US008858955B2

(12) United States Patent
Biemans et al.

(10) Patent No.: US 8,858,955 B2
(45) Date of Patent: Oct. 14, 2014

(54) PROCESS FOR MANUFACTURING VACCINES

(75) Inventors: Ralph Leon Biemans, Rixensart (BE); Pierre Duvivier, Rixensart (BE)

(73) Assignee: GlaxoSmithKline Biologicals s.a. (BE)

(*) Notice: Subject to any disclaimer, the term of this patent is extended or adjusted under 35 U.S.C. 154(b) by 577 days.

(21) Appl. No.: 12/521,797

(22) PCT Filed: Jan. 2, 2008

(86) PCT No.: PCT/EP2008/050011
§ 371 (c)(1),
(2), (4) Date: Jun. 30, 2009

(87) PCT Pub. No.: WO2008/081014
PCT Pub. Date: Jul. 10, 2008

(65) Prior Publication Data
US 2010/0143399 A1  Jun. 10, 2010

(30) Foreign Application Priority Data
Jan. 4, 2007   (GB) .................................. 0700136.5

(51) Int. Cl.
| A61K 39/385 | (2006.01) |
| C07K 1/00 | (2006.01) |
| C07H 1/00 | (2006.01) |
| A61K 39/02 | (2006.01) |
| A61K 47/48 | (2006.01) |
| A61K 39/00 | (2006.01) |

(52) U.S. Cl.
CPC ............ *A61K 39/385* (2013.01); *A61K 47/4833* (2013.01); *A61K 47/48261* (2013.01); *A61K 2039/627* (2013.01); *A61K 2039/6037* (2013.01); *Y10S 424/831* (2013.01); *Y10S 530/807* (2013.01)
USPC ................. 424/197.11; 424/193.1; 424/194.1; 424/831; 530/807; 530/405; 536/123.1; 536/124

(58) Field of Classification Search
None
See application file for complete search history.

(56) References Cited

U.S. PATENT DOCUMENTS

| 4,365,170 | A | 12/1982 | Okuhara et al. |
| 4,376,760 | A | 3/1983 | Jung et al. |
| 4,673,574 | A | 6/1987 | Anderson et al. |
| 5,180,815 | A | 1/1993 | Masuda |
| 8,329,184 | B2 * | 12/2012 | Biemans et al. ........... 424/184.1 |
| 2008/0095777 | A1 * | 4/2008 | Castado et al. ........... 424/139.1 |
| 2010/0215686 | A1 | 8/2010 | Biemans et al. |
| 2013/0004532 | A1 | 1/2013 | Biemans et al. |

FOREIGN PATENT DOCUMENTS

| EP | 0 208 375 A2 | 1/1987 |
| EP | 0 161 188 B1 | 4/1991 |
| EP | 0 497 525 A2 | 1/1992 |
| EP | 0 378 881 B1 | 6/1993 |
| EP | 0 427 347 B1 | 2/1995 |
| EP | 0 477 508 B1 | 7/1995 |
| EP | 0 471 177 B1 | 10/1995 |
| WO | WO 91/01146 | 2/1991 |
| WO | WO 93/15760 | 8/1993 |
| WO | WO 93/17712 | 9/1993 |
| WO | WO 94/03208 | 2/1994 |
| WO | WO 95/08348 | 3/1995 |
| WO | WO 96/29094 | 9/1996 |
| WO | WO 96/40242 | 12/1996 |
| WO | WO 98/26799 | 6/1998 |
| WO | WO 98/58668 | 12/1998 |
| WO | WO 00/56360 | 9/2000 |
| WO | WO 00/61761 | 10/2000 |
| WO | WO 01/72337 A1 | 10/2001 |
| WO | WO 02/091998 A2 | 11/2002 |
| WO | WO 03/007985 A2 | 1/2003 |
| WO | WO 2004/014417 A2 | 2/2004 |
| WO | WO 2004/014418 A2 | 2/2004 |
| WO | WO 2004/014419 A2 | 2/2004 |
| WO | WO 2006032475 * | 3/2006 |
| WO | WO 2007/000341 A2 | 1/2007 |
| WO | WO 2007/000342 A2 | 1/2007 |
| WO | WO 2008/011201 A2 | 1/2008 |

OTHER PUBLICATIONS

Beuvery et al. Infect. Immun. 37: 15-22, 1982.*
Bartoloni, et al., Vaccine, 13(5): 463-470 (1995).
Chibber, et al., J. Med. Microbiol. 53:705-709, 2004.
Chu, et al., Infect. Immun. 40(1):245-256 (1983).
Corbel, Biologicals, 22:353-360, 1994.
Costantino, et al., Vaccine 10(10): 691-698 (1982).
Devi, et al., PNAS, 88:7175-7179 (1991).
Dintzis, Rational of Conjugate Vaccines, Pediatric Research 32(4):376-385 (1992).
Falugi, et al., Eur. Journal of Immunology, 31:3816-3824 (2001).
Gu & Tsai, Infect. Immun. 61(5):1873-1880 (1993).
Halsey, et al., Combination Vaccines, Clinical Infectious Diseases, vol. 33(suppl 4); S312-S318, 2001.

(Continued)

*Primary Examiner* — S. Devi
(74) *Attorney, Agent, or Firm* — Jason C. Fedon; William T. Han

(57) ABSTRACT

The present application discloses a method for making an immunogenic composition comprising an improved way of conducting saccharide-protein conjugation reactions using carbodiimide condensation chemistry. Depending on the nature of the saccharide or protein carrier involved, the quality of the conjugate may be improved by adding one of the reaction components slowly to the reaction mixture. In addition, the conjugate is mixed with a staphylococcal antigen. Immunogenic compositions are further provided comprising the saccharide-protein conjugates made by the methods disclosed.

8 Claims, 46 Drawing Sheets

(56) References Cited

OTHER PUBLICATIONS

Hoare, et al., Journal Biological Chemistry, 242(10):2447-2453 (1967).
Jin, et al., Infect. Immun, 71(9):5115-5120 (2003).
Kossaczka, et al., Infect. Immun. 68(9):5037-5043 (2000).
Kuo, et al., Infect. Immun. 63(7): 2706-2713 (1995).
Lindberg, Vaccine 17:S28-S36 (1999).
Nakajima & Ikada, Bioconjugate Chemistry, 6(1): 123-130 (1995).
Pierce, Cross linking reagents Technical Handbook, pp. 1-48 (2005).
Que, et al., Infect. Immun. 56(10):2645-2649 (1988).
Schneerson, et al., Infect. Immun. 52(2):519-528 (1986).
Schneerson, et al., Infect. Immuno. 60(9): 3528-3532 (1992).
Schneerson, et al., Journal of Experimental Medicine, 152:361-376 (1980).
Shen, et al., Vaccine, 19: 850-861 (2001).
Szu, et al., Carbohydrate research 152:7-20 (1986).
Wang, et al., An active Immunozation Approach to Generate Protective Catalytic Antibodies, Biochemical Journal, vol. 360, p. 151-157, 2001.
Wilkinson, et al., Poultry Science, 82:1565-1572 (2003).
Beuvery, et al., Preperation and Immunochemical Characterization of Meningococcal Group C polysaccbaride-teanus Toxoid Conjugates as a new generation of vaccines, Infection and Immunity, 40(1) pp. 39-45, 1983.
Kossaczka, Z. et al., American society for Microbiology, Synthesis and Immunological Properties of VI and Di-Omicron-Acetyl pectin Protein Conjugates with Adipic Acid Dihydrazide as the Linker, Americant Society for Microbiology, vol. 65, No. 6, pp. 2088-2093 (Jun. 1997).

* cited by examiner

Figure 1

SEQ ID NO:1 polypeptide sequence
MLQVTDVSLRFGDRKLFEDVNIKFTEGNCYGLIGANGAGKSTFLKILSGELDSQTGHVSLGKNERLAVLKQDHYAYEDERV
LDVVIKGHERLYEVMKEKDEIYMKPDFSDEDGIRAAELEGEFAEMNGWNAEADAANLLSGLGIDPTLHDKKMAELENNQKI
KVLLAQSLFGEPDVLLLDEPTNGLDIPAISWLEDFLINFDNTVIVVSHDRHFLNNVCTHIADLDFGKIKVYVGNYDFW
YQSSQLAQKMAQEQNKKKEEKMKELQDFIARFSANASKSKQATSRKKQLEKIELDDIQPSSRRYPFVKFTPEREIGNDLLI
VQNLSKTIDGEKVLDNVSFTMNPNDKAILIGDSEIAKTTLLKILAGEMEPDEGSFKWGVTTSLSYFPKDNSEFFEGVNMNL
VDWLRQYAPEDEQTETFLRGFLGRMLFSGEEVKKASVLSGGEKVRCMLSKMMLSSANVLLLDEPTNHLDLESITAVN
DGLKSFKGSIIFTSYDFEFINTIANRVIDLNKQGGVSKEIPYEEYLQEIGVLK

SEQ ID NO:2 polypeptide sequence
MLQVTDVSLRFGDRKLFEDVNIKFTEGNCYGLIGANGAGKSTFLKILSGEIDSQTGHVSLGKDERLAVLKQDHFAYEDERV
LDVVIKGHERLYQVMKEKDEIYMKPDFSDEDGIRAAELEGEFAEMNGWNAEADAANLLSGLGIEPDLHDKNMSELENNQKV
KVLLAQSLFGDPDVLLLDEPTNGLDIPAISWLEDFLINFENTVIVVSHDRHFLNNVCTHIADLDFGKIKLYVGNYDFW
YQSSQLAQKMAQEQNKKKEEKMKELQDFIARFSANASKSKQATSRKKQLEKIELDDIQPSSRRYPYVKFTPEREIGNDLLT
VENLSKTIDGEKVLDNVSFTMNPNDKAILVGDSEIAKTTLLKILAGEMEPDEGTFKWGVTTSLSYFPKDNSEFFDGVDMNL
VEWLRQYAPEDEQTETFLRGFLGRMLFSGEEVKKASVLSGGEKVRCMLSKMMLSSANVLLLDEPTNHLDLESITAVN
DGLKSFKGSIIFTSYDFEFINTIANRVIDLNQAGALSKEVPYEEYLQEIGVLQNN

SEQ ID NO:3 polypeptide sequence
MPIITDVYAREVLDSRGNPTVEVEVLTESGAFGRALVPSGASTGEHEAVELRDGDKSRYLGKGVTKAVENVNEIIAPEIIE
GEFSVLDQVSIDKMMIALDGTPNKGKLGANAILGVSIAVARAAADLLGQPLYKYLGGFNGKQLPVPMMNIVNGGSHSDAPI
AFQEFMILPVGATTFKESLRWGTEIFHNLKSILSKRGLETAVGDEGGFAPKFEGTEDAVETIIQAIEAAGYKPGEEVF
LGFDCASSEFYENGVYDYSKFEGEHGAKRTAAEQVDYLEQLVDKYPIITIEDGMDENDWDGWKQLTERIGDRVQLVGDDLF
VTNTEILAKGIENGIGNSILIKVNQIGTLTETFDAIEMAQKAGYTAVVSHRSGETEDTTIADIAVATNAGQIKTGSLSRTD
RIAKYNQLLRIEDELFET
AKYDGIKSFYNLDK

SEQ ID NO:4 polypeptide sequence
MPIITDVYAREVLDSRGNPTVEVEVLTESGAFGRALVPSGASTGEHEAVELRDGDKSRYLGKGVTKAVENVNEMIAPEIVE
GEFSVLDQVSIDKMMIQLDGTHNKGKLGANAILGVSIAVARAAADLLGQPLYKYLGGFNGKQLPVPMMNIVNGGSHSDAPI
AFQEFMILPVGAESFKESLRWGAEIFHNLKSILSERGLETAVGDEGGFAPRFEGTEDAVETIIKAIEKAGYKPGEDVF
LGFDCASSEFYENGVYDYTKFEGEHGAKRSAAEQVDYLEELIGKYPIITIEDGMDENDWEGWKQLTDRIGDKVQLVGDDLF
VTNTEILSKGIEQGIGNSILIKVNQIGTLTETFDAIEMAQKAGYTAVVSHRSGETEDTTIADIAVATNAGQIKTGSLSRTD
RIAKYNQLLRIEDELYETAKFEGIKSFYNLDK

SEQ ID NO:5 polypeptide sequence
MKKIVTATIATAGLATIAFAGHDAQAAEQNNNGYNSNDAQSYSYTYTIDAQGNYHYTWTGNWNPSQLTQNNTYYYNNYNT
YSYNNASYNNYYNHSYQYNNYTNNSQTATNNYYTGGSGASYSTTSNNVHVTTTAAPSSNGRSISNGYASGSNLYTSGQCT
YYVFDRVGGKIGSTWGNASNWANAAASSGYTVNNTPKVGAIMQTTQGYYGHVAYVEGVNSNGSVRVSEMNYGHGAGVVTS
RTISANQAGSYNFIH

SEQ ID NO:6 polypeptide sequence
MKKIATATIATAGFATIAIASGNQAHASEQDNYGYNPNDPTSYSYTYTIDAQGNYHYTWKGNWHPSQLNQDNGYYSYYYY
NGYNNYNNYNNGYSYNNYSRYNNYSNNNQSYNYNNYNSYNTNSYRTGGLGASYSTSSNNVQVTTTMAPSSNGRSISSGYT
SGRNLYTSGQCTYYVFDRVGGKIGSTWGNASNWANAAARAGYTVNNTPKAGAIMQTTQGAYGHVAYVESVNSNGSVRVSE
MNYGYGPGVVTSRTISASQAAGYNFIH

SEQ ID NO:7 polypeptide sequence
MKKIATATIATAGIATFAFAHHDAQAAEQNNDGYNPNDPYSYSYTYTIDAEGNYHYTWKGNWSPDRVNTSYNYNNYNNYN
YYGYNNYSNYNNYSNYNNYNNYQSNNTQSQRTTQPTGGLGASYSTSSSNVHVTTTSAPSSNGVSLSNARSASGNLYTSGQ
CTYYVFDRVGGKIGSTWGNANNWANAAAARSGYTVNNSPAKGAILQTSQGAYGHVAYVEGVNSNGSIRVSEMNYGHGAGVV

Figure 1 cont.

TSRTISASQAASYNYIH

SEQ ID NO:8 polypeptide sequence
MKKLVPLLLALLLLVAACGTGGKQSSDKSNGKLKVVTTNSILYDMAKNVGGDNVDIHSIVPVGQDPHEYEVKPKDIKKLTD
ADVILYNGLNLETGNGWFEKALEQAGKSLKDKKVIAVSKDVKPIYLNGEEGNKDKQDPHAWLSLDNGIKYVKTIQQTFIDN
DKKHKADYEKQGNKYIAQLEKLNNDSKDKFNDIPKEQRAMITSEGAFKYFSKQYGITPGYIWEINTEKQGTPEQMRQA
IEFVKKHKLKHLLVETSVDKKAMESLSEETKKDIFGEVYTDSIGKEGTKGDSYYKMMKSNIETVHGSMK

SEQ ID NO:9 polypeptide sequence
MKKILALAIAFLIILAACGNHSNHEHHSHEGKLKVVTTNSILYDMVKRVGGNKVDVHSIVPVGQDPHEYEVKPKDIKALTD
ADVVFYNGLNLETGNGWFEKALDQAGKSTKDKNVIAASNNVKPIYLNGEEGNKNKQDPHAWLSLENGIKYVKTIQKSLEHH
DKKDKSTYEKQGNAYISKLEELNKDSKNKFDDIPKNQRAMMTSEGAFKYFAQQFDVKPGYIWEINTEKQGTPGQMKQA
IKFVKDNHLKHLLVETSVDKKAMQSLSEETKKDIYGEVFTDSIGKEGTKGDSYYKMMKSNIDTIHGSMK

SEQ ID NO:10 polypeptide sequence
MKKTIMASSLAVALGVTGYAAGTGHQAHAAEVNVDQAHLVDLAHNHQDQLNAAPIKDGAYDIHFVKDGFQYNFTSNGTTW
SWSYEAANGQTAGFSNVAGADYTTSYNQGSDVQSVSYNAQSSNSNVEAVSAPTYHNYSTSTTSSSVRLSNGNTAGATGSS
AAQIMAQRTGVSASTWAAIIARESNGQVNAYNPSGASGLFQTMPGWGPTNTVDQQINAAVKAYKAQGLGAWGF

SEQ ID NO:11 polypeptide sequence
MKKTVIASTLAVSLGIAGYGLSGHEAHASETTNVDKAHLVDLAQHNPEELNAKPVQAGAYDIHFVDNGYQYNFTSNGSEWS
WSYAVAGSDADYTESSSNQEVSANTQSSNTNVQAVSAPTSSESRSYSTSTTSYSAPSHNYSSHSSSVRLSNGNTAGSVGSY
AAAQMAARTGVSASTWEHIIARESNGQLHARNASGAAGLFQTMPGWGSTGSVNDQINAAYKAYKAQGLSAWGM

SEQ ID NO:12 polypeptide sequence
MNYRDKIQKFSIRKYTVGTFSTVIATLVFLGFNTSQAHAAETNQPASVVKQKQQSNNEQTENRESQVQNSQNSQNSQSLS
ATHENEQPNNSQANLVNQKVAQSSTTNDEQPASQNVNTKKDSATAATTQPDKEESKHKQNESQSANKNGNDNRAAHVENH
EANVVTASDSSDNGNVQHDRNELQAFFDANYHDYRFIDRENADSGTFNYVKGIFDKINTLLGSNDPINNKDLQLAYKELE
QAVALIRTMPQRQQTSRRSNRIQTRSVESRAAEPRSVSDYQNANSSYYVENANDGSGYPVGTYINASSKGAPYNLPTTPW
NTLKASDSKEIALMTAKQTGDGYQWVIKFNKGHAPHQNMIFWFALPADQVPVGRTDFVTVNSDGTNVQWSHGAGAGANKP
LQQMWEYGVNDPDRSHDFKIRNRSGQVIYSWPTVHVYSLEDLSRASDYFSEAGATPATKAFGRQNFEYINGQKPAESPGV
PKVYTFIGQGDASYTISFKTQGPTVNKLYYAAGGRALEYNQLFMYSQLYVESTQDHQQRLNGLRQVVNRTYRIGTTKRVE
VSQGNVQTKKVLESTNLNIDDFVDDPLSYVKTPSNKVLGFYPTNANTNAFRPGGVQELNEYQLSQLFTDQKLQEAARTRN
PIRLMIGFDYPDGYGNSETLVPVNLTVLPEIQHNIKFFKNDDTQNIAEKPFSKQAGHPVFYVYAGNQGNASVNLGGSVTS
IQPLRINLTSNENFTDKDWQITGIPRTLHIENSTNRTNNARERNIELVGNLLPGDYFGTIRFGRKEQLFEIRVKPHTPTI
TTTAEQLRGTALQKVPVNISGIPLDPSALVYLVAPTNQTTNGGSEADQIPSGYTILATGTPDGVHNTITIRPQDYVVFIP
PVGKQIRAVVYYNKVVASNMSNAVTILPDDIPPTINNPVGINAKYYRGDEVNFTMGVSDRHSGIKNTTITTLPSGWTSNL
TKSDNKNGSLAITGRVSMNQAFNSDITFKVSATDNVNNTTNDSQSKHVSIHVGKISEDAHPIVLGNTEKVVVVNPTAVSN
DEKQSIITAFMNKNQNIRGYLASTDPVTVDNNGNVTLHYRDGSSTTLDATNVMTYEPVVKSEYQTANAAKTATVTIAKGQ
SFNIGDIKQYFTLSNGQAIPNGTFTNITSDRTIPTAQEVSQMNAGTQLYHIVASNAYHKDTEDFYISLKIVDVKQPEGDQ
RVYRTSTYDLTTDEISKVKQAFINANRDVITLAEGDISVTNTPNGANVSTITVNINKGRLTKSFASNLANMNFLRWVNFP
QDYTVTWTNAKIANRPTDGGLSWSDDHKSLIYRYDATLGTQITTNDILTMLKATTTVPGLRNNITGNEKAQAEAGGRPNY
RTTGYSQSNATTDGQRQFTLNGQVIQILDIINPSNGYGGQPVTNSNTRANHSNSTVVNVNEPAANGAGAFTIDHVVKSNS
THNASDAVYKAQLYLTPYGPKQYVEHLNQNTGNTTDAINIYFVPSDLVNPTISVGNYTNHQVFSGETFTNTITANDNFGV
QSVTVPNTSQITGTVDNNHQHVSATAPNVTSATSKTINLLATDTSGNTATTSFNVTVKPLRDKYRVGTSSTAANPVRIAN
ISNNATVSQADQTTIINSLTFTSNAPNRNYATASANEITSKTVSNVSRTGNNANVTVTVTHQDGTTSTVTVPVKHVIPEI
VAHSHYTVQGQDFPAGNGSSAADYFKLSNGSAIPDATITWVSGQAPNKDNTRIGEDITVTAHILIDGETTPITKTATYKV
VRTVPKHVFETARGVLYPGVSDMYDAKQYVKPVNNSWSTNAQHMNFQFVGTYGPNKDVVGISTRLIRVTYDNRQTEDLTI
LSKVKPDPPRIDANSVTYKAGLTNQEIKVNNVLNNSSVKLFKADNTPLNVTNITHGSGFSSVVTVSDALPNGGIKAKSSI
SMNNVTYTTQDEHGQVVTVTRNESVDSNDSASVTVTPQLQATTEGAVFIKGGDGFDFGHVERFIQNPPHGATVAWHDSPD
TWKNTVGNTHKTAVVTLPSGQGTRNVEVPVKVYPVANAKAPSRDVKGQNLTHGTNAIDYITFDPNTNTNGITAAWANRQQ
PNNQQAGVQHLNVDVTYPGISAAKRVPVTVNVYQFEFPQTTYTTTVGGTLASGTQASGYAHMQNASGLPTDGFTYKWNRD
TTGTNDANWAAMNKPNTAQVVNAKYDVIYNGHTFATSLPAKFVVKDVQPAKPTVTETAAGAITIAPGANQTVNTHAGNVT
TYADKLVIKRNGNVVTFTRRNNTSPWVKEASADNVTGIVGTNNGITVAAGTFNPADTIQVVATQGSGETISDEQRSDDF
TVVAPQPNQATTKIWQNGHIDITPNNPSGHLINPTQAMDIAYTEKVGNGAEHSKTINVVRGQNNQWTIANKPDYVTLDAQ
TGKVTFNANTIKPNSSITITPKAGTGHSVSSNPSTLTAPAAHTVNTTEIVKDYGSNVTAAEINNAVQVANKRTATIKNGT

Figure 1 cont.

AMPTNLAGGSTTTIPVTVTYNDGSTEEVQESIFTKADKRELITAKNHLDDPVSTEGKKPGTITQYNNAMHNAQQQINTAK
TEAQQVINNERATPQQVSDALTKVRAAQTKIDQAKALLQNKEDNSQLVTSKNNLQSSVNQVPSTAGMTQQSIDNYNAKKR
EAETEITAAQRVIDNGDATAQQISDEKHRVDNALTALNQAKHDLTADTHALEQAVQQLNRTGTTTGKKPASITAYNNSIR
ALQSDLTSAKNSANAIIQKPIRTVQEVQSALTNVNRVNERLTQAINQLVPLADNSALRTAKTKLDEEINKSVTTDGMTQS
SIQAYENAKRAGQTETTNAQNVINNGDATDQQIAAEKTKVEEKYNSLKQAIAGLTPDLAPLQTAKTQLQNDIDQPTSTTG
MTSASVAAFNDKLSAARTKIQEIDRVLASHPDVATIRQNVTAANAAKTALDQARNGLTVDKAPLENAKNQLQHSIDTQTS
TTGMTQDSINAYNAKLTAARNKVQQINQVLAGSPTVDQINTNTSAANQAKSDLDHARQALTPDKAPLQNAKTQLEQSINQ
PTDTTGMTTASLNAYNQKLQAARQKLTEINQVLNGNPTVQNINDKVAEANQAKDQLNTARQGLTLDRQPALTTLHGASNL
NQAQQNNFTQQINAAQNHAALETIKSNITALNTAMTKLKDSVADNNTIKSGQNYTDATPANKQAYDNAVNAAKGVIGETT
NPTMDVNTVNQKAASVKSTKDALDGQQNLQRAKTEATNAITHASDLNQAQKNALTQQVNSAQNVQAVNDIKQTTQSLNTA
MTGLKRGVANHNQVVQSDNYVNADTNKKNDYNNAYNHANDIINGNAQHPVITPSDVNNALSNVTSKEHALNGEAKLNAAK
QEANTALGHLNNLNNVQRQNLQSQINGAHQIDAVNTIKQNATNLNSAMGNLRQAVADKDQVKRTEDYADADTAKQNAYNS
AVSSAETIINQTANPTMSVDDVNRATSAVTTNKNALNGDEKLVQSKTDAARAIDALPHLNNAQKADVKSKINAASNIAGV
NTVKQQGTDLNTAMGNLQGAINDEQTTLNSQNYQDATPSKKTAYTNAVQAAKDILNKSNGQNKTKDQVTEAMNQVNSAKN
NLDGTRLLDQAKQTAKQQLNNMTHLTTAQKTNLTNQINSGTTVAGVHTVQSNANTLDQAMNTLRQSIANNDATKASEDYV
DANNDKQTAYNNAVAAAETIINANSNPEMNPSTITQKAEQVNSSKTALNGDENLATAKQNAKTYLNTLTSITDAQKNNLI
SQISSATRVSGVDTVKQNAQHLDQAMANLQNGINNESQVKSSEKYRDADTNKQQEYDNAITAAKAILNKSTGPNTAQNAV
EAALQRVNTAKDALNGDAKLIAAQNAAKQHLGTLTHITTAQRNDLTNQIS

SEQ ID NO:13 polypeptide sequence
MGNLQTAINDKSGTLASQNFLDADEQKRNAYNQAISAAETILNKQTGPNTAKTAVEQALNNVNSAKHALNGTQNLNNAKQ
AAITAINGASDLNQKQKDALKAQANGAQRVSNANDVQRNATELNTAMGQLQHAIADKTNTLASSKYVNADSTKQNAYTTK
VTNAEHIISGTPTVVTTPSEVTAAANQVNSAKQELNGDERLRVAKQNANTAIDALTQLNTPQKAKLKEQVGQANRLEDVQ
SVQTNGQSLNNAMKGLRDSIANETTVKASQNYTDASPNNQSTYNSAVSNAKGIINQTNNPTMDTSAITQATTQVNNAKNG
LNGAENLRNAQNTAKQNLNTLSHLTNNQKSAISSQIDRAGHVSEVTAAKNAATELNAQMGNLEQAIHDQNTVKQGVNFTD
ADKAKRDAYTNAVSRAETILNKTQGANTSKQDVEAAIQNVTSAKNALNGDQNVTNAKNAAKNALNNLTSINNAQKRDLTT
KIDQATTVAGVEAVSNTGTQLNTAMANLQNGINDKANTLASENYHDADSDKKTAYTQAVTNAENILNKNSGSNLDKAAVE
NALSQVTNAKGALNGNHNLEQAKSNANTTINGLQHLTTAQKDKLKQQVQQAQNVAGVDTVKSSANTLNGAMGTLRNSIQD
NTATKNGQNYLDATERNKTNYNNAVDSANGVINATSNPNMDANAINQIATQVTSTKNALDGTHNLTQAKQTATNAIDGAT
NLNKAQKDALKAQVTSAQRVANVTSIQQTANELNTAMGQLQHGIDDENATKQTQKYRDAEQSKKTAYDQAVAAAKAILNK
QTGSNSDKAAVDRALQQVTSTKDALNGDAKLAEAKAAARQNLGTLNHITNAQRTALEGQINQATTVDGVNTVKTNANTLD
GAMNSLQGAINDKDATLRNQNYLDADESKRNAYTQAVTAAEGILNKQTGGNTSKADVDNALNAVTRAKAALNGAENLRNA
KTSATNTINGLPNLTQLQKDNLKHQVEQAQNVVGVNGVKDKGNTLNTAMGALRTSIQNDNTTKTSQNYLDASDSNKNNYN
TAVNNANGVINATNNPNMDANAINDMANQVNTTKAALNGAQNLAQAKTNATNTINNAQDLNQKQKDALKTQVNNAQRVSD
ANNVQHTATELNGAMTALKAAIADKERTKASGNYVNADQEKRQAYDSKVTNAENIINGTPNATLTVNDVNSAASQVNAAK
TALNGDNNLRVAKEHANNTIDGLAQLNNVQKAKLKEQVQSATTLDGVQTVKNSSQTLNTAMKGLRDSIANEATIKAGQNY
TDASPNNREYDSAVTAAKAIINQTSNPTMEPNTITQATSQVTTKEHALNGAQNLAQAKTTAKNNLNNLTSINNAQKDAL
TRNIDGATTVAGVNQETAKATELNNAMHSLQNGINDETQTKQTQKYLDAEPSKKSAYDQAVNAAKAILTKASGQNVDKAA
VEQALQNVNSTKTALNGDAKLNEAKAAAKQTLGTLTHINNAQRNALDNEITQATNVEGVNTVKAKAQQLDGAMGQLETSI
RDKDTTLQSQNYQDADDAKRTAYSQAVNAAATILNKTAGGNTPKADVERAMQAVTQANTALNGIQNLERAKQAANTAITN
ASDLNTKQKEALKAQVTSAGRVSAANGVEHTATELNTAMTALKRAIADKADTKASGNYVNADANKRQAYDEKVTAAEHIV
SGTPTPTLTPSDVTNAATQVTNAKTQLNGNHNLEVAKQNANTAIDGLTSLNGPQKAKLKEQVGQATTLPNVQTVRDNAQT
LNTAMKGLRDSIANEATIKAGQNYTDASQNKQNDYNNAVTAAKAIIGQTTSPSMIAQEINQAKDQVTAKQQALNGQENLR
TAQTNAKQHLNGLSDLTNAQKDAAKRQIEGATHVNEVTQAQNNADALNTAMTNLKNGIQDQNTIKQGVNFTDADEAKRNA
YTNAVTQAEQILNKAQGPNTAKDGVETALQNVQRAKNELNGNQNVANAKTTAKNALNNLTSINNAQKAALKSQIEGATTV
AGVNQVSTMASELNTAMSNLQRGINDEAATKAAQKYTEADRDKQTAYNDAVTAAKTLLDKTAGSNDNKVAVEQALQRVNT
AKTALNGDARLNEAKNTAKQQLATMSHLTNAQKANLTEQIERGTTVAGVQGIQANAGTLNQAMNQLRQSIASKDATKSSE
DYQDANADLQNAYNDAVTNAEGIISATNNPEMNPDTINQKASQVNSAKSALNGDEKLAAVKQTAKSDIGRLTDLNNAQRT
AANAEVDQAPNLAAVTAAKNKATSLNTAMGNLKHALAEKDNTKRSVNYTDADQPKQQAYDTAVTQAEAITNANGSNANET
QVQAALNQLNQAKNDLNGDNKVAQAKETAKRALASYSNLNNAQSTAATSQIDNATTVADVTAAQNTANELNTAMGQLQNG
INDQNTVKQQVNFTDADQGKKDAYTNAVTNAQGILDKANGQNMTKAQVEAALNQVTTAKNALNGDANVRQAKSDAKANLG
TLTHLNNAQKQDLTSQIEGATTVNGVNSVKTKAQDLDGAMQRLESAIANKDQTKASENYIDADPTKKTAFDNAITQAESY
LNKDHGTNKDKQAVEQAIQSVTSTENALNGDANLQCAKTEATQAIDNLTQLNTPQKTALKQQVNAAQRVSGVTDLKNSAT
SLNNAMDQLKQAIGDHDTIVAGGNYTNASPDKQGAYTDAYNAAKNIVNGSPNVITNAADVTAATQRVNNAETSLNGDTNL
ATAKQQAKDALRQMTHLSDAQKQSITGQIDSATQVTGVQSVKDNATNLDNAMNQLRNSIANKDEVKASQPYVDADTDKQN
AYNTAVTSAENIINATSQPTLDPSAVTQAANQVNTNKTALNGAQNLANKKQETTANINRLSHLNNAQKQDLNTQVTNAPN
ISTVNQVKTKAEQLDQAMERLINGIQDKDQVKQSVNFTDADPEKQTAYNNAVTAAENIINQANGTNANQSQVEAALSTVT
TTKQALNGDRKVTDAKNNANQTLSTLDNLNNAQKGAVTGNINQAHTVAEVTQAIQTAQELNTAMGNLKNSLNDKDTTLGS

Figure 1 cont.

QNFADADPEKKNAYNEAVRNAENILNKSTGTNVPKDQVEAAMNQVNTTKAALNGTQNLEKAKQHANTAIDGLSHLTNAQK
EALKQLVQQSTTVAEAQGNEQKANNVDAAMDKLRQSIADNATTKQNQNYTDASPNKKDAYNNAVTTAQGIIDQTTNPSLD
PTVINQAAGQVSTSKNALNGNENLEAAKQQATQSLGSLDNLNNAQKQAVTNQINGAHTVDEANQIKQNAQNLNTAMGNLK
QAIADKDATKATVNFTDADQAKQQAYNTAVTNAENIISKANGGNATQTEVEQAIQQVNAAKQALNGNANVQHAKDEATAL
INNSNDLNQAQKDALKQQVQNATTVAGVNNVKQTAQELNNAMTQLKQGIADKEQTKADGNFVNADSDKQNAYNQAVAKAE
ALISGTPDVVVTPSEITAALNKVTQAKNDLNGNTNLATAKQNVQHAIDQLPNLNQAQRDEYSKQITQATLVPNVNAIQQA
ATTLNDAMTQLKQGIANKAQIKGSENYHDADTDKQTAYDNAVTKAEELLKQTTNPTMDPNTIQQALTKVNDTNQALNGNQ
KLADAKQDAKTTLGTLDHLNDAQKQALTTQVEQAPDIATVNNVKQNAQNLNNAMTNLNNALQDKTETLNSINFTDADQAK
KDDYTNAVSHAEGILSKANGSNASQTEVEQAMQRVNEAKQALNGNDNVQRAKDAAKQVITNANDLNQAQKDALKQQVDAA
QTVANVNTIKQTAQDLNQAMTQLKQGIADKDQTKANGNFVNADTDKQNAYNNAVAHAEQIISGTPNANVDPQQVAQALQQ
VNQAKGDLNGNHNLQVAKDNANTAIDQLPNLNQPQKTALKDQVSHAELVTGVNAIKQNADALNNAMGTLKQQIQANSQVP
QSVDFTQADQDKQQAYNNAANQAQQIANGTPTPVLAPDTVTKAVTTMNQAKDALNGDEKLAQAKQDALANLDTLRDLNQP
QRDALRNQINQAQALATVEQTKQNAQNVNTAMGNLKQGIANKDTVKASENYHDADVDKQTAYTNAVSQAEGIINQTTNPT
LNPDDITRALTQVTDAKNSLNGEAKLATEKQNAKDAVSGMTHLNDAQKQALKGQIDQSPEIATVNQVKQTATSLDQAMDQ
LSQAINDKDQILADGNYLNADPDKQNAYKQAVAKAEALLNKQSGTNEVQAQVESITNEVNAAKQALNGNDNLANAKQQAK
QQLANLTHLNDAQKQSFESQITQAPLVTDVTTINQKAQTLDHAMELLRNSVADNQTTLASEDYHDATAQRQNDYNKAVTA
ANNIINQTTSPTMNPDDVNGATTQVNNTKVALDGDENLAAAKQQANNRLDQLDHLNNAQKQQLQSQITQSSDIAAVNGHK
QTAESLNTAMGNLINAIADHQAVEQRGNFINADTDKQTAYNTAVNEAAAMINKQTGQNANQTEVEQAITKVQTTLQALNG
DHNLQVAKTNATQAIDVLTSLNDPQKTALKDQVTAATLVTAVHQIEQNANTLNQAMHGLRQSIQDNAATKANSKYINEDQ
PEQQNYDQAVQAANNIINEQTATLDNNAINQVAATVNTTKAALHGDVKLQNDKDHAKQTVSQLAHLNNAQKHMEDTLIDS
ETTRTAVKQDLTEVQALDQLMDALQQSIADKDATRASSAYVNAEPNKKQAYDEAVQNAESIIAGLNNPTINKGNVSSATQ
AVISSKNALDGVERLAQDKQTAGNSLNHLDQLTPAQQQALENQINNATTCDKVAEIIAQAQALNEAMKALKESIKDQPQT
EASSKFINEDQAQKDAYTQAVQHAKDLINKTTDPTLAKSIIDQATQAVTDAKNNLHGDQKLAQDKQRATETLNNLSNLNT
PQRQALENQINNAATRGEVAQKLTEAQALNQAMEALRNSIQDQQQTESGSKFINEDKPQKDAYQAAVQNAKDLINQTGNP
TLDKAQVEQLTHAFKQAKDNLHGDQKLADDKQHAVTDLNQLNGLNNPQRQALESQINNAATRGEVAQKLAEAKALDQAMQ
ALRNSIQDQQQTEAGSKFINEDKPQKDAYQAAVQNAKDLINQTGNPTLDKSQVEQLTQAVTTAKDNLHGDQKLARDQQQA
VTTVNALPNLNHAQQQTLTDAINAAPTRTEVAQHVQTATELDHAMETLKNKVDQVNTDKAQPNYTEASTDKKEAVDQALQ
AAQSITDPTNGSNANKDAVEQALTKLQEKVNELNGNERVAEAKTQAKQTIDQLTHLNADQIATAKQNIDQATKLQPIAEL
VDQATQLNQSMDQLQQAVNEHANVEQTIDYTQADSDKQKAYKQAIADAENVLKQNANKQQVDQALQNILNAKQALNGDER
VALAKTNGKHDIDQLNALNNAQQDGFKGRIDQSNDLNQIQQIVDEAKALNRAMDQLSQEITGNEGRTKGSTNYVNADTQV
KQVYDEAVDKAKQALDKSSGQNLTAEQVIKLNDAVTAAKKALNGEERLNNRKAEALQRLDQLTHLNNAQRQLAIQQINNA
ETLNKASRAINRATKLDNAMGAVQQYIDEQHLGVISSTNYINADDNLKANYDNAIANAAHELDKVQGNAIAKAEAEQLKQ
NIIDAQNALNGDQNLANAKDKANAFVNSLNGLNQQQQDLAHKAINNADTVSDVTDIVNNQIDLNDAMETLKHLVDNEIPN
AEQTVNYQNADDNAKTNFDDAKRLANTLLNSDNTNVNDINGAIQAVNDAIHNLNGDQRLQDAKDKAIQSINQALANKLKE
IEASNATDQDKLIAKNKAEELANSIINNNINKATSNQAVSQVQTAGNHAIEQVHANEIPKAKIDANKDVDKQVQALIDEID
RNPNLTDKEKQALKDRINQILQQGHNDINNALTKEEIEQAKAQLAQALQDIKDLVKAKEDAKQDVDKQVQALIDEIDQNP
NLTDKEKQALKDRINQILQQGHNGINNAMTKEEIEQAKAQLAQALKEIKDLVKAKENAKQDVDKQVQALIDEIDQNPNLT
DKEKQALKDRINQILQQGHNDINNAMTKEEIEQAKAQLAQALQDIKDLVKAKEDAKNAIKALANAKRDQINSNPDLTPEQ
KAKALKEIDEAEKRALQNVENAQTIDQLNRGLNLGLDDIRNTHVWEVDEQPAVNEIFEATPEQILVNGELIVHRDDIITE
QDILAHINLIDQLSAEVIDTPSTATISDSLTAKVEVTLLDGSKVIVNVPVKVVEKELSVVKQQAIESIENAAQQKIDEIN
NSVTLTLEQKEAAIAEVNKLKQQAIDHVNNAPDVHSVEEIQQQEQAYIEQFNPEQFTIEQAKSNAIKSIEDAIQHMIDEI
KARTDLTDKEKQEAIAKLNQLKEQAIQAIQRAQSISEITEQLEQFKAQMKAANPTAKELAKRKQEAISRIKDFSNEKINS
IRNSEIGTADEKQAAMNQINEIVLETIRDINNAHTLQQVEAALNNGIARISAVQIVISDRAKQSSSTGNESNSHLTIGYG
TANHPFNSSTIGHKKKLDEDDDIDPLHMRHFSNNFGNVIKNAIGVVGISGLLASFWFFIAKRRRKEDEEEELEIRDNNKD
SIKETLDDTKHLPLLFAKRRRKEDEEDVTVEEKDSLNNGESLDKVKHTPFFLPKRRRKEDEEDVEVTNENTDEKVLKDNE
HSPLLFAKRRRKDKEEDVETTTSIESKDEDVPLLLAKKKNQKDNQSKDKKSASKNTSKKVAAKKKKKKSKKNKK

SEQ ID NO:14 polypeptide sequence
MNNRDKLQKFSIRKYAIGTFSTVIATLVFMGINTNHASADELNQNQKLIKQLNQTDDDDSNTHSQEIENNKQNSSGQTES
LRSSTSQNQANARLSDQFKDTNETSQQLPTNVSDDSINQSHSEANMNNEPLKVDNSTMQAHSKIVSDSDGNASENKHHKL
TENVLAESRASKNDKEKENLQEKDKSQQVHPPLDKNALQAFFDASYHNYRMIDRDRADATEYQKVKSTFDYVNDLLGNNQ
NIPSEQLVSAYQQLEKALELARTLPQQSTTEKRGRRSTRSVVENRSSRSDYLDARTEYYVSKDDDDSGFPPGTFFHASNR
RWPYNLPRSRNILRASDVQGNAYITTKRLKDGYQWDILFNSNHKGHEYMYYWFGLPSDQTPTGPVTFTIINRDGSSTSTG
GVGFGSGAPLPQFWRSAGAINSSVANDFKHGSATNYAFYDGVNNFSDFARGGELYFDREGATQTNKYYGDENFALLNSEK
PDQIRGLDTIYSFKGSGDVSYRISFKTQGAPTARLYYAAGARSGEYKQATNYNQLYVEPYKNYRNRVQSNVQVKNRTLHL
KRTIRQFDPTLQRTTDVPILDSDGSGSIDSVYDPLSYVKNVTGTVLGIYPSYLPYNQERWQGANAMNAYQIEELFSQENL
QNAARSGRPIQFLVGFDVEDSHHNPETLLPVNLYVKPELKHTIELYHDNEKQDRKEFSVSK

Figure 1 cont.

SEQ ID NO:15 polypeptide sequence
```
MSGTLHNTVGSGILPYQQEIRIKLTSNEPIKDSEWSITGYPNTLTLQNAVGRTNNATEKNLALVGHIDPGNYFITVKFGD
KVEQFEIRSKPTPPRIITTANELRGNPNHKPEIRVTDIPNDTTAKIKLVMGGTDGDHDPEINPYTVPENYTVVAEAYHDN
DPSKNGVLTFRSSDYLKDLPLSGELKAIVYYNQYVQSNFSKSVPFSSDTTPPTINEPAGLVHKYYRGDHVEITLPVTDNT
GGSGLRDVNVNLPQGWTKTFTINPNNNTEGTLKLIGNIPSNEAYNTTYHFNITATDNSGNTTNPAKTFILNVGKLADDLN
PVGLSRDQLQLVTDPSSLSNSEREEVKRKISEANANIRSYLLQNNPILAGVNGDVTFYYRDGSVDIDAENVITYEPERK
SIFSENGNTNKKEAVITIARGQNYTIGPNLRKYFSLSNGSDLPNRDFTSISAIGSLPSSSEISRLNVGNYNYRVNAKNAY
HKTQQELNLKLKIVEVNAPTGNNRVYRVSTYNLTNDEINKIKQAFKAANSGLNLNDNDITVSNNFDHRNVSSVTVTIRKG
DLIKEFSSNLNNMNFLRWVNIRDDYTISWTSSKIQGRNTDGGLEWSPDHKSLIYKYDATLGRQINTNDVLTLLQATAKNS
NLRSNINSNEKQLAERGSNGYSKSIIRDDGEKSYLLNSNPIQVLDLVEPDNGYGGRQVSHSNVIYNEKNSSIVNGQVPEA
NGASAFNIDKVVKANAANNGIMGVIYKAQLYLAPYSPKGYIEKLGQNLSNTNNVINVYFVPSDKVNPSITVGNYDHHTVY
SGETFKNTINVNDNYGLNTVASTSDSAITMTRNNNELVGQAPNVTNSINKIVKVKATDKSGNESIVSFTVNIKPLNEKYR
ITTSSSNQTPVRISNIQNNANLSIEDQNRVKSSLSMTKILGTRNYVNESNNDVRSQVVSKVNRSGNNATVNVTTTFSDGT
TNTITVPVKHVLLEVVPTTRTTVRGQQFPTGKGTSPNDFFSLRTGGPVDARIVWVNNQGPDINSNQIGRDLTLHAEIFFD
GETTPIRKDTTYKLSQSIPKQIYETTINGRFNSSGDAYPGNFVQAVNQYWPEHMDFRWAQGSGTPSSRNAGSFTKTVTVV
YQNGQTENVNVLFKVKPNKPVIDSNSVISKGQLNGQQILVRNVPQNAQVTLYQSNGTVIPNTNTTIDSNGIATVTIQGTL
PTGNITAKTSMTNNVTYTKQNSSGIASNTTEDISVFSENSDQVNVTAGMQAKNDGIKIIKGTNYNFNDPNSFISNIPAHS
TLTWNEEPNSWKNNIGTTTKTVTVTLPNHQGTRTVDIPITIYPTVTAKNPVRDQKGRNLTNGTDVYNYIIFENNNRLGGT
ASWKDNRQPDKNIAGVQNLIALVNYPGISTPLEVPVKVWVYNFDFTQPIYKIQVGDTFPKGTWAGYYKHLENGEGLPIDG
WKFYWNQQSTGTTSDQWQSLAYTRTPFVKTGTYDVVNPSNWGVWQTSQSAKFIVTNAKPNQPTITQSKTGDVTVTPGAVR
NILISGTNDYIQASADKIVINKNGNKLTTFVKNNDGRWTVETGSPDINGIGPTNNGTAISLSRLAVRPGDSIEAIATEGS
GETISTSATSEIYIVKAPQPEQVATHTYDNGTFDILPDNSRNSLNPTERVEINYTEKLNGNETQKSFTITKNNNGKWTIN
NKPNYVEFNQDNGKVVFSANTIKPNSQITITPKAGQGNTENTNPTVIQAPAQHTLTINEIVKEQGQNVTNDDINNAVQVP
NKNRVAIKQGNALPTNLAGGSTSHIPVVIYYSDGSSEEATETVRTKVNKTELINARRRLDEEISKENKTPSSIRNFDQAM
NRAQSQINTAKSDADQVIGTEFATPQQVNSALSKVQAAQNKINEAKALLQNKADNSQLVRAKEQLQQSIQPAASTDGMTQ
DSTRNYNNKRQAAEQAIQHANSVINNGDATSQQINDAKNTVEQAQRDYVEAKSNLRADKSQLQSAYDTLNRDVLTNDKKP
ASVRRYNEAISNIRKELDTAKADASSTLRNTNPSVEQVRDALNKINTVQPKVNQAIALLQPKENNSELVQAKKRLQDAVN
DIPQTQGMTQQTINNYNDKQREAERALTSAQRVIDNGDATTQEITSEKSKVEQAMQALTNAKSNLRADKNELQTAYNKLI
ENVSTNGKKPASIRQYETAKARIQNQINDAKNEAERILGNDNPQVSQVTQALNKIKAIQPKLTEAINMLQNKENNTELVN
AKNRLENAVNDTDPTHGMTQETINNYNAKKREAQNEIQKANMIINNGDATAQDISSEKSKVEQVLQALQNAKNDLRADKR
ELQTAYNKLIQNVNTNGKKPSSIQNYKSARRNIENQYNTAKNEAHNVLENTNPTVNAVEDALRKINAIQPEVTKAINILQ
DKEDNSELVRAKEKLDQAINSQPSLNGMTQESINNYTTKRREAQNIASSADTIINNGDASIEQITENKIRVEEATNALNE
AKQHLTADTTSLKTEVRKLSRRGDTNNKKPSSVSAYNNTIHSLQSEITQTENRANTIINKPIRSVEEVNNALHEVNQLNQ
RLTDTINLLQPLANKESLKEARNRLESKINETVQTDGMTQQSVENYKQAKIKAQNESSIAQTLINNGDASDQEVSTEIEK
LNQKLSELTNSINHLTVNKEPLETAKNQLQANIDQKPSTDGMTQQSVQSYERKLQEAKDKINSINNVLANNPDVNAIRTN
KVETEQINNELTQAKQGLTVDKQPLINAKTALQQSLDNQPSTTGMTEATIQNYNAKRQKAEQVIQNANKIIENAQPSVQQ
VSDEKSKVEQALSELNNAKSALRADKQELQQAYNQLIQPTDLNNKKPASITAYNQRYQQFSNELNSTKTNTDRILKEQNP
SVADVNNALNKVREVQQKLNEARALLQNKEDNSALVRAKEQLQQAVDQVPSTEGMTQQTKDDYNSKQQAAQQEISKAQQV
IDNGDATTQQISNAKTNVERALEALNNAKTGLRADKEELQNAYNQLTQNIDTSGKTPASIRKYNEAKSRIQTQIDSAKNE
ANSILTNDNPQVSQVTAALNKIKAVQPELDKAIAMLKNKENNNALVQAKQQLQQIVNEVDPTQGMTTDTANNYKSKKREA
EDEIQKAQQIINNGDATEQQITNETNRVNQAINAINKAKNDLRADKSQLENAYNQLIQNVDTNGKKPASIQQYQAARQAI
ETQYNNAKSEAHQILENSNPSVNEVAQALQKVEAVQLKVNDAIHILQNKENNSALVTAKNQLQQSVNDQPLTTGMTQDSI
NNYEAKRNEAQSAIRNAEAVINNGDATAKQISDEKSKVEQALAHLNDAKQQLTADTTELQTAVQQLNRRGDTNNKKPRSI
NAYNKAIQSLETQITSAKDNANAVIQKPIRTVQEVNNALQQVNQLNQQLTEAINQLQPLSNNDALKAARLNLENKINQTV
QTDGMTQQSIEAYQNAKRVAQNESNTALALINNGDADEQQITTETDRVNQQTTNLTQAINGLTVNKEPLETAKTALQNNI
DQVPSTDGMTQQSVANYNQKLQIAKNEINTINNVLANNPDVNAIKTNKAEAERISNDLTQAKNNLQVDTQPLEKIKRQLQ
DEIDQGTNTDGMTQDSVDNYNDSLSAAIIEKGKVNKLLKRNPTVEQVKESVANAQQVIQDLQNARTSLVPDKTQLQEAKN
RLENSINQQTDTDGMTQDSLNNYNDKLAKARQNLEKISKVLGGQPTVAEIRQNTDEANAHKQALDTARSQLTLNREPYIN
HINNESHLNNAQKDNFKAQVNSAPNHNTLETIKNKADTLNQSMTALSESIADYENQKQQENYLDASNNKRQDYDNAVNAA
KGILNQTQSPTMSADVIDQKAEDVKRTKTALDGNQRLEVAKQQALNHLNTLNDLNDAQRQTLTDTINHSPNINSVNQAKE
KANTVNTAMTQLKQTIANYDDELHDGNYINADKDKKDAYNNAVNNAKQLINQSDANQAQLDPAEINKVTQRVNTTKNDLN
GNDKLAEAKRDANTTIDGLTYLNEAQRNKAKENVGKASTKTNITSQLQDYNQLNIAMQALRNSVNDVNNVKANSNYINED
NGPKEAYNQAVTHAQTLINAQSNPEMSRDVVNQKTQAVNTAHQNLHGQQKLEQAQSSANTEIGNLPNLTNTQKAKEKELV
NSKQTRTEVQEQLNQAKSLDSSMGTLKSLVAKQPTVQKTSVYINEDQPEQSAYNDSITMGQTIINKTADPVLDKTLVDNA
ISNISTKENALHGEQKLTTAKTEAINALNTLADLNTPQKEAIKTAINTAHTRTDVTAEQSKANQINSAMHTLRQNISDNE
SVTNESNYINAEPEKQHAFTEALNNAKEIVNEQQATLDANSINQKAQAILTTKNALDGEEQLRRAKENADQEINTLNQLT
DAQRNSEKGLVNSSQTRTEVASQLAKAKELNKVMEQLNHLINGKNQMINSSKFINEDANQQQAYSNAIASAEALKNKSQN
PELDKVTIEQAINNINSAINNLNGEAKLTKAKEDAVASINNLSGLTNEQKTKENQAVNGAQTRDQVANKLRDAEALDQSM
```

Figure 1 cont.

```
QTLRDLVNNQNAIHSTSNYFNEDSTQKNTYDNAIDNGSTYITGQHNPELNKSTIDQTISRINTAKNDLHGVEKLQRDKGT
ANQEIGQLGYLNDPQKSGEESLVNGSNTRSEVEEHLNEAKSLNNAMKQLRDKVAEKTNVKQSSDYINDSTEHQRGYDQAL
QEAENIINEIGNPTLNKSEIEQKLQQLTDAQNALQGSHLLEEAKNNAITGINKLTALNDAQRQKAIENVQAQQTIPAVNQ
QLTLDREINTAMQALRDKVGQQNNVHQQSNYFNEDEQPKHNYDNSVQAGQTIIDKLQDPIMNKNEIEQAINQINTTQTAL
SGENKLHTDQESTNRQIEGLSSLNTAQINAEKDLVNQAKTRTDVAQKLAAAKEINSAMSNLRDGIQNKEDIKRSSAYINA
DPTKVTAYDQALQNAENIINATPNVELNKATIEQALSRVQQAQQDLDGVQQLANAKQQATQTVNGLNSLNDGQKRELNLL
INSANTRTKVQEELNKATELNHAMEALRNSVQNVDQVKQSSNYVNEDQPEQHNYDNAVNEAQATINNNAQPVLDKLAIER
LTQTVNTTKDALHGAQKLTQDQQAAETGIRGLTSLNEPQKNAEVAKVTAATTRDEVRNIRQEATTLDTAMLGLRKSIKDK
NDTKNSSKYINEDHDQQQAYDNAVNNAQQVIDETQATLSSDTINQLANAVTQAKSNLHGDTKLQHDKDSAKQTIAQLQNL
NSAQKHMEDSLIDNESTRTQVQHDLTEAQALDGLMGALKESIKDYTNIVSNGNYINAEPSKKQAYDAAVQNAQNIINGTN
QPTINKGNVTTATQTVKNTKDALDGDHRLEEAKNNANQTIRNLSNLNNAQKDAEKNLVNSASTLEQVQQNLQTAQQLDNA
MGELRQSIAKKDQVKADSKYLNEDPQIKQNYDDAVQRVETIINETQNPELLKANIDQATQSVQNAEQALHGAEKLNQDKQ
TSSTELDGLTDLTDAQREKLREQINTSNSRDDIKQKIEQAKALNDAMKKLKEQVAQKDGVHANSDYTNEDSAQKDAYNNA
LKQAEDIINNSSNPNLNAQDITNALNNIKQAQDNLHGAQKLQQDKNTTNQAIGNLNHLNQPQKDALIQAINGATSRDQVA
EKLKEAEALDEAMKQLEDQVNQDDQISNSSPFINEDSDKQKTYNDKIQAAKEIINQTSNPTLDKQKIADTLQNIKDAVNN
LHGDQKLAQSKQDANNQLNHLDDLTEEQKNHFKPLINNADTRDEVNKQLEIAKQLNGDMSTLHKVINDKDQIQHLSNYIN
ADNDKKQNYDNAIKEAEDLIHNHPDTLDHKALQDLLNKIDQAHNELNGESRFKQALDNALNDIDSLNSLNVPQRQTVKDN
INHVTTLESLAQELQKAKELNDAMKAMRDSIMNQEQIRKNSNYTNEDLAQQNAYNHAVDKINNIIGEDNATMDPQIIKQA
TQDINTAINGLNGDQKLQDAKTDAKQQITNFTGLTEPQKQALENIINQQTSRANVAKQLSHAKFLNGKMEELKVAVAKAS
LVRQNSNYINEDVSEKEAYEQAIAKGQEIINSENNPTISSTDINRTIQEINDAEQNLHGDNKLRQAQEIAKNEIQNLDGL
NSAQITKLIQDIGRTTTKPAVTQKLEEAKAINQAMQQLKQSIADKDATLNSSNYLNEDSEKKLAYDNAVSQAEQLINQLN
DPTMDISNIQAITQKVIQAKDSLHGANKLAQNQADSNLIINQSTNLNDKQKQALNDLINHAQTKQQVAEIIAQANKLNNE
MGTLKTLVEEQSNVHQQSKYINEDPQVQNIYNDSIQKGREILNGTTDDVLNNNKIADAIQNIHLTKNDLHGDQKLQKAQQ
DATNELNYLTNLNNSQRQSEHDEINSAPSRTEVSNDLNHAKALNEAMRQLENEVALENSVKKLSDFINEDEAAQNEYSNA
LQKAKDIINGVPSSTLDKATIEDALLELQNARESLHGEQKLQEAKNQAVAEIDNLQALNPGQVLAEKTLVNQASTKPEVQ
EALQKAKELNEAMKALKTEINKKEQIKADSRYVNADSGLQANYNSALNYGSQIIATTQPPELNKDVINRATQTIKTAENN
LNGQSKLAEAKSDGNQSIEHLQGLTQSQKDQHDLINQAQTKQQVDDIVNNSKQLDNSMNQLQQIVNNDNTVKQNSDFIN
EDSSQQDAYNHAIQAAKDLITAHPTIMDKNQIDQAIENIKQALNDLHGSNKLSEDKKEASEQLQNLNSLTNGQKDTILNH
IFSAPTRSQVGEKIASAKQLNNTMKALRDSIADNNEILQSSKYFNEDSEQQNAYNQAVNKAKNIINDQPTPVMANDEIQS
VLNEVKQTKDNLHGDQKLANDKTDAQATLNALNYLNQAQRGNLETKVQNSNSRPEVQKVVQLANQLNDAMKKLDDALTGN
DAIKQTSNYINEDTSQQVNFDEYTDRGKNIVAEQTNPNMSPTNINTIADKITEAKNDLHGVQKLKQAQQQSINTINQMTG
LNQAQKEQLNQEIQQTQTRSEVHQVINKAQALNDSMNTLRQSITDEHEVKQTSNYINETVGNQTAYNNAVDRVKQIINQT
SNPTMNPLEVERATSNVKISKDALHGERELNDNKNSKTFAVNHLDNLNQAQKEALTHEIEQATIVSQVNNIYNKAKALNN
DMKKLKDIVAQQDNVRQSNNYINEDSTPQNMYNDTINHAQSIIDQVANPTMSHDEIENAINNIKHAINALDGEHKLQQAK
ENANLLINSLNDLNAPQRDAINRLVNEAQTREKVAEQLQSAQALNDAMKHLRNSIQNQSSVRQESKYINASDAKKEQYNH
AVREVENIINEQHPTLDKEIIKQLTDGVNQANNDLNGVELLDADKQNAHQSIPTLMHLNQAQQNALNEKINNAVTRTEVA
AIIGQAKLLDHAMENLEESIKDKEQVKQSSNYINEDSDVQETYDNAVDHVTEILNQTVNPTLSIEDIEHAINEVNQAKKQ
LRGKQKLYQTIDLADKELSKLDDLTSQQSSSISNQIYTAKTRTEVAQAIEKAKSLNHAMKALNKVYKNADKVLDSSRFIN
EDQPEKKAYQQAINHVDSIIHRQTNPEMDPTVINSITHELETAQNNLHGDQKLAHAQQDDAANVINGLIHLNVAQREVMIN
TNTNATTREKVAKNLDNAQALDKAMETLQQVVAHKNNILNDSKYLNEDSKYQQQYDRVIADAEQLLNQTTNPTLEPYKVD
IVKDNVLANEKILFGAEKLSYDKSNANDEIKHMNYLNNAQKQSIKDMISHAALRTEVKQLLQQAKILDEAMKSLEDKTQV
VITDTTLPNYTEASEDKKEKVDQTVSHAQAIIDKINGSNVSLDQVRQALEQLTQASENLDGDQRVEEAKVHANQTIDQLT
HLNSLQQQTAKESVKNATKLEEIATVSNNAQALNKVMGKLQEQFINHADSVENSDNYRQADDDKIIAYDEALEHGQDIQKT
NATQNETKQALQQLIYAETSLNGFERLNHARPRALEYIKSLEKINNAQKSALEDKVTQSHDLLELEHIVNEGTNLNDIMG
ELANAIVNNYAPTKASINYINADNLRKDNFTQAINNARDALNKTQGQNLDFNAIDTFKDDIFKTKDALNGIERLTAAKSK
AEKLIDSLKFINKAQFTHANDEIMNTNSIAQLSRIVNQAFDLNDAMKSLRDELNNQAFPVQASSNYINSDEDLKQQFDHA
LSNARKVLAKENGKNLDEKQIQGLKQVIEDTKDALNGIQRLSKAKAKAIQYVQSLSYINDAQRHIAENNIHNSDDLSSLA
NTLSKASDLDNAMKDLRDTIESNSTSVPNSVNYINADKNLQIEFDEALQQASATSSKTSENPATIEEVLGLSQAIYDTKN
ALNGEQRLATEKSKDLKLIKGLKDLNKAQLEDVTNKVNSANTLTELSQLTQSTLELNDKMKLLRDKLKTLVNPVKASLNY
RNADYNLKRQFNKALKEAKGVLNKNSGTNVNINDIQHLLTQIDNAKDQLNGERRLKEHQQKSEVFIIKELDILNNAQKAA
IINQIRASKDIKIINQIVDNAIELNDAMQGLKEHVAQLTATTKDNIEYLNADEDHKLQYDYAINLANNVLDKENGTNKDA
NIIIGMIQNMDDARALLNGIERLKDAQTKAHNDIKDTLKRQLDEIEHANATSNSKAQAKQMVNEEARKALSNINDATSND
LVNQAKDEGQSAIEHIHADELPKAKLDANQMIDQKVEDINHLISQNPNLSNEEKNKLISQINKLVNGIKNEIQQAINKQQ
IENATTKLDEVIETTKKLIIAKAEAKQMIKELSQKKRDAINNNTDLTPSQKAHALADIDKTEKDALQHIENSNSIDDINN
NKEHAFNTLAHIIIWDTDQQPLVFELPELSLQNALVTSEVVVHRDETISLESIIGAMTLTDELKVNIVSLPNTDKVADHL
TAKVKVILADGSYVTVNVPVKVVEKELQIAKDDAIKTIDVLVKQKIKDIDSNNELTSTQREDAKAEIERLKKQAIDKVNH
SKSIKDIETVKRTDFEEIDQFDPKRFTLNKAKKDIITDVNTQIQNGFKEIETIKGLTSNEKTQFDKQLTALQKEFLEKVE
HAHNLVELNQLQQEFNNRYKHILNQAHLLGEKHIAEHKLGYVVVNKTQQILNNQSASYFIKQWALDRIKQIQLETMNSIR
GAHTVQDVHKALLQGIEQILKVNVSIINQSFNDSLHNFNYLHSKFDARLREKDVANHIVQTETFKEVLKGTGVEPGKINK
```

Figure 1 cont.

ETQQPKLHKNDNDSLFKHLVDNFGKTVGVITLTGLLSSFWLVLAKRRKKEEEEKQSIKNHHKDIRLSDTDKIDPIVITKR
KIDKEEQIQNDDKHSIPVAKHKKSKEKQLSEEDIHSIPVVKRKQNSDNKDTKQKKVTSKKKKTPQSTKKVVKTKKRSKK

SEQ ID NO:16 polypeptide sequence
MRDKKGPVNKRVDFLSNKLNKYSIRKFTVGTASILIGSLMYLGTQQEAEAAENNIENPTTLKDNVQSKEVKIEEVTNKDT
APQGVEAKSEVTSNKDTIEHEASVKAEDISKKEDTPKEVANVAEVQPKSSVTHNAEAPKVRKARSVDEGSFDITRDSKNV
VESTPITIQGKEHFEGYGSVDIQKNPTDLGVSEVTRFNVGNESNGLIGALQLKNKIDFSKDFNFKVRVANNHQSNTTGAD
GWGFLFSKGNAEEYLTNGGILGDKGLVNSGGFKIDTGYIYTSSMDKTEKQAGQGYRGYGAFVKNDSSGNSQMVGENIDKS
KTNFLNYADNSTNTSDGKFHGQRLNDVILTYVASTGKMRAEYAGKTWETSITDLGLSKNQAYNFLITSSQRWGLNQGINA
NGWMRTDLKGSEFTFTPEAPKTITELEKKVEEIPFKKERKFNPDLAPGTEKVTREGQKGEKTITTPTLKNPLTGEIISKG
ESKEEITKDPINELTEYGPETIAPGHRDEFDPKLPTGEKEEVPGKPGIKNPETGDVVRPPVDSVTKYGPVKGDSIVEKEE
IPFEKERKFNPDLAPGTEKVTREGQKGEKTITTPTLKNPLTGEIISKGESKEEITKDPINELTEYGPETIAPGHRDEFDP
KLPTGEKEEVPGKPGIKNPETGDVVRPPVDSVTKYGPVKGDSIVEKEEIPFKKERKFNPDLAPGTEKVTREGQKGEKTIT
TPTLKNPLTGEIISKGESKEEITKDPINELTEYGPETITPGHRDEFDPKLPTGEKEEVPGKPGIKNPETGDVVRPPVDSV
TKYGPVKGDSIVEKEEIPFKERKFNPDLAPGTEKVTREGQKGEKTITTPTLKNPLTGEIISKGESKEEITKDPVNELTE
FGGEKIPQGHKDIFDPNLPTDQTEKVPGKPGIKNPDTGKVIEEPVDDVIKHGPKTGTPETKTVEIPFETKREFNPKLQPG
EERVKQEGQPGSKTITTPITVNPLTGEKVGEGQPTEEITKQPVDKIVEFGGEKPKDPKGPENPEKPSRPTHPSGPVNPNN
PGLSKDRAKPNGPVHSMDKNDKVKKSKIAKESVANQEKKRAELPKTGLESTQKGLIFSSIIGIAGLMLLARRRKN

SEQ ID NO:17 polypeptide sequence
MGKRRQGPINKKVDFLPNKLNKYSIRKFTVGTASILLGSTLIFGSSSHEAKAAEEKQVDPITQANQNDSSERSLENTNQPT
VNNEAPQMSSTLQAEEGSNAEAPNVPTIKANSDNDTQTQFSEAPTRNDLARKEDIPAVSKNEELQSSQPNTDSKIEPTTSE
PVNLNYSSPFMSLLSMPADSSSNNTKNTIDIPPTTVKGRDNYDFYGRVDIQSNPTDLNATNLTRYNYGQPPGTTTAGA
VQFKNQVSFDKDFDFNIRVANNRQSNTTGADGWGFMFSKKDGDDFLKNGGILREKGTPSAAGFRIDTGYYNNDPLDKIQKQ
AGQGYRGYGTFVKNDSQGNTSKVGSGTPSTDFLNYADNTTNDLDGKFHGQKLNNVNLKYNASNQTFTATYAGKTWTATLSE
LGLSPTDSYNFLVTSSQYGNGNSGTYADGVMRADLDGATLTYTPKAVDGDPITSTKEIPFNKKREFDPNLAPGTEKVV
QKGEPGIETTTTPTYVNPNTGEKVGEGTPTTKITKQPVDEIVHYGGEEIKPGHKDEFDPNAPKGSQTTQPGKPGVKNPDTG
EVVTPPVDDVTKYGPVDGDPITSTEEIPFDKKREFNPDLKPGEERVKQKGEPGTKTITTPTTKNPLTGEKVGEGEPTEKIT
KQPVDEITEYGGEEIKPGHKDEFDPNAPKGSQEDVPGKPGVKNPDTGEVVTPPVDDVTKYGPVDGDPITSTEEIPFDK
KREFDPNLAPGTEKVVQKGEPGTKTITTPTTKNPLTGEKVGEGEPTEKITKQPVDEIVHYGGEEIKPGHKDEFDPNAPKGS
QEDVPGKPGVKNPDTGEVVTPPVDDVTKYGPVDGDPITSTEEIPFDKKREFNPDLKPGEERVKQKGEPGTKTITTPTTKNP
LTGEKVGEGEPTEKVTKQPVDEIVHYGGEEIKPGHKDEFDPNAPKGSQEDVPGKPGVKNPDTGEVVTPPVDDVTKYGP
VDGDPITSTEEIPFDKKREFDPNLAPGTEKVVQKGEPGTKTITTPTTKNPLTGEKVGEGEPTEKITKQPVDEIVHYGGEEI
KPGHKDEFDPNAPKGSQTTQPGKPGVKNPDTGEVVTPPVDDVTKYGPVDGDPITSTEEIPFDKKREFDPNLAPGTEKVVQK
GEPGTKTITTPTTKNPLTGEKVGEGEPTEKITKQPVDEIVHYGGEQIPQGHKDEFDPNAPVDSKTEVPGKPGVKNPDT
GEVVTPPVDDVTKYGPKVGNPITSTEEIPFDKKRVFNPDLKPGEERVKQKGEPGTKTITTPILVNPITGEKVGEGKSTEKV
TKQPVDEIVEYGPTKAEPGKPAEPGKPAEPGKPAEPGKPAEPGTPAEPGKPAEPGKPAEPGKPAEPGKPAEPGKPAEPGTP
AEPGKPAEPGKPAEPGKPAEPGTPAEPGKPAEPGTPAEPGKPAEPGTPTQSGAPEQPNRSMHSTDNKNQLPDTGENRQ
ANEGTLVGSLLAIVGSLFIFGRRKKGNEK

SEQ ID NO:18 polypeptide sequence
MKKLYTSYGTYGFLHQIKINNPTHQLFQFSASDTSVIFEETDGETVLKSPSIYEVIKEIGEFSEHHFYCAIFIPSTEDHAY
QLEKKLISVDDNFRNFGGFKSYRLLRPAKGTTYKIYFGFADRHAYEDFKQSDAFNDHFSKDALSHYFGSSGQHSSYFERYL
YPIKE

SEQ ID NO:19 polypeptide sequence
MYLYTSYGTYQFLNQIKLNHQERSLFQFSTNDSSIILEESEGKSILKHPSAYQVIDSTGEFNEHHFYSAIFVPTSEDHRQQ
LEKKLLLVDVPLRNFGGFKSYRLLKPTEGSTYKIYFGFANRTAYEDFKASDIFNENFSKDALSQYFGASGQHSSYFERYLY
PIEDH

SEQ ID NO:20 polypeptide sequence
MINRDNKKAITKKGMISNRLNKFSIRKYTVGTASILVGTTLIFGLGNQEAKAAENTSTENAKQDDATTSDNKEVVSETEN
NSTTENDSTNPIKKETNTDSQPEAKEESTTSSTQQQQNNVTATTETKPQNIEKENVKPSTDKTATEDTSVILEEKKAPNY
TNNDVTTKPSTSEIQTKPTTPQESTNIENSQPQPTPSKVDNQVTDATNPKEPVNVSKEELKNNPEKLKELVRNDNNTDRS
TKPVATAPTSVAPKRLNAKMRFAVAQPAAVASNNVNDLITVTKQTIKVGDGKDNVAAAHDGKDIEYDTEFTIDNKVKKGD
TMTINYDKNVIPSDLTDKNDPIDITDPSGEVIAKGTFDKATKQITYTFTDYVDKYEDIKARLTLYSYIDKQAVPNETSLN

Figure 1 cont.

```
LTFATAGKETSQNVSVDYQDPMVHGDSNIQSIFTKLDENKQTIEQQIYVNPLKKTATNTKVDIAGSQVDDYGNIKLGNGS
TIIDQNTEIKVYKVNPNQQLPQSNRIYDFSQYEDVTSQFDNKKSFSNNVATLDFGDINSAYIIKVVSKYTPTSDGELDIA
QGTSMRTTDKYGYYNYAGYSNFIVTSNDTGGGDGTVKPEEKLYKIGDYVWEDVDKDGVQGTDSKEKPMANVLVTLTYPDG
TTKSVRTDANGHYEFGGLKDGETYTVKFETPAGYLPTKVNGTTDGEKDSNGSSITVKINGKDDMSLDTGFYKEPKYNLGD
YVWEDTNKDGIQDANEPGIKDVKVTLKDSTGKVIGTTTTDASGKYKFTDLDNGNYTVEFETPAGYTPTVKNTTAEDKDSN
GLTTTGVIKDADNMTLDSGFYKTPKYSLGDYVWYDSNKDGKQDSTEKGIKDVKVTLLNEKGEVIGTTKTDENGKYRFDNL
DSGKYKVIFEKPAGLTQTVTNTTEDDKDADGGEVDVTITDHDDFILDNGYFEEDTSDSDSDSDSDSDSDSDSDSDSDSDS
DSDSDSDSDSDSDSDSDSDSDSDSDSDSDSDSDSDSDSDSDSDSDSDSDSDSDSDSDSDSDSDSDSDSDSDSDSDSDSDS
DSDSDSDSDSDSDSDSDSDSDSDSDSDSDSDSDSDSDAGKHTPVKPMSTTKDHHNKAKALPETGSENNGSNNATLF
GGLFAALGSLLLFGRRKKQNK
```

SEQ ID NO:21 polypeptide sequence
```
MINKKNNLLTKKKPIANKSNKYAIRKFTVGTASIVIGATLLFGLGHNEAKAEENSVQDVKDSNTDDELSDSNDQSSDEEKN
DVINNNQSINTDDNNQIIKKEETNNYDGIEKRSEDRTESTTNVDENEATFLQKTPQDNTHLTEEEVKESSSVESSNSSIDT
AQQPSHTTINREESVQTSDNVEDSHVSDFANSKIKESNTESGKEENTIEQPNKVKEDSTTSQPSGYTNIDEKISNQDE
LLNLPINEYENKARPLSTTSAQPSIKRVTVNQLAAEQGSNVNHLIKVTDQSITEGYDDSEGVIKAHDAENLIYDVTFEVDD
KVKSGDTMTVDIDKNTVPSDLTDSFTIPKIKDNSGEIIATGTYDNKNKQITYTFTDYVDKYENIKAHLKLTSYIDKSKVPN
NNTKLDVEYKTALSSVNKTITVEYQRPNENRTANLQSMFTNIDTKNHTVEQTIYINPLRYSAKETNVNISGNGDEGST
IIDDSTIIKVYKVGDNQNLPDSNRIYDYSEYEDVTNDDYAQLGNNNDVNINFGNIDSPYIIKVISKYDPNKDDYTTIQQTV
TMQTTINEYTGEFRTASYDNTIAFSTSSGQGQGDLPPEKTYKIGDYVWEDVDKDGIQNTNDNEKPLSNVLVTLTYPDGTSK
SVRTDEDGKYQFDGLKNGLTYKITFETPEGYTPTLKHSGTNPALDSEGNSVWVTINGQDDMTIDSGFYQTPKYSLGNY
VWYDTNKDGIQGDDEKGISGVKVTLKDENGNIISTTTTDENGKYQFDNLNSGNYIVHFDKPSGMTQTTTDSGDDDEQDADG
EEVHVTITDHDDFSIDNGYYDDESDSDSDSDSDSDSDSDSDSDSDSDSDSDSDSDSDSDSDSDSDSDSDSDSDSDSDSD
SDSDSDSDSDSDSDSDSDSDSDSDSDSDSDSDSDSDSDSDSDSDSDSDSDSDSDSDSDSDSDSDSDSDSDSDSDSDSD
SDSDSDSDSDSDSDSDSDSDSDSDSDSDSDSDSDSDNDSDLGNSSDKSTKDKLPDTGANEDYGSKGTLLGTLFAGLG
ALLLGKRRKNRKNKN
```

SEQ ID NO:22 polypeptide sequence
```
MSNNFKDDFEKNRQSIDTNSHQDHTEDVEKDQSELEHQDTIENTEQQFPPRNAQRRKRRRDLATNHNKQVHNESQTSEDNV
QNEAGTIDDRQVESSHSTESQEPSHQDSTPQHEEEYYNKNAFAMDKSHPEPIEDNDKHETIKDAENNTEHSTVSDKSIAEQ
SQQPKPYFATGANQANTSKDKHDDVTVKQDKDESKDHHSGKKGAAIGAGTAGVAGAAGAMGVSKAKKHSNDAQNKSNS
DKSNNSTEDKASQDKSKDHHNGKKGAAIGAGTAGLAGGAASKSASAASKPHASNNASQNHDEHDNHDRDKERKKGGMAKVL
LPLIAAVLIIGALAIFGGMALNNHNNGTKENKIANTNKNNADESKDKDTSKDASKDKSKSTDSDKSKEDQDKATKDESDND
QNNANQANNQAQNNQNQQQANQNQQQQQQRQGGGQRHTVNGQENLYRIAIQYYGSGSPENVEKIRRANGLSGNNIRNG
QQIVIP
```

SEQ ID NO:23 polypeptide sequence
```
MIELIKMEGMIVVSNNNFKDDFEKNRQSINPDEQQTELKEDDKTNENKKEADSQNSLSNNSNQQFPPRNAQRRKRRRETAT
NQSKQQDDKHQKNSDAKTTEGSLDDRYDEAQLQQQHDKSQQQNKTEKQSQDNRMKDGKDAAIVNGTSESPEHKSKSTQNRP
GPKAQQQKRKSESTQSKPSTNKDKKAATGAGIAGAAGVGAGAAETSKRHHNKKDKQDSKHSNHENDEKSVKNDDQKQSK
KGKKAAVGAGAAAGVGAAGVAHHNNQNKHHNEEKNSNQNNQYNDQSEGKKKGGFMKILLPLIAAILILGAIAIFGGMALNN
HNDSKSDDQKIANQSKKDSDKKDGAQSEDNKDKKSDSNKDKKSDSDKNADDDSDNSSSNPNATSTNNNDNVANNNSNYTNQ
NQQDNANQNSNNQQATQGQQSHTVYGQENLYRIAIQYYGEGTQANVDKIKRANGLSSNNIHNGQTLVIPQ
```

SEQ ID NO:24 polypeptide sequence
```
MKNKLIAKSLLTIAAIGITTTTIASTADASEGYGPREKKPVSINHNIVEYNDGTFKYQSRPKFNSTPKYIKFKHDYNILEF
NDGTFEYGARPQFNKPAAKTDATIKKEQKLIQAQNLVREFEKTHTVSAHRKAQKAVNLVSFEYKVKKMVLQERIDNVLKQG
LVR
```

SEQ ID NO:25 polypeptide sequence
```
MKTRIVSSVTTTLLLGSILMNPVANAADSDINIKTGTTDIGSNTTVKTGDLVTYDKENGMHKKVFYSFIDDKNHNKKLLVI
RTKGTIAGQYRVYSEEGANKSGLAWPSAFKVQLQLPDNEVAQISDYYPRNSIDTKEYMSTLTYGFNGNVTGDDTGKIGGLI
GANVSIGHTLKYVQPDFKTILESPTDKKVGWKVIFNNMVNQNWGPYDRDSWNPVYGNQLFMKTRNGSMKAAENFLDPN
KASSLLSSGFSPDFATVITMDRKASKQQTNIDVIYERVRDDYQLHWTSTNWKGTNTKDKWTDRSSERYKIDWEKEEMTN
```

SEQ ID NO:26 polypeptide sequence

Figure 1 cont.

MHMKNKYISKLLVGAATITLATMISNGEAKASENTQQTSTKHQTTQNNYVTDQQKAFYQVLHLKGITEEQRNQYIKTLREH
PERAQEVFSESLKDSKNPDRRVAQQNAFYNVLKNDNLTEQEKNNYIAQIKENPDRSQQVWVESVQSSKAKERQNIENADKA
IKDFQDNKAPHDKSAAYEANSKLPKDLRDKNNRFVEKVSIEKAIVRHDERVKSANDAISKLNEKDSIENRRLAQREVNKAP
MDVKEHLQKQLDALVAQKDAEKKVAPKVEAPQIQSPQIEKPKAESPKVEVPQSKLLGYYQSLKDSFNYGYKYLTDTYKSYK
EKYDTAKYYYNTYYKYKGAIDQTVLTVLGSGSKSYIQPLKVDDKNGYLAKSYAQVRNYVTESINTGKVLYTFYQNPTLVKT
AIKAQETASSIKNTLSNLLSFWK

SEQ ID NO:27 polypeptide sequence
MTKHYLNSKYQSEQRSSAMKKITMGTASIILGSLVYIGADSQQVNAATEATNATNNQSTQVSQATSQPINFQVQKDGSSE
KSHMDDYMQHPGKVIKQNNKYYFQTVLNNASFWKEYKFYNANNQELATTVVNDNKKADTRTINVAVEPGYKSLTTKVHIV
VPQINYNHRYTTHLEFEKAIPTLADAAKPNNVKPVQPKPAQPKTPTEQTKPVQPKVEKVKPTVTTTSKVEDNHSTKVVST
DTTKDQTKTQTAHTVKTAQTAQEQNKVQTPVKDVATAKSESNNQAVSDNKSQQTNKVTKHNETPKQASKAKELPKTGLTS
VDNFISTVAFATLALLGSLSLLLFKRKESK

SEQ ID NO:28 polypeptide sequence
MNKQQKEFKSFYSIRKSSLGVASVAISTLLLLMSNGEAQAAAEETGGTNTEAQPKTEAVASPTTTSEKAPETKPVANAVSV
SNKEVEAPTSETKEAKEVKEVKAPKETKAVKPAAKATNNTYPILNQELREAIKNPAIKDKDHSAPNSRPIDFEMKKENGEQ
QFYHYASSVKPARVIFTDSKPEIELGLQSGQFWRKFEVYEGDKKLPIKLVSYDTVKDYAYIRFSVSNGTKAVKIVSST
HFNNKEEKYDYTLMEFAQPIYNSADKFKTEEDYKAEKLLAPYKKAKTLERQVYELNKIQDKLPEKLKAEYKKKLEDTKKAL
DEQVKSAITEFQNVQPTNEKMTDLQDTKYVVYESVENNESMMDTFVKHPIKTGMLNGKKYMVMETTNDDYWKDFMVEGQRV
RTISKDAKNNTRTIIFPYVEGKTLYDAIVKVHVKTIDYDGQYHVRIVDKEAFTKANTDKSNKKEQQDNSAKKEATPAT
PSKPTPSPVEKESQKQDSQKDDNKQLPSVEKENDASSESGKDKTPATKPTKGEVESSSTTPTKVVSTTQNVAKPTTASSKT
TKDVVQTSAGSSEAKDSAPLQKANIKNTNDGHTQSQNNKNTQENKAKSLPQTGEESNKDMTLPLMALLALSSIVAFVLPRK
RKN

SEQ ID NO:29 polypeptide sequence
MNNKKTATNRKGMIPNRLNKFSIRKYSVGTASILVGTTLIFGLSGHEAKAAEHTNGELNQSKNETTAPSENKTTEKVDSR
QLKDNTQTATADQPKVTMSDSATVKETSSNMQSPQNATASQSTTQTSNVTTNDKSSTTYSNETDKSNLTQAKNVSTTPKT
TTIKQRALNRMAVNTVAAPQQGTNVNDKVHFTNIDIAIDKGHVNKTTGNTEFWATSSDVLKLKANYTIDDSVKEGDTFTF
KYGQYFRPGSVRLPSQTQNLYNAQGNIIAKGIYDSKTNTTTYTFTNYVDQYTNVSGSFEQVAFAKRENATTDKTAYKMEV
TLGNDTYSKDVIVDYGNQKGQQLISSTNYINNEDLSRNMTVYVNQPKKTYTKETFVTNLTGYKFNPDAKNFKIYEVTDQN
QFVDSFTPDTSKLKDVTGQFDVIYSNDNKTATVDLLNGQSSSDKQYIIQQVAYPDNSSTDNGKIDYTLETQNGKSSWSNS
YSNVNGSSTANGDQKKYNLGDYVWEDTNKDGKQDANEKGIKGVYVILKDSNGKELDRTTTDENGKYQFTGLSNGTYSVEF
STPAGYTPTTANAGTDDAVDSDGLTTTGVIKDADNMTLDSGFYKTPKYSLGDYVWYDSNKDGKQDSTEKGIKGVKVTLQN
EKGEVIGTTETDENGKYRFDNLDSGKYKVIFEKPAGLTQTGTNTTEDDKDADGGEVDVTIIDHDDFTLDNGYYEEETSDS
DSDSDSDSDSDSDSDSDSDSDSDSDSDSDSDSDSDSDSDSDSDSESDSDSDSDSDSDSDSDSDSDSDS
DSDSDSDSDSDSDSDSDSDSDNDSDSDSDSDSDSDSDSDSDSDSDSDSDSDSDSDSDSDSDSDSDSDSDS
DSDSDSDSDSDAGKHTPTKPMSTVKDQHKTAKALPETGSENNNSNNGTLFGGLFAALGSLLLFGRRKKQNK

SEQ ID NO:30 polypeptide sequence
MNMKKKEKHAIRKKSIGVASVLVGTLIGFGLLSSKEADASENSVTQSDSASNESKSNDSSSVSAAPKTDDTNVSDTKTSSN
TNNGETSVAQNPAQQETTQSSSTNATTEETPVTGEATTTTTNQANTPATTQSSNTNAEELVNQTSNETTSNDTNTVSSVNS
PQNSTNAENVSTTQDTSTEATPSNNESAPQNTDASNKDVVSQAVNPSTPRMRAFSLAAVAADAPAAGTDITNQLTDVK
VTIDSGTTVYPHQAGYVKLNYGFSVPNSAVKGDTFKITVPKELNLNGVTSTAKVPPIMAGDQVLANGVIDSDGNVIYTFTD
YVDNKENVTANITMPAYIDPENVTKTGNVTLTTGIGTNTASKTVLIDYEKYGQFHNLSIKGTIDQIDKTNNTYRQTIYVNP
SGDNVVLPALTGNLIPNTKSNALIDAKNTDIKVYRVDNANDLLSESYYVNPSDFEDVTNQVRISFPNANQYKVEFPTDD
DQITTPYIVVVNGHIDPASTGDLALRSTFYGYDSNFIWRSMSWDNEVAFNNGSGSGDGIDKPVVPEQPEDPGEIEPIPEDS
DSDPGSDSGSDSNSDSGSDSGSDSTSDSGSDSASDSDSASDSDSASDSDSASDSDSASDSDSASDSDSASDSDSA
SDSDSASDSDSASDSDSASDSDSASDSDSDSDSDSDSDSDSDSDSDSDSDSDSDSDSDSDSDSDSDSDSD
SDSDSDSDSDSDSDSDSDSDSDSDSDSDSDSDSDSDSDSDSDSASDSDSDSDSESDSDSDSDSDSDSDSDSDS
ESDSDSDSDSDSESDSDSDSDSDSASDSDSGSDSDSSSDSDSTSDTGSDNDSDSDSNSDSESGSNNNVVPPNSPKNG
TNASNKNEAKDSKEPLPDTGSEDEANTSLIWGLLASLGSLLLFRRKKENKDKK

SEQ ID NO:31 polypeptide sequence
MKNNLRYGIRKHKLGAASVFLGTMIVVGMGQDKEAAASEQKTTTVEENGNSATDNKTSETQTTATNVNHIEETQSYNATVT
EQPSNATQVTTEEAPKAVQAPQTAQPANVETVKEEEKPQVKETTQPQDNSGNQRQVDLTPKKVTQNQGTETQVEVAQPRTA
SESKPRVTRSADVAEAKEASDVSEVKGTDVTSKVTVESGSIEAPQGNKVEPHAGQRVVLKYKLKFADGLKRGDYFDFT

Figure 1 cont.

```
LSNNVNTYGVSTARKVPEIKNGSVVMATGEILGNGNIRYTFTNEIEHKVEVTANLEINLFIDPKTVQSNGEQKITSKLNGE
ETEKTIPVVYNPGVSNSYTNVNGSIETFNKESNKFTHIAYIKPMNGNQSNTVSVTGTLTEGSNLAGGQPTVKVYEYLGKKD
ELPQSVYANTSDTNKFKDVTKEMNGKLSVQDNGSYSLNLDKLDKTYVIHYTGEYLQGSDQVNFRTELYGYPERAYKSY
YVYGGYRLTWDNGLVLYSNKADGNGKNGQIIQDNDFEYKEDTAKGTMSGQYDAKQIIETEENQDNTPLDIDYHTAIDGEGG
YVDGYIETIEETDSSAIDIDYHTAVDSEVGHVGGYTESSEESNPIDFEESTHENSKHHADVVEYEEDTNPGGGQVTTESNL
VEFDEESTKGIVTGAVSDHTTIEDTKEYTTESNLIELVDELPEEHGQAQGPIEEITENNHHISHSGLGTENGHGNYGV
IEEIEENSHVDIKSELGYEGGQNSGNQSFEEDTEEDKPKYEQGGNIVDIDFDSVPQIHGQNKGDQSFEEDTEKDKPKYEHG
GNIIDIDFDSVPQIHGFNKHNEIIEEDTNKDKPNYQFGGHNSVDFEEDTLPKVSGQNEGQQTIEEDTTPPTPPTEVPSEP
ETPMPPTEVPSEPETPTPPTPEVPSEPETPTPPTPEVPSEPETPTPPTPEVPSEPETPTPPTPEVPAEPGKPVPPAK
EEPKKPSKPVEQGKVVTPVIEINEKVKAVAPTKKAQSKKSELPETGGEESTNKGMLFGGLFSILGLALLRRNKKNNKA
```

SEQ ID NO:32 polypeptide sequence
```
MKKRIDYLSNKQNKYSIRRFTVGTTSVIVGATILFGIGNHQAQASEQSNDTTQSSKNNASADSEKNNMIETPQLNTTANDT
SDISANTNSANVDSTTKPMSTQTSNTTTTEPASTNETPQPTAIKNQATAAKMQDQTVPQEANSQVDNKTTNDANSIATNSE
LKNSQTLDLPQSSPQTISNAQGTSKPSVRTRAVRSLAVAEPVVNAADAKGTNVNDKVTASNFKLEKTTFDPNQSGNTF
MAANFTVTDKVKSGDYFTAKLPDSLTGNGDVDYSNSNNTMPIADIKSTNGDVVAKATYDILTKTYTFVFTDYVNNKENING
QFSLPLFTDRAKAPKSGTYDANINIADEMFNNKITYNYSSPIAGIDKPNGANISSQIIGVDTASGQNTYKQTVFVNPKQRV
LGNTWVYIKGYQDKIEESSGKVSATDTKLRIFEVNDTSKLSDSYYADPNDSNLKEVTDQFKNRIYYEHPNVASIKFGD
ITKTYVVLVEGHYDNTGKNLKTQVIQENVDPVTNRDYSIFGWNNENVVRYGGGSADGDSAVNPKDPTPGPPVDPEPSPDPE
PEPTPDPEPSPDPEPEPSPDPDPDSDSDSDSGSDSDSGSDSDSESDSDSDSDSDSDSDSDSESDSDSESDSDSDSDSDS
DSDSESDSDSDSDSDSDSDSESDSDSESDSESDSDSDSDSDSDSDSDSDSDSDSDSDSDSDSDSDSESDSDSDS
DSDSDSDSDSDSDSDSDSDSDSDSDSDSDSDSDSDSDSDSDSDSDSDSDSDSDSDSDSDSDSDSDSDSDSDSDSD
SDSRVTPPNNEQKAPSNPKGEVNHSNKVSKQHKTDALPETGDKSENTNATLFGAMMALLGSLLLFRKRKQDHKEKA
```

SEQ ID NO:33 polypeptide sequence
```
MKKQIISLGALAVASSLFTWDNKADAIVTKDYSKESRVNEKSKKGATVSDYYYWKIIDSLEAQFTGAIDLLEDYKYGDPIY
KEAKDRLMTRVLGEDQYLLKKKIDEYELYKKWYKSSNKNTNMLTFHKYNLYNLTMNEYNDIFNSLKDAVYQFNKEVKEIEH
KNVDLKQFDKDGEDKATKEVYDLVSEIDTLVVTYYADKDYGEHAKELRAKLDLILGDTDNPHKITNERIKKEMIDDLN
SIIDDFFMETKQNRPNSITKYDPTKHNFKEKSENKPNFDKLVEETKKAVKEADESWKNKTVKKYEETVTKSPVVKEEKKVE
EPQLPKVGNQQEVKTTAGKAEETTQPVAQPLVKIPQETIYGETVKGPEYPTMENKTLQGEIVQGPDFLTMEQNRPSLSDNY
TQPTTPNPILEGLEGSSSKLEIKPQGTESTLKGIQGESSDIEVKPQATETTEASQYGPRPQFNKTPKYVKYRDAGTGI
REYNDGTFGYEARPRFNKPSETNAYNVTTNQDGTVSYGARPTQNKPSETNAYNVTTHANGQVSYGARPTQKKPSKTNAYNV
TTHANGQVSYGARPTQKKPSKTNAYNVTTHANGQVSYGARPTYKKPSETNAYNVTTHANGQVSYGARPTQKKPSETNAYNV
TTHADGTATYGPRVTK
```

SEQ ID NO:67 polypeptide sequence
```
MKSNLRYGIRKHKLGAASVFLGTMIVVGMGQEKEAAASEQNNTTVEESGSSATESKASETQTTTNNVNTIDETQSYSATST
EQPSKSTQVTTEEAPTTVQAPKVETEMKSQEDLPSEKVADKETTGTQVDIAQPSNVSEIKPRMKRSADVTAVSEKEVAEEA
KATGTDVTNKVEVTESSLEGHNKDSNIVNPHNAQRVTLKYKWKFGEGIKAGDYFDFTLSDNVETHGISTLRKVPEIKS
STEDKVMANGQVINERTIRYTFTDYINNKKDLTAELNLNLFIDPTTVTKQGSQKVEVTLGQNKVSKEFDIKYLDGVKDRMG
VTVNGRIDTLNKEEGKFSHFAYVKPNNQSLTSVTVTGQVTSGYKQSANNPTVKVYKHIGSDELAESVYAKLDDTSKFEDVT
EKVNLSYTSNGGYTLNLGDLDNSKDYVIKYEGEYDQNAKDLNFRTHLSGYHKYYPYYPYYPVQLTWNNGVAFYSN
NAKGDGKDKPNDPIIEKSEPIDLDIKSEPPVEKHELTGTIEESNDSKPIDFEYHTAVEGAEGHAEGIIETEEDSIHVDFEE
STHENSKHHADVVEYEEDTNPGGGQVTTESNLVEFDEESTKGIVTGAVSDHTTVEDTKEYTTESNLIELVDELPEEHGQAQ
GPIEEITENNHHISHSGLGTENGHGNYGVIDEIEENSHVDIKSELGYEGGQNSGNQSFEEDTEEDKPKYEQGGNIVDI
DFDSVPQIHGQNNGNQSFEEDTEEDKPKYEQGGNIIDIDFDSVPQIHGFNKHNEIIEEDTNKDKPNYQFGGHNSVDFEEDT
LPKVSGQNEGQQTIEEDTTPPTPPTEVPSEPETPTPPTPEVPSEPGEPTPPKPEVPSEPETPVPPTPEVPSEPGKPVPPA
KEEPKKPSKPVEQGKVVTPVIEINEKVKAVAPTKQKQSKKSELPETGGEESTNKGMLFGGLFSILGLVLLRRNKKNNK
A
```

Figure 1 cont.

SEQ ID NO:68 polypeptide sequence

MKFSLITTTLALGVIASTGANFNTNEASAAAKPLDKSSSTLHHGHSNIQIPYTITVNGTSQNILSSLTFNKNQNISYKD
IENKVKSVLYFNRGISDIDLRLSKQAEYTVHFKNGTKRVIDLKSGIYTADLINTSDIKAISVNVDTKKQPKDKAKANVQV
PYTITVNGTSQNILSNLTFNKNQNISYKDLEGKVKSVLESNRGITDVDLRLSKQAKYTVNFKNGTKKVIDLKSGIYTANL
INSSDIKSININVDTKKHIENKAKRNYQVPYSINLNGTSTNILSNLSFSNKPWTNYKNLTSQIKSVLKHDRGISEQDLKY
AKKAYYTVYFKNGGKRILQLNSKNYTANLVHAKDVKRIEITVKTGTKAKADRYVPYTIAVNGTSTPILSKLKISNKQLIS
YKYLNDKVKSVLKSERGISDLDLKFAKQAKYTVYFKNGKKQVVNLKSDIFTPNLFSAKDIKKIDIDVKQYTKSKKKINKS
NNVKFPVTINKFENIVSNEFVFYNASKITINDLSIKLKSAMANDQGITKHDIGLAERAVYKVYFKNGSSKYVDLKTEYKD
ERVFKATDIKKVDIELKF

SEQ ID NO:69 polypeptide sequence

MNKHHPKLRSFYSIRKSTLGVASVIVSTLFLITSQHQAQAAENTNTSDKISENQNNNATT
TQPPKDTNQTQPATQPANTAKNYPAADESLKDAIKDPALENKEHDIGPREQVNFQLLDKN
NETQYYHFFSIKDPADVYYTKKKAEVELDINTASTWKKFEVYENNQKLPVRLVSYSPVPE
DHAYIRFPVSDGTQELKIVSSTQIDDGEETNYDYTKLVFAKPIYNDPSLVKSDTNDAVVT
NDQSSSVASNQTNTNTSNQNISTINNANNQPQATTNMSQPAQPKSSTNADQASSQPAHET
NSNGNTNDKTNESSNQSDVNQQYPPADESLQDAIKNPAIIDKEHTADNWRPIDFQMKNDK
GERQFYHYASTVEPATVIFTKTGPIIELGLKTASTWKKFEVYEGDKKLPVELVSYDSDKD
YAYIRFPVSNGTREVKIVSSIEYGENIHEDYDYTLMVFAQPITNNPDDYVDEETYNLQKL
LAPYHKAKTLERQVYELEKLQEKLPEKYKAEYKKKLDQTRVELADQVKSAVTEFENVTPT
NDQLTDLQEAHFVVFESEENSESVMDGFVEHPFYTATLNGQKYVVMKTKDDSYWKDLIVE
GKRVTTVSKDPKNNSRTLIFPYIPDKAVYNAIVKVVVANIGYEGQYHVRIINQDINTKDD
DTSQNNTSEPLNVQTGQEGKVADTDVAENSSTATNPKDASDKADVIEPESDVVKDADNNI
DKDVQHDVDHLSDMSDNNHFDKYDLKEMDTQIAKDTDRNVDKDADNSVGMSSNVDTDKDS
NKNKDKVIQLNHIADKNNHTGKAAKLDVVKQNYNNTDKVTDKKTTEHLPSDIHKTVDKTV
KTKEKAGTPSKENKLSQSKMLPKTGETTSSQSWWGLYALLGMLALFIPKFRKESK

SEQ ID NO:70 polypeptide sequence

MAETTQDQTTNKNVLDSNKVKATTEQAKAEVKNPTQNISGTQVYQDPAIVQPKTANNKTG
NAQVSQKVDTAQVNGDTRANQSATTNNTQPVAKSTSTTAPKTNTNVTNAGYSLVDDEDDN
SENQINPELIKSAAKPAALETQYKTAAPKAATTSAPKAKTEATPKVTTFSASAQPRSVAA
TPKTSLPKYKPQVNSSINDYICKNNLKAPKIEEDYTSYFPKYAYRNGVGRPEGIVVHDTA
NDRSTINGEISYMKNNYQNAFVHAFVDGDRIIETAPTDYLSWGVGAVGNPRFINVEIVHT
HDYASFARSMNNYADYAATQLQYYGLKPDSAEYDGNGTVWTHYAVSKYLGGTDHADPHGY
LRSHNYSYDQLYDLINEKYLIKMGKVAPWGTQSTTTPTTPSKPTTPSKPSTGKLTVAANN
GVAQIKPTNSGLYTTVYDKTGKATNEVQKTFAVSKTATLGNQKFYLVQDYNSGNKFGWVK
EGDVVYNTAKSPVNVNQSYSIKPGTKLYTVPWGTSKQVAGSVSGSGNQTFKASKQQQIDK
SIYLYGSVNGKSGWVSKAYLVDTAKPTPTPTPKPSTPTTNNKLTVSSLNGVAQINAKNNG
LFTTVYDKTGKPTKEVQKTFAVTKEASLGGNKFYLVKDYNSPTLIGWVKQGDVIYNNAKS
PVNVMQTYTVKPGTKLYSVPWGTYKQEAGAVSGTGNQTFKATKQQQIDKSIYLFGTVNGK
SGWVSKAYLAVPAAPKKAVAQPKTAVK

SEQ ID NO: 71 polypeptide sequence

MAYTVTKPQTTQTVSKIAQVKPNNTGIRASVYEKTAKNGAKYADRTFYVTKERAHGNETY
VLLNNTSHNIPLGWFNVKDLNVQNLGKEVKTTQKYTVNKSNNGLSMVPWGTKNQVILTGN
NIAQGTFNATKQVSVGKDVYLYGTINNRTGWVNAKDLTAPTAVKPTTSAAKDYNYTYVIK
NGNGYYYVTPNSDTAKYSLKAFNEQPFAVVKEQVINGQTWYYGKLSNGKLAWIKSTDLAK
ELIKYNQTGMTLNQVAQIQAGLQYKPQVQRVPGKWTDAKFNDVKHAMDTKRLAQDPALKY
QFLRLDQPQNISIDKINQFLKGKGVLENQGAAFNKAAQMYGINEVYLISHALLETGNGTS

Figure 1 cont.

QLAKGADVVNNKVVTNSNTKYHNVFGIAAYDNDPLREGIKYAKQAGWDTVSKAIVGGAKF
IGNSYVKAGQNTLYKMRWNPAHPGTHQYATDVDWANINAKIIKGYYDKIGEVGKYFDIPQ
YK

SEQ ID NO:72 polypeptide sequence
DRVLASHPDVATIRQNVTAANAAKSALDQARNGLTVDKAPLENAKNQLQHSIDTQTSTTG
MTQDSINAYNAKLTAARNKIQQINQVLAGSPTVEQINTNTSTANQAKSDLDHARQALTPD
KAPLQTAKTQLEQSINQPTDTTGMTTASLNAYNQKLQAARQKLTEINQVLNGNPTVQNIN
DKVTEANQAKDQLNTARQGLTLDRQPALTTLHGASNLNQAQQNNFTQQINAAQNHAALET
IKSNITALNTAMTKLKDSVADNNTIKSDQNYTDATPANKQAYDNAVNAAKGVIGETTNPT
MDVNTVNQKAASVKSTKDALDGQQNLQRAKTEATNAITHASDLNQAQKNALTQQVNSAQN
VQAVNDIKQTTQSLNTAMTGLKRGVANHNQVVQSDNYVNADTNKKNDYNNAYNHANDIIN
GNAQHPVITPSDVNNALSNVTSKEHALNGEAKLNAAKQEANTALGHLNNLNNAQRQNLQS
QINGAHQIDAVNTIKQNATNLNSAMGNLRQAVADKDQVKRTEDYADADTAKQNAYNSAVS
SAETIINQTTNPTMSVDDVNRATSAVTSNKNALNGYEKLAQSKTDAARAIDALPHLNNAQ
KADVKSKINAASNIAGVNTVKQQGTDLNTAMGNLQGAINDEQTTLNSQNYQDATPSKKTA
YTNAVQAAKDILNKSNGQNKTKDQVTEAMNQVNSAKNNLDGTRLLD

SEQ ID NO: 73 polypeptide sequence
ASTQHTVQSGESLWSIAQKYNTSVESIKQNNQLDNNLVFPGQVISVGGSDAQNTSNTSPQ
AGSASSHTVQAGESLNIIASRYGVSVDQLMAANNLRGYLIMPNQTLQIPNGGSGGTTPTA
TTGSNGNASSFNHQNLYTAGQCTWYVFDRRAQAGSPISTYWSDAKYWAGNAANDGYQVNN
TPSVGSIMQSTPGPYGHVAYVERVNGDGSILISEMNYTYGPYNMNYRTIPASEVSSYAFI
H

SEQ ID NO: 74 polypeptide sequence
MNNKKTATNRKGMIPNRLNKFSIRKYSVGTASILVGTTLIFGLSGHEAKAAEHTNGELNQ
SKNETTAPSENKTTKKVDSRQLKDNTQTATADQPKVTMSDSATVKETSSNMQSPQNATAN
QSTTKTSNVTTNDKSSTTYSNETDKSNLTQAKDVSTTPKTTTIKPRTLNRMAVNTVAAPQ
QGTNVNDKVHFSNIDIAIDKGHVNQTTGKTEFWATSSDVLKLKANYTIDDSVKEGDTFTF
KYGQYFRPGSVRLPSQTQNLYNAQGNIIAKGIYDSTTNTTYTFTNYVDQYTNVRGSFEQ
VAFAKRKNATTDKTAYKMEVTLGNDTYSEEIIVDYGNKKAQPLISSTNYINNEDLSRNMT
AYVNQPKNTYTKQTFVTNLTGYKFNPNAKNFKIYEVTDQNQFVDSFTPDTSKLKDVTDQF
DVIYSNDNKTATVDLMKGQTSSNKQYIIQQVAYPDNSSTDNGKIDYTLDTDKTKYSWSNS
YSNVNGSSTANGDQKKYNLGDYVWEDTNKDGKQDANEKGIKGVYVILKDSNGKELDRTTT
DENGKYQFTGLSNGTYSVEFSTPAGYTPTTANVGTDDAVDSDGLTTTGVIKDADNMTLDS
GFYKTPKYSLGDYVWYDSNKDGKQDSTEKGIKGVKVTLQNEKGEVIGTTETDENGKYRFD
NLDSGKYKVIFEKPAGLTQTGTNTTEDDKDADGGEVDVTITDHDDFTLDNGYYEEETSDS
DSDSDSDSDSDSDSDSDSDSDSDSDSDSDSDSDSDSDSDSDSDSDSDSDSDSDSDSDSDS
DSDSDSDSDSDSDSDSDSDSDSDSDSDSDSDSDSDSDSDSDSDSDSDSDSDSDSDSDSDS
DSDSDSDSDSDSDSDNDSDSDSDSDSDSDSDSDSDSDSDSDSDSDSDSDSDSDSDSDSDS
DSDSDSDSDSDSDSDSDSDSDNDSDSDSDSDAGKHTPAKPMSTVKDQHKTAKALPE
TGSENNNSNNGTLFGGLFAALGSLLLFGRRKKQNK

SEQ ID NO: 75 polypeptide sequence
MNLLKKNKYSIRKYKVGIFSTLIGTVLLLSNPNGAQALTTDNNVQSDTNQATPVNSQDKD
VANNRGLANSAQNTPNQSATTNQATNQALVNHNNGSIVNQATPTSVQSSTPSAQNNHTD
GNTTATETVSNANNNDVVSNNTALNVPTKTNENGSGGHLTLKEIQEDVRHSSNKPELVAI
AEPASNRPKKRSRRAAPADPNATPADPAAAAVGNGGAPVAITAPYTPTTDPNANNAGQNA
PNEVLSFDDNGIRPSTNRSVPTVNVVNNLPGFTLINGGKVGVFSHAMVRTSMFDSGDNKN
YQAQGNVIALGRIHGTDTNDHGDFNGIEKALTVNPNSELIFEFNTMTTKNGQGATNVIIK
NADTNDTIAEKTVEGGPTLRLFKVPDNVRNLKIQFVPKNDAITDARGIYQLKDGYKYYSF
VDSIGLHSGSHVFVERRTMDPTATNNKEFTVTTSLKNNGNSGASLDTNDFVYQVQLPEGV
EYVNNSLTKDFPSNNSGVDVNDMNVTYDAANRVITIKSTGGGTANSPARLMPDKILDLRY
KLRVNNVPTPRTVTFNETLTYKTYTQDFINSAAESHTVSTNPYTIDIIMNKDALQAEVDR
RIQQADYTFASLDIFNGLKRRAQTILDENRNNVPLNKRVSQAYIDSLTNQMQHTLIRSVD

Figure 1 cont.

```
AENAVNKKVDQMEDLVNQNDELTDEEKQAAIQVIEEHKNEIIGNIGDQTTDDGVTRIKDQ
GIQTLSGDTATPVVKPNAKKAIRDKATKQREIINATPDATEDEIQDALNQLATDETDAID
NVTNATTNADVETAKNNGINTIGAVVPQVTHKKAARDAINQATATKRQQINSNREATQEE
KNAALNELTQATNHALEQINQATTNANVDNAKGDGLNAINPIAPVTVVKQAARDAVSHDA
QQHIAEINANPDATQEERQAAIDKVNAAVTAANTNILNANTNADVEQVKTNAIQGIQAIT
PATKVKTDAKNAIDKSAETQHNTIFNNNDATLEEQQAAQQLLDQAVATAKQNINAADTNQ
EVAQAKDQGTQNIVVIQPATQVKTDTRNVVNDKAREAITNINATTGATREEKQEAINRVN
TLKNRALTDIGVTSTTAMVNSIRDDAVNQIGAVQPHVTKKQTATGVLNDLATAKKQEINQ
NTNATTEEKQVALNQVDQELATAINNINQADTNAEVDQAQQLGTKAINAIQPNIVKKPAA
LAQINQHYNAKLAEINATPDATNDEKNAAINTLNQDRQQAIESIKQANTNAEVDQAATVA
ENNIDAVQVDVVKKQAARDKITAEVAKRIEAVKQTPNATDEEKQAAVNQINQLKDQAINQ
INQNQTNDQVDTTTNQAVNAIDNVEAEVVIKTKAIADIEKAVKEKQQQIDNSLDSTDNEK
EVASQALAKEKEKALAAIDQAQTNSQVNQAATNGVSAIKIIQPETKVKPAAREKINQKAN
ELRAKINQDKEATAEERQVALDKINEFVNQAMTDITNNRTNQQVDDTTSQALDSIALVTP
DHIVRAAARDAVKQQYEAKKREIEQAEHATDEEKQVALNQLANNEKRALQNIDQAIANND
VKRVETNGIATLKGVQPHIVIKPEAQQAIKASAENQVESIKDTPHATVDELDEANQLISD
TLKQAQQEIENTNQDAAVTDVRNQTIKAIEQIKPKVRRKRAALDSIEENNKNQLDAIRNT
LDTTQDERDVAIDTLNKIVNTIKNDIAQNKTNAEVDRTETDGNDNIKVILPKVQVKPAAR
QSVGVKAEAQNALIDQSDLSTEEERLAAKHLVEQALNQAIDQINHADKTAQVNQDSINAQ
NIISKIKPATTVKATALQQIQNIATNKINLIKANNEATDEEQNIAIAQVEKELIKAKQQI
ASAVTNADVAYLLHDEKNEIREIEPVINRKASAREQLTTLFNDKKQAIEANIQATVEERN
SILAQLQNIYDTAIGQIDQDRSNAQVDKTASLNLQTIHDLDVHPIKKPDAEKTINDDLAR
VTALVQNYRKVSNRNKADALKAITALKLQMDEELKTARTNADVDAVLKRFNVALSDIEAV
ITEKENSLLRIDNIAQQTYAKFKAIATPEQLAKVKVLIDQYVADGNRMIDEDATLNDIKQ
HTQFIVDEILAIKLPAEATKVSPKEIQPAPKVCTPIKKEETHESRKVEKELPNTGSEGMD
LPLKEFALITGAALLARRRTKNEKES
```

SEQ ID NO: 76 polypeptide sequence
```
EENSVQDVKDSNTDDELSDSNDQSSDEEKNDVINNNQSINTDDNNQIIKKEETNNYDGIE
KRSEDRTESTTNVDENEATFLQKTPQDNTHLTEEEVKESSSVESSNSSIDTAQQPSHTTI
NREESVQTSDNVEDSHVSDFANSKIKESNTESGKEENTIEQPNKVKEDSTTSQPSGYTNI
DEKISNQDELLNLPINEYENKARPLSTTSAQPSIKRVTVNQLAAEQGSNVNHLIKVTDQS
ITEGYDDSEGVIKAHDAENLIYDVTFEVDDKVKSGDTMTVDIDKNTVPSDLTDSFTIPKI
KDNSGEIIATGTYDNKNKQITYTFTDYVDKYENIKAHLKLTSYIDKSKVPNNNTKLDVEY
KTALSSVNKTITVEYQRPNENRTANLQSMFTNIDTKNHTVEQTIYINPLRYSAKETNVNI
SGNGDEGSTIIDDSTIIKVYKVGDNQNLPDSNRIYDYSEYEDVTNDDYAQLGNNNDVNIN
FGNIDSPYIIKVISKYDPNKDDYTTIQQTVTMQTTINEYTGEFRTASYDNTIAFSTSSGQ
GQGDLPPEKTYKIGDYVWEDVDKDGIQNTNDNEKPLSNVLVTLTYPDGTSKSVRTDEDGK
YQFDGLKNGLTYKITFETPEGYTPTLKHSGTNPALDSEGNSVWVTINGQDDMTIDSGFYQ
TPKYSLGNYVWYDTNKDGIQGDDEKGISGVKVTLKDENGNIISTTTTDENGKYQFDNLNS
GNYIVHFDKPSGMTQTTTDSGDDDEQDADGEEVHVTITDHDDFSIDNGYYDDE
```

Figure 2

SEQ ID NO:34 polynucleotide sequence
ATGTTACAAGTAACTGATGTGAGTTTACGTTTTGGAGATCGTAAACTATTTGAAGATGTAAATATTAAATTTACAGAAGG
TAATTGTTATGGATTAATTGGTGCGAATGGTGCAGGTAAATCAACATTCTTAAAAATATTATCTGGTGAATTAGATTCTC
AAACAGGACATGTTTCATTAGGTAAAAATGAACGTCTAGCTGTTTTAAAACAGGACCACTATGCTTATGAAGATGAACGC
GTGCTTGATGTTGTAATTAAAGGTCACGAACGTCTTTATGAGGTTATGAAAGAAAAAGATGAAATCTATATGAAGCCAGA
TTTCAGTGATGAAGATGGTATCCGTGCTGCTGAACTTGAAGGTGAATTTGCAGAAATGAATGGTTGGAATGCTGAAGCTG
ATGCTGCTAACCTTTTATCTGGTTTAGGTATCGATCCAACTTTACACGATAAAAAAATGGCTGAATTAGAAAACAACCAA
AAAATTAAAGTATTATTAGCGCAAAGTTTATTCGGTGAACCAGACGTACTATTACTGGATGAGCCTACTAACGGTCTCGA
TATTCCAGCAATCAGTTGGTTAGAAGATTTCTTAATTAACTTTGATAATACTGTTATCGTAGTATCGCATGACCGTCATT
TCTTAAATAATGTATGTACTCATATCGCTGATTTAGACTTCGGTAAAATTAAAGTTTATGTTGGTAACTATGATTTTTGG
TATCAATCTAGTCAGTTAGCTCAAAAGATGGCTCAAGAACAAAACAAGAAAAAAGAAGAAAAATGAAAGAGTTACAGGA
CTTTATTGCACGTTTCTCAGCTAACGCTTCTAAATCTAAACAAGCAACAAGTCGTAAAAAACAACTTGAGAAAATTGAAT
TAGATGATATTCAACCATCATCAAGAAGATATCCTTTCGTTAAATTCACGCCTGAGCGTGAGATTGGTAACGACTTATTA
ATCGTTCAAAATCTTTCTAAAACAATTGACGGCGAAAAAGTATTAGATAATGTATCATTCACAATGAATCCAAATGATAA
AGCGATTTTAATTGGAGATAGTGAAATTGCAAAAACAACATTACTTAAAATATTAGCTGGCGAAATGGAACCAGACGAAG
GTTCATTTAAATGGGGTGTTACTACATCATTAAGTTACTTCCCTAAAGATAACTCAGAGTTCTTTGAGGGTGTAAATATG
AATCTCGTTGATTGGTTAAGACAATATGCTCCTGAAGATGAACAAACAGAAACATTTTTACGTGGTTTCTTAGGTCGTAT
GTTATTAGTGGTGAAGAAGTTAAGAAAAAAGCTAGTGTGCTTTCAGGTGGAGAAAAAGTACGTTGTATGCTAAGTAAAA
TGATGTTATCAAGTGCGAATGTACTTTTACTTGACGAACCTACTAACCACTTAGACTTAGAAAGTATTACTGCTGTCAAT
GATGGTCTTAAATCATTTAAAGGTTCTATCATCTTTACTTCTTATGACTTCGAATTTATCAACACGATTGCAAACCGTGT
TATCGATTTAAATAAACAAGGCGGCGTTTCAAAAGAAATTCCATATGAAGAATACTTGCAAGAAATCGGCGTTTTAAAAT
AA

SEQ ID NO:35 polynucleotide sequence
ATGTTACAAGTAACTGATGTAAGTTTACGTTTTGGTGATCGTAAACTATTTGAAGATGTAAATATAAAATTTACAGAGGG
TAATTGTTATGGATTAATTGGTGCAAATGGTGCTGGGAAATCTACATTCTTGAAGATTTTATCAGGCGAAATTGATTCAC
AGACTGGTCATGTATCTCTAGGTAAAGATGAGCGTTTGGCTGTGTTAAAACAAGATCATTTTGCTTATGAAGATGAACGT
GTTTTAGATGTTGTGATTAAAGGACATGAACGTTTGTATCAAGTGATGAAAGAAAGATGAAATTTATATGAAACCTGA
TTTCAGCGATGAGGACGGTATTCGCGCTGCAGAACTTGAAGGAGAATTTGCAGAAATGAACGGTTGGAATGCTGAAGCTG
ATGCTGCTAACTTATTATCAGGATTAGGCATAGAACCTGACTTACATGATAAAAATATGTCTGAACTTGAAAATAATCAA
AAAGTTAAGGTATTGTTAGCTCAAAGTTTATTTGGTGATCCTGACGTTCTTTTACTAGATGAGCCTACCAATGGTTTAGA
TATACCAGCAATAAGTTGGTTAGAAGACTTTTTAATTAATTTTGAAAATACTGTCATTGTCGTTTCGCATGACCGTCACT
TCTTAAATAATGTTTGTACTCATATTGCTGATTTAGACTTTGGCAAAATTAAACTTTATGTTGGTAACTATGATTTTTGG
TATCAATCAAGTCAATTAGCACAAAAAATGGCACAAGAACAAAATAAGAAAAAAGAAGAAAAATGAAAGAGTTACAGGA
TTTCATCGCACGCTTCTCAGCAAATGCTTCTAAATCTAAACAGGCAACAAGTCGTAAGAAACAATTAGAAAAAATTGAAT
TAGATGATATCCAGCCATCATCTCGTAGATACCCTTACGTGAAATTTACTCCTGAACGTGAAATTGGAAATGATTTACTT
ACAGTAGAAAATCTTTCTAAAACAATTGACGGCGAAAAAGTACTAGACAATGTTTCATTCACTATGAATCCTAATGATAA
AGCTATTTTAGTTGGTGATAGCGAAATTGCTAAAACAACATTGTTAAAAATTTTAGCTGGAGAAATGGAACCAGATGAAG
GTACATTTAAATGGGGTGTAACGACATCTTTAAGTTACTTCCCTAAAGATAACTCTGAGTTCTTTGATGGTGTCGATATG
AATTTAGTTGAATGGTTACGTCAATACGCTCCAGAAGATGAACAAACTGAAACATTTTTACGTGGTTTCTTAGGTCGCAT
GTTATTAGTGGTGAGGAAGTTAAGAAAAAAGCAAGCGTGCTTTCAGGTGGAGAAAAAGTACGTTGCATGTTAAGTAAAA
TGATGTTATCAAGTGCTAACGTACTTTTACTTGATGAGCCAACAAACCATTTAGATTTGGAAAGTATCACTGCTGTAAAT
GACGGATTAAAATCATTTAAAGGTTCTATCATCTTCACTTCTTATGATTTTGAATTTATTAATACAATCGCAAATCGAGT
GATTGACTTGAATCAAGCTGGTGCCCTTTCTAAAGAAGTACCTTATGAGGAATACTTACAAGAAATTGGTGTATTACAAA
ATAATTAA

SEQ ID NO:36 polynucleotide sequence
ATGCCAATTATTACAGATGTTTACGCTCGCGAAGTCTTAGACTCTCGTGGTAACCCAACTGTTGAAGTAGAAGTATTAAC
TGAAAGTGGCGCATTTGGTCGTGCATTAGTACCATCAGGTGCTTCAACTGGTGAACACGAAGCTGTTGAATTACGTGATG
GAGACAAATCACGTTATTTAGGTAAAGGTGTTACTAAAGCAGTTGAAAACGTTAATGAAATCATCGCACCAGAAATTATT
GAAGGTGAATTTCAGTATTAGATCAAGTATCTATTGATAAATGATGATCGCATTAGACGGTACTCCAAACAAAGGTAA
ATTAGGTGCAAATGCTATTTTAGGTGTATCTATCGCAGTAGCACGTGCAGCAGCTGACTTATTAGGTCAACCACTTTACA
AATATTTAGGTGGATTTAATGGTAAGCAGTTACCAGTACCAATGATGAACATCGTTAATGGTGGTTCTCACTCAGATGCT
CCAATTGCATTCCAAGAATTCATGATTTTACCTGTAGGTGCTACAACGTTCAAAGAATCATTACGTTGGGGTACTGAAAT
TTTCCACAACTTAAAATCAATTTTAAGCAAACGTGGTTTAGAAACTGCAGTAGGTGACGAAGGTGGTTTCGCTCCTAAAT
TTGAAGGTACTGAAGATGCTGTTGAAACAATTATCCAAGCAATCGAAGCAGCTGGTTACAAACCAGGTGAAGAAGTATTC

Figure 2 cont.

TTAGGATTTGACTGTGCATCATCAGAATTCTATGAAAATGGTGTATATGACTACAGTAAGTTCGAAGGCGAACACGGTGC
AAAACGTACAGCTGCAGAACAAGTTGACTACTTAGAACAATTAGTAGACAAATATCCTATCATTACAATTGAAGACGGTA
TGGACGAAAACGACTGGGATGGTTGGAAACAACTTACAGAACGTATCGGTGACCGTGTACAATTAGTAGGTGACGATTTA
TTCGTAACAAACACTGAAATTTTAGCAAAAGGTATTGAAAACGGAATTGGTAACTCAATCTTAATTAAAGTTAACCAAAT
CGGTACATTAACTGAAACATTTGATGCAATCGAAATGGCTCAAAAAGCTGGTTACACAGCAGTAGTTTCTCACCGTTCAG
GTGAAACAGAAGATACAACAATTGCTGATATTGCTGTTGCTACAAACGCTGGTCAAATTAAAACTGGTTCATTATCACGT
ACTGACCGTATTGCTAAATACAATCAATTATTACGTATCGAAGATGAATTATTTGAAACTGCTAAATATGACGGTATCAA
ATCATTCTATAACTTAGATAAATAA

SEQ ID NO:37 polynucleotide sequence
ATGCCAATTATTACAGATGTTTACGCTCGCGAAGTCTTAGACTCACGTGGTAACCCAACAGTTGAAGTTGAAGTATTAAC
TGAAAGCGGTGCTTTCGGACGTGCATTAGTACCTTCTGGTGCTTCTACTGGTGAACATGAAGCAGTTGAATTACGTGATG
GAGATAAATCACGTTATTTAGGTAAAGGTGTGACTAAAGCGGTAGAAAATGTTAACGAAATGATCGCACCAGAAATCGTT
GAAGGTGAATTTTCAGTTTTAGATCAAGTATCTATTGATAAATGATGATTCAATTAGACGGTACACACAACAAAGGTAA
ATTAGGTGCAAATGCCATTTTAGGTGTTTCTATTGCCGTAGCTCGTGCAGCTGCTGACTTATTAGGTCAACCATTATATA
AATATTTAGGTGGATTTAATGGTAAACAATTGCCAGTACCTATGATGAATATTGTTAATGGTGGTTCTCACTCAGATGCA
CCAATTGCTTTCCAAGAGTTCATGATTTTACCTGTAGGTGCTGAGTCATTCAAAGAATCATTACGTTGGGGTGCAGAAAT
CTTCCATAACCTTAAATCAATCTTAAGTGAACGTGGTTTAGAAACTGCAGTAGGTGATGAAGGTGGTTTCGCTCCTAGAT
TTGAAGGCACTGAAGACGCTGTAGAAACTATTATTAAAGCTATCGAAAAAGCAGGATACAAACCAGGTGAAGATGTATTC
TTAGGATTTGACTGTGCTTCTTCTGAATTCTATGAAAATGGTGTTTATGATTACACTAAATTCGAAGGTGAACACGGTGC
TAAACGTAGTGCAGCAGAGCAAGTTGACTACTTAGAAGAATTAATTGGTAAATATCCAATCATCACTATTGAAGATGGTA
TGGATGAAAACGATTGGGAAGGTTGGAAACAATTAACTGCTGTATCGGTGATAAAGTTCAATTAGTTGGTGATGATTTA
TTCGTAACTAACACTGAAATTTTATCTAAAGGTATCGAACAAGGTATTGGTAACTCAATCTTAATCAAAGTAAACCAAAT
CGGTACATTAACTGAAACATTCGATGCTATTGAAATGGCTCAAAAAGCTGGATATACTGCGGTTGTATCTCACCGTTCTG
GTGAAACTGAAGATACTACAATTGCTGATATCGCAGTTGCTACAAATGCAGGCCAAATTAAAACAGGTTCATTATCTAGA
ACTGACCGTATTGCTAAATACAATCAATTATTACGTATTGAAGATGAATTATACGAAACAGCTAAATTTGAAGGAATTAA
ATCTTTCTACAATTTAGATAAATAA

SEQ ID NO:38 polynucleotide sequence
ATGAAAAAAATCGTTACAGCTACAATCGCTACAGCAGGACTTGCCACTATCGCATTTGCAGGACATGATGCACAAGCCGC
AGAACAAAATAACAATGGATATAATTCTAATGACGCTCAATCATACAGCTATACGTATACAATTGATGCACAAGGTAATT
ATCATTACACTTGGACAGGAAATTGGAATCCAAGTCAATTAACGCAAAACAACACATACTACTACAACAACTACAATACT
TATAGTTATAACAATGCATCTTACAATAACTACTATAATCATTCATATCAATACAATAACTATACAAACAATAGCCAAAC
AGCAACAAATAACTATTATACTGGTGGTTCAGGTGCAAGTTATAGCACAACAAGTAATAATGTTCATGTGACTACAACTG
CAGCGCCATCTTCAAATGGTCGTTCAATTTCTAATGGTTATGCATCAGGAAGTAACTTATATACTTCAGGACAATGTACT
TATTATGTATTTGATCGTGTTGGTGGGAAAATTGGTTCAACATGGGGTAACGCAAGTAATTGGGCTAACGCAGCTGCATC
ATCTGGCTATACAGTGAACAATACACCAAAAGTTGGTGCTATCATGCAAACAACACAAGGCTATTACGGTCATGTTGCTT
ACGTTGAAGGCGTTAACAGCAACGGTTCTGTTCGTGTTTCAGAAATGAACTATGGACATGGTGCTGGTGTGGTTACGTCT
CGTACAATTTCAGCAAACCAAGCAGGTTCATATAATTTCATTCATTAA

SEQ ID NO:39 polynucleotide sequence
ATGAAGAAAATCGCTACAGCTACTATCGCAACTGCAGGATTCGCTACAATCGCAATTGCATCAGGAAATCAAGCTCATGC
TTCTGAGCAAGATAACTACGGTTATAATCCAAACGACCCAACATCATATAGCTATACTTACACTATTGATGCACAAGGTA
ACTACCATTACACATGGAAAGGTAACTGGCATCCAAGTCAATTAAACCAAGATAATGGCTACTACAGCTATTACTACTAC
AATGGCTACAATAACTACAACAATTACAACAATGGTTATAGCTACAATAATTACAGCCGTTACAACAACTACTCAAATAA
TAATCAATCATATAACTACAATAACTATAATAGTTACAACACAAACAGCTACCGTACTGGTGGTTTAGGTGCAAGCTACA
GCACTTCAAGCAACAATGTTCAAGTAACTACAACTATGGCTCCATCATCAAATGGCCGTTCAATCTCAAGTGGTTATACT
TCAGGACGTAACTTATACACTTCTGGTCAATGTACATACTACGTATTTGATCGTGTAGGTGGTAAAATCGGTTCAACTTG
GGGCAATGCAAGTAACTGGGCTAACGCAGCTGCAAGAGCTGGTTACACAGTGAACAATACACCAAAAGCTGGTGCAATTA
TGCAAACAACTCAAGGTGCATACGGTCACGTTGCATACGTTGAAAGTGTTAACAGCAATGGTTCAGTAAGAGTTTCAGAA
ATGAACTATGGTTATGGCCCAGGTGTTGTAACTTCACGTACAATCTCAGCTAGCCAAGCTGCTGGTTATAACTTCATTCA
CTAA

SEQ ID NO:40 polynucleotide sequence
ATGAAAAAAATCGCTACAGCTACAATTGCAACTGCAGGAATCGCTACTTTCGCATTTGCACACCATGACGCACAAGCAGC
AGAACAAAATAATGATGGGTACAATCCAAACGACCCTTATTCATATAGCTACACTTACACAATCGATGCTGAAGGTAACT
ACCACTACACTTGGAAAGGTAACTGGAGTCCAGATCGTGTAAATACTTCATATAACTATAATAATTATAATAACTACAAC

Figure 2 cont.

TACTATGGTTACAATAACTATAGCAACTACAATAACTACAGTAATTACAACAATTACAACAACTATCAATCAAACAACAC
GCAATCACAAAGAACAACTCAACCGACTGGTGGTTTAGGCGCAAGCTATTCAACATCAAGTAGTAATGTTCACGTTACAA
CAACTTCTGCGCCATCATCAAACGGTGTATCTTTATCAAACGCTCGCTCAGCATCTGGTAACTTATACACTTCAGGTCAA
TGTACATATTATGTATTTGACAGAGTAGGTGGCAAAATCGGTTCAACGTGGGGTAACGCAAACAACTGGGCAAACGCTGC
AGCACGTTCTGGTTACACAGTAAACAATTCGCCTGCTAAAGGTGCAATCTTACAAACGTCACAAGGTGCATACGGACACG
TAGCATACGTTGAAGGTGTAAACAGCAATGGTTCAATCAGAGTTTCAGAAATGAACTACGGTCACGGTGCAGGTGTTGTC
ACTTCACGTACAATCTCTGCGAGCCAAGCTGCTTCATATAACTATATTCACTAA

SEQ ID NO:41 polynucleotide sequence
ATGAAAAAATTAGTACCTTTATTATTAGCCTTATTACTTCTAGTTGCTGCATGTGGTACTGGTGGTAAACAAAGCAGTGA
TAAGTCAAATGGCAAATTAAAAGTAGTAACGACGAATTCAATTTTATATGATATGGCTAAAAATGTTGGTGGAGACAACG
TCGATATTCATAGTATTGTACCTGTTGGTCAAGATCCTCATGAATATGAAGTTAAACCTAAAGATATTAAAAAGTTAACT
GACGCTGACGTTTATTTTATACAACGGATTAAATTTAGAGACTGGTAACGGTTGGTTTGAAAAAGCCTTAGAACAGGCTGG
TAAATCATTAAAAGATAAAAAAGTTATCGCAGTATCAAAAGATGTTAAACCTATCTATTTAAACGGTGAAGAAGGCAACA
AAGATAAACAAGATCCACACGCATGGTTAAGTTTAGATAATGGTATTAAATACGTAAAACAATTCAACAAACATTTATC
GATAACGACAAAAAACATAAAGCAGATTATGAAAGCAAGGTAACAAATACATTGCTCAATTGGAAAAATTAAATAATGA
CAGTAAAGACAAATTTAATGACATTCCAAAAGAACAACGTGCCATGATTACAAGTGAAGGTGCCTTCAAGTACTTCTCAA
AACAATACGGTATTACACCAGGTTATATTTGGGAAATTAACACTGAAAAACAAGGTACACCTGAACAAATGAGACAAGCT
ATTGAGTTTGTTAAAAAGCACAAATTAAAACACTTATTAGTAGAAACAAGTGTTGATAAGAAAGCAATGGAAAGTTTATC
TGAAGAAACGAAGAAAGATATCTTTGGTGAAGTGTACACAGATTCAATCGGTAAAGAAGGCACTAAAGGTGACTCTTACT
ACAAAATGATGAAATCAAATATTGAAACTGTACACGGAAGCATGAAATAA

SEQ ID NO:42 polynucleotide sequence
GTGAAAAAAATTCTCGCTTTAGCAATAGCATTTTTAATTATCCTTGCCGCATGTGGGAATCACAGTAACCATGAACATCA
CTCACATGAAGGAAAATTAAAAGTTGTAACTACAAACTCTATTCTCTATGACATGGTTAAACGTGTCGGTGGAAATAAGG
TCGATGTTCATAGCATCGTTCCAGTAGGACAAGACCCACATGAATATGAGGTTAAACCTAAAGATATTAAAGCATTAACA
GATGCTGACGTTGTATTTTATAACGGTTTAAACCTAGAAACTGGAAATGGTTGGTTTGAAAAAGCACTTGACCAAGCAGG
AAAATCAACAAAAGATAAAAATGTGATAGCAGCATCAAATAATGTTAAACCAATATACTTAAATGGTGAGGAAGGTAACA
AAAACAAACAAGATCCACATGCATGGTTAAGTTTAGAGAATGGAATTAAATACGTAAAAACAATACAAAAATCACTAGAA
CATCATGATAAAAAGATAAGTCTACATATGAAAAACAAGGGAATGCATATATATCAAAATTAGAAGAACTTAATAAAGA
TAGTAAAAATAAATTTGATGACATACCCAAAAATCAACGTGCCATGATGACAAGTGAAGGTGCATTTAAATATTTTGCTC
AACAATTCGATGTTAAACCAGGTTATATTTGGGAGATAAACACAGAAAAACAAGGTACACCTGGTCAAATGAAACAAGCC
ATTAAATTTGTTAAAGATAATCATTTAAAACATTTATTAGTCGAAACAAGCGTAGATAAAAAAGCTATGCAAAGTTTATC
AGAAGAAACTAAGAAAGATATTTATGGTGAAGTATTTACCGACTCTATAGGTAAGGAAGGTACTAAAGGTGACTCATACT
ATAAAATGATGAAATCTAATATTGATACAATACATGGTAGTATGAAATAA

SEQ ID NO:43 polynucleotide sequence
ATGAAAAAGACAATTATGGCATCATCATTAGCAGTGGCATTAGGTGTAACAGGTTACGCAGCAGGTACAGGACATCAAGC
ACACGCTGCTGAAGTAAACGTTGATCAAGCACACTTAGTTGACTTAGCGCATAATCACCAAGATCAATTAAATGCAGCTC
CAATCAAAGATGGTGCATATGACATCCACTTTGTAAAAGATGGTTTCCAATATAACTTTACTTCAAATGGTACTACATGG
TCATGGAGCTATGAAGCAGCTAATGGTCAAACTGCTGGTTTCTCAAACGTTGCAGGTGCAGACTACACTACTTCATACAA
CCAAGGTTCAGATGTACAATCAGTAAGCTACAATGCACAATCAAGTAACTCAAACGTTGAAGCTGTTTCAGCTCCAACTT
ACCATAACTACAGCACTTCAACTACTTCAAGTTCAGTGAGATTAAGCAATGGTAATACTGCAGGTGCTACTGGTTCATCA
GCAGCTCAAATCATGGCTCAACGTACTGGTGTTTCAGCTTCTACATGGGCTGCAATCATCGCTCGTGAATCAAATGGTCA
AGTAAATGCTTACAACCCCATCAGGTGCTTCAGGTTTATTCCAAACTATGCCAGGTTGGGGTCCGACAAACACTGTTGACC
AACAAATCAACGCAGCTGTTAAAGCATACAAAGCACAAGGTTTAGGTGCTTGGGGATTCTAA

SEQ ID NO:44 polynucleotide sequence
ATGAAAAAAACAGTTATCGCTTCTACATTAGCAGTATCTTTAGGAATTGCAGGTTACGGTTTATCAGGACATGAAGCACA
CGCTTCAGAAACTACAAACGTTGATAAAGCACACTTAGTAGATTTAGCACAACATAATCCTGAAGAATTAAATGCTAAAC
CAGTTCAAGCTGGTGCTTACGATATTCATTTCGTAGACAATGGATACCAATACAACTTCACTTCAAATGGTTCTGAATGG
TCATGGAGCTACGCTGTAGCTGGTTCAGATGCTGATTACACAGAATCATCATCAAACCAAGAAGTAAGTGCAAATACACA
ATCTAGTAACACAAATGTACAAGCTGTTTCAGCTCCAACTTCTTCAGAAAGTCGTAGCTACAGCACATCAACTACTTCAT
ACTCAGCACCAAGCCATAACTACAGCTCTCACAGTAGTTCAGTAAGATTATCAAATGGTAATACTGCTGGTTCTGTAGGT
TCATATGCTGCTGCTCAAATGGCTGCACGTACTGGTGTATCTGCTTCAACATGGGAACACATCATTGCTAGAGAATCAAA
TGGTCAATTACATGCACGTAATGCTTCAGGTGCTGCTGGATTATTCCAAACTATGCCAGGTTGGGGTTCAACTGGTTCAG
TAAATGATCAAATCAATGCCGCTTATAAAGCATATAAAGCACAAGGTTTATCTGCTTGGGGTATGTAA

Figure 2 cont.

SEQ ID NO:45 polynucleotide sequence
GTGAATTATCGTGATAAAATTCAAAAGTTTAGTATTCGTAAATATACAGTTGGTACATTTTCAACTGTCATTGCGACATT
GGTATTTTTAGGATTCAATACATCACAAGCACATGCTGCTGAAACAAATCAACCAGCAAGCGTGGTTAAACAGAAACAAC
AAAGTAATAATGAACAGACTGAGAATCGAGAATCTCAAGTACAAAATTCTCAAAATTCACAAAATAGTCAATCATTATCC
GCTACTCATGAAAATGAGCAACCAAATAATAGTCAAGCTAATTTAGTAAATCAAAAGTAGCGCAATCATCTACTACTAA
TGATGAACAACCAGCATCTCAAAATGTAAATACAAAGAAAGATTCGGCAACGGCTGCGACAACACAACCAGATAAAGAAG
AAAGTAAGCATAAACAAAACGAAAGTCAATCTGCTAATAAAAATGGAAACGACAATAGAGCGGCTCATGTAGAAAATCAT
GAAGCAAATGTAGTAACAGCTTCAGATTCATCTGATAATGGTAACGTACAACATGACCGAAATGAATTACAAGCATTTTT
TGATGCAAATTATCATGATTATCGCTTTATTGACCGTGAAAATGCAGATTCTGGCACATTTAACTATGTAAAAGGCATTT
TTGACAAGATTAATACTTTATTAGGCAGTAATGATCCAATTAACAATAAAGACTTGCAACTTGCATACAAAGAATTGGAA
CAAGCTGTTGCTTTAATTCGTACAATGCCTCAACGTCAACAAACTAGCCGTCGATCAAACAGAATTCAAACGCGTTCTGT
TGAGTCTAGAGCTGCAGAGCCTAGATCAGTATCAGACTATCAAAATGCAAATTCATCATATTATGTTGAAAATGCTAATG
ATGGTTCAGGATATCCTGTAGGTACATATATCAATGCTTCTAGTAAAGGGGCGCCATATAATTTACCAACTACACCATGG
AATACATTGAAGGCCTCTGACTCAAAGGAAATTGCTCTTATGACAGCGAAACAAACTGGAGATGGCTACCAATGGGTTAT
TAAGTTTAATAAAGGACATGCTCCACATCAAAATATGATTTTCTGGTTTGCATTACCAGCAGACCAAGTGCCAGTAGGAA
GAACTGACTTTGTAACAGTTAATTCAGATGGAACAAATGTACAATGGAGTCATGGAGCAGGAGCAGGTGCAAATAAACCA
CTTCAACAAATGTGGGAATATGGAGTAAATGATCCTGATCGTTCACATGACTTTAAAATAAGAAATAGAAGTGGCCAAGT
AATATATAGCTGGCCAACTGTCCATGTTTATTCTTTAGAAGATTTATCTAGAGCGAGTGATTATTTTAGTGAAGCTGGAG
CGACACCTGCTACTAAAGCATTTGGTAGACAAAATTTTGAATATATTAATGGTCAAAAACCTGCTGAATCACCGGGTGTT
CCTAAAGTTTATACTTTCATCGGTCAAGGTGATGCAAGTTATCAAATTTCATTTAAAACACAAGGTCCAACTGTTAATAA
ATTGTATTATGCAGCAGGTGGGCGTGCTTTAGAGTACAATCAATTATTTATGTACAGTCAACTATACGTCGAATCAACGC
AAGACCATCAACAACGTCTTAATGGTTTAAGACAAGTGGTTAATCGTACATATCGCATAGGTACAACTAAACGTGTAGAA
GTGAGTCAAGGAAATGTACAAACGAAAAAGGTATTAGAAAGTACAAACCTAAATATAGATGATTTTGTTGATGATCCTTT
AAGTTATGTTAAGACGCCGAGTAATAAAGTGTTAGGTTTTTACCCAACTAATGCAAATACTAACGCTTTTAGACCGGGGG
GCGTTCAAGAATTAAATGAATATCAATTAAGTCAATTATTTACTGATCAAAAATTACAAGAAGCAGCAAGAACTAGAAAC
CCAATAAGATTAATGATTGGTTTCGACTATCCTGATGGTTATGGTAATAGTGAAACTTTAGTTCCTGTTAACTTAACGGT
ATTACCTGAAATCCAACATAATATTAAATTCTTTAAAAATGACGATACTCAAAATATTGCTGAAAAACCATTTTCAAAAC
AAGCTGGGCATCCAGTTTTCTATGTATATGCAGGTAACCAAGGGAATGCTTCCGTGAATTTAGGTGGTAGCGTAACATCT
ATTCAACCATTACGTATTAATTTAACAAGTAATGAGAATTTTACAGATAAAGATTGGCAAATTACAGGTATTCCGCGTAC
ATTACACATTGAAAACTCGACAAATAGAACTAATAATGCTAGAGAACGTAACATTGAACTTGTTGGTAATTTATTACCAG
GGGATTACTTTGGTACGATACGTTTTGGACGTAAAGAACAATTATTTGAAATTCGTGTTAAACCACATACACCAACAATT
ACAACGACAGCTGAGCAATTAAGAGGTACAGCATTACAAAAAGTGCCTGTTAATATTTCGGGAATACCGTTGGATCCATC
GGCATTGGTTTATTTAGTTGCACCAACAAATCAAACTACGAATGGTGGTAGTGAGGCAGATCAAATACCATCTGGTTATA
CGATACTTGCGACTGGTACACCTGATGGGGTGCATAATACAATTACTATACGACCGCAAGATTATGTTGTATTCATACCA
CCTGTAGGTAAACAAATTAGAGCAGTAGTTTATTATAATAAAGTAGTTGCATCTAATATGAGTAATGCTGTTACTATTTT
GCCAGATGACATTCCACCAACAATCAATAATCCTGTTGGAATAAATGCCAAATACTATCGAGGCGACGAAGTCAACTTTA
CAATGGGAGTCTCTGATAGACATTCTGGTATAAAAAATACAACTATTACTACTTTGCCAAGTGGTTGGACATCAAATTTA
ACTAAATCCGACAACAAAAACGGCTCATTAGCTATTACAGGTAGAGTCTCTATGAATCAGGCATTTAACAGTGATATTAC
ATTTAAAGTATCAGCGACAGACAATGTCAATAATACGACAAATGATAGTCAATCTAAACATGTGTCAATTCATGTAGGTA
AAATTAGTGAAGATGCTCATCCGATTGTATTAGGAAATACTGAGAAAGTTGTAGTAGTCAATCCGACTGCTGTATCTAAT
GATGAAAAGCAAAGCATAATTACTGCCTTTATGAATAAAAACCAAAATATAAGAGGATATTTAGCATCAACTGATCCAGT
AACTGTCGATAATAATGGTAACGTCACATTACATTACCGTGATGGCTCATCAACAACGCTTGATGCTACAAATGTGATGA
CATACGAACCAGTTGTGAAATCTGAATTCAAACTGCCAATGCTGCTAAAACAGCAACGGTAACGATTGCTAAAGGACAA
TCATTTAATATTGGTGATATTAAACAATATTTTACTTTAAGTAATGGACAAGCTATTCCAAATGGCACATTTACAAATAT
TACATCTGATAGAACTATTCCAACTGCACAAGAAGTTAGTCAAATGAATGCAGGTACGCAGTTATATCATATAGTTGCTT
CAAATGCATATCATAAAGACACTGAAGATTTCTATATTAGTTTAAAAATCGTTGATGTGAAACAACCTGAAGGCGATCAA
CGTGTCTATCGTACGTCAACATATGATTTAACCACTGATGAAATCTCAAAAGTAAAACAAGCTTTTATTAATGCAAATAG
AGATGTAATTACGCTTGCCGAAGGTGATATTTCAGTTACAAATACACCTAATGGTGCTAATGTAAGTACTATTACAGTAA
ATATTAATAAAGGTCGATTAACGAAATCATTCGCGTCTAACCTAGCTAATATGAATTTCTTGCGTTGGGTTAATTTCCCA
CAAGATTATACAGTGACATGGACGAATGCAAAAATTGCAAACAGACCAACAGATGGTGGTTTATCATGGTCCGATGACCA
TAAATCTTTAATTTATCGTTATGATGCTACATTAGGCACACAAATTACAACTAATGATATTTTAACGATGCTAAAGCGA
CTACTACAGTGCCTGGATTGCGTGAATAATATTACTGGTAATGAAAAAGCACAAGCAGAAGCAGGTGGAAGACCAAACTAT
AGAACAACTGGTTATTCACAATCAAATGCGACAACTGATGGTCAACGTCAATTTACGTTGAATGGTCAAGTGATTCAAAT
ATTAGACATCATCAACCCTTCAAACGGTTATGGTGGGCAACCTGTTACAAATTCAAATACTCGTGCAAACCATAGTAACT
CAACTGTTGTTAACGTAAACGAACCGGCAGCTAATGGTGCTGGCGCATTTACAATTGACCACGTTGTAAAAAGTAATTCT
ACACATAATGCAAGTGATGCAGTTTATAAAGCGCAGTTATACTTAACGCCATATGGTCCAAAACAATATGTTGAACATTT
AAATCAAAATACAGGAAATACTACTGACGCTATTAACATTTATTTTGTACCAAGTGACTTAGTGAATCCAACAATTTCAG

Figure 2 cont.

```
TAGGTAATTACACTAATCATCAAGTGTTCTCAGGTGAAACATTTACAAATACGATTACAGCGAATGATAACTTTGGTGTG
CAATCGGTAACTGTACCAAATACATCACAAATTACAGGTACTGTTGATAATAACCATCAACATGTTTCTGCAACGGCACC
AAATGTGACATCAGCAACTAGTAAGACAATCAATTTATTAGCAACTGATACAAGTGGTAATACAGCTACAACTTCATTCA
ATGTAACAGTGAAACCTTTGCGTGATAAATATCGAGTTGGTACTTCATCAACGGCTGCTAATCCTGTTAGAATTGCCAAT
ATTTCGAATAATGCGACAGTATCACAAGCTGATCAAACGACAATTATTAATTCGTTAACGTTTACAAGTAATGCACCAAA
TAGAAACTATGCAACAGCAAGCGCAAATGAAATCACTAGTAAAACAGTTAGTAATGTCAGTCGTACTGGAAATAATGCCA
ATGTCACAGTAACTGTTACTCATCAAGATGGAACAACATCAACAGTGACTGTACCTGTAAAGCATGTCATTCCAGAAATC
GTTGCACATTCGCATTACACTGTACAAGGCCAAGACTTCCCAGCAGGTAATGGTTCTAGTGCAGCAGATTACTTTAAGTT
ATCTAATGGTAGTGCCATTCCAGATGCAACGATTACATGGGTAAGTGGACAAGCGCCAAATAAAGATAATACACGTATTG
GTGAAGATATAACAGTAACTGCACATATCTTAATTGATGGCGAAACAACGCCGATTACGAAAACAGCAACATATAAAGTA
GTAAGAACTGTACCGAAACATGTCTTTGAAACAGCCAGAGGTGTTTTATACCCAGGTGTTTCAGATATGTATGATGCGAA
ACAATATGTTAAGCCAGTAAATAATTCTTGGTCGACAAATGCGCAACATATGAATTTTCAATTTGTTGGAACATATGGTC
CTAACAAAGATGTTGTAGGTATATCAACGCGTCTTATTAGAGTGACTTATGATAATAGACAAACTGAAGATTTAACTATT
TTATCTAAAGTTAAACCTGACCCACCAAGAATTGACGCAAACTCTGTGACATATAAAGCAGGTCTTACAAACCAAGAAAT
TAAAGTTAATAACGTATTAAATAACTCGTCAGTAAAATTATTTAAAGCAGATAATACACCATTAAATGTCACAAATATTA
CTCATGGTAGTGGTTTTAGTTCGGTTGTGACAGTAAGTGACGCGTTACCAAATGGCGGAATTAAAGCAAAATCTTCAATT
TCAATGAACAATGTGACGTATACGACGCAAGACGAACATGGTCAAGTTGTTACAGTAACAAGAAATGAATCTGTTGATTC
AAATGATAGTGCTTCTGTTACAGTAACACCACAATTACAAGCAACTACTGAAGGCGCTGTATTTATTAAAGGTGGCGACG
GTTTTGATTTCGGTCATGTAGAACGATTTATTCAAAATCCGCCACATGGGGCAACGGTCGCATGGCATGATAGTCCAGAT
ACATGGAAGAATACAGTCGGCAACACACATAAAACTGCGGTTGTAACATTACCTAGTGGTCAAGGTACGCGTAATGTTGA
AGTTCCAGTCAAAGTTTATCCAGTTGCTAATGCTAAGGCGCCATCACGTGATGTGAAAGGTCAAAATTTGACACATGGTA
CAAACGCTATTGATTACATTACATTTGATCCAAATACTAATACGAATGGTATTACAGCAGCATGGGCAAATAGACAACAA
CCAAATAACCAGCAAGCAGGCGTTCAACATTTAAATGTCGATGTCACATATCCAGGTATTTCAGCTGCTAAACGAGTTCC
TGTAACTGTGAACGTATATCAATTTGAATTCCCTCAAACTACTTATACAACAACAGTTGGTGGCACTTTAGCAAGTGGTA
CGCAAGCATCAGGATATGCACATATGCAAAACGCTTCAGGTTTACCAACAGATGGATTTACGTATAAATGGAATCGTGAT
ACTACGGGTACAAACGATGCAAACTGGGCAGCAATGAATAAACCAAATACTGCACAAGTCGTTAATGCAAAATATGATGT
CATCTATAATGGACATACATTTGCAACATCTTTACCAGCGAAATTTGTAGTAAAAGATGTTCAACCAGCGAAACCAACTG
TCACTGAAACAGCGGCAGGAGCGATTACAATTGCACCTGGTGCGAACCAAACAGTCAATACTCATGCTGGTAATGTTACG
ACATATGCTGACAAATTAGTTATTAAACGTAATGGAAATGTTGTAACGACATTTACACGTCGTAATAATACGAGCCCATG
GGTGAAAGAAGCATCAGCAGATAATGTAACAGGTATTGTTGGAACTAATAATGGTATTACTGTGGCAGCAGGTACTTTCA
ATCCTGCTGATACAATTCAAGTTGTTGCAACACAAGGTAGTGCGAAACAATCAGTGACGAGCAACGTAGTGATGATTTC
ACAGTTGTCGCACCACAACCGAACCAAGCGACTACGAAAATTTGGCAAAATGGTCATATTGATATCACGCCTAATAATCC
ATCAGGACATTTAATTAATCCAACACAAGCAATGGATATTGCTTACACTGAAAAAGTGGGTAATGGTGCAGAACATAGTA
AGACAATTAATGTTGTTCGTGGTCAAAATAATCAATGGACAATTGCGAATAAGCCTGACTATGTAACGTTAGATGCACAA
ACTGGTAAAGTGACGTTCAATGCCAATACTATAAAACCAAATTCATCAATCACAATTACTCCGAAAGCAGGTACAGGTCA
CTCAGTAAGTAGTAATCCAAGTACATTAACTGCACCGGCAGCTCATACTGTCAACACAACTGAAATTGTGAAAGATTATG
GTTCAAATGTAACAGCAGCTGAAATTAACAATGCAGTTCAAGTTGCTAATAAACGTACTGCAACGATTAAAAATGGCACA
GCAATGCCTACTAATTTAGCTGGTGGTAGCACAACGACGATTCCTGTGACAGTAACTTACAATGATGGTAGTACTGAAGA
AGTACAAGAGTCCATTTTCACAAAAGCGGATAAACGTGAGTTAATCACAGCTAAAAATCATTTAGATGATCCAGTAAGCA
CTGAAGGTAAAAAGCCAGGTACAATTACGCAGTACAATAATGCAATGCATAATGCGCAACAACAAATCAATACCGCGAAA
ACAGAAGCACAACAAGTGATTAATAATGAGCGTGCAACACCACAACAAGTTTCTGACGCACTAACTAAAGTTCGTGCAGC
ACAAACTAAGATTGATCAAGCTAAAGCATTACTTCAAAATAAAGAAGATAATAGCCAATTAGTAACGTCTAAAAATAACT
TACAAAGTTCTGTGAACCAAGTACCATCAACTGCTGGTATGACGCAACAAAGTATTGATAACTATAATGCGAAGAAGCGT
GAAGCAGAAACTGAAATAACTGCAGCTCAACGTGTTATTGACAATGGCGATGCAACTGCACAACAAATTTCAGATGAAAA
ACATCGTGTCGATAACGCATTAACAGCATTAAACCAAGCGAAACATGATTTAACTGCAGATACACATGCCTTAGAGCAAG
CAGTGCAACAATTGAATCGCACAGGTACAACGACTGGTAAGAAGCCGGCAAGTATTACTGCTTACAATAATTCGATTCGT
GCACTTCAAAGTGACTTAACAAGTGCTAAAAATAGCGCTAATGCTATCATTCAGAAGCCAATAAGAACAGTGCAAGAGGT
ACAATCTGCGTTAACAAATGTAAATCGTGTCAATGAGCGATTAACGCAAGCAATTAATCAATTAGTACCTTTAGCTGATA
ATAGTGCTTTAAGAACTGCTAAGACGAAACTTGATGAAGAAATCAATAAATCAGTAACTACTGATGGTATGACACAATCA
TCAATCCAAGCATATGAAAATGCTAAACGTGCAGGTCAAACAGAAACAACAAATGCACAAAATGTTATTAACAATGGTGA
CGCGACAGACCAACAAATTGCCGCAGAAAAAACAAAAGTAGAAGAAAATATAATAGCTTAAAACAAGCAATTGCTGGAT
TAACACCAGACTTGGCACCATTACAAACTGCAAAAACTCAGTTGCAAAATGATATTGATCAGCCAACGAGTACGACTGGT
ATGACAAGCGCATCTGTTGCTGCATTTAATGACAAACTTTCAGCAGCTAGAACTAAAATTCAAGAAATTGATCGCGTACT
AGCATCTCATCCAGATGTAGCAACGATTCGTCAAAACGTGACAGCAGCGAATGCTGCTAAAACAGCACTTGATCAAGCGC
GCAATGGCTTAACAGTCGATAAAGCACCTTTAGAAAATGCGAAAAATCAACTCAACATAGTATTGATACGCAAACAAGT
ACAACTGGTATGACAAGACTCTATAAATGCATACAATGCGAAGTTAACAGCTGCACGTAATAAGGTTCAACAAATCAA
TCAAGTATTAGCAGGTTCACCTACTGTAGATCAAATTAATACAAATACGTCTGCAGCAAATCAAGCGAAATCTGATTTAG
ATCATGCACGTCAAGCGTTAACACCAGATAAAGCGCCGCTTCAAAATGCGAAAACGCAATTAGAACAAAGCATTAATCAA
CCAACAGATACAACAGGTATGACAACCGCTTCGTTAAATGCATACAACCAAAAATTACAAGCAGCACGTCAAAAGTTAAC
```

Figure 2 cont.

TGAAATTAATCAAGTGTTGAATGGCAACCCAACTGTCCAAAATATCAATGATAAAGTGGCAGAGGCAAACCAAGCTAAGG
ATCAATTAAATACAGCACGTCAAGGTTTAACATTAGATAGACAGCCAGCGTTAACAACATTACATGGTGCATCTAACTTA
AACCAAGCACAACAAAATAATTTCACGCAACAAATTAATGCTGCTCAAAATCATGCTGCGCTTGAAACAATTAAGTCTAA
CATTACGGCTTTAAATACTGCGATGACGAAATTAAAAGACAGTGTTGCGGATAATAATACAATTAAATCAGGTCAAAATT
ACACTGACGCAACACCAGCTAATAAACAAGCCTATGATAATGCAGTTAATGCGGCTAAAGGTGTCATTGGAGAAACGACT
AATCCAACGATGGATGTTAACACAGTGAACCAAAAAGCAGCATCTGTTAAATCGACGAAAGATGCTTTAGATGGTCAACA
AAACTTACAACGTGCGAAAACAGAAGCAACAAATGCGATTACGCATGCAAGTGATTTAAACCAAGCACAAAAGAATGCAT
TAACACAACAAGTGAATAGTGCACAAAACGTGCAAGCAGTAAATGATATTAAACAAACGACTCAAAGCTTAAATACTGCT
ATGACAGGTTTAAAACGTGGCGTTGCTAATCATAACCAAGTCGTACAAAGTGATAATTATGTCAACGCAGATACTAATAA
GAAAAATGATTACAACAATGCATACAACCATGCGAATGACATTATTAATGGTAATGCACAACATCCAGTTATAACACCAA
GTGATGTTAACAATGCTTTATCAAATGTCACAAGTAAAGAACATGCATTGAATGGTGAAGCTAAGTTAAATGCTGCGAAA
CAAGAAGCGAATACTGCATTAGGTCATTTAAACAATTTAAATAATGTACAACGTCAAAACTTACAATCGCAAATTAATGG
TGCGCATCAAATTGATGCAGTTAATACAATTAAGCAAAATGCAACAAACTTGAATAGTGCAATGGGTAACTTAAGACAAG
CTGTTGCAGATAAAGATCAAGTGAAACGTACAGAAGATTATGCGGATGCAGATACAGCTAAACAAAATGCATATAACAGT
GCAGTTTCAAGTGCTGAAACAATTATTAATCAAACAGCTAATCCGACAATGTCTGTTGATGATGTTAATCGTGCAACTTC
AGCTGTTACTACTAATAAAAATGCATTAAATGGTGATGAAAAATTAGTACAATCTAAAACAGATGCTGCAAGAGCAATTG
ATGCATTACCACATTTAAATAATGCACAAAAAGCAGATGTTAAATCTAAAATTAATGCTGCATCAAATATTGCTGGTGTA
AATACCGTTAAACAACAAGGTACAGATTTAAATACAGCGATGGGTAACTTGCAGGGTGCAATCAATGATGAACAAACGAC
GCTTAATAGTCAAAATTATCAAGATGCGACACCTAGTAAGAAAACAGCATACACAAATGCGGTGCAAGCTGCGAAAGATA
TTTTAAATAAATCAAATGGTCAAAATAAAACGAAAGATCAAGTTACTGAAGCGATGAATCAAGTGAATTCGGCTAAAAAT
AACTTAGATGGTACGCGTTTATTAGATCAAGCGAAGCAAACAGCGAAACAGCAGTTAAATAATATGACGCATTTAACAAC
TGCACAAAAAACGAATTTAACAAATCAAATTAATAGTGGTACTACTGTTGCTGGTGTTCATACGGTTCAATCAAATGCCA
ACACATTAGATCAAGCGATGAATACGTTAAGACAAAGTATTGCTAACAATGATGCGACTAAAGCAAGTGAAGATTACGTA
GATGCTAATAATGATAAGCAAACAGCATATAACAACGCGGTAGCTGCTGCTGAAACGATTATTAATGCGAATAGTAATCC
AGAAATGAATCCAAGTACGATTACACAAAAAGCAGAGCAAGTGAATAGTTCTAAAACGGCACTTAACGGTGATGAAAACT
TAGCTACGGCAAAACAAATGCGAAAACGTACTTAAACACATTAACGAGTATTACAGATGCTCAAAAGAACAATTTGATT
AGTCAAATTAGTAGTGCGACAAGAGTGAGTGGTGTTGATACTGTAAAACAAAATGCACAACATTTAGATCAAGCTATGGC
TAACTTACAAAATGGTATTAACAACGAATCTCAAGTGAAATCATCTGAGAAATATCGTGATGCTGATACAAATAAACAAC
AAGAGTATGATAATGCTATTACTGCAGCGAAAGCGATTTTAAATAAATCGACAGGTCCAAACACTGCGCAAAATGCAGTT
GAAGCAGCATTGCAACGTGTTAATACTGCGAAAGATGCATTGAATGGTGATGCAAAATTAATTGCAGCTCAAAACGCAGC
GAAACAACATTTAGGTACTTTAACGCATATCACTACAGCACAACGCAATGATTTAACAAATCAAATTTCA

SEQ ID NO:46 polynucleotide sequence
ATGGGTAACTTACAACGGCTATCAACGATAAGTCAGGAACATTAGCGAGCCAAAACTTCTTGGATGCTGATGAGCAAAA
ACGTAATGCTTACAATCAAGCTATATCAGCTGCCGAAACCATTTTAAATAAACAAACTGGACCGAATACAGCGAAAACAG
CGGTTGAACAAGCACTTAATAATGTTAATAGTGCGAAACATGCATTAAATGGTACGCAAAACTTAAATAATGCGAAACAA
GCAGCGATTACAGCAATTAATGGCGCATCTGATTTAAATCAAAAACAAAAGATGCATTAAAAGCACAAGCTAATGGTGC
TCAACGCGTATCTAATGCAAATGATGTACAACGTAATGCGACTGAACTGAACACGGCAATGGGTCAATTACAACATGCCA
TCGCAGATAAGACGAATACGTTAGCAAGCAGTAAATATGTCAACGCCGATAGCACTAAACAAATGCTTACACAACTAAA
GTTACCAATGCTGAACATATTATTAGCGGTACGCCAACGGTTGTTACAACACCTTCAGAAGTAACAGCTGCAGCTAATCA
AGTAAACAGCGCGAAACAAGAATTAAATGGTGACGAAAGATTACGTGTTGCAAAACAAAACGCCAATACTGCTATTGATG
CATTAACGCAATTAAATACTCCTCAAAAAGCTAAATTAAAAGAACAAGTGGGACAAGCCAATAGATTAGAAGACGTACAA
TCTGTTCAAACAAATGGACAATCATTGAACAATGCAATGAAAGGCTTAAGAGATAGTATTGCTAACGAAACAACAGTCAA
AGCAAGTCAAAACTATACAGACGCAAGTCCGAATAACCAATCAACATATAATAGCGCTGTGTCAAATGCGAAAGGTATCA
TTAATCAAACTAACAATCCAACTATGGATACTAGTGCGATTACCCAAGCTACAACACAAGTGAATAATGCTAAAAATGGT
TTAAACGGTGCTGAAAACTTAAGAAATGCACAAAACACTGCTAAGCAAAACTTAAATACGTTATCACACTTAACAAATAA
CCAAAAATCTGCAATCTCATCACAAATTGATCGTGCAGGTCATGTGAGTGAGGTAACAGCTGCTAAAAATGCAGCAACTG
AGTTAAACGCGCAAATGGGCAACTTGGAACAAGCTATCCATGATCAAAACACAGTTAAACAAGGTGTTAACTTCACTGAT
GCAGATAAAGCTAAACGTGATGCTTATACAAATGCGGTAAGCAGAGCAGAAACAATTCTGAATAAAACGCAAGGTGCAAA
TACGTCTAAACAAGATGTTGAAGCGGCTATTCAAATGTTACAAGTGCTAAAAATGCATTGAATGGTGATCAAAACGTTA
CAAATGCGAAGAATGCAGCTAAAAATGCATTAAATAACTTAACGTCAATTAATAATGCACAAAAACGTGACTTAACAACT
AAAATTGATCAAGCAACAACAGTAGCTGGTGTTGAAGCGGTATCTAATACAGGTACACAATTGAATACAGCGATGGCTAA
CTTGCAAAATGGTATTAATGATAAAGCGAATACTTTAGCGAGCGAAAACTATCATGATGCTGATTCAGATAAGAAAACTG
CTTATACTCAAGCCGTTACGAACGCAGAAAATATTTTAAATAAAAATAGTGGATCAAATTTAGATAAAGCTGCCGTTGAA
AACGCGTTGTCACAAGTGACAAATGCGAAAGGTGCCCTAAATGGTAACCATAATTTAGAGCAAGCTAAATCAAATGCAAA
CACTACTATAAACGGCCTTCAACATTTAACAACAGCACAAAAAGATAAATTGAAACAACAAGTGCAACAAGCACAAAATG
TTGCAGGTGTAGATACTGTTAAATCAAGTGCCAACACATTAAATGGTGCTATGGGTACGTTAAGAAATAGCATACAAGAT
AACACAGCTACGAAAAATGGCCAAAACTATCTTGATGCTACAGAACGTAACAAAACAAACTATAACAATGCTGTTGATAG

Figure 2 cont.

```
TGCTAATGGTGTCATTAATGCAACAAGCAATCCAAATATGGATGCTAATGCAATTAACCAAATCGCTACACAAGTGACAT
CAACGAAAAATGCATTAGATGGTACACATAATTTAACGCAAGCGAAACAAACAGCAACAAATGCCATCGATGGTGCTACT
AACTTAAATAAAGCGCAAAAAGATGCGTTAAAAGCACAAGTTACAAGTGCGCAACGTGTTGCAAATGTAACAAGTATCCA
ACAAACTGCAAATGAACTTAATACAGCTATGGGTCAATTACAACATGGTATTGATGATGAAAATGCAACAAAACAAACTC
AAAAATATCGTGACGCTGAACAAAGTAAGAAAACTGCTTATGATCAAGCTGTAGCTGCTGCGAAAGCAATTTTAAATAAA
CAAACAGGTTCCAATTCAGATAAAGCAGCAGTTGACCGTGCATTACAACAAGTAACAAGTACGAAAGATGCATTGAATGG
GGATGCTAAACTGGCAGAAGCGAAAGCGGCAGCTAGACAAAACTTAGGTACTTTAAACCATATTACGAATGCACAACGTA
CTGCGTTAGAAGGTCAAATCAATCAAGCGACGACTGTTGATGGCGTTAATACTGTAAAAACAAATGCCAATACATTAGAC
GGCGCTATGAATAGCTTACAAGGTGCAATCAATGATAAAGATGCGACATTAAGAAATCAAAATTATCTTGATGCAGATGA
ATCAAAACGAAATGCATATACGCAAGCTGTCACAGCGGCTGAAGGCATTTTAAATAAACAAACAGGTGGTAACACATCTA
AAGCAGACGTTGATAATGCATTAAATGCAGTTACAAGAGCGAAAGCGGCTTTAAATGGTGCTGAAAACTTAAGAAATGCG
AAAACTTCAGCAACAAATACGATTAATGGTTTACCTAACTTAACACAATTACAAAAAGACAACTTGAAGCATCAAGTTGA
ACAAGCGCAAAATGTAGTTGGTGTAAATGGTGTTAAAGATAAAGGTAATACATTAAATACTGCCATGGGTGCATTACGTA
CAAGTATCCAAAATGATAATACGACGAAAACAAGTCAAAATTATCTTGATGCATCTGATAGCAACAAAAATAATTACAAT
ACTGCTGTAAATAATGCAAATGGTGTTATTAATGCAACGACAATCCAAATATGGATGCTAATGCGATTAATGACATGGC
AAATCAAGTCAATACAACAAAAGCAGCGTTAAATGGTGCACAAAACTTAGCTCAAGCTAAAACAAATGCGACGAACACAA
TTAACAACGCGCAAGACTTAAACCAAAAACAAAAAGATGCATTAAAAACACAAGTTAACAATGCACAACGTGTATCTGAT
GCAAATAACGTTCAACATACAGCTACTGAATTGAACGGTGCGATGACAGCACTTAAAGCAGCTATTGCGGATAAAGAAAG
AACAAAAGCAAGCGGTAATTATGTCAATGCTGATCAAGAAAAACGTCAAGCGTATGATTCAAAAGTGACTAACGCTGAAA
ATATCATTAATGGTACACCAAATGCGACATTAACAGTCAATGACGTAAATAGTGCGGCATCACAAGTCAATGCGGCTAAA
ACAGCATTAAATGGTGATAACAACTTACGTGTAGCGAAAGAGCATGCTAACAATACAATTGACGGCTTAGCACAATTGAA
TAATGTACAAAAAGCAAAATTAAAAGAACAAGTTCAAAGTGCAACTACATTAGATGGTGTTCAAACTGTTAAAAATAGTT
CTCAAACGTTGAATACAGCGATGAAAGGCTTAAGAGATAGTATTGCGAATGAAGCAACGATTAAAGCAGGTCAAAACTAC
ACTGACGCAAGTCCAAATAATCGTAACGAGTACGACAGCGCAGTTACTGCAGCAAAAGCAATCATTAATCAAACATCGAA
CCCAACGATGGAACCAAATACTATTACGCAAGCAACATCACAAGTGACAACTAAAGAACATGCATTAAATGGTGCGCAAA
ACTTAGCTCAAGCTAAGACAACAGCGAAAAACAACTTGAATAACTTAACATCAATTAACAATGCACAAAAAGATGCGTTA
ACGCGTAACATTGATGGTGCAACTACAGTAGCTGGTGTAAATCAAGAAACTGCAAAAGCAACAGAATTAAATAACGCAAT
GCACAGTTTACAAAATGGTATCAATGATGAGACACAAACAAAACAAACTCAGAAATACCTAGATGCTGAGCCAAGTAAGA
AATCAGCTTATGATCAAGCAGTAAATGCAGCAAAAGCAATTTTAACAAAAGCTAGTGGTCAAAATGTAGACAAAGCAGCA
GTTGAACAAGCATTACAAAATGTGAACAGTACGAAGACGGCGTTGAACGGTGATGCGAAATTAAATGAAGCTAAAGCTGC
TGCGAAACAAACGTTAGGTACATTAACACACATTAATAATGCACAACGTAATGCGTTAGATAATGAAATTACACAAGCAA
CAAATGTTGAAGGTGTTAATACAGTTAAAGCCAACGCAATTAGATGGTGCTATGGGTCAATTAGAAACATCAATT
CGTGATAAAGACACGACGTTACAAAGTCAAAATTATCAAGATGCTGATGATGCTAAACGAACGGCTTATTCTCAAGCAGT
AAATGCAGCAGCAACTATTTTAAATAAAACAGCTGGAGGAAATACACCTAAAGCAGATGTCGAAAGAGCAATGCAAGCTG
TTACACAAGCCAATACTGCATTAAACGGTATTCAAAACTTAGAACGTGCGAAACAGGCTGCGAACACAGCGATTACAAAT
GCTTCGGACTTAAATACAAAACAAAAAGAAGCATTGAAAGCACAAGTAACAAGTGCAGGACGCGTATCTGCAGCAAATGG
TGTTGAACATACTGCGACTGAATTAAATACTGCGATGACAGCTTTAAAACGTGCCATTGCTGATAAAGCTGACACAAAAG
CTAGTGGTAATTATGTCAATGCTGATGCGAATAAACGCCAAGCATATGATGAAAAGTGACAGCTGCAGAACATATCGTT
AGTGGTACACCAACACCAACGTTAACACCATCAGATGTTACAAATGCAGCAACGCAAGTAACGAATGCGAAGACGCAGTT
AAACGGTAATCATAATTTAGAAGTAGCGAAACAAAATGCTAACACAGCAATTGATGGTTTAACTTCTTTAAATGGTCCGC
AAAAAGCAAAACTTAAAGAACAAGTGGGTCAAGCGACGACGTTGCCAAATGTTCAAACTGTTCGTGATAATGCACAAACA
TTAAACACTGCAATGAAAGGTCTACGAGATAGCATTGCGAATGAAGCAACGATTAAAGCAGGTCAAAACTACACAGATGC
AAGTCAAAACAAACAAAATGACTACAACAATGCAGTCACTGCAGCAAAAGCAATCATTGGTCAAACAACTAGTCCATCAA
TGATTGCGCAAGAAATTAATCAAGCGAAAGACCAAGTGACAGCTAAACAACAAGCGTTAAACGGTCAAGAAAACTTAAGA
ACTGCGCAAACAAATGCGAAGCAACATTTGAATGGCTTAAGTGACTTAACTAATGCACAAAAAGATGCAGCGAAACGCCA
AATCGAAGGTGCAACGCATGTTAATGAAGTAACACAAGCGCAAAATAATGCGGACGCATTAAATACAGCTATGACGAACT
TGAAAAATGGTATTCAAGATCAAAATACGATTAAGCAAGGTGTTAACTTCACTGATGCAGATGAAGCGAAACGTAATGCA
TATACAAATGCAGTGACGCAAGCTGAACAAATTTTAAATAAAGCACAAGGTCCAAATACTGCAAAAGACGGTGTCGAAAC
TGCGTTACAAAATGTACAACGTGCTAAAAACGAATTGAACGGTAATCAAAATGTTGCGAACGCTAAGACAACTGCGAAAA
ATGCATTGAATAACCTTACATCAATTAATAATGCACAAAAAGCAGCATTGAAATCACAAATTGAAGGTGCGACAACAGTT
GCAGGTGTAAATCAAGTGTCTACAATGGCATCTGAATTAAATACTGCAATGAGCAACTTACAACGTGGTATTAATGACGA
AGCAGCTACAAAAGCAGCTCAGAAATATACTGAAGCAGATAGAGATAAACAAACTGCATACAATGATGCTGTAACAGCAG
CTAAAACGTTATTAGATAAAACAGCTGGTTCAAATGACAATAAAGTAGCCGTTGAACAAGCATTACAACGTGTGAATACT
GCTAAAACAGCCATTAAATGGTGACGCGCGATTAAATGAACGCAAGAACACAGCTAAACAACAATTAGCGACAATGTCACA
TTTAACTAATGCTCAAAAAGCAAACTTAACAGAACAAATTGAACGTGGTACAACTGTTGCTGGTTCAAGGCATCCAAG
CAAATGCTGGTACTTTAAATCAAGCAATGAATCAATTAAGACAAAGTATTGCTTCTAAAGATGCGACTAAATCAAGCGAA
GATTATCAAGACGCGAATGCAGATTTACAAAATGCATACAATGATGCGGTAACTAATGCTGAAGGTATTATTAGTGCAAC
GAATAACCCTGAAATGAATCCTGATACAATTAACCAAAAAGCGAGCCAAGTGAACAGTGCGAAGTCTGCATTGAACGGTG
ATGAAAAATTAGCAGCAGTAAAACAAACTGCGAAATCAGATATCGGTCGTTTGACAGACTTGAACAATGCACAACGAACT
```

Figure 2 cont.

```
GCGGCAAATGCTGAAGTGGATCAAGCACCAAATCTTGCAGCTGTCACAGCGGCTAAAAATAAAGCAACATCGTTAAACAC
AGCGATGGGTAATTTGAAACATGCACTTGCTGAAAAGGATAATACGAAACGTAGTGTCAATTACACAGATGCGGATCAAC
CAAAACAACAAGCGTATGATACTGCAGTTACACAAGCAGAAGCAATTACTAATGCAAATGGCAGTAACGCGAATGAAACA
CAAGTTCAAGCAGCGCTTAACCAATTGAATCAAGCTAAAAACGACTTGAATGGTGATAATAAAGTTGCTCAAGCGAAAGA
AACAGCAAAACGTGCATTAGCTTCATATAGTAACTTGAATAACGCGCAATCAACTGCAGCAACTAGTCAAATTGACAATG
CAACGACAGTAGCAGACGTAACTGCTGCACAAAATACTGCTAATGAATTAAATACAGCAATGGGTCAACTTCAAAATGGT
ATTAATGACCAAAACACTGTTAAACAACAAGTGAACTTTACAGATGCTGACCAAGGTAAGAAAGATGCTTACACAAATGC
TGTTACGAATGCTCAAGGTATTTTAGATAAAGCAAACGGTCAAAATATGACAAAAGCACAAGTTGAAGCTGCATTAAATC
AAGTAACGACTGCTAAGAATGCTTTAAACGGTGATGCAAATGTAAGACAAGCAAAATCAGATGCGAAAGCAAACTTAGGT
ACATTAACACACTTAAATAATGCACAAAAACAAGATTTAACATCACAAATCGAAGGTGCAACAACAGTCAACGGTGTAAA
TAGTGTTAAAACGAAAGCACAAGACTTAGATGGTGCAATGCAACGATTAGAGTCAGCAATCGCAAATAAAGATCAAACTA
AAGCGAGCGAAAACTACATTGACGCAGATCCAACTAAGAAAACAGCATTTGATAATGCCATCACACAAGCTGAATCTTAC
TTAAATAAAGATCATGGTACGAATAAAGATAAGCAAGCTGTTGAACAAGCAATTCAAAGTGTAACGTCTACTGAAAATGC
TTTGAACGGTGACGCGAACTTACAATGCGCTAAAACTGAAGCTACACAAGCTATCGATAACTTGACACAATTGAATACAC
CGCAAAAAACAGCATTGAAACAACAAGTGAATGCTGCACAACGCGTATCAGGTGTAACTGATCTGAAAAATAGTGCTACA
TCACTTAATAATGCGATGGATCAATTAAAACAAGCAATTGGTGATCATGACACAATTGTAGCTGGTGGTAATTACACTAA
CGCAAGTCCTGATAAACAAGGTGCTTACACTGATGCATATAATGCTGCGAAGAATATCGTAAATGGTTCACCTAATGTGA
TTACAAATGCAGCAGATGTTACTGCGGCAACACAACGTGTCAATAATGCTGAAACAAGTTTAAATGGTGATACAAACTTA
GCAACTGCGAAGCAACAAGCTAAAGATGCATTACGTCAAATGACACATTTATCTGATGCACAAAAACAAAGTATTACTGG
TCAAATTGATAGCGCGACACAAGTAACTGGTGTACAAAGTGTGAAAGACAATGCAACAAATCTTGACAATGCAATGAATC
AACTTCGAAATAGTATTGCGAATAAAGATGAAGTAAAAGCGAGTCAACCATATGTTGATGCAGATACAGATAAACAAAAT
GCATACAATACAGCAGTTACAAGTGCTGAAAATATCATTAATGCAACGAGTCAGCCAACACTTGATCCATCTGCAGTAAC
ACAAGCAGCTAATCAAGTGAACACTAACAAAACTGCGCTTAATGGTGCGCAAAACTTAGCAAATAAAAAGCAAGAAACAA
CTGCTAACATCAACCGATTAAGTCATTTAAACAATGCTCAAAAGCAAGATTTAAATACACAAGTGACAAATGCACCAAAT
ATTAGCACAGTAAATCAAGTGAAAACTAAAGCTGAACAATTAGATCAAGCAATGGAACGTTTAATCAACGGAATCCAAGA
CAAAGATCAAGTGAAACAAAGTGTTAACTTTACAGATGCAGATCCAGAAAAACAAACAGCATACAACAATGCGGTAACTG
CTGCTGAAAATATTATTAATCAAGCAAATGGTACAAATGCGAACCAATCACAAGTTGAAGCAGCACTTTCAACTGTAACA
ACTACTAAACAAGCGTTGAATGGTGATAGAAAAGTAACAGATGCTAAAAACAATGCAAACCAAACATTATCTACGTTAGA
TAACTTAAACAATGCACAAAAAGGTGCTGTTACTGGAAACATCAATCAAGCGCACACTGTAGCTGAAGTAACGCAAGCCA
TTCAAACCGCTCAGGAACTCGAATACAGCGATGGGTAACTTGAAAAATAGCTTGAATGATAAAGACACTACACTTGGCAGT
CAAAACTTTGCAGATGCAGATCCAGAGAAGAAAAATGCATACAATGACAACGGGTTCGTAATGCTGAAAATATTTTAAATAA
ATCTACAGGTACGAACGTGCCTAAAGATCAAGTTGAAGCAGCTATGAATCAAGTGAATACTACAAAAGCAGCGCTTAATG
GTACTCAAAACCTTGAAAAAGCGAAACAACACGCAAATACAGCAATTGACGGTTTAAGCCATTTAACAAATGCACAAAAA
GAGGCATTAAAACAATTGGTACAACAATCGACTACTGTTGCAGAAGCACAAGGTAATGAACAAAAAGCAAACAATGTTGA
TGCAGCAATGGACAAATTACGTCAAAGTATTGCAGATAATGCGACAACAAAACAAAACCAAAATTATACTGATGCAAGTC
CGAATAAAAAGGATGCGTACAATAATGCTGTCACAACTGCACAAGGTATTATTGATCAAACTACAAACCCTTCATTAGAT
CCGACTGTTATCAATCAAGCTGCTGGACAAGTAAGCACGTCTAAAAATGCTTTAAATGGTAATGAAAACTTAGAGGCAGC
GAAGCAACAAGCAACGCAATCTTTAGGTTCATTAGACAACTTAAATAATGCGCAAAAACAAGCTGTTACTAATCAAATTA
ATGGCGCGCATACTGTTGATGAAGCAAATCAAATTAAGCAAATGCGCAAAACTTAAATACTGCGATGGGTAACTTGAAA
CAAGCGATAGCTGATAAAGATGCTACGAAAGCAACAGTTAACTTCACTGATGCAGATCAAGCAAAACAACAAGCATATAA
CACTGCAGTTACAAATGCTGAAAATATCATTTCAAAAGCTAATGGTGGTAATGCAACACAAACTGAAGTTGAACAAGCAA
TCCAACAAGTAAATGCAGCAAAACAAGCATTAAATGGTAATGCCAACGTTCAACATGCAAAAGACGAAGCAACAGCATTA
ATTAATAACTCTAATGATCTTAACCAAGCACAGAAAGATGCATTAAAACAACAAGTACAAAATGCAACTACTGTAGCTGG
TGTAAACAATGTTAAACAAACGGCGCAAGAGTTAAACAATGCGATGACACAATTAAAACAAGGCATTGCAGATAAAGAAC
AAACAAAAGCTGATGGTAACTTTGTCAATGCAGATTCTGACAAGCAAAATGCATATAATCAAGCAGTAGCGAAAGCTGAA
GCATTAATTAGTGGTACGCCTGATGTTGTCGTTACACCTAGCGAAATTACTGCAGCGTTAAATAAAGTTACGCAAGCTAA
AAATGATTTAAATGGTAATACAAACTTAGCAACGGCGAAACAAAATGTTCAACATGCTATTGATCAATTGCCAAACTTAA
ACCAAGCGCAACGTGATGAATACAGCAAACAAATCACGCAAGCAACACTTGTACCAAACGTCAATGCTATTCAACAAGCG
GCAACAACGCTTAATGACGCGATGACACAATTGAAACAAGGTATTGCGAATAAAGCACAAATTAAAGGTAGCGAGAACTA
TCACGATGCTGATACTGACAAGCAAACAGCATATGATAATGCAGTAACAAAAGCAGAAGAATTGTTAAAACAAACAACAA
ATCCAACAATGGATCCAAATACAATTCAACAAGCATTAACTAAAGTGAATGACACAAATCAAGCACTTAACGGTAATCAA
AAATTAGCTGATGCCAAACAAGATGCTAAGACAACACTTGGTACACTAGATCATTTAAATGATGCTCAAAAACAAGCGCT
AACAACTCAAGTTGAACAAGCACCAGATATTGCAACAGTTAATAATGTTAAGCAAAATGCTCAAATCTGAATAATGCTA
TGACTAACTTAAACAATGCATTACAAGATAAAACTGAGACATTAAATAGCATTAACTTTACTGATGCAGATCAAGCTAAG
AAAGATGATTATACTAATGCGGTTTCACATGCAGAAGGTATTTTATCTAAAGCAAATGGCAGCAATGCAAGTCAAACTGA
AGTGGAACAAGCGATGCAACGTGTGAACGAAGCGAAACAAGCATTGAATGGTAATGACAATGTACAACGTGCAAAAGATG
CAGCGAAACAAGTAATTACAAATGCAAATGATTTAAATCAAGCGCAAAAAGATGCATTAAAACAACAAGTCGATGCTGCG
CAAACTGTTGCAAATGTAAACACGATTAAGCAAACAGCACAAGATTTAAATCAAGCAATGACACAATTGAAACAAGGTAT
TGCAGATAAAGACCAAACTAAAGCAAATGGTAACTTTGTCAATGCTGATACTGATAAGCAAAATGCATATAACAATGCGG
```

Figure 2 cont.

```
TAGCGCATGCTGAACAAATCATTAGTGGTACACCAAATGCAAACGTGGATCCACAACAAGTGGCTCAAGCGTTACAACAA
GTGAATCAAGCTAAGGGTGATTTAAACGGTAACCACAACTTACAAGTTGCTAAAGACAATGCAAATACAGCCATTGATCA
GTTACCAAACTTAAATCAACCACAAAAAACAGCATTAAAAGACCAAGTGTCGCATGCAGAACTTGTTACAGGTGTTAATG
CTATTAAGCAAAATGCTGATGCGTTAAATAATGCAATGGGTACGTTGAAACAACAAATTCAAGCGAATAGTCAAGTACCA
CAATCAGTTGACTTTACACAAGCGGATCAAGACAAACAACAAGCTTATAACAATGCAGCTAACCAAGCGCAACAAATCGC
AAATGGCACACCAACACCTGTATTGGCGCCTGATACAGTAACAAAAGCAGTTACAACTATGAATCAAGCGAAAGATGCAT
TAAACGGTGATGAAAAATTAGCGCAAGCGAAACAAGATGCTTTAGCAAATCTTGATACGTTACGTGACTTAAATCAACCA
CAACGTGATGCATTACGAAACCAAATCAATCAAGCACAAGCTTTAGCTACAGTTGAACAAACTAAACAAAATGCACAAAA
TGTGAATACAGCAATGGGTAACTTGAAACAAGGTATTGCAAATAAAGATACTGTGAAAGCAAGTGAGAACTACCACGATG
CTGATGTCGATAAGCAAACAGCATATACAAATGCAGTGTCTCAAGCGGAAGGTATTATCAATCAAACGACAAATCCAACG
CTTAACCCAGATGACATTACTCGTGCATTAACTCAAGTGACTGATGCTAAAAATAGCTTAAACGGTGAAGCTAAATTAGC
CACTGAAAAGCAAAATGCTAAAGATGCCGTAAGTGGAATGACGCATTTAAACGATGCTCAAAAACAAGCATTAAAAGGTC
AAATCGATCAATCGCCTGAAATTGCTACAGTGAACCAAGTTAAACAAACAGCAACGAGCCTAGATCAAGCAATGGATCAA
TTATCACAAGCTATTAATGATAAAGATCAAATATTAGCGGACGGTAATTACTTAAATGCAGATCCTGACAAACAAAATGC
GTATAAACAGGCAGTAGCAAAAGCTGAAGCATTATTGAATAAACAAAGTGGTACTAATGAAGTACAAGCACAAGTTGAAA
GCATCACTAATGAAGTGAACGCAGCGAAACAAGCATTAAATGGTAATGACAATTTGGCAAATGCAAAACAACAAGCAAAA
CAACAATTGGCGAACTTAACACACTTAAATGATGCACAAAAACAATCATTTGAAAGTCAAATTACACAAGCGCCACTTGT
TACAGATGTCACTACGATTAATCAAAAAGCACAAACGTTAGATCATGCGATGGAATTATTAAGAAATAGTGTTGCGGATA
ATCAAACGACATTAGCGTCTGAAGATTATCATGATGCAACTGCGCAAAGACAAAATGACTATAACAAAGCTGTAACAGCT
GCTAATAATATCATTAATCAAACTACATCGCCTACGATGAATCCAGATGATGTTAATGGTGCAACGACACAAGTGAATAA
TACGAAAGTTGCATTAGATGGTGATGAAAACCTTGCAGCAGCTAAACAACAAGCAAACAACAGACTTGATCAATTAGATC
ATTTGAATAATGCGCAAAAGCAACAGTTACAATCACAAATTACGCAATCATCTGATATTGCTGCAGTTAATGGTCACAAA
CAAACAGCAGAATCTTTAAATACTGCGATGGGTAACTTAATTAATGCGATTGCAGATCATCAAGCCGTTGAACAACGTGG
TAACTTCATCAATGCTGATACTGATAAACAAACTGCTTATAATACAGCGGTAAATGAAGCAGCAGCAATGATTAACAAAC
AAACTGGTCAAAATGCGAACCAAACAGAAGTAGAACAAGCTATTACTAAAGTTCAAACAACACTTCAAGCGTTAAATGGA
GATCATAATTTACAAGTTGCTAAAACAAATGCGACGCAAGCAATTGATGTTTTAACAAGCTTAAATGATCCTCAAAAAAC
AGCATTAAAAGACCAAGTTACAGCTGCAACTTTAGTAACTGCAGTTCATCAAATTGAACAAAATGCGAATACGCTTAACC
AAGCAATGCATGGTTTAAGACAGAGCATTCAAGATAACGCAGCAACTAAAGCAAATAGCAAATATATCAACGAAGATCAA
CCAGAGCAACAAAACTATGATCAAGCTGTTCAAGCCGCAAATAATATTATCAATGAACAAACTGCAACATTAGATAATAA
TGCGATTAATCAAGTAGCGGCAACTGTGAATACAACGAAAGCAGCATTACATGGTGATGTGAAATTACAAATGATAAAG
ATCATGCTAAACAAACGGTTAGCCAATTAGCACATCTAAACAATGCACAAAAACATATGGAAGATACGTTAATTGATAGT
GAAACAACTAGAACAGCAGTTAAGCAAGATTTGACTGAAGTACAAGCATTAGATCAACTTATGGATGCATTACAACAAAG
TATTGCTGACAAAGATGCAACACGTGCGAGCAGTGCATATGTCAATGCAGAACCGAATAAAAAACAAGCCTATGATGAAG
CAGTTCAAAATGCTGAGTCTATCATTGCAGGATTAAATAATCCAACTATCAATAAAGGTAATGTATCAAGTGCGACTCAA
GCAGTAATATCATCTAAAAATGCATTAGATGGTGTTGAACGATTAGCTCAAGATAAGCAAACTGCTGGAAATTCTCTAAA
TCATTTAGATCAATTAACACCAGCTCAACAACAAGCGCTAGAAAATCAAATTAATAATGCAACAACTTGTGATAAAGTGG
CTGAAATCATTGCACAAGCGCAAGCATTAAATGAAGCGATGAAAGCATTAAAAGAAGTATTAAGGATCAACCACAAACT
GAAGCAAGTAGTAAATTTATTAACGAGGATCAAGCGCAAAAAGATGCATATACGCAAGCAGTACAACACGCGAAAGATTT
GATTAACAAAACAACTGATCCTACATTAGCTAAATCAATCATTGATCAAGCGACACAGGCAGTGACTGATGCTAAAAACA
ATTTACATGGTGATCAAAAACTAGCTCAAGATAAGCAACGTGCAACAGAAACGTTAAATAACTTGTCTAACTTGAATACA
CCACAACGTCAAGCACTTGAAAATCAAATCAATAATGCAGCAACTCGTGGTGAAGTAGCACAAAAATTAACTGAAGCACA
AGCACTTAACCAAGCAATGGAAGCTTTACGTAATAGCATTCAAGATCAACAACAAACAGAATCTGGTAGCAAGTTTATTA
ATGAAGATAAACCGCAAAAAGATGCTTACCAAGCAGCAGTTCAAAATGCAAAAGATTTAATTAACCAAACAGGTAATCCA
ACGCTTGATAAAGCACAAGTTGAACAATTGACACATGCTTTTAAACAAGCTAAAGATAACCTACACGGTGATCAAAAACT
TGCAGACGATAAACAACATGCGGTTACTGATTTAAATCAATTAAATGGTTTGAATAATCCGCAACGTCAAGCACTTGAAA
GCCAAATAAACAACGCAGCAACTCGTGGCGAAGTAGCGCAAAAATTAGCTGAAGCAAAAGCGCTTGATCAAGCAATGCAA
GCATTACGAAATAGTATTCAAGATCAACAACAAACGGAAGCGGGTAGCAAGTTTATCAATGAAGATAAACCGCAAAAGA
TGCTTACCAAGCAGCAGTTCAAAATGCAAAAGATTTAATTAACCAAACAGGTAATCCAACACTCGACAAATCACAAGTAG
AACAATTAACACAAGCAGTAACAACTGCAAAAGATAATCTACATGGTGATCAAAAACTTGCTCGTGATCAACAACAAGCA
GTAACAACTGTAAATGCATTGCCAAACTTAAATCATGCACAACAACAAACATTAACTGATGCTATAAATGCAGCGCCTAC
AAGAACAGAGGTTGCACAACATGTTCAAACTGCTACTGAACTTGATCACGCGATGGAAACATTGAAAAATAAAGTTGATC
AAGTGAATACAGATAAGGCTCAACCCAAATTACACTGAAGCGTCAACTGATAAAAAGAAGCAGTAGATCAAGCGTTACAA
GCTGCACAAAGCATTACAGATCCAATCTAATGGTTCAAATGCAATAAAGACGCTGTAGAACAAGCATTAACTAAGCTTCA
AGAAAAGTGAATGAGTTAAATGGTAATGAGAGAGTCGCTGAAGCTAAAACACAAGCGAAACAAACTATTGACCAATTAA
CACATTTAAATGCTGATCAAATTGCAACTGCTAAACAAAATATTGATCAAGCGACGAAACTTCAACCAATCGCTGAATTA
GTAGATCAAGCAACGCAATTGAACCAATCAATGGATCAATTACAACAAGCAGTTAATGAACATGCTAACGTTGAGCAAAC
TATAGATTACACACAAGCAGATTCAGATAAGCAAAAGGCTTATAAACAAGCGATTGCTGATGCTGAAAATGTATTGAAAC
AAAATGCGAATAAGCAACAAGTGGATCAAGCACTTCAAAATATTTTAAATGCAAAACAAGCATTAAATGGTGATGAACGT
GTAGCACTTGCTAAAACAAATGGTAAACATGACATCGACCAATTGAATGCATTAAACAATGCTCAACAAGATGGATTTAA
```

Figure 2 cont.

```
AGGTCGCATCGATCAATCAAACGATTTAAATCAAATCCAACAAATTGTAGATGAGGCTAAGGCACTTAATCGTGCAATGG
ATCAATTGTCACAAGAAATCACTGGCAATGAAGGACGCACGAAAGGTAGCACGAACTATGTCAATGCAGATACACAAGTC
AAACAAGTATATGATGAAGCGGTTGATAAAGCGAAACAAGCACTTGATAAATCGTCTGGGCAAAACTTAACTGCAGAACA
AGTTATCAAATTAAATGATGCAGTCACTGCAGCTAAGAAAGCATTAAATGGTGAAGAAAGACTTAATAATCGTAAAGCTG
AAGCATTACAAAGATTGGATCAATTAACACATCTAAACAATGCTCAAAGACAATTAGCAATCCAACAAATTAATAATGCT
GAAACGCTAAATAAAGCATCTCGAGCAATTAATAGAGCAACTAAATTAGATAATGCAATGGGTGCAGTACAACAATATAT
TGACGAACAGCACCTTGGTGTTATCAGCAGCACAAATTACATCAATGCAGATGACAATTTGAAAGCAAATTATGATAATG
CAATTGCGAATGCAGCACATGAGTTAGATAAAGTGCAAGGTAATGCAATTGCAAAAGCTGAAGCAGAGCAATTGAAACAA
AATATTATCGATGCTCAAAATGCATTAAATGGAGACCAAAACCTTGCAAATGCCAAAGATAAAGCAAATGCGTTTGTTAA
TTCGTTAAATGGATTAAATCAACAGCAACAAGATCTTGCACATAAAGCAATTAACAATGCCGATACTGTATCAGATGTAA
CAGATATTGTTAATAATCAAATTGACTTAAATGATGCAATGGAAACATTGAAACATTTAGTTGACAATGAAATTCCAAAT
GCAGAGCAAACTGTCAATTACCAAAACGCTGACGATAATGCTAAAACAAACTTCGATGATGCCAAACGTCTAGCAAATAC
ATTGCTAAATAGTGATAACACAAATGTGAATGATATCAATGGCGCAATCCAAGCAGTCAATGATGCAATCCATAATCTTA
ATGGTGATCAACGACTACAAGATGCTAAAGACAAGGCAATTCAATCAATTAATCAAGCTTTAGCTAATAAGCTAAAAGAA
ATCGAAGCTTCAAATGCGACGGATCAAGACAAGCTTATTGCGAAAAATAAAGCAGAAGAATTGGCAAACAGCATCATCAA
CAACATTAATAAAGCAACAAGTAATCAGGCTGTATCTCAAGTTCAAACAGCAGGCAACCACGCGATTGAACAAGTGCATG
CTAATGAAATACCAAAAGCAAAAATTGATGCCAATAAAGACGTTGATAAGCAAGTTCAAGCATTAATTGACGAAATTGAT
CGAAATCCAAATCTAACAGATAAGGAAAAACAAGCACTTAAAGATCGTATTAATCAAATACTTCAACAAGGTCATAACGA
CATTAACAATGCGCTGACTAAAGAAGAAATTGAACAAGCTAAAGCACAACTTGCGCAAGCATTACAAGACATCAAAGATT
TAGTGAAAGCTAAAGAAGATGCGAAACAAGATGTTGATAAACAAGTTCAAGCATTAATTGACGAAATCGATCAAAATCCA
AATCTAACAGATAAGGAAAAACAAGCACTTAAAGATCGTATTAATCAAATACTTCAACAAGGTCATAACGGCATTAACAA
TGCGATGACTAAAGAAGAAATTGAACAAGCCAAAGCACAACTTGCACAAGCATTAAAAGAAATTAAAGATTTAGTGAAAG
CTAAAGAAATGCGAAACAAGATGTTGATAAACAAGTTCAAGCATTAATTGACGAAATCGATCAAAATCCAAATCTAACA
GATAAGGAAAAACAAGCGCTTAAAGATCGAATCAATCAAATACTGCAACAAGGTCATAACGACATTAACAATGCGATGAC
TAAAGAAGAAATTGAACAAGCCAAAGCACAACTTGCACAAGCATTACAAGACATCAAAGATTTAGTGAAAGCTAAAGAAG
ATGCGAAAAATGCAATAAAAGCCTTAGCTAATGCGAAGCGTGATCAAATCAATTCAAATCCAGATTTAACACCTGAGCAA
AAAGCAAAAGCGCTCAAAGAAATTGACGAAGCTGAAAAACGAGCACTACAAAACGTTGAGAATGCTCAAACTATAGATCA
ATTAAATCGAGGATTAAACTTAGGTTTAGATGACATTAGAAATACACATGTATGGGAGGTTGATGAACAACCTGCTGTAA
ATGAAATTTTTGAAGCAACACCTGAGCAAATCCTAGTTAATGGTGAACTCATTGTACATCGTGATGACATCATTACAGAA
CAAGATATTCTTGCACACATAAACTTAATTGATCAGCTTTCAGCAGAAGTTATTGATACACCATCAACTGCAACGATTTC
TGATAGCTTAACAGCAAAAGTTGAAGTTACATTGCTTGATGGATCAAAAGTGATTGTTAATGTTCCTGTAAAAGTTGTAG
AAAAAGAATTGTCAGTAGTCAAACAACAGGCAATTGAATCAATCGAAAATGCGGCACAACAAAAGATTGATGAAATCAAT
AATAGTGTGACATTAACACTGGAACAAAAAGAAGCTGCAATTGCAGAAGTTAATAAGCTTAAACAACAAGCAATTGATCA
TGTTAACAATGCACCTGATGTTCATTCAGTTGAAGAAATTCAACAACAAGAACAAGCGTATATTGAACAATTTAATCCAG
AACAATTTACGATTGAACAAGCAAAATCAAATGCAATTAAATCGATTGAAGATGCAATTCAACATATGATTGATGAAATC
AAAGCTCGTACTGATCTAACAGATAAAGAGAAGCAAGAAGCTATTGCTAAGTTAAATCAATTAAAAGAACAAGCAATTCA
AGCGATTCAACGTGCGCAAAGCATCAGTGAAATAACTGAGCAATTGGAACAATTTAAAGCTCAAATGAAAGCAGCTAATC
CAACAGCAAAAGAACTAGCTAAACGCAAGCAAGAAGCTATTAGTAGAATTAAAGACTTTTCAAATGAAAAATAAATAGT
ATTCGAAATAGTGAAATTGGCACAGCTGATGAAAACAAGCAGCAATGAATCAAATTAACGAAATTGTGCTTGAAACAAT
TAGAGATATTAATAATGCGCATACATTACAGCAAGTTGAGGCTGCATTGAACAATGGTATTGCTCGAATTTCAGCAGTAC
AAATTGTAATATCTGATCGTGCTAAACAATCGTCAAGTACTGGAAATGAATCTAATAGCCATTTAACAATTGGTTATGGA
ACTGCAAATCATCCATTTAACAGTTCGACTATTGGACATAAAAAGAAACTTGATGAAGATGATGACATTGATCCACTTCA
TATGCGTCACTTTAGTAATAATTTCGGTAATGTTATTAAAAACGCTATTGGTGTGGTGGGTATCTCTGGCTTACTAGCTA
GTTTCTGGTTCTTCATTGCCAAACGTCGTCGTCGTAAAGAAGATGAAGGAAGCAATTAGAAATAAGAGATAATAATAAGAT
TCAATAAAAGAGACTTTAGACGATACAAAACATTTACCACTTTTATTTGCGAAACGTCGCAGAAAAGAAGATGAAGAAGA
TGTTACTGTTGAAGAAAAGATTCGCTAAATAATGGCGAGTCACTCGATAAAGTTAAACATACGCCGTTCTTCTTACCAA
AACGTCGTCGTAAAGAAGATGAAGAAGATGTGGAAGTTACAAATGAAAACACAGATGAAAAAGTGTTGAAAGATAACGAA
CATTCACCACTCTTATTCGCAAAACGACGCAAAGATAAAGAGGAAGATGTTGAAACAACAACTAGTATTGAATCTAAAGA
TGAGGACGTTCCTTTATTATTGGCTAAAAAGAAAAATCAAAAGATAACCAATCCAAAGACAAAAAGTCAGCATCAAAAA
ATACTTCTAAAAAGGTAGCAGCTAAAAAGAAGAAAAAGAAATCTAAGAAAAAATAAAAAA
```

SEQ ID NO:47 polynucleotide sequence
```
TTGAATAATCGTGATAAATTACAAAAATTTAGTATTCGAAAATACGCAATTGGAACATTTTCTACTGTGATTGCAACACT
TGTGTTCATGGGTATCAATACAAACCATGCAAGTGCCGACGAGTTGAATCAAATCAAAAGTTAATTAAACAATTAAATC
AAACAGATGATGATGATTCGAATACGCATAGTCAAGAAATCGAAAATAACAAACAAATTCTAGTGGGCAGACTGAATCA
TTACGTTCATCAACTAGTCAAAATCAAGCAAATGCACGACTGTCGGATCAATTCAAAGACACTAATGAAACATCGCAACA
ATTACCTACAAATGTTTCGGATGATAGTATCAATCAATCGCATAGTGAAGCAAATATGAATAACGAACCATTGAAAGTTG
ATAATAGTACTATGCAAGCACATAGTAAAATAGTAAGCGATAGCGATGGGAATGCTTCTGAAAATAAACATCATAAACTA
```

Figure 2 cont.

ACAGAAAATGTACTTGCAGAAAGCCGAGCAAGTAAAAATGACAAAGAGAAAGAGAATCTACAAGAGAAAGATAAATCGCA
GCAAGTACATCCACCATTAGATAAAAATGCATTACAAGCTTTTTTTGACGCATCATATCACAATTACAGAATGATTGATA
GAGATCGTGCGGATGCAACAGAATATCAAAAAGTCAAATCTACTTTTGACTACGTCAATGACTTACTAGGTAATAATCAA
AATATTCCTTCAGAACAGCTTGTTTCGGCATATCAACAATTAGAGAAAGCATTAGAACTTGCACGTACGTTACCACAACA
ATCTACTACAGAAAAACGTGGTAGAAGAAGTACGAGAAGTGTTGTTGAGAATCGTTCATCAAGAAGCGATTACTTAGATG
CTAGAACTGAATATTATGTTTCAAAAGACCATGATGATTCTGGTTTCCCTCCTGGTACTTTCTTCCATGCTTCAAATAGA
AGATGGCCTTATAATTTACCAAGATCTAGGAACATCTTACGTGCTTCTGATGTACAAGGTAATGCTTATATCACTACAAA
ACGACTTAAAGATGGATATCAATGGGATATTTTATTTAATAGTAATCATAAAGGGCATGAATATATGTACTATTGGTTTG
GACTTCCAAGTGATCAAACACCAACTGGTCCAGTAACTTTCACTATTATCAACCGTGATGGTTCAAGTACATCTACTGGT
GGCGTTGGATTTGGATCAGGTGCACCACTACCTCAATTTTGGAGATCAGCAGGTGCTATTAATTCTAGCGTAGCGAATGA
TTTTAAACATGGCTCCGCTACAAATTATGCATTTTATGATGGTGTTAATAATTTTTCTGACTTTGCTAGAGGGGGAGAAT
TATACTTCGACAGAGAAGGCGCTACACAAACTAATAAATATTATGGCGATGAAAACTTCGCATTGCTAAATAGTGAGAAA
CCAGATCAAATAAGAGGATTAGATACAATATATAGTTTTAAAGGTAGTGGTGATGTAAGTTATCGTATTTCATTTAAAAC
TCAAGGAGCTCCAACTGCAAGATTGTATTATGCTGCTGGCGCGCGTTCTGGTGAATATAAACAAGCAACGAACTATAACC
AACTCTATGTCGAACCTTATAAGAATTATCGAAATCGAGTACAGTCAAATGTCCAAGTTAAAAATCGTACACTTCATTTA
AAAAGAACAATCAGACAATTCGATCCTACATTACAGAGAACTACTGATGTTCCTATTTTGGATAGTGACGGTTCCGGAAG
TATTGATTCGGTATACGACCCATTAAGTTATGTAAAGAATGTGACTGGTACAGTCCTAGGTATTTATCCATCTTATCTTC
CTTATAATCAGGAAAGATGGCAGGGAGCTAATGCAATGAATGCCTATCAAATTGAAGAACTTTTTTCACAAGAAATCTT
CAAAATGCAGCACGTTCAGGCCGTCCAATTCAATTTCTTGTAGGTTTTGATGTTGAAGATAGCCATCATAACCCTGAAAC
TCTTTTACCAGTAAATTTATATGTAAAACCTGAGTTAAAACATACAATTGAGTTATATCACGATAATGAAAAACAAGATA
GAAAGGAATTTTCAGTATCGAAA

SEQ ID NO:48 polynucleotide sequence
ATGAGTGGAACGCTTCATAACACTGTAGGATCAGGAATATTACCTTATCAACAAGAGATACGTATCAAACTTACTAGTAA
TGAACCAATTAAAGATAGTGAATGGTCTATTACAGGATATCCTAACACGCTTACATTACAAAACGCTGTGGGTAGAACAA
ATAATGCTACTGAAAAAAACTTAGCTCTTGTTGGTCATATTGATCCAGGAAATTATTTCATCACTGTTAAGTTTGGTGAT
AAAGTAGAACAATTTGAAATTAGATCAAAACCAACTCCACCAAGAATCATTACAACTGCTAATGAATTACGTGGAAATCC
TAACCATAAGCCTGAAATAAGAGTAACAGATATACCAAATGATACTACTGCTAAAATCAAACTTGTGATGGGCGGAACCG
ATGGCGATCATGATCCAGAAATAAATCCATATACTGTCCCTGAAAACTACACAGTAGTTGCAGAAGCATACCATGATAAT
GATCCAAGTAAAAATGGGGTCTTAACATTCCGTTCATCAGACTACCTTAAAGATCTACCATTAAGCGGTGAATTAAAGGC
AATTGTTTATTACAATCAATATGTACAATCAAACTTTAGTAAAAGCGTTCCGTTTAGTAGCGATACAACACCACCTACAA
TTAATGAACCGGCAGGACTAGTTCATAAGTATTACAGGGGAGATCATGTAGAAATTACTCTTCCAGTCACTGATAATACT
GGCGGTTCAGGTTTAAGAGATGTAAACGTCAATTTACCTCAAGGTTGGACAAAAACCTTTACAATCAATCCTAATAATAA
TACTGAGGGTACGCTTAAGTTAATTGGTAATATACCTAGTAATGAAGCATATAATACGACATATCATTTCAATATTACTG
CAACCGATAATTCTGGAAATACAACAAATCCAGCTAAAACCTTTATTTTAAATGTTGGTAAGTTGGCTGATGATTTAAAT
CCAGTCGGATTATCTAGAGATCAACTACAATTAGTGACAGACCCTTCTTCATTATCTAATTCCGAACGAGAAGAGGTAAA
AAGAAAAATAAGTGAAGCAAATGCTAATATAAGATCATATTTTATTACAAAATAACCCAATACTCGCTGGAGTAAACGGCG
ATGTTACATTTTATTATAGAGATGGTTCTGTAGATGTTATTGATGCTGAAAATGTAATCACATATGAGCCCGAAAGAAAA
TCCATTTTCAGTGAAAATGGTAACAAATAAAAAAGAAGCAGTAATCACTATTGCTAGAGGACAAAACTATACCATTGG
TCCAAACTTAAGAAAATATTTCTCATTAAGTAATGGTTCGGATTTACCTAATAGAGATTTCACCTCTATATCAGCTATTG
GATCTTTACCTTCATCGAGTGAAATTAGTCGACTCAATGTTGGAAATTATAACTATAGAGTTAATGCTAAAAATGCTTAT
CATAAGACTCAACAAGAACTTAATTTAAAACTTAAAATAGTAGAGGTTAATGCACCTACTGGTAATAATCGTGTATATAG
AGTTAGTACTTATAATTTAACTAATGATGAAATCAATAAAATCAAACAAGCATTTAAAGCAGCTAATTCTGGACTTAATT
TAAACGATAACGATATCACTGTTTCGAATAACTTTGACCATAGAAATGTTAGTAGTGTGACAGTAACTATACGTAAGGGC
GATTTGATAAAAGAGTTTTCATCAAATCTCAATAATATGAATTTCTTACGTTGGGTTAATATAAGGGATGATTATACCAT
TTCGTGGACTTCTAGTAAGATTCAAGGTAGAAATACAGATGGTGGATTAGAATGGTCACCAGATCATAAATCACTTATTT
ATAAATATGATGCAACATTAGGTAGACAAATAAATACTAATGACGTGTTAACTTTACTTCAAGCAACAGCTAAAAACTCA
AATTTACGTTCAAATATCAATAGTAATGAAAAACAGTTAGCAGAACGAGGGTCTAATGGGTATTCTAAATCTATAATTAG
AGATGATGGCGAGAAATCTTATTTACTTAACTCAAATCCTATTCAAGTATTAGACTTAGTAGAACCAGATAATGGTTACG
GTGGACGTCAAGTCAGTCATTCTAACGTTATATATAATGAAAAAATTCTTCTATCGTAAATGGTCAAGTTCCAGAAGCT
AATGGGGCATCCGCTTTTAACATTATGAAAAGTTGTTAAAGCTAATGCGGCAAATAATGGTATTGGGTGTTATCTATAA
GGCACAATTATACTTAGCACCATACAGTCCAAAAGGTTACATTGAAAAATTAGGCCAAAATTTAAGCAATCAATAACG
TGATTAATGTTTATTTTGTGCCTTCTGATAAAGTAAATCCTAGTATAACTGTAGGTAATTACGACCATCATACGGTATAT
TCTGGTGAAACATTTAAAAATACTATCAATGTAAATGATAATTATGGATTAAATACAGTAGCTTCTACAAGTGATAGTGC
AATTACTATGACCAGAAACAACAACGAGTTAGTAGGTCAGGCTCCTAATGTTACTAATAGCATAAATAAAATTGTAAAAG
TTAAAGCCACAGATAAAAGTGGAAATGAAAGTATTGTTTCTTTCACAGTAAATATAAAACCATTAAACGAGAAATATAGA
ATAACAACTTCATCAAGTAATCAAACACCAGTGAGAATTAGTAATATTCAAAACAATGCTAACCTTTCAATTGAAGATCA
AAATAGAGTAAAATCTTCACTCAGCATGACTAAAATTTTAGGTACAAGAAATTATGTCAATGAGTCAAATAATGACGTTC

Figure 2 cont.

```
GTAGTCAAGTTGTAAGTAAAGTAAATAGAAGTGGGAACAATGCTACAGTTAATGTTACAACTACATTTTCTGATGGTACA
ACTAATACAATAACCGTTCCAGTTAAACATGTGTTATTAGAAGTTGTACCTACTACTAGAACAACAGTAAGAGGACAACA
ATTTCCAACCGGCAAAGGAACTTCCCCAAATGATTTCTTTAGTTTAAGAACGGGAGGTCCAGTTGATGCGAGAATAGTTT
GGGTTAATAATCAGGGACCCGATATAAATAGTAATCAAATTGGTAGAGATTTAACATTACACGCTGAAATATTCTTTGAT
GGTGAAACAACACCAATTAGAAAAGATACTACTTACAAACTTAGTCAATCTATTCCAAAGCAAATATATGAAACAACTAT
CAATGGTCGATTTAATTCATCAGGTGATGCATATCCAGGAAATTTTGTTCAAGCAGTAAATCAATATTGGCCAGAACATA
TGGACTTCAGATGGGCCCAAGGATCAGGCACACCAAGTTCTCGTAATGCAGGTTCATTTACTAAAACAGTTACGGTAGTT
TATCAAAACGGCCAAACTGAAAACGTTAATGTACTATTCAAAGTCAAACCAAATAAACCTGTTATTGATAGTAATAGTGT
GATTTCAAAAGGACAATTAAATGGTCAACAAATTTTAGTTCGAAATGTTCCACAAAATGCACAAGTCACTCTATATCAAT
CAAATGGAACTGTTATTCCTAATACAAATACAACTATAGATTCTAATGGTATAGCTACTGTAACAATTCAAGGCACTCTA
CCAACCGGAAATATTACTGCTAAAACCTCAATGACAAATAATGTAACGTACACTAAACAAAATAGTAGTGGAATTGCTTC
AAATACAACTGAAGATATAAGTGTTTTTTCAGAAAACAGTGATCAAGTAAATGTTACCGCTGGCATGCAAGCTAAAAATG
ATGGTATTAAAATAATTAAAGGTACAAACTATAATTTTAATGACTTCAATAGTTTCATAAGTAATATACCAGCCCATTCT
ACTCTTACATGGAACGAGGAGCCTAATAGTTGGAAAAACAACATCGGTACTACAACAAAAACTGTTACAGTTACTCTACC
TAATCATCAAGGTACGAGAACTGTAGATATTCCAATAACAATCTATCCAACAGTTACAGCTAAGAATCCAGTAAGAGATC
AAAAAGGACGAAACTTAACCAATGGTACTGACGTTTATAATTATATTATTTTTGAAAATAATAACCGTCTTGGAGGAACA
GCTTCTTGGAAAGACAATCGTCAACCTGATAAAAACATAGCCGGTGTACAAAATTTAATTGCACTTGTTAATTATCCTGG
CATATCTACACCATTAGAAGTTCCTGTTAAAGTGTGGGTATATAATTTTGATTTCACTCAACCTATCTACAAAATTCAAG
TAGGAGATACATTCCCTAAAGGAACATGGGCAGGCTATTACAACATCTTGAAAATGGAGAGGGATTACCAATAGATGGT
TGGAAATTTTATTGGAACCAGCAAAGTACAGGAACTACTAGTGATCAATGGCAATCATTAGCATATACTAGAACTCCTTT
TGTTAAAACTGGTACTTATGATGTCGTTAATCCTAGCAACTGGGGTGTTTGGCAAACATCACAATCAGCTAAATTTATAG
TTACAAATGCTAAACCTAATCAACCAACCATAACTCAGTCTAAAACTGGTGATGTAACAGTAACACCTGGTGCTGTGCGT
AATATACTAATAAGTGGGACAAATGATTATATCCAAGCATCTGCAGATAAGATTGTTATTAATAAAAATGGAAATAAATT
AACTACATTTGTTAAAAATAATGATGGTCGTTGGACTGTTGAAACTGGGTCACCTGACATAAATGGTATCGGACCAACAA
ATAACGGAACTGCTATATCTTTAAGTCGATTAGCAGTTAGACCTGGGGATTCAATAGAAGCAATAGCGACTGAAGGTTCC
GGAGAAACTATAAGTACTTCAGCAACTAGTGAAATTTATATTGTCAAAGCTCCACAACCTGAACAAGTAGCAACTCATAC
TTATGATAATGGAACATTCGATATATTACCTGACAATTCACGTAATTCTTTAAATCCAACTGAACGTGTCGAAATTAATT
ACACTGAAAAATTAAATGGCAATGAAACACAAAAATCATTCACTATTACTAAAAATAACAACGGCAAATGGACGATAAAT
AATAAACCAAATTATGTCGAGTTCAATCAGGATAATGGTAAAGTTGTATTTTCGGCCAATACAATTAAACCTAATTCTCA
AATTACAATAACTCCTAAAGCAGGTCAGGGTAACACTGAAAACACAAATCCTACTGTAATTCAAGCACCTGCGCAACATA
CTTTAACAATCAATGAAATTGTTAAAGAACAGGGTCAAATGTGACTAATGATGATATTAATAATGCGGTTCAAGTGCCA
AATAAAAATAGAGTTGCGATTAAACAAGGAAACGCTCTTCCAACAAATTTAGCTCGTGGTGGTAGTACATCACATATTCCAGT
AGTTATTTATTACAGTGATGGAAGTTCTGAAGAAGCTACTGAGACTGTTAGAACTAAAGTTAATAAAACCGAATTAATCA
ATGCTCGTCGTCGACTAGATGAAGAAATTAGTAAAGAGAACAAAACACCATCAAGTATCAGAAACTTTGATCAAGCTATG
AATCGTGCTCAATCACAAATTAATACAGCTAAAAGTGATGCTGACCAAGTTATAGGCACAGAATTTGCAACACCTCAACA
AGTAAATTCAGCTTTATCTAAAGTTCAAGCGGCACAAAATAAAATAAATGAAGCTAAAGCATTATTACAAAACAAGGCTG
ATAATAGTCAACTTGTGAGAGCAAAAGAACAATTACAACAATCGATTCAACCAGCCGCTTCAACTGATGGTATGACTCAA
GATAGCACAAGGAACTACAACAATAAACGCCAAGCAGCTGAACAAGCAATACAACATGCAAATAGCGTTATAAATAATGG
AGATGCAACATCCCAACAAATTAATGATGCTAAAAACACAGTTGAACAGGCACAGAGAGATTATGTTGAAGCTAAAAGCA
ACTTACGTGCTGATAAGTCACAGTTACAAAGCGCTTATGATACGTTAAATAGAGATGTTTTAACAAATGATAAAAAGCCA
GCATCTGTAAGACGCTATAATGAAGCCATTTCAAATATTAGAAAAGAATTAGATACAGCTAAAGCGGATGCAAGTAGTAC
TTTGCGAAACACCAATCCTTCCGTTGAACAAGTTAGAGACGCTTTAAATAAAATAAATACTGTTCAACCTAAAGTGAATC
AAGCAATTGCTTTACTTCAACCAAAAGAAAATAATTCAGAACTTGTACAAGCTAAAAAACGTTTACAAGACGCTGTAAAT
GACATACCTCAAACACAAGGTATGACACAACAAACAATTAATAATTATAATGACAAACAACGTGAAGCTGAAAGAGCACT
TACATCTGCACAAAGAGTGATTGATAATGGGGATGCTACAACTCAAGAAATTACTTCTGAAAAATCTAAAGTAGAGCAAG
CAATGCAAGCTTTAACTAATGCTAAAAGTAATCTGAGAGCTGATAAGAATGAGTTACAGACTGCATATAACAAATTAATT
GAGAACGTATCTACCAATGGTAAAAAACCGGCGAGTATACGTCAATACGAAACAGCCAAAGCCAGAATACAAAATCAAAT
TAATGATGCTAAAAATGAAGCGGAGCGAATTTTAGGTAATGATAATCCACAAGTATCACAAGTAACTCAAGCATTGAACA
AAATCAAAGCTATTCAACCAAAATTAACAGAAGCTATCAACATGCTTCAAAACAAAGAAAATAATACAGAATTAGTCAAT
GCTAAAAACAGACTTGAAAATGCAGTAAATGATACAGATCCAACACACGGTATGACTCAAGAAACAATTAATAATTACAA
CGCTAAAAAGCGAGAAGCTCAAAATGAAATACAAAAAGCGAACATGATTATTAATAATGGAGATGCTACTGCTCAAGATA
TTTCTTCTGAAAAATCTAAAGTAGAGCAAGTATTACAAGCATTACAAAATGCTAAGAATGACTTAAGAGCTGATAAAAGA
GAATTACAGACTGCATACAATAAACTTATACAAAATGTTAATACCAATGGTAAAAAACCATCTAGTATTCAAAACTATAA
GTCTGCAAGACGAAATATCGAAACCAATATAATACCGCTAAAAATGAAGCACATAATGTTCTTGAAAATACAAACCCTA
CTGTAAATGCAGTAGAAGATGCTTTACGTAAGATAAATGCAATTCAACCAGAGGTTACAAAAGCTATTAATATACTTCAA
GATAAAGAAGATAATAGCGAACTTGTTAGAGCAAAAGAAAATTAGATCAAGCGATTAATAGTCAACCATCACTAAATGG
TATGACTCAAGAATCTATTAATAATTACACAACAAAACGTAGAGAAGCACAAAATATAGCAAGTTCTGCTGACACTATTA
TTAATAATGGGGATGCATCTATTGAACAAATAACAGAAAATAAAATTCGAGTTGAAGAGGCAACTAATGCACTTAACGAA
GCAAAACAACATTTAACGGCAGATACAACTTCTTTAAAAACTGAAGTACGGAAATTAAGTAGGAGAGGCGACACAAACAA
```

Figure 2 cont.

```
CAAAAAGCCTAGCAGTGTTAGTGCTTATAACAATACTATTCATTCGCTACAATCTGAAATTACACAGACTGAAAATAGAG
CAAATACTATCATCAATAAGCCTATTCGTTCTGTTGAAGAAGTAAATAATGCATTGCATGAAGTAAACCAATTGAACCAA
CGCTTAACAGATACAATTAACTTATTACAACCTTTAGCGAATAAAGAAAGCTTAAAAGAAGCTCGTAATCGACTTGAAAG
TAAAATTAATGAAACCGTTCAAACAGACGGTATGACTCAACAATCTGTTGAGAATTATAAGCAAGCTAAAATAAAAGCTC
AAAATGAATCTAGTATTGCACAAACTCTTATTAATAATGGTGATGCATCTGATCAAGAAGTTTCTACAGAAATAGAAAAA
TTAAATCAAAAGCTGTCTGAATTAACAAATTCAATCAATCACTTAACAGTTAATAAAGAACCTTTAGAAACTGCCAAAAA
TCAGTTACAAGCAAATATTGACCAAAAACCTAGCACTGATGGTATGACGCAACAATCTGTACAAAGCTATGAACGTAAAC
TACAAGAAGCCAAAGATAAAATAAACTCAATTAATAATGTCTTAGCTAACAATCCAGATGTTAATGCTATCAGAACAAAC
AAAGTTGAGACGGAACAAATCAATAATGAATTAACACAGGCGAAACAAGGTCTTACTGTTGATAAACAACCATTGATTAA
TGCAAAAACTGCTTTGCAACAAAGTCTAGATAATCAACCAAGTACTACTGGTATGACTGAAGCAACAATTCAAAATTATA
ACGCTAAACGTCAAAAAGCAGAGCAAGTTATACAAATGCAAATAAAATTATTGAAAACGCTCAACCTAGTGTACAACAA
GTGTCTGATGAGAAATCTAAGGTAGAGCAAGCACTCAGTGAATTGAACAACGCCAAATCAGCGCTTAGAGCTGATAAACA
AGAATTACAGCAAGCATATAATCAGTTGATTCAACCAACGGATTTAAATAATAAGAAACCAGCTTCTATCACTGCGTACA
ATCAAAGATATCAACAATTTAGTAACGAATTGAACAGCACTAAAACAAATACAGATCGCATTTTAAAAGAGCAAAATCCA
AGTGTAGCTGATGTCAACAATGCACTAAATAAAGTAAGAGAAGTACAACAAAATTAAACGAAGCCAGAGCACTTTTACA
AAATAAAGAAGATAATAGTGCACTAGTTCGAGCCAAAGAACAACTTCAACAGGCAGTTGACCAAGTCCCTTCAACAGAAG
GTATGACGCAACAAACTAAAGATGATTACAATTCAAAACAACAAGCTGCTCAACAAGAAATATCAAAAGCACAACAAGTT
ATCGATAATGGCGATGCGACTACACAACAAATTTCTAACGCCAAAACAAATGTTGAACGCGCTTTAGAAGCATTAAATAA
TGCAAAAACTGGTTTAAGAGCAGATAAAGAGGAACTTCAAAATGCATATAATCAATTAACTCAAAATATTGATACGAGCG
GTAAAACGCCTGCAAGTATCAGGAAATACAATGAAGCTAAGTCACGTATTCAAACTCAAATTGATTCAGCTAAAAATGAA
GCAAACAGTATTTTAACAAATGACAATCCTCAAGTATCACAAGTGACTGCTGCGTTAAACAAAATAAAAGCTGTTCAACC
TGAATTAGATAAAGCGATAGCAATGCTTAAAAATAAAGAGAATAATAATGCATTGGTTCAAGCGAAACAACAACTTCAAC
AAATTGTTAATGAAGTAGATCCAACACAAGGCATGACAACAGATACTGCTAATAACTATAAATCAAAAAAACGTGAAGCT
GAAGATGAAATACAAAAAGCTCAACAAATCATTAACAATGGCGATGCCACTGAGCAACAAATTACTAACGAAACAAATAG
AGTAAATCAAGCGATTAATGCAATAAACAAAGCCAAAAACGATTTACGTGCTGATAAGTCTCAATTGGAAAATGCTTATA
ACCAATTAATACAAAATGTTGATACAAATGGTAAAAAACCTGCTAGTATTCAACAATACCAAGCTGCTCGACAAGCTATT
GAGACGCAATACAATAACGCTAAATCAGAAGCACATCAAATTCTTGAAAATAGTAACCCTTCAGTTAATGAAGTAGCACA
AGCATTACAAAAAGTTGAAGCTGTACAACTTAAAGTTAATGACGCGATTCATATACTTCAAAATAAAGAGAATAATAGTG
CACTTGTCACAGCTAAAAATCAACTTCAGCAATCAGTTAATGATCAACCATTAACAACAGGTATGACTCAAGATTCTATT
AATAACTATGAAGCTAAGAGAAATGAGGCTCAAAGTGCTATCAGAAATGCAGAAGCTGTCATCAACAATGGCGATGCAAC
TGCAAAACAAATTTCAGACGAGAAATCTAAAGTTGAACAAGCACTAGCACATTTGAATGATGCTAAACAGCAATTAACTG
CAGATACTACTGAATTACAAACAGCAGTTCAACAATTAAACAGAAGAGGCGATACAAATAATAAAAGCCAAGAAGTATC
AATGCATATAATAAAGCAATTCAATCATTAGAAACACAAATTACTTCTGCTAAAGATAATGCCAACGCTGTGATACAAAA
ACCTATACGTACTGTTCAAGAGGTAAATAATGCATTACAACAAGTAAATCAGTTGAATCAACAATTAACTGAAGCAATTA
ATCAACTTCAACCGCTATCAAATAATGATGCATTAAAAGCTGCAAGATTAAATTTAGAAAATAAAATTAATCAAACTGTA
CAAACTGATGGTATGACACAACAATCTATAGAGGCTTATCAAAACGCTAAACGCGTAGCCCAAAATGAATCTAACACTGC
TTTAGCATTAATTAATAACGGCGATGCCGATGAACAACAAATTACAACTGAAACAGACCGAGTCAATCAGCAAACTACAA
ACTTAACTCAAGCAATTAACGGGTTAACAGTTAATAAAGAACCATTAGAAACCGCTAAAACAGCGTTACAAAATAACATC
GACCAGGTACCTAGTACAGATGGTATGACTCAGCAATCTGTTGCAAATTATAATCAAAAACTACAAATAGCTAAAAACGA
AATTAACACAATTAATAACGTTTTAGCGAACAATCCAGATGTTAATGCAATCAAAACGAATAAAGCAGAAGCGGAACGAA
TCAGTAACGATTTAACACAAGCTAAGAATAACTTACAAGTTGATACTCAACCTTTAGAAAAAATAAAAAGACAACTTCAA
GATGAAATTGATCAAGGTACTAACACAGATGGAATGACTCAAGATTCAGTGGATAATTACAATGATAGCTTAAGTGCAGC
AATTATAGAAAAAGGCAAAGTAAATAAATTACTTAAACGTAATCCGACAGTAGAACAAGTTAAAGAGAGCGTTGCTAATG
CACAACAAGTCATACAAGATTTACAAAATGCTCGAACTTCACTTGTTCCAGACAAAACTCAACTTCAAGAAGCTAAAAAT
AGATTAGAAAACAGTATTAACCAACAAACAGATACTGACGGCATGACTCAAGATTCGCTTAACAATTATAATGATAAATT
AGCAAAAGCTAGACAAAACCTTGAAAAAATATCTAAAGTTTTAGGTGGTCAACCTACTGTAGCTGAAATTAGACAAAATA
CAGATGAAGCAAATGCACATAAACAAGCATTAGACACTGCACGTTCTCAACTTACATTAAATAGAGAGCCATATATCAAT
CATATTAATAATGAAAGTCATTTAAATAACGCGCAAAAAGATAATTTTAAAGCTCAAGTTAACTCAGCACCTAATCATAA
TACTTTAGAAACGATTAAAAATAAGGCTGATACTTTAAATCAATCTATGACAGCATTAAGTGAAAGTATTGCAGATTACG
AAAATCAAAAACAACAAGAAAATTATTTAGATGCATCTAACAATAAACGTCAAGACTATGCAATGCAGTCAATGCGGCT
AAAGGTATTTTAAACCAAACTCAAAGTCCGACAATGAGTGCTGATGTGATTGATCAAAAAGCTGAAGATGTTAAACGTAC
GAAAACTGCGTTAGATGGAAATCAAAGATTAGAAGTTGCTAAACAACAAGCACTTAATCATTTAAATACCTTAAATGATT
TAAACGATGCTCAGCGACAAACTTTAACTGATACTATAAATCACTCTCCAAACATCAATTCAGTGAATCAAGCTAAAGAA
AAAGCTAATACTGTTAACACAGCAATGACTCAACTGAAACAAACTATTGCTAACTATGACGATGAATTGCATGACGGCAA
TTACATTAATGCAGATAAAGACAAAAAAGATGCTTATAATAACGCTGTTAACAATGCTAAACAACTGATTAATCAATCTG
ATGCTAATCAAGCACAACTTGATCCAGCTGAAATTAATAAAGTTACACAAAGAGTCAATACGACTAAAAATGATCTAAAT
GGTAATGACAAATTGGCTGAAGCTAAAAGAGATGCTAATACAACCATTGATGGTTTAACTTATCTAAATGAAGCTCAACG
TAACAAAGCTAAAGAAAATGTAGGCAAAGCTTCTACAAAAACAAATATTACGAGTCAGTTACAAGATTACAATCAATTGA
```

Figure 2 cont.

```
ATATTGCTATGCAAGCATTACGTAACAGTGTGAACGACGTTAACAATGTTAAAGCAAATAGCAATTATATAAATGAAGAT
AATGGTCCAAAAGAAGCTTACAATCAAGCCGTTACTCATGCTCAAACATTGATAAATGCACAATCTAACCCTGAAATGAG
CCGTGACGTAGTAAATCAAAAAACACAAGCAGTAAATACTGCCCATCAGAATTTACATGGACAACAAAAGTTAGAACAAG
CACAAAGTAGTGCTAATACAGAAATCGGTAACTTACCAAACTTAACTAATACTCAAAAAGCTAAAGAAAAGGAACTGGTA
AATAGTAAACAAACTCGTACGGAAGTACAAGAACAACTTAACCAAGCTAAGTCACTAGATAGTTCTATGGGCACGTTAAA
ATCATTAGTTGCTAAACAACCTACAGTACAAAAAACAAGTGTTTATATTAACGAAGATCAACCTGAGCAATCTGCCTACA
ATGATTCCATTACAATGGGACAAACTATAATTAATAAAACAGCTGATCCAGTACTTGATAAAACTTTAGTTGATAACGCA
ATCAGTAACATTTCAACTAAAGAGAATGCACTGCATGGTGAACAAAAATTAACAACTGCTAAAACGGAAGCAATTAATGC
ACTTAATACATTAGCTGATTTAAACACACCTCAGAAAGAGGCTATTAAAACAGCTATTAACACTGCTCATACAAGAACTG
ATGTAACTGCAGAGCAAAGTAAGGCTAATCAAATAAATAGTGCAATGCACACGTTGAGACAAAACATTTCTGACAACGAA
TCAGTAACAAACGAAAGTAATTATATTAACGCTGAACCCGAAAAACAACATGCCTTTACTGAGGCTCTAAATAATGCTAA
AGAAATAGTTAATGAACAACAAGCCACTCTTGATGCCAATTCAATTAACCAAAAAGCACAAGCGATTCTTACTACTAAAA
ATGCTTTAGATGGTGAAGAACAATTACGTCGTGCTAAAGAAATGCCGATCAAGAAATCAATACGTTAAATCAATTGACT
GATGCGCAAAGAAATAGTGAAAAAGGTTTAGTCAACAGTTCTCAAACTAGAACAGAAGTTGCTTCTCAATTAGCAAAAGC
TAAAGAACTAAATAAGGTGATGGAACAACTGAATCACCTTATCAATGGTAAAAACCAAATGATAAATAGCAGTAAATTTA
TCAATGAAGATGCGAACCAACAACAAGCATATTCAAATGCGATTGCAAGTGCAGAAGCGCTTAAAAACAAATCACAAAAC
CCTGAATTAGATAAAGTAACAATTGAACAAGCAATTAATAATATTAATTCTGCAATTAACAATCTAAACGGTGAAGCTAA
ACTGACTAAAGCTAAAGAAGATGCTGTTGCTTCAATAAACAACCTAAGCGGATTAACAAACGAGCAAAAAACAAAAGAAA
ATCAAGCCGTTAATGGCGCTCAAACTAGAGACCAAGTTGCTAATAAATTACGTGATGCTGAAGCATTAGATCAATCAATG
CAAACATTACGTGACTTAGTTAACAATCAAAATGCAATACATTCAACAAGTAATTATTTTAACGAGGATTCAACTCAAAA
GAATACTTATGATAATGCAATTGATAATGGCTCGACATATATATAACTGGTCAACACAATCCAGAATTAAATAAATCTACTA
TTGATCAAACGATTAGCCGAATTAACACAGCTAAAAATGATTTTACATGGTGTAGAAAAGTTACAAAGAGATAAGGGAACT
GCTAATCAAGAAATTGGACAATTAGGTTATTTAAATGACCCTCAAAAATCTGGTGAGGAATCCTTAGTCAACGGTTCAAA
TACACGTTCTGAAGTAGAAGAGCATCTTAATGAAGCTAAATCATTAAATAATGCAATGAAACAATTAAGAGATAAAGTAG
CTGAAAAGACTAATGTCAAACAAAGTAGCGATTACATTAATGATTCAACTGAACATCAACGTGGGTATGATCAAGCACTT
CAAGAAGCAGAAAATATTATTAATGAAATCGGTAATCCAACATTAAATAAATCGGAAATTGAACAAAAGTTACAACAATT
GACTGACGCTCAAAATGCGTTACAAGGTTCACATCTATTAGAAGAAGCTAAAAATAATGCGATTACTGGAATCAATAAAC
TTACAGCATTAAATGATGCACAACGTCAAAAAGCAATTGAAAATGTTCAAGCACAGCAGACAATCCAGCAGTTAATCAA
CAATTAACTTTGGATAGAGAAATAAATACTGCAATGCAAGCTTTACGAGATAAAGTAGGCCAACAAATAACGTTCACCA
ACAAAGTAATTATTTCAATGAAGATGAACAACCAAAACATAACTATGATAATTCTGTACAAGCCGGTCAAACTATTATTG
ATAAACTTCAAGATCCAATCATGAACAAAAATGAAATTGAGCAGGCTATTAATCAAATCAATACGACTCAAACAGCGTTA
AGTGGAGAAAATAAATTACACACTGACCAAGAAGCACAAATAGACAATAGAAGGTTTATCTAGTTTGAACACAGCTCA
AATCAACGCCGAAAAAGATTTAGTCAATCAAGCTAAAACAAGAACAGATGTTGCTCAAAAGTTAGCTGCAGCTAAAGAAA
TAAATTCTGCTATGAGTAATTTAAGAGATGGCATTCAAAATAAAGAGGACATCAAACGTAGCAGTGCATATATCAACGCA
GATCCGACTAAAGTTACAGCTTACGATCAAGCACTACAGAACGCAGAAAATATCATCAATGCCACACCAAACGTAGAGCT
TAATAAAGCTACAATTGAACAAGCGCTATCACGCGTTCAACAAGCACAACAAGATCTTGATGGTGTTCAACAATTAGCTA
ATGCTAAACAACAAGCTACACAAACTGTCAATGGGTTAAATAGCTTAAATGACGGTCAAAAGCGTGAATTAAATCTATTA
ATTAATTCAGCTAATACCCGTACAAAAGTACAAGAAGAATTAAACAAAGCAACTGAATTGAACCATGCGATGGAAGCTTT
AAGAAACAGTGTTCAAAACGTTGATCAAGTAAAACAAAGTAGCAATTATGTCAATGAAGATCAACCTGAACAGCACAATT
ATGATAATGCTGTCAATGAAGCTCAAGCTACAATCAACAACAATGCTCAACCTGTTCTAGACAAATTAGCTATAGAACGT
TTAACTCAAACTGTTAACACTACAAAAGATGCATTACATGGTGCTCAAAAACTGACACAAGACCAACAAGCTGCTGAAAC
TGGAATACGTGGTTTAACGAGTCTCAATGAACCTCAGAAAAATGCTGAAGTAGCTAAAGTAACTGCAGCAACAACACGTG
ATGAAGTGAGAAATATTCGTCAAGAAGCAACAACATTAGATACTGCAATGCTTGGTTTACGTAAAAGCATTAAAGATAAA
AACGATACTAAAAATAGTAGTAAATATATTAATGAGGATCATGACCAACAACAAGCTTATGCAATGCTGTAAATAATGC
TCAACAAGTTATCGATGAAACTCAAGCAACGTTAAGCTCAGATACAATCAATCAATTGGCAAATGCCGTAACTCAAGCTA
AATCTAATCTTCATGGAGATACTAAACTACAACACGATAAAGATAGTGCTAAACAAACGATTGCTCAATTACAGAATTTG
AATTCAGCTCAAAAACATATGGAAGATTCTTTAATTGATAATGAATCTACACGTACGCAAGTCCAACACGATTTAACAGA
AGCTCAAGCTTTAGATGGTTTAATGGGTGCCTTAAAAGAAAGTATTAAAGATTATACTAATATTGTTTCAAACGGTAATT
ACATCAATGCGGAACCATCTAAGAAACAAGCATATGATGCAGCTGTACAAAATGCTCAAAATATAATAAATGGAACGAAT
CAACCAACAATTAATAAAGGTAATGTCACTACAGCAACACAAACCGTGAAAAATACTAAAGATGCCTTAGACGGTGATCA
TAGATTAGAGGAAGCTAAAAATAATGCCAATCAAACAATCAGAAATCTATCTAATTTGAACAATGCCCAAAAAGATGCAG
AGAAAAATCTAGTTAATAGCGCATCAACATTAGAACAAGTTCAACAAAACTTACAAACCGCTCAACAATTAGATAATGCT
ATGGGTGAGTTACGACAAAGTATTGCTAAAAAAGATCAAGTGAAAGCAGATAGTAAATATCTAAATGAAGATCCTCAAAT
TAAGCAAAACTATGATGATGCAGTTCAACGTGTTGAAACATTATTAACGAACACTCAAAACCCTGAATTACTTAAAGCAA
ACATTGACCAAGCAACTCAATCCGTTCAAAAATGCAGAACAAGCTTTACATGGTGCTGAAAATTAAATCAAGACAAACAA
ACGTCTTCGACAGAACTAGATGGATTAACAGATTTAACAGATGCACAACGTGAAAAACTCAGAGAACAAATTAACACTTC
TAATAGTAGAGATGATATTAAGCAAAAAATTGAGCAAGCAAAGCACTAAATGACGCAATGAAAAAACTTAAAGAACAAG
TTGCGCAAAAAGATGGTGTTCATGCTAACAGTGATTATACAAATGAAGATTCTGCACAAAAAGATGCGTATAATAATGCA
CTTAAACAAGCGGAAGACATTATTAATAACAGCTCAAATCCTAACTTAAATGCACAAGACATTACTAATGCTTTAAATAA
```

Figure 2 cont.

```
TATTAAACAAGCACAAGATAACCTTCATGGAGCTCAAAAATTACAGCAAGACAAAAATACAACTAATCAAGCCATTGGTA
ACTTAAATCATCTTAATCAACCTCAAAAAGATGCGCTTATACAAGCTATTAATGGAGCTACATCTAGGGACCAAGTTGCA
GAAAAACTTAAAGAGGCCGAAGCGCTTGATGAAGCTATGAAACAACTTGAAGATCAAGTGAATCAAGATGATCAAATTTC
AAATAGCAGCCCATTCATAAATGAAGACTCAGACAAACAAAAAACTTATAATGATAAATCCAAGCTGCAAAAGAAATAA
TTAATCAAACATCTAATCCAACCTTAGATAAACAAAAAATTGCTGATACACTTCAAAATATTAAAGATGCAGTGAATAAT
TTACATGGTGATCAAAAATTAGCTCAATCTAAACAAGATGCTAATAATCAATTAAATCATTTAGATGACTTAACCGAAGA
ACAAAAAAACCATTTTAAACCGTTAATTAATAATGCTGATACTCGAGATGAGGTAAATAAACAACTAGAGATTGCTAAAC
AATTAAATGGTGATATGAGTACACTTCATAAAGTCATAAATGATAAAGATCAAATTCAACATTTAAGCAATTACATTAAT
GCTGATAATGATAAAAAACAAAATTATGATAATGCTATTAAAGAAGCTGAGGATTTAATTCATAATCATCCAGATACATT
AGATCATAAAGCATTACAAGATTTATTAAACAAGATAGACCAAGCGCATAACGAATTAAATGGAGAATCCAGATTTAAAC
AGGCTTTAGACAATGCTTTAAACGACATAGATAGCTTAAACAGTCTCAATGTTCCACAACGCCAAACTGTTAAGGATAAC
ATCAACCATGTGACAACTCTAGAAAGTTTAGCTCAAGAATTGCAGAAAGCAAAAGAGCTTAATGATGCTATGAAAGCAAT
GAGAGATAGCATTATGAATCAAGAGCAAATTCGTAAAAATAGCAATTATACTAATGAAGACTTAGCTCAACAAAATGCCT
ATAATCATGCAGTAGATAAAATAAATAACATTATTGGTGAAGACAATGCGACGATGGATCCTCAAATAATCAAACAAGCA
ACTCAAGATATAAATACAGCTATAAATGGATTAAATGGAGATCAAAAACTTCAAGATGCAAAGACAGATGCTAAACAACA
AATTACTAACTTTACTGGTTTAACTGAACCACAAAAACAAGCATTGGAAAACATCATTAACCAACAAACAAGCAGAGCAA
ATGTTGCTAAACAGTTAAGTCATGCTAAATTCTTAAATGGAAAAATGGAAGAATTAAAAGTTGCAGTAGCCAAAGCGTCA
TTAGTAAGACAAAATAGTAACTATATTAATGAAGATGTCTCTGAAAAAGAAGCATATGAACAAGCTATCGCAAAAGGTCA
GGAAATAATTAATTCAGAAAATAATCCAACAATAAGTAGTACTGATATCAATCGTACCATTCAAGAAATTAATGATGCTG
AACAAAATCTTCATGGTGATAATAAATTAAGACAAGCACAGGAAATTGCAAAGAATGAAATACAAAATCTAGACGGATTA
AATTCAGCTCAAATAACAAAATTAATCCAAGATATAGGCAGAACAACAACTAAACCTGCAGTAACTCAGAAACTAGAAGA
AGCAAAAGCAATAAACCAAGCTATGCAACAACTTAAACAAAGTATAGCCGATAAGGATGCTACTCTAAATTCTAGTAACT
ATCTCAATGAAGATTCTGAGAAAAAGTTAGCGTACGATAATGCTGTAAGCCAAGCTGAACAACTCATAAATCAACTTAAC
GACCCAACTATGGATATAAGTAATATTCAAGCTATTACTCAAAAGGTCATTCAAGCAAAGATTCATTGCACGGTGCGAA
TAAACTTGCACAAAATCAAGCAGATTCAAATTTAATAATAAATCAATCAACAAATTTAAATGATAAACAAAAGCAAGCAT
TAAATGACTTAATTAATCATGCTCAAACTAAACAGCAAGTGGCAGAAATAATTGCACAAGCTAATAAGTTAAATAACGAA
ATGGGCACACTAAAAACACTCGTAGAAGAACAGTCAAACGTTCATCAACAAAGTAAATATATTAATGAAGATCCGCAAGT
TCAAAATATTTATAATGACTCCATTCAAAAAGGTCGAGAAATATTAAACGGCACTACAGATGATGTTTTAAACAACAATA
AAATAGCAGATGCCATTCAAAACATTCATTTAACTAAAAACGATTTACATGGTGATCAAAAATTACAAAAAGCACAACAA
GATGCAACCAATGAATTAAACTATTTAACAAATCTAAACAATTCTCAAAGACAAAGCGAGCATGATGAGATTAACTCTGC
TCCTTCAAGAACTGAAGTTTCTAATGATTTAAATCATGCTAAAGCACTTAATGAAGCTATGCGTCAACTTGAGAATGAAG
TTGCTCTTGAAAACAGTGTTAAAAAATTAAGCGACTTTATCAATGAAGATGAAGCGGCACAAAATGAATATAGTAATGCA
CTTCAAAAAGCTAAAGACATTATCAACGGCGTTCCAAGTAGCACTTTAGATAAAGCTACAATTGAAGATGCTTTATTAGA
ATTGCAAAATGCTAGAGAAAGTTTACATGGTGAGCAAAAACTTCAAGAGGCTAAAAATCAAGCTGTTGCTGAAATTGATA
ATTTACAAGCATTAAATCCTGGACAGGTTCTTGCTGAAAAAACATTAGTTAACCAAGCATCAACCAAACCAGAAGTTCAA
GAAGCCTTACAAAAAGCAAAAGAACTTAATGAAGCTATGAAAGCACTGAAAACTGAAATAAATAAAAAGAACAAATCAA
GGCTGATAGTAGATATGTAAATGCTGACAGTGGTCTTCAAGCAAATTACAATTCTGCGTTAAATTATGGTTCTCAAATTA
TTGCAACTACCCAACCACCAGAGCTTAATAAAGATGTAATAAATAGAGCAACTCAAACGATTAAAACTGCTGAAAATAAT
TTAAATGGGCAATCTAAATTAGCAGAGGCTAAGTCAGACGGAAATCAAAGCATCGAACATTTGCAAGGATTAACACAATC
ACAAAAAGATAAACAACATGATTTAATTAATCAAGCTCAAACTAAACAACAGGTAGATGATATCGTAAATAACTCTAAAC
AATTAGATAACTCTATGAATCAACTACAACAAATTGTTAACAATGACAATACAGTAAAACAAAATAGTGATTTCATTAAT
GAAGATTCCAGCCAACAGGATGCTTATAATCATGCAATTCAAGCAGCAAAAGATTTGATAACTGCTCATCCAACTATCAT
GGATAAAAATCAAATAGATCAAGCTATTGAAAATATCAACAAGCACTTAATGATTTACACGGTAGTAATAAACTATCAG
AAGATAAAAAAGAAGCTTCAGAACAACTACAAAACCTTAATAGCTTGACGAACGGGCAAAAGATACGATTTTAAATCAT
ATTTTCAGTGCACCAACAAGAAGCCAAGTAGGAGAAAAAATTGCAAGTGCTAAACAATTAAATAATACAATGAAAGCACT
TAGAGATTCTATTGCTGATAATAATGAAATTTTACAAAGTAGTAAGTACTTCAATGAAGATTCTGAACAACAAAATGCTT
ATAATCAAGCCGTAAATAAAGCTAAAAATATAATTAATGATCAACCAACACCAGTAATGGCAAATGATGAGATTCAAAGT
GTCCTAAATGAAGTTAAACAAACTAAAGATAATTTACATGGTGATCAAAAACTTGCTAACGACAAGACAGATGCTCAAGC
AACATTAAATGCGTTAAATTACTTAAATCAAGCGCAAAGAGGTAATCTTGAAACTAAAGTTCAAAACTCTAATTCTAGAC
CAGAAGTACAAAAAGTAGTTCAATTAGCAAATCAACTTAATGATGCGATGAAAAAATTAGATGATGCTTTAACTGGTAAT
GACGCAATAAAACAAACGAGTAATTATATTAATGAAGATACTTCTCAACAAGTTAACTTTGATGAGTATACAGATAGAGG
TAAAAACATAGTTGCTGAACAAACAAATCCAAATATGTCTCCAACTAATATTAACACTATTGCTGATAAAATTACTGAAG
CTAAAAACGATTTACATGGCGTACAAAAACTAAAACAAGCTCAACAACAGTCCATCAATACTATTAATCAAATGACTGGT
CTAAACCAAGCTCAAAAAGAACAATTAAATCAAGAAATTCAACAAACTCAAACCCGTTCTGAAGTACATCAAGTAATTAA
TAAAGCACAAGCTTTAAATGATTCAATGAATACTTTACGTCAAAGTATTACTGATGAACATGAAGTTAAACAAACAAGTA
ACTACATCAATGAAACTGTTGGTAATCAAACTGCATATAACAATGCCGTTGATCGTGTAAAACAAATAATCAATCAAACA
TCTAATCCAACTATGAATCCTTTAGAGGTGGAACGTGCAACATCAAATGTAAAAATTTCTAAAGATGCACTTCATGGTGA
ACGTGAATTGAATGACAATAAAAATTCAAAAACTTTTGCAGTCAATCACTTAGATAACCTCAATCAAGCTCAAAAAGAAG
CATTAACTCATGAAATTGAACAAGCAACTATAGTTTCACAAGTAAATAATATCTATAACAAAGCGAAAGCTTTAAATAAT
```

Figure 2 cont.

```
GATATGAAAAAACTTAAAGATATCGTTGCTCAACAAGATAATGTGAGACAATCAAACAATTATATAAACGAGGATAGTAC
ACCTCAAAATATGTACAACGATACAATTAATCATGCACAATCAATCATTGATCAAGTAGCAAACCCTACGATGTCTCATG
ACGAAATAGAGAATGCAATCAATAACATAAAGCATGCCATCAATGCACTCGATGGAGAACATAAATTACAACAAGCAAAA
GAAAATGCAAACTTATTGATTAATAGTTTAAACGATTTAAATGCACCACAAAGAGATGCCATAAATAGATTGGTTAATGA
AGCTCAAACAAGAGAAAAAGTAGCTGAACAACTTCAAAGTGCTCAAGCTTTAAATGACGCTATGAAGCATTTAAGAAACA
GCATTCAAAATCAATCATCCGTAAGACAAGAGAGCAAATATATTAATGCAAGTGATGCTAAAAAAGAGCAATATAATCAC
GCAGTTAGAGAAGTCGAAAATATTATCAATGAACAACATCCAACATTGGATAAAGAAATAATTAAGCAACTAACGGATGG
TGTAAATCAAGCGAATAATGACTTAAATGGCGTTGAATTATTAGATGCTGATAAGCAAAACGCACATCAATCGATACCTA
CATTGATGCACTTAAATCAAGCACAACAAAACGCATTAAATGAAAAAATTAATAACGCAGTTACCAGAACTGAAGTTGCG
GCTATTATTGGCCAAGCAAAACTACTCGATCATGCTATGGAGAATTTAGAAGAAAGTATCAAAGATAAAGAGCAAGTCAA
ACAGTCAAGTAACTATATTAATGAAGATTCTGATGTTCAAGAAACATACGATAACGCCGTTGATCATGTGACAGAAATAC
TTAATCAAACAGTAAATCCAACTTTATCTATTGAAGATATAGAGCATGCTATCAACGAAGTTAATCAAGCGAAAAAACAA
CTCAGAGGTAAACAAAAACTTTATCAAACTATCGATTTAGCTGATAAAGAATTAAGTAAATTGGATGATTTAACATCACA
ACAAAGCAGTTCAATATCTAATCAAATATATACTGCTAAAACGAGAACAGAAGTTGCCCAAGCAATTGAAAAAGCAAAAT
CATTAAATCATGCAATGAAAGCACTTAACAAAGTATATAAAAATGCAGATAAAGTGTTAGATAGTAGTCGATTCATTAAC
GAAGATCAACCTGAAAAAAAGGCGTATCAACAAGCTATAAATCATGTTGATTCAATCATTCATAGACAAACAAATCCTGA
AATGGATCCAACAGTAATCAATAGCATAACTCATGAACTCGAAACAGCTCAAAATAACTTACATGGTGATCAGAAACTTG
CTCATGCACAACAAGATGCCGCTAATGTAATTAATGGTCTAATTCATCTTAATGTTGCTCAACGTGAGGTAATGATAAAT
ACGAATACAAATGCTACAACACGCGAAAAAGTTGCAAGACTTAGATAATGCTCAAGCTCTTGATAAAGCTATGGAAAC
ACTACAACAAGTAGTTGCTCATAAAAATAATATATTGAACGATAGTAAATATTTAAATGAAGATTCAAAATATCAACAAC
AATACGATCGAGTTATTGCTGATGCCGAACAACTACTTAATCAGACAACAAATCCAACATTAGAACCTTATAAAGTCGAT
ATTGTTAAGGATAATGTCCTAGCTAACGAAAAAATACTATTTGGCGCAGAAAAACTATCATATGACAAATCAAATGCAAA
TGATGAAATTAAACATATGAATTATCTTAATAATGCACAAAAGCAATCTATAAAAGATATGATTTCTCACGCAGCATTAA
GAACTGAAGTTAAACAACTTCTGCAACAAGCTAAAATCCTTGATGAAGCCATGAAATCACTTGAAGATAAAACTCAAGTA
GTGATTACAGATACTACTTTGCCTAATTACACTGAAGCTTCAGAGGATAAAAGGAAAAAGTAGACCAAACTGTATCACA
TGCTCAAGCGATTATTGATAAAATAAATGGCTCAAATGTAAGTTTAGATCAAGTACGACAAGCACTAGAACAATTAACTC
AAGCATCAGAAAACCTCGATGGTGATCAGCGAGTTGAAGAAGCTAAAGTTCATGCTAATCAAACAATTGATCAATTAACA
CATCTTAATTCATTACAACAACAAACTGCGAAAGAAAGTGTTAAAAACGCAACAAAACTAGAAGAAATCGCTACTGTTAG
TAACAATGCTCAGGCATTAAACAAAGTAATGGGTAAATTAGAACAATTCATTAATCATGCTGATTCTGTTGAAAATAGTG
ATAATTATAGACAAGCCGACGACGACAAAATCATCGCTTATGATGACGCACTTGAACATGGACAAGATATACAAAAAACT
AACGCAACCCAAAATGAAACAAAACAAGCGTTACAACAATTAATATATGCAGAAACATCGTTAAATGGTTTCGAAAGATT
AAATCATGCTAGACCACGAGCTTTAGAATATATCAAATCACTAGAAAAAATAAACAATGCTCAAAAGTCTGCTTTAGAGG
ATAAAGTAACGCAATCGCATGATTTATTAGAATTAGAACATATTGTCAACGAGGGCACAAACCTCAATGACATTATGGGT
GAATTAGCTAACGCAATCGTTAATAACTATGCTCCAACCAAAGCAAGTATAAATTATATTAACGCCGATAACCTACGCAA
AGATAACTTTACTCAAGCTATCAACAATGCACGTGATGCACTCAACAAAACTCAAGGTCAGAACTTAGATTTCAATGCAA
TTGATACATTTAAAGATGATATATTCAAAACTAAAGATGCACTTAACGGTATTGAACGTTTAACAGCTGCAAAATCAAAA
GCAGAAAAACTAATTGATAGTTTAAAATTTATTAATAAAGCTCAATTCACACATGCAAATGATGAAATTATGAATACTAA
TTCTATTGCACAATTGTCTAGAATCGTGAATCAAGCATTTGATTTAAATGATGCAATGAAATCTTTAAGAGATGAACTTA
ATAATCAAGCTTTTCCTGTCCAAGCAAGCTCAAATTATATAAATTCAGATGAAGATTTAAAACAACAATTTGACCATGCT
TTAAGTAATGCTCGAAAAGTTCTTGCAAAAGAAAATGGTAAAAATTTAGATGAAAAACAAATTCAGGGACTCAAACAAGT
GATTGAGGATACTAAAGATGCTTTAAATGGTATCCAACGTTTATCAAAAGCTAAAGCTAAAGCAATTCAATACGTACAAT
CTTTATCTTATATCAATGATGCACAGCGTCATATTGCTGAAAATAATATTCACAACTCTGATGATTTATCATCTTTAGCA
AATACATTATCTAAAGCTAGTGATTTAGATAATGCAATGAAAGACTTACGAGATACTATAGAAAGTAATTCAACTTCTGT
TCCAAATAGTGTGAATTATATTAATGCTGATAAGAATTTACAAATTGAATTTGATGAGGCGCTACAACAAGCAAGTGCAA
CAAGTTCTAAAACTTCAGAAAATCCAGCAACGATTGAAGAAGTATTAGGTCTTAGTCAAGCCATTTACGATACAAAAAAT
GCATTAAATGGTGAACAACGACTTGCAACTGAGAAGAGCAAAGATCTAAAATTAATAAAAGGATTAAAAGATTTAAATAA
AGCACAACTTGAAGATGTCACAAACAAGGTAAATTCAGCAAATACTTTAACAGAGTTATCTCAGCTCACTCAATCAACGT
TAGAATTAAACGATAAAATGAAATTATTGAGAGATAAGCTTAAAACTTTAGTAAATCCTGTTAAAGCAAGTTTAAATTAT
AGAAACGCTGATTATAATTTAAAACGTCAATTTAACAAAGCTTTAAAAGAAGCTAAAGGCGTATTAAATAAAAATAGCGG
TACAAATGTCAATATCAATGACATTCAACATCTTTTAACACAAATAGATAATGCTAAAGACCAATTAAATGGTGAACGAC
GTCTAAAAGAACATCAACAAAAATCTGAAGTATTTATTATTAAAGAATTAGATATACTTAATAATGCTCAAAAAGCTGCA
ATAATTAATCAGATTAGAGCGTCTAAAGACATTAAAATAATTAATCAAATCGTTGATAATGCAATAGAATTAAATGATGC
TATGCAAGGTTTAAAAGAACATGTAGCTCAATTAACAGCAACTACAAAAGACAACATTGAATATTTAAATGCTGATGAAG
ACCATAAATTACAATATGATTACGCTATCAACTTAGCGAATAATGTTCTTGACAAAGAAAACGGTACAAATAAAGACGCT
AATATCATAATTGGAATGATTCAAAACATGGATGATGCTAGAGCACTTCTAAATGGAATTGAAAGACTTAAAGATGCTCA
AACAAAAGCACATAATGACATTAAAGATACGCTCAAACGTCAACTTGATGAAATTGAACACGCTAATGCAACATCAAATT
CTAAAGCTCAAGCTAAACAAATGGTAAATGAGGAAGCTAGAAAAGCGCTTTCTAATATTAATGACGCAACATCAAATGAT
TTAGTTAATCAAGCAAAAGATGAAGGGCAATCTGCAATTGAACACATCATGCAGATGAATTACCTAAAGCAAAACTAGA
TGCTAATCAAATGATTGACCAAAAAGTTGAAGATATAAATCACTTAATTAGTCAAAATCCAAACTTATCAAATGAAGAAA
```

Figure 2 cont.

```
AAAATAAACTAATATCTCAAATTAATAAGTTAGTAAATGGAATTAAGAATGAAATTCAACAAGCTATAAACAAACAACAA
ATAGAAAATGCTACAACAAAACTAGATGAAGTCATTGAAACTACTAAAAAATTAATTATCGCCAAAGCAGAAGCTAAACA
AATGATAAAAGAGTTATCACAAAAGAAACGAGATGCAATAAATAACAACACTGATTTAACACCTTCTCAAAAGGCACATG
CTTTAGCAGATATTGATAAAACAGAAAAAGATGCACTTCAACATATCGAAAATTCTAATTCAATTGATGATATCAATAAC
AATAAAGAGCATGCATTTAATACTTTAGCTCATATCATTATTTGGGATACTGATCAGCAACCATTAGTTTTTGAACTACC
TGAATTGAGCCTTCAAAATGCTCTAGTAACAAGTGAGGTGGTTGTTCACAGAGATGAAACTATTTCATTAGAATCTATAA
TTGGAGCTATGACTTTAACTGATGAACTTAAAGTCAATATTGTTTCATTACCGAACACTGATAAAGTAGCTGATCACCTA
ACCGCTAAAGTTAAGGTTATTTTAGCTGATGGCTCATATGTCACTGTAAATGTTCCAGTCAAAGTTGTAGAAAAAGAATT
ACAAATAGCTAAAAAGGATGCTATAAAAACAATTGATGTTCTGGTAAAACAAAAAATCAAAGATATAGATTCTAATAACG
AATTAACGTCTACTCAACGTGAAGATGCAAAAGCTGAAATTGAAAGATTGAAAAAGCAAGCCATCGATAAAGTGAATCAT
TCAAATCGATTAAAGATATTGAAACAGTAAACGAACTGATTTTGAAGAAATAGATCAGTTTGATCCTAAACGCTTTAC
GCTAAATAAAGCTAAAAAGGATATCATTACTGATGTTAATACTCAAATCCAAAATGGTTTCAAAGAAATTGAAACAATAA
AAGGTTTAACTTCTAATGAAAAAACTCAGTTTGATAAACAATTAACTGCACTACAAAAGAATTTTTAGAAAAAGTCGAG
CATGCTCATAATTTAGTAGAATTAAATCAATTACAACAAGAGTTTAATAATAGATATAAACATATTTTAAACCAAGCACA
TTTACTAGGTGAAAAACATATAGCAGAACATAAATTAGGATATGTTGTAGTAAACAAAACTCAGCAAATACTAAATAATC
AATCTGCTTCTTACTTTATAAAACAATGGGCACTTGATAGAATTAAACAAATTCAACTAGAAACGATGAATTCAATTCGT
GGTGCGCATACCGTACAAGATGTACACAAAGCATTATTACAAGGTATAGAGCAAATCTTGAAAGTAAATGTAAGTATTAT
AAATCAATCTTTCAACGATTCCTTGCATAACTTTAATTATCTTCATTCAAAATTTGATGCTAGATTAAGAGAAAAGGATG
TTGCAAACCATATCGTACAAACTGAAACATTCAAAGAAGTTCTAAAAGGAACGGGTGTTGAACCAGGTAAAATCAACAAA
GAAACACAGCAACCAAAACTTCATAAGAATGATAATGATAGCCTATTCAAACATTTAGTTGATAATTTCGGCAAAACTGT
AGGTGTTATTACATTAACTGGTTTACTTTCTAGTTTCTGGTTAGTTTTGGCTAAAAGACGTAAAAAAGAAGAAGAAGAAA
AACAATCGATAAAAAATCATCACAAAGATATTCGTCTTTCAGATACTGATAAAATAGATCCAATTGTAATAACTAAGCGT
AAAATAGATAAAGAAGAACAAATTCAAAACGATGACAAACATTCAATTCCAGTTGCTAAACATAAGAAATCTAAAGAAAA
GCAATTGAGTGAAGAGGATATTCATTCAATCCCCGTCGTTAAGCGTAAACAAAACAGTGATAACAAAGATACAAAACAGA
AGAAAGTTACTTCTAAAAAGAAGAAAACGCCTCAGTCAACTAAAAAAGTTGTAAAAACCAAAAAGCGTTCTAAAAAG
```

SEQ ID NO:49 polynucleotide sequence
```
ATGAGAGATAAGAAAGGACCGGTAAATAAAGAGTAGATTTTCTATCAAATAAATTGAATAAATATTCAATAAGAAAATT
TACAGTTGGAACAGCATCTATTTTAATTGGCTCACTAATGTATTTGGGAACTCAACAAGAAGCAGAAGCAGCTGAAAACA
ATATTGAGAATCCAACTACATTAAAAGATAATGTCCAATCAAAAGAAGTGAAGATTGAAGAAGTAACAAACAAAGACACT
GCACCACAAGGTGTAGAAGCTAAATCTGAAGTAACTTCAAACAAAGACACAATCGAACATGAAGCATCAGTAAAAGCTGA
AGATATATCAAAAAAGGAGGATACACCAAAAGAAGTAGCTAATGTTGCTGAAGTTCAGCCGAAATCGTCAGTCACTCATA
ACGCAGAGGCACCTAAGGTTAGAAAAGCTCGTTCTGTTGATGAAGGCTCTTTTGATATTACAAGAGATTCTAAAAATGTA
GTTGAATCTACCCCAATTACAATTCAAGGTAAAGAACATTTTGAAGGTTACGGAAGTGTTGATATACAAAAAAACCCAAC
AGATTTAGGGGTATCAGAGGTAACCAGGTTTAATGTTGGTAATGAAAGTAATGGTTTGATAGGAGCTTTACAATTAAAAA
ATAAAATAGATTTTAGTAAGGATTTCAATTTTAAAGTTAGAGTGGCAAATAACCATCAATCAAATACCACAGGTGCTGAT
GGTTGGGGGTTCTTATTTAGTAAAGGAAATGCAGAAGAATATTGTAATAATGGTGGAATCCTTGGGGATAAAGGTCTGGT
AAATTCAGGCGGATTTAAAATTGATACTGGATACATTTATACAAGTTCCATGGACAAAACTGAAAAGCAAGCTGGACAAG
GTTATAGAGGATACGGAGCTTTTGTGAAAAATGACAGTTCTGGTAATTCACAAATGGTTGGAGAAAATATTGATAAATCA
AAAACTAATTTTTTAAACTATGCGGACAATTCAACTAATACATCAGATGGAAAGTTTCATGGGCAACGTTTAAATGATGT
CATCTTAACTTATGTTGCTTCAACTGGTAAAATGAGAGCAGAATATGCTGGTAAAACTTGGGAGACTTCAATAACAGATT
TAGGTTTATCTAAAAATCAGGCATATAATTTCTTAATTACATCTAGTCAAAGATGGGGCCTTAATCAAGGGATAAATGCA
AATGGCTGGATGAGAACTGACTTGAAAGGTTCAGAGTTTACTTTTACACCAGAAGCGCCAAAAACAATAACAGAATTAGA
AAAAAAAGTTGAAGAGATTCCATTCAAGAAAGAACGTAAATTTAATCCGGATTTAGCACCAGGGACAGAAAAAGTAACAA
GAGAAGGACAAAAAGGTGAGAAGACAATAACAACACCAACACTAAAAAATCCATTAACTGGAGAAATTATTAGTAAAGGT
GAATCGAAAGAAGAGATCACAAAAGATCCGATTAATGAATTAACAGAATACGGACCAGAAACGATAGCACCAGGTCATCG
AGACGAATTTGATCCGAAGTTACCAACAGGAGAGAAAGAAGAAGTTCCAGGTAAACCAGGAATTAAGAATCCAGAACAG
GAGACGTAGTTAGACCACCGGTCGATAGTGTGAACAAAATATGGACCTGTAAAAGGAGACTCGATTGTAGAAAAGAAGAA
ATTCCATTCGAGAAAGAACGTAAATTTAATCCTGATTTAGCACCAGGAACAGAAAAAGTAACAAGAGAAGGACAAAAAGG
TGAGAAGACAATAACGACACCAACACTAAAAAATCCATTAACTGGAGAAATTATTAGTAAAGGTGAATCGAAAGAAGAGA
TCACAAAAGATCCGATTAATGAATTAACAGAATACGGACCTGAAACAATAGCGCCAGGTCATCGAGACGAATTTGATCCG
AAGTTACCAACAGGAGAGAAGAAGAAGTTCCAGGTAAACCAGGAATTAAGAATCCAGAAACAGGAGACGTAGTTAGACC
GCCGGTCGATAGCGTAACAAAATATGGACCTGTAAAAGGAGACTCGATTGTAGAAAAGAAGAAATTCCATTCAAGAAAG
AACGTAAATTTAATCCTGATTTAGCACCAGGGACAGAAAAAGTAACAAGAGAAGGACAAAAAGGTGAGAAGACAATAACG
ACGCCAACACTAAAAAATCCATTAACTGGAGAAATTATTAGTAAAGGTGAATCGAAAGAAGAAATCACAAAAGATCCGAT
TAATGAATTAACAGAATACGGACCAGAAACGATAACACCAGGTCATCGAGACGAATTTGATCCGAAGTTACCAACAGGAG
AGAAAGAGGAAGTTCCAGGTAAACCAGGAATTAAGAATCCAGAAACAGGAGATGTAGTTAGACCACCGGTCGATAGCGTA
ACAAAATATGGACCTGTAAAAGGAGACTCGATTGTAGAAAAGAAGAAATTCCATTCGAGAAAGAACGTAAATTTAATCC
```

Figure 2 cont.

TGATTTAGCACCAGGGACAGAAAAAGTAACAAGAGAAGGACAAAAAGGTGAGAAGACAATAACGACGCCAACACTAAAAA
ATCCATTAACTGGAGAAATTATTAGTAAAGGTGAATCGAAAGAAGAAATCACAAAAGATCCAGTTAATGAATTAACAGAA
TTCGGTGGCGAGAAAATACCGCAAGGTCATAAAGATATCTTTGATCCAAACTTACCAACAGATCAAACGGAAAAAGTACC
AGGTAAACCAGGAATCAAGAATCCAGACACAGGAAAAGTGATCGAAGAGCCAGTGGATGATGTGATTAAACACGGACCAA
AAACGGGTACACCAGAAACAAAAACAGTAGAGATACCGTTTGAAACAAAACGTGAGTTTAATCCAAAATTACAACCTGGT
GAAGAGCGAGTGAAACAAGAAGGACAACCAGGAAGTAAGACAATCACAACACCAATCACAGTGAACCCATTAACAGGTGA
AAAAGTTGGCGAGGGTCAACCAACAGAAGAGATCACAAAACAACCAGTAGATAAGATTGTAGAGTTCGGTGGAGAGAAAC
CAAAAGATCCAAAAGGACCTGAAAACCCAGAGAAGCCGAGCAGACCAACTCATCCAAGTGGCCCAGTAAATCCTAACAAT
CCAGGATTATCGAAAGACAGAGCAAAACCAAATGGCCCAGTTCATTCAATGGATAAAAATGATAAAGTTAAAAAATCTAA
AATTGCTAAAGAATCAGTAGCTAATCAAGAGAAAAAACGAGCAGAATTACCAAAAACAGGTTTAGAAAGCACGCAAAAAG
GTTTGATCTTTAGTAGTATAATTGGAATTGCTGGATTAATGTTATTGGCTCGTAGAAGAAAGAATTAA

SEQ ID NO:50 polynucleotide sequence
ATGGGCAAACGTAGACAAGGTCCTATTAATAAAAAGTGGATTTTTTACCTAACAAATTAAACAAGTATTCTATAAGAAA
ATTCACTGTTGGTACGGCCTCAATATTACTTGGTTCGACACTTATTTTTGGAAGTAGTAGCCATGAAGCGAAAGCTGCAG
AAGAAAAACAAGTTGATCCAATTACACAAGCTAATCAAAATGATAGTAGTGAAAGATCACTTGAAAACACAAATCAACCT
ACTGTAAACAATGAAGCACCACAGATGTCTTCTACATTGCAAGCAGAAGAAGGAAGCAATGCAGAAGCACCGAATGTTCC
AACTATCAAAGCTAATTCAGATAATGATACACAAACACAATTTTCAGAAGCCCCTACAAGAAATGACCTAGCTAGAAAAG
AAGATATCCCTGCTGTTTCTAAAAACGAGGAATTACAATCATCACAACCAAACACTGACAGTAAAATAGAACCTACAACT
TCAGAACCTGTGAATTTAAATTATAGTTCTCCGTTTATGTCCTTATTAAGCATGCCTGCTGATAGTTCATCCAATAACAC
TAAAAATACAATAGATATACCGCCAACTACGGTTAAAGGTAGAGATAATTACGATTTTTACGGTAGAGTAGATATCCAAA
GTAATCCTACAGATTTAAATGCGACAAATTTAACGAGATATAATTATGGACAGCCACCTGGTACAACAACAGCTGGTGCA
GTTCAATTTAAAAATCAAGTTAGTTTTGATAAAGATTTCGACTTTAACATTAGAGTAGCAAACAATCGTCAAAGTAATAC
AACTGGTGCAGATGGTTGGGGCTTTATGTTCAGCAAGAAAGATGGGGATGATTTCCTAAAAAACGGTGGTATCTTACGTG
AAAAAGGTACACCTAGTGCAGCTGGTTTCAGAATTGATACAGGATATTATAATAACGATCCATTAGATAAAATACAGAAA
CAAGCTGGTCAAGGCTATAGAGGGTATGGGACATTTGTTAAAAATGACTCCCAAGGTAATACTTCTAAAGTAGGATCAGG
TACTCCATCAACAGATTTTCTTAACTACGCAGATAATACTACTAATGATTTAGATGGTAAATTCCATGGTCAAAAATTAA
ATAATGTTAATTTGAAATATAATGCTTCAAATCAAACTTTTACAGCTACTTATGCTGGTAAAACTTGGACGGCTACGTTA
TCTGAATTAGGATTGAGTCCAACTGATAGTTACAATTTTTTAGTTACATCAAGTCAATATGGAAATGGTAATAGTGGTAC
ATACGCAGATGGCGTTATGAGAGCTGATTTAGATGGTGCAACATTGACATATACTCCTAAAGCAGTCGATGGAGACCCAA
TTACATCAACTAAGGAAATACCATTTAATAAAAAACGCGAATTTGATCCAAACTTAGCGCCAGGTACAGAAAAGTCGTT
CAAAAAGGTGAACCAGGAATTGAAACAACAACAACACCAACTTATGTCAATCCTAATACTGGAGAAAAAGTAGGTGAAGG
CACACCTACAACAAAGATCACTAAACAACCAGTGGATGAAATCGTTCATTATGGTGGCGAAGAAATCAAGCCAGGACATA
AAGATGAATTTGATCCAAATGCACCGAAAGGTAGTCAAACAACGCAACCAGGTAAGCCAGGAGTTAAAAATCCTGATACA
GGCGAAGTAGTCACACCACCAGTGGATGATGTGACAAAATATGGTCCAGTTGATGGAGATCCGATTACGTCAACGGAAGA
AATTCCATTCGACAAGAAACGTGAATTCAATCCTGATTTAAAACCAGGTGAAGAGCGTGTTAAACAAAAGGTGAACCAG
GAACAAAAACAATTACAACACCAACAACTAAGAACCCATTAACAGGGGAAAAAGTTGGCGAAGGTGAACCAACAGAAAAA
ATAACAAAACAACCAGTAGATGAAATCACAGAATATGGTGGCGAAGAAATCAAGCCAGGCCATAAGGATGAATTTGATCC
GAACGCACCGAAAGGTAGCCAAGAGGACGTTCCAGGTAAACCAGGAGTTAAAAATCCTGATACAGGCGAAGTAGTCACAC
CACCAGTGGATGATGTGACAAAATATGGTCCAGTTGATGGAGATCCGATTACGTCAACGGAAGAAATTCCGTTTGATAAA
AAACGCGAATTTGATCCAAACTTAGCGCCAGGTACAGAGAAAGTCGTTCAAAAAGGTGAACCAGGAACAAAAACAATTAC
AACACCAACAACTAAGAACCCATTAACAGGAGAAAAAGTTGGCGAAGGTGAACCAACAGAAAAAATAACAAAACAACCAG
TGGATGAAATCGTTCATTATGGTGGCGAAGAAATCAAGCCAGGCCATAAGGATGAATTTGATCCGAACGCACCGAAAGGT
AGCCAAGAGGACGTTCCAGGTAAGCCAGGAGTTAAAAATCCTGATACAGGCGAAGTAGTCACACCACCAGTGGATGATGT
GACAAAATATGGTCCAGTTGATGGAGATCCGATTACGTCAACGGAAGAAATTCCATTCGACAAGAAACGTGAATTCAATC
CTGATTTAAAACCAGGTGAAGAGCGTGTTAAACAAAAGGTGAACCAGGAACAAAAACAATTACAACACCAACAACTAAG
AACCCATTAACAGGGGAAAAAGTTGGCGAAGGTGAACCAACAGAAAAAGTAACAAAACAACCAGTGGATGAAATCGTTCA
TTATGGTGGCGAAGAAATCAAGCCAGGCCATAAGGATGAATTTGATCCAAATGCACCGAAAGGTAGCCAAGAAGACGTTC
CAGGTAAACCAGGAGTTAAAAACCCTGATACAGGCGAAGTAGTTACTCCACCAGTGGATGATGTGACAAAATATGGTCCA
GTTGATGGAGATCCGATTACGTCAACGGAAGAAATTCCGTTTGATAAAAAACGCGAATTTGATCCAAACTTAGCGCCAGG
TACAGAGAAAGTCGTTCAAAAAGGTGAACCAGGAACAAAAACAATTACAACACCAACAACTAAGAACCCATTAACAGGAG
AAAAAGTTGGCGAAGGTGAACCAACAGAAAAAATAACAAAACAACCAGTGGATGAGATCGTTCATTATGGTGGCGAAGAA
ATCAAGCCAGGCCATAAGGATGAATTTGATCCGAACGCACCGAAAGGTAGTCAAACAACGCAACCAGGTAAGCCAGGAGT
TAAAAATCCTGATACAGGCGAAGTAGTCACACCACCAGTGGATGATGTGACAAAATATGGTCCAGTTGATGGAGATCCGA
TTACGTCAACGGAAGAAATTCCGTTTGATAAAAAACGCGAATTTGATCCAAACTTAGCGCCAGGTACAGAGAAAGTCGTT
CAAAAAGGTGAACCAGGAACAAAAACAATTACAACGCCAACAACTAAGAACCCATTAACAGGAGAAAAGTTGGCGAAGG
TGAACCAACAGAAAAAATAACAAAACAACCAGTGGATGAGATTGTTCATTATGGTGGTGAACAAATACCACAAGGTCATA
AAGATGAATTTGATCCAAATGCACCTGTAGATAGTAAAACTGAAGTTCCAGGTAAACCAGGAGTTAAAAATCCTGATACA

Figure 2 cont.

GGTGAAGTTGTTACCCCACCAGTGGATGATGTGACAAAATATGGTCCGAAAGTTGGTAATCCAATCACATCAACGGAAGA
GATTCCATTTGATAAGAAACGTGTATTTAATCCTGATTTAAAACCAGGTGAAGAGCGCGTTAAACAAAAAGGTGAACCAG
GAACAAAAACAATTACAACACCAATATTAGTTAATCCTATTACAGGAGAAAAAGTTGGCGAAGGTAAATCAACAGAAAAA
GTCACTAAACAACCTGTTGACGAAATTGTTGAGTATGGTCCAACAAAAGCAGAACCAGGTAAACCAGCGGAACCAGGTAA
ACCAGCGGAACCAGGTAAACCAGCGGAACCAGGTAAACCAGCGGAACCAGGTACGCCAGCAGAACCAGGTAAACCAGCGG
AACCAGGTAAACCAGCGGAACCAGGTAAACCAGCGGAACCAGGTAAACCAGCGGAACCAGGTAAACCAGCGGAACCAGGT
ACGCCAGCAGAACCAGGTAAACCAGCGGAACCAGGTAAACCAGCGGAACCAGGTAAACCAGCGGAACCAGGTACGCCAGC
AGAACCAGGTAAACCAGCGGAACCAGGTACGCCAGCAGAACCAGGTAAACCAGCGGAACCAGGTACGCCAACACAATCAG
GTGCACCAGAACAACCAAATAGATCAATGCATTCAACAGATAATAAAAATCAATTACCTGATACAGGTGAAAATCGTCAA
GCTAATGAGGGAACTTTAGTCGGATCTCTATTAGCAATTGTCGGATCATTGTTCATATTTGGTCGTCGTAAAAAGGTAA
TGAAAAATAA

SEQ ID NO:51 polynucleotide sequence
ATGAAGAAACTATATACATCTTATGGCACTTATGGATTTTTACATCAAATAAAAATCAATAACCCGACCCATCAACTATT
CCAATTTTCAGCATCAGATACTTCAGTTATTTTTGAAGAAACTGATGGTGAGACTGTTTTAAAATCACCTTCAATATATG
AAGTTATTAAAGAAATTGGTGAATTCAGTGAACATCATTTCTATTGTGCAATCTTCATTCCTTCAACAGAAGATCATGCA
TATCAACTTGAAAAGAAACTGATTAGTGTAGACGATAATTTCAGAAACTTTGGTGGCTTTAAAAGCTATCGTTTGTTAAG
ACCTGCTAAAGGTACAACATATAAAATTTATTTCGGATTTGCTGATCGACATGCATACGAAGACTTTAAGCAATCTGATG
CCTTTAATGACCATTTTTCAAAAGACGCATTAAGTCATTACTTTGGTTCAAGCGGACAACATTCAAGTTATTTTGAAAGA
TATCTATACCCAATAAAAGAATAG

SEQ ID NO:52 polynucleotide sequence
ATGTATTTATATACATCTTATGGGACTTACCAATTTTTAAATCAAATTAAACTTAATCATCAAGAACGTAGTTTATTTCA
ATTTTCCACTAATGATTCCTCAATAATCTTAGAAGAGTCTGAGGGAAAATCAATCTTAAAACATCCTAGTGCATATCAAG
TGATTGATAGCACAGGTGAATTTAACGAACATCATTTTTATAGTGCTATTTTTGTCCCTACATCTGAAGATCATCGTCAA
CAGCTAGAGAAAAAATTATTACTCGTAGACGTACCTTTAAGAAATTTTGGTGGTTTTAAAAGCTATCGTTTATTAAAACC
CACTGAGGGGTCTACCTACAAAATTTACTTTGGTTTTGCAAATCGAACAGCATATGAAGATTTCAAAGCTTCTGATATAT
TTAATGAAAACTTTTCAAAAGATGCATTGAGCCAATACTTTGGTGCTAGTGGTCAACATTCTAGCTACTTTGAAAGATAT
TTATATCCAATAGAAGATCATTAA

SEQ ID NO:53 polynucleotide sequence
ATGATTAACAGGGATAATAAAAAGGCAATAACAAAAAAGGGTATGATTTCAAATCGCTTAAACAAATTTTCGATTAGAAA
GTATACTGTAGGAACTGCATCGATTTTAGTAGGTACGACATTGATTTTTGGTCTAGGGAACCAAGAAGCTAAAGCTGCTG
AAAACACTAGTACAGAAAATGCGAAACAAGATGATGCAACGACTAGTGATAATAAAGAAGTAGTGTCGGAAACTGAAAAT
AATTCGACAACAGAAAATGATTCAACAAATCCAATTAAGAAAGAAACAAATACTGATTCACAACCAGAAGCTAAAGAAGA
ATCAACTACATCAAGTACTCAACAACAGCAAAATAACGTTACAGCTACAACTGAAACTAAGCCTCAAAACATTGAAAAAG
AAAATGTTAAACCTTCAACTGATAAAACTGCCGACAGAAGATACATCTGTTATTTTAGAAGAGAAGAAAGCACCAAATTAT
ACAAATAACGATGTAACTACAAAACCATCTACAAGTGAAATTCAAACAAAACCAACTACACCTCAAGAATCTACAAAATAT
TGAAAATTCACAACCGCAACCAACGCCTTCAAAAGTAGACAATCAAGTTACAGATGCAACTAATCCAAAAGAACCAGTAA
ATGTGTCAAAAGAAGAACTTAAAAATAATCCTGAGAAATTAAAAGAATTAGTTAGAAATGATAACAATACAGATCGTTCA
ACTAAACCAGTTGCTACAGCTCCAACAAGTGTTGCACCAAAACGATTAAATGCGAAAATGCGTTTTGCAGTTGCACAACC
AGCAGCAGTTGCTTCAAATAATGTAAATGACTTAATTACAGTTACGAAACAGACGATCAAAGTTGGCGATGGTAAAGATA
ATGTGGCAGCAGCGCATGACGGTAAAGATATTGAATATGATACAGAGTTTACAATTGACAATAAAGTCAAAAAAGGCGAT
ACAATGACGATTAATTATGATAAGAATGTAATTCCTTCGGATTTAACAGATAAAAATGATCCTATCGATATTACTGATCC
ATCAGGAGAGGTCATTGCCAAAGGAACATTTGATAAGGCGACTAAGCAAATCACATATACATTTACAGATTATGTAGATA
AATATGAAGATATAAAAGCACGTTTAACTTTATACTCATATATTGATAAGCAAGCAGTACCTAATGAAACTAGTTTGAAT
TTAACGTTTGCAACAGCAGGTAAAGAAACTAGCCAAAACGTTTCTGTTGATTATCAAGACCCAATGGTTCATGGTGATTC
AAACATTCAATCTATCTTTACAAAGTTAGATGAAAACAAACAAACTATTGAACAACAATTTATGTTAATCCTTTGAAAA
AAACAGCAACTAACACTAAAGTTGATATAGCTGGTAGTCAAGTAGATGATTATGGAAATATTAAACTAGGAAATGGTAGT
ACCATTATTGACCAAAATACAGAAATAAAAGTTTATAAAGTTAACCCTAATCAACAATTGCCTCAAAGTAATAGAATCTA
TGATTTTAGTCAATACGAAGATGTAACAAGTCAATTTGATAATAAAAAATCATTTAGTAATAATGTAGCAACATTGGATT
TTGGTGATATTAATTCAGCCTATATTATCAAAGTTGTTAGTAAATATACACCTACATCAGATGGCGAACTAGATATTGCT
CAAGGTACTAGTATGAGAACAACTGATAAATATGGTTATTATAATTATGCAGGATATTCAAACTTCATCGTAACTTCTAA
TGACACTGGCGGTGGCGACGGTACTGTTAAACCTGAAGAAAAGTTATACAAAATTGGTGACTATGTATGGGAAGACGTTG
ATAAAGACGGTGTCCAAGGTACAGATTCGAAAGAAAGCCAATGGCAAACGTTTTAGTTACATTAACTTACCCGGACGGT
ACTACAAAATCAGTAAGAACAGATGCTAACGGTCATTATGAATTCGGTGGTTTGAAAGACGGAGAAACTTATACAGTTAA
ATTCGAAACGCCAGCTGGATATCTTCCAACAAAAGTAAATGGAACAACTGATGGTGAAAAAGACTCAAATGGTAGTTCTA

Figure 2 cont.

TAACTGTTAAAATTAATGGTAAAGATGATATGTCTTTAGACACTGGTTTTTATAAAGAACCTAAATATAATCTTGGTGAC
TATGTATGGGAAGATACAAATAAAGATGGTATCCAAGATGCTAATGAACCTGGTATCAAAGATGTTAAGGTTACATTAAA
AGATAGTACTGGAAAAGTTATTGGTACAACTACTACTGATGCCTCGGGTAAATATAAATTTACAGATTTAGATAATGGTA
ACTATACAGTAGAATTTGAAACACCAGCAGGTTACACGCCAACGGTTAAAAATACTACAGCTGAAGATAAAGATTCTAAT
GGTTTAACAACAACAGGTGTCATTAAAGATGCAGATAATATGACATTAGACAGTGGTTTCTATAAAACACCAAAATACAG
TTTAGGTGATTATGTTTGGTACGACAGTAATAAAGACGGTAAACAAGATTCAACTGAAAAGGTATCAAAGATGTTAAAG
TTACTTTATTAAATGAAAAAGGCGAAGTAATTGGAACAACTAAAACAGATGAAAATGGTAAATATCGTTTCGATAATTTA
GATAGCGGTAAATACAAAGTTATTTTTGAAAAGCCTGCTGGCTTAACACAAACAGTTACAAATACAACTGAAGATGATAA
AGATGCCGATGGTGGCGAAGTTGACGTAACAATTACGGATCATGATGATTTCATACTTGATAACGGATACTTCGAAGAAG
ATACATCAGACAGTGATTCAGACTCAGACAGTGATTCAGACTCAGACAGCGACTCAGATTCAGACAGTGATTCAGACTCA
GATAGCGATTCAGATTCAGACAGCGACTCAGACTCAGATAGCGACTCAGACTCAGACAGCGACTCAGACTCAGATAGCGA
CTCAGATTCGGACAGCGATTCAGACTCAGATAGCGACTCAGATTCAGACAGCGATTCAGACTCAGATAGCGACTCAGATT
CAGACAGTGACTCAGACTCAGATAGCGACTCAGACTCAGACAGTGACTCAGACTCAGACAGCGATTCAGATTCAGATAGC
GACTCAGATTCGGACAGTGATTCAGACTCAGATAGCGACTCAGATTCAGACAGCGACTCAGACTCAGATAGCGACTCAGA
CTCAGACAGTGATTCAGACTCAGATAGCGATTCGGACTCGGATGCAGGAAAACATACACCTGTTAAACCAATGAGTACTA
CTAAAGACCATCACAATAAAGCAAAAGCATTACCAGAAACAGGTAGTGAAAATAACGGCTCAAATAACGCAACGTTATTT
GGTGGATTATTTGCAGCATTAGGTTCATTATTGTTATTCGGTCGTCGCAAAAAACAAACAAATAA

SEQ ID NO:54 polynucleotide sequence
ATGATTAATAAAAAAAATAATTTACTAACTAAAAAGAAACCTATAGCAAATAAATCCAATAAATATGCAATTAGAAAATT
CACAGTAGGTACAGCGTCTATTGTAATAGGTGCAACATTATTGTTTGGTTTAGGTCATAATGAGGCCAAAGCCGAGGAGA
ATTCAGTACAAGACGTTAAAGATTCGAATACGGATGATGAATTATCAGACAGCAATGATCAGTCTAGTGATGAAGAAAAG
AATGATGTGATCAATAATAATCAGTCAATAAACACCGACGATAATAACCAAATAATTAAAAAAGAAGAAACGAATAACTA
CGATGGCATAGAAAAACGCTCAGAAGATAGAACAGAGTCAACAACAAATGTAGATGAAAACGAAGCAACATTTTTACAAA
AGACCCCTCAAGATAATACTCATCTTACAGAAGAGAGGTAAAAGAATCCTCATCAGTCGAATCCTCAAATTCATCAATT
GATACTGCCCAACAACCATCTCACACAACAATAAATAGAGAAGAATCTGTTCAAACAAGTGATAATGTAGAAGATTCACA
CGTATCAGATTTTGCTAACTCTAAAATAAAAGAGAGTAACACTGAATCTGGTAAAGAAGAGAATACTATAGAGCAACCTA
ATAAAGTAAAAGAAGATTCAACAACAAGTCAGCCGTCTGGCTATACAAATATAGATGAAAAATTTCAAATCAAGATGAG
TTATTAAATTTACCAATAAATGAATATGAAAATAAGGCTAGACCATTATCTACAACATCTGCCCAACCATCGATTAAACG
TGTAACCGTAAATCAATTAGCGGCGGAACAAGGTTCGAATGTTAATCATTTAATTAAAGTTACTGATCAAAGTATTACTG
AAGGATATGATGATAGTGAAGGTGTTATTAAAGCACATGATGCTGAAAACTTAATCTATGATGTAACTTTTGAAGTAGAT
GATAAGGTGAAATCTGGTGATACGATGACAGTGGATATAGATAAGAATACAGTTCCATCAGATTTAACCGATAGCTTTAC
AATACCAAAAATAAAAGATAATTCTGGAGAAAATCATCGCTACAGGTACTTATGATAACAAAAATAAACAAATCACCTATA
CTTTTACAGATTATGTAGATAAGTATGAAAATATTAAAGCACACCTTAAATTAACGTCATACATTGATAAATCAAAGGTT
CCAAATAATAATACCAAGTTAGATGTAGAATATAAAACGGCCCTTTCATCAGTAAATAAAACAATTACGGTTGAATATCA
AAGACCTAACGAAAATCGGACTGCTAACCTTCAAAGTATGTTTACAAACATAGATACGAAAAATCATACAGTTGAGCAAA
CGATTTATATTAACCCTCTCTTCGTTATTCAGCCAAGGAACAAATGTAAATATTTCAGGGAATGGTGATGAAGGTTCAACA
ATTATAGACGATAGCACAATAATTAAAGTTTATAAGGTTGGAGATAATCAAAATTTACCAGATAGTAACAGAATTTATGA
TTACAGTGAATATGAAGATGTCACAAATGATGATTATGCCCAATTAGGGAAATAATAATGATGTGAATATTAATTTTGGTA
ATATAGATTCACCATATATTATTAAAGTTATTAGTAAATATGACCCTAATAAGGATGATTACACGACTATACAGCAAACT
GTGACAATGCAGACGACTATAAATGAGTATACTGGTGAGTTTAGAACAGCATCCTATGATAATACAATTGCTTTCTCTAC
AAGTTCAGGTCAAGGACAAGGTGACTTGCCTCCTGAAAAAACTTATAAAATCGGAGATTACGTATGGGAAGATGTAGATA
AAGATGGTATTCAAATACAAATGATAATGAAAACCGCTTAGTAATGTATTGGTAACTTTGACGTATCCTGATGGAACT
TCAAAATCAGTCAGAACAGATGAAGATGGGAAATATCAATTTGATGGATTGAAAAACGGATTGACTTATAAAATTACATT
CGAAACACCTGAAGGATATACGCCGACGCTTAAACATTCAGGAACAAATCCTGCACTAGACTCAGAAGGTAATTCTGTAT
GGGTAACTATTAATGGACAAGACGATATGACGATTGATAGTGGATTTATCAAACACCTAAATACAGCTTAGGGAACTAT
GTATGGTATGACACTAATAAAGATGGTATTCAAGGTGATGATGAAAAAGGAATCTCTGGAGTTAAAGTGACGTTAAAAGA
TGAAAACGGAAATATCATTAGTACAACTACAACCGATGAAAATGGAAAGTATCAATTTGATAATTTAAATAGTGGTAATT
ATATTGTTCATTTTGATAAAACCTTCAGGTATGACTCAAACAACAACAGATTCTGGTGATGATGACGAACAGGATGCTGAT
GGGGAAGAAGTTCATGTAACAATTACTGATCATGATGACTTTAGTATAGATAACGGATACTATGATGACGAATCGGATTC
CGATAGTGACTCAGACAGCGACTCAGATTCCGATAGTGATTCAGACTCCGATAGCGACTCGGATTCAGACAGCGACTCAG
ATTCAGACAGCGACTCGGATTCTGATAGCGACTCGGATTCAGACAGCGACTCAGACTCAGACAGTGATTCAGATTCAGAC
AGCGACTCAGATTCCGATAGTGATTCAGACTCAGACAGCGACTCAGATTCTGATAGTGATTCAGACTCAGACAGTGATTC
AGATTCAGACAGCGACTCAGATTCCGATAGTGATTCAGACTCAGACAGCGACTCAGATTCCGATAGTGATTCAGACTCAG
ACAGCGACTCAGATTCTGATAGTGATTCAGACTCAGACAGTGATTCAGATTCCGATAGTGATTCAGACTCCGATAGCGAC
TCAGACTCGGATAGTGACTCAGATTCTGATAGTGATTCAGACTCAGACAGTGATTCGGATTCCGATAGTGATTCAGACTC
AGACAGCGACTCAGATTCTGATAGTGATTCAGACTCAGACAACGACTCAGATTTAGGCAATAGCTCAGATAAGAGTACAA
AAGATAAATTACCTGATACAGGAGCTAATGAAGATTATGGCTCTAAAGGCACGTTACTTGGAACTCTGTTTGCAGGTTTA

Figure 2 cont.

GGAGCGTTATTATTAGGGAAACGTCGCAAAAATAGAAAAAATAAAAATTAA

SEQ ID NO:55 polynucleotide sequence
ATGTCTAATAATTTTAAAGATGACTTTGAAAAAAATCGTCAATCGATAGACACAAATTCACATCAAGACCATACGGAAGA
TGTTGAAAAAGACCAATCAGAATTAGAACATCAGGATACAATAGAGAATACGGAGCAACAGTTTCCGCCAAGAAATGCCC
AAAGAAGAAAAAGACGCCGTGATTTAGCAACGAATCATAATAAACAAGTTCACAATGAATCACAAACATCTGAAGACAAT
GTTCAAAATGAGGCTGGCACAATAGATGATCGTCAAGTCGAATCATCACACAGTACTGAAAGTCAAGAACCTAGCCATCA
AGACAGTACACCTCAACATGAAGAGGAATATTATAATAAGAATGCTTTTGCAATGGATAAATCACATCCAGAACCAATCG
AAGACAATGATAAACACGAGACTATTAAAGATGCAGAAAATAACACTGAGCATTCAACAGTTTCTGATAAGAGTATAGCT
GAACAATCTCAGCAACCTAAACCATATTTTGCAACAGGTGCTAACCAAGCAAATACATCAAAAGATAAACATGATGATGT
AACTGTTAAGCAAGACAAAGATGAATCTAAAGATCATCATAGTGGTAAAAAAGGCGCAGCAATTGGTGCTGGAACAGCGG
GTGTTGCAGGTGCAGCTGGTGCAATGGGTGTTTCTAAAGCTAAGAAACATTCAAATGACGCTCAAAACAAAGTAATTCT
GACAAGTCGAATAACTCGACTGAGGATAAAGCGTCTCAAGATAAGTCTAAAGATCATCATAATGGCAAAAAAGGTGCAGC
GATCGGTGCTGGAACAGCAGGTTTGGCTGGAGGCGCAGCAAGTAAAAGTGCTTCTGCCGCTTCAAAACCACATGCCTCTA
ATAATGCAAGCCAAAACCATGATGAACATGACAATCATGACAGAGATAAAGAACGTAAAAAAGGTGGCATGGCCAAAGTA
TTGTTACCATTAATTGCAGCTGTACTAATTATCGGTGCATTAGCGATATTTGGAGGCATGGCATTAAACAATCATAATAA
TGGTACAAAAGAAAATAAAATCGCGAATACAAATAAAAATAATGCTGATGAAAGTAAAGACAAAGACACATCTAAAGACG
CTTCTAAAGATAAATCAAAATCTACAGACAGTGATAAATCAAAAGAGGATCAAGACAAAGCGACTAAAGATGAATCTGAT
AATGATCAAAACAACGCTAATCAAGCGAACAATCAAGCACAAAATAATCAAAATCAACAACAAGCTAATCAAAATCAACA
ACAGCAACAACAACGTCAAGGTGGTGGCCAAAGACATACAGTGAATGGTCAAGAAAACTTATACCGTATCGCAATTCAAT
ACTACGGTTCAGGTTCACCGGAAAATGTTGAAAAAATTAGACGTGCCAATGGTTTAAGTGGTAACAATATTAGAAACGGT
CAACAAATCGTTATTCCATAA

SEQ ID NO:56 polynucleotide sequence
GTGATTGAATTAATTAAAATGGAAGGGATGATAGTTGTGTCTAATAATAATTTTAAAGATGATTTCGAAAAGAATCGTCA
ATCTATTAATCCAGACGAACAGCAAACAGAATTAAAAGAAGATGATAAAACAAATGAAAATAAAAAAGAAGCTGACTCTC
AAAAACAGTTTATCTAATAACTCAAATCAACAATTTCCTCCGAGAAATGCCCAACGACGAAAAAGACGTAGAGAGACAGCA
ACTAATCAAAGCAAACAACAAGACGACAAACATCAAAAAAATAGTGACGCTAAAACTACAGAAGGTTCATTAGATGACCG
TTATGACGAAGCACAGTTACAGCAACAACATGATAAATCGCAACAACAAAATAAAACTGAAAAACAATCACAAGATAATA
GAATGAAAGATGGAAAAGATGCAGCTATTGTAAATGGAACATCTGAGTCACCAGAACATAAATCAAATCAACACAAAAT
AGACCCGGCCCTAAAGCTCAACAACAAAAGCGTAAATCGAAGATACGCAATCAAAACCGTCAACAAACAAAGATAAAAA
AGCAGCTACAGGTGCTGGAATAGCTGGTGCAGCTGGTGTTGCTGGTGCAGCAGAAACATCCAAACGTCATCATAATAAAA
AAGATAAACAAGATTCTAAACACTCAAACCATGAGAATGACGAAAATCTGTTAAAAATGATGACCAAAAGCAATCTAAA
AAAGGCAAAAAAGCAGCAGTCGGTGCTGGCGCAGCTGCAGGAGTTGGTGCGGCTGGTGTTGCGCATCATAATAATCAAAA
TAAACATCATAATGAGGAAAAAAATTCTAATCAAAACAATCAGTACAATGACCAATCAGAAGGTAAGAAAAAAGGTGGTT
TCATGAAAATCTTGTTACCACTTATAGCAGCCATTCTTATTCTAGGTGCAATAGCAATATTCGGTGGTATGGCTCTAAAT
AATCACAACGATAGTAAAAGTGATGACCAAAAAATAGCGAATCAAAGTAAGAAAGACTCAGATAAAAAAGATGGTGCGCA
ATCCGAAGATAACAAAGACAAAAAATCTGATAGTAACAAAGACAAAAAATCTGATTCTGATAAGAACGCAGATGATGACT
CTGATAATAGTTCCTCAAATCCTAACGCTACTTCAACTAATAATAACGATAATGTAGCCAATAATAACTCAAATTATACA
AACCAAAATCAACAAGATAATGCAAACCAAAATAGCAATAATCAACAGGCAACTCAAGGTCAACAATCACATACAGTATA
CGGTCAAGAAACTTATATCGTATCGCCATACAATATTATGGAGAAGGAACTCAAGCTAACGTAGATAAAATTAAACGTG
CGAATGGATTAAGCAGTAATAATATTCATAATGGTCAAACATTAGTTATTCCTCAATAA

SEQ ID NO:57 polynucleotide sequence
ATGAAAAATAAATTGATAGCAAAATCTTTATTAACAATAGCGGCAATTGGTATTACTACAACTACAATTGCGTCAACAGC
AGATGCGAGCGAAGGATACGGTCCAAGAGAAAAGAAACCAGTGAGTATTAATCACAATATCGTAGAGTACAATGATGGTA
CTTTTAAATATCAATCTAGACCAAAATTTAACTCAACACCTAAATATATTAAATTCAAACATGACTATATAATTTTAGAA
TTTAACGATGGTACATTCGAATATGGTGCACGTCCACAATTTAATAAACCAGCAGCGAAAACTGATGCAACTATTAAAAA
AGAACAAAAATTGATTCAAGCTCAAAATCTTGTGAGAGAATTTGAAAAAACACATACTGTCAGTGCACACAGAAAAGCAC
AAAAGGCAGTCAACTTAGTTTCGTTTGAATACAAAGTGAAGAAAATGGTCTTACAAGAGCGAATTGATAATGTATTAAAA
CAAGGATTAGTGAGATAA

SEQ ID NO:58 polynucleotide sequence
ATGAAAACACGTATAGTCAGCTCAGTAACAACAACACTATTGCTAGGTTCCATATTAATGAATCCTGTCGCTAATGCCGC
AGATTCTGATATTAATATTAAAACCGGTACTACAGATATTGGAAGCAATACTACAGTAAAAACAGGTGATTTAGTCACTT
ATGATAAAGAAATGGCATGCACAAAAAAGTATTTTATAGTTTTATCGATGATAAAAATCACAATAAAAAACTGCTAGTT
ATTAGAACGAAAGGTACCATTGCTGGTCAATATAGAGTTTATAGCGAAGAAGGTGCTAACAAAAGTGGTTTAGCCTGGCC

Figure 2 cont.

TTCAGCCTTTAAGGTACAGTTGCAACTACCTGATAATGAAGTAGCTCAAATATCTGATTACTATCCAAGAAATTCGATTG
ATACAAAAGAGTATATGAGTACTTTAACTTATGGATTCAACGGTAATGTTACTGGTGATGATACAGGAAAAATTGGCGGC
CTTATTGGTGCAAATGTTTCGATTGGTCATACACTGAAATATGTTCAACCTGATTTCAAAACAATTTTAGAGAGCCCAAC
TGATAAAAAAGTAGGCTGGAAAGTGATATTTAACAATATGGTGAATCAAAATTGGGGACCATATGATAGAGATTCTTGGA
ACCCGGTATATGGCAATCAACTTTTCATGAAAACTAGAAATGGTTCTATGAAAGCAGCAGAGAACTTCCTTGATCCTAAC
AAAGCAAGTTCTCTATTATCTTCAGGGTTTTCACCAGACTTCGCTACAGTTATTACTATGGATAGAAAAGCATCCAAACA
ACAAACAAATATAGATGTAATATACGAACGAGTTCGTGATGACTACCAATTGCATTGGACTTCAACAAATTGGAAAGGTA
CCAATACTAAAGATAAATGGACAGATCGTTCTTCAGAAAGATATAAAATCGATTGGGAAAAAGAAGAAATGACAAATTAA

SEQ ID NO:59 polynucleotide sequence
ATACACATGAAAAATAAATATATCTCGAAGTTGCTAGTTGGGGCAGCAACAATTACTTTAGCTACAATGATTTCAAATGG
GGAAGCAAAAGCGAGTGAAAACACGCAACAAACTTCAACTAAGCACCAAACAACTCAAAACAACTACGTAACAGATCAAC
AAAAAGCTTTTTATCAAGTATTACATCTAAAAGGTATCACAGAAGAACAACGTAACCAATACATCAAAACATTACGCGAA
CACCCAGAACGTGCACAAGAAGTATTCTCTGAATCACTTAAAGACAGCAAGAACCCAGACCGACGTGTTGCACAACAAA
CGCTTTTTACAATGTTCTTAAAAATGATAACTTAACTGAACAAGAAAAAAATAATTACATTGCACAAATTAAAGAAAACC
CTGATAGAAGCCAACAAGTTTGGGTAGAATCAGTACAATCTTCTAAAGCTAAAGAACGTCAAAATATTGAAAATGCGGAT
AAAGCAATTAAAGATTTCCAAGATAACAAAGCACCACACGATAAATCAGCAGCATATGAAGCTAACTCAAAATTACCTAA
AGATTTACGCGATAAAAATAACCGCTTTGTAGAAAAAGTTTCAATTGAAAAAGCAATCGTTCGTCATGATGAGCGTGTGA
AATCAGCAAATGATGCAATCTCAAAATTAAATGAAAAAGATTCAATTGAAAACAGACGTTTAGCACAACGTGAAGTTAAC
AAAGCACCTATGGATGTAAAAGAGCATTTACAGAAACAATTAGACGCATTAGTAGCTCAAAAAGATGCTGAAAAGAAAGT
GGCGCCAAAAGTTGAGGCTCCTCAAATTCAATCACCACAAATTGAAAAACCTAAAGCAGAATCACCAAAAGTTGAAGTCC
CTCAATCTAAATTATTAGGTTACTACCAATCATTAAAAGATTCATTTAACTATGGTTACAAGTATTTAACAGATACTTAT
AAAAGCTATAAAGAAAAATATGATACAGCAAAGTACTACTATAATACGTACTATAAATACAAAGGTGCGATTGATCAAAC
AGTATTAACAGTACTAGGTAGTGGTTCTAAATCTTACATCCAACCATTGAAAGTTGATGATAAAAACGGCTACTTAGCTA
AATCATATGCACAAGTAAGAAACTATGTAACTGAGTCAATCAATACTGGTAAAGTATTATATACTTTCTACCAAAACCCA
ACATTAGTAAAAACAGCTATTAAAGCTCAAGAAACTGCATCATCAATCAAAAATACATTAAGTAATTTATTATCATTCTG
GAAATAA

SEQ ID NO:60 polynucleotide sequence
ATGACAAAACATTATTTAAACAGTAAGTATCAATCAGAACAACGTTCATCAGCTATGAAAAAGATTACAATGGGTACAGC
ATCTATCATTTTAGGTTCCCTTGTATACATAGGCGCAGACAGCCAACAAGTCAATGCGGCAACAGAAGCTACGAACGCAA
CTAATAATCAAAGCACACAAGTTTCTCAAGCAACATCACAACCAATTAATTTCCAAGTGCAAAAAGATGGCTCTTCAGAG
AAGTCACACATGGATGACTATATGCAACACCCTGGTAAAGTAATTAAACAAAATAATAAATATTATTTCCAAACCGTGTT
AAACAATGCATCATTCTGGAAAGAATACAAATTTTACAATGCAAACAATCAAGAATTAGCAACAACTGTTGTTAACGATA
ATAAAAAAGCGGATACTAGAACAATCAATGTTGCAGTTGAACCTGGATATAAGAGCTTAACTACTAAAGTACATATTGTC
GTGCCACAAATTAATTACAATCATAGATATACTACGCATTTGGAATTTGAAAAAGCAATTCCTACATTAGCTGACGCAGC
AAAACCAAACAATGTTAAACCGGTTCAACCAAAACCAGCTCAACCTAAAACACCTACTGAGCAAACTAAACCAGTTCAAC
CTAAAGTTGAAAAAGTTAAACCTACTGTAACTACAACAAGCAAAGTTGAAGACAATCACTCTACTAAAGTTGTAAGTACT
GACACAACAAAAGATCAAACTAAAACACAAACTGCTCATACAGTTAAAACAGCACAAACTGCTCAAGAACAAAATAAAGT
TCAAACACCTGTTAAAGATGTTGCAACAGCGAAATCTGAAAGCAACAATCAAGCTGTAAGTGATAATAAATCACAACAAA
CTAACAAAGTTACAAAACATAACGAAACGCCTAAACAAGCATCTAAAGCTAAAGAATTACCAAAAACTGGTTTAACTTCA
GTTGATAACTTTATTAGCACAGTTGCCTTCGCAACACTTGCCCTTTTAGGTTCATTATCTTTATTACTTTTCAAAAGAAA
AGAATCTAAATAA

SEQ ID NO:61 polynucleotide sequence
ATGAACAAACAGCAAAAGAATTTAAATCATTTTATTCAATTAGAAAGTCATCACTAGGCGTTGCATCTGTAGCGATTAG
TACACTTTTATTATTAATGTCAAATGGCGAAGCACAAGCAGCAGCTGAAGAAACAGGTGGTACAAATACAGAAGCACAAC
CAAAAACTGAAGCAGTTGCAAGTCCAACAACAACATCTGAAAAAGCTCCAGAAACTAAACCAGTAGCTAATGCTGTCTCA
GTATCTAATAAAGAAGTTGAGGCCCCTACTTCTGAAACAAAAGAAGCTAAAGAAGTTAAAGAAGTTAAAGCCCCTAAGGA
AACAAAAGCAGTTAAACCAGCAGCAAAAGCCACTAACAATACATATCCTATTTTGAATCAGGAACTTAGAGAAGCGATTA
AAAAACCCTGCAATAAAAGATAAAGATCATAGCGCACCAAACTCTCGTCCAATTGATTTTGAAATGAAAAAGAAAATGGT
GAGCAACAATTTTATCATTATGCCAGCTCTGTTAAACCTGCTAGAGTTATTTTCACTGATTCAAAACCAGAAATTGAATT
AGGATTACAATCAGGTCAATTTTGGAGAAAATTTGAAGTTTATGAAGGTGACAAAAGTTGCCAATTAAATTAGTATCAT
ACGATACTGTTAAAGATTACGCTTACATTCGCTTCTCTGTTTCAAATGGAACAAAAGCCGTTAAAATTGTAAGTTCAACT
CACTTCAATAACAAAGAAGAAAAATACGATTACACATTAATGGAATTCGCACAACCAATTTATAACAGTGCAGATAAATT
CAAAACTGAAGAAGATTATAAAGCTGAAAAATTATTAGCGCCATATAAAAAAGCGAAAACACTAGAAAGACAAGTTTATG
AATTAAATAAAATTCAAGATAAACTTCCTGAAAAATTAAAGGCTGAGTACAAGAAGAAATTAGAGGATACAAAGAAAGCT

Figure 2 cont.

TTAGATGAGCAAGTGAAATCAGCTATTACTGAATTCCAAAATGTACAACCAACAAATGAAAAAATGACTGATTTACAAGA
TACAAAATATGTTGTTTATGAAAGTGTTGAGAATAACGAATCTATGATGGATACTTTTGTTAAACACCCTATTAAAACAG
GTATGCTTAACGGCAAAAAATATATGGTCATGGAAACTACTAATGACGATTACTGGAAAGATTTCATGGTTGAAGGTCAA
CGTGTTAGAACTATAAGCAAAGATGCTAAAAATAATACTAGAACAATTATTTTCCCATATGTTGAAGGTAAAACTCTATA
TGATGCTATCGTTAAAGTTCACGTAAAAACGATTGATTATGATGGACAATACCATGTCAGAATCGTTGATAAAGAAGCAT
TTACAAAAGCCAATACCGATAAATCTAACAAAAAAGAACAACAAGATAACTCAGCTAAGAAGGAAGCTACTCCAGCTACG
CCTAGCAAACCAACACCATCACCTGTTGAAAAAGAATCACAAAAACAAGACAGCCAAAAAGATGACAATAAACAATTACC
AAGTGTTGAAAAAGAAATGACGCATCTAGTGAGTCAGGTAAAGACAAAACGCCTGCTACAAAACCAACTAAAGGTGAAG
TAGAATCAAGTAGTACAACTCCAACTAAGGTAGTATCTACGACTCAAAATGTTGCAAAACCAACAACTGCTTCATCAAAA
ACAACAAAAGATGTTGTTCAAACTTCAGCAGGTTCTAGCGAAGCAAAAGATAGTGCTCCATTACAAAAAGCAAACATTAA
AAACACAAATGATGGACACACTCAAAGCCAAAACAATAAAAATACACAAGAAAATAAAGCAAATCATTACCACAAACTG
GTGAAGAATCAAATAAAGATATGACATTACCATTAATGGCATTACTAGCTTTAAGTAGCATCGTTGCATTCGTATTACCT
AGAAAACGTAAAAACTAA

SEQ ID NO:62 polynucleotide sequence
ATGAATAATAAAAAGACAGCAACAAATAGAAAAGGCATGATACCAAATCGATTAAACAAATTTTCGATAAGAAAGTATTC
TGTAGGTACTGCTTCAATTTTAGTAGGGACAACATTGATTTTTGGGTTAAGTGGTCATGAAGCTAAAGCGGCAGAACATA
CGAATGGAGAATTAAATCAATCAAAAAATGAAACGACAGCCCCAAGTGAGAATAAAACAACTGAAAAAGTTGATAGTCGT
CAACTAAAAGACAATACGCAAACTGCAACTGCAGATCAGCCTAAAGTGACAATGAGTGATAGTGCAACAGTTAAAGAAAC
TAGTAGTAACATGCAATCACCACAAAACGCTACAGCTAGTCAATCTACTACACAAACTAGCAATGTAACAACAAATGATA
AATCATCAACTACATATAGTAATGAAACTGATAAAGTAATTTAACACAAGCAAAAAACGTTTCAACTACACCTAAAACA
ACGACTATTAAACAAAGAGCTTTAAATCGCATGGCAGTGAATACTGTTGCAGCTCCACAACAAGGAACAAATGTTAATGA
TAAAGTACATTTTACGAACATTGATATTGCGATTGATAAAGGACATGTTAATAAAACAACAGGAAATACTGAATTTTGGG
CAACTTCAAGTGATGTTTTAAAATTAAAAGCGAATTACACAATCGATGATTCTGTTAAAGAGGGCGATACATTTACTTTT
AAATATGGTCAATATTTCCGTCCAGGTTCTGTAAGATTACCTTCACAAACTCAAAATTTATATAATGCCCAAGGTAATAT
TATTGCAAAAGGTATTTACGATAGTAAAACAAATACAACAACGTATACTTTTACGAATTATGTAGATCAATACACAAATG
TTAGCGGTAGCTTTGAACAAGTCGCATTTGCGAAACGTGAAATGCAACAACTGATAAAACTGCTTATAAAATGGAAGTA
ACTTTAGGTAATGATACATATAGTAAAGATGTCATTGTCGATTATGGTAATCAAAAAGGTCAACAACTTATTCGAGTAC
AAATTATATTAATAATGAAGATTTGTCACGTAATATGACTGTTTATGTAAATCAACCTAAAAAGACCTATACAAAAGAAA
CATTTGTAACAAATTTAACTGGTTATAAATTTAATCCAGATGCTAAAAACTTCAAAATTTACGAAGTGACAGATCAAAAT
CAATTTGTGGATAGTTTCACCCCAGATACTTCAAAACTTAAAGATGTTACTGGTCAATTCGATGTTATTTATAGTAATGA
TAATAAGACGGCGACAGTAGATTTATTGAATGGTCAATCTAGTAGTGATAAACAGTACATCATTCAACAAGTTGCTTATC
CAGATAATAGTTCAACAGATAATGGGAAATTGATTATACTTTAGAAACACAAAATGGAAAAGTAGTTGGTCAAACAGT
TATTCAAATGTGAATGGCTCATCAACTGCAAATGGCGACCAAAAGAAATATAATCTAGGTGACTATGTATGGGAAGATAC
AAATAAAGATGGTAAACAAGATGCCAATGAAAAAGGGATTAAAGGTGTTTATGTCATTCTTAAAGATAGTAACGGTAAAG
AATTAGATCGTACGACAACAGATGAAAATGGTAAATATCAGTTCACTGGTTTAAGCAATGGAACTTATAGTGTAGAGTTT
TCAACACCAGCCGGTTATACACCGACAACTGCAAATGCAGGTACAGATGATGCTGTAGATTCTGATGGACTAACTACAAC
AGGTGTCATTAAAGACGCTGACAACATGACATTAGATAGTGGATTCTACAAAACACCAAAATATAGTTTAGGTGATTATG
TTTGGTACGACAGTAACAAAGATGGTAAACAAGATTCGACTGAAAAAGGAATTAAAGGTGTTAAAGTTACTTTGCAAAAC
GAAAAAGGCGAAGTAATTGGTACAACTGAAACAGATGAAAATGGTAAATACCGCTTTGATAATTTAGATAGTGGTAAATA
CAAAGTTATCTTTGAAAAGCCTGCTGGTTTAACTCAAACAGGTACAAATACAACTGAAGATGATAAAGATGCCGATGGTG
GCGAAGTTGATGTAACAATTACGGATCATGATGATTTCACACTTGATAATGGCTACTACGAAGAAGAAACATCAGATAGT
GACTCAGATTCGGACAGCGATTCAGACTCAGATAGCGACTCAGATTCAGATAGTGACTCAGACTCAGATAGCGACTCAGA
CTCAGATAGCGACTCAGACAGCGACTCAGACTCAGATAGTGATTCAGATTCGGACAGCGACTCAGATTCAGACAGCGAAT
CAGATTCGGATAGCGACTCAGACTCAGATAGCGACTCAGACAGCGACTCAGATTCAGACAGTGACTCAGACTCAGACAGC
GACTCAGATTCAGACAGCGATTCAGATTCGGATAGCGACTCAGATTCAGATAGCGATTCGGACTCAGACAACGACTCAGA
TTCTGACAGCGATTCAGACTCAGATAGCGACTCAGATTCAGACAGCGACTCAGATTCAGACAGCGATTCAGATTCAGATA
GCGATTCAGATTCAGACAGCGACTCAGATTCAGATAGCGACTCAGACAGCGACTCAGACTCAGATAGCGACTCA
GACAGCGATTCAGATTCGGATAGCGATTCAGATTCAGATGCAGGTAAACATACTCCGACTAAACCAATGAGTACGGTTAA
AGATCAGCATAAAACGCTAAAGCATTACCAGAAACAGGTAGTGAAAATAATAATTCAAATAATGGCACATTATTCGGTG
GATTATTCGCGGCATTAGGATCATTATTGTTATTCGGTCGTCGTAAAAAACAAAATAAATAA

SEQ ID NO:63 polynucleotide sequence
ATGAATATGAAGAAAAAGAAAAACACGCAATTCGGAAAAAATCGATTGGCGTGGCTTCAGTGCTTGTAGGTACGTTAAT
CGGTTTTGGACTACTCAGCAGTAAAGAAGCAGATGCAAGTGAAAATAGTGTTACGCAATCTGATAGCGCAAGTAACGAAA
GCAAAAGTAATGATTCAAGTAGCGTTAGTGCTGCACCTAAAACAGACGACACAAACGTGAGTGATACTAAAACATCGTCA
AACACTAATAATGGCGAAACGAGTGTGGCGCAAAATCCAGCACAACAGGAAACGACACAATCATCATCAACAAATGCAAC
TACGGAAGAAACGCCGGTAACTGGTGAAGCTACTACTACGACAACGAATCAAGCTAATACACCGGCAACAACTCAATCAA

Figure 2 cont.

```
GCAATACAAATGCGGAGGAATTAGTGAATCAAACAAGTAATGAAACGACTTCTAATGATACTAATACAGTATCATCTGTA
AATTCACCTCAAAATTCTACAAATGCGGAAAATGTTTCAACAACGCAAGATACTTCAACTGAAGCAACACCTTCAAACAA
TGAATCAGCTCCACAGAATACAGATGCAAGTAATAAAGATGTAGTTAGTCAAGCGGTTAATCCAAGTACGCCTAGAATGA
GAGCATTTAGTTTAGCGGCAGTAGCTGCAGATGCACCGGCAGCTGGCACAGATATTACGAATCAGTTGACAGATGTGAAA
GTTACTATTGACTCTGGTACGACTGTGTATCCGCACCAAGCAGGTTATGTCAAACTGAATTATGGTTTTTCAGTGCCTAA
TTCTGCTGTTAAAGGTGACACATTCAAAATAACTGTACCTAAAGAATTAAACTTAAATGGTGTAACTTCAACTGCTAAAG
TGCCACCAATTATGGCTGGAGATCAAGTATTGGCAAATGGTGTAATCGATAGTGATGGTAATGTTATTTATACATTTACA
GACTATGTTGATAATAAGAAAATGTAACAGCTAATATTACTATGCCAGCTTATATTGACCCTGAAAATGTTACAAGAC
AGGTAATGTGACATTGACAACTGGCATAGGAACCAATACTGCTAGTAAGACAGTATTAATCGACTATGAGAAATATGGAC
AATTCCATAATTTATCAATTAAAGGTACGATTGATCAAATCGATAAAACAAATAATACGTATCGCCAAACAATTTATGTC
AATCCAAGCGGAGATAACGTTGTGTTACCTGCCTTAACAGGTAATTTAATTCCTAATACAAAGAGTAATGCGTTAATAGA
TGCAAAAAACACTGATATTAAAGTTTATAGAGTCGATAATGCTAATGATTTATCTGAAAGTTATTATGTGAATCCTAGCG
ATTTTGAAGATGTAACTAATCAAGTTAGAATTTCATTTCCAAATGCTAATCAATACAAAGTAGAATTTCCTACGGACGAT
GACCAAATTACAACACCGTATATTGTAGTTGTTAATGGCCATATTGATCCTGCTAGTACAGGTGATTTAGCACTACGTTC
GACATTTTATGGTTATGATTCTAATTTTATATGGAGATCTATGTCATGGGACAACGAAGTAGCATTTAATAACGGATCAG
GTTCTGGTGACGGTATCGATAAACCAGTTGTTCCTGAACAACCTGATGAGCCTGGTGAAATTGAACCAATTCCAGAGGAT
TCAGATTCTGACCCAGGTTCAGATTCTGGCAGCGATTCTAATTCAGATAGCGGTTCAGATTCTGGCAGTGATTCTACATC
AGATAGTGGTTCAGATTCAGCGAGTGATTCAGATTCAGCAAGTGATTCAGACTCAGCGAGTGATTCAGATTCAGCAAGTG
ATTCAGATTCAGCAAGTGATTCAGATTCAGCAAGTGATTCAGACTCAGCAAGTGATTCAGATTCAGCAAGTGATTCAGAT
TCAGCAAGCGATTCAGATTCAGCGAGCGATTCAGATTCAGCGAGCGATTCAGATTCAGCGAGTGATTCCGACTCAGCGAG
CGATTCAGACTCAGATAGTGACTCAGATTCCGATAGCGATTCCGACTCAGATAGCGACTCAGATTCAGACAGCGATTCTG
ACTCAGACAGCGATTCTGACTCAGACAGTGACTCAGATTCCGATAGCGATTCTGACTCAGACAGTGACTCAGATTCCGAT
AGCGATTCAGATTCAGACAGTGATTCAGACTCAGATAGCGATTCAGATTCCGACAGTGACTCAGACTCAGACAGCGATTC
AGATTCCGATAGCGATTCAGATTCCGACAGTGACTCAGATTCCGATAGTGACTCGGATTCAGCGAGTGATTCAGATTCAG
ATAGCGATTCAGAATCAGATAGTGACTCAGACTCAGACAGTGATTCAGATTCAGATAGTGACTCAGACTCAGACAGCGAT
TCAGAATCAGATAGTGACTCCGATTCAGACAGCGATTCAGAATCAGATAGTGACTCCGATTCAGATAGCGATTCGGATTC
AGCGAGTGATTCAGACTCAGGTAGTGACTCCGATTCATCAAGTGATTCAGATTCCGATTCAACGAGTGACACAGGATCAG
ACAACGACTCAGACAGTGATTCAAATAGCGATTCCGAGTCAGGTTCTAACAATAATGTAGTTCCGCCTAATTCACCTAAA
AATGGTACTAATGCTTCTAATAAAAATGAGGCTAAAGATAGTAAAGAACCATTACCAGATACAGGTTCTGAAGATGAAGC
GAATACGTCACTAATTTGGGGATTATTAGCATCATTAGGTTCATTACTACTTTTCAGAAGAAAAAAAGAAAATAAGATA
AGAAATAA
```

SEQ ID NO:64 polynucleotide sequence
```
GTGAAAAACAATCTTAGGTACGGCATTAGAAAACATAAATTGGGAGCAGCATCAGTATTCTTAGGAACAATGATCGTTGT
TGGGATGGGACAAGATAAAGAAGCTGCAGCATCAGAACAAAAGACAACTACAGTAGAAGAAAATGGGAATTCAGCTACTG
ATAATAAAACAAGTGAAACACAAACAACTGCTACTAACGTTAATCATATAGAAGAAACTCAATCATATAACGCAACAGTA
ACAGAACAACCGTCAAACGCAACACAAGTAACAACTGAAGAAGCACCAAAAGCAGTACAAGCACCACAAACTGCACAACC
AGCAAATGTAGAAACAGTTAAAGAAGAAGAGAAACCTCAAGTTAAGGAAACGACACAACCTCAAGACAATAGCGGAAATC
AAAAGACAAGTAGATTTAACACCTAAAAAGGTTACACAAAATCAAGGGACAGAAACACAAGTTGAAGTGGCACAGCCAAGA
ACGGCATCAGAAAGTAAGCCACGTGTGACAAGATCAGCAGATGTAGCGGAAGCTAAGGAAGCTAGTGACGTTTCAGAAGT
TAAAGGCACAGATGTTACAAGTAAAGTTACAGTAGAAAGTGGTTCTATTGAGGCACCTCAAGGAAATAAAGTAGAGCCAC
ATGCTGGTCAACGTGTCGTATTGAAATACAAATTGAAATTCGCAGATGGATTAAAAAGAGGAGATTATTTTGATTTTACA
TTATCAAATAATGTAAATACTTATGGGGTTTCAACAGCTAGAAAGGTACCAGAGATTAAAAATGGCTCAGTTGTAATGGC
TACAGGTGAGATCTTAGGGAATGGTAACATAAGATATACATTTACTAACGAAATTGAACACAAGGTAGAGGTAACAGCTA
ATTTAGAAATCAACTTATTTATTGACCCTAAAACTGTACAAAGCAATGGAGAACAAAAGATTACTTCTAAATTAAATGGT
GAAGAAACAGAAAAAACAATACCAGTTGTTTATAATCCAGGTGTTAGCAATAGTTATACAAATGTAAATGGATCAATTGA
ACATTTAATAAAGAATCTAATAAATTTACACATATAGCTTATATTAAGCCAATGAATGGAAACCAGTCAAACACTGTAT
CAGTAACAGGGACGTTGACTGAAGGTAGTAATTTAGCTGGTGGACAACCTACTGTTAAAGTATATGAATATCTAGGGAAA
AAAGATGAATTGCCACAAAGTGTTTTATGCAAATACATCAACATCTAACAAATTCAAAGATGTAACAAAGGAAATGAATGG
AAAATTGAGTGTGCAAGACAATGGTAGTTACTCATTGAATTTAGATAAGTTGGATAAAACGTATGTCATTCATTATACAG
GTGAATATTTGCAAGGGTCAGATCAGGTTAATTTTAGAACTGAATTATATGGGTATCCAGAACGAGCATATAAATCTTAC
TATGTTTATGGGGATATCGTTTAACTTGGGATAATGGTTTAGTTTTATATAGCAATAAAGCTGACGGCAATGGTAAAAA
TGGACAAATTATTCAAGATAATGATTTTGAATATAAAGAAGTACTGCAAAAGGAACTATGAGCGGGCAGTACGATGCCA
AGCAAATTATTGAAACAGAAGAAAATCAAGACAATACACCGCTTGACATTGATTACCACACAGCTATAGATGGTGAGGGT
GGTTATGTTGATGGGTATATTGAAACAATAGAAGAAACGGATTCATCAGCTATTGATATCGATTACCATACTGCTGTGGA
TAGTGAAGTGGGTCACGTTGGAGGATACACTGAGTCCTCTGAGGAATCAAATCCAATTGACTTTGAAGAATCGACACATG
AAAAATTCAAAACATCACGCTGATGTTGTTGAATATGAAGAGGATACAAATCCAGGTGGTGGCCAAGTAACAACTGAGTCT
AACTTAGTTGAATTTGACGAAGAGTCTACAAAAGGTATTGTAACTGGCGCAGTGAGCGACCATACAACAATTGAAGATAC
```

Figure 2 cont.

GAAAGAATATACGACTGAAAGTAATCTGATTGAACTAGTAGATGAACTACCTGAAGAACATGGTCAAGCACAAGGACCAA
TCGAGGAAATTACTGAAAACAATCATCATATTTCTCATTCTGGTTTAGGAACTGAAAATGGTCACGGTAATTATGGCGTG
ATTGAAGAAATCGAAGAAAATAGCCACGTTGATATTAAGAGTGAATTAGGTTACGAAGGTGGCCAAAATAGCGGTAACCA
GTCATTCGAGGAAGACACAGAAGAAGACAAACCTAAATATGAACAAGGTGGCAATATCGTAGATATCGATTTCGACAGTG
TACCTCAAATTCATGGTCAAAATAAAGGTGACCAGTCATTCGAAGAAGATACAGAGAAAGACAAGCCTAAATATGAACAT
GGCGGTAATATCATTGATATCGACTTCGACAGTGTGCCACAAATTCATGGATTCAATAAGCATAATGAAATTATTGAAGA
AGATACAAACAAAGATAAACCTAATTATCAATTCGGTGGACACAATAGTGTTGACTTTGAAGAAGATACACTTCCAAAAG
TAAGCGGCCAAAATGAAGGTCAACAAACGATTGAAGAAGATACAACGCCGCCAACGCCACCGACACCAGAAGTACCGAGT
GAGCCGGAAACACCAATGCCACCGACACCAGAAGTACCGAGTGAGCCGGAAACACCAACGCCACCAACACCAGAGGTACC
AAGTGAGCCGGAAACACCAACACCACCGACTCCGGAAGTACCAAGTGAGCCGGAAACACCAACACCACCGACACCAGAAG
TGCCGAGTGAGCCAGAAACACCAACACCGCCAACACCAGAGGTACCAGCTGAACCTGGTAAACCAGTACCACCCGCAAAA
GAAGAACCTAAAAAGCCTTCTAAACCAGTGGAACAAGGTAAAGTAGTAACACCTGTTATTGAAATCAATGAAAAGGTTAA
AGCAGTGGCACCAACTAAAAAAGCACAATCTAAGAAATCTGAACTACCTGAAACAGGTGGAGAAGAATCAACAAACAAAG
GTATGTTGTTCGGCGGATTATTCAGCATTCTAGGTTTAGCATTATTACGCAGAAATAAAAAGAATAACAAAGCATAA

SEQ ID NO:65 polynucleotide sequence
TTGAAAAAAGAATTGATTATTTGTCGAATAAGCAGAATAAGTATTCGATTAGACGTTTTACAGTAGGTACCACATCAGT
AATAGTAGGGGCAACTATACTATTTGGGATAGGCAATCATCAAGCACAAGCTTCAGAACAATCGAACGATACAACGCAAT
CTTCGAAAAATAATGCAAGTGCAGATTCCGAAAAAAACAATATGATAGAAACACCTCAATTAAATACAACGGCTAATGAT
ACATCTGATATTAGTGCAAACACAAACAGTGCGAATGTAGATAGCACAACAAAACCAATGTCTACACAAACGAGCAATAC
CACTACAACAGAGCCAGCTTCAACAAATGAAACACCTCAACCGACGGCAATTAAAAATCAAGCAACTGCTGCAAAAATGC
AAGATCAAACTGTTCCTCAAGAAGCAAATTCTCAAGTAGATAATAAAACAACGAATGATGCTAATAGCATAGCAACAAAC
AGTGAGCTTAAAAATTCTCAAACATTAGATTTACCACAATCATCACCACAAACGATTTCCAATGCGCAAGGAACTAGTAA
ACCAAGTGTTAGAACGAGAGCTGTACGTAGTTTAGCTGTTGCTGAACCGGTAGTAAATGCTGCTGATGCTAAAGGTACAA
ATGTAAATGATAAAGTTACGGCAAGTAATTTCAAGTTAGAAAAGACTACATTTGACCCTAATCAAAGTGGTAACACATTT
ATGGCGGCAAATTTTACAGTGACAGATAAAGTGAAATCAGGGGATTATTTTACAGCGAAGTTACCAGATAGTTTAACTGG
TAATGGAGACGTGGATTATTCTAATTCAAATAATACGATGCCAATTGCAGACATTAAAAGTACGAATGGCGATGTTGTAG
CTAAAGCAACATATGATATCTTGACTAAGACGTATACATTTGTCTTTACAGATTATGTAAATAATAAAGAAAATATTAAC
GGACAATTTTCATTACCTTTATTTACAGACCGAGCAAAGGCACCTAAATCAGGAACATATGATGCGAATATTAATATTGC
GGATGAAATGTTTAATAATAAAATTACTTATAACTATAGTTCGCCAATTGCAGGAATTGATAAACCAATGGCGCGAACA
TTTCTTCTCAAATTATTGGTGTAGATACAGCTTCAGGTCAAAACACATACAAGCAAACAGTATTTGTTAACCCTAAGCAA
CGAGTTTTAGGTAATACGTGGGTGTATATTAAAGGCTACCAAGATAAAATCGAAGAAAGTAGCGGTAAAGTAAGTGCTAC
AGATACAAAACTGAGAATTTTTGAAGTGAATGATACATCTAAATTATCAGATAGCTACTATGCAGATCCAAATGACTCTA
ACCTTAAAGAAGTAACAGACCAATTTAAAAATAGAATCTATTATGAGCATCCAAATGTAGCTAGTATTAAATTTGGTGAT
ATTACTAAAACATATGTAGTAGTAGTAGAAGGGCATTACGACAATACAGGTAAGAACTTAAAAACTCAGGTTATTCAAGA
AAATGTTGATCCTGTAACAAATAGAGACTACAGTATTTTCGGTTGGAATAATGAGAATGTTGTACGTTATGGTGGTGGAA
GTGCTGATGGTGATTCAGCAGTAAATCCGAAAGACCCAACTCCAGGGCCGCCGGTTGACCCAGAACCAAGTCCAGACCCA
GAACCAGAACCAACGCCAGATCCAGAACCAAGTCCAGACCCAGAACCGGAACCAAGCCCAGACCCGGATCCGGATTCGGA
TTCAGACAGTGACTCAGGCTCAGACAGCGACTCAGGTTCAGATAGCGACTCAGAATCAGATAGCGATTCGGATTCAGACA
GTGATTCAGATTCAGACAGCGACTCAGAATCAGATAGCGATTCAGAATCAGATAGCGACTCAGATTCAGATAGCGATTCA
GATTCAGATAGCGATTCAGAATCAGATAGCGATTCGGATTCAGACAGTGATTCAGATTCAGACAGCGACTCAGAATCAGA
TAGCGACTCAGAATCAGATAGTGAGTCAGATTCAGACAGTGACTCGGACTCAGACAGTGATTCAGACTCAGATAGCGATT
CAGACTCAGATAGCGATTCAGACTCAGACAGCGATTCAGATTCAGACAGCGACTCAGAATCAGACAGCGACTCAGACTCA
GATAGCGACTCAGACTCAGACAGCGACTCAGATTCAGATAGCGATTCAGACTCAGACAGCGACTCAGACTCAGACAGCGA
CTCAGACTCAGATAGCGATTCAGACTCAGACAGCGACTCAGATTCAGATAGCGATTCGGACTCAGACAGCGATTCAGATT
CAGACAGCGACTCAGACTCGGATAGCGATTCAGATTCAGACAGCGACTCAGACTCGGATAGCGACTCGGATTCAGATAGT
GACTCCGATTCAAGAGTTACACCACCAAATAATGACAGAAAGCACCATCAAATCCTAAAGGTGAAGTAAACCATTCTAA
TAAGGTATCAAAACAACACAAAACTGATGCTTTACCAGAAACAGGAGATAAGAGCGAAAACACAAATGCAACTTTATTTG
GTGCAATGATGGCATTATTAGGATCATTACTATTGTTTAGAAAACGCAAGCAAGATCATAAAGAAAAAGCGTAA

SEQ ID NO:66 polynucleotide sequence
ATGAAAAAGCAAATAATTTCGCTAGGCGCATTAGCAGTTGCATCTAGCTTATTTACATGGGATAACAAAGCAGATGCGAT
AGTAACAAAGGATTATAGTAAAGAATCAAGAGTGAATGAGAAAGTAAAAGGGAGCTACTGTTTCAGATTATTACTATT
GGAAAATAATTGATAGTTTAGAGGCACAATTTACTGGAGCAATAGACTTATTGGAAGATTATAAATATGGAGATCCTATC
TATAAAGAAGCGAAAGATAGATTGATGACAAGAGTATTAGGAGAAGACCAGTATTTATTAAAGAAAAAGATTGATGAATA
TGAGCTTTATAAAAAGTGGTATAAAAGTTCAAATAAGAACACTAATATGCTTACTTTCCATAAATATAATCTTTACAATT
TAACAATGAATGAATATAACGATATTTTTAACTCTTTGAAAGATGCAGTTTATCAATTTAATAAAGAAGTTAAAGAAATA
GAGCATAAAAATGTTGACTTGAAGCAGTTTGATAAAGATGGAGAAGACAAGGCAACTAAAGAAGTTTATGACCTTGTTTC

Figure 2 cont.

TGAAATTGATACATTAGTTGTAACTTATTATGCTGATAAGGATTATGGGGAGCATGCGAAAGAGTTACGAGCAAAACTGG
ACTTAATCCTTGGAGATACAGACAATCCACATAAAATTACAAATGAGCGTATAAAAAAAGAAATGATCGATGACTTAAAT
TCAATTATAGATGATTTCTTTATGGAGACTAAACAAAATAGACCGAATTCTATAACAAAATATGATCCAACAAAACACAA
TTTTAAAGAGAAGAGTGAAAATAAACCTAATTTTGATAAATTAGTTGAAGAAACAAAAAAAGCAGTTAAAGAAGCAGACG
AATCTTGGAAAAATAAAACTGTCAAAAAATACGAGGAAACTGTAACAAAATCTCCTGTTGTAAAAGAAGAGAAGAAAGTT
GAAGAACCTCAATTACCTAAAGTTGGAAACCAGCAAGAGGTTAAAACTACGGCTGGTAAAGCTGAAGAAACAACACAACC
AGTGGCACAGCCATTAGTAAAAATTCCACAAGAAACAATCTATGGTGAAACTGTAAAAGGTCCAGAATATCCAACGATGG
AAAATAAAACGTTACAAGGTGAAATCGTTCAAGGTCCCGATTTTCTAACAATGGAACAAAACAGACCATCTTTAAGCGAT
AATTATACTCAACCGACGACACCGAACCCTATTTTAGAAGGTCTTGAAGGTAGCTCATCTAAACTTGAAATAAAACCACA
AGGTACTGAATCAACGTTGAAAGGTATTCAAGGAGAATCAAGTGATATTGAAGTTAAACCTCAAGCAACTGAAACAACAG
AAGCTTCTCAATATGGTCCGAGACCGCAATTTAACAAAACACCTAAGTATGTGAAATATAGAGATGCTGGTACAGGTATC
CGTGAATACAACGATGGAACATTTGGATATGAAGCGAGACCAAGATTCAACAAGCCAAGTGAAACAAATGCATACAACGT
AACGACAAATCAAGATGGCACAGTATCATACGGAGCTCGCCCAACACAAAACAAGCCAAGTGAAACAAACGCATATAACG
TAACAACACATGCAAATGGTCAAGTATCATACGGTGCTCGCCCAACACAAAAAAAGCCAAGCAAAACAAATGCATACAAC
GTAACAACACATGCAAATGGTCAAGTATCATATGGCGCTCGCCCGACACAAAAAAAGCCAAGCAAAACAAATGCATATAA
CGTAACAACACATGCAAATGGTCAAGTATCATACGGAGCTCGCCCGACATACAAGAAGCCAAGCGAAACAAATGCATACA
ACGTAACAACACATGCAAATGGTCAAGTATCATATGGCGCTCGCCCGACACAAAAAAAGCCAAGCGAAACAAACGCATAT
AACGTAACAACACATGCAGATGGTACTGCGACATATGGGCCTAGAGTAACAAAATAA

SEQ ID NO:77 polynucleotide sequence
GTGAAAAGCAATCTTAGATACGGCATAAGAAAACACAAATTGGGAGCGGCCTCAGTATTCTTAGGAACAATGATCGTTGT
TGGAATGGGACAAGAAAAGAAGCTGCAGCATCGGAACAAAACAATACTACAGTAGAGGAAAGTGGGAGTTCAGCTACTG
AAAGTAAAGCAAGCGAAACACAAACAACTACAAATAACGTTAATACAATAGATGAAACACAATCATACAGCGCGACATCA
ACTGAGCAACCATCAAAATCAACTCAAGTAACAACAGAAGAAGCACCAACAACTGTGCAAGCACCAAAAGTAGAAACCGA
AATGAAATCACAAGAAGATTTACCATCAGAAAAAGTTGCTGATAAGGAAACTACAGGAACTCAAGTTGACATAGCTCAAC
CAAGTAACGTCTCAGAAATTAAACCAAGAATGAAAAGATCAGCTGACGTTACAGCAGTTTCAGAGAAAGAAGTAGCGGAA
GAAGCTAAAGCGACAGGTACAGATGTAACAAATAAAGTGGAAGTTACTGAAAGCTCTTTAGAAGGACATAATAAAGATTC
GAATATTGTTAATCCGCATAATGCTCAAAGAGTAACTTTAAAATACAAATGGAAATTTGGAGAAGGAATTAAGGCAGGAG
ATTATTTTGATTTCACATTAAGTGATAATGTTGAAACACATGGTATATCAACACTGCGTAAAGTTCCGGAGATAAAAAGT
TCAACAGAAGATAAAGTTATGGCAAATGGTCAAGTTATAAATGAACGTACAATTCGCTATACATTTACTGATTATATAAA
TAACAAAAAGATTTAACTGCTGAATTAAACTTAAACCTATTCATTGACCCAACAACAGTGACAAAGCAAGGGAGTCAAA
AAGTTGAAGTAACACTAGGTCAAAATAAAGTCTCAAAAGAATTTGATATCAAATATTTAGACGGCGTTAAAGATAGAATG
GGTGTTACTGTTAATGGTCGTATTGATACTTTGAATAAAGAAGAGGGTAAATTTAGCCATTTTGCATATGTGAAGCCTAA
CAACCAGTCGTTAACTTCTGTCACAGTAACTGGTCAAGTAACATCTGGATATAAACAAAGTGCTAATAATCCAACAGTCA
AAGTATATAAACACATTGGTTCAGATGAATTAGCTGAAAGTGTTTATGCAAAGCTTGATGATACCAGTAAATTTGAAGAT
GTGACTGAAAAAGTAAATCTATCTTACACAAGTAATGGTGGGTACACATTGAACCTTGGCGATTTAGATAATTCGAAAGA
CTATGTAATTAAATATGAAGGTGAATATGATCAAAATGCTAAGGATCTAAATTTCCGAACACATCTTTCAGGATATCATA
AATACTACCCATACTATATCCTTATTACCCGTATTATCCAGTTCAATTAACTTGGAACAACGGTGTTGCATTTTACTCTAAT
AATGCTAAAGGCGATGGTAAAGATAAACCAAATGATCCTATCATTGAGAAGAGTGAACCAATTGATTTAGACATTAAATC
AGAGCCACCAGTGGAGAAGCATGAATTGACTGGTACAATCGAAGAAAGTAACGATTCTAAGCCAATTGATTTTGAATATC
ATACAGCTGTTGAAGGTGCAGAAGGTCATGCAGAAGGTATTATTGAAACTGAAGAAGATTCTATTCATGTGGATTTTGAA
GAATCTACACATGAAAATTCAAAACATCACGCTGATGTTGTTGAATATGAAGAGGATACAAACCCAGGTGGTGGCCAAGT
AACAACTGAGTCTAACTTAGTTGAATTTGACGAAGAGTCTACAAAAGGTATTGTAACTGGCGCAGTGAGCGACCATACAA
CAGTTGAAGATACGAAAGAATATACAACTGAAAGTAATCTGATTGAATTAGTGGATGAATTACCTGAAGAACATGGTCAA
GCACAAGGGCCAATCGAGGAAATTACTGAAAACAATCATCATATTTCTCATTCTGGTTTAGGAACTGAAAATGGTCACGG
TAATTATGGCGTGATTGATGAAATCGAAGAAAATAGCCACGTTGATATTAAGAGTGAATTAGGTTATGAAGGTGGCCAAA
ATAGCGGTAATCAGTCATTCGAGGAAGACACAGAAGAAGATAAACCTAAATATGAACAAGGTGGTAATATCGTAGATATC
GATTTCGACAGTGTACCTCAAATTCATGGTCAAAATAATGGTAACCAGTCATTCGAGGAAGACACAGAAGAAGACAAGCC
TAAGTATGAACAAGGTGGTAACATCATTGATATCGACTTCGACAGTGTGCCACAAATTCATGGATTCAATAAGCATAATG
AAATTATTGAAGAAGATACAAACAAAGATAAACCTAATTATCAATTTGGTGGACACACAGTGTTGATTTTGAAGAAGAT
ACACTTCCAAAAGTAAGTGGTCAAAATGAAGGTCAACAAACGATTGAAGAAGATACAACGCCGCCAACACCGCCAACACC
AGAGGTACCAAGTGAGCCGGAAACACCAACACCACCAACACCAGAAGTACCGAGTGAGCCAGGCGAACCAACGCCACCAA
AACCGGAAGTACCAAGTGAGCCGGAAACACCAGTACCACCAACACCAGAGGTACCATCTGAACCTGGTAAACCAGTACCA
CCTGCTAAAGAAGAACCTAAAAAACCTTCTAAACCAGTGGAACAAGGTAAGGTAGTAACACCTGTTATTGAAATCAATGA
AAAGGTTAAAGCAGTGGCACCAACTAAACAAAAACAATCTAAGAAATCTGAACTACCTGAAACAGGTGGAGAAGAATCAA
CAAACAAAGGTATGTTGTTCGGCGGATTATTCAGCATTCTAGGTTTAGTATTATTACGCAGAAATAAAAAGAATAACAAA
GCATAA

Figure 2 cont.

SEQ ID NO:78 polynucleotide sequence
ATGAAATTTAAGTCATTGATTACAACAACATTAGCATTAGGCGTTATAGCATCAACAGGAGCAAACTTTAATACTAACGA
AGCATCTGCCGCAGCTAAGCCATTAGATAAATCATCAAGTACATTACACCATGGACATTCTAACATCCAGATTCCATATA
CAATTACTGTGAACGGTACAAGCCAAAACATTTTATCAAGCTTAACATTTAATAAGAATCAAAATATTAGTTATAAAGAT
ATAGAGAATAAAGTTAAATCAGTTTTATACTTTAATAGAGGTATTAGTGATATCGATTTAAGACTTTCAAAGCAAGCGGA
ATATACGGTTCATTTTAAAAATGGAACAAAAAGAGTTATCGATTTGAAATCAGGTATCTACACAGCTGACTTAATCAATA
CAAGTGACATTAAAGCTATCAGTGTTAACGTAGATACTAAAAAGCAACCTAAAGATAAAGCTAAAGCAAATGTTCAAGTG
CCATATACAATCACAGTGAACGGCACAAGCCAAAACATTTTATCAAACCTAACATTTAATAAAAATCAAATATTAGTTA
CAAAGATTTAGAGGGTAAAGTTAAATCAGTTTTAGAATCAAATAGAGGTATTACTGATGTTGATTTAAGACTTTCGAAGC
AAGCGAAATATACAGTTAATTTTAAAAATGGAACGAAGAAAGTTATCGATTTGAAATCAGGTATTTACACAGCGAATTTA
ATCAATTCAAGTGATATTAAAAGTATCAATATTAACGTAGATACAAAAAAACATATCGAAAATAAAGCTAAAAGAAACTA
TCAAGTTCCATATTCAATTAATCTAAATGGTACATCTACAAACATTTTATCGAATCTTTCATTTTCAAATAAACCTTGGA
CAAATTACAAAAATTTAACTAGTCAAATAAAATCAGTACTGAAGCATGATAGAGGTATTAGTGAACAAGATTTAAAATAT
GCTAAGAAAGCTTATTATACTGTTTATTTTAAAAATGGTGGTAAAAGAATCTTACAGTTAAATTCAAAAAATTACACAGC
AAACTTAGTTCATGCGAAAGATGTTAAGAGAATTGAAATTACTGTTAAAACAGGAACTAAAGCGAAAGCAGACAGATATG
TACCATACACAATTGCAGTAAATGGCACATCAACACCAATTTTATCAAAACTAAAAATTTCGAATAAACAATTAATTAGT
TACAAATATTTAAACGACAAAGTGAAATCTGTATTAAAAAGTGAAAGAGGTATCAGTGATCTTGACTTAAAATTTGCGAA
ACAAGCAAAATATACAGTATATTTCAAAAATGGAAAGAAACAAGTAGTGAATTTAAAATCAGACATCTTTACACCTAATT
TATTTAGTGCCAAAGATATTAAAAAGATTGATATTGATGTAAAACAATACACTAAATCAAAAAAAAAAATAAATAAATCT
AATAATGTGAAATTCCCAGTAACAATAAATAAATTTGAAAACATAGTTTCAAATGAATTTGTGTTCTATAATGCAAGCAA
AATTACAATTAATGATTTAAGTATAAAACTTAAATCAGCAATGGCAAATGATCAAGGGATAACTAAACATGACATAGGAC
TTGCTGAACGCGCAGTGTATAAAGTGTATTTTAAAAATGGTTCGTCAAAATATGTAGACTTAAAAACTGAGTATAAAGAT
GAAAGAGTATTTAAAGCAACTGACATTAAAAAGGTAGATATTGAACTTAAATTCTAA

SEQ ID NO:79 polynucleotide sequence
ATGAACAAACATCACCCAAAATTAAGGTCTTTCTATTCTATTAGAAAATCAACTCTAGGC
GTTGCATCGGTCATTGTCAGTACACTATTTTTAATTACTTCTCAACATCAAGCACAAGCA
GCAGAAAATACAAATACTTCAGATAAAATCTCGCAAAATCAAAATAATAATGCAACTACA
ACTCAGCCACCTAAGGATACAAATCAAACACAACCTGCTACGCAACCAGCAAACACTGCG
AAAAACTATCCTGCAGCGGATGAATCACTTAAAGATGCAATTAAAGATCCTGCATTAGAA
AATAAAGAACATGATATAGGTCCAAGAGAACAAGTCAATTTCCAGTTATTAGATAAAAAC
AATGAAACGCAGTACTATCACTTTTTCAGCATCAAAGATCCAGCAGATGTGTATTACACT
AAAAAGAAAGCAGAAGTTGAATTAGACATCAATACTGCTTCAACATGGAAGAAGTTTGAA
GTCTATGAAAACAATCAAAAATTGCCAGTGAGACTTGTATCATATAGTCCTGTACCAGAA
GACCATGCCTATATTCGATTCCCAGTTTCAGATGGCACACAAGAATTGAAAATTGTTTCT
TCGACTCAAATTGATGATGGAGAAGAAACAAATTATGATTATACTAAATTAGTATTTGCT
AAACCTATTTATAACGATCCTTCACTTGTAAAATCAGATACAAATGATGCAGTAGTAACG
AATGATCAATCAAGTTCAGTCGCAAGTAATCAAACAAACACGAATACATCTAATCAAAAT
ATATCAACGATCAACAATGCTAATAATCAACCGCAGGCAACGACCAATATGAGTCAACCT
GCACAACCAAAATCGTCAACGAATGCAGATCAAGCGTCAAGCCAACCAGCTCATGAAACA
AATTCTAATGGTAATACTAACGATAAAACGAATGAGTCAAGTAATCAGTCGGATGTTAAT
CAACAGTATCCACCAGCAGATGAATCACTACAAGATGCAATTAAAAACCCGGCTATCATC
GATAAAGAACATACAGCTGATAATTGGCGACCAATTGATTTTCAAATGAAAATGATAAA
GGTGAAAGACAGTTCTATCATTATGCTAGTACTGTTGAACCAGCAACTGTCATTTTTACA
AAAACAGGACCAATAATTGAATTAGGTTTAAAGACAGCTTCAACATGGAAGAAATTTGAA
GTTTATGAAGGTGACAAAAAGTTACCAGTCGAATTAGTATCATATGATTCTGATAAAGAT
TATGCCTATATTCGTTTCCCAGTATCTAATGGTACGAGAGAAGTTAAAATTGTGTCATCT
ATTGAATATGGTGAGAACATCCATGAAGACTATGATTATACGCTAATGGTCTTTGCACAG
CCTATTACTAATAACCCAGACGACTATGTGGATGAAGAAACATACAATTTACAAAAATTA
TTAGCTCCGTATCACAAAGCTAAAACGTTAGAAAGACAAGTTTATGAATTAGAAAAATTA
CAAGAGAAATTGCCAGAAAAATATAAGGCGGAATATAAAAAGAAATTAGATCAAACTAGA
GTAGAGTTAGCTGATCAAGTTAAATCAGCAGTGACGGAATTTGAAAATGTTACACCTACA
AATGTCAATTAACAGATTTACAAGAAGCGCATTTTGTTGTTTTTGAAAGTGAAGAAAAT
AGTGAGTCAGTTATGGACGGCTTTGTTGAACATCCATTCTATACAGCAACTTTAAATGGT
CAAAAATATGTAGTGATGAAAACAAAGGATGACAGTTACTGGAAAGATTTAATTGTAGAA
GGTAAACGTGTCACTACTGTTTCTAAAGATCCTAAAAATAATTCTAGAACGCTGATTTTC
CCATATATACCTGACAAAGCAGTTTACAATGCGATTGTTAAGTCGTTGTGGCAAACATT
GGTTATGAAGGTCAATATCATGTCAGAATTATAAATCAGGATATCAATACAAAAGATGAT

Figure 2 cont.

GATACATCACAAAATAACACGAGTGAACCGCTAAATGTACAAACAGGACAAGAAGGTAAG
GTTGCTGATACAGATGTAGCTGAAAATAGCAGCACTGCAACAAATCCTAAAGATGCGTCT
GATAAAGCAGATGTGATAGAACCAGAGTCTGACGTGGTTAAAGATGCTGATAATAATATT
GATAAAGATGTGCAACATGATGTTGATCATTTATCCGATATGTCGGATAATAATCACTTC
GATAAATATGATTTAAAAGAAATGGATACTCAAATTGCCAAAGATACTGATAGAAATGTG
GATAAAGATGCCGATAATAGCGTTGGTATGTCATCTAATGTCGATACTGATAAAGACTCT
AATAAAAATAAAGACAAAGTCATACAGCTGAATCATATTGCCGATAAAAATAATCATACT
GGAAAAGCAGCAAAGCTTGACGTAGTGAAACAAAATTATAATAATACAGACAAAGTTACT
GACAAAAAAACAACTGAACATCTGCCGAGTGATATTCATAAAACTGTAGATAAAACAGTG
AAAACAAAAGAAAAGCCGGCACACCATCGAAAGAAAACAAACTTAGTCAATCTAAAATG
CTACCAAAAACTGGAGAAACAACTTCAAGCCAATCATGGTGGGGCTTATATGCGTTATTA
GGTATGTTAGCTTTATTCATTCCTAAATTCAGAAAAGAATCTAAATAA

SEQ ID NO:80 polynucleotide sequence
GCTGAGACGACACAAGATCAAACTACTAATAAAAACGTTTTAGATAGTAATAAAGTTAAA
GCAACTACTGAACAAGCAAAAGCTGAGGTAAAAAATCCAACGCAAAACATTTCTGGCACT
CAAGTATATCAAGACCCTGCTATTGTCCAACCAAAAACAGCAAATAACAAAACAGGCAAT
GCTCAAGTAAGTCAAAAAGTTGATACTGCACAAGTAAATGGTGACACTCGTGCTAATCAA
TCAGCGACTACAAATAATACGCAGCCTGTTGCAAAGTCAACAAGCACTACAGCACCTAAA
ACTAACACTAATGTTACAAATGCTGGTTATAGTTTAGTTGATGATGAAGATGATAATTCA
GAAAATCAAATTAATCCAGAATTAATTAAATCAGCTGCTAAACCTGCAGCTCTTGAAACG
CAATATAAAACCGCAGCACCTAAAGCTGCAACTACATCAGCACCTAAAGCTAAAACTGAA
GCGACACCTAAAGTAACTACTTTTAGCGCTTCAGCACAACCAAGATCAGTTGCTGCAACA
CCAAAAACGAGTTTGCCAAAATATAAACCACAAGTAAACTCTTCAATTAACGATTACATT
TGTAAAAATAACTTAAAAGCACCTAAAATTGAAGAAGATTATACATCTTACTTCCCTAAA
TACGCATACCGTAACGGCGTAGGTCGTCCTGAAGGTATCGTAGTTCATGATACAGCTAAT
GATCGTTCGACGATAAATGGTGAAATTAGTTATATGAAAATAACTATCAAAACGCATTC
GTACATGCATTTGTTGATGGGGATCGTATAATCGAAACAGCACCAACGGATTACTTATCT
TGGGGTGTCGGTGCAGTCGGTAACCCTAGATTCATCAATGTTGAAATCGTACACACACAC
GACTATGCTTCATTTGCACGTTCAATGAATAACTATGCTGACTATGCAGCTACACAATTA
CAATATTATGGTTTAAAACCAGACAGTGCTGAGTATGATGGAAATGGTACAGTATGGACT
CACTACGCTGTAAGTAAATATTTAGGTGGTACTGACCATGCCGATCCACATGGATATTTA
AGAAGTCATAATTATAGTTATGATCAATTATATGACTTAATTAATGAAAATATTTAATA
AAAATGGGTAAAGTGGCGCCATGGGTACGCAATCTACAACTACCCCTACTACACCATCA
AAACCAACAACACCGTCGAAACCATCAACTGGTAAATTAACAGTTGCTGCAAACAATGGT
GTCGCACAAATCAAACCAACAAATAGTGGTTTATATACTACTGTATACGACAAAACTGGT
AAAGCAACTAATGAAGTTCAAAAAACATTTGCTGTATCTAAAACAGCTACATTAGGTAAT
CAAAAATTCTATCTTGTTCAAGATTACAATTCTGGTAATAAATTTGGTTGGGTTAAAGAA
GGCGATGTGGTTTACAACACAGCTAAATCACCTGTAAATGTAAATCAATCATATTCAATC
AAACCTGGTACGAAACTTTATACAGTACCTTGGGGTACATCTAAACAAGTTGCTGGTAGT
GTGTCTGGCTCTGGAAACCAAACATTTAAGGCTTCAAAGCAACAACAAATTGATAAATCA
ATTTATTTATATGGCTCTGTGAATGGTAAATCTGGTTGGGTAAGTAAAGCATATTTAGTT
GATACTGCTAAACCTACGCCTACACCAACACCTAAGCCATCAACACCTACAACAAATAAT
AAATTAACAGTTTCATCATTAAACGGTGTTGCTCAAATTAATGCTAAAAACAATGGCTTA
TTCACTACAGTTTATGACAAAACTGGTAAGCCAACGAAAGAAGTTCAAAAAACATTTGCT
GTAACAAAAGAAGCAAGTTTAGGTGGAAACAAATTCTACTTAGTTAAAGATTACAATAGT
CCAACTTTAATTGGTTGGGTTAAACAAGGTGACGTTATTTATAACAATGCAAAATCACCT
GTAAATGTAATGCAAACATATACAGTAAAACCAGGCACTAAATTATATTCAGTACCTTGG
GGCACTTATAAACAAGAAGCTGGTGCAGTTTCTGGTACAGGTAACCAAACTTTTAAAGCG
ACTAAGCAACAACAAATTGATAAATCTATCTATTTATTTGGAACTGTAAATGGTAAATCT
GGTTGGGTAAGTAAAGCATATTTAGCTGTACCTGCTGCACCTAAAAAAGCAGTAGCACAA
CCAAAAACAGCTGTAAAA

SEQ ID NO: 81 polynucleotide sequence
GCTTATACTGTTACTAAACCACAAACGACTCAAACAGTTAGCAAGATTGCTCAAGTTAAA

Figure 2 cont.

```
CCAAACAACACTGGTATTCGTGCTTCTGTTTATGAAAAAACAGCGAAAAACGGTGCGAAA
TATGCAGACCGTACGTTCTATGTAACAAAAGAGCGTGCTCATGGTAATGAAACGTATGTA
TTATTAAACAATACAAGCCATAACATCCCATTAGGTTGGTTCAATGTAAAAGACTTAAAT
GTTCAAAACTTAGGCAAAGAAGTTAAAACGACTCAAAAATATACTGTTAATAAATCAAAT
AACGGCTTATCAATGGTTCCTTGGGGTACTAAAAACCAAGTCATTTTAACAGGCAATAAC
ATTGCTCAAGGTACATTTAATGCAACGAAACAAGTATCTGTAGGCAAAGATGTTTATTTA
TACGGTACTATTAATAACCGCACTGGTTGGGTAAATGCAAAAGATTTAACTGCACCAACT
GCTGTGAAACCAACTACATCAGCTGCCAAAGATTATAACTACACTTATGTAATTAAAAAT
GGTAATGGTTATTACTATGTAACACCAAATTCTGATACAGCTAAATACTCATTAAAAGCA
TTTAATGAACAACCATTCGCAGTTGTTAAAGAACAAGTCATTAATGGACAAACTTGGTAC
TATGGTAAATTATCTAACGGTAAATTAGCATGGATTAAATCAACTGATTTAGCTAAAGAA
TTAATTAAGTATAATCAAACAGGTATGACATTAAACCAAGTTGCTCAAATACAAGCTGGT
TTACAATATAAACCACAAGTACAACGTGTACCAGGTAAGTGGACAGATGCTAAATTTAAT
GATGTTAAGCATGCAATGGATACGAAGCGTTTAGCTCAAGATCCAGCATTAAAATATCAA
TTCTTACGCTTAGACCAACCACAAAATATTTCTATTGATAAAATTAATCAATTCTTAAAA
GGTAAAGGTGTATTAGAAAACCAAGGTGCTGCATTTAACAAAGCTGCTCAAATGTATGGC
ATTAATGAAGTTTATCTTATCTCACATGCCCTATTAGAAACAGGTAACGGTACTTCTCAA
TTAGCGAAAGGTGCAGATGTAGTGAACAACAAAGTTGTAACTAACTCAAACACGAAATAC
CATAACGTATTTGGTATTGCTGCATATGATAACGATCCTTTACGTGAAGGTATTAAATAT
GCTAAACAAGCTGGTTGGGACACAGTATCAAAAGCAATCGTTGGTGGTGCTAAATTCATC
GGCAACTCATATGTAAAAGCTGGTCAAAATACACTTTACAAAATGAGATGGAATCCTGCA
CATCCAGGAACACACCAATATGCTACAGATGTAGATTGGGCTAACATCAATGCTAAAATC
ATCAAAGGCTACTATGATAAAATTGGCGAAGTCGGCAAATACTTCGACATCCCACAATAT
AAA
```

SEQ ID NO: 82 polynucleotide sequence
```
GATCGTGTATTAGCCTCACATCCAGATGTTGCGACAATACGTCAAAACGTGACAGCAGCG
AATGCCGCTAAATCAGCACTTGATCAAGCACGTAATGGCTTAACAGTCGATAAAGCGCCT
TTAGAAAATGCGAAAAATCAACTACAACATAGTATTGACACGCAAACAAGTACAACTGGT
ATGACACAAGACTCTATAAATGCATACAATGCGAAGTTAACAGCTGCACGTAATAAGATT
CAACAAATCAATCAAGTATTAGCAGGTTCACCGACTGTAGAACAAATTAATACAAATACG
TCTACAGCAAATCAAGCTAAATCTGATTTAGATCATGCACGTCAAGCTTTAACACCAGAT
AAAGCGCCGCTTCAAACTGCGAAAACGCAATTAGAACAAAGCATTAATCAACCAACGGAT
ACAACAGGTATGACGACCGCTTCGTTAAATGCGTACAACCAAAAATTACAAGCAGCGCGT
CAAAAGTTAACTGAAATTAATCAAGTGTTGAATGGCAACCCAACTGTCCAAAATATCAAT
GATAAAGTGACAGAGGCAAACCAAGCTAAGGATCAATTAAATACAGCACGTCAAGGTTTA
ACATTAGATAGACAGCCAGCGTTAACAACATTACATGGTGCATCTAACTTAAACCAAGCA
CAACAAAATAATTTCACGCAACAAATTAATGCTGCTCAAAATCATGCTGCGCTTGAAACA
ATTAAGTCTAACATTACGGCTTTAAATACTGCGATGACGAAATTAAAAGACAGTGTTGCG
GATAATAATACAATTAAATCAGATCAAAATTACACTGACGCAACACCAGCTAATAAACAA
GCGTATGATAATGCAGTTAATGCGGCTAAAGGTGTCATTGGAGAAACGACTAATCCAACG
ATGGATGTTAACACAGTGAACCAAAAAGCAGCATCTGTTAAATCGACGAAAGATGCTTTA
GATGGTCAACAAAACTTACAACGTGCGAAAACAGAAGCAACAAATGCGATTACGCATGCA
AGTGATTTAAACCAAGCACAAAAGAATGCATTAACACAACAAGTGAATAGTGCACAAAAC
GTGCAAGCAGTAAATGATATTAAACAAACGACTCAAAGCTTAAATACTGCTATGACAGGT
TTAAAACGTGGCGTTGCTAATCATAACCAAGTCGTACAAAGTGATAATTATGTCAACGCA
GATACTAATAAGAAAAATGATTACAACAATGCATACAACCATGCGAATGACATTATTAAT
GGTAATGCACAACATCCAGTTATAACACCAAGTGATGTTAACAATGCTTTATCAAATGTC
ACAAGTAAAGAACATGCATTGAATGGTGAAGCTAAGTTAAATGCTGCGAAACAAGAAGCG
AATACTGCATTAGGTCATTTAAACAATTTAAATAATGCACAACGTCAAAACTTACAATCG
CAAATTAATGGTGCGCATCAAATTGATGCAGTTAATACAATTAAGCAAAATGCAACAAAC
TTGAATAGTGCAATGGGTAACTTAAGACAAGCTGTTGCAGATAAAGATCAAGTGAAACGT
ACAGAAGATTATGCGGATGCAGATACAGCTAAACAAAATGCATATAACAGTGCAGTTTCA
AGTGCCGAAACAATCATTAATCAAACAACAAATCCAACGATGTCTGTTGATGATGTTAAT
```

Figure 2 cont.

CGTGCAACTTCAGCTGTTACTTCTAATAAAAATGCATTAAATGGTTATGAAAAATTAGCA
CAATCTAAAACAGATGCTGCAAGAGCAATTGATGCATTACCACATTTAAATAATGCACAA
AAAGCAGATGTTAAATCTAAAATTAATGCTGCATCAAATATTGCTGGCGTAAATACTGTT
AAACAACAAGGTACAGATTTAAATACAGCGATGGGTAACTTGCAAGGTGCAATCAATGAT
GAACAAACGACGCTTAATAGTCAAAACTATCAAGATGCGACACCTAGTAAGAAAACAGCA
TACACAAATGCGGTACAAGCTGCGAAAGATATTTTAAATAAATCAAATGGTCAAAATAAA
ACGAAAGATCAAGTTACTGAAGCGATGAATCAAGTGAATTCTGCTAAAAATAACTTAGAT
GGTACGCGTTTATTAGAT

SEQ ID NO: 83 polynucleotide sequence
GCTTCTACACAACATACAGTACAATCTGGTGAATCATTATGGAGTATTGCTCAAAAATAC
AACACTTCAGTAGAGAGTATTAAACAAAATAACCAATTAGATAACAACTTGGTATTCCCT
GGTCAAGTTATCTCAGTAGGTGGAAGTGATGCACAAAATACGTCAAACACTTCTCCACAA
GCTGGTTCAGCATCATCTCATACTGTACAAGCTGGTGAATCATTAAATATCATTGCTAGC
AGATATGGTGTTTCAGTTGATCAATTAATGGCAGCCAATAACTTACGTGGTTATTTAATT
ATGCCTAACCAAACATTACAAATTCCTAATGGTGGATCAGGTGGTACAACACCAACAGCT
ACAACAGGTAGCAATGGCAATGCATCATCTTTTAATCACCAAAATTTATACACTGCTGGT
CAATGTACATGGTACGTATTTGACCGTCGTGCTCAAGCTGGTAGTCCAATTAGCACATAT
TGGTCAGACGCTAAGTATTGGGCTGGTAACGCAGTCAATGATGGTTACCAAGTAAACAAC
ACACCATCAGTTGGTTCAATTATGCAAAGCACACCTGGTCCATATGGTCATGTTGCTTAT
GTTGAACGTGTCAATGGTGATGGTAGTATCTTGATTTCTGAAATGAATTACACATATGGT
CCATACAATATGAACTACCGTACAATTCCAGCTTCAGAAGTTTCTAGCTATGCATTCATC
CATTAA

SEQ ID NO:84 polynucleotide sequence
ATGAATAATAAAAAGACAGCAACAAATAGAAAAGGCATGATACCAAATCGATTAAACAAA
TTTTCGATAAGAAAGTATTCTGTAGGTACTGCTTCAATTTTAGTAGGGACAACATTGATT
TTTGGGTTAAGTGGTCATGAAGCTAAAGCGGCAGAACATACGAATGGAGAATTAAATCAA
TCAAAAAATGAAACGACAGCCCCAAGTGAGAATAAAACAACTAAAAAAGTTGATAGTCGT
CAACTAAAAGACAATACGCAAACTGCAACTGCAGATCAGCCTAAAGTGACAATGAGTGAT
AGTGCAACAGTTAAAGAAACTAGTAGTAACATGCAATCACCACAAAACGCTACAGCTAAT
CAATCTACTACAAAAACTAGCAATGTAACAACAAATGATAAATCATCAACTACATATAGT
AATGAAACTGATAAAAGTAATTTAACACAAGCAAAAGATGTTTCAACTACACCTAAAACA
ACGACTATTAAACCAAGAACTTTAAATCGCATGGCAGTGAATACTGTTGCAGCTCCACAA
CAAGGAACAAATGTTAATGATAAAGTACATTTTTCAAATATTGACATTGCGATTGATAAA
GGACATGTTAATCAGACTACTGGTAAAACTGAATTTTGGGCAACTTCAAGTGATGTTTTA
AAATTAAAAGCAAATTACACAATCGATGATTCTGTTAAAGAGGGCGATACATTTACTTTT
AAATATGGTCAATATTTCCGTCCAGGATCAGTAAGATTACCTTCACAAACTCAAAATTTA
TATAATGCCCAAGGTAATATTATTGCAAAAGGTATTTATGATAGTACAACAAACACAACA
ACATATACTTTTACGAACTATGTAGATCAATATACAAATGTTAGAGGTAGCTTTGAACAA
GTTGCATTTGCGAAACGTAAAAATGCAACAACTGATAAAACAGCTTATAAAATGGAAGTA
ACTTTAGGTAATGATACATATAGCGAAGAAATCATTGTCGATTATGGTAATAAAAAGCA
CAACCGCTTATTTCAAGTACAAACTATATTAACAATGAAGATTTATCGCGTAATATGACT
GCATATGTAAATCAACCTAAAAATACATATCTAAACAAACGTTTGTTACTAATTTAACT
GGATATAAATTTAATCCAAATGCAAAAAACTTCAAAATTTACGAAGTGACAGATCAAAAT
CAATTTGTGGATAGTTTCACCCCTGATACTTCAAAACTTAAAGATGTTACTGATCAATTC
GATGTTATTTATAGTAATGATAATAAAACAGCTACAGTCGATTTAATGAAAGGCCAAACA
AGCAGCAATAAACAATACATCATTCAACAAGTTGCTTATCCAGATAATAGTTCAACAGAT
AATGGAAAATTGATTATACTTTAGACACTGACAAAACTAAATATAGTTGGTCAAATAGT
TATTCAAATGTGAATGGCTCATCAACTGCTAATGGCGACCAAAAGAAATATAATCTAGGT
GACTATGTATGGGAAGATACAAATAAAGATGGTAAACAAGATGCCAATGAAAAAGGGATT
AAAGGTGTTTATGTCATTCTTAAAGATAGTAACGGTAAAGAATTAGATCGTACGACAACA
GATGAAAATGGTAAATATCAGTTCACTGGTTTAAGCAATGGAACTTATAGTGTAGAGTTT
TCAACACCAGCCGGTTATACACCGACAACTGCAAATGTAGGTACAGATGATGCTGTAGAT
TCTGATGGACTAACTACAACAGGTGTCATTAAAGACGCTGACAACATGACATTAGATAGT
GGATTCTACAAAACACCAAAATATAGTTTAGGTGATTATGTTTGGTACGACAGTAATAAA

Figure 2 cont.

GATGGTAAACAAGATTCGACTGAAAAAGGAATTAAAGGTGTTAAAGTTACTTTGCAAAAC
GAAAAAGGCGAAGTAATTGGTACAACTGAAACAGATGAAAATGGTAAATACCGCTTTGAT
AATTTAGATAGTGGTAAATACAAAGTTATCTTTGAAAAACCTGCTGGCTTAACTCAAACA
GGTACAAATACAACTGAAGATGATAAAGATGCCGATGGTGGCGAAGTTGATGTAACAATT
ACGGATCATGATGATTTCACACTTGATAATGGCTACTACGAAGAAGAAACATCAGATAGC
GACTCAGATTCTGACAGCGATTCAGACTCAGATAGCGACTCAGATTCAGATAGCGACTCA
GATTCAGACAGCGATTCAGACAGCGACTCAGACTCAGATAGCGATTCAGATTCAGACAGC
GACTCAGACTCAGACAGCGATTCAGACTCGGATAGCGACTCAGACTCAGATAGCGACTCA
GATTCGGATAGCGACTCAGACTCAGATAGCGATTCAGATTCAGATAGCGATTCGGACTCA
GACAGTGATTCAGATTCAGACTCAGATAGCGACTCAGATTCTGACAGCGATTCAGACTCA
GACAGCGACTCAGACTCAGACAGTGATTCAGATTCAGACAGCGACTCAGATTCAGATAGC
GACTCAGACTCAGATAGCGACTCAGATTCAGATAGCGATTCGGACTCAGACAACGACTCA
GATTCAGATAGCGATTCAGATTCAGATAGCGACTCAGATTCGGACAGCGATTCAGACTCA
GATAGCGATTCAGACTCAGACAGCGATTCAGATTCAGATAGCGACTCAGACTCAGATAGC
GACTCAGACTCGGATAGCGATTCAGATTCAGACAGCGACTCAGATTCAGATAGCGATTCG
GACTCAGACAACGACTCAGATTCAGATAGCGATTCAGATTCAGATGCAGGTAAACATACT
CCGGCTAAACCAATGAGTACGGTTAAAGATCAGCATAAAACAGCTAAAGCATTACCAGAA
ACAGGTAGTGAAAATAATAATTCAAATAATGGCACATTATTCGGTGGATTATTCGCGGCA
TTAGGATCATTATTGTTATTCGGTCGTCGTAAAAAACAAAATAAATAA

SEQ ID NO: 85 polynucleotide sequence
ATGAATTTGTTAAAGAAAAATAAATATAGTATTAGGAAGTATAAAGTAGGCATATTCTCT
ACTTTAATCGGAACAGTTTTATTACTTTCAAACCCAAATGGTGCACAAGCCTTAACTACG
GATAATAATGTACAAAGCGATACTAATCAAGCAACACCTGTAAATTCACAAGATAAAGAT
GTTGCTAATAATAGAGGTTTAGCAAATAGTGCGCAGAATACACCTAATCAATCTGCAACA
ACCAATCAAGCAACGAATCAAGCATTGGTTAATCATAATAATGGTAGTATAGTAAATCAA
GCTACGCCAACATCAGTGCAATCAAGTACGCCTTCAGCACAAAACAATAATCATACAGAT
GGCAATACAACAGCAACTGAGACAGTGTCAAACGCTAATAATAATGATGTAGTGTCGAAT
AATACCGCATTAAATGTACCAACTAAAACAAATGAAAATGGTTCAGGAGGACATCTAACT
TTAAAGGAAATTCAAGAAGATGTTCGTCATTCTTCAAATAAACCAGAGCTAGTTGCAATT
GCTGAACCAGCATCTAATAGACCGAAAAAGAGAAGTAGACGTGCGGCACCGGCAGATCCT
AATGCAACTCCAGCAGATCCAGCGGCTGCAGCGGTAGGAAACGGTGGTGCACCAGTTGCA
ATTACAGCGCCATATACGCCAACAACTGATCCTAATGCCAATAATGCAGGACAAAATGCA
CCTAACGAAGTGCTGTCATTTGATGACAATGGTATTAGACCAAGTACCAACCGTTCTGTG
CCAACAGTAAACGTTGTTAATAACTTGCCGGGCTTCACACTAATCAATGGTGGCAAAGTA
GGGGTGTTTAGTCATGCAATGGTAAGAACGAGCATGTTTGATTCAGGAGATAATAAGAAC
TATCAAGCACAAGGAAATGTAATTGCATTAGGTCGTATACATGGAACTGATACGAATGAC
CATGGCGATTTTAATGGTATCGAGAAAGCATTAACAGTAAATCCGAATTCTGAATTAATC
TTTGAATTTAATACAATGACTACTAAAAACGGTCAAGGCGCAACAAATGTTATTATCAAA
AATGCTGATACTAATGATACGATTGCTGAAAAGACTGTTGAAGGCGGTCCAACTTTGCGT
TTATTTAAAGTACCTGATAATGTGAGAAATCTCAAAATTCAATTTGTACCTAAAAATGAC
GCAATAACAGATGCGCGTGGCATTTATCAACTAAAAGATGGTTACAAATACTATAGCTTT
GTTGACTCTATCGGACTTCATTCTGGGTCACATGTTTTTGTTGAAAGACGAACAATGGAT
CCAACAGCAACAAATAATAAAGAGTTTACTGTAACAACATCATTAAAGAATAATGGTAAT
TCTGGTGCTTCTCTAGATACAAATGACTTTGTATATCAAGTTCAATTACCTGAAGGTGTT
GAATATGTGAACAATTCATTGACTAAAGATTTTCCAAGTAACAATTCAGGCGTTGATGTT
AATGATATGAATGTTACATATGATGCAGCAAATCGTGTGATAACAATTAAAAGTACTGGA
GGAGGTACAGCAAACTCTCCGGCACGACTTATGCCTGATAAAATACTCGATTTAAGATAT
AAATTACGTGTAAATAATGTGCCGACACCAAGAACAGTAACATTTAACGAGACATTAACG
TATAAAACATATACACAAGATTTCATTAATTCAGCTGCAGAAAGTCATACTGTAAGTACA
AATCCATATACTATCGATATCATCATGAATAAAGATGCATTACAAGCCGAAGTTGACAGA
CGTATTCAACAAGCTGATTATACATTTGCGTCATTAGATATCTTTAATGGTCTGAAACGA
CGCGCACAAACGATTTTAGATGAAATCGTAACAATGTACCATTAAATAAAAGAGTTTCT
CAAGCATATATTGATTCATTAACTAATCAAATGCAACATACGTTAATTCGAAGTGTTGAT
GCTGAAAATGCAGTTAATAAAAAAGTTGACCAAATGGAAGATTTAGTTAATCAAATGAT
GAATTGACAGATGAAGAAAAACAAGCAGCAATACAAGTTATCGAGGAACATAAAAATGAA

Figure 2 cont.

```
ATAATTGGTAATATTGGTGACCAAACGACTGATGATGGCGTTACTAGAATCAAAGATCAA
GGTATACAGACCTTAAGTGGGGATACTGCAACACCGGTTGTTAAACCAAATGCTAAAAAA
GCAATACGTGATAAAGCAACGAAACAAAGGGAAATTATCAATGCAACACCAGATGCTACT
GAAGACGAGATTCAAGATGCACTAAATCAATTAGCTACGGATGAAACAGATGCTATTGAT
AATGTTACGAATGCTACTACAAATGCTGACGTTGAAACAGCTAAAAATAATGGCATCAAT
ACTATTGGAGCAGTTGTTCCTCAAGTAACTCATAAAAAAGCTGCAAGAGATGCAATTAAC
CAAGCAACAGCAACGAAAAGACAACAAATAAATAGTAATAGAGAAGCAACTCAGGAAGAG
AAAAATGCAGCATTGAACGAATTAACTCAAGCAACCAACCATGCTTTAGAACAAATCAAT
CAAGCAACAACAAATGCTAATGTTGATAACGCCAAAGGAGATGGTCTAAATGCCATTAAT
CCAATTGCTCCTGTAACTGTTGTTAAGCAAGCTGCAAGGGATGCCGTATCACATGATGCA
CAACAACATATCGCAGAGATCAATGCTAATCCTGATGCGACTCAAGAAGAAAGACAAGCA
GCAATTGACAAAGTGAATGCTGCTGTAACTGCAGCAAACACAAACATTTTAAACGCTAAT
ACCAATGCTGATGTTGAACAAGTAAAGACAAATGCGATTCAAGGAATACAAGCAATTACA
CCAGCTACAAAAGTAAAAACAGATGCAAAAAATGCCATCGATAAAAGTGCGGAAACGCAA
CATAATACGATATTTAATAATAATGATGCGACGCTCGAAGAACAACAAGCAGCACAACAA
TTACTTGATCAAGCTGTAGCCACAGCGAAGCAAAATATTAATGCAGCAGATACGAATCAA
GAAGTTGCACAAGCAAAGATCAGGGCACACAAAATATAGTAGTGATTCAACCGGCAACA
CAAGTTAAAACGGATACTCGCAATGTTGTAAATGATAAAGCGCGAGAGGCGATAACAAAT
ATCAATGCTACAACTGGCGCGACTCGAGAAGAGAAACAAGAAGCGATAAATCGTGTCAAT
ACACTTAAAAATAGAGCATTAACTGATATTGGTGTGACGTCTACTACTGCGATGGTCAAT
AGTATTAGAGACGATGCAGTCAATCAAATCGGCGCAGTTCAACCGCATGTAACGAAGAAA
CAAACTGCTACAGGTGTATTAAATGATTTAGCAACTGCTAAAAAGCAAGAAATTAATCAA
AACACAAATGCAACAACTGAAGAAAAGCAAGTGGCTTTAAATCAAGTGGATCAAGAGTTA
GCAACGGCAATTAATAATATAAATCAAGCTGATACAAATGCGGAAGTAGATCAAGCGCAA
CAATTAGGTACAAAAGCAATTAATGCGATTCAGCCAAATATTGTTAAAAAACCTGCAGCA
TTAGCACAAATCAATCAGCATTATAATGCTAAATTAGCTGAAATCAATGCTACACCAGAT
GCAACGAATGATGAGAAAAATGCTGCGATCAATACTTTAAATCAAGACAGACAACAAGCT
ATTGAAAGTATTAAACAAGCTAACACAAATGCAGAAGTAGACCAAGCTGCGACAGTAGCA
GAGAATAATATCGATGCTGTTCAAGTTGATGTAGTAAAAAAACAAGCAGCGCGAGATAAA
ATCACTGCTGAAGTGGCGAAGCGTATTGAAGCGGTTAAACAAACACCTAATGCAACTGAC
GAAGAAAAGCAGGCTGCTGTTAATCAAATCAATCAACTTAAAGATCAAGCAATTAATCAA
ATTAATCAAAACCAAACAAATGATCAGGTAGACACAACTACAAATCAAGCGGTAAATGCT
ATAGATAATGTTGAAGCTGAAGTAGTAATTAAAACAAAGGCAATTGCAGATATTGAAAAA
GCTGTTAAAGAAAAGCAACAGCAAATTGATAATAGTCTTGATTCAACAGATAATGAGAAA
GAAGTTGCTTCACAAGCATTAGCTAAAGAAAAAGAAAAAGCACTTGCAGCTATTGACCAA
GCTCAAACGAATAGTCAGGTGAATCAAGCAGCAACAAATGGTGTATCAGCGATTAAAATT
ATTCAACCTGAAACAAAAGTTAAACCAGCTGCACGTGAAAAAATCAATCAAAAAGCGAAT
GAATTACGTGCTAAGATTAATCAGGATAAAGAAGCAACAGCAGAAGAAAGACAAGTAGCA
CTAGATAAAATCAATGAATTTGTAAATCAAGCCATGACAGATATTACGAATAATAGAACA
AATCAACAAGTTGATGATACAACAAGTCAAGCGCTTGATAGCATTGCTTTAGTGACGCCT
GACCATATTGTTAGAGCAGCTGCTAGAGATGCAGTTAAGCAACAATATGAAGCTAAAAAG
CGCGAAATTGAGCAAGCGGAACATGCGACTGATGAAGAAAACAAGTTGCTTTAAATCAA
TTAGCGAATAATGAAAAACGTGCATTACAAAACATCGATCAAGCAATAGCGAATAATGAT
GTGAAACGTGTTGAAACAAATGGCATTGCTACACTAAAAGGTGTACAACCTCATATTGTA
ATTAAGCCTGAAGCACAACAAGCAATTAAAGCAAGTGCAGAAAATCAAGTAGAATCAATA
AAAGATACACCACATGCAACAGTTGATGAATTAGATGAAGCGAATCAATTAATTAGCGAC
ACACTCAAACAAGCGCAACAAGAAATAGAAATACAAATCAAGATGCTGCTGTTACTGAT
GTTAGAAATCAAACAATCAAGGCAATAGAGCAAATAAAACCTAAAGTAAGACGTAAACGA
GCTGCGCTTGATAGCATTGAAGAAAATAATAAAAATCAACTCGATGCAATCCGAAATACG
TTGGATACTACTCAAGATGAAAGAGATGTTGCTATTGATACTTTAAATAAAATTGTAAAT
ACAATTAAAAATGACATTGCACAAAACAAAACGAATGCAGAAGTGGATCGAACTGAGACT
GATGGCAACGACAACATCAAAGTGATTTTACCTAAAGTTCAAGTTAAACCAGCAGCGCGT
CAATCTGTTGGTGTAAAAGCCGAAGCTCAAATGCACTAATCGATCAAAGCGATTTATCA
ACTGAAGAAGAAAGACTAGCTGCTAAACATTTAGTAGAACAAGCACTTAATCAGGCTATT
GATCAGATCAATCATGCAGATAAGACTGCCCAAGTTAATCAAGATAGTATAAATGCTCAA
AATATTATTTCAAAAATTAAACCAGCGACAACAGTTAAAGCAACAGCATTACAACAAATT
CAAAATATCGCTACAAATAAATTAATTTAATTAAAGCAAATAACGAAGCGACAGATGAA
GAACAAAATATTGCAATAGCACAAGTTGAAAAAGAGTTAATTAAAGCTAAACAACAAATT
GCTAGTGCAGTGACTAATGCAGATGTGGCATATTTATTGCATGATGAGAAAAACGAAATT
```

Figure 2 cont.

CGTGAAATCGAACCTGTTATTAACAGAAAGGCGTCTGCTCGAGAACAATTGACAACATTA
TTCAACGATAAAAAACAAGCAATTGAAGCGAATATTCAAGCAACGGTAGAAGAAAGAAAT
AGTATATTAGCACAGTTACAAAATATTTATGACACTGCTATTGGACAAATTGATCAAGAT
CGTAGCAATGCACAAGTTGATAAAACAGCATCATTAAATCTACAAACAATACATGATTTA
GATGTACATCCTATTAAAAAGCCAGATGCTGAAAAAACGATTAATGATGATCTTGCACGC
GTCACTGCTTTAGTGCAAAATTATCGAAAAGTAAGTAATCGTAATAAGGCTGATGCATTA
AAAGCTATAACTGCTTTAAAATTACAAATGGATGAAGAATTAAAAACAGCACGCACTAAT
GCTGATGTTGATGCAGTTTTAAAACGATTTAATGTTGCATTAAGCGATATAGAAGCAGTA
ATTACTGAAAAAGAAAATAGCTTACTGCGAATTGATAACATTGCTCAACAAACATATGCG
AAATTCAAAGCGATCGCAACACCAGAACAATTAGCTAAAGTAAAAGTATTAATTGATCAA
TATGTTGCAGATGGCAATAGAATGATTGATGAAGATGCGACATTAAATGACATCAAACAA
CACACGCAATTCATTGTTGATGAAATTTTAGCAATTAAATTACCAGCTGAAGCGACGAAA
GTATCACCAAAAGAAATTCAGCCAGCTCCAAAAGTTTGTACGCCTATTAAAAAAGAAGAG
ACACATGAATCGCGCAAAGTTGAAAAAGAACTTCCAAATACAGGTTCTGAAGGAATGGAT
TTACCATTGAAAGAATTTGCACTGATTACAGGTGCGGCTTTGTTAGCTAGAAGACGTACT
AAAAACGAAAAGAATCATAA

SEQ ID NO: 86 polynucleotide sequence
GAGGAGAATTCAGTACAAGACGTTAAAGATTCGAATACGGATGATGAATTATCAGACAGC
AATGATCAGTCTAGTGATGAAGAAAAGAATGATGTGATCAATAATAATCAGTCAATAAAC
ACCGACGATAATAACCAAATAATTAAAAAGAAGAAACGAATAACTACGATGGCATAGAA
AAACGCTCAGAAGATAGAACAGAGTCAACAACAAATGTAGATGAAAACGAAGCAACATTT
TTACAAAAGACCCCTCAAGATAATACTCATCTTACAGAAGAAGAGGTAAAAGAATCCTCA
TCAGTCGAATCCTCAAATTCATCAATTGATACTGCCCAACAACCATCTCACACAACAATA
AATAGAGAAGAATCTGTTCAAACAAGTGATAATGTAGAAGATTCACACGTATCAGATTTT
GCTAACTCTAAAATAAAAGAGAGTAACACTGAATCTGGTAAAGAAGAGAATACTATAGAG
CAACCTAATAAAGTAAAAGAAGATTCAACAACAAGTCAGCCGTCTGGCTATACAAATATA
GATGAAAAAATTTCAAATCAAGATGAGTTATTAAATTTACCAATAAATGAATATGAAAAT
AAGGCTAGACCATTATCTACAACATCTGCCCAACCATCGATTAAACGTGTAACCGTAAAT
CAATTAGCGGCGGAACAAGGTTCGAATGTTAATCATTTAATTAAAGTTACTGATCAAAGT
ATTACTGAAGGATATGATGATAGTGAAGGTGTTATTAAAGCACATGATGCTGAAAACTTA
ATCTATGATGTAACTTTTGAAGTAGATGATAAGGTGAAATCTGGTGATACGATGACAGTG
GATATAGATAAGAATACAGTTCCATCAGATTTAACCGATAGCTTTACAATACCAAAAATA
AAAGATAATTCTGGAGAAATCATCGCTACAGGTACTTATGATAACAAAAATAAACAAATC
ACCTATACTTTTACAGATTATGTAGATAAGTATGAAAATATTAAAGCACACCTTAAATTA
ACGTCATACATTGATAAATCAAAGGTTCCAAATAATAATACCAAGTTAGATGTAGAATAT
AAAACGGCCCTTTCATCAGTAAATAAAACAATTACGGTTGAATATCAAAGACCTAACGAA
AATCGGACTGCTAACCTTCAAAGTATGTTTACAAACATAGATACGAAAAATCATCACAGTT
GAGCAAACGATTTATATTAACCCTCTTCGTTATTCAGCCAAGGAAACAAATGTAAATATT
TCAGGGAATGGTGATGAAGGTTCAACAATTATAGACGATAGCACAATAATTAAAGTTTAT
AAGGTTGGAGATAATCAAAATTTACCAGATAGTAACAGAATTTATGATTACAGTGAATAT
GAAGATGTCACAAATGATGATTATGCCCAATTAGGAAATAATAATGATGTGAATATTAAT
TTTGGTAATATAGATTCACCATATATTATTAAAGTTATTAGTAAATATGACCCTAATAAG
GATGATTACACGACTATACAGCAAACTGTGACAATGCAGACGACTATAAATGAGTATACT
GGTGAGTTTAGAACAGCATCCTATGATAATACAATTGCTTTCTCTACAAGTTCAGGTCAA
GGACAAGGTGACTTGCCTCCTGAAAAAACTTATAAAATCGGAGATTACGTATGGGAAGAT
GTAGATAAAGATGGTATTCAAAATACAAATGATAATGAAAAACCGCTTAGTAATGTATTG
GTAACTTTGACGTATCCTGATGGAACTTCAAATCAGTCAGAACAGATGAAGATGGGAAA
TATCAATTTGATGGATTGAAAAACGGATTGACTTATAAAATTACATTCGAAACACCTGAA
GGATATACGCCGACGCTTAAACATTCAGGAACAAATCCTGCACTAGACTCAGAAGGTAAT
TCTGTATGGGTAACTATTAATGGACAAGACATATGACGATTGATAGTGGATTTTATCAA
ACACCTAAATACAGCTTAGGGAACTATGTATGGTATGACACTAATAAAGATGGTATTCAA
GGTGATGATGAAAAAGGAATCTCTGGAGTTAAAGTGACGTTAAAAGATGAAACGGAAAT
ATCATTAGTACAACTACAACCGATGAAAATGGAAAGTATCAATTTGATAATTTAAATAGT
GGTAATTATATTGTTCATTTGATAAACCTTCAGGTATGACTCAAACAACAACAGATTCT
GGTGATGATGACGAACAGGATGCTGATGGGGAAGAAGTTCATGTAACAATTACTGATCAT
GATGACTTTAGTATAGATAACGGATACTATGATGACGAA

PROCESS FOR MANUFACTURING VACCINES

This application is filed pursuant to 35 U.S.C. §371 as a United States National Phase Application of International Patent Application Serial No. PCT/EP2008/050011 filed Jan. 2, 2008, which claims priority to Great Britain Application No. 0700136.5 filed in the United Kingdom on Jan. 4, 2007, the content of which is incorporated herein by reference.

The present invention relates to improved methods of making immunogenic compositions by conducting carbodiimide condensation reactions. In particular, it relates to the conjugation of saccharides (particularly staphylococcal saccharides) and proteins using carbodiimide condensation. It also relates to immunogenic compositions that may be made comprising the saccharide-protein conjugates of the invention.

The use of bacterial capsular polysaccharides has been widely used in immunology for many years for the prevention of bacterial disease. A problem with such a use, however, is the T-independent nature of the immune response. These antigens are thus poorly immunogenic in young children. This problem has been overcome through conjugating the polysaccharide antigens to a protein carrier (a source of T-helper epitopes) which may then by used to elicit a T-dependent immune response, even in the first year of life.

Various conjugation techniques are known in the art. Conjugates can be prepared by direct reductive amination methods as described in U.S. Pat. No. 4,365,170 (Jennings) and U.S. Pat. No. 4,673,574 (Anderson). Other methods are described in EP-0-161-188, EP-208375 and EP-0-477508. The conjugation method may alternatively rely on activation of hydroxyl groups of the saccharide with 1-cyano-4-dimethylamino pyridinium tetrafluoroborate (CDAP) to form a cyanate ester. The activated saccharide may thus be coupled directly or via a spacer (linker) group to an amino group on the carrier protein. For example, the cyanate ester can be coupled with hexane diamine or adipic acid dihydrazide (ADH or AH) and the amino-derivatised saccharide is conjugated to the carrier protein using carbodiimide (e.g. EDAC or EDC) chemistry via a carboxyl group on the protein carrier. Such conjugates are described in PCT published application WO 93/15760 Uniformed Services University and WO 95/08348 and WO 96/29094. See also Chu C. et al Infect. Immunity, 1983 245 256.

In general the following types of chemical groups on a protein carrier can be used for coupling/conjugation:

A) Carboxyl (for instance via aspartic acid or glutamic acid) which may be conjugated to natural or derivatised amino groups on saccharide moieties using carbodiimide chemistry;

B) Amino group (for instance via lysine) which may be conjugated to natural or derivatised carboxyl groups on saccharide moieties using carbodiimide chemistry;

C) Sulphydryl (for instance via cysteine);
  D) Hydroxyl group (for instance via tyrosine);
  E) Imidazolyl group (for instance via histidine);
  F) Guanidyl group (for instance via arginine); and
  G) Indolyl group (for instance via tryptophan).

On a saccharide, in general the following groups can be used for a coupling: OH, COOH or NH2. Staphylococcal saccharides, for example S. aureus capsular saccharides (such as those form serotypes 5 and/or 8) contain OH and COOH groups. Aldehyde groups can be generated after different treatments known in the art such as: periodate, acid hydrolysis, hydrogen peroxide, etc.

Direct Coupling Approaches:
  Saccharide-OH+CNBr or CDAP→cyanate ester+NH2-Prot→conjugate
  Saccharide-aldehyde+NH2-Prot→Schiff base+NaCNBH3→conjugate
  Saccharide-COOH+NH2-Prot+EDAC→conjugate
  Saccharide-NH2+COOH-Prot+EDAC→conjugate
  Indirect coupling via spacer (linker) approaches:
  Saccharide-OH+CNBr or CDAP→cyanate ester+NH2→NH2→saccharide-NH2+COOH-Prot+EDAC→conjugate
  Saccharide-OH+CNBr or CDAP→cyanate ester+NH2-SH→saccharide-SH+SH-Prot (native Protein with an exposed cysteine or obtained after modification of amino groups of the protein by SPDP for instance)→saccharide-S—S-Prot
  Saccharide-OH+CNBr or CDAP→cyanate ester+NH2-SH→saccharide-SH+maleimide-Prot (modification of amino groups)→conjugate
  Saccharide-COOH+EDAC+NH2-NH2→saccharide-NH2+EDAC+COOH-Prot→conjugate
  Saccharide-COOH+EDAC+NH2-SH→saccharide-SH+SH-Prot (native Protein with an exposed cysteine or obtained after modification of amino groups of the protein by SPDP for instance)→saccharide-S—S-Prot
  Saccharide-COOH+EDAC+NH2-SH→saccharide-SH+maleimide-Prot (modification of amino groups)→conjugate
  Saccharide-Aldehyde+NH2-NH2→saccharide-NH2+EDAC+COOH-Prot→conjugate As can be observed carbodiimide chemistry (e.g. using EDAC) is very convenient for conjugation reactions as it makes use of groups on the saccharide and/or protein which may be naturally present or easily inserted by derivatisation. It also conveniently links moieties through a peptide bond.

Carbodiimides (RN=C=NR') are unsaturated compounds with an allene structure (Nakajima and Ikada 1995 Bioconjugate Chem. 6:123-130; Hoare and Koshland 1967 JBC 242:2447-2453). The chemical is relatively unstable at its reaction pH (4.5-6.5), and therefore all components of the saccharide/protein/carbodiimide conjugation reaction tend to be added together in the art.

The present inventors have found that depending on the nature of the saccharide and protein to be conjugated, better characteristics of the final conjugate for vaccine use may be achieved by adding a certain component of the reaction slowly to the mix. In so doing one or more benefits/improvements may be realised such as: saccharide yield in the conjugate, sterile filterability of the conjugate, better control of the conjugation, easier reproducibility, and/or prevention of intra-moiety cross-links.

Accordingly, in one embodiment there is provided a method of making an immunogenic composition comprising a conjugation step of conjugating a saccharide to a protein carrier to make a saccharide-protein conjugate using carbodiimide condensation chemistry, wherein the saccharide comprises (for instance as part of its repeating unit), or has been derivatised to comprise, amino and/or carboxyl groups, and wherein the protein carrier comprises, or has been derivatised to comprise, amino and/or carboxyl groups, comprising the steps of:

I)— if the protein carrier comprises both amino and carboxyl groups and the saccharide comprises either amino or carboxyl groups:
    a) mixing the saccharide and aliquot of carbodiimide required to perform the conjugation, and b) adding the aliquot of protein carrier required over a period of 35 seconds to 6 hours to form the saccharide-protein conjugate;

II)— if the saccharide comprises both amino and carboxyl groups and the protein carrier comprises either amino or carboxyl groups:
a) mixing the protein carrier and aliquot of carbodiimide required to perform the conjugation, and
b) adding the aliquot of saccharide required over a period of 35 seconds to 6 hours to form the saccharide-protein conjugate; or III)— if the saccharide comprises both amino and carboxyl groups and the protein carrier comprises both amino and carboxyl groups:
a) mixing the protein carrier and saccharide, and
b) adding the aliquot of carbodiimide required to perform the conjugation over a period of 35 seconds to 6 hours to form the saccharide-protein conjugate;

and adding a further step to I, II or III of mixing the saccharide-protein conjugate (so formed) with an antigen, for example a staphylococcal antigen.

DESCRIPTION OF FIGURES

FIG. 1—Polypeptide sequences of preferred proteins. Table 2 provides information on which protein is represented by each SEQ ID.

FIG. 2—Nucleotide sequences encoding preferred proteins. Table 2 provides information on which protein is encoded by each SEQ ID.

DETAILED DESCRIPTION

Any suitable carbodiimide may be used in the conjugation step as long as it is capable of conjugating saccharides and proteins in an aqueous medium. In one embodiment the carbodiimide may be EDAC (1-ethyl-3-(3-dimethyl-aminopropyl) carbodiimide) [also known as EDC] or it may be a carbodiimide other than EDAC.

The term "saccharide" throughout this specification may indicate polysaccharide or oligosaccharide and includes both. It may indicate lipopolysaccharide (LPS) or lipooliogosaccharide (LOS). Before use Polysaccharides (such as bacterial polysaccharides) may be isolated from a source strain (e.g. of bacteria) or isolated from the source strain and sized to some degree by known methods (see for example EP497524 and EP497525; Shousun Chen Szu et al.—Carbohydrate Research Vol 152 p7-20 (1986)) for instance by microfluidisation. Polysaccharides can be sized in order to reduce viscosity in polysaccharide samples and/or to improve filterability for conjugated products. Oligosaccharides have a low number of repeat units (typically 5-30 repeat units) and are typically hydrolysed polysaccharides.

The term "protein carrier" is intended to cover both small peptides and large polypeptides (>10 kDa). Clearly large polypeptides are more likely to contain both reactive amino and carboxyl groups without any modification.

For the purposes of the invention, "native polysaccharide" refers to a saccharide that has not been subjected to a process, the purpose of which is to reduce the size of the saccharide. A polysaccharide can become slightly reduced in size during normal purification procedures. Such a saccharide is still native. Only if the polysaccharide has been subjected to sizing techniques would the polysaccharide not be considered native.

For the purposes of the invention, "sized by a factor up to ×2" means that the saccharide is subject to a process intended to reduce the size of the saccharide but to retain a size more than half the size of the native polysaccharide. ×3, ×4 etc. are to be interpreted in the same way i.e. the saccharide is subject to a process intended to reduce the size of the polysaccharide but to retain a size more than a third, a quarter etc. the size of the native polysaccharide.

By "a further step of mixing the saccharide-protein conjugate with a staphylococcal antigen" it is meant that the saccharide-protein conjugate (which may itself contain a staphylococcal saccharide and/or a staphylococcal protein) is mixed with a further staphylococcal antigen which is not present in the saccharide-protein conjugate.

The 35 second to 6 hour time period in step b) of the method for the addition of the full aliquot of the final component can be 50 seconds to 5 hours, 1 minute to 4 hours, 2 minutes to 3 hours, 3 minutes to 2 hours, 4 to 60 minutes, 5 to 50 minutes, 6 to 40 minutes, 7 to 30 minutes or 8 to 20 minutes. It may be 1 minute to 5 hours, 10 minutes to 4 hours, 20 minutes to 3 hours, 30 minutes to 2 hours, 40 to 90 minutes, or 50 to 70 minutes. This time can be adjusted according to the precise saccharide and protein being conjugated.

In one embodiment the aliquot of the final component of the conjugation step (e.g. of carbodiimide, saccharide or protein) is added to the reaction mixture at a constant rate during the time period (this is conveniently achieved using a pump operating at a constant rate). Alternatively it may be added in stages over the time period. Although this may be done in many ways, in general parts of the aliquot should be added throughout the period. For instance at least one quarter of the aliquot may be added over the first half of the period, and at least one quarter of the aliquot over the second half of the period. The total amount of the aliquot 'a' measured, for instance, in mL or mg may be added in 4-100 stages ('s') throughout the period. In one embodiment the stages are arranged such that an even amount (a/s) is introduced at all the stages. In one embodiment the stages are evenly spaced throughout the period 'p' (in seconds). Thus if one stage takes place at time zero of the period 'p', then each subsequent stage could take place at a time which is $p/(s-1)$. The volume of the aliquot of the final component added in step b) may be adjusted in terms of ease of addition of the aliquot to the reaction within the desired time period. The carbodiimide may be added as an aqueous solution (typically buffered at pH 7.5 before being added to the reaction) or as solid powder (EDAC for instance is highly soluble in aqueous media). Of course if the carbodiimide is the last component added to the reaction (situation III step b)), a slow dissolving carbodiimide may be used such that the entire aliquot of powder is added to the reaction all at once but it dissolves at a rate consistent with the desired period over which the aliquot is to be made available to the reaction.

If the protein and/or saccharide has no amino or carboxyl groups (or only has one of these), it may be derivatised to give it one (or to give it the other it does not already have). For instance for a saccharide only comprising reactive hydroxyl groups (e.g. meningococcal serogroup A capsular saccharide), such a group should be used for derivatising on amino or carboxyl groups so that EDAC condensation may be carried out. This may take place within a repeat subunit, or may be a group only present at the end of the saccharide molecule.

It should be noted that where derivatisation takes place, it can be beneficial to only partially derivatise the moiety. For saccharides with repeating subunits, the target epitope may be present in each repeat. Therefore if partial derivatisation takes place (for this it is meant 0.5-20, 1-15, 3-12, or 5-10% of the targeted reactive group is actually derivatised) this can have the benefit of conserving the majority of the epitopes, and preventing too much cross-linking.

If a saccharide or protein already has amino or carboxyl groups only (e.g. Vi saccharide from *Salmonella typhi* which naturally has carboxyl but not amino groups), derivatisation can take place to give it the other type of group (i.e. amino groups for Vi). It should be noted, however, that as derivatisation can be partial this action can change the preferred reaction of the invention from a type I to a type III. For instance if Vi saccharide is conjugated to a protein carrier comprising both amino and carboxyl groups situation I adds the aliquot of protein slowly in step b). If the Vi saccharide carboxyl group is partially derivatised with amino groups it will have both carboxyl and amino groups, thus situation III adding the aliquot of carbodiimide slowly in step b) becomes most relevant.

Derivatisation may occur through the addition of a hetero- or homo-bifunctional linker. It may take place with similar chemistry as described above for saccharide-protein conjugation step (e.g. CDAP or carbodiimide chemistry). The linker may have between 4 and 20, 4 and 12, or 5 and 10 carbon atoms. It may have two reactive amino groups, two reactive carboxyl groups, or one of each (e.g. hexane diamine, 6-aminocaproic acid, or adipic acid dihydrazide). Typically derivatization takes place through reacting a large excess of the linker with the saccharide and/or protein carrier to be derivatised. This allows derivatization to take place with minimal intra-moiety cross-linking (which otherwise might be possible if for instance a carboxyl group on a saccharide was being derivatised with amino groups using carbodiimide condensation). Excess linker is readily removed using techniques such as diafiltration.

In one embodiment the saccharide comprises a reactive hydroxyl group as part of its repeating unit which is partially derivatised via an amino group on the linker (e.g. with CDAP chemistry). In another embodiment the saccharide comprises a reactive amino group as part of its repeating unit which is partially derivatised via a carboxyl group on the linker (e.g. with carbodiimide chemistry). In a further embodiment the saccharide comprises a reactive carboxyl group as part of its repeating unit which is partially derivatised via an amino group on the linker (e.g. with carbodiimide chemistry).

The aliquot of carbodiimide required to perform the conjugation (whether present in step a) or b) of the reaction of the invention) is 0.01 to 3, 0.05 to 2, or 0.09 to 1 mg carbodiimide/mg saccharide. Although these numbers are calculated in respect of EDAC being the carbodiimide, these numbers may be adjusted if any other carbodiimide is used by multiplying the numbers in the range by: (molecular weight of other carbodiimide)/(molecular weight of EDAC).

In general, the saccharide may be present in the methods of the invention at a final concentration of 0.5-50 mg/ml in step b). This will depend on the size and nature of the saccharide, and the extent of any derivatisation. For instance for oligosaccharides a larger concentration will be required, but for large polysaccharides a much smaller concentration will be more appropriate. If it is towards the high end of partially derivatised with amino or carboxyl groups a smaller concentration may be appropriate to reduce the possibility of any cross-linking. The protein carrier may be present at a final concentration of 1-50 mg/ml in step b).

The initial ratio of protein carrier to saccharide in the methods of the invention can be 5:1 to 1:5, 4:1 to 1:1, or 3:1 to 2:1 (w/w). Again this will depend on the size and nature of the saccharide, and the extent of any derivatisation.

Salt conditions (e.g. NaCl) may also be varied according to the nature of the saccharide/protein. Usually around 0.2M NaCl may be present in step b) of the methods of the invention, but may be 0-2, 0.1-1 or 0.2-0.5 M.

In terms of pH in step b) of the methods of the invention, the reaction pH may be any pH where the carbodiimide is activated—for instance pH 4.5-6.5, 4.7-6.0, or 5-5.5. This pH is typically maintained throughout the reaction by addition of acid/base as required. EDAC is usually stable at pH 7.5, though if the conjugation requires to be done at higher pH compounds which are known to keep the reaction intermediate stable (such as N-hydroxysuccinimide) may also be present in the reaction in step b), in which case the reaction pH in step b) may be maintained at pH 4.5-7.5.

The reaction temperature during step b) of the methods of the invention can be 4-37, 10-32, 17-30, or 22-27° C., and is typically maintained throughout the reaction.

In the methods of the invention, once the entire aliquot has been added in step b) the reaction is typically maintained for a further 10 minutes to 72 hours, 20 minutes to 48 hours, 30 minutes to 24 hours, 40 minutes to 12 hours, 50 minutes to 6 hours, or 1-3 hours. Once the reaction is completed the pH is adjusted to 7.5-9 (towards the higher end of this if N-hydroxysuccinimide is present) to go back to the stable pH range of carbodiimide.

Once conjugated, the saccharide-protein conjugate may be purified from: unreacted components, free saccharide, etc by injecting it on a size exclusion chromatography column (for instance SEPHACRYL® S400HR, Pharmacia). This is typically carried out at 2-8° C. The conjugate may be sterile filtered then stored. Ultimately an effective dose (for instance 1-20, 2-15, or 3-10 µg saccharide/dose) of the saccharide-protein conjugate can be formulated with a pharmaceutically acceptable excipient (for instance a salt or adjuvant) to manufacture an immunogenic composition or vaccine.

In terms of the saccharides of the invention, any saccharide of viral, fungal, bacterial or eukaryotic source may be conjugated using the conjugation step of the methods of the invention. It may be the Vi saccharide from *Salmonella typhi*, or a saccharide other than Vi. It may be the capsular saccharide Hib from *H. influenzae* type b, or may be a saccharide other than Hib. In one embodiment the saccharide is a bacterial capsular saccharide, for instance derived from a bacterium selected from a list consisting of: *N. meningitidis* serogroup A (MenA), B (MenB), C (MenC), W135 (MenW) or Y (MenY), *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20, 22F, 23F or 33F, Group B *Streptococcus* group Ia, Ib, II, III, IV, V, VI, or VII, *Staphylococcus aureus* type 5, *Staphylococcus aureus* type 8, *Salmonella typhi* (Vi saccharide), *Vibrio cholerae*, or *H. influenzae* type b.

The weight-average molecular weight of the saccharide may be 1000-2000000, 5000-1000000, 10000-500000, 50000-400000, 75000-300000, or 100000-200000. The molecular weight or average molecular weight of a saccharide herein refers to the weight-average molecular weight (Mw) of the saccharide measured prior to conjugation and is measured by MALLS. The MALLS technique is well known in the art and is typically carried out as described in example 2. For MALLS analysis of saccharides, two columns (TSKG6000 and 5000PWxl) may be used in combination and the saccharides are eluted in water. Saccharides are detected using a light scattering detector (for instance Wyatt Dawn DSP equipped with a 10 mW argon laser at 488 nm) and an inferometric refractometer (for instance Wyatt Otilab DSP equipped with a P100 cell and a red filter at 498 nm). In an embodiment, the polydispersity of the saccharide is 1-1.5, 1-1.3, 1-1.2, 1-1.1 or 1-1.05 and after conjugation to a carrier protein, the polydispersity of the conjugate is 1.0-2.5, 1.0-2.0, 1.0-1.5, 1.0-1.2, 1.5-2.5, 1.7-2.2 or 1.5-2.0. All polydispersity measurements are by MALLS.

The saccharide may be either a native polysaccharide or may have been sized by a factor of no more than 2, 4, 6, 8, 10 or 20 fold (for instance by microfluidization [e.g. by EMULSIFLEX® C-50 apparatus] or other known technique [for instance heat, chemical, oxidation, sonication methods]). Oligosaccharides may have been sized substantially further [for instance by known heat, chemical, or oxidation methods].

The structures of most of these saccharides are known (and therefore whether they naturally have any amino or carboxyl groups for carbodiimide chemistry, or any other reactive group which may be derivatised with amino or carboxyl groups (see table 1 below).

TABLE 1

|  | Natural NH2 group | Natural COOH group | Other reactive group |
|---|---|---|---|
| S. aureus | | | |
| PS5 | No | Yes | OH |
| PS8 | No | Yes | OH |
| N. meningitidis | | | |
| MenA | No | No | OH |
| MenC | No | Yes | OH |
| MenW135 | No | Yes | OH |
| MenY | No | Yes | OH |
| MenB | No (can be generated if de-N-acetylated) | Yes | OH/N-propyl |
| Gp. B Streptococcus | | | |
| Ia, Ib | No | Yes | OH |
| II | No | Yes | OH |
| III | No | Yes | OH |
| IV | No | Yes | OH |
| V | No | Yes | OH |
| VI | No | Yes | OH |
| VII | No | Yes | OH |
| S. typhi | | | |
| Vi | No | Yes | No |
| S. pneumoniae | | | |
| PS1 | Yes | Yes | OH |
| PS3, 4, 5, 8, 9, 12F | No | Yes | OH |
| Vibrio cholorea | | | |
| Capsular saccharide | yes | No | OH |
| H. influenzae B Hib | No | No | OH |
| LOS | | | |
| Nmen/Mcat/Hi | Yes on PEA | Yes on KDO | OH |

The protein carrier may be any peptide or protein. In an embodiment it is a staphylococcal protein, optionally selected from the staphylococcal proteins listed below. It may comprise one or more T-helper epitopes. In one embodiment of the invention the protein carrier is selected from the group consisting of: TT, DT, CRM197, fragment C of TT, protein D of H. influenzae, pneumococcal PhtD, and pneumococcal Pneumolysin. The carrier protein may be tetanus toxoid (TT), tetanus toxoid fragment C, non-toxic mutants of tetanus toxin [note all such variants of TT are considered to be the same type of carrier protein for the purposes of this invention], diphtheria toxoid (DT), CRM197, other non-toxic mutants of diphtheria toxin [such as CRM176, CRM 197, CRM228, CRM 45 (Uchida et al J. Biol. Chem. 218; 3838-3844, 1973); CRM 9, CRM 45, CRM102, CRM 103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or U.S. Pat. No. 4,950,740; mutation of at least one or more residues Lys 516, Lys 526, Phe 530 and/or Lys 534 and other mutations disclosed in U.S. Pat. No. 5,917, 017 or U.S. Pat. No. 6,455,673; or fragment disclosed in U.S. Pat. No. 5,843,711] (note all such variants of DT are considered to be the same type of carrier protein for the purposes of this invention), pneumococcal pneumolysin (Kuo et al (1995) Infect Immun 63; 2706-13), OMPC (meningococcal outer membrane protein—usually extracted from N. meningitidis serogroup B—EP0372501), synthetic peptides (EP0378881, EP0427347), heat shock proteins (WO 93/17712, WO 94/03208), pertussis proteins (WO 98/58668, EP0471177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998), iron uptake proteins (WO 01/72337), toxin A or B of C. difficile (WO 00/61761), H. influenzae Protein D (EP594610 and WO 00/56360), pneumococcal PhtA (WO 98/18930, also referred to Sp36), pneumococcal PhtD (disclosed in WO 00/37105, and is also referred to Sp036D), pneumococcal PhtB (disclosed in WO 00/37105, and is also referred to Sp036B), or PhtE (disclosed in WO00/30299 and is referred to as BVH-3).

The method of the invention includes a further step of mixing the saccharide-protein conjugate with an antigen, for example a staphylococcal antigen. A staphylococcal antigen may be chosen from the antigens described below, although this list is not exclusive of other antigens derived from staphylococci. In an embodiment, the staphylococcal antigen is a saccharide, teichoic acid or lipoteichoic acid (LTA), any of which is/are optionally conjugated, optionally using a conjugation method described herein. In an embodiment, the staphylococcal antigen is a protein, optionally as described herein.

Capsular Saccharides from S. aureus

In an embodiment, the method of the invention comprises the step of mixing the saccharide-protein conjugate of the invention with S. aureus capsular saccharides (for example capsular saccharides from S. aureus type 5 and/or type 8). In a further embodiment, the method of the invention conjugates a S. aureus capsular saccharide (for example capsular saccharides from S. aureus type 5 and/or type 8) to a protein a make a saccharide-protein conjugate according to the invention.

Most strains of S. aureus that cause infection in man contain either Type 5 or Type 8 polysaccharides. Approximately 60% of human strains are Type 8 and approximately 30% are Type 5. The structures of Type 5 and Type 8 capsular polysaccharide antigens are described in Moreau et al Carbohydrate Res. 201; 285 (1990) and Fournier et al Infect. Immun. 45; 87 (1984). Both have FucNAcp in their repeat unit as well as ManNAcA which can be used to introduce a sulfhydryl group.

Recently (Jones Carbohydrate Research 340, 1097-1106 (2005)) NMR spectroscopy revised the structures of the capsular polysaccharides to:

Type 5
→4)-β-D-ManNAcA-(1→4)-α-L-FucNAc(3OAc)-(1→3)-β-D-FucNAc-(1→

Type 8
→3)-β-D-ManNAcA(4OAc)-(1→3)-α-L-FucNAc (1→3)-α-D-FucNAc(1→

Saccharides may be extracted from the appropriate strain of S. aureus using method well known to the skilled man, for instance as described in U.S. Pat. No. 6,294,177. For example, ATCC 12902 is a Type 5 *S. aureus* strain and ATCC 12605 is a Type 8 *S. aureus* strain.

Saccharides are of native size or alternatively may be sized, for instance by microfluidisation, ultrasonic irradiation or by chemical treatment. The invention also covers oligosaccharides derived from the type 5 and 8 polysaccharides from *S. aureus*.

The weight-average molecular weight of the saccharide may be 1000-2000000, 5000-1000000, 10000-500000, 50000-400000, 75000-300000, or 100000-200000. The molecular weight or average molecular weight of a saccharide herein refers to the weight-average molecular weight (Mw) of the saccharide measured prior to conjugation and is measured by MALLS. The MALLS technique is well known in the art and is typically carried out as described in example 2. For MALLS analysis of saccharides, two columns (TSKG6000 and 5000PWxl) may be used in combination and the saccharides are eluted in water. Saccharides are detected using a light scattering detector (for instance Wyatt Dawn DSP equipped with a 10 mW argon laser at 488 nm) and an inferometric refractometer (for instance Wyatt Otilab DSP equipped with a P100 cell and a red filter at 498 nm). In an embodiment, the polydispersity of the saccharide is 1-1.5, 1-1.3, 1-1.2, 1-1.1 or 1-1.05 and after conjugation to a carrier protein, the polydispersity of the conjugate is 1.0-2.5, 1.0-2.0. 1.0-1.5, 1.0-1.2, 1.5-2.5, 1.7-2.2 or 1.5-2.0. All polydispersity measurements are by MALLS.

The type 5 and/or 8 capsular polysaccharide or oligosaccharides included in the process or immunogenic composition of the invention are optionally O-acetylated. In an embodiment, the degree of O-acetylation of type 5 capsular polysaccharide or oligosaccharide is 10-100%, 20-100%, 30-100%, 40-100%, 50-100%. 60-100%, 70-100%, 80-100%, 90-100%, 50-90%, 60-90%, 70-90% or 80-90%. In an embodiment, the degree of O-acetylation of type 8 capsular polysaccharide or oligosaccharide is 10-100%, 20-100%, 30-100%, 40-100%, 50-100%. 60-100%, 70-100%, 80-100%, 90-100%, 50-90%, 60-90%, 70-90% or 80-90%. In an embodiment, the degree of O-acetylation of type 5 and type 8 capsular polysaccharides or oligosaccharides is 10-100%, 20-100%, 30-100%, 40-100%, 50-100%. 60-100%, 70-100%, 80-100%, 90-100%, 50-90%, 60-90%, 70-90% or 80-90%. In an embodiment, the type 5 and/or 8 capsular saccharides are de-O-acetylated.

The degree of O-acetylation of the polysaccharide or oligosaccharide can be determined by any method known in the art, for example, by proton NMR (Lemercinier and Jones 1996, Carbohydrate Resarch 296; 83-96, WO 05/033148 or WO 00/56357).

O-acetyl groups can be removed by hydrolysis, for example by treatment with a base such as anhydrous hydrazine (Konadu et al 1994; Infect. Immun. 62; 5048-5054) or treatment with 0.1N NaOH for 1-8 hours. In order to maintain high levels of O-acetylation on type 5 and/or 8 polysaccharide or oligosaccharide, treatments which would lead to hydrolysis of the O-acetyl groups are minimised. For example treatment at extremes of pH are minimised.

In an embodiment, the O-acetylated staphylococcal saccharides as described above are conjugated using the conjugation step of the method of the invention and is mixed with a further staphylococcal antigen in the method of the invention.

Poly N-Acetylated Glucosamine (PNAG)

In an embodiment, the method of the invention comprises the step of mixing the saccharide-protein conjugate of the invention with poly N-acetylated glucosamine (PNAG) antigen.

PNAG is a polysaccharide intercellular adhesin and is composed of a polymer of β-(1→6)-linked glucosamine, optionally substituted with N-acetyl and O-succinyl constituents. This polysaccharide is present in both *S. aureus* and *S. epidermidis* and can be isolated from either source (Joyce et al 2003, Carbohydrate Research 338; 903; Maira-Litran et al 2002, Infect. Imun. 70; 4433). For example, PNAG may be isolated from *S. aureus* strain MN8m (WO 04/43407).

The polysaccharide previously known as poly-N-succinyl-β-(1→6)-glucosamine (PNSG) was recently shown not to have the expected structure since the identification of N-succinylation was incorrect (Maira-Litran et al 2002, Infect. Imun. 70; 4433). Therefore the polysaccharide formally known as PNSG and now found to be PNAG is also encompassed by the term PNAG.

PNAG may be of different sizes varying from over 400 kDa to between 75 and 400 kDa to between 10 and 75 kDa to oligosaccharides composed of up to 30 repeat units (of β-(1→6)-linked glucosamine, optionally substituted with N-acetyl and O-succinyl constituents). Any size of PNAG polysaccharide or oligosaccharide may be use in an immunogenic composition of the invention, for example a size of over 40 kDa can be used. Sizing may be achieved by any method known in the art, for instance by microfluidisation, ultrasonic irradiation or by chemical cleavage (WO 03/53462, EP497524, EP497525).

Size ranges of PNAG are for example 40-400 kDa, 50-350 kDa, 40-300 kDa, 60-300 kDa, 50-250 kDa and 60-200 kDa.

PNAG can have different degree of acetylation due to substitution on the amino groups by acetate. PNAG produced in vitro is almost fully substituted on amino groups (95-100%). Alternatively, a deacetylated PNAG can be used having less than 50%, 40%, 30%, 20%, 10% or 5% N-acetylation. Use of a deacetylated PNAG allows opsonic killing of Gram positive bacteria, preferably *S. aureus* and/or *S. epidermidis* (WO 04/43405). In an embodiment, the PNAG has a size between 40 kDa and 300 kDa and is deacetylated so that less than 50%, 40%, 30%, 20%, 10% or 5% of amino groups are N acetylated.

In an embodiment, the PNAG is not O-succinylated or is O-succinylated on less than 25, 20, 15, 10, 5, 2, 1 or 0.1% of residues.

The term deacetylated PNAG (dPNAG) refers to a PNAG polysaccharide or oligosaccharide in which less than 50%, 40%, 30%, 20%, 10% or 5% of the amino groups are acetylated.

As used herein, the term PNAG encompasses both acetylated and deacetylated forms of the saccharide.

In an embodiment, PNAG is deacetylated to form dPNAG by chemically treating the native polysaccharide. For example, the native PNAG is treated with a basic solution such that the pH rises to above 10. For instance the PNAG is treated with 0.1-5M, 0.2-4M, 0.3-3M, 0.5-2M, 0.75-1.5M or 1M NaOH, KOH or NH$_4$OH. Treatment is for at least 10 or 30 minutes, or 1, 2, 3, 4, 5, 10, 15 or 20 hours at a temperature of 20-100, 25-80, 30-60 or 30-50 or 35-45° C. dPNAG may be prepared as described in WO 04/43405.

In an embodiment, the polysaccharide(s) included in the process of the invention are conjugated to a carrier protein as described below or alternatively unconjugated.

S. aureus 336 Antigen

In an embodiment, the method of the invention comprises the step of mixing the saccharide-protein conjugate of the invention with S. aureus 336 antigen (as described in U.S. Pat. No. 6,294,177).

The 336 antigen comprises β-linked hexosamine, contains no O-acetyl groups and specifically binds to antibodies to S. aureus Type 336 deposited under ATCC 55804.

In an embodiment, the 336 antigen is a polysaccharide which is of native size or alternatively may be sized, for instance by microfluidisation, ultrasonic irradiation or by chemical treatment. The invention also covers oligosaccharides derived from the 336 antigen.

The 336 antigen, where included in the process of the invention is preferably conjugated to a carrier protein as described below or are alternatively unconjugated.

Strains ATCC-31432, SE-360 and SE-10 of S. epidermidis are characteristic of three different capsular types, I, II and III respectively (Ichiman and Yoshida 1981, J. Appl. Bacteriol. 51; 229). Capsular polysaccharides extracted from each serotype of S. epidermidis constitute Type I, II and III polysaccharides. Polysaccharides may be extracted by serval methods including the method described in U.S. Pat. No. 4,197,290 or as described in Ichiman et al 1991, J. Appl. Bacteriol. 71; 176.

In one embodiment of the invention, the process comprises mixing the saccharide-protein conjugate with type I and/or II and/or III polysaccharides or oligosaccharides from S. epidermidis.

Polysaccharides are of native size or alternatively may be sized, for instance by microfluidisation, ultrasonic irradiation or chemical cleavage. The invention also covers oligosaccharides extracted from S. epidermidis strains.

These polysaccharides are unconjugated or are preferably conjugated as described herein.

Conjugation of Polysaccharides

Amongst the problems associated with the use of polysaccharides in vaccination, is the fact that polysaccharides per se are poor immunogens. Strategies, which have been designed to overcome this lack of immunogenicity, include the linking of the polysaccharide to large protein carriers, which provide bystander T-cell help. It is preferred that the polysaccharides utilised in the invention are linked to a protein carrier which provide bystander T-cell help. Examples of these carriers which may be used for coupling to polysaccharide or oligosaccharide immunogens include the Diphtheria and Tetanus toxoids (DT, DT Crm197 and TT), Keyhole Limpet Haemocyanin (KLH), Pseudomonas aeruginosa exoprotein A (rEPA) and the purified protein derivative of Tuberculin (PPD), protein D from Haemophilus influenzae, pneumolysin or fragments of any of the above. Fragments suitable for use include fragments encompassing T-helper epitopes. In particular protein D fragment will preferably contain the N-terminal ⅓ of the protein. Protein D is an IgD-binding protein from Haemophilus influenzae (EP 0 594 610 B1).

An alternative carrier protein to use in the processes of the invention is a single staphylococcal protein or fragment thereof or a fusion protein comprising at least or exactly 1, 2, 3 or 4 or more of the staphylococcal proteins or fragments thereof listed in the section below.

A new carrier protein that would be particularly advantageous to use in the context of a staphylococcal vaccine is staphylococcal alpha toxoid. The native form may be conjugated to a polysaccharide since the process of conjugation reduces toxicity. Preferably a genetically detoxified alpha toxin such as the His35Leu or His 35 Arg variants are used as carriers since residual toxicity is lower. Alternatively the alpha toxin is chemically detoxified by treatment with a cross-linking reagent, formaldehyde or glutaraldehyde. A genetically detoxified alpha toxin is optionally chemically detoxified, preferably by treatment with a cross-linking reagent, formaldehyde or glutaraldehyde to further reduce toxicity.

Proteins

The method of the invention optionally comprises a step of mixing the saccharide-protein conjugate of the invention with a staphylococcal protein, for example a protein from S. aureus or S. epidermidis. Some embodiments of the invention contain proteins from both S. aureus and S. epidermidis.

In an independent embodiment of the method of the invention, a staphylococcal protein is used as the protein carrier to which the saccharide is conjugated in the method of the invention.

Accordingly the invention provides a method of conjugating a saccharide to a staphylococcal protein carrier using carbodiimide condensation chemistry, wherein the saccharide comprises (for instance as part of its repeating unit), or has been derivatised to comprise, amino and/or carboxyl groups, and wherein the protein carrier comprises, or has been derivatised to comprise, amino and/or carboxyl groups, comprising the steps of:

I)— if the staphylococcal protein carrier comprises both amino and carboxyl groups and the saccharide comprises either amino or carboxyl groups:
 a) mixing the saccharide and aliquot of carbodiimide required to perform the conjugation, and
 b) adding the aliquot of staphylococcal protein carrier required over a period of 35 seconds to 6 hours;

II)— if the saccharide comprises both amino and carboxyl groups and the protein carrier comprises either amino or carboxyl groups:
 a) mixing the staphylococcal protein carrier and aliquot of carbodiimide required to perform the conjugation, and
 b) adding the aliquot of saccharide required over a period of 35 seconds to 6 hours;

III)— if the saccharide comprises both amino and carboxyl groups and the protein carrier comprises both amino and carboxyl groups:
 a) mixing the staphylococcal protein carrier and saccharide, and
 b) adding the aliquot of carbodiimide required to perform the conjugation over a period of 35 seconds to 6 hours.

In an embodiment, the methods of the invention use an isolated protein which comprises an amino acid sequence which has at least 85% identity, preferably at least 90% identity, more preferably at least 95% identity, most preferably at least 97-99% or exact identity, to that of any sequence of FIG. 1.

Where a protein is specifically mentioned herein, it is optionally a reference to a native or recombinant, full-length protein or optionally a mature protein in which any signal sequence has been removed. The protein may be isolated directly from the staphylococcal strain or produced by recombinant DNA techniques. Immunogenic fragments of the protein may be incorporated into the immunogenic composition of the invention. These are fragments comprising at least 10 amino acids, preferably 20 amino acids, more preferably 30 amino acids, more preferably 40 amino acids or 50 amino acids, most preferably 100 amino acids, taken contiguously from the amino acid sequence of the protein. In addition, such immunogenic fragments are typically immunologically reactive with antibodies generated against the Staphylococcal proteins or with antibodies generated by infection of a mammalian host with Staphylococci or contain T cell epitopes. Immunogenic fragments also includes fragments that when administered at an effective dose, (either alone or as a hapten bound to a carrier), elicit a protective immune response against Staphylococcal infection, optionally it is protective against *S. aureus* and/or *S. epidermidis* infection. Such an immunogenic fragment may include, for example, the protein lacking an N-terminal leader sequence, and/or a transmembrane domain and/or a C-terminal anchor domain. In an embodiment, the immunogenic fragment according to the invention comprises substantially all of the extracellular domain of a protein which has at least 85%, 90%, 95%, 97% or 99% identity, to that a sequence selected from FIG. 1 over the entire length of the fragment sequence.

In an embodiment, the methods of the invention may use fusion proteins of Staphylococcal proteins, or fragments of staphylococcal proteins. Such fusion proteins may be made recombinantly and may comprise one portion of at least 2, 3, 4, 5 or 6 staphylococcal proteins. Alternatively, a fusion protein may comprise multiple portions of at least 2, 3, 4 or 5 staphylococcal proteins. These may combine different Staphylococcal proteins or fragments thereof in the same protein. Alternatively, the invention also includes individual fusion proteins of Staphylococcal proteins or fragments thereof, as a fusion protein with heterologous sequences such as a provider of T-cell epitopes or purification tags, for example: β-galactosidase, glutathione-S-transferase, green fluorescent proteins (GFP), epitope tags such as FLAG, myc tag, poly histidine, or viral surface proteins such as influenza virus haemagglutinin, or bacterial proteins such as tetanus toxoid, diphtheria toxoid, CRM197.

Proteins

In an embodiment, the methods of the invention use one or more of the proteins mentioned below. Many of the proteins fall into the categories of extracellular component binding proteins, transporter proteins or toxins and regulators of virulence. The methods of the invention optionally use a staphylococcal extracellular component binding protein or a staphylococcal transporter protein or a staphylococcal toxin or regulator of virulence. The methods of the invention optionally use at least or exactly 1, 2, 3, 4, 5 or 6 staphylococcal proteins.

The following table (table 2) sets out the SEQ ID numbers of protein sequences and DNA sequences that are found in FIG. 1 and FIG. 2 respectively. SA indicates a sequence from *S. aureus* and SE indicates a sequence from *S. epidermidis*.

TABLE 2

| Name | Protein sequence | DNA sequence |
|---|---|---|
| Immunodominant ABC transporter | | |
| SA | SEQ ID 1 | SEQ ID 34 |
| SE | SEQ ID 2 | SEQ ID 35 |
| Laminin receptor | | |
| SA | SEQ ID 3 | SEQ ID 36 |
| SE | SEQ ID 4 | SEQ ID 37 |
| Secretory Antigen A SsaA | | |
| SA 1 | SEQ ID 5 | SEQ ID 38 |
| SA 2 | SEQ ID 6 | SEQ ID 39 |
| SE | SEQ ID 7 | SEQ ID 40 |
| SitC | | |
| SA | SEQ ID 8 | SEQ ID 41 |
| SE | SEQ ID 9 | SEQ ID 42 |

TABLE 2-continued

| Name | Protein sequence | DNA sequence |
|---|---|---|
| IsaA/PisA (IssA) | | |
| SA | SEQ ID 10 | SEQ ID 43 |
| SE | SEQ ID 11 | SEQ ID 44 |
| EbhA/B | | |
| SA EbhA | SEQ ID 12 | SEQ ID 45 |
| SA EbhB | SEQ ID 13 | SEQ ID 46 |
| SE EbhA | SEQ ID 14 | SEQ ID 47 |
| SE EbhB | SEQ ID 15 | SEQ ID 48 |
| Accumulation-assoc pro Aap | | |
| SA | SEQ ID 16 | SEQ ID 49 |
| SE | SEQ ID 17 | SEQ ID 50 |
| RNA III activating protein RAP | | |
| SA | SEQ ID 18 | SEQ ID 51 |
| SE | SEQ ID 19 | SEQ ID 52 |
| FIG/SdrG | | |
| SA | SEQ ID 20 | SEQ ID 53 |
| SE | SEQ ID 21 | SEQ ID 54 |
| Elastin binding protein EbpS | | |
| SA | SEQ ID 22 | SEQ ID 55 |
| SE | SEQ ID 23 | SEQ ID 56 |
| Extracellular protein EFB SA | SEQ ID 24 | SEQ ID 57 |
| alpha toxin SA | SEQ ID 25 | SEQ ID 58 |
| SBI SA | SEQ ID 26 | SEQ ID 59 |
| IsdA SA | SEQ ID 27 | SEQ ID 60 |
| IsdB SA | SEQ ID 28 | SEQ ID 61 |
| SdrC SA | SEQ ID 29 | SEQ ID 62 |
| ClfA SA | SEQ ID 30 | SEQ ID 63 |
| FnbA SA | SEQ ID 31 | SEQ ID 64 |
| ClfB SA | SEQ ID 32 | SEQ ID 65 |
| Coagulase SA | SEQ ID 33 | SEQ ID 66 |
| FnbB SA | SEQ ID 67 | SEQ ID 77 |
| MAP SA | SEQ ID 68 | SEQ ID 78 |
| HarA SA | SEQ ID 69 | SEQ ID 79 |
| Autolysin glucosaminidase SA | SEQ ID 70 | SEQ ID 80 |
| Autolysin amidase SA | SEQ ID 71 | SEQ ID 81 |
| Ebh fragment SA | SEQ ID 72 | SEQ ID 82 |
| Autolysin Ant SA | SEQ ID 73 | SEQ ID 83 |
| SdrC SA | SEQ ID 74 | SEQ ID 84 |
| MRPII SA | SEQ ID 75 | SEQ ID 85 |
| SdrG SA | SEQ ID 76 | SEQ ID 86 |

Extracellular Component Binding Proteins

Extracellular component binding proteins are proteins that bind to host extracellular components. The term includes, but is not limited to adhesins.

Examples of extracellular component binding proteins include laminin receptor (Naidu et al J. Med. Microbiol. 1992, 36; 177), Protein A, SitC/MntC/saliva binding protein (U.S. Pat. No. 5,801,234, Wiltshire and Foster Infec. Immun. 2001, 69; 5198), EbhA (Williams et al Infect. Immun. 2002, 70; 6805), EbhB, Elastin binding protein (EbpS) (Park et al 1999, J. Biol. Chem. 274; 2845), EFB (FIB) (Wastfelt and Flock 1995, J. Clin. Microbiol. 33; 2347), SBI (Zhang et al FEMS Immun. Med. Microbiol. 2000, 28; 211), protein A (PCT/EP2006/069944), autolysin (Rupp et al 2001, J. Infect. Dis. 183; 1038), ClfA (U.S. Pat. No. 6,008,341, McDevitt et al Mol. Microbiol. 1994, 11; 237), SdrC (WO 99/27109), SdrD (WO 99/27109), SdrE (WO 99/27109), SdrG (McCrea et al Microbiology 2000, 146; 1535), SdrH (McCrea et al Microbiology 2000, 146; 1535), Lipase GehD (US2002/0169288), SasA (WO 06/121664, Mazmanian et al Molecular Microbiology 40; 1049, 2001 and WO 06/121664), FnbA (Flock et al Mol Microbiol. 1994, 12; 599, U.S. Pat. No. 6,054,572), FnbB (WO 97/14799, Booth et al 2001 Infec. Immun. 69; 345), collagen binding protein Cna (Visci et al 2000, J. Biol. Chem. 275; 39837), ClfB (WO 99/27109), FbpA (Phonimdaeng et al 1988 J. Gen Microbiol. 134; 75), Npase (Flock 2001 J. Bacteriol. 183; 3999), IsaA/PisA (Lonenz et al FEMS Immuno. Med. Microbiol. 2000, 29; 145), SsaA (Lang et al FEMS Immunol. Med. Microbiol. 2000, 29; 213), EPB (Hussain and Hermann symposium on Staph Denmark 14-17th 2000), SasH (Robertson et al Antimicrobial agents and chemotherapy 47; 3926, 2003) SSP-1 (Veenstra et al 1996, J. Bacteriol. 178; 537), SSP-2 (Veenstra et al 1996, J. Bacteriol. 178; 537), 17 kDa heparin binding protein HBP (Fallgren et al 2001, J. Med. Microbiol. 50; 547), Vitronectin binding protein (Li et al 2001, Curr. Microbiol. 42; 361), fibrinogen binding protein, coagulase, Fig (WO 97/48727) and MAP (U.S. Pat. No. 5,648,240)

SitC/MntC/Saliva Binding Protein

This is an ABC transporter protein which is a homologue of adhesin PsaA in *S. pneumoniae*. It is a highly immunogenic 32 kDa lipoprotein which is distributed through the bacterial cell wall (Cockayne et al Infect. Immun. 1998 66; 3767). It is expressed in *S. aureus* and *S. epidermidis* as a 32 kDa lipoprotein and a 40 kDa homologue is present in *S. hominis*. In *S. epidermidis*, it is a component of an iron-regulated operon. It shows considerable homology to both adhesins including FimA of *Streptococcus* parasanguis, and with lipoproteins of a family of ABC transporters with proven or putative metal iron transport functions. Therefore SitC is included as an extracellular biding protein and as a metal ion transporter.

The saliva binding protein disclosed in U.S. Pat. No. 5,801,234 is also a form of SitC and can be included in an immunogenic composition of the invention.

ClfA and ClfB

Both these proteins have fibrinogen binding activity and trigger *S. aureus* to form clumps in the presence of plasma. They contain a LPXTG (SEQ ID NO: 102) motif common to wall associated proteins.

ClfA is described in U.S. Pat. No. 6,008,341 and ClfB is described in WO 99/27109.

Coagulase (FbpA)

This is a fibrinogen binding protein which triggers *S. aureus* to form clumps in the presence of plasma. It is described in references related to Coagulase: Phonimdaeng et al (J. Gen. Microbio. 1988, 134:75-83), Phonimdaeng et al. (Mol Microbiol 1990; 4:393-404), Cheung et al. (Infect Immun 1995; 63:1914-1920) and Shopsin et al. (J. CLin. Microbiol. 2000; 38:3453-3456).

Preferred fragments for inclusion in the immunogenic composition of the invention include the mature protein in which the signal peptide has been removed (amino acids 27 to the C-terminus).

Coagulase has three distinct domains. Amino acids 59-297 which is a coiled coil region, amino acids 326-505 which is a proline and glycine rich region and the C-terminal domain from amino acid 506 to 645 which has a beta sheet conformation. Each of these domains is a fragment which may be incorporated into the immunogenic composition of the invention.

SdrG

This protein is described in WO 00/12689. SdrG is found in coagulase negative staphylococci and is a cell wall associated protein containing a LPXTG (SEQ ID NO: 102) sequence.

SdrG contains a signal peptide (amino acids 1-51), a region containing fibrinogen binding sites and collagen binding sites (amino acids 51-825), two CnaB domains (amino acids 627-698 and 738-809), a SD repeat region (amino acids 825-1000) and an anchor domain (amino acids 1009-1056).

Preferred fragments of SdrG include polypeptides in which the signal peptide and/or the SD repeats and the anchor domain have been removed. These include polypeptides comprising or consisting of amino acids 50-825, amino acids 50-633, amino acids 50-597 (SEQ ID NO 2 of WO 03/76470), amino acids 273-597 (SEQ ID NO 4 of WO 03/76470), amino acids 273-577 (SEQ ID NO 6 of WO 03/76470) amino acids 1-549, amino acids 219-549, amino acids 225-549, amino acids 219-528, amino acids 225-528 of SEQ ID NO: 70 or 20 or 21.

Preferably, an SdrG polypeptide having a sequence at least 80%, 85%, 90%, 92%, 95%, 97%, 98%, 99% or 100% homologous to the sequence of SEQ ID NO: 70, 20 or 21 is incorporated into the immunogenic composition of the invention.

The compositions of the invention optionally comprise a fragment of the SdrG polypeptides described above.

In an embodiment fragments have the signal peptide and/or the SD repeat domain and/or the anchoring domain deleted. For example sequences corresponding to amino acids 1-713, 1-549, 225-549, 225-529, 24-717, 1-707, 1-690, 1-680, 1-670, 1-660, 1-650, 1-640, 1-630, 1-620, 1-610, 1-600, 34-707, 44-697, 36-689 of SEQ ID 70 or sequences having 85%, 90%, 92%, 95%, 97%, 98%, 99% or 100% identity to SEQ ID 70 or 20 or 21.

In an embodiment, fragments with the signal peptide deleted have a methionine residue at the N-terminus of the fragment to ensure correct translation.

In an embodiment, the fragment has the following sequence (SEQ ID NO:87):—

MEENSVQDVKDSNTDDELSDSNDQSSDEEKNDVINNNQSINTDDNNQIIK

KEETNNYDGIEKRSEDRTESTTNVDENEATFLQKTPQDNTHLTEEEVKES

SSVESSNSSIDTAQQPSHTTINREESVQTSDNVEDSHVSDFANSKIKESN

TESGKEENTIEQPNKVKEDSTTSQPSGYTNIDEKISNQDE

LLNLPINEYENKARPLSTTSAQPSIKRVTVNQLAAEQGSNVNHLIKVTDQ

SITEGYDDSEGVIKAHDAENLIYDVTFEVDDKVKSGDTMTVDIDKNTVPS

DLTDSFTIPKIKDNSGEIIATGTYDNKNKQITYTFTDYVDKYENIKAHLK

LTSYIDKSKVPNNNTKLDVEYKTALSSVNKTITVEYQRPNENRTANLQSM

FTNIDTKNHTVEQTIYINPLRYSAKETNVNISGNGDEGST

IIDDSTIIKVYKVGDNQNLPDSNRIYDYSEYEDVTNDDYAQLGNNNDVNI

NFGNIDSPYIIKVISKYDPNKDDYTTIQQTVTMQTTINEYTGEFRTASYD

NTIAFSTSSGQGQGDLPPEKTYKIGDYVWEDVDKDGIQNTNDNEKPLSNV

LVTLTYPDGTSKSVRTDEDGKYQFDGLKNGLTYKITFETPEGYTPTLKHS

GTNPALDSEGNSVWVTINGQDDMTIDSGFYQTPKYSLGNY

VWYDTNKDGIQGDDEKGISGVKVTLKDENGNIISTTTTDENGKYQFDNLN

SGNYIVHFDKPSGMTQTTTDSGDDDEQDADGEEVHVTITDHDDFSIDNGY

YDDE

EbhA and EbhB

EbhA and EbhB are proteins that are expressed in both *S. aureus* and *S. epidermidis* (Clarke and Foster Infect. Immun. 2002, 70; 6680, Williams et al Infect. Immun. 2002, 20; 6805) and which bind to fibronectin. Since fibronectin is an important component of extracellular matrix, EbhA and EbhB have an important function in adhering staphylococci to host extracellular matrix.

The Ebh proteins are large, having a molecular weight of 1.1 megadaltons. It is advantageous to use a fragment of the Ebh protein rather than the complete sequence due to ease of production and formulation. The central region of the protein contains imperfect repeats which contain fibronectin binding sites. Fragments containing one or more of the repeat domains described below are preferred fragments for incorporation into the immunogenic composition of the invention.

Ebh proteins contain imperfect repeats units of 127 amino acids in length which are characterised by containing the consensus sequence:—

```
L.G.{10}A.{13}Q.{26}L...M..L.{33}A
or

.{19}L.G.{10}A.{13}Q.{26}L...M..L.{33}A.{12}
or

.....I/V..A...I/V..AK.ALN/DG..NL..AK..A.{6}L..LN.A
QK..L..QI/V..A..V..V.{6}A..LN/D.AM..L...I/V.D/E...
TK.S.NY/F.N/DAD..K..AY/F..AV..A..I/V.N/D.......

Where '.' means any amino acid and '.{10}' means
any 10 amino acids and I/V indicates alternative
choices of amino acid.
```

By reference to the sequence disclosed in Kuroda et al (2001) Lancet 357; 1225-1240, and Table 3, the repeat sequences within Ebh proteins are readily deduced.

In an embodiment, fragments to be included in the immunogenic composition of the invention include proteins containing of one, two, three, four, five, six, seven, eight, nine, ten or more than 10 of the 127 amino acid repeat units. Such fragments may consist of 1, 2, 3, 4, 5, 6, 7, 8, 9, 10 or more repeats of the 127 amino acid repeat region or may consist of 1, 2, 3, 4, 5, 6, 7, 8, 9, 10 or more repeats with additional amino acid residues present at either or both ends of the fragment. Optionally the fragment is the H2 polypeptide of about 44 kDa spaning three repeats (amino acids 3202-3595) as described in Clarke et al Infection and Immunity 70, 6680-6687, 2002. Such fragments will preferably be able to bind fibronectin and/or to elicit antibodies that are reactive against the whole Ebh protein.

The Ebh proteins are capable of binding to fibronectin. Preferred fragments of these polypeptides sequences retain the ability to bind to fibronectin. Binding to fibronectin can be assessed by ELISA as described by Clarke et al (Infection and Immunity 70; 6680-6687 2002).

In an embodiment, the fragment is one which comprises a B-cell or T-helper epitope, for example those fragments/peptides described in Tables 4 and 5.

TABLE 3

Repeat sequences in the full-length sequence of Ebh.
The full-length sequence of Ebh is disclosed in Kuroda et al (2001) Lancet 357; 1225-1240. The following table shows the amino acid residues at which the 127 amino acid repeats begin and end within the full length sequence.

|  | Begin | End |
|---|---|---|
| 1 | 3204 | 3330 |
| 2 | 3331 | 3457 |
| 3 | 3457 | 3583 |
| 4 | 3583 | 3709 |
| 5 | 3709 | 3835 |
| 6 | 3835 | 3961 |
| 7 | 3961 | 4087 |
| 8 | 4200 | 4326 |
| 9 | 4326 | 4452 |
| 10 | 4452 | 4578 |
| 11 | 4578 | 4704 |
| 12 | 4704 | 4830 |
| 13 | 4830 | 4956 |
| 14 | 4956 | 5082 |

TABLE 3-continued

Repeat sequences in the full-length sequence of Ebh.
The full-length sequence of Ebh is disclosed in Kuroda et al (2001) Lancet 357; 1225-1240. The following table shows the amino acid residues at which the 127 amino acid repeats begin and end within the full length sequence.

|  | Begin | End |
|---|---|---|
| 15 | 5082 | 5208 |
| 16 | 5208 | 5334 |
| 17 | 5334 | 5460 |
| 18 | 5460 | 5586 |
| 19 | 5585 | 5711 |
| 20 | 5711 | 5837 |
| 21 | 5837 | 5963 |
| 22 | 5963 | 6089 |
| 23 | 6089 | 6215 |
| 24 | 6215 | 6341 |
| 25 | 6341 | 6467 |
| 26 | 6467 | 6593 |
| 27 | 6593 | 6719 |
| 28 | 6719 | 6845 |
| 29 | 6845 | 6971 |
| 30 | 6971 | 7097 |
| 31 | 7097 | 7223 |
| 32 | 7223 | 7349 |
| 33 | 7349 | 7475 |
| 34 | 7475 | 7601 |
| 35 | 7601 | 7727 |
| 36 | 7727 | 7853 |
| 37 | 7852 | 7978 |
| 38 | 7978 | 8104 |
| 39 | 8104 | 8230 |
| 40 | 8230 | 8356 |
| 41 | 8356 | 8482 |
| 42 | 8482 | 8608 |
| 43 | 8604 | 8730 |
| 44 | 8858 | 8984 |

TABLE 4

B-cell epitope prediction for a 127 amino acid repeat:

The full-length sequence is disclosed in Kuroda et al (2001) Lancet 357; 1225-1240. One of these repeats, encoded by amino acids 3204-3331 of the full-length sequence was chosen to carry out an epitope prediction:-

MDVNTVNQKAASVKSTKDALDGQQNLQRAKTEATNAITHASDLNQAQKNA
LTQQVNSAQNVHAVNDIKQTTQSLNTAMTGLKRGVANHNQVVQSDNYVNA
DTNKKNDYNNAYNHANDIINGNAQHPVI

| Begin | End | Epitope sequence | Start | Stop |
|---|---|---|---|---|
| 5 | 10 | TVNQKA | 3208 | 3213 |
| 14 | 19 | KSTKDA | 3217 | 3222 |
| 21 | 33 | DGQQNLQRAKTEA | 3224 | 3236 |
| 42 | 51 | DLNQAQKNAL | 3245 | 3254 |
| 66 | 74 | DIKQTTQSL | 3269 | 3277 |
| 100 | 112 | ADTNKKNDYNNAY | 3303 | 3315 |
| 117 | 123 | DIINGNA | 3320 | 3326 |

The "Begin" and "End" columns present the position of the predicted B-cell epitopes in the 127 amino acid repeat
The "Start" and "Stop" columns present the position of the predicted B-cell epitopes in the Ebh full length sequence

TABLE 5

T-helper cell epitope prediction in Ebh:

The full-length sequence is disclosed in TrEMBL database, sequence reference Q8NWQ6. One of these repeats, encoded by amino acids 3204-3331 of the full-length sequence was chosen to carry out an epitope prediction:-

MDVNTVNQKAASVKSTKDALDGQQNLQRAKTEATNAITHASDLNQAQKNA
LTQQVNSAQNVHAVNDIKQTTQSLNTAMTGLKRGVANHNQVVQSDNYVNA
DTNKKNDYNNAYNHANDIINGNAQHPVI

| Position repeat | Epitope sequence | Position sequence |
|---|---|---|
| 1 | MDVNTVNQK | 3204 |
| 3 | VNTVNQKAA | 3206 |
| 6 | VNQKAASVK | 3209 |
| 26 | LQRAKTEAT | 3229 |
| 37 | ITHASDLNQ | 3240 |
| 43 | LNQAQKNAL | 3246 |
| 51 | LTQQVNSAQ | 3254 |
| 55 | VNSAQNVHA | 3258 |
| 61 | VHAVNDIKQ | 3264 |
| 64 | VNDIKQTTQ | 3267 |
| 67 | IKQTTQSLN | 3270 |
| 74 | LNTAMTGLK | 3277 |
| 78 | MTGLKRGVA | 3281 |
| 81 | LKRGVANHN | 3284 |
| 85 | VANHNQVVQ | 3288 |
| 91 | VVQSDNYVN | 3294 |
| 92 | VQSDNYVNA | 3295 |
| 97 | YVNADTNKK | 3301 |
| 98 | VNADTNKKN | 3302 |
| 108 | YNNAYNHAN | 3311 |
| 112 | YNHANDIIN | 3315 |
| 118 | IINGNAQHP | 3321 |
| 119 | INGNAQHPV | 3322 |

The "Position repeat" column presents the position of the predicted T-cell epitopes in the repeat
The "Position sequence" column presents the position of the predicted T-cell epitopes in the Ebh full length sequence Fragments of the proteins of the invention may be employed for producing the corresponding full-length polypeptide by peptide synthesis; therefore, these fragments may be employed as intermediates for producing the full-length proteins of the invention.

In an embodiment, variants are used in which several, 5-10, 1-5, 1-3, 1-2 or 1 amino acids are substituted, deleted, or added in any combination.

Elastin Binding Protein (EbpS)

EbpS is a protein containing 486 amino acids with a molecular weight of 83 kDa. It is associated with the cytoplasmic membrane of S. aureus and has three hydrophobic regions which hold the protein in the membrane (Downer et al 2002, J. Biol. Chem. 277; 243; Park et al 1996, J. Biol. Chem. 271; 15803).

Two regions between amino acids 1-205 and 343-486 are surface exposed on the outer face of the cytoplasmic membrane. The ligand binding domain of EbpS is located between residues 14-34 at the N-terminus (Park et al 1999, J. Biol. Chem. 274; 2845).

In an embodiment, the fragment to be incorporated into the immunogenic composition of the invention is the surface exposed fragment containing the elastin binding region (amino acids 1-205). Optionally the fragments do not contain the entire exposed loop but should contain the elastin binding region (amino acids 14-34). An alternative fragment which could be used consists of amino acids forming the second surface exposed loop (amino acids 343-486). Alternative fragments containing up to 1, 2, 5, 10, 20, 50 amino acids less at one or both ends are also possible.

Laminin Receptors

The laminin receptor of S. aureus plays an important role in pathogenicity. A characteristic feature of infection is bloodstream invasion which allows widespread metastatic abscess formation. Bloodstream invasion requires the ability to extravasate across the vascular basement membrane. This is achieved through binding to laminin through the laminin receptor (Lopes et al Science 1985, 229; 275).

Laminin receptors are surface exposed and are present in many strains of staphylococci including S. aureus and S. epidermidis.

SBI

Sbi is a second IgG binding protein in addition to protein A and it is expressed in most strains of S. aureus (Zhang et al 1998, Microbiology 144; 985).

The N-terminus of the sequence of Sbi has a typical signal sequence with a cleavage site after amino acid 29. Therefore a fragment of Sbi which could be used in an immunogenic composition of the invention starts at amino acid residue 30, 31, 32 or 33 and continues to the C-terminus of Sbi, for example of SEQ ID NO: 26.

The IgG binding domain of Sbi has been identified as a region towards the N-terminus of the protein from amino acids 41-92. This domain is homologous to the IgG binding domains of protein A.

The minimal IgG binding domain of Sbi contains the following sequence (SEQ ID NO:89):—

```
QTTQNNYVTDQQKAFYQVLHLKGITEEQRNQYIKTLREHPERAQEVFSES
 ** ***  *           ***  *   *      *           *

LK
 *
```

*denotes amino acids which are similar between IgG binding domains

In an embodiment, a fragment of Sbi to be included in the immunogenic composition of the invention contains an IgG binding domain. This fragment contains the consensus sequence for an IgG binding domain as designated by * as shown in the above sequence. Optionally the fragment contains or consists of the complete sequence shown above. Optionally, the fragment contains or consists of amino acids 30-92, 33-92, 30-94, 33-94, 30-146, 33-146, 30-150, 33-150, 30-160, 33-160, 30-170, 33-180, 33-190, 33-200, 33-205 or 33-210 of Sbi, for example of SEQ ID NO:26.

A fragment may contain 1, 2, 3, 4, 5, 6, 7, 8, 9, 10 amino acid substitutions from the sequences indicated.

A fragments may contain multiple repeats (2, 3, 4, 5, 6, 7, 8, 9 or 10) of the IgG binding domain.

EFB-FIB

Fib is a 19 kDa fibrinogen binding protein which is secreted into the extracellular medium by *S. aureus*. It is produced by all *S. aureus* isolates tested (Wastfelt and Flock 1995, J. Clin. Microbiol. 33; 2347).

*S. aureus* clumps in the presence of fibrinogen and binds to fibrinogen coated surfaces. This ability facilitates staphylococcal colonisation of catheters and endothelial cells.

Fib contains a signal sequence at the N-terminus of the protein with a putative cleavage site at about amino acid 30. In an embodiment, the immunogenic composition of the invention comprises or consists of the sequence of the mature protein (from about amino acid 30 to the C-terminus of the protein).

Fbe-EfB/FIG

Fbe is a fibrinogen binding protein that is found in many isolates of *S. epidermidis* and has a deduced molecular weight of 119 kDa (Nilsson et al 1998. Infect. Immun. 66; 2666). Its sequence is related to that of clumping factor from *S. aureus* (ClfA). Antibodies against Fbe can block the binding of *S. epidermidis* to fibrinogen coated plates and to catheters (Pei and Flock 2001, J. Infect. Dis. 184; 52).

Fbe has a putative signal sequence with a cleavage site between amino acids 51 and 52. Therefore a preferred fragment of Fbe contains the mature form of Fbe extending from amino acid 52 to the C-terminus (amino acid 1,092).

The domain of Fbe from amino acid 52 to amino acid 825 is responsible for fibrinogen binding. In an embodiment, the fragment of Fbe consists of or contains amino acids 52-825.

The region between amino acid 373 and 516 of Fbe shows the most conservation between Fbe and ClfA. In an embodiment, the fragment contains amino acids 373-516 of Fbe.

Amino acids 825-1041 of Fbe contains a highly repetitive region composed of tandemly repeated aspartic acid and serine residues.

IsaA/PisA

IsaA is a 29 kDa protein, also known as PisA has been shown to be a immunodominant staphylococcal protein during sepsis in hospital patients (Lorenz et al 2000, FEMS Immunol. Med. Microb. 29; 145).

The first 29 amino acids of the IsaA sequence are thought to be a signal sequence. In an embodiment, the fragment of IsaA to be included in an immunogenic composition of the invention contains amino acid residues 30 onwards, to the end of the coded sequence.

Fibronectin Binding Protein

Fibronectin binding protein A contains several domains that are involved in binding to fibronectin (WO 94/18327). These are called D1, D2, D3 and D4. In an embodiment fragments of fibronectin binding protein A or B comprise or consist of D1, D2, D3, D4, D1-D2, D2-D3, D3-D4, D1-D3, D2-D4 or D1-D4.

Fibronectin binding protein contains a 36 amino acid signal sequence. For example:
VKNNLRYGIRKHKLGAASVFLGTMIVVG-MGQDKEAA (SEQ ID NO: 90)

Optionally, the mature protein omitting this signal sequence is included in the immunogenic composition of the invention.

Transporter Proteins

The cell wall of Gram positive bacteria acts as a barrier preventing free diffusion of metabolites into the bacterium. A family of proteins orchestrates the passage of essential nutrients into the bacterium and are therefore essential for the viability of the bacterium. The term transporter protein covers proteins involved in the initial step of binding to metabolites such as iron as well as those involved in actually transporting the metabolite into the bacterium.

Molecular iron is an essential co-factor for bacterial growth. Siderophores are secreted that bind free iron and then are captured by bacterial surface receptors that deliver iron for transport across the cytoplasmic membrane. Iron acquisition is critical for the establishment of human infections so that the generation of an immune response against this class of proteins leads to a loss of staphylococcal viability.

Examples of transporter proteins include Immunodominant ABC transporter (Burnie et al 2000 Infect. Imun. 68; 3200), IsdA (Mazmanian et al 2002 PNAS 99; 2293), IsdB (Mazmanian et al 2002 PNAS 99; 2293, WO 05/09378), IsdC (WO 06/59247), -IsdH/HarA (Pilpa et al 2006, J. Mol. Biol. 360; 435; WO 05/09379) Mg2+ transporter, SitC (Wiltshire and Foster 2001 Infect. Immun. 69; 5198) and Ni ABC transporter.

Immunodominant ABC Transporter

Immunodominant ABC transporter is a well conserved protein which may be capable of generating an immune response that is cross-protective against different staphylococcal strains (Mei et al 1997, Mol. Microbiol. 26; 399). Antibodies against this protein have been found in patients with septicaemia (Burnie et al 2000, Infect. Immun. 68; 3200).

Optional fragments of immunodominant ABC transporter will include the peptides DRHFLN (SEQ ID NO:91), GNYD (SEQ ID NO:92), RRYPF (SEQ ID NO:93), KTTLLK (SEQ ID NO:94), GVTTSLS (SEQ ID NO:95), VDWLR (SEQ ID NO 96), RGFL (SEQ ID NO:97), more preferably KIKVYVGNYDFWYQS (SEQ ID NO:98), TVIWSH-DRHFLYNNV (SEQ ID NO:99) and/or TETFLRGFLGRM-LFS (SEQ ID NO:100) since these sequences contain epitopes that are recognised by the human immune system.

IsdA-IsdB

The isd genes (iron-regulated surface determinant) of *S. aureus* encode proteins responsible for haemoglobin binding and passage of haem iron to the cytoplasm, where it acts as an essential nutrient. IsdA and IsdB are located in the cell wall of staphylococci. IsdA appear to be exposed on the surface of bacterium since it is susceptible to proteinase K digestion. IsdB was partially digested suggesting that it is partially exposed on the surface of the bacterium (Mazmanian et al 2003 Science 299; 906).

IsdA and IsdB are both 29 kDa proteins which bind heme. Their expression is regulated by the availability of iron via the Fur repressor. Their expression will be high during infection in a host where the concentration of iron will be low.

They are also known as FrpA and FrpB (Morrissey et al 2002, Infect. Immun. 70; 2399). FrpA and FrpB are major surface proteins with a high charge. They have been shown to provide a major contribution to adhesion to plastic.

In an embodiment, the immunogenic composition of the invention comprises a fragment of IsdA and/or IsdB which is described in WO 01/98499 or WO 03/11899.

HarA

HarA is a further iron-regulated protein. It contains a signal peptide of amino acids 1-40. Optionally, the HarA present in the immunogenic compositions of the invention omits the signal peptide.

HarA contains three NEAT domains from amino acid 101-232, from amino acid 341-471 and from amino acid 539-664. For example, a fragment of HarA comprises or consists of amino acids 101-232, 101-471, 101-664, 341-471. 341-664 or 539-664, optionally from the sequence of SEQ ID NO 69.

HarA contains a Gram plus anchor domain: from aa 853 to aa 892. Optionally, a fragment of HarA omits this domain.

Signal peptide length: 40 amino acids—underlined in first row of sequence

NEAT domains—three underlined internal regions.

Gram+anchor domain—underlined region on bottom line of sequence.

staphylococci and activates the expression and subsequent release of virulence factors such as hemolysin, enterotoxin B and TSST-1.

Other Immunodominant Proteins

Accumulation-Associated Protein (Aap)

Aap is a 140 kDa protein which is essential for the accumulation of *S. epidermidis* strains on surfaces (Hussain et al

```
MNKHHPKLRSFYSIRKSTLGVASVIVSTLFLITSQHQAQAAENTNTSDKISENQNNNATT
TQPPKDTNQTQPATQPANTAKNYPAADESLKDAIKDPALENKEHDTGPREQVNFQLLDKN
NETQYYHFRSIKDPADVYYTKKKAEVELDINTASTWKKFEVYENNQKLPVRLVSYSPVPF
DHAYIRFPVSDGTQFLKTVSSTQIDDGEFTNYDYTKLVFAKPIYNDPSLVKSDTNDAVVT
NDQSSSVASNQTNTNTSNQNISTINNANNQPQATTNMSQPAQPKSSTNADQASSQPAHET
NSNGNTNDKTNESSNQSDVNQQYPPADESLQDAIKNPAIIDKEHTADNWRPIDFQMKNDK
GERQPYHYASTVEPATVIFTKTGPIIBLGLKTASTWKKPEVYEGDKKLPVELVGYDSDKD
YAYIRFPVSNGTREVKTVSSIEYGENTHEDYDYTLMVFAQPITNNPDDYVDEETYNLQKL
LAPYHKAKTLERQVYELEKLQEKLPEKYKAEYKKKLDQTRVELADQVKSAVTEFENVTPT
NDQLTDLQEAHFVVFESEENSESVMDGFVEHPFYTATLNGQKYVVMKTKDDSYWKDLIVE
GKRVTTVSKDPKNNSRTLIFPYIPDKAVYNAIVKVVVANIGYEGQYHVRIINQDINTKDD
DTSQNNTSEPLNVQTGQEGKVADTDVAENSSTATNPKDASDKADVIEPESDVVKDADNNI
DKDVQHDVDHLSDMSDNNHFDKYDLKEMDTQIAKDTDRNVDKDADNSVGMSSNVDTDKDS
NKNKDKVIQLNHIADKNNHTGKAAKLDVVKQNYNNTDKVTDKKTTEHLPSDIHKTVDKTV
KTKEKAGTPSKENKLSQSKMLPKTGETTSSQSWWGLYALLGMLALFIPKFRKESK
(SEQ ID NO: 101)
```

Toxins and Regulators of Virulence

Members of this family of proteins include toxin such as alpha toxin, hemolysin, enterotoxin B, Panton Valentine Leucocidin (VPL) (Morinaga et al Microbiol. Immunol. 47; 81-90, 2003) and TSST-1 as well as proteins that regulate the production of toxins such as RAP.

Alpha Toxin (Hla)

Alpha toxin is an important virulence determinant produced by most strains of *S. aureus*. It is a pore forming toxin with haemolytic activity. Antibodies against alpha toxin have been shown to neutralise the detrimental and lethal effects of alpha toxin in animal models (Adlam et al 1977 Infect. Immun. 17; 250). Human platelets, endothelial cells and mononuclear cells are susceptible to the effects of alpha toxin.

The high toxicity of alpha toxin requires that it should be detoxified before being used as an immunogen. This can be achieved by chemical treatment, for instance by treating with formaldehyde, glutaraldehyde of other cross-linking reagents or by chemically conjugating it to bacterial polysaccharides as described below.

A further way of removing toxicity is to introduce point mutations that remove toxicity while retaining the antigenicity of the toxin. The introduction of a point mutation at amino acid 35 of alpha toxin where a histidine residue is replaced with a leucine residue results in the removal of toxicity whilst retaining immunogenicity (Menzies and Kernodle 1996; Infect. Immun. 64; 1839). Histidine 35 appears to be critical for the proper oligomerization required for pore formation and mutation of this residue leads to loss of toxicity.

When incorporated into immunogenic compositions of the invention, alpha toxin is optionally detoxified by mutation of His 35, for example by replacing His 35 with Leu or Arg. In an alternative embodiment, alpha toxin is detoxified by conjugation to other components of the immunogenic composition, for example capsular polysaccharides or PNAG, most preferably to *S. aureus* type 5 polysaccharide and/or *S. aureus* Type 8 polysaccharide and/or PNAG.

RNA III Activating Protein (RAP)

RAP is not itself a toxin, but is a regulator of the expression of virulence factors. RAP is produced and secreted by staphylococci. It activates the agr regulatory system of other Infect. Immun. 1997, 65; 519). Strains expressing this protein produced significantly larger amounts of biofilm and Aap appear to be involved in biofilm formation. Antibodies against Aap are able to inhibit biofilm formation and inhibit the accumulation of *S. epidermidis*. Sequences which could be added to a vaccine are disclosed in WO 05/86663.

Staphylococcal Secretory Antigen SsaA

SsaA is a strongly immunogenic protein of 30 kDa found in both *S. aureus* and *S. epidermidis* (Lang et al 2000 FEMS Immunol. Med. Microbiol. 29; 213). Its expression during endocarditis suggested a virulence role specific to the pathogenesis of the infectious disease.

SsaA contains an N-terminal leader sequence and a signal peptidase cleavage site. The leader peptide is followed by a hydrophilic region of approximately 100 amino acids from residue 30 to residue 130.

An optional fragment of SsaA to be incorporated into the immunogenic composition of the invention is made up of the mature protein (amino acids 27 to the C-terminus or amino acids 30 to the C-terminus).

A further optional fragments contains the hydrophilic area of SsaA from amino acid 30 to amino acid 130. Further optional sequences and fragments are disclosed in WO 05/115113, Penicillin Binding Protein 4

Penicillin binding protein 4 is described in Henze et al Antimicrobial Agents and Chemotherapy 38: 2415, 1995 and WO 06/33918.

Preferred Combinations

Staphylococcal infections progress through several different stages. For example, the staphylococcal life cycle involves commensal colonisation, initiation of infection by accessing adjoining tissues or the bloodstream, anaerobic multiplication in the blood, interplay between *S. aureus* virulence determinants and the host defense mechanisms and induction of complications including endocarditis, metastatic abscess formation and sepsis syndrome. Different molecules on the surface of the bacterium will be involved in different steps of the infection cycle. By targeting the immune response against a combination of particular antigens involved in different processes of Staphylococcal infection, multiple aspects of staphylococcal function are affected and this can result in good vaccine efficacy.

In particular, combinations of certain antigens from different classes, some of which are involved in adhesion to host cells, some of which are involved in iron acquisition or other transporter functions, some of which are toxins or regulators of virulence and immunodominant antigens can elicit an immune response which protects against multiple stages of infection.

Some combinations of antigens are particularly effective at inducing an immune response. This can be measured either in animal model assays as described in the examples and/or using an opsonophagocytic assay as described in the examples. Without wishing to be bound by theory, such effective combinations of antigens are thought to be enabled by a number of characteristics of the immune response to the antigen combination. The antigens themselves are usually exposed on the surface of Staphylococcal cells, they tend to be conserved but also tend not to be present in sufficient quantity on the surface cell for an optimal bactericidal response to take place using antibodies elicited against the single antigen. Combining the antigens of the invention can result in a formulation eliciting an advantageous combination of antibodies which interact with the Staphylococcal cell beyond a critical threshold. At this critical level, sufficient antibodies of sufficient quality bind to the surface of the bacterium to allow either efficient killing by complement or neutralisation of the bacterium. This can be measured in either an animal challenge model or an opsonisation assay as described in the examples.

In an embodiment, processes of the invention mix a plurality of proteins selected from at least two different categories of protein, having different functions within Staphylococci. Examples of such categories of proteins are extracellular binding proteins, transporter proteins such as Fe acquisition proteins, toxins or regulators of virulence and other immunodominant proteins, thus making an immunogenic composition of the invention.

In an embodiment, the process or immunogenic composition of the invention further use/comprises a number of proteins equal to or greater than 2, 3, 4, 5 or 6 selected from 2 or 3 different groups selected from;
Group a) extracellular component binding proteins;
Group b) transporter proteins;
Group c) toxins or regulators of virulence.

In an embodiment, the immunogenic composition of the invention further comprises a number of proteins equal to or greater than 2, 3, 4, 5 or 6 selected from 2 or 3 of the following groups:
group a)—at least one staphylococcal extracellular component binding protein or fragment thereof selected from the group consisting of laminin receptor, SitC/MntC/saliva binding protein, Protein A, EbhA, EbhB, Elastin binding protein (EbpS), EFB (FIB), SBI, autolysin, ClfA, SdrC, SdeD, SdrE, SdrG, SdrH, Lipase GehD, SasA, FnbA, FnbB, Cna, ClfB, FbpA, Npase, IsaA/PisA, SsaA, SasH, EPB, SSP-1, SSP-2, HBP, Vitronectin binding protein, fibrinogen binding protein, coagulase, Fig and MAP;
group b)—at least one staphylococcal transporter protein or fragment thereof selected from the group consisting of Immunodominant ABC transporter, IsdA, IsdB, IsdH/HarA Mg2+ transporter, SitC and Ni ABC transporter;
group c)—at least one staphylococcal regulator of virulence, toxin or fragment thereof selected from the group consisting of alpha toxin (Hla), alpha toxin H35R mutant, RNA III activating protein (RAP);
group d)—at least one staphylococcal structural protein or immunogenic fragment thereof selected from the group consisting of MRPII and autolysin.

These particular immunogenic composition may include at least one staphylococcal saccharide and/or protein as part of the saccharide-protein conjugate of the invention and at least one staphylococcal antigen which is not part of the saccharide-protein conjugate of the invention in order to complete the combination.

In an embodiment, the immunogenic composition of the invention contains at least one protein selected from group a) and an additional protein selected from group b) and/or group c).

In a further embodiment, the immunogenic composition of the invention contains at least one antigen selected from group b) and an additional protein selected from group c) and/or group a).

In a further embodiment, the immunogenic composition of the invention contains at least one antigen selected from group c) and an additional protein selected from group a) and/or group b).

In a further embodiment, the process of the invention involves the addition of any of the staphylococcal proteins listed in WO 02/59148, WO 05/09378, WO 05/09379, WO 05/86663, WO 05/115113, WO 06/33918, WO 06/78680, WO 06/121664, WO 07/01361, WO 02/94868, U.S. Pat. No. 6,380,370, WO 04/87746, WO 01/98499 or WO 03/11899.

In an embodiment, the immunogenic composition of the invention comprises a dose of each saccharide conjugate between 0.1 and 20 μg, 2 and 10 μg, 2 and 6 μg or 4 and 7 μg of saccharide per administered dose. In an embodiment, the method of the invention mixes between 0.1 and 20 μg, 2 and 10 μg, 2 and 6 μg or 4 and 7 μg of each saccharide.

"Around" or "approximately" are defined as within 10% more or less of the given figure for the purposes of the invention.

In an embodiment, the immunogenic composition of the invention is adjusted to or buffered at, or adjusted to between pH 7.0 and 8.0, pH 7.2 and 7.6 or around or exactly pH 7.4.

The immunogenic composition or vaccines of the invention are optionally lyophilised in the presence of a stabilising agent for example a polyol such as sucrose or trehalose.

Optionally, the immunogenic composition or vaccine of the invention contains an amount of an adjuvant sufficient to enhance the immune response to the immunogen. Suitable adjuvants include, but are not limited to, aluminium salts (aluminium phosphate or aluminium hydroxide), squalene mixtures (SAF-1), muramyl peptide, saponin derivatives, mycobacterium cell wall preparations, monophosphoryl lipid A, mycolic acid derivatives, non-ionic block copolymer surfactants, Quil A, cholera toxin B subunit, polyphosphazene and derivatives, and immunostimulating complexes (IS-COMs) such as those described by Takahashi et al. (1990) Nature 344:873-875. Equally, the method of the invention optionally comprises a step of adding at least one of the above adjuvants.

As with all immunogenic compositions or vaccines, the immunologically effective amounts of the immunogens must be determined empirically. Factors to be considered include the immunogenicity, whether or not the immunogen will be complexed with or covalently attached to an adjuvant or carrier protein or other carrier, route of administrations and the number of immunising dosages to be administered.

The active agent can be present in varying concentrations in the pharmaceutical composition or vaccine of the invention. Typically, the minimum concentration of the substance is an amount necessary to achieve its intended use, while the maximum concentration is the maximum amount that will remain in solution or homogeneously suspended within the initial mixture. For instance, the minimum amount of a therapeutic agent is optionally one which will provide a single therapeutically effective dosage. For bioactive substances, the minimum concentration is an amount necessary for bioactivity upon reconstitution and the maximum concentration is at the point at which a homogeneous suspension cannot be maintained. In the case of single-dosed units, the amount is that of a single therapeutic application. Generally, it is expected that each dose will comprise 1-100 μg of protein antigen, optionally 5-50 μg or 5-25 μg. For example, doses of bacterial saccharides are 10-20 μg, 5-10 μg, 2.5-5 μg or 1-2.5 μg of saccharide in the conjugate.

The vaccine preparations of the present invention may be used to protect or treat a mammal (for example a human patient) susceptible to infection, by means of administering said vaccine via systemic or mucosal route. A human patient is optionally an infant (under 12 months), a toddler (12-24, 12-16 or 12-14 months), a child (2-10, 3-8 or 3-5 years) an adolescent (12-21, 14-20 or 15-19 years) or an adult. These administrations may include injection via the intramuscular, intraperitoneal, intradermal or subcutaneous routes; or via mucosal administration to the oral/alimentary, respiratory, genitourinary tracts. Intranasal administration of vaccines for the treatment of pneumonia or otitis media is preferred (as nasopharyngeal carriage of pneumococci can be more effectively prevented, thus attenuating infection at its earliest stage). Although the vaccine of the invention may be administered as a single dose, components thereof may also be co-administered together at the same time or at different times (for instance if saccharides are present in a vaccine these could be administered separately at the same time or 1-2 weeks after the administration of a bacterial protein vaccine for optimal coordination of the immune responses with respect to each other). In addition to a single route of administration, 2 different routes of administration may be used. For example, viral antigens may be administered ID (intradermal), whilst bacterial proteins may be administered IM (intramuscular) or IN (intranasal). If saccharides are present, they may be administered IM (or ID) and bacterial proteins may be administered IN (or ID). In addition, the vaccines of the invention may be administered IM for priming doses and IN for booster doses.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

In a further aspect of the invention there is provided an immunogenic composition comprising a saccharide-protein carrier conjugate and a staphylococcal antigen obtainable or obtained by the method of the invention.

A use of the immunogenic composition or vaccine of the invention in the manufacture of a medicament for the prevention or treatment of disease, and a method of preventing or treating disease comprising the step of administering an effective dose of the immunogenic composition or vaccine of the invention to a patient in need thereof is further provided. The use or method may be such that the disease is caused by a bacterium selected from a list consisting of: *N. meningitidis, Streptococcus pneumoniae, M. catarrhalis*, Group B *Streptococcus, Staphylococcus aureus, Salmonella typhi, Vibrio cholerae, E. coli*, and *H. influenzae*.

The terms "comprising", "comprise" and "comprises" herein are intended by the inventors to be optionally substitutable with the terms "consisting of", "consist of" and "consists of", respectively, in every instance.

All references or patent applications cited within this patent specification are incorporated by reference herein.

The invention is illustrated in the accompanying examples. The examples below are carried out using standard techniques, which are well known and routine to those of skill in the art, except where otherwise described in detail. The examples are illustrative, but do not limit the invention.

EXAMPLES

Example 1

Preparation of Polysaccharide Conjugates

*S. aureus* Capsular Polysaccharide Type 8-TT Conjugate:
PS Derivatization

Activation and coupling were performed at room temperature under continuous stirring. 30 mg of native polysaccharide were diluted to obtain a final polysaccharide concentration of 5 mg/ml in water. The solution was adjusted to pH 5.0 with 0.5N HCl and then 66 μg of ADH were added (2.2 mg/mg PS). After complete dissolution, 60 mg of EDAC were added (2 mg/mg PS). After 70 min the pH was raised to pH 7.5 with 1N NaOH to stop the reaction. Free ADH was removed by purification on SEPHACRYL® S100HR (XK 16/40). The flow-rate was fixed at 60 ml/h using 0.2 M NaCl as elution buffer. A size reduction was done by sonication of 15 min allowing a sterile filtration on millex filter (0.22 μm).

Coupling

Tetanus toxoid was added to 5 to 10 mg of derivatized polysaccharide in 0.2M NaCl and the pH was adjusted to pH 5.0 or pH 6.0 by addition of 0.5N HCl. EDAC was dissolved in 0.1M Tris buffer pH 7.5 and then added over a period of 10 min (⅕ vol each 2 min). According to the conditions used (see Table 6), the reaction was stopped after between 30 and 180 minutes by addition of 1M Tris-HCl pH 7.5. Prior to purification on SEPHACRYL® S400HR, the conjugate was clarified using a 5 μm Minisart filter. Alternatively, the conjugate was clarified by a 5 minute sonication step. The conjugate was then injected on SEPHACRYL® S400HR (XK50/100). The flow-rate was fixed at 30 ml/h using 150 mM NaCl as elution buffer. The elution pool was selected on the basis of resorcinol and μBCA profiles (which measure polysaccharide and protein dosage respectively). The conjugate was filtered on a 0.22 μm sterilizing membrane (Millipack 20) at 10 ml/min.

TABLE 6

| Conjugate | Coupling time | [PS (AH)] (mg/ml) | [TT (AH)] (mg/ml) | [reagent EDAC] (mg/mg PS) |
|---|---|---|---|---|
| SA08-TT011 | 40 min | 5 | 10 | 0.5/1 |
| SA08-TT015* | 180 min | 2.5 | 5.0 | 0.25/1 |
| SA08-TT017 | 30 min | 3.75 | 7.5 | 0.25/1 |
| SA08-TT018 | 50 min | 3.75 | 7.5 | 0.10/1 |

*coupling done at pH 6.0

The resulting conjugates have the following characteristics shown in Table 7:

TABLE 7

| Conjugate | In. TT/PS ratio(w/w) | F. TT/PS ratio(w/w) | Y. PS rec (%) | Filtr. Yield (%) |
|---|---|---|---|---|
| SA08-TT011 | 2/1 | 2.43/1 | 48 | 99 |
| SA08-TT015 | 2/1 | 2.40/1 | 53 | 104 |

TABLE 7-continued

| Conjugate | In. TT/PS ratio(w/w) | F. TT/PS ratio(w/w) | Y. PS rec (%) | Filtr. Yield (%) |
|---|---|---|---|---|
| SA08-TT017 | 2/1 | 2.41/1 | 44 | 107 |
| SA08-TT018 | 2/1 | 2.40/1 | 42 | 106 |

*S. aureus* polysaccharide type 8 was also treated by microfluidization before derivatization with ADH PS Derivatization Activation and coupling are performed at room temperature under continuous stirring. 200 mg of sized polysaccharide are diluted to obtain a final PS concentration of 10 mg/ml in water. Then 440 mg of ADH were added (2.2 mg/mg PS). The solution was adjusted to pH 4.7 with 1N HCl before the addition of 400 mg of EDAC (2 mg/mg PS). After 60 min the pH was raised to pH 7.5 with 5M NaOH to stop the reaction. The mixture was concentrated on Amicon Ultra (cut-off 10.000 MWCO). Prior to purification on SEPHACRYL® S200HR (XK16/100), the conjugate was clarified using a 5 µm Minisart filter. The flow-rate was fixed at 30 ml/h using 0.150 M NaCl as elution buffer.

Coupling 100 mg of TT was added to 50 mg of derivatized polysaccharide in 0.15M NaCl. The pH was adjusted to pH 5.0±0.02 by addition of 0.3N HCl. EDAC was dissolved in 0.1M Tris buffer pH 7.5 and then added over a period of 10 min (1/10 vol each minute). According to the conditions used (see Table 8), the reaction was stopped after between 30 and 180 minutes by addition of 1M Tris-HCl pH 7.5. Prior to purification on SEPHACRYL® S400HR, the conjugate was clarified using a 5 µm Minisart filter. The conjugate was then injected on SEPHACRYL® S400HR (XK50/100). The flow-rate was fixed at 60 ml/h using 150 mM NaCl as elution buffer. The elution pool was selected on the basis of resorcinol and µBCA profiles (which measure polysaccharide and protein dosage respectively). Then, the conjugate was filtered on a 0.22 µm sterilizing membrane (Millipack 20) at 10 ml/min.

TABLE 8

| Conjugate | Coupling time | [PS-AH] (mg/ml) | [TT] (mg/ml) | [EDAC] (mg/mg PS) |
|---|---|---|---|---|
| SA08-TT045 | 65 min | 3.75 | 7.5 | 0.1 |
| SA08-TT046 | 45 min | 3.75 | 7.5 | 0.2 |
| SA08-TT047 | 30 min | 5.0 | 15.0 | 0.2 |
| SA08-TT048 | 120 min | 5.0 | 10.0 | 0.05 |
| SA08-TT049* | 50 min | 5.0 | 10.0 | 0.1 |

*EDAC added in "one time"

TABLE 9

| Conjugate | In. TT/PS ratio(w/w) | F. TT/PS ratio(w/w) | Y. PS rec (%) | Filtr. Yield (%) |
|---|---|---|---|---|
| SA08-TT045 | 2/1 | 2.20/1 | 57 | 101 |
| SA08-TT046 | 2/1 | 2.80/1 | | |
| SA08-TT047 | 3/1 | Gel- Not purified | — | — |
| SA08-TT048 | 2/1 | 3.35 | 30 | 101 |
| SA08-TT049 | 2/1 | 3.5 | 24 | 106 |

Example 1a

Preparation of Meningococcal MenA and MenC Capsular Polysaccharide Conjugate According to the Invention MenC-TT conjugates were produced using native polysaccharides (of over 150 kDa as measured by MALLS) or were slightly microfluidised. MenA-TT conjugates were produced using either native polysaccharide or slightly microfluidised polysaccharide of over 60 kDa as measured by the MALLS method of example 2. Sizing was by microfluidisation using a homogenizer EMULSIFLEX® C-50 apparatus. The polysaccharides were then filtered through a 0.2 µm filter.

In order to conjugate MenA capsular polysaccharide to tetanus toxoid via a spacer, the following method was used. The covalent binding of the polysaccharide and the spacer (ADH) is carried out by a coupling chemistry by which the polysaccharide is activated under controlled conditions by a cyanylating agent, 1-cyano-4-dimethylamino-pyridinium tetrafluoroborate (CDAP). The spacer reacts with the cyanylated PS through its hydrazino groups, to form a stable isourea link between the spacer and the polysaccharide.

A 10 mg/ml solution of MenA (pH 6.0) [3.5 g] was treated with a freshly prepared 100 mg/ml solution of CDAP in acetonitrile/water (50/50 (v/v)) to obtain a CDAP/MenA ratio of 0.75 (w/w). After 1.5 minutes, the pH was raised to pH 10.0. Three minutes later, ADH was added to obtain an ADH/MenA ratio of 8.9. The pH of the solution was decreased to 8.75 and the reaction proceeded for 2 hours maintaining this pH (with temperature kept at 25° C.).

The PSA$_{AH}$ solution was concentrated to a quarter of its initial volume and then diafiltered with 30 volumes of 0.2M NaCl using a Filtron Omega membrane with a cut-off of 10 kDa, and the retentate was filtered.

Prior to the conjugation (carbodiimide condensation) reaction, the purified TT solution and the PSA$_{AH}$ solution were diluted to reach a concentration of 10 mg/ml for PSA$_{AH}$ and 10 mg/ml for TT.

EDAC (1-ethyl-3-(3-dimethyl-aminopropyl) carbodiimide) was added to the PS$_{AH}$ solution (2 g saccharide) in order to reach a final ratio of 0.9 mg EDAC/mg PSA$_{AH}$. The pH was adjusted to 5.0. The purified tetanus toxoid was added with a peristaltic pump (in 60 minutes) to reach 2 mg TT/mg PSA$_{AH}$. The resulting solution was left 60 min at +25° C. under stirring to obtain a final coupling time of 120 min. The solution was neutralised by addition of 1M Tris-Hcl pH 7.5 (1/10 of the final volume) and left 30 minutes at +25° C. then overnight at +2° C. to +8° C.

The conjugate was clarified using a 10 µm filter and was purified using a SEPHACRYL® S400HR column (Pharmacia, Sweden). The column was equilibrated in 10 mM Tris-HCl (pH 7.0), 0.075 M NaCl and the conjugate (approx. 660 mL) was loaded on the column (+2° C. to +8° C.). The elution pool was selected as a function of optical density at 280 nm. Collection started when absorbance increased to 0.05. Harvest continued until the Kd reached 0.30. The conjugate was filter sterilised at +20° C., then stored at +2° C. to +8° C. The resultant conjugate had a polysaccharide:protein ratio of 1:2-1:4 (w/w).

In order to conjugate MenC capsular polysaccharide to tetanus toxoid via a spacer, the following method was used. The covalent binding of the polysaccharide and the spacer (ADH) is carried out by a coupling chemistry by which the polysaccharide is activated under controlled conditions by a cyanylating agent, 1-cyano-4-dimethylamino-pyridinium tetrafluoroborate (CDAP). The spacer reacts with the cyanylated PS through its hydrazino groups, to form a stable isourea link between the spacer and the polysaccharide.

A 20 mg/ml solution of MenC (pH6.0) (3.5 g) was treated with a freshly prepared 100 mg/ml solution of CDAP in acetonitrile/water (50/50 (v/v)) to obtain a CDAP/MenC ratio of 1.5 (w/w). After 1.5 minutes, the pH was raised to pH 10.0. At activation pH 5M NaCl was added to achieve a final concentration of 2M NaCl. Three minutes later, ADH was added to obtain an ADH/MenC ratio of 8.9. The pH of the solution was decreased to 8.75 and the reaction proceeded for 2 hours (retained at 25° C.).

The PSC$_{AH}$ solution was concentrated to a minimum of 150 mL and then diafiltered with 30 volumes of 0.2M NaCl using a Filtron Omega membrane with a cut-off of 10 kDa, and the retentate was filtered.

Prior to the conjugation reaction, the purified TT solution and the PSC$_{AH}$ solution (2 g scale) were diluted in 0.2M NaCl to reach a concentration of 15 mg/ml for PSC$_{AH}$ and 20 mg/ml for TT.

The purified tetanus toxoid was added to the PSC$_{AH}$ solution in order to reach 2 mg TT/mg PSC$_{AH}$. The pH was adjusted to 5.0. EDAC (16.7 mg/ml in Tris 0.1M pH 7.5) was added with a peristaltic pump (in 10 minutes) to reach a final ratio of 0.5 mg EDAC/mg PSC$_{AH}$. The resulting solution was left 110 min at +25° C. under stirring and pH regulation to obtain a final coupling time of 120 min. The solution was then neutralized by addition of 1M Tris-Hcl pH 9.0 (1/10 of final volume) and left 30 minutes at +25° C. then overnight at +2° C. to +8° C.

The conjugate was clarified using a 10 μm filter and was purified using a SEPHACRYL® S400HR column (Pharmacia, Sweden). The column was equilibrated in 10 mM Tris-HCl (pH 7.0), 0.075 M NaCl and the conjugate (approx. 460 mL) was loaded on the column (+2° C. to +8° C.). The elution pool was selected as a function of optical density at 280 nm. Collection started when absorbance increased to 0.05. Harvest continued until the Kd reached 0.20. The conjugate was filter sterilised at +20° C., then stored at +2° C. to +8° C. The resultant conjugate had a polysaccharide:protein ratio of 1:2-1:4 (w/w).

Various experiments adding EDAC over 10-45 minutes were carried out—in each case good quality MenC conjugates resulted. If, however the TT carrier was added last slowly to the MenC-ADH+EDAC mix this led to a gel—a conjugate that could not be purified.

Experiments were also carried out adding the EDAC all at once into the reaction but the final TT/PS ratio (2.7/1) (w/w) of the conjugate was lower than for the conjugate obtained via the reaction where EDAC was added over 10 minutes (3.3/1); furthermore the αTT and aPS antigenicity were both lower than that measured in respect of the conjugate made by the reaction where EDAC was added over 10 minutes.

Note on Approximate % Derivatisation of the Polysaccharides

MenCAH: after CDAP treatment with ADH about 3.47% of hydroxyl groups were derivatized with ADH (with an estimation of two available hydroxyl groups per repeat subunit). For MenA: about 11.5% of hydroxyl groups derivatized with ADH (considering there is only one available hydroxyl group per repeat unit).

Example 2

Determination of Molecular Weight Using MALLS

Detectors were coupled to a HPLC size exclusion column from which the samples were eluted. On one hand, the laser light scattering detector measured the light intensities scattered at 16 angles by the macromolecular solution and on the other hand, an interferometric refractometer placed on-line allowed the determination of the quantity of sample eluted. From these intensities, the size and shape of the macromolecules in solution can be determined.

The mean molecular weight in weight (M$_w$) is defined as the sum of the weights of all the species multiplied by their respective molecular weight and divided by the sum of weights of all the species.

a) Weight-average molecular weight: -Mw- $$M_w = \frac{\sum W_i \cdot M_i}{\sum W_i} = \frac{m_2}{m_1}$$

b) Number-average molecular weight: -Mn- $$M_n = \frac{\sum N_i \cdot M_i}{\sum N_i} = \frac{m_1}{m_0}$$

c) Root mean square radius: -Rw- and R$^2$w is the square radius defined by:

$$R^2 w \text{ or } (r^2)w = \frac{\sum m_i \cdot r_i^2}{\sum m_i}$$

(-m$_i$- is the mass of a scattering centre i and -r$_i$- is the distance between the
scattering centre i and the center of gravity of the macromolecule).

d) The polydispersity is defined as the ratio -Mw/Mn-.

Meningococcal polysaccharides were analysed by MALLS by loading onto two HPLC columns (TSKG6000 and 5000PWxl) used in combination. 250 of the polysaccharide were loaded onto the column and was eluted with 0.75 ml of filtered water. The polyaccharides are detected using a light scattering detector (Wyatt Dawn DSP equipped with a 10 mW argon laser at 488 nm) and an inferometric refractometer (Wyatt Otilab DSP equipped with a P100 cell and a red filter at 498 nm).

The molecular weight polydispersities and recoveries of all samples were calculated by the Debye method using a polynomial fit order of 1 in the Astra 4.72 software.

Example 3

Immunogenicity of *S. aureus* PS8-TT and dPNAG-TT Conjugates

Groups of 30 mice were inoculated subcutaneously with *S. aureus* PS8-TT conjugate at a saccharide dose of 3 μg, either unadjuvanted or combined with adjuvant A, on days 0, 14, 28 and 42. On day 0, the mice received a first saccharide dose including between 0.001 and 0.013 μg. The further three immunisations were done with a dose of 0.3 μg in saline. On day 55 serum was collected from the mice and each serum sample was tested by ELISA to assess the immune response against PS8. Groups of 10 mice were used in the control groups and these were inoculated with either saline or saline containing adjuvant A.

The purified PS8 was coated at 2 μg/ml in phosphate buffered saline (PBS) on high binding microtitre plates (Nunc Maxisorp) overnight at 4° C. The plates were blocked with PBS-BSA 1% for 30 min at room temperature with agitation. The mice antisera were prediluted 1/100, then further twofold dilutions were made in microplates which were incubated at 37° C. for 1 hour. After washing, bound murine antibody was detected using Jackson ImmunoLaboratories Inc. peroxidase-conjugated affiniPure Goat Anti-Mouse IgG (H+L) (ref: 115-035-003) diluted 1:5000 in PBS-TWEEN® 0.05%. The detection antibodies were incubated for 30 minutes at room temperature with agitation. The color was developed using 4 mg OPD (Sigma)+5 µl H2O2 per 10 ml pH 4.5 0.1M citrate buffer for 15 minutes in the dark at room temperature. The reaction was stopped with 50 µl HCl, and the optical density was read at 490 nm relative to 650 nm.

The results were expressed in mid-point titers and the GMT was calculated for the 30 samples (10 for controls). The results are shown in Table 14 below.

TABLE 14

| Conjugate | Anti-PS8 titre (GMT) nonadsorbed | Anti-PS8 titre (GMT) Adjuvant A |
| --- | --- | --- |
| SA08-TT011 | 4714 | 2109 |
| SA08-TT015 | 2806 | 5631 |

TABLE 14-continued

| Conjugate | Anti-PS8 titre (GMT) nonadsorbed | Anti-PS8 titre (GMT) Adjuvant A |
| --- | --- | --- |
| SA08-TT017 | 3770 | 4396 |
| SA08-TT018 | 5349 | 4748 |
| Control | 50 | 50 |

Groups of 30 mice were inoculated subcutaneously with *S. aureus* dPNAG-TT conjugates (containing dPNAG which was between 10% and 30% N-acetylated) at a saccharide dose of 0.3 µg in 200 mM NaCl, either unadjuvanted or combined with adjuvant A. The mice received three inoculations on days 0, 14 and 28. On day 41 or 42 serum was collected from the mice and each serum sample was tested by ELISA to assess the immune response against PNAG. Groups of 10 mice were used in the control groups and these were inoculated with saline or with adjuvant alone.

The invention claimed is:

1. A method of making an immunogenic composition comprising a conjugation step of conjugating a saccharide to a protein carrier to make a saccharide-protein conjugate using carbodiimide condensation chemistry, wherein the saccharide comprises, or has been derivatised to comprise, amino and/or carboxyl groups, and wherein the protein carrier comprises, or has been derivatised to comprise, amino and/or carboxyl groups, comprising the steps of:

I) if the protein carrier comprises both amino and carboxyl groups and the saccharide comprises either amino or carboxyl groups:
 a) mixing the saccharide and aliquot of carbodiimide required to perform the conjugation, and
 b) adding aliquot of the protein carrier required over a time period of 35 seconds to 6 hours to form a saccharide-protein conjugate;

II) if the saccharide comprises both amino and carboxyl groups and the protein carrier comprises either amino or carboxyl groups:
 a) mixing the protein carrier and aliquot of carbodiimide required to perform the conjugation, and
 b) adding aliquot of saccharide required over a time period of 10 minutes to 4 hours to form a saccharide-protein conjugate; and III) if the saccharide comprises both amino and carboxyl groups and the protein carrier comprises both amino and carboxyl groups:
 a) mixing the protein carrier and the saccharide, and
 b) adding aliquot of carbodiimide required to perform the conjugation over a time period of 35 seconds to 6 hours to form a saccharide-protein conjugate;
and a further step of mixing the saccharide-protein conjugate of I), II), or III) with a staphylococcal antigen.

2. The method of claim 1, wherein the carbodiimide is EDAC (1-ethyl-3-(3-dimethyl-aminopropyl)carbodiimide).

3. The method of claim 1, wherein the saccharide and/or the protein carrier has been derivatised to comprise the amino or the carboxyl groups.

4. The method of claim 1, wherein in step b) the aliquot of the carbodiimide, the aliquot of the saccharide or the aliquot of the protein carrier is added at a constant rate using a pump.

5. The method of claim 1, wherein in step b) the aliquot of carbodiimide, the aliquot of saccharide or the aliquot of protein carrier is added in stages over the time period.

6. The method of claim 5, wherein at least one quarter of the aliquot is added over the first half of the time period, and at least one quarter of the aliquot over the second half of the time period.

7. The method of claim 5, wherein the aliquot is added in 4-100 stages.

8. The method of claim 7, wherein if one of the stages takes place at time zero of the time period, each subsequent stage takes place at a time period which is evenly spaced throughout the time period.

* * * * *

SEQUENCE LISTING

```
<160> NUMBER OF SEQ ID NOS: 102

<210> SEQ ID NO 1
<211> LENGTH: 533
<212> TYPE: PRT
<213> ORGANISM: S. aureus

<400> SEQUENCE: 1

Met Leu Gln Val Thr Asp Val Ser Leu Arg Phe Gly Asp Arg Lys Leu
1               5                   10                  15

Phe Glu Asp Val Asn Ile Lys Phe Thr Glu Gly Asn Cys Tyr Gly Leu
            20                  25                  30

Ile Gly Ala Asn Gly Ala Gly Lys Ser Thr Phe Leu Lys Ile Leu Ser
        35                  40                  45

Gly Glu Leu Asp Ser Gln Thr Gly His Val Ser Leu Gly Lys Asn Glu
    50                  55                  60

Arg Leu Ala Val Leu Lys Gln Asp His Tyr Ala Tyr Glu Asp Glu Arg
65                  70                  75                  80

Val Leu Asp Val Val Ile Lys Gly His Glu Arg Leu Tyr Glu Val Met
                85                  90                  95

Lys Glu Lys Asp Glu Ile Tyr Met Lys Pro Asp Phe Ser Asp Glu Asp
            100                 105                 110

Gly Ile Arg Ala Ala Glu Leu Glu Gly Glu Phe Ala Glu Met Asn Gly
        115                 120                 125

Trp Asn Ala Glu Ala Asp Ala Ala Asn Leu Leu Ser Gly Leu Gly Ile
    130                 135                 140

Asp Pro Thr Leu His Asp Lys Lys Met Ala Glu Leu Glu Asn Asn Gln
145                 150                 155                 160

Lys Ile Lys Val Leu Leu Ala Gln Ser Leu Phe Gly Glu Pro Asp Val
                165                 170                 175

Leu Leu Leu Asp Glu Pro Thr Asn Gly Leu Asp Ile Pro Ala Ile Ser
            180                 185                 190

Trp Leu Glu Asp Phe Leu Ile Asn Phe Asp Asn Thr Val Ile Val Val
        195                 200                 205

Ser His Asp Arg His Phe Leu Asn Asn Val Cys Thr His Ile Ala Asp
    210                 215                 220

Leu Asp Phe Gly Lys Ile Lys Val Tyr Val Gly Asn Tyr Asp Phe Trp
```

```
            225                 230                 235                 240
        Tyr Gln Ser Ser Gln Leu Ala Gln Lys Met Ala Gln Glu Gln Asn Lys
                        245                 250                 255
        Lys Lys Glu Glu Lys Met Lys Glu Leu Gln Asp Phe Ile Ala Arg Phe
                        260                 265                 270
        Ser Ala Asn Ala Ser Lys Ser Lys Gln Ala Thr Ser Arg Lys Lys Gln
                        275                 280                 285
        Leu Glu Lys Ile Glu Leu Asp Asp Ile Gln Pro Ser Ser Arg Arg Tyr
                290                 295                 300
        Pro Phe Val Lys Phe Thr Pro Glu Arg Glu Ile Gly Asn Asp Leu Leu
        305                 310                 315                 320
        Ile Val Gln Asn Leu Ser Lys Thr Ile Asp Gly Lys Val Leu Asp
                        325                 330                 335
        Asn Val Ser Phe Thr Met Asn Pro Asn Asp Lys Ala Ile Leu Ile Gly
                        340                 345                 350
        Asp Ser Glu Ile Ala Lys Thr Thr Leu Leu Lys Ile Leu Ala Gly Glu
                        355                 360                 365
        Met Glu Pro Asp Glu Gly Ser Phe Lys Trp Gly Val Thr Thr Ser Leu
                370                 375                 380
        Ser Tyr Phe Pro Lys Asp Asn Ser Glu Phe Phe Glu Gly Val Asn Met
        385                 390                 395                 400
        Asn Leu Val Asp Trp Leu Arg Gln Tyr Ala Pro Glu Asp Glu Gln Thr
                        405                 410                 415
        Glu Thr Phe Leu Arg Gly Phe Leu Gly Arg Met Leu Phe Ser Gly Glu
                        420                 425                 430
        Glu Val Lys Lys Lys Ala Ser Val Leu Ser Gly Gly Glu Lys Val Arg
                        435                 440                 445
        Cys Met Leu Ser Lys Met Met Leu Ser Ser Ala Asn Val Leu Leu Leu
                        450                 455                 460
        Asp Glu Pro Thr Asn His Leu Asp Leu Glu Ser Ile Thr Ala Val Asn
        465                 470                 475                 480
        Asp Gly Leu Lys Ser Phe Lys Gly Ser Ile Ile Phe Thr Ser Tyr Asp
                        485                 490                 495
        Phe Glu Phe Ile Asn Thr Ile Ala Asn Arg Val Ile Asp Leu Asn Lys
                        500                 505                 510
        Gln Gly Gly Val Ser Lys Glu Ile Pro Tyr Glu Glu Tyr Leu Gln Glu
                        515                 520                 525
        Ile Gly Val Leu Lys
                530

<210> SEQ ID NO 2
<211> LENGTH: 535
<212> TYPE: PRT
<213> ORGANISM: S. epidermidis

<400> SEQUENCE: 2

Met Leu Gln Val Thr Asp Val Ser Leu Arg Phe Gly Asp Arg Lys Leu
        1               5                   10                  15
        Phe Glu Asp Val Asn Ile Lys Phe Thr Glu Gly Asn Cys Tyr Gly Leu
                        20                  25                  30
        Ile Gly Ala Asn Gly Ala Gly Lys Ser Thr Phe Leu Lys Ile Leu Ser
                        35                  40                  45
        Gly Glu Ile Asp Ser Gln Thr Gly His Val Ser Leu Gly Lys Asp Glu
                50                  55                  60
```

-continued

```
Arg Leu Ala Val Leu Lys Gln Asp His Phe Ala Tyr Glu Asp Glu Arg
 65                  70                  75                  80

Val Leu Asp Val Val Ile Lys Gly His Glu Arg Leu Tyr Gln Val Met
                 85                  90                  95

Lys Glu Lys Asp Glu Ile Tyr Met Lys Pro Asp Phe Ser Asp Glu Asp
            100                 105                 110

Gly Ile Arg Ala Ala Glu Leu Glu Gly Glu Phe Ala Glu Met Asn Gly
        115                 120                 125

Trp Asn Ala Glu Ala Asp Ala Ala Asn Leu Leu Ser Gly Leu Gly Ile
130                 135                 140

Glu Pro Asp Leu His Asp Lys Asn Met Ser Glu Leu Glu Asn Asn Gln
145                 150                 155                 160

Lys Val Lys Val Leu Leu Ala Gln Ser Leu Phe Gly Asp Pro Asp Val
                165                 170                 175

Leu Leu Leu Asp Glu Pro Thr Asn Gly Leu Asp Ile Pro Ala Ile Ser
            180                 185                 190

Trp Leu Glu Asp Phe Leu Ile Asn Phe Glu Asn Thr Val Ile Val Val
        195                 200                 205

Ser His Asp Arg His Phe Leu Asn Asn Val Cys Thr His Ile Ala Asp
210                 215                 220

Leu Asp Phe Gly Lys Ile Lys Leu Tyr Val Gly Asn Tyr Asp Phe Trp
225                 230                 235                 240

Tyr Gln Ser Ser Gln Leu Ala Gln Lys Met Ala Gln Glu Gln Asn Lys
                245                 250                 255

Lys Lys Glu Glu Lys Met Lys Glu Leu Gln Asp Phe Ile Ala Arg Phe
            260                 265                 270

Ser Ala Asn Ala Ser Lys Ser Lys Gln Ala Thr Ser Arg Lys Lys Gln
        275                 280                 285

Leu Glu Lys Ile Glu Leu Asp Asp Ile Gln Pro Ser Ser Arg Arg Tyr
290                 295                 300

Pro Tyr Val Lys Phe Thr Pro Glu Arg Glu Ile Gly Asn Asp Leu Leu
305                 310                 315                 320

Thr Val Glu Asn Leu Ser Lys Thr Ile Asp Gly Glu Lys Val Leu Asp
                325                 330                 335

Asn Val Ser Phe Thr Met Asn Pro Asn Asp Lys Ala Ile Leu Val Gly
            340                 345                 350

Asp Ser Glu Ile Ala Lys Thr Thr Leu Leu Lys Ile Leu Ala Gly Glu
        355                 360                 365

Met Glu Pro Asp Glu Gly Thr Phe Lys Trp Gly Val Thr Thr Ser Leu
370                 375                 380

Ser Tyr Phe Pro Lys Asp Asn Ser Glu Phe Phe Asp Gly Val Asp Met
385                 390                 395                 400

Asn Leu Val Glu Trp Leu Arg Gln Tyr Ala Pro Glu Asp Glu Gln Thr
                405                 410                 415

Glu Thr Phe Leu Arg Gly Phe Leu Gly Arg Met Leu Phe Ser Gly Glu
            420                 425                 430

Glu Val Lys Lys Lys Ala Ser Val Leu Ser Gly Gly Glu Lys Val Arg
        435                 440                 445

Cys Met Leu Ser Lys Met Met Leu Ser Ser Ala Asn Val Leu Leu Leu
450                 455                 460

Asp Glu Pro Thr Asn His Leu Asp Leu Glu Ser Ile Thr Ala Val Asn
465                 470                 475                 480

Asp Gly Leu Lys Ser Phe Lys Gly Ser Ile Ile Phe Thr Ser Tyr Asp
```

```
                         485                 490                 495
Phe Glu Phe Ile Asn Thr Ile Ala Asn Arg Val Ile Asp Leu Asn Gln
                500                 505                 510

Ala Gly Ala Leu Ser Lys Glu Val Pro Tyr Glu Glu Tyr Leu Gln Glu
            515                 520                 525

Ile Gly Val Leu Gln Asn Asn
        530                 535

<210> SEQ ID NO 3
<211> LENGTH: 434
<212> TYPE: PRT
<213> ORGANISM: S. aureus

<400> SEQUENCE: 3

Met Pro Ile Ile Thr Asp Val Tyr Ala Arg Glu Val Leu Asp Ser Arg
 1               5                  10                  15

Gly Asn Pro Thr Val Glu Val Glu Val Leu Thr Glu Ser Gly Ala Phe
                20                  25                  30

Gly Arg Ala Leu Val Pro Ser Gly Ala Ser Thr Gly Glu His Glu Ala
            35                  40                  45

Val Glu Leu Arg Asp Gly Asp Lys Ser Arg Tyr Leu Gly Lys Gly Val
        50                  55                  60

Thr Lys Ala Val Glu Asn Val Asn Glu Ile Ile Ala Pro Glu Ile Ile
65                  70                  75                  80

Glu Gly Glu Phe Ser Val Leu Asp Gln Val Ser Ile Asp Lys Met Met
                85                  90                  95

Ile Ala Leu Asp Gly Thr Pro Asn Lys Gly Lys Leu Gly Ala Asn Ala
            100                 105                 110

Ile Leu Gly Val Ser Ile Ala Val Ala Arg Ala Ala Ala Asp Leu Leu
        115                 120                 125

Gly Gln Pro Leu Tyr Lys Tyr Leu Gly Gly Phe Asn Gly Lys Gln Leu
    130                 135                 140

Pro Val Pro Met Met Asn Ile Val Asn Gly Gly Ser His Ser Asp Ala
145                 150                 155                 160

Pro Ile Ala Phe Gln Glu Phe Met Ile Leu Pro Val Gly Ala Thr Thr
                165                 170                 175

Phe Lys Glu Ser Leu Arg Trp Gly Thr Glu Ile Phe His Asn Leu Lys
            180                 185                 190

Ser Ile Leu Ser Lys Arg Gly Leu Glu Thr Ala Val Gly Asp Glu Gly
        195                 200                 205

Gly Phe Ala Pro Lys Phe Glu Gly Thr Glu Asp Ala Val Glu Thr Ile
    210                 215                 220

Ile Gln Ala Ile Glu Ala Ala Gly Tyr Lys Pro Gly Glu Glu Val Phe
225                 230                 235                 240

Leu Gly Phe Asp Cys Ala Ser Ser Glu Phe Tyr Glu Asn Gly Val Tyr
                245                 250                 255

Asp Tyr Ser Lys Phe Glu Gly Glu His Gly Ala Lys Arg Thr Ala Ala
            260                 265                 270

Glu Gln Val Asp Tyr Leu Glu Gln Leu Val Asp Lys Tyr Pro Ile Ile
        275                 280                 285

Thr Ile Glu Asp Gly Met Asp Glu Asn Asp Trp Asp Gly Trp Lys Gln
    290                 295                 300

Leu Thr Glu Arg Ile Gly Asp Arg Val Gln Leu Val Gly Asp Asp Leu
305                 310                 315                 320
```

-continued

```
Phe Val Thr Asn Thr Glu Ile Leu Ala Lys Gly Ile Glu Asn Gly Ile
                325                 330                 335

Gly Asn Ser Ile Leu Ile Lys Val Asn Gln Ile Gly Thr Leu Thr Glu
            340                 345                 350

Thr Phe Asp Ala Ile Glu Met Ala Gln Lys Ala Gly Tyr Thr Ala Val
        355                 360                 365

Val Ser His Arg Ser Gly Glu Thr Glu Asp Thr Thr Ile Ala Asp Ile
    370                 375                 380

Ala Val Ala Thr Asn Ala Gly Gln Ile Lys Thr Gly Ser Leu Ser Arg
385                 390                 395                 400

Thr Asp Arg Ile Ala Lys Tyr Asn Gln Leu Leu Arg Ile Glu Asp Glu
                405                 410                 415

Leu Phe Glu Thr Ala Lys Tyr Asp Gly Ile Lys Ser Phe Tyr Asn Leu
            420                 425                 430

Asp Lys

<210> SEQ ID NO 4
<211> LENGTH: 434
<212> TYPE: PRT
<213> ORGANISM: S. epidermidis

<400> SEQUENCE: 4

Met Pro Ile Ile Thr Asp Val Tyr Ala Arg Glu Val Leu Asp Ser Arg
1               5                   10                  15

Gly Asn Pro Thr Val Glu Val Glu Val Leu Thr Glu Ser Gly Ala Phe
            20                  25                  30

Gly Arg Ala Leu Val Pro Ser Gly Ala Ser Thr Gly Glu His Glu Ala
        35                  40                  45

Val Glu Leu Arg Asp Gly Asp Lys Ser Arg Tyr Leu Gly Lys Gly Val
    50                  55                  60

Thr Lys Ala Val Glu Asn Val Asn Glu Met Ile Ala Pro Glu Ile Val
65                  70                  75                  80

Glu Gly Glu Phe Ser Val Leu Asp Gln Val Ser Ile Asp Lys Met Met
                85                  90                  95

Ile Gln Leu Asp Gly Thr His Asn Lys Gly Lys Leu Gly Ala Asn Ala
            100                 105                 110

Ile Leu Gly Val Ser Ile Ala Val Ala Arg Ala Ala Ala Asp Leu Leu
        115                 120                 125

Gly Gln Pro Leu Tyr Lys Tyr Leu Gly Gly Phe Asn Gly Lys Gln Leu
    130                 135                 140

Pro Val Pro Met Met Asn Ile Val Asn Gly Gly Ser His Ser Asp Ala
145                 150                 155                 160

Pro Ile Ala Phe Gln Glu Phe Met Ile Leu Pro Val Gly Ala Glu Ser
                165                 170                 175

Phe Lys Glu Ser Leu Arg Trp Gly Ala Glu Ile Phe His Asn Leu Lys
            180                 185                 190

Ser Ile Leu Ser Glu Arg Gly Leu Glu Thr Ala Val Gly Asp Glu Gly
        195                 200                 205

Gly Phe Ala Pro Arg Phe Glu Gly Thr Glu Asp Ala Val Glu Thr Ile
    210                 215                 220

Ile Lys Ala Ile Glu Lys Ala Gly Tyr Lys Pro Gly Glu Asp Val Phe
225                 230                 235                 240

Leu Gly Phe Asp Cys Ala Ser Ser Glu Phe Tyr Glu Asn Gly Val Tyr
                245                 250                 255
```

```
Asp Tyr Thr Lys Phe Glu Gly Glu His Gly Ala Lys Arg Ser Ala Ala
                260                 265                 270

Glu Gln Val Asp Tyr Leu Glu Glu Leu Ile Gly Lys Tyr Pro Ile Ile
            275                 280                 285

Thr Ile Glu Asp Gly Met Asp Glu Asn Asp Trp Glu Gly Trp Lys Gln
        290                 295                 300

Leu Thr Asp Arg Ile Gly Asp Lys Val Gln Leu Val Gly Asp Asp Leu
305                 310                 315                 320

Phe Val Thr Asn Thr Glu Ile Leu Ser Lys Gly Ile Glu Gln Gly Ile
                325                 330                 335

Gly Asn Ser Ile Leu Ile Lys Val Asn Gln Ile Gly Thr Leu Thr Glu
            340                 345                 350

Thr Phe Asp Ala Ile Glu Met Ala Gln Lys Ala Gly Tyr Thr Ala Val
        355                 360                 365

Val Ser His Arg Ser Gly Glu Thr Glu Asp Thr Thr Ile Ala Asp Ile
        370                 375                 380

Ala Val Ala Thr Asn Ala Gly Gln Ile Lys Thr Gly Ser Leu Ser Arg
385                 390                 395                 400

Thr Asp Arg Ile Ala Lys Tyr Asn Gln Leu Leu Arg Ile Glu Asp Glu
                405                 410                 415

Leu Tyr Glu Thr Ala Lys Phe Glu Gly Ile Lys Ser Phe Tyr Asn Leu
            420                 425                 430

Asp Lys

<210> SEQ ID NO 5
<211> LENGTH: 255
<212> TYPE: PRT
<213> ORGANISM: S. aureus

<400> SEQUENCE: 5

Met Lys Lys Ile Val Thr Ala Thr Ile Ala Thr Ala Gly Leu Ala Thr
1               5                   10                  15

Ile Ala Phe Ala Gly His Asp Ala Gln Ala Ala Glu Gln Asn Asn Asn
            20                  25                  30

Gly Tyr Asn Ser Asn Asp Ala Gln Ser Tyr Ser Tyr Thr Tyr Thr Ile
        35                  40                  45

Asp Ala Gln Gly Asn Tyr His Tyr Thr Trp Thr Gly Asn Trp Asn Pro
    50                  55                  60

Ser Gln Leu Thr Gln Asn Asn Thr Tyr Tyr Asn Asn Tyr Asn Thr
65                  70                  75                  80

Tyr Ser Tyr Asn Asn Ala Ser Tyr Asn Tyr Asn His Ser Tyr
                85                  90                  95

Gln Tyr Asn Asn Tyr Thr Asn Asn Ser Gln Thr Ala Thr Asn Asn Tyr
            100                 105                 110

Tyr Thr Gly Gly Ser Gly Ala Ser Tyr Ser Thr Thr Ser Asn Asn Val
        115                 120                 125

His Val Thr Thr Thr Ala Ala Pro Ser Ser Asn Gly Arg Ser Ile Ser
    130                 135                 140

Asn Gly Tyr Ala Ser Gly Ser Asn Leu Tyr Thr Ser Gly Gln Cys Thr
145                 150                 155                 160

Tyr Tyr Val Phe Asp Arg Val Gly Gly Lys Ile Gly Ser Thr Trp Gly
                165                 170                 175

Asn Ala Ser Asn Trp Ala Asn Ala Ala Ser Ser Gly Tyr Thr Val
            180                 185                 190
```

```
Asn Asn Thr Pro Lys Val Gly Ala Ile Met Gln Thr Gln Gly Tyr
            195                 200                 205

Tyr Gly His Val Ala Tyr Val Glu Gly Val Asn Ser Asn Gly Ser Val
210                 215                 220

Arg Val Ser Glu Met Asn Tyr Gly His Gly Ala Gly Val Val Thr Ser
225                 230                 235                 240

Arg Thr Ile Ser Ala Asn Gln Ala Gly Ser Tyr Asn Phe Ile His
            245                 250                 255
```

```
<210> SEQ ID NO 6
<211> LENGTH: 267
<212> TYPE: PRT
<213> ORGANISM: S. aureus

<400> SEQUENCE: 6

Met Lys Lys Ile Ala Thr Ala Thr Ile Ala Thr Ala Gly Phe Ala Thr
1               5                   10                  15

Ile Ala Ile Ala Ser Gly Asn Gln Ala His Ala Ser Glu Gln Asp Asn
                20                  25                  30

Tyr Gly Tyr Asn Pro Asn Asp Pro Thr Ser Tyr Ser Tyr Thr Tyr Thr
            35                  40                  45

Ile Asp Ala Gln Gly Asn Tyr His Tyr Thr Trp Lys Gly Asn Trp His
50                  55                  60

Pro Ser Gln Leu Asn Gln Asp Asn Gly Tyr Tyr Ser Tyr Tyr Tyr Tyr
65                  70                  75                  80

Asn Gly Tyr Asn Asn Tyr Asn Asn Tyr Asn Asn Gly Tyr Ser Tyr Asn
                85                  90                  95

Asn Tyr Ser Arg Tyr Asn Asn Tyr Ser Asn Asn Asn Gln Ser Tyr Asn
            100                 105                 110

Tyr Asn Asn Tyr Asn Ser Tyr Asn Thr Asn Ser Tyr Arg Thr Gly Gly
        115                 120                 125

Leu Gly Ala Ser Tyr Ser Thr Ser Ser Asn Asn Val Gln Val Thr Thr
130                 135                 140

Thr Met Ala Pro Ser Ser Asn Gly Arg Ser Ile Ser Ser Gly Tyr Thr
145                 150                 155                 160

Ser Gly Arg Asn Leu Tyr Thr Ser Gly Gln Cys Thr Tyr Tyr Val Phe
                165                 170                 175

Asp Arg Val Gly Gly Lys Ile Gly Ser Thr Trp Gly Asn Ala Ser Asn
            180                 185                 190

Trp Ala Asn Ala Ala Arg Ala Gly Tyr Thr Val Asn Asn Thr Pro
        195                 200                 205

Lys Ala Gly Ala Ile Met Gln Thr Thr Gln Gly Ala Tyr Gly His Val
210                 215                 220

Ala Tyr Val Glu Ser Val Asn Ser Asn Gly Ser Val Arg Val Ser Glu
225                 230                 235                 240

Met Asn Tyr Gly Tyr Gly Pro Gly Val Val Thr Ser Arg Thr Ile Ser
                245                 250                 255

Ala Ser Gln Ala Ala Gly Tyr Asn Phe Ile His
            260                 265
```

```
<210> SEQ ID NO 7
<211> LENGTH: 257
<212> TYPE: PRT
<213> ORGANISM: S. epidermidis

<400> SEQUENCE: 7
```

Met Lys Lys Ile Ala Thr Ala Thr Ile Ala Thr Ala Gly Ile Ala Thr
1               5                   10                  15

Phe Ala Phe Ala His His Asp Ala Gln Ala Ala Glu Gln Asn Asn Asp
            20                  25                  30

Gly Tyr Asn Pro Asn Asp Pro Tyr Ser Tyr Ser Tyr Thr Tyr Thr Ile
        35                  40                  45

Asp Ala Glu Gly Asn Tyr His Tyr Thr Trp Lys Gly Asn Trp Ser Pro
50                      55                  60

Asp Arg Val Asn Thr Ser Tyr Asn Tyr Asn Asn Tyr Asn Asn Tyr Asn
65                  70                  75                  80

Tyr Tyr Gly Tyr Asn Asn Tyr Ser Asn Tyr Asn Tyr Ser Asn Tyr
                85                  90                  95

Asn Asn Tyr Asn Asn Tyr Gln Ser Asn Asn Thr Gln Ser Gln Arg Thr
            100                 105                 110

Thr Gln Pro Thr Gly Gly Leu Gly Ala Ser Tyr Ser Thr Ser Ser Ser
            115                 120                 125

Asn Val His Val Thr Thr Thr Ser Ala Pro Ser Ser Asn Gly Val Ser
            130                 135                 140

Leu Ser Asn Ala Arg Ser Ala Ser Gly Asn Leu Tyr Thr Ser Gly Gln
145                 150                 155                 160

Cys Thr Tyr Tyr Val Phe Asp Arg Val Gly Gly Lys Ile Gly Ser Thr
                165                 170                 175

Trp Gly Asn Ala Asn Asn Trp Ala Asn Ala Ala Ala Arg Ser Gly Tyr
            180                 185                 190

Thr Val Asn Asn Ser Pro Ala Lys Gly Ala Ile Leu Gln Thr Ser Gln
            195                 200                 205

Gly Ala Tyr Gly His Val Ala Tyr Val Glu Gly Val Asn Ser Asn Gly
            210                 215                 220

Ser Ile Arg Val Ser Glu Met Asn Tyr Gly His Gly Ala Gly Val Val
225                 230                 235                 240

Thr Ser Arg Thr Ile Ser Ala Ser Gln Ala Ala Ser Tyr Asn Tyr Ile
                245                 250                 255

His

<210> SEQ ID NO 8
<211> LENGTH: 309
<212> TYPE: PRT
<213> ORGANISM: S. aureus

<400> SEQUENCE: 8

Met Lys Lys Leu Val Pro Leu Leu Leu Ala Leu Leu Leu Leu Val Ala
1               5                   10                  15

Ala Cys Gly Thr Gly Gly Lys Gln Ser Ser Asp Lys Ser Asn Gly Lys
            20                  25                  30

Leu Lys Val Val Thr Thr Asn Ser Ile Leu Tyr Asp Met Ala Lys Asn
        35                  40                  45

Val Gly Gly Asp Asn Val Asp Ile His Ser Ile Val Pro Val Gly Gln
50                  55                  60

Asp Pro His Glu Tyr Glu Val Lys Pro Lys Asp Ile Lys Lys Leu Thr
65                  70                  75                  80

Asp Ala Asp Val Ile Leu Tyr Asn Gly Leu Asn Leu Glu Thr Gly Asn
                85                  90                  95

Gly Trp Phe Glu Lys Ala Leu Glu Gln Ala Gly Lys Ser Leu Lys Asp
            100                 105                 110

```
Lys Lys Val Ile Ala Val Ser Lys Asp Val Lys Pro Ile Tyr Leu Asn
            115                 120                 125

Gly Glu Glu Gly Asn Lys Asp Lys Gln Asp Pro His Ala Trp Leu Ser
        130                 135                 140

Leu Asp Asn Gly Ile Lys Tyr Val Lys Thr Ile Gln Gln Thr Phe Ile
145                 150                 155                 160

Asp Asn Asp Lys Lys His Lys Ala Asp Tyr Glu Lys Gln Gly Asn Lys
                165                 170                 175

Tyr Ile Ala Gln Leu Glu Lys Leu Asn Asn Asp Ser Lys Asp Lys Phe
            180                 185                 190

Asn Asp Ile Pro Lys Glu Gln Arg Ala Met Ile Thr Ser Glu Gly Ala
        195                 200                 205

Phe Lys Tyr Phe Ser Lys Gln Tyr Gly Ile Thr Pro Gly Tyr Ile Trp
    210                 215                 220

Glu Ile Asn Thr Glu Lys Gln Gly Thr Pro Glu Gln Met Arg Gln Ala
225                 230                 235                 240

Ile Glu Phe Val Lys Lys His Lys Leu Lys His Leu Leu Val Glu Thr
                245                 250                 255

Ser Val Asp Lys Lys Ala Met Glu Ser Leu Ser Glu Glu Thr Lys Lys
            260                 265                 270

Asp Ile Phe Gly Glu Val Tyr Thr Asp Ser Ile Gly Lys Glu Gly Thr
        275                 280                 285

Lys Gly Asp Ser Tyr Tyr Lys Met Met Lys Ser Asn Ile Glu Thr Val
    290                 295                 300

His Gly Ser Met Lys
305

<210> SEQ ID NO 9
<211> LENGTH: 309
<212> TYPE: PRT
<213> ORGANISM: S. epidermidis

<400> SEQUENCE: 9

Met Lys Lys Ile Leu Ala Leu Ala Ile Ala Phe Leu Ile Ile Leu Ala
1               5                   10                  15

Ala Cys Gly Asn His Ser Asn His Glu His His Ser His Glu Gly Lys
            20                  25                  30

Leu Lys Val Val Thr Thr Asn Ser Ile Leu Tyr Asp Met Val Lys Arg
        35                  40                  45

Val Gly Gly Asn Lys Val Asp Val His Ser Ile Val Pro Val Gly Gln
    50                  55                  60

Asp Pro His Glu Tyr Glu Val Lys Pro Lys Asp Ile Lys Ala Leu Thr
65                  70                  75                  80

Asp Ala Asp Val Val Phe Tyr Asn Gly Leu Asn Leu Glu Thr Gly Asn
                85                  90                  95

Gly Trp Phe Glu Lys Ala Leu Asp Gln Ala Gly Lys Ser Thr Lys Asp
            100                 105                 110

Lys Asn Val Ile Ala Ala Ser Asn Asn Val Lys Pro Ile Tyr Leu Asn
        115                 120                 125

Gly Glu Glu Gly Asn Lys Asn Lys Gln Asp Pro His Ala Trp Leu Ser
    130                 135                 140

Leu Glu Asn Gly Ile Lys Tyr Val Lys Thr Ile Gln Lys Ser Leu Glu
145                 150                 155                 160

His His Asp Lys Lys Asp Lys Ser Thr Tyr Glu Lys Gln Gly Asn Ala
                165                 170                 175
```

```
Tyr Ile Ser Lys Leu Glu Glu Leu Asn Lys Asp Ser Lys Asn Lys Phe
        180                 185                 190

Asp Asp Ile Pro Lys Asn Gln Arg Ala Met Met Thr Ser Glu Gly Ala
            195                 200                 205

Phe Lys Tyr Phe Ala Gln Gln Phe Asp Val Lys Pro Gly Tyr Ile Trp
210                 215                 220

Glu Ile Asn Thr Glu Lys Gln Gly Thr Pro Gly Gln Met Lys Gln Ala
225                 230                 235                 240

Ile Lys Phe Val Lys Asp Asn His Leu Lys His Leu Leu Val Glu Thr
                245                 250                 255

Ser Val Asp Lys Lys Ala Met Gln Ser Leu Ser Glu Glu Thr Lys Lys
            260                 265                 270

Asp Ile Tyr Gly Glu Val Phe Thr Asp Ser Ile Gly Lys Glu Gly Thr
        275                 280                 285

Lys Gly Asp Ser Tyr Tyr Lys Met Met Lys Ser Asn Ile Asp Thr Ile
    290                 295                 300

His Gly Ser Met Lys
305

<210> SEQ ID NO 10
<211> LENGTH: 233
<212> TYPE: PRT
<213> ORGANISM: S. aureus

<400> SEQUENCE: 10

Met Lys Lys Thr Ile Met Ala Ser Ser Leu Ala Val Ala Leu Gly Val
  1               5                  10                  15

Thr Gly Tyr Ala Ala Gly Thr Gly His Gln Ala His Ala Ala Glu Val
             20                  25                  30

Asn Val Asp Gln Ala His Leu Val Asp Leu Ala His Asn His Gln Asp
         35                  40                  45

Gln Leu Asn Ala Ala Pro Ile Lys Asp Gly Ala Tyr Asp Ile His Phe
     50                  55                  60

Val Lys Asp Gly Phe Gln Tyr Asn Phe Thr Ser Asn Gly Thr Thr Trp
 65                  70                  75                  80

Ser Trp Ser Tyr Glu Ala Ala Asn Gly Gln Thr Ala Gly Phe Ser Asn
                 85                  90                  95

Val Ala Gly Ala Asp Tyr Thr Thr Ser Tyr Asn Gln Gly Ser Asp Val
            100                 105                 110

Gln Ser Val Ser Tyr Asn Ala Gln Ser Ser Asn Ser Val Glu Ala
        115                 120                 125

Val Ser Ala Pro Thr Tyr His Asn Tyr Ser Thr Ser Thr Ser Ser
    130                 135                 140

Ser Val Arg Leu Ser Asn Gly Asn Thr Ala Gly Ala Thr Gly Ser Ser
145                 150                 155                 160

Ala Ala Gln Ile Met Ala Gln Arg Thr Gly Val Ser Ala Ser Thr Trp
                165                 170                 175

Ala Ala Ile Ile Ala Arg Glu Ser Asn Gly Gln Val Asn Ala Tyr Asn
            180                 185                 190

Pro Ser Gly Ala Ser Gly Leu Phe Gln Thr Met Pro Gly Trp Gly Pro
        195                 200                 205

Thr Asn Thr Val Asp Gln Gln Ile Asn Ala Ala Val Lys Ala Tyr Lys
    210                 215                 220

Ala Gln Gly Leu Gly Ala Trp Gly Phe
```

```
                  225                 230

<210> SEQ ID NO 11
<211> LENGTH: 235
<212> TYPE: PRT
<213> ORGANISM: S. epidermidis

<400> SEQUENCE: 11

Met Lys Lys Thr Val Ile Ala Ser Thr Leu Ala Val Ser Leu Gly Ile
1               5                   10                  15

Ala Gly Tyr Gly Leu Ser Gly His Glu Ala His Ala Ser Glu Thr Thr
            20                  25                  30

Asn Val Asp Lys Ala His Leu Val Asp Leu Ala Gln His Asn Pro Glu
        35                  40                  45

Glu Leu Asn Ala Lys Pro Val Gln Ala Gly Ala Tyr Asp Ile His Phe
    50                  55                  60

Val Asp Asn Gly Tyr Gln Tyr Asn Phe Thr Ser Asn Gly Ser Glu Trp
65                  70                  75                  80

Ser Trp Ser Tyr Ala Val Ala Gly Ser Asp Ala Asp Tyr Thr Glu Ser
                85                  90                  95

Ser Ser Asn Gln Glu Val Ser Ala Asn Thr Gln Ser Ser Asn Thr Asn
            100                 105                 110

Val Gln Ala Val Ser Ala Pro Thr Ser Ser Glu Ser Arg Ser Tyr Ser
        115                 120                 125

Thr Ser Thr Thr Ser Tyr Ser Ala Pro Ser His Asn Tyr Ser Ser His
    130                 135                 140

Ser Ser Ser Val Arg Leu Ser Asn Gly Asn Thr Ala Gly Ser Val Gly
145                 150                 155                 160

Ser Tyr Ala Ala Ala Gln Met Ala Ala Arg Thr Gly Val Ser Ala Ser
                165                 170                 175

Thr Trp Glu His Ile Ile Ala Arg Glu Ser Asn Gly Gln Leu His Ala
            180                 185                 190

Arg Asn Ala Ser Gly Ala Ala Gly Leu Phe Gln Thr Met Pro Gly Trp
        195                 200                 205

Gly Ser Thr Gly Ser Val Asn Asp Gln Ile Asn Ala Ala Tyr Lys Ala
    210                 215                 220

Tyr Lys Ala Gln Gly Leu Ser Ala Trp Gly Met
225                 230                 235

<210> SEQ ID NO 12
<211> LENGTH: 3890
<212> TYPE: PRT
<213> ORGANISM: S. aureus

<400> SEQUENCE: 12

Met Asn Tyr Arg Asp Lys Ile Gln Lys Phe Ser Ile Arg Lys Tyr Thr
1               5                   10                  15

Val Gly Thr Phe Ser Thr Val Ile Ala Thr Leu Val Phe Leu Gly Phe
            20                  25                  30

Asn Thr Ser Gln Ala His Ala Ala Glu Thr Asn Gln Pro Ala Ser Val
        35                  40                  45

Val Lys Gln Lys Gln Ser Asn Asn Glu Gln Thr Glu Asn Arg Glu
    50                  55                  60

Ser Gln Val Gln Asn Ser Gln Asn Ser Gln Ser Gln Ser Leu Ser
65                  70                  75                  80

Ala Thr His Glu Asn Glu Gln Pro Asn Asn Ser Gln Ala Asn Leu Val
```

```
                              85                  90                  95
Asn Gln Lys Val Ala Gln Ser Ser Thr Thr Asn Asp Glu Gln Pro Ala
                100                 105                 110

Ser Gln Asn Val Asn Thr Lys Lys Asp Ser Ala Thr Ala Ala Thr Thr
            115                 120                 125

Gln Pro Asp Lys Glu Ser Lys His Lys Gln Asn Glu Ser Gln Ser
        130                 135                 140

Ala Asn Lys Asn Gly Asn Asp Asn Arg Ala Ala His Val Glu Asn His
145                 150                 155                 160

Glu Ala Asn Val Val Thr Ala Ser Asp Ser Asp Asn Gly Asn Val
                165                 170                 175

Gln His Asp Arg Asn Glu Leu Gln Ala Phe Phe Asp Ala Asn Tyr His
                180                 185                 190

Asp Tyr Arg Phe Ile Asp Arg Glu Asn Ala Asp Ser Gly Thr Phe Asn
            195                 200                 205

Tyr Val Lys Gly Ile Phe Asp Lys Ile Asn Thr Leu Leu Gly Ser Asn
        210                 215                 220

Asp Pro Ile Asn Asn Lys Asp Leu Gln Leu Ala Tyr Lys Glu Leu Glu
225                 230                 235                 240

Gln Ala Val Ala Leu Ile Arg Thr Met Pro Gln Arg Gln Thr Ser
                245                 250                 255

Arg Arg Ser Asn Arg Ile Gln Thr Arg Ser Val Glu Ser Arg Ala Ala
            260                 265                 270

Glu Pro Arg Ser Val Ser Asp Tyr Gln Asn Ala Asn Ser Ser Tyr Tyr
        275                 280                 285

Val Glu Asn Ala Asn Asp Gly Ser Gly Tyr Pro Val Gly Thr Tyr Ile
    290                 295                 300

Asn Ala Ser Ser Lys Gly Ala Pro Tyr Asn Leu Pro Thr Thr Pro Trp
305                 310                 315                 320

Asn Thr Leu Lys Ala Ser Asp Ser Lys Glu Ile Ala Leu Met Thr Ala
                325                 330                 335

Lys Gln Thr Gly Asp Gly Tyr Gln Trp Val Ile Lys Phe Asn Lys Gly
            340                 345                 350

His Ala Pro His Gln Asn Met Ile Phe Trp Phe Ala Leu Pro Ala Asp
        355                 360                 365

Gln Val Pro Val Gly Arg Thr Asp Phe Val Thr Val Asn Ser Asp Gly
    370                 375                 380

Thr Asn Val Gln Trp Ser His Gly Ala Gly Ala Gly Ala Asn Lys Pro
385                 390                 395                 400

Leu Gln Gln Met Trp Glu Tyr Gly Val Asn Asp Pro Asp Arg Ser His
                405                 410                 415

Asp Phe Lys Ile Arg Asn Arg Ser Gly Gln Val Ile Tyr Ser Trp Pro
            420                 425                 430

Thr Val His Val Tyr Ser Leu Glu Asp Leu Ser Arg Ala Ser Asp Tyr
        435                 440                 445

Phe Ser Glu Ala Gly Ala Thr Pro Ala Thr Lys Ala Phe Gly Arg Gln
    450                 455                 460

Asn Phe Glu Tyr Ile Asn Gly Gln Lys Pro Ala Glu Ser Pro Gly Val
465                 470                 475                 480

Pro Lys Val Tyr Thr Phe Ile Gly Gln Gly Asp Ala Ser Tyr Thr Ile
                485                 490                 495

Ser Phe Lys Thr Gln Gly Pro Thr Val Asn Lys Leu Tyr Tyr Ala Ala
            500                 505                 510
```

```
Gly Gly Arg Ala Leu Glu Tyr Asn Gln Leu Phe Met Tyr Ser Gln Leu
        515                 520                 525

Tyr Val Glu Ser Thr Gln Asp His Gln Gln Arg Leu Asn Gly Leu Arg
530                 535                 540

Gln Val Val Asn Arg Thr Tyr Arg Ile Gly Thr Thr Lys Arg Val Glu
545                 550                 555                 560

Val Ser Gln Gly Asn Val Gln Thr Lys Lys Val Leu Glu Ser Thr Asn
                565                 570                 575

Leu Asn Ile Asp Asp Phe Val Asp Asp Pro Leu Ser Tyr Val Lys Thr
                580                 585                 590

Pro Ser Asn Lys Val Leu Gly Phe Tyr Pro Thr Asn Ala Asn Thr Asn
        595                 600                 605

Ala Phe Arg Pro Gly Gly Val Gln Glu Leu Asn Glu Tyr Gln Leu Ser
610                 615                 620

Gln Leu Phe Thr Asp Gln Lys Leu Gln Glu Ala Ala Arg Thr Arg Asn
625                 630                 635                 640

Pro Ile Arg Leu Met Ile Gly Phe Asp Tyr Pro Asp Gly Tyr Gly Asn
                645                 650                 655

Ser Glu Thr Leu Val Pro Val Asn Leu Thr Val Leu Pro Glu Ile Gln
                660                 665                 670

His Asn Ile Lys Phe Phe Lys Asn Asp Asp Thr Gln Asn Ile Ala Glu
        675                 680                 685

Lys Pro Phe Ser Lys Gln Ala Gly His Pro Val Phe Tyr Val Tyr Ala
690                 695                 700

Gly Asn Gln Gly Asn Ala Ser Val Asn Leu Gly Ser Val Thr Ser
705                 710                 715                 720

Ile Gln Pro Leu Arg Ile Asn Leu Thr Ser Asn Glu Asn Phe Thr Asp
                725                 730                 735

Lys Asp Trp Gln Ile Thr Gly Ile Pro Arg Thr Leu His Ile Glu Asn
                740                 745                 750

Ser Thr Asn Arg Thr Asn Asn Ala Arg Glu Arg Asn Ile Glu Leu Val
        755                 760                 765

Gly Asn Leu Leu Pro Gly Asp Tyr Phe Gly Thr Ile Arg Phe Gly Arg
770                 775                 780

Lys Glu Gln Leu Phe Glu Ile Arg Val Lys Pro His Thr Pro Thr Ile
785                 790                 795                 800

Thr Thr Thr Ala Glu Gln Leu Arg Gly Thr Ala Leu Gln Lys Val Pro
                805                 810                 815

Val Asn Ile Ser Gly Ile Pro Leu Asp Pro Ser Ala Leu Val Tyr Leu
                820                 825                 830

Val Ala Pro Thr Asn Gln Thr Thr Asn Gly Gly Ser Glu Ala Asp Gln
        835                 840                 845

Ile Pro Ser Gly Tyr Thr Ile Leu Ala Thr Gly Thr Pro Asp Gly Val
850                 855                 860

His Asn Thr Ile Thr Ile Arg Pro Gln Asp Tyr Val Val Phe Ile Pro
865                 870                 875                 880

Pro Val Gly Lys Gln Ile Arg Ala Val Val Tyr Tyr Asn Lys Val Val
                885                 890                 895

Ala Ser Asn Met Ser Asn Ala Val Thr Ile Leu Pro Asp Asp Ile Pro
                900                 905                 910

Pro Thr Ile Asn Asn Pro Val Gly Ile Asn Ala Lys Tyr Tyr Arg Gly
        915                 920                 925
```

Asp Glu Val Asn Phe Thr Met Gly Val Ser Asp Arg His Ser Gly Ile
930                 935                 940

Lys Asn Thr Thr Ile Thr Thr Leu Pro Ser Gly Trp Thr Ser Asn Leu
945                 950                 955                 960

Thr Lys Ser Asp Asn Lys Asn Gly Ser Leu Ala Ile Thr Gly Arg Val
            965                 970                 975

Ser Met Asn Gln Ala Phe Asn Ser Asp Ile Thr Phe Lys Val Ser Ala
            980                 985                 990

Thr Asp Asn Val Asn Asn Thr Asn Asp Ser Gln Ser Lys His Val
            995                 1000                1005

Ser Ile His Val Gly Lys Ile Ser Glu Asp Ala His Pro Ile Val Leu
    1010                1015                1020

Gly Asn Thr Glu Lys Val Val Val Asn Pro Thr Ala Val Ser Asn
    1025                1030                1035                1040

Asp Glu Lys Gln Ser Ile Ile Thr Ala Phe Met Asn Lys Asn Gln Asn
                1045                1050                1055

Ile Arg Gly Tyr Leu Ala Ser Thr Asp Pro Val Thr Val Asp Asn Asn
                1060                1065                1070

Gly Asn Val Thr Leu His Tyr Arg Asp Gly Ser Ser Thr Thr Leu Asp
    1075                1080                1085

Ala Thr Asn Val Met Thr Tyr Glu Pro Val Val Lys Ser Glu Tyr Gln
    1090                1095                1100

Thr Ala Asn Ala Ala Lys Thr Ala Thr Val Thr Ile Ala Lys Gly Gln
1105                1110                1115                1120

Ser Phe Asn Ile Gly Asp Ile Lys Gln Tyr Phe Thr Leu Ser Asn Gly
                1125                1130                1135

Gln Ala Ile Pro Asn Gly Thr Phe Thr Asn Ile Thr Ser Asp Arg Thr
                1140                1145                1150

Ile Pro Thr Ala Gln Glu Val Ser Gln Met Asn Ala Gly Thr Gln Leu
            1155                1160                1165

Tyr His Ile Val Ala Ser Asn Ala Tyr His Lys Asp Thr Glu Asp Phe
    1170                1175                1180

Tyr Ile Ser Leu Lys Ile Val Asp Val Lys Gln Pro Glu Gly Asp Gln
1185                1190                1195                1200

Arg Val Tyr Arg Thr Ser Thr Tyr Asp Leu Thr Thr Asp Glu Ile Ser
            1205                1210                1215

Lys Val Lys Gln Ala Phe Ile Asn Ala Asn Arg Asp Val Ile Thr Leu
            1220                1225                1230

Ala Glu Gly Asp Ile Ser Val Thr Asn Thr Pro Asn Gly Ala Asn Val
    1235                1240                1245

Ser Thr Ile Thr Val Asn Ile Asn Lys Gly Arg Leu Thr Lys Ser Phe
    1250                1255                1260

Ala Ser Asn Leu Ala Asn Met Asn Phe Leu Arg Trp Val Asn Phe Pro
1265                1270                1275                1280

Gln Asp Tyr Thr Val Thr Trp Thr Asn Ala Lys Ile Ala Asn Arg Pro
            1285                1290                1295

Thr Asp Gly Gly Leu Ser Trp Ser Asp His Lys Ser Leu Ile Tyr
            1300                1305                1310

Arg Tyr Asp Ala Thr Leu Gly Thr Gln Ile Thr Asn Asp Ile Leu
            1315                1320                1325

Thr Met Leu Lys Ala Thr Thr Thr Val Pro Gly Leu Arg Asn Asn Ile
    1330                1335                1340

Thr Gly Asn Glu Lys Ala Gln Ala Glu Ala Gly Gly Arg Pro Asn Tyr

```
                1345                1350                1355                1360
Arg Thr Thr Gly Tyr Ser Gln Ser Asn Ala Thr Thr Asp Gly Gln Arg
                    1365                1370                1375
Gln Phe Thr Leu Asn Gly Gln Val Ile Gln Ile Leu Asp Ile Ile Asn
                1380                1385                1390
Pro Ser Asn Gly Tyr Gly Gly Gln Pro Val Thr Asn Ser Asn Thr Arg
            1395                1400                1405
Ala Asn His Ser Asn Ser Thr Val Val Asn Val Asn Glu Pro Ala Ala
        1410                1415                1420
Asn Gly Ala Gly Ala Phe Thr Ile Asp His Val Val Lys Ser Asn Ser
1425                1430                1435                1440
Thr His Asn Ala Ser Asp Ala Val Tyr Lys Ala Gln Leu Tyr Leu Thr
                1445                1450                1455
Pro Tyr Gly Pro Lys Gln Tyr Val Glu His Leu Asn Gln Asn Thr Gly
            1460                1465                1470
Asn Thr Thr Asp Ala Ile Asn Ile Tyr Phe Val Pro Ser Asp Leu Val
        1475                1480                1485
Asn Pro Thr Ile Ser Val Gly Asn Tyr Thr Asn His Gln Val Phe Ser
    1490                1495                1500
Gly Glu Thr Phe Thr Asn Thr Ile Thr Ala Asn Asp Asn Phe Gly Val
1505                1510                1515                1520
Gln Ser Val Thr Val Pro Asn Thr Ser Gln Ile Thr Gly Thr Val Asp
                1525                1530                1535
Asn Asn His Gln His Val Ser Ala Thr Ala Pro Asn Val Thr Ser Ala
            1540                1545                1550
Thr Ser Lys Thr Ile Asn Leu Leu Ala Thr Asp Thr Ser Gly Asn Thr
        1555                1560                1565
Ala Thr Thr Ser Phe Asn Val Thr Val Lys Pro Leu Arg Asp Lys Tyr
    1570                1575                1580
Arg Val Gly Thr Ser Thr Ala Ala Asn Pro Val Arg Ile Ala Asn
1585                1590                1595                1600
Ile Ser Asn Asn Ala Thr Val Ser Gln Ala Asp Gln Thr Thr Ile Ile
                1605                1610                1615
Asn Ser Leu Thr Phe Thr Ser Asn Ala Pro Asn Arg Asn Tyr Ala Thr
            1620                1625                1630
Ala Ser Ala Asn Glu Ile Thr Ser Lys Thr Val Ser Asn Val Ser Arg
        1635                1640                1645
Thr Gly Asn Asn Ala Asn Val Thr Val Thr Val Thr His Gln Asp Gly
    1650                1655                1660
Thr Thr Ser Thr Val Thr Val Pro Val Lys His Val Ile Pro Glu Ile
1665                1670                1675                1680
Val Ala His Ser His Tyr Thr Val Gln Gly Gln Asp Phe Pro Ala Gly
                1685                1690                1695
Asn Gly Ser Ser Ala Ala Asp Tyr Phe Lys Leu Ser Asn Gly Ser Ala
            1700                1705                1710
Ile Pro Asp Ala Thr Ile Thr Trp Val Ser Gly Gln Ala Pro Asn Lys
        1715                1720                1725
Asp Asn Thr Arg Ile Gly Glu Asp Ile Thr Val Thr Ala His Ile Leu
    1730                1735                1740
Ile Asp Gly Glu Thr Thr Pro Ile Thr Lys Thr Ala Thr Tyr Lys Val
1745                1750                1755                1760
Val Arg Thr Val Pro Lys His Val Phe Glu Thr Ala Arg Gly Val Leu
                1765                1770                1775
```

```
Tyr Pro Gly Val Ser Asp Met Tyr Asp Ala Lys Gln Tyr Val Lys Pro
            1780                1785                1790

Val Asn Asn Ser Trp Ser Thr Asn Ala Gln His Met Asn Phe Gln Phe
        1795                1800                1805

Val Gly Thr Tyr Gly Pro Asn Lys Asp Val Val Gly Ile Ser Thr Arg
    1810                1815                1820

Leu Ile Arg Val Thr Tyr Asp Asn Arg Gln Thr Glu Asp Leu Thr Ile
1825                1830                1835                1840

Leu Ser Lys Val Lys Pro Asp Pro Arg Ile Asp Ala Asn Ser Val
            1845                1850                1855

Thr Tyr Lys Ala Gly Leu Thr Asn Gln Glu Ile Lys Val Asn Asn Val
        1860                1865                1870

Leu Asn Asn Ser Ser Val Lys Leu Phe Lys Ala Asp Asn Thr Pro Leu
    1875                1880                1885

Asn Val Thr Asn Ile Thr His Gly Ser Gly Phe Ser Ser Val Val Thr
1890                1895                1900

Val Ser Asp Ala Leu Pro Asn Gly Gly Ile Lys Ala Lys Ser Ser Ile
1905                1910                1915                1920

Ser Met Asn Asn Val Thr Tyr Thr Thr Gln Asp Glu His Gly Gln Val
            1925                1930                1935

Val Thr Val Thr Arg Asn Glu Ser Val Asp Ser Asn Asp Ser Ala Ser
        1940                1945                1950

Val Thr Val Thr Pro Gln Leu Gln Ala Thr Thr Glu Gly Ala Val Phe
    1955                1960                1965

Ile Lys Gly Gly Asp Gly Phe Asp Phe Gly His Val Glu Arg Phe Ile
1970                1975                1980

Gln Asn Pro Pro His Gly Ala Thr Val Ala Trp His Asp Ser Pro Asp
1985                1990                1995                2000

Thr Trp Lys Asn Thr Val Gly Asn Thr His Lys Thr Ala Val Val Thr
            2005                2010                2015

Leu Pro Ser Gly Gln Gly Thr Arg Asn Val Glu Val Pro Val Lys Val
        2020                2025                2030

Tyr Pro Val Ala Asn Ala Lys Ala Pro Ser Arg Asp Val Lys Gly Gln
    2035                2040                2045

Asn Leu Thr His Gly Thr Asn Ala Ile Asp Tyr Ile Thr Phe Asp Pro
2050                2055                2060

Asn Thr Asn Thr Asn Gly Ile Thr Ala Ala Trp Ala Asn Arg Gln Gln
2065                2070                2075                2080

Pro Asn Asn Gln Gln Ala Gly Val Gln His Leu Asn Val Asp Val Thr
            2085                2090                2095

Tyr Pro Gly Ile Ser Ala Ala Lys Arg Val Pro Val Thr Val Asn Val
        2100                2105                2110

Tyr Gln Phe Glu Phe Pro Gln Thr Thr Tyr Thr Thr Val Gly Gly
    2115                2120                2125

Thr Leu Ala Ser Gly Thr Gln Ala Ser Gly Tyr Ala His Met Gln Asn
2130                2135                2140

Ala Ser Gly Leu Pro Thr Asp Gly Phe Thr Tyr Lys Trp Asn Arg Asp
2145                2150                2155                2160

Thr Thr Gly Thr Asn Asp Ala Asn Trp Ala Ala Met Asn Lys Pro Asn
            2165                2170                2175

Thr Ala Gln Val Val Asn Ala Lys Tyr Asp Val Ile Tyr Asn Gly His
        2180                2185                2190
```

-continued

```
Thr Phe Ala Thr Ser Leu Pro Ala Lys Phe Val Val Lys Asp Val Gln
        2195                2200                2205

Pro Ala Lys Pro Thr Val Thr Glu Thr Ala Ala Gly Ala Ile Thr Ile
2210                2215                2220

Ala Pro Gly Ala Asn Gln Thr Val Asn Thr His Ala Gly Asn Val Thr
2225                2230                2235                2240

Thr Tyr Ala Asp Lys Leu Val Ile Lys Arg Asn Gly Asn Val Val Thr
        2245                2250                2255

Thr Phe Thr Arg Arg Asn Asn Thr Ser Pro Trp Val Lys Glu Ala Ser
        2260                2265                2270

Ala Asp Asn Val Thr Gly Ile Val Gly Thr Asn Gly Ile Thr Val
        2275                2280                2285

Ala Ala Gly Thr Phe Asn Pro Ala Asp Thr Ile Gln Val Val Ala Thr
        2290                2295                2300

Gln Gly Ser Gly Glu Thr Ile Ser Asp Glu Gln Arg Ser Asp Asp Phe
2305                2310                2315                2320

Thr Val Val Ala Pro Gln Pro Asn Gln Ala Thr Thr Lys Ile Trp Gln
        2325                2330                2335

Asn Gly His Ile Asp Ile Thr Pro Asn Asn Pro Ser Gly His Leu Ile
        2340                2345                2350

Asn Pro Thr Gln Ala Met Asp Ile Ala Tyr Thr Glu Lys Val Gly Asn
        2355                2360                2365

Gly Ala Glu His Ser Lys Thr Ile Asn Val Val Arg Gly Gln Asn Asn
        2370                2375                2380

Gln Trp Thr Ile Ala Asn Lys Pro Asp Tyr Val Thr Leu Asp Ala Gln
2385                2390                2395                2400

Thr Gly Lys Val Thr Phe Asn Ala Asn Thr Ile Lys Pro Asn Ser Ser
        2405                2410                2415

Ile Thr Ile Thr Pro Lys Ala Gly Thr Gly His Ser Val Ser Ser Asn
        2420                2425                2430

Pro Ser Thr Leu Thr Ala Pro Ala Ala His Thr Val Asn Thr Thr Glu
        2435                2440                2445

Ile Val Lys Asp Tyr Gly Ser Asn Val Thr Ala Ala Glu Ile Asn Asn
        2450                2455                2460

Ala Val Gln Val Ala Asn Lys Arg Thr Ala Thr Ile Lys Asn Gly Thr
2465                2470                2475                2480

Ala Met Pro Thr Asn Leu Ala Gly Gly Ser Thr Thr Ile Pro Val
        2485                2490                2495

Thr Val Thr Tyr Asn Asp Gly Ser Thr Glu Glu Val Gln Glu Ser Ile
        2500                2505                2510

Phe Thr Lys Ala Asp Lys Arg Glu Leu Ile Thr Ala Lys Asn His Leu
        2515                2520                2525

Asp Asp Pro Val Ser Thr Glu Gly Lys Lys Pro Gly Thr Ile Thr Gln
        2530                2535                2540

Tyr Asn Asn Ala Met His Asn Ala Gln Gln Ile Asn Thr Ala Lys
2545                2550                2555                2560

Thr Glu Ala Gln Gln Val Ile Asn Asn Glu Arg Ala Thr Pro Gln Gln
        2565                2570                2575

Val Ser Asp Ala Leu Thr Lys Val Arg Ala Ala Gln Thr Lys Ile Asp
        2580                2585                2590

Gln Ala Lys Ala Leu Leu Gln Asn Lys Glu Asp Asn Ser Gln Leu Val
        2595                2600                2605

Thr Ser Lys Asn Asn Leu Gln Ser Ser Val Asn Gln Val Pro Ser Thr
```

```
                2610                2615                2620

Ala Gly Met Thr Gln Gln Ser Ile Asp Asn Tyr Asn Ala Lys Lys Arg
2625                2630                2635                2640

Glu Ala Glu Thr Glu Ile Thr Ala Ala Gln Arg Val Ile Asp Asn Gly
                2645                2650                2655

Asp Ala Thr Ala Gln Gln Ile Ser Asp Glu Lys His Arg Val Asp Asn
                2660                2665                2670

Ala Leu Thr Ala Leu Asn Gln Ala Lys His Asp Leu Thr Ala Asp Thr
                2675                2680                2685

His Ala Leu Glu Gln Ala Val Gln Gln Leu Asn Arg Thr Gly Thr Thr
                2690                2695                2700

Thr Gly Lys Lys Pro Ala Ser Ile Thr Ala Tyr Asn Asn Ser Ile Arg
2705                2710                2715                2720

Ala Leu Gln Ser Asp Leu Thr Ser Ala Lys Asn Ser Ala Asn Ala Ile
                2725                2730                2735

Ile Gln Lys Pro Ile Arg Thr Val Gln Glu Val Gln Ser Ala Leu Thr
                2740                2745                2750

Asn Val Asn Arg Val Asn Glu Arg Leu Thr Gln Ala Ile Asn Gln Leu
            2755                2760                2765

Val Pro Leu Ala Asp Asn Ser Ala Leu Arg Thr Ala Lys Thr Lys Leu
            2770                2775                2780

Asp Glu Glu Ile Asn Lys Ser Val Thr Thr Asp Gly Met Thr Gln Ser
2785                2790                2795                2800

Ser Ile Gln Ala Tyr Glu Asn Ala Lys Arg Ala Gly Gln Thr Glu Thr
                2805                2810                2815

Thr Asn Ala Gln Asn Val Ile Asn Asn Gly Asp Ala Thr Asp Gln Gln
                2820                2825                2830

Ile Ala Ala Glu Lys Thr Lys Val Glu Glu Lys Tyr Asn Ser Leu Lys
                2835                2840                2845

Gln Ala Ile Ala Gly Leu Thr Pro Asp Leu Ala Pro Leu Gln Thr Ala
                2850                2855                2860

Lys Thr Gln Leu Gln Asn Asp Ile Asp Gln Pro Thr Ser Thr Thr Gly
2865                2870                2875                2880

Met Thr Ser Ala Ser Val Ala Ala Phe Asn Asp Lys Leu Ser Ala Ala
                2885                2890                2895

Arg Thr Lys Ile Gln Glu Ile Asp Arg Val Leu Ala Ser His Pro Asp
                2900                2905                2910

Val Ala Thr Ile Arg Gln Asn Val Thr Ala Ala Asn Ala Ala Lys Thr
                2915                2920                2925

Ala Leu Asp Gln Ala Arg Asn Gly Leu Thr Val Asp Lys Ala Pro Leu
                2930                2935                2940

Glu Asn Ala Lys Asn Gln Leu Gln His Ser Ile Asp Thr Gln Thr Ser
2945                2950                2955                2960

Thr Thr Gly Met Thr Gln Asp Ser Ile Asn Ala Tyr Asn Ala Lys Leu
                2965                2970                2975

Thr Ala Ala Arg Asn Lys Val Gln Gln Ile Asn Gln Val Leu Ala Gly
                2980                2985                2990

Ser Pro Thr Val Asp Gln Ile Asn Thr Asn Thr Ser Ala Ala Asn Gln
                2995                3000                3005

Ala Lys Ser Asp Leu Asp His Ala Arg Gln Ala Leu Thr Pro Asp Lys
                3010                3015                3020

Ala Pro Leu Gln Asn Ala Lys Thr Gln Leu Glu Gln Ser Ile Asn Gln
                3025                3030                3035                3040
```

```
Pro Thr Asp Thr Thr Gly Met Thr Thr Ala Ser Leu Asn Ala Tyr Asn
            3045                3050                3055
Gln Lys Leu Gln Ala Ala Arg Gln Lys Leu Thr Glu Ile Asn Gln Val
        3060                3065                3070
Leu Asn Gly Asn Pro Thr Val Gln Asn Ile Asn Asp Lys Val Ala Glu
    3075                3080                3085
Ala Asn Gln Ala Lys Asp Gln Leu Asn Thr Ala Arg Gln Gly Leu Thr
3090                3095                3100
Leu Asp Arg Gln Pro Ala Leu Thr Thr Leu His Gly Ala Ser Asn Leu
3105                3110                3115                3120
Asn Gln Ala Gln Gln Asn Asn Phe Thr Gln Gln Ile Asn Ala Ala Gln
            3125                3130                3135
Asn His Ala Ala Leu Glu Thr Ile Lys Ser Asn Ile Thr Ala Leu Asn
        3140                3145                3150
Thr Ala Met Thr Lys Leu Lys Asp Ser Val Ala Asp Asn Asn Thr Ile
    3155                3160                3165
Lys Ser Gly Gln Asn Tyr Thr Asp Ala Thr Pro Ala Asn Lys Gln Ala
3170                3175                3180
Tyr Asp Asn Ala Val Asn Ala Ala Lys Gly Val Ile Gly Glu Thr Thr
3185                3190                3195                3200
Asn Pro Thr Met Asp Val Asn Thr Val Asn Gln Lys Ala Ala Ser Val
            3205                3210                3215
Lys Ser Thr Lys Asp Ala Leu Asp Gly Gln Gln Asn Leu Gln Arg Ala
        3220                3225                3230
Lys Thr Glu Ala Thr Asn Ala Ile Thr His Ala Ser Asp Leu Asn Gln
    3235                3240                3245
Ala Gln Lys Asn Ala Leu Thr Gln Gln Val Asn Ser Ala Gln Asn Val
3250                3255                3260
Gln Ala Val Asn Asp Ile Lys Gln Thr Thr Gln Ser Leu Asn Thr Ala
3265                3270                3275                3280
Met Thr Gly Leu Lys Arg Gly Val Ala Asn His Asn Gln Val Val Gln
            3285                3290                3295
Ser Asp Asn Tyr Val Asn Ala Asp Thr Asn Lys Lys Asn Asp Tyr Asn
        3300                3305                3310
Asn Ala Tyr Asn His Ala Asn Asp Ile Ile Asn Gly Asn Ala Gln His
    3315                3320                3325
Pro Val Ile Thr Pro Ser Asp Val Asn Asn Ala Leu Ser Asn Val Thr
3330                3335                3340
Ser Lys Glu His Ala Leu Asn Gly Glu Ala Lys Leu Asn Ala Ala Lys
3345                3350                3355                3360
Gln Glu Ala Asn Thr Ala Leu Gly His Leu Asn Leu Asn Asn Val
            3365                3370                3375
Gln Arg Gln Asn Leu Gln Ser Gln Ile Asn Gly Ala His Gln Ile Asp
        3380                3385                3390
Ala Val Asn Thr Ile Lys Gln Asn Ala Thr Asn Leu Asn Ser Ala Met
    3395                3400                3405
Gly Asn Leu Arg Gln Ala Val Ala Asp Lys Asp Gln Val Lys Arg Thr
3410                3415                3420
Glu Asp Tyr Ala Asp Ala Asp Thr Ala Lys Gln Asn Ala Tyr Asn Ser
3425                3430                3435                3440
Ala Val Ser Ser Ala Glu Thr Ile Ile Asn Gln Thr Ala Asn Pro Thr
            3445                3450                3455
```

```
Met Ser Val Asp Asp Val Asn Arg Ala Thr Ser Ala Val Thr Thr Asn
            3460                3465                3470

Lys Asn Ala Leu Asn Gly Asp Glu Lys Leu Val Gln Ser Lys Thr Asp
        3475                3480                3485

Ala Ala Arg Ala Ile Asp Ala Leu Pro His Leu Asn Asn Ala Gln Lys
        3490                3495                3500

Ala Asp Val Lys Ser Lys Ile Asn Ala Ala Ser Asn Ile Ala Gly Val
3505                3510                3515                3520

Asn Thr Val Lys Gln Gln Gly Thr Asp Leu Asn Thr Ala Met Gly Asn
            3525                3530                3535

Leu Gln Gly Ala Ile Asn Asp Glu Gln Thr Thr Leu Asn Ser Gln Asn
            3540                3545                3550

Tyr Gln Asp Ala Thr Pro Ser Lys Lys Thr Ala Tyr Thr Asn Ala Val
            3555                3560                3565

Gln Ala Ala Lys Asp Ile Leu Asn Lys Ser Asn Gly Gln Asn Lys Thr
        3570                3575                3580

Lys Asp Gln Val Thr Glu Ala Met Asn Gln Val Asn Ser Ala Lys Asn
3585                3590                3595                3600

Asn Leu Asp Gly Thr Arg Leu Leu Asp Gln Ala Lys Gln Thr Ala Lys
            3605                3610                3615

Gln Gln Leu Asn Asn Met Thr His Leu Thr Thr Ala Gln Lys Thr Asn
            3620                3625                3630

Leu Thr Asn Gln Ile Asn Ser Gly Thr Thr Val Ala Gly Val His Thr
            3635                3640                3645

Val Gln Ser Asn Ala Asn Thr Leu Asp Gln Ala Met Asn Thr Leu Arg
3650                3655                3660

Gln Ser Ile Ala Asn Asn Asp Ala Thr Lys Ala Ser Glu Asp Tyr Val
3665                3670                3675                3680

Asp Ala Asn Asn Asp Lys Gln Thr Ala Tyr Asn Asn Ala Val Ala Ala
            3685                3690                3695

Ala Glu Thr Ile Ile Asn Ala Asn Ser Asn Pro Glu Met Asn Pro Ser
            3700                3705                3710

Thr Ile Thr Gln Lys Ala Glu Gln Val Asn Ser Ser Lys Thr Ala Leu
            3715                3720                3725

Asn Gly Asp Glu Asn Leu Ala Thr Ala Lys Gln Asn Ala Lys Thr Tyr
        3730                3735                3740

Leu Asn Thr Leu Thr Ser Ile Thr Asp Ala Gln Lys Asn Asn Leu Ile
3745                3750                3755                3760

Ser Gln Ile Ser Ser Ala Thr Arg Val Ser Gly Val Asp Thr Val Lys
            3765                3770                3775

Gln Asn Ala Gln His Leu Asp Gln Ala Met Ala Asn Leu Gln Asn Gly
            3780                3785                3790

Ile Asn Asn Glu Ser Gln Val Lys Ser Ser Glu Lys Tyr Arg Asp Ala
            3795                3800                3805

Asp Thr Asn Lys Gln Gln Glu Tyr Asp Asn Ala Ile Thr Ala Ala Lys
            3810                3815                3820

Ala Ile Leu Asn Lys Ser Thr Gly Pro Asn Thr Ala Gln Asn Ala Val
3825                3830                3835                3840

Glu Ala Ala Leu Gln Arg Val Asn Thr Ala Lys Asp Ala Leu Asn Gly
            3845                3850                3855

Asp Ala Lys Leu Ile Ala Ala Gln Asn Ala Ala Lys Gln His Leu Gly
            3860                3865                3870

Thr Leu Thr His Ile Thr Thr Ala Gln Arg Asn Asp Leu Thr Asn Gln
```

Ile Ser
    3890

<210> SEQ ID NO 13
<211> LENGTH: 6713
<212> TYPE: PRT
<213> ORGANISM: S. aureus

<400> SEQUENCE: 13

Met Gly Asn Leu Gln Thr Ala Ile Asn Asp Lys Ser Gly Thr Leu Ala
1               5                   10                  15

Ser Gln Asn Phe Leu Asp Ala Asp Glu Gln Lys Arg Asn Ala Tyr Asn
            20                  25                  30

Gln Ala Ile Ser Ala Ala Glu Thr Ile Leu Asn Lys Gln Thr Gly Pro
        35                  40                  45

Asn Thr Ala Lys Thr Ala Val Glu Gln Ala Leu Asn Asn Val Asn Ser
    50                  55                  60

Ala Lys His Ala Leu Asn Gly Thr Gln Asn Leu Asn Ala Lys Gln
65                  70                  75                  80

Ala Ala Ile Thr Ala Ile Asn Gly Ala Ser Asp Leu Asn Gln Lys Gln
                85                  90                  95

Lys Asp Ala Leu Lys Ala Gln Ala Asn Gly Ala Gln Arg Val Ser Asn
            100                 105                 110

Ala Asn Asp Val Gln Arg Asn Ala Thr Glu Leu Asn Thr Ala Met Gly
        115                 120                 125

Gln Leu Gln His Ala Ile Ala Asp Lys Thr Asn Thr Leu Ala Ser Ser
130                 135                 140

Lys Tyr Val Asn Ala Asp Ser Thr Lys Gln Asn Ala Tyr Thr Thr Lys
145                 150                 155                 160

Val Thr Asn Ala Glu His Ile Ile Ser Gly Thr Pro Thr Val Val Thr
                165                 170                 175

Thr Pro Ser Glu Val Thr Ala Ala Asn Gln Val Asn Ser Ala Lys
            180                 185                 190

Gln Glu Leu Asn Gly Asp Glu Arg Leu Arg Val Ala Lys Gln Asn Ala
        195                 200                 205

Asn Thr Ala Ile Asp Ala Leu Thr Gln Leu Asn Thr Pro Gln Lys Ala
    210                 215                 220

Lys Leu Lys Glu Gln Val Gly Gln Ala Asn Arg Leu Glu Asp Val Gln
225                 230                 235                 240

Ser Val Gln Thr Asn Gly Gln Ser Leu Asn Asn Ala Met Lys Gly Leu
                245                 250                 255

Arg Asp Ser Ile Ala Asn Glu Thr Thr Val Lys Ala Ser Gln Asn Tyr
            260                 265                 270

Thr Asp Ala Ser Pro Asn Asn Gln Ser Thr Tyr Asn Ser Ala Val Ser
        275                 280                 285

Asn Ala Lys Gly Ile Ile Asn Gln Thr Asn Asn Pro Thr Met Asp Thr
    290                 295                 300

Ser Ala Ile Thr Gln Ala Thr Thr Gln Val Asn Asn Ala Lys Asn Gly
305                 310                 315                 320

Leu Asn Gly Ala Glu Asn Leu Arg Asn Ala Gln Asn Thr Ala Lys Gln
                325                 330                 335

Asn Leu Asn Thr Leu Ser His Leu Thr Asn Asn Gln Lys Ser Ala Ile
            340                 345                 350

-continued

```
Ser Ser Gln Ile Asp Arg Ala Gly His Val Ser Glu Val Thr Ala Ala
        355                 360                 365
Lys Asn Ala Ala Thr Glu Leu Asn Ala Gln Met Gly Asn Leu Glu Gln
    370                 375                 380
Ala Ile His Asp Gln Asn Thr Val Lys Gln Gly Val Asn Phe Thr Asp
385                 390                 395                 400
Ala Asp Lys Ala Lys Arg Asp Ala Tyr Thr Asn Ala Val Ser Arg Ala
                405                 410                 415
Glu Thr Ile Leu Asn Lys Thr Gln Gly Ala Asn Thr Ser Lys Gln Asp
                420                 425                 430
Val Glu Ala Ala Ile Gln Asn Val Thr Ser Ala Lys Asn Ala Leu Asn
            435                 440                 445
Gly Asp Gln Asn Val Thr Asn Ala Lys Asn Ala Lys Asn Ala Leu
    450                 455                 460
Asn Asn Leu Thr Ser Ile Asn Asn Ala Gln Lys Arg Asp Leu Thr Thr
465                 470                 475                 480
Lys Ile Asp Gln Ala Thr Thr Val Ala Gly Val Glu Ala Val Ser Asn
                485                 490                 495
Thr Gly Thr Gln Leu Asn Thr Ala Met Ala Asn Leu Gln Asn Gly Ile
            500                 505                 510
Asn Asp Lys Ala Asn Thr Leu Ala Ser Glu Asn Tyr His Asp Ala Asp
    515                 520                 525
Ser Asp Lys Lys Thr Ala Tyr Thr Gln Ala Val Thr Asn Ala Glu Asn
    530                 535                 540
Ile Leu Asn Lys Asn Ser Gly Ser Asn Leu Asp Lys Ala Ala Val Glu
545                 550                 555                 560
Asn Ala Leu Ser Gln Val Thr Asn Ala Lys Gly Ala Leu Asn Gly Asn
                565                 570                 575
His Asn Leu Glu Gln Ala Lys Ser Asn Ala Asn Thr Thr Ile Asn Gly
            580                 585                 590
Leu Gln His Leu Thr Thr Ala Gln Lys Asp Lys Leu Lys Gln Gln Val
        595                 600                 605
Gln Gln Ala Gln Asn Val Ala Gly Val Asp Thr Val Lys Ser Ser Ala
    610                 615                 620
Asn Thr Leu Asn Gly Ala Met Gly Thr Leu Arg Asn Ser Ile Gln Asp
625                 630                 635                 640
Asn Thr Ala Thr Lys Asn Gly Gln Asn Tyr Leu Asp Ala Thr Glu Arg
                645                 650                 655
Asn Lys Thr Asn Tyr Asn Asn Ala Val Asp Ser Ala Asn Gly Val Ile
                660                 665                 670
Asn Ala Thr Ser Asn Pro Asn Met Asp Ala Asn Ala Ile Asn Gln Ile
            675                 680                 685
Ala Thr Gln Val Thr Ser Thr Lys Asn Ala Leu Asp Gly Thr His Asn
    690                 695                 700
Leu Thr Gln Ala Lys Gln Thr Ala Thr Asn Ala Ile Asp Gly Ala Thr
705                 710                 715                 720
Asn Leu Asn Lys Ala Gln Lys Asp Ala Leu Lys Ala Gln Val Thr Ser
                725                 730                 735
Ala Gln Arg Val Ala Asn Val Thr Ser Ile Gln Gln Thr Ala Asn Glu
                740                 745                 750
Leu Asn Thr Ala Met Gly Gln Leu Gln His Gly Ile Asp Asp Glu Asn
            755                 760                 765
Ala Thr Lys Gln Thr Gln Lys Tyr Arg Asp Ala Glu Gln Ser Lys Lys
```

```
            770                 775                 780
Thr Ala Tyr Asp Gln Ala Val Ala Ala Lys Ala Ile Leu Asn Lys
785                 790                 795                 800

Gln Thr Gly Ser Asn Ser Asp Lys Ala Ala Val Asp Arg Ala Leu Gln
                805                 810                 815

Gln Val Thr Ser Thr Lys Asp Ala Leu Asn Gly Asp Ala Lys Leu Ala
                820                 825                 830

Glu Ala Lys Ala Ala Arg Gln Asn Leu Gly Thr Leu Asn His Ile
                835                 840                 845

Thr Asn Ala Gln Arg Thr Ala Leu Glu Gly Gln Ile Asn Gln Ala Thr
850                 855                 860

Thr Val Asp Gly Val Asn Thr Val Lys Thr Asn Ala Asn Thr Leu Asp
865                 870                 875                 880

Gly Ala Met Asn Ser Leu Gln Gly Ala Ile Asn Asp Lys Asp Ala Thr
                885                 890                 895

Leu Arg Asn Gln Asn Tyr Leu Asp Ala Asp Glu Ser Lys Arg Asn Ala
                900                 905                 910

Tyr Thr Gln Ala Val Thr Ala Ala Glu Gly Ile Leu Asn Lys Gln Thr
                915                 920                 925

Gly Gly Asn Thr Ser Lys Ala Asp Val Asp Asn Ala Leu Asn Ala Val
                930                 935                 940

Thr Arg Ala Lys Ala Ala Leu Asn Gly Ala Glu Asn Leu Arg Asn Ala
945                 950                 955                 960

Lys Thr Ser Ala Thr Asn Thr Ile Asn Gly Leu Pro Asn Leu Thr Gln
                965                 970                 975

Leu Gln Lys Asp Asn Leu Lys His Gln Val Glu Gln Ala Gln Asn Val
                980                 985                 990

Val Gly Val Asn Gly Val Lys Asp Lys Gly Asn Thr Leu Asn Thr Ala
                995                1000                1005

Met Gly Ala Leu Arg Thr Ser Ile Gln Asn Asp Asn Thr Thr Lys Thr
                1010                1015                1020

Ser Gln Asn Tyr Leu Asp Ala Ser Asp Ser Asn Lys Asn Asn Tyr Asn
1025                1030                1035                1040

Thr Ala Val Asn Asn Ala Asn Gly Val Ile Asn Ala Thr Asn Asn Pro
                1045                1050                1055

Asn Met Asp Ala Asn Ala Ile Asn Asp Met Ala Asn Gln Val Asn Thr
                1060                1065                1070

Thr Lys Ala Ala Leu Asn Gly Ala Gln Asn Leu Ala Gln Ala Lys Thr
                1075                1080                1085

Asn Ala Thr Asn Thr Ile Asn Asn Ala Gln Asp Leu Asn Gln Lys Gln
                1090                1095                1100

Lys Asp Ala Leu Lys Thr Gln Val Asn Asn Ala Gln Arg Val Ser Asp
1105                1110                1115                1120

Ala Asn Asn Val Gln His Thr Ala Thr Glu Leu Asn Gly Ala Met Thr
                1125                1130                1135

Ala Leu Lys Ala Ala Ile Ala Asp Lys Glu Arg Thr Lys Ala Ser Gly
                1140                1145                1150

Asn Tyr Val Asn Ala Asp Gln Glu Lys Arg Gln Ala Tyr Asp Ser Lys
                1155                1160                1165

Val Thr Asn Ala Glu Asn Ile Ile Asn Gly Thr Pro Asn Ala Thr Leu
                1170                1175                1180

Thr Val Asn Asp Val Asn Ser Ala Ala Ser Gln Val Asn Ala Ala Lys
1185                1190                1195                1200
```

```
Thr Ala Leu Asn Gly Asp Asn Leu Arg Val Ala Lys Glu His Ala
            1205                1210                1215

Asn Asn Thr Ile Asp Gly Leu Ala Gln Leu Asn Asn Val Gln Lys Ala
        1220                1225                1230

Lys Leu Lys Glu Gln Val Gln Ser Ala Thr Thr Leu Asp Gly Val Gln
    1235                1240                1245

Thr Val Lys Asn Ser Ser Gln Thr Leu Asn Thr Ala Met Lys Gly Leu
1250                1255                1260

Arg Asp Ser Ile Ala Asn Glu Ala Thr Ile Lys Ala Gly Gln Asn Tyr
1265                1270                1275                1280

Thr Asp Ala Ser Pro Asn Asn Arg Asn Glu Tyr Asp Ser Ala Val Thr
            1285                1290                1295

Ala Ala Lys Ala Ile Ile Asn Gln Thr Ser Asn Pro Thr Met Glu Pro
        1300                1305                1310

Asn Thr Ile Thr Gln Ala Thr Ser Gln Val Thr Thr Lys Glu His Ala
    1315                1320                1325

Leu Asn Gly Ala Gln Asn Leu Ala Gln Ala Lys Thr Thr Ala Lys Asn
1330                1335                1340

Asn Leu Asn Asn Leu Thr Ser Ile Asn Asn Ala Gln Lys Asp Ala Leu
1345                1350                1355                1360

Thr Arg Asn Ile Asp Gly Ala Thr Thr Val Ala Gly Val Asn Gln Glu
            1365                1370                1375

Thr Ala Lys Ala Thr Glu Leu Asn Asn Ala Met His Ser Leu Gln Asn
        1380                1385                1390

Gly Ile Asn Asp Glu Thr Gln Thr Lys Gln Thr Gln Lys Tyr Leu Asp
    1395                1400                1405

Ala Glu Pro Ser Lys Lys Ser Ala Tyr Asp Gln Ala Val Asn Ala Ala
1410                1415                1420

Lys Ala Ile Leu Thr Lys Ala Ser Gly Gln Asn Val Asp Lys Ala Ala
1425                1430                1435                1440

Val Glu Gln Ala Leu Gln Asn Val Asn Ser Thr Lys Thr Ala Leu Asn
            1445                1450                1455

Gly Asp Ala Lys Leu Asn Glu Ala Lys Ala Ala Ala Lys Gln Thr Leu
        1460                1465                1470

Gly Thr Leu Thr His Ile Asn Asn Ala Gln Arg Asn Ala Leu Asp Asn
    1475                1480                1485

Glu Ile Thr Gln Ala Thr Asn Val Glu Gly Val Asn Thr Val Lys Ala
1490                1495                1500

Lys Ala Gln Gln Leu Asp Gly Ala Met Gly Gln Leu Glu Thr Ser Ile
1505                1510                1515                1520

Arg Asp Lys Asp Thr Thr Leu Gln Ser Gln Asn Tyr Gln Asp Ala Asp
            1525                1530                1535

Asp Ala Lys Arg Thr Ala Tyr Ser Gln Ala Val Asn Ala Ala Ala Thr
        1540                1545                1550

Ile Leu Asn Lys Thr Ala Gly Gly Asn Thr Pro Lys Ala Asp Val Glu
    1555                1560                1565

Arg Ala Met Gln Ala Val Thr Gln Ala Asn Thr Ala Leu Asn Gly Ile
1570                1575                1580

Gln Asn Leu Glu Arg Ala Lys Gln Ala Ala Asn Thr Ala Ile Thr Asn
1585                1590                1595                1600

Ala Ser Asp Leu Asn Thr Lys Gln Lys Glu Ala Leu Lys Ala Gln Val
            1605                1610                1615
```

```
Thr Ser Ala Gly Arg Val Ser Ala Ala Asn Gly Val Glu His Thr Ala
        1620                1625                1630

Thr Glu Leu Asn Thr Ala Met Thr Ala Leu Lys Arg Ala Ile Ala Asp
        1635                1640                1645

Lys Ala Asp Thr Lys Ala Ser Gly Asn Tyr Val Asn Ala Asp Ala Asn
        1650                1655                1660

Lys Arg Gln Ala Tyr Asp Glu Lys Val Thr Ala Ala Glu His Ile Val
1665                1670                1675                1680

Ser Gly Thr Pro Thr Pro Thr Leu Thr Pro Ser Asp Val Thr Asn Ala
        1685                1690                1695

Ala Thr Gln Val Thr Asn Ala Lys Thr Gln Leu Asn Gly Asn His Asn
        1700                1705                1710

Leu Glu Val Ala Lys Gln Asn Ala Asn Thr Ala Ile Asp Gly Leu Thr
        1715                1720                1725

Ser Leu Asn Gly Pro Gln Lys Ala Lys Leu Lys Glu Gln Val Gly Gln
        1730                1735                1740

Ala Thr Thr Leu Pro Asn Val Gln Thr Val Arg Asp Asn Ala Gln Thr
1745                1750                1755                1760

Leu Asn Thr Ala Met Lys Gly Leu Arg Asp Ser Ile Ala Asn Glu Ala
        1765                1770                1775

Thr Ile Lys Ala Gly Gln Asn Tyr Thr Asp Ala Ser Gln Asn Lys Gln
        1780                1785                1790

Asn Asp Tyr Asn Asn Ala Val Thr Ala Ala Lys Ala Ile Ile Gly Gln
        1795                1800                1805

Thr Thr Ser Pro Ser Met Ile Ala Gln Glu Ile Asn Gln Ala Lys Asp
        1810                1815                1820

Gln Val Thr Ala Lys Gln Gln Ala Leu Asn Gly Gln Glu Asn Leu Arg
1825                1830                1835                1840

Thr Ala Gln Thr Asn Ala Lys Gln His Leu Asn Gly Leu Ser Asp Leu
        1845                1850                1855

Thr Asn Ala Gln Lys Asp Ala Ala Lys Arg Gln Ile Glu Gly Ala Thr
        1860                1865                1870

His Val Asn Glu Val Thr Gln Ala Gln Asn Asn Ala Asp Ala Leu Asn
        1875                1880                1885

Thr Ala Met Thr Asn Leu Lys Asn Gly Ile Gln Asp Gln Asn Thr Ile
        1890                1895                1900

Lys Gln Gly Val Asn Phe Thr Asp Ala Asp Glu Ala Lys Arg Asn Ala
1905                1910                1915                1920

Tyr Thr Asn Ala Val Thr Gln Ala Glu Gln Ile Leu Asn Lys Ala Gln
        1925                1930                1935

Gly Pro Asn Thr Ala Lys Asp Gly Val Glu Thr Ala Leu Gln Asn Val
        1940                1945                1950

Gln Arg Ala Lys Asn Glu Leu Asn Gly Asn Gln Asn Val Ala Asn Ala
        1955                1960                1965

Lys Thr Thr Ala Lys Asn Ala Leu Asn Asn Leu Thr Ser Ile Asn Asn
        1970                1975                1980

Ala Gln Lys Ala Ala Leu Lys Ser Gln Ile Glu Gly Ala Thr Thr Val
1985                1990                1995                2000

Ala Gly Val Asn Gln Val Ser Thr Met Ala Ser Glu Leu Asn Thr Ala
        2005                2010                2015

Met Ser Asn Leu Gln Arg Gly Ile Asn Asp Glu Ala Ala Thr Lys Ala
        2020                2025                2030

Ala Gln Lys Tyr Thr Glu Ala Asp Arg Asp Lys Gln Thr Ala Tyr Asn
```

```
              2035                2040                2045
Asp Ala Val Thr Ala Ala Lys Thr Leu Leu Asp Lys Thr Ala Gly Ser
              2050                2055                2060
Asn Asp Asn Lys Val Ala Val Glu Gln Ala Leu Gln Arg Val Asn Thr
2065                2070                2075                2080
Ala Lys Thr Ala Leu Asn Gly Asp Ala Arg Leu Asn Glu Ala Lys Asn
                  2085                2090                2095
Thr Ala Lys Gln Gln Leu Ala Thr Met Ser His Leu Thr Asn Ala Gln
                  2100                2105                2110
Lys Ala Asn Leu Thr Glu Gln Ile Glu Arg Gly Thr Thr Val Ala Gly
                  2115                2120                2125
Val Gln Gly Ile Gln Ala Asn Ala Gly Thr Leu Asn Gln Ala Met Asn
              2130                2135                2140
Gln Leu Arg Gln Ser Ile Ala Ser Lys Asp Ala Thr Lys Ser Ser Glu
2145                2150                2155                2160
Asp Tyr Gln Asp Ala Asn Ala Asp Leu Gln Asn Ala Tyr Asn Asp Ala
                  2165                2170                2175
Val Thr Asn Ala Glu Gly Ile Ile Ser Ala Thr Asn Asn Pro Glu Met
                  2180                2185                2190
Asn Pro Asp Thr Ile Asn Gln Lys Ala Ser Gln Val Asn Ser Ala Lys
                  2195                2200                2205
Ser Ala Leu Asn Gly Asp Glu Lys Leu Ala Ala Val Lys Gln Thr Ala
              2210                2215                2220
Lys Ser Asp Ile Gly Arg Leu Thr Asp Leu Asn Asn Ala Gln Arg Thr
2225                2230                2235                2240
Ala Ala Asn Ala Glu Val Asp Gln Ala Pro Asn Leu Ala Ala Val Thr
                  2245                2250                2255
Ala Ala Lys Asn Lys Ala Thr Ser Leu Asn Thr Ala Met Gly Asn Leu
              2260                2265                2270
Lys His Ala Leu Ala Glu Lys Asp Asn Thr Lys Arg Ser Val Asn Tyr
              2275                2280                2285
Thr Asp Ala Asp Gln Pro Lys Gln Gln Ala Tyr Asp Thr Ala Val Thr
              2290                2295                2300
Gln Ala Glu Ala Ile Thr Asn Ala Asn Gly Ser Asn Ala Asn Glu Thr
2305                2310                2315                2320
Gln Val Gln Ala Ala Leu Asn Gln Leu Asn Gln Ala Lys Asn Asp Leu
                  2325                2330                2335
Asn Gly Asp Asn Lys Val Ala Gln Ala Lys Glu Thr Ala Lys Arg Ala
                  2340                2345                2350
Leu Ala Ser Tyr Ser Asn Leu Asn Asn Ala Gln Ser Thr Ala Ala Thr
              2355                2360                2365
Ser Gln Ile Asp Asn Ala Thr Thr Val Ala Asp Val Thr Ala Ala Gln
              2370                2375                2380
Asn Thr Ala Asn Glu Leu Asn Thr Ala Met Gly Gln Leu Gln Asn Gly
2385                2390                2395                2400
Ile Asn Asp Gln Asn Thr Val Lys Gln Gln Val Asn Phe Thr Asp Ala
                  2405                2410                2415
Asp Gln Gly Lys Lys Asp Ala Tyr Thr Asn Ala Val Thr Asn Ala Gln
                  2420                2425                2430
Gly Ile Leu Asp Lys Ala Asn Gly Gln Asn Met Thr Lys Ala Gln Val
              2435                2440                2445
Glu Ala Ala Leu Asn Gln Val Thr Ala Lys Asn Ala Leu Asn Gly
              2450                2455                2460
```

```
Asp Ala Asn Val Arg Gln Ala Lys Ser Asp Ala Lys Ala Asn Leu Gly
2465                2470                2475                2480

Thr Leu Thr His Leu Asn Asn Ala Gln Lys Gln Asp Leu Thr Ser Gln
            2485                2490                2495

Ile Glu Gly Ala Thr Thr Val Asn Gly Val Asn Ser Val Lys Thr Lys
        2500                2505                2510

Ala Gln Asp Leu Asp Gly Ala Met Gln Arg Leu Glu Ser Ala Ile Ala
    2515                2520                2525

Asn Lys Asp Gln Thr Lys Ala Ser Glu Asn Tyr Ile Asp Ala Asp Pro
2530                2535                2540

Thr Lys Lys Thr Ala Phe Asp Asn Ala Ile Thr Gln Ala Glu Ser Tyr
2545                2550                2555                2560

Leu Asn Lys Asp His Gly Thr Asn Lys Asp Lys Gln Ala Val Glu Gln
            2565                2570                2575

Ala Ile Gln Ser Val Thr Ser Thr Glu Asn Ala Leu Asn Gly Asp Ala
        2580                2585                2590

Asn Leu Gln Cys Ala Lys Thr Glu Ala Thr Gln Ala Ile Asp Asn Leu
    2595                2600                2605

Thr Gln Leu Asn Thr Pro Gln Lys Thr Ala Leu Lys Gln Gln Val Asn
2610                2615                2620

Ala Ala Gln Arg Val Ser Gly Val Thr Asp Leu Lys Asn Ser Ala Thr
2625                2630                2635                2640

Ser Leu Asn Asn Ala Met Asp Gln Leu Lys Gln Ala Ile Gly Asp His
            2645                2650                2655

Asp Thr Ile Val Ala Gly Gly Asn Tyr Thr Asn Ala Ser Pro Asp Lys
        2660                2665                2670

Gln Gly Ala Tyr Thr Asp Ala Tyr Asn Ala Ala Lys Asn Ile Val Asn
    2675                2680                2685

Gly Ser Pro Asn Val Ile Thr Asn Ala Ala Asp Val Thr Ala Ala Thr
2690                2695                2700

Gln Arg Val Asn Asn Ala Glu Thr Ser Leu Asn Gly Asp Thr Asn Leu
2705                2710                2715                2720

Ala Thr Ala Lys Gln Gln Ala Lys Asp Ala Leu Arg Gln Met Thr His
            2725                2730                2735

Leu Ser Asp Ala Gln Lys Gln Ser Ile Thr Gly Gln Ile Asp Ser Ala
        2740                2745                2750

Thr Gln Val Thr Gly Val Gln Ser Val Lys Asp Asn Ala Thr Asn Leu
    2755                2760                2765

Asp Asn Ala Met Asn Gln Leu Arg Asn Ser Ile Ala Asn Lys Asp Glu
2770                2775                2780

Val Lys Ala Ser Gln Pro Tyr Val Asp Ala Asp Thr Asp Lys Gln Asn
2785                2790                2795                2800

Ala Tyr Asn Thr Ala Val Thr Ser Ala Glu Asn Ile Ile Asn Ala Thr
            2805                2810                2815

Ser Gln Pro Thr Leu Asp Pro Ser Ala Val Thr Gln Ala Ala Asn Gln
        2820                2825                2830

Val Asn Thr Asn Lys Thr Ala Leu Asn Gly Ala Gln Asn Leu Ala Asn
    2835                2840                2845

Lys Lys Gln Glu Thr Thr Ala Asn Ile Asn Arg Leu Ser His Leu Asn
2850                2855                2860

Asn Ala Gln Lys Gln Asp Leu Asn Thr Gln Val Thr Asn Ala Pro Asn
2865                2870                2875                2880
```

Ile Ser Thr Val Asn Gln Val Lys Thr Lys Ala Glu Gln Leu Asp Gln
            2885                2890                2895

Ala Met Glu Arg Leu Ile Asn Gly Ile Gln Asp Lys Asp Gln Val Lys
        2900                2905                2910

Gln Ser Val Asn Phe Thr Asp Ala Asp Pro Glu Lys Gln Thr Ala Tyr
        2915                2920                2925

Asn Asn Ala Val Thr Ala Ala Glu Asn Ile Ile Asn Gln Ala Asn Gly
        2930                2935                2940

Thr Asn Ala Asn Gln Ser Gln Val Glu Ala Ala Leu Ser Thr Val Thr
2945                2950                2955                2960

Thr Thr Lys Gln Ala Leu Asn Gly Asp Arg Lys Val Thr Asp Ala Lys
            2965                2970                2975

Asn Asn Ala Asn Gln Thr Leu Ser Thr Leu Asp Asn Leu Asn Asn Ala
        2980                2985                2990

Gln Lys Gly Ala Val Thr Gly Asn Ile Asn Gln Ala His Thr Val Ala
        2995                3000                3005

Glu Val Thr Gln Ala Ile Gln Thr Ala Gln Glu Leu Asn Thr Ala Met
        3010                3015                3020

Gly Asn Leu Lys Asn Ser Leu Asn Asp Lys Asp Thr Thr Leu Gly Ser
3025                3030                3035                3040

Gln Asn Phe Ala Asp Ala Asp Pro Glu Lys Lys Asn Ala Tyr Asn Glu
            3045                3050                3055

Ala Val Arg Asn Ala Glu Asn Ile Leu Asn Lys Ser Thr Gly Thr Asn
        3060                3065                3070

Val Pro Lys Asp Gln Val Glu Ala Ala Met Asn Gln Val Asn Thr Thr
        3075                3080                3085

Lys Ala Ala Leu Asn Gly Thr Gln Asn Leu Glu Lys Ala Lys Gln His
        3090                3095                3100

Ala Asn Thr Ala Ile Asp Gly Leu Ser His Leu Thr Asn Ala Gln Lys
3105                3110                3115                3120

Glu Ala Leu Lys Gln Leu Val Gln Ser Thr Thr Val Ala Glu Ala
            3125                3130                3135

Gln Gly Asn Glu Gln Lys Ala Asn Asn Val Asp Ala Ala Met Asp Lys
        3140                3145                3150

Leu Arg Gln Ser Ile Ala Asp Asn Ala Thr Thr Lys Gln Asn Gln Asn
        3155                3160                3165

Tyr Thr Asp Ala Ser Pro Asn Lys Lys Asp Ala Tyr Asn Asn Ala Val
        3170                3175                3180

Thr Thr Ala Gln Gly Ile Ile Asp Gln Thr Thr Asn Pro Ser Leu Asp
3185                3190                3195                3200

Pro Thr Val Ile Asn Gln Ala Ala Gly Gln Val Ser Thr Ser Lys Asn
        3205                3210                3215

Ala Leu Asn Gly Asn Glu Asn Leu Glu Ala Ala Lys Gln Gln Ala Thr
        3220                3225                3230

Gln Ser Leu Gly Ser Leu Asp Asn Leu Asn Asn Ala Gln Lys Gln Ala
        3235                3240                3245

Val Thr Asn Gln Ile Asn Gly Ala His Thr Val Asp Glu Ala Asn Gln
        3250                3255                3260

Ile Lys Gln Asn Ala Gln Asn Leu Asn Thr Ala Met Gly Asn Leu Lys
3265                3270                3275                3280

Gln Ala Ile Ala Asp Lys Asp Ala Thr Lys Ala Thr Val Asn Phe Thr
        3285                3290                3295

Asp Ala Asp Gln Ala Lys Gln Gln Ala Tyr Asn Thr Ala Val Thr Asn

```
                 3300                3305                3310
Ala Glu Asn Ile Ile Ser Lys Ala Asn Gly Gly Asn Ala Thr Gln Thr
             3315                3320                3325
Glu Val Glu Gln Ala Ile Gln Gln Val Asn Ala Lys Gln Ala Leu
         3330                3335                3340
Asn Gly Asn Ala Asn Val Gln His Ala Lys Asp Glu Ala Thr Ala Leu
3345                3350                3355                3360
Ile Asn Asn Ser Asn Asp Leu Asn Gln Ala Gln Lys Asp Ala Leu Lys
             3365                3370                3375
Gln Gln Val Gln Asn Ala Thr Thr Val Ala Gly Val Asn Asn Val Lys
         3380                3385                3390
Gln Thr Ala Gln Glu Leu Asn Asn Ala Met Thr Gln Leu Lys Gln Gly
         3395                3400                3405
Ile Ala Asp Lys Glu Gln Thr Lys Ala Asp Gly Asn Phe Val Asn Ala
     3410                3415                3420
Asp Ser Asp Lys Gln Asn Ala Tyr Asn Gln Ala Val Ala Lys Ala Glu
3425                3430                3435                3440
Ala Leu Ile Ser Gly Thr Pro Asp Val Val Thr Pro Ser Glu Ile
             3445                3450                3455
Thr Ala Ala Leu Asn Lys Val Thr Gln Ala Lys Asn Asp Leu Asn Gly
         3460                3465                3470
Asn Thr Asn Leu Ala Thr Ala Lys Gln Asn Val Gln His Ala Ile Asp
     3475                3480                3485
Gln Leu Pro Asn Leu Asn Gln Ala Gln Arg Asp Glu Tyr Ser Lys Gln
     3490                3495                3500
Ile Thr Gln Ala Thr Leu Val Pro Asn Val Asn Ala Ile Gln Gln Ala
3505                3510                3515                3520
Ala Thr Thr Leu Asn Asp Ala Met Thr Gln Leu Lys Gln Gly Ile Ala
             3525                3530                3535
Asn Lys Ala Gln Ile Lys Gly Ser Glu Asn Tyr His Asp Ala Asp Thr
         3540                3545                3550
Asp Lys Gln Thr Ala Tyr Asp Asn Ala Val Thr Lys Ala Glu Glu Leu
     3555                3560                3565
Leu Lys Gln Thr Thr Asn Pro Thr Met Asp Pro Asn Thr Ile Gln Gln
     3570                3575                3580
Ala Leu Thr Lys Val Asn Asp Thr Asn Gln Ala Leu Asn Gly Asn Gln
3585                3590                3595                3600
Lys Leu Ala Asp Ala Lys Gln Asp Ala Lys Thr Thr Leu Gly Thr Leu
             3605                3610                3615
Asp His Leu Asn Asp Ala Gln Lys Gln Ala Leu Thr Thr Gln Val Glu
         3620                3625                3630
Gln Ala Pro Asp Ile Ala Thr Val Asn Asn Val Lys Gln Asn Ala Gln
     3635                3640                3645
Asn Leu Asn Asn Ala Met Thr Asn Leu Asn Asn Ala Leu Gln Asp Lys
     3650                3655                3660
Thr Glu Thr Leu Asn Ser Ile Asn Phe Thr Asp Ala Asp Gln Ala Lys
3665                3670                3675                3680
Lys Asp Asp Tyr Thr Asn Ala Val Ser His Ala Glu Gly Ile Leu Ser
             3685                3690                3695
Lys Ala Asn Gly Ser Asn Ala Ser Gln Thr Glu Val Glu Gln Ala Met
         3700                3705                3710
Gln Arg Val Asn Glu Ala Lys Gln Ala Leu Asn Gly Asn Asp Asn Val
     3715                3720                3725
```

```
Gln Arg Ala Lys Asp Ala Ala Lys Gln Val Ile Thr Asn Ala Asn Asp
    3730                3735                3740
Leu Asn Gln Ala Gln Lys Asp Ala Leu Lys Gln Gln Val Asp Ala Ala
3745                3750                3755                3760
Gln Thr Val Ala Asn Val Asn Thr Ile Lys Gln Thr Ala Gln Asp Leu
            3765                3770                3775
Asn Gln Ala Met Thr Gln Leu Lys Gln Gly Ile Ala Asp Lys Asp Gln
        3780                3785                3790
Thr Lys Ala Asn Gly Asn Phe Val Asn Ala Asp Thr Asp Lys Gln Asn
    3795                3800                3805
Ala Tyr Asn Asn Ala Val Ala His Ala Glu Gln Ile Ile Ser Gly Thr
3810                3815                3820
Pro Asn Ala Asn Val Asp Pro Gln Gln Val Ala Gln Ala Leu Gln Gln
3825                3830                3835                3840
Val Asn Gln Ala Lys Gly Asp Leu Asn Gly Asn His Asn Leu Gln Val
            3845                3850                3855
Ala Lys Asp Asn Ala Asn Thr Ala Ile Asp Gln Leu Pro Asn Leu Asn
        3860                3865                3870
Gln Pro Gln Lys Thr Ala Leu Lys Asp Gln Val Ser His Ala Glu Leu
    3875                3880                3885
Val Thr Gly Val Asn Ala Ile Lys Gln Asn Ala Asp Ala Leu Asn Asn
3890                3895                3900
Ala Met Gly Thr Leu Lys Gln Gln Ile Gln Ala Asn Ser Gln Val Pro
3905                3910                3915                3920
Gln Ser Val Asp Phe Thr Gln Ala Asp Gln Asp Lys Gln Gln Ala Tyr
            3925                3930                3935
Asn Asn Ala Ala Asn Gln Ala Gln Gln Ile Ala Asn Gly Thr Pro Thr
        3940                3945                3950
Pro Val Leu Ala Pro Asp Thr Val Thr Lys Ala Val Thr Thr Met Asn
    3955                3960                3965
Gln Ala Lys Asp Ala Leu Asn Gly Asp Glu Lys Leu Ala Gln Ala Lys
    3970                3975                3980
Gln Asp Ala Leu Ala Asn Leu Asp Thr Leu Arg Asp Leu Asn Gln Pro
3985                3990                3995                4000
Gln Arg Asp Ala Leu Arg Asn Gln Ile Asn Gln Ala Gln Ala Leu Ala
            4005                4010                4015
Thr Val Glu Gln Thr Lys Gln Asn Ala Gln Asn Val Asn Thr Ala Met
        4020                4025                4030
Gly Asn Leu Lys Gln Gly Ile Ala Asn Lys Asp Thr Val Lys Ala Ser
    4035                4040                4045
Glu Asn Tyr His Asp Ala Asp Val Asp Lys Gln Thr Ala Tyr Thr Asn
    4050                4055                4060
Ala Val Ser Gln Ala Glu Gly Ile Ile Asn Gln Thr Thr Asn Pro Thr
4065                4070                4075                4080
Leu Asn Pro Asp Asp Ile Thr Arg Ala Leu Thr Gln Val Thr Asp Ala
            4085                4090                4095
Lys Asn Ser Leu Asn Gly Glu Ala Lys Leu Ala Thr Glu Lys Gln Asn
        4100                4105                4110
Ala Lys Asp Ala Val Ser Gly Met Thr His Leu Asn Asp Ala Gln Lys
    4115                4120                4125
Gln Ala Leu Lys Gly Gln Ile Asp Gln Ser Pro Glu Ile Ala Thr Val
    4130                4135                4140
```

-continued

Asn Gln Val Lys Gln Thr Ala Thr Ser Leu Asp Gln Ala Met Asp Gln
4145                4150                4155                4160

Leu Ser Gln Ala Ile Asn Asp Lys Asp Gln Ile Leu Ala Asp Gly Asn
            4165                4170                4175

Tyr Leu Asn Ala Asp Pro Asp Lys Gln Asn Ala Tyr Lys Gln Ala Val
            4180                4185                4190

Ala Lys Ala Glu Ala Leu Leu Asn Lys Gln Ser Gly Thr Asn Glu Val
        4195                4200                4205

Gln Ala Gln Val Glu Ser Ile Thr Asn Glu Val Asn Ala Ala Lys Gln
        4210                4215                4220

Ala Leu Asn Gly Asn Asp Asn Leu Ala Asn Ala Lys Gln Gln Ala Lys
4225                4230                4235                4240

Gln Gln Leu Ala Asn Leu Thr His Leu Asn Asp Ala Gln Lys Gln Ser
            4245                4250                4255

Phe Glu Ser Gln Ile Thr Gln Ala Pro Leu Val Thr Asp Val Thr Thr
            4260                4265                4270

Ile Asn Gln Lys Ala Gln Thr Leu Asp His Ala Met Glu Leu Leu Arg
        4275                4280                4285

Asn Ser Val Ala Asp Asn Gln Thr Thr Leu Ala Ser Glu Asp Tyr His
        4290                4295                4300

Asp Ala Thr Ala Gln Arg Gln Asn Asp Tyr Asn Lys Ala Val Thr Ala
4305                4310                4315                4320

Ala Asn Asn Ile Ile Asn Gln Thr Thr Ser Pro Thr Met Asn Pro Asp
            4325                4330                4335

Asp Val Asn Gly Ala Thr Thr Gln Val Asn Asn Thr Lys Val Ala Leu
            4340                4345                4350

Asp Gly Asp Glu Asn Leu Ala Ala Ala Lys Gln Gln Ala Asn Asn Arg
        4355                4360                4365

Leu Asp Gln Leu Asp His Leu Asn Asn Ala Gln Lys Gln Gln Leu Gln
        4370                4375                4380

Ser Gln Ile Thr Gln Ser Ser Asp Ile Ala Ala Val Asn Gly His Lys
4385                4390                4395                4400

Gln Thr Ala Glu Ser Leu Asn Thr Ala Met Gly Asn Leu Ile Asn Ala
            4405                4410                4415

Ile Ala Asp His Gln Ala Val Glu Gln Arg Gly Asn Phe Ile Asn Ala
            4420                4425                4430

Asp Thr Asp Lys Gln Thr Ala Tyr Asn Thr Ala Val Asn Glu Ala Ala
        4435                4440                4445

Ala Met Ile Asn Lys Gln Thr Gly Gln Asn Ala Asn Gln Thr Glu Val
        4450                4455                4460

Glu Gln Ala Ile Thr Lys Val Gln Thr Thr Leu Gln Ala Leu Asn Gly
4465                4470                4475                4480

Asp His Asn Leu Gln Val Ala Lys Thr Asn Ala Thr Gln Ala Ile Asp
            4485                4490                4495

Val Leu Thr Ser Leu Asn Asp Pro Gln Lys Thr Ala Leu Lys Asp Gln
            4500                4505                4510

Val Thr Ala Ala Thr Leu Val Thr Ala Val His Gln Ile Glu Gln Asn
        4515                4520                4525

Ala Asn Thr Leu Asn Gln Ala Met His Gly Leu Arg Gln Ser Ile Gln
        4530                4535                4540

Asp Asn Ala Ala Thr Lys Ala Asn Ser Lys Tyr Ile Asn Glu Asp Gln
4545                4550                4555                4560

Pro Glu Gln Gln Asn Tyr Asp Gln Ala Val Gln Ala Ala Asn Asn Ile

```
                    4565              4570              4575
Ile Asn Glu Gln Thr Ala Thr Leu Asp Asn Asn Ala Ile Asn Gln Val
                4580              4585              4590
Ala Ala Thr Val Asn Thr Thr Lys Ala Ala Leu His Gly Asp Val Lys
                4595              4600              4605
Leu Gln Asn Asp Lys Asp His Ala Lys Gln Thr Val Ser Gln Leu Ala
                4610              4615              4620
His Leu Asn Asn Ala Gln Lys His Met Glu Asp Thr Leu Ile Asp Ser
4625              4630              4635              4640
Glu Thr Thr Arg Thr Ala Val Lys Gln Asp Leu Thr Glu Val Gln Ala
                4645              4650              4655
Leu Asp Gln Leu Met Asp Ala Leu Gln Gln Ser Ile Ala Asp Lys Asp
                4660              4665              4670
Ala Thr Arg Ala Ser Ser Ala Tyr Val Asn Ala Glu Pro Asn Lys Lys
                4675              4680              4685
Gln Ala Tyr Asp Glu Ala Val Gln Asn Ala Glu Ser Ile Ile Ala Gly
4690              4695              4700
Leu Asn Asn Pro Thr Ile Asn Lys Gly Asn Val Ser Ser Ala Thr Gln
4705              4710              4715              4720
Ala Val Ile Ser Ser Lys Asn Ala Leu Asp Gly Val Glu Arg Leu Ala
                4725              4730              4735
Gln Asp Lys Gln Thr Ala Gly Asn Ser Leu Asn His Leu Asp Gln Leu
                4740              4745              4750
Thr Pro Ala Gln Gln Ala Leu Glu Asn Gln Ile Asn Asn Ala Thr
                4755              4760              4765
Thr Cys Asp Lys Val Ala Glu Ile Ile Ala Gln Ala Gln Ala Leu Asn
                4770              4775              4780
Glu Ala Met Lys Ala Leu Lys Glu Ser Ile Lys Asp Gln Pro Gln Thr
4785              4790              4795              4800
Glu Ala Ser Ser Lys Phe Ile Asn Glu Asp Gln Ala Gln Lys Asp Ala
                4805              4810              4815
Tyr Thr Gln Ala Val Gln His Ala Lys Asp Leu Ile Asn Lys Thr Thr
                4820              4825              4830
Asp Pro Thr Leu Ala Lys Ser Ile Ile Asp Gln Ala Thr Gln Ala Val
                4835              4840              4845
Thr Asp Ala Lys Asn Asn Leu His Gly Asp Gln Lys Leu Ala Gln Asp
                4850              4855              4860
Lys Gln Arg Ala Thr Glu Thr Leu Asn Asn Leu Ser Asn Leu Asn Thr
4865              4870              4875              4880
Pro Gln Arg Gln Ala Leu Glu Asn Gln Ile Asn Asn Ala Ala Thr Arg
                4885              4890              4895
Gly Glu Val Ala Gln Lys Leu Thr Glu Ala Gln Ala Leu Asn Gln Ala
                4900              4905              4910
Met Glu Ala Leu Arg Asn Ser Ile Gln Asp Gln Gln Thr Glu Ser
                4915              4920              4925
Gly Ser Lys Phe Ile Asn Glu Asp Lys Pro Gln Lys Asp Ala Tyr Gln
                4930              4935              4940
Ala Ala Val Gln Asn Ala Lys Asp Leu Ile Asn Gln Thr Gly Asn Pro
4945              4950              4955              4960
Thr Leu Asp Lys Ala Gln Val Glu Gln Leu Thr His Ala Phe Lys Gln
                4965              4970              4975
Ala Lys Asp Asn Leu His Gly Asp Gln Lys Leu Ala Asp Asp Lys Gln
                4980              4985              4990
```

```
His Ala Val Thr Asp Leu Asn Gln Leu Asn Gly Leu Asn Asn Pro Gln
        4995                5000                5005

Arg Gln Ala Leu Glu Ser Gln Ile Asn Asn Ala Ala Thr Arg Gly Glu
    5010                5015                5020

Val Ala Gln Lys Leu Ala Glu Ala Lys Ala Leu Asp Gln Ala Met Gln
5025                5030                5035                5040

Ala Leu Arg Asn Ser Ile Gln Asp Gln Gln Thr Glu Ala Gly Ser
            5045                5050                5055

Lys Phe Ile Asn Glu Asp Lys Pro Gln Lys Asp Ala Tyr Gln Ala Ala
        5060                5065                5070

Val Gln Asn Ala Lys Asp Leu Ile Asn Gln Thr Gly Asn Pro Thr Leu
    5075                5080                5085

Asp Lys Ser Gln Val Glu Gln Leu Thr Gln Ala Val Thr Thr Ala Lys
5090                5095                5100

Asp Asn Leu His Gly Asp Gln Lys Leu Ala Arg Asp Gln Gln Gln Ala
5105                5110                5115                5120

Val Thr Thr Val Asn Ala Leu Pro Asn Leu Asn His Ala Gln Gln Gln
            5125                5130                5135

Thr Leu Thr Asp Ala Ile Asn Ala Ala Pro Thr Arg Thr Glu Val Ala
        5140                5145                5150

Gln His Val Gln Thr Ala Thr Glu Leu Asp His Ala Met Glu Thr Leu
    5155                5160                5165

Lys Asn Lys Val Asp Gln Val Asn Thr Asp Lys Ala Gln Pro Asn Tyr
        5170                5175                5180

Thr Glu Ala Ser Thr Asp Lys Lys Glu Ala Val Asp Gln Ala Leu Gln
5185                5190                5195                5200

Ala Ala Gln Ser Ile Thr Asp Pro Thr Asn Gly Ser Asn Ala Asn Lys
            5205                5210                5215

Asp Ala Val Glu Gln Ala Leu Thr Lys Leu Gln Glu Lys Val Asn Glu
        5220                5225                5230

Leu Asn Gly Asn Glu Arg Val Ala Glu Ala Lys Thr Gln Ala Lys Gln
        5235                5240                5245

Thr Ile Asp Gln Leu Thr His Leu Asn Ala Asp Gln Ile Ala Thr Ala
        5250                5255                5260

Lys Gln Asn Ile Asp Gln Ala Thr Lys Leu Gln Pro Ile Ala Glu Leu
5265                5270                5275                5280

Val Asp Gln Ala Thr Gln Leu Asn Gln Ser Met Asp Gln Leu Gln Gln
            5285                5290                5295

Ala Val Asn Glu His Ala Asn Val Glu Gln Thr Ile Asp Tyr Thr Gln
        5300                5305                5310

Ala Asp Ser Asp Lys Gln Lys Ala Tyr Lys Gln Ala Ile Ala Asp Ala
        5315                5320                5325

Glu Asn Val Leu Lys Gln Asn Ala Asn Lys Gln Gln Val Asp Gln Ala
    5330                5335                5340

Leu Gln Asn Ile Leu Asn Ala Lys Gln Ala Leu Asn Gly Asp Glu Arg
5345                5350                5355                5360

Val Ala Leu Ala Lys Thr Asn Gly Lys His Asp Ile Asp Gln Leu Asn
            5365                5370                5375

Ala Leu Asn Asn Ala Gln Gln Asp Gly Phe Lys Gly Arg Ile Asp Gln
        5380                5385                5390

Ser Asn Asp Leu Asn Gln Ile Gln Gln Ile Val Asp Glu Ala Lys Ala
        5395                5400                5405
```

```
Leu Asn Arg Ala Met Asp Gln Leu Ser Gln Glu Ile Thr Gly Asn Glu
    5410                5415                5420

Gly Arg Thr Lys Gly Ser Thr Asn Tyr Val Asn Ala Asp Thr Gln Val
5425                5430                5435                5440

Lys Gln Val Tyr Asp Glu Ala Val Asp Lys Ala Lys Gln Ala Leu Asp
                5445                5450                5455

Lys Ser Ser Gly Gln Asn Leu Thr Ala Glu Gln Val Ile Lys Leu Asn
                5460                5465                5470

Asp Ala Val Thr Ala Ala Lys Lys Ala Leu Asn Gly Glu Glu Arg Leu
            5475                5480                5485

Asn Asn Arg Lys Ala Glu Ala Leu Gln Arg Leu Asp Gln Leu Thr His
        5490                5495                5500

Leu Asn Asn Ala Gln Arg Gln Leu Ala Ile Gln Gln Ile Asn Asn Ala
5505                5510                5515                5520

Glu Thr Leu Asn Lys Ala Ser Arg Ala Ile Asn Arg Ala Thr Lys Leu
                5525                5530                5535

Asp Asn Ala Met Gly Ala Val Gln Gln Tyr Ile Asp Glu Gln His Leu
            5540                5545                5550

Gly Val Ile Ser Ser Thr Asn Tyr Ile Asn Ala Asp Asp Asn Leu Lys
        5555                5560                5565

Ala Asn Tyr Asp Asn Ala Ile Ala Asn Ala Ala His Glu Leu Asp Lys
    5570                5575                5580

Val Gln Gly Asn Ala Ile Ala Lys Ala Glu Ala Gln Leu Lys Gln
5585                5590                5595                5600

Asn Ile Ile Asp Ala Gln Asn Ala Leu Asn Gly Asp Gln Asn Leu Ala
                5605                5610                5615

Asn Ala Lys Asp Lys Ala Asn Ala Phe Val Asn Ser Leu Asn Gly Leu
            5620                5625                5630

Asn Gln Gln Gln Gln Asp Leu Ala His Lys Ala Ile Asn Asn Ala Asp
        5635                5640                5645

Thr Val Ser Asp Val Thr Asp Ile Val Asn Asn Gln Ile Asp Leu Asn
    5650                5655                5660

Asp Ala Met Glu Thr Leu Lys His Leu Val Asp Asn Glu Ile Pro Asn
5665                5670                5675                5680

Ala Glu Gln Thr Val Asn Tyr Gln Asn Ala Asp Asp Asn Ala Lys Thr
                5685                5690                5695

Asn Phe Asp Asp Ala Lys Arg Leu Ala Asn Thr Leu Leu Asn Ser Asp
            5700                5705                5710

Asn Thr Asn Val Asn Asp Ile Asn Gly Ala Ile Gln Ala Val Asn Asp
        5715                5720                5725

Ala Ile His Asn Leu Asn Gly Asp Gln Arg Leu Gln Asp Ala Lys Asp
    5730                5735                5740

Lys Ala Ile Gln Ser Ile Asn Gln Ala Leu Ala Asn Lys Leu Lys Glu
5745                5750                5755                5760

Ile Glu Ala Ser Asn Ala Thr Asp Gln Asp Lys Leu Ile Ala Lys Asn
                5765                5770                5775

Lys Ala Glu Glu Leu Ala Asn Ser Ile Ile Asn Asn Ile Asn Lys Ala
            5780                5785                5790

Thr Ser Asn Gln Ala Val Ser Gln Val Gln Thr Ala Gly Asn His Ala
        5795                5800                5805

Ile Glu Gln Val His Ala Asn Glu Ile Pro Lys Ala Lys Ile Asp Ala
    5810                5815                5820

Asn Lys Asp Val Asp Lys Gln Val Gln Ala Leu Ile Asp Glu Ile Asp
```

```
                    5825           5830           5835           5840
Arg Asn Pro Asn Leu Thr Asp Lys Glu Lys Gln Ala Leu Lys Asp Arg
                    5845           5850           5855
Ile Asn Gln Ile Leu Gln Gln Gly His Asn Asp Ile Asn Asn Ala Leu
                    5860           5865           5870
Thr Lys Glu Glu Ile Glu Gln Ala Lys Ala Gln Leu Ala Gln Ala Leu
                    5875           5880           5885
Gln Asp Ile Lys Asp Leu Val Lys Ala Lys Glu Asp Ala Lys Gln Asp
                    5890           5895           5900
Val Asp Lys Gln Val Gln Ala Leu Ile Asp Glu Ile Asp Gln Asn Pro
5905                5910           5915                5920
Asn Leu Thr Asp Lys Glu Lys Gln Ala Leu Lys Asp Arg Ile Asn Gln
                    5925           5930           5935
Ile Leu Gln Gln Gly His Asn Gly Ile Asn Asn Ala Met Thr Lys Glu
                    5940           5945           5950
Glu Ile Glu Gln Ala Lys Ala Gln Leu Ala Gln Ala Leu Lys Glu Ile
                    5955           5960           5965
Lys Asp Leu Val Lys Ala Lys Glu Asn Ala Lys Gln Asp Val Asp Lys
                    5970           5975           5980
Gln Val Gln Ala Leu Ile Asp Glu Ile Asp Gln Asn Pro Asn Leu Thr
5985                5990           5995                6000
Asp Lys Glu Lys Gln Ala Leu Lys Asp Arg Ile Asn Gln Ile Leu Gln
                    6005           6010           6015
Gln Gly His Asn Asp Ile Asn Asn Ala Met Thr Lys Glu Glu Ile Glu
                    6020           6025           6030
Gln Ala Lys Ala Gln Leu Ala Gln Ala Leu Gln Asp Ile Lys Asp Leu
                    6035           6040           6045
Val Lys Ala Lys Glu Asp Ala Lys Asn Ala Ile Lys Ala Leu Ala Asn
                    6050           6055           6060
Ala Lys Arg Asp Gln Ile Asn Ser Asn Pro Asp Leu Thr Pro Glu Gln
6065                6070           6075                6080
Lys Ala Lys Ala Leu Lys Glu Ile Asp Glu Ala Glu Lys Arg Ala Leu
                    6085           6090           6095
Gln Asn Val Glu Asn Ala Gln Thr Ile Asp Gln Leu Asn Arg Gly Leu
                    6100           6105           6110
Asn Leu Gly Leu Asp Asp Ile Arg Asn Thr His Val Trp Glu Val Asp
                    6115           6120           6125
Glu Gln Pro Ala Val Asn Glu Ile Phe Glu Ala Thr Pro Glu Gln Ile
                    6130           6135           6140
Leu Val Asn Gly Glu Leu Ile Val His Arg Asp Asp Ile Ile Thr Glu
6145                6150           6155                6160
Gln Asp Ile Leu Ala His Ile Asn Leu Ile Asp Gln Leu Ser Ala Glu
                    6165           6170           6175
Val Ile Asp Thr Pro Ser Thr Ala Thr Ile Ser Asp Ser Leu Thr Ala
                    6180           6185           6190
Lys Val Glu Val Thr Leu Leu Asp Gly Ser Lys Val Ile Val Asn Val
                    6195           6200           6205
Pro Val Lys Val Val Glu Lys Glu Leu Ser Val Lys Gln Gln Ala
                    6210           6215           6220
Ile Glu Ser Ile Glu Asn Ala Ala Gln Gln Lys Ile Asp Glu Ile Asn
6225                6230           6235                6240
Asn Ser Val Thr Leu Thr Leu Glu Gln Lys Glu Ala Ala Ile Ala Glu
                    6245           6250           6255
```

```
Val Asn Lys Leu Lys Gln Gln Ala Ile Asp His Val Asn Asn Ala Pro
            6260                6265                6270

Asp Val His Ser Val Glu Glu Ile Gln Gln Glu Gln Gln Ala Tyr Ile
            6275                6280                6285

Glu Gln Phe Asn Pro Gln Phe Thr Ile Gln Ala Lys Ser Asn
            6290                6295            6300

Ala Ile Lys Ser Ile Glu Asp Ala Ile Gln His Met Ile Asp Glu Ile
6305            6310                6315                6320

Lys Ala Arg Thr Asp Leu Thr Asp Lys Glu Lys Gln Glu Ala Ile Ala
            6325                6330                6335

Lys Leu Asn Gln Leu Lys Glu Gln Ala Ile Gln Ala Ile Gln Arg Ala
            6340                6345                6350

Gln Ser Ile Ser Glu Ile Thr Glu Gln Leu Glu Gln Phe Lys Ala Gln
            6355                6360                6365

Met Lys Ala Ala Asn Pro Thr Ala Lys Glu Leu Ala Lys Arg Lys Gln
    6370                6375                6380

Glu Ala Ile Ser Arg Ile Lys Asp Phe Ser Asn Glu Lys Ile Asn Ser
6385            6390                6395                6400

Ile Arg Asn Ser Glu Ile Gly Thr Ala Asp Glu Lys Gln Ala Ala Met
            6405                6410                6415

Asn Gln Ile Asn Glu Ile Val Leu Glu Thr Ile Arg Asp Ile Asn Asn
            6420                6425                6430

Ala His Thr Leu Gln Gln Val Glu Ala Ala Leu Asn Asn Gly Ile Ala
            6435                6440                6445

Arg Ile Ser Ala Val Gln Ile Val Ile Ser Asp Arg Ala Lys Gln Ser
            6450                6455                6460

Ser Ser Thr Gly Asn Glu Ser Asn Ser His Leu Thr Ile Gly Tyr Gly
6465            6470                6475                6480

Thr Ala Asn His Pro Phe Asn Ser Ser Thr Ile Gly His Lys Lys Lys
            6485                6490                6495

Leu Asp Glu Asp Asp Asp Ile Asp Pro Leu His Met Arg His Phe Ser
            6500                6505                6510

Asn Asn Phe Gly Asn Val Ile Lys Asn Ala Ile Gly Val Val Gly Ile
            6515                6520                6525

Ser Gly Leu Leu Ala Ser Phe Trp Phe Phe Ile Ala Lys Arg Arg Arg
            6530                6535                6540

Lys Glu Asp Glu Glu Glu Leu Glu Ile Arg Asp Asn Asn Lys Asp
6545            6550                6555                6560

Ser Ile Lys Glu Thr Leu Asp Asp Thr Lys His Leu Pro Leu Leu Phe
            6565                6570                6575

Ala Lys Arg Arg Arg Lys Glu Asp Glu Glu Asp Val Thr Val Glu Glu
            6580                6585                6590

Lys Asp Ser Leu Asn Asn Gly Glu Ser Leu Asp Lys Val Lys His Thr
            6595                6600                6605

Pro Phe Phe Leu Pro Lys Arg Arg Arg Lys Glu Asp Glu Glu Asp Val
            6610                6615                6620

Glu Val Thr Asn Glu Asn Thr Asp Glu Lys Val Leu Lys Asp Asn Glu
6625            6630                6635                6640

His Ser Pro Leu Leu Phe Ala Lys Arg Arg Lys Asp Lys Glu Glu Asp
            6645                6650                6655

Val Glu Thr Thr Ser Ile Glu Ser Lys Asp Glu Asp Val Pro Leu
            6660                6665                6670
```

```
Leu Leu Ala Lys Lys Asn Gln Lys Asp Asn Gln Ser Lys Asp Lys
        6675            6680            6685

Lys Ser Ala Ser Lys Asn Thr Ser Lys Lys Val Ala Ala Lys Lys Lys
        6690            6695            6700

Lys Lys Lys Ser Lys Lys Asn Lys Lys
6705            6710

<210> SEQ ID NO 14
<211> LENGTH: 701
<212> TYPE: PRT
<213> ORGANISM: S. epidermidis

<400> SEQUENCE: 14

Met Asn Asn Arg Asp Lys Leu Gln Lys Phe Ser Ile Arg Lys Tyr Ala
1               5                   10                  15

Ile Gly Thr Phe Ser Thr Val Ile Ala Thr Leu Val Phe Met Gly Ile
            20                  25                  30

Asn Thr Asn His Ala Ser Ala Asp Glu Leu Asn Gln Asn Gln Lys Leu
        35                  40                  45

Ile Lys Gln Leu Asn Gln Thr Asp Asp Asp Ser Asn Thr His Ser
    50                  55                  60

Gln Glu Ile Glu Asn Asn Lys Gln Asn Ser Ser Gly Gln Thr Glu Ser
65                  70                  75                  80

Leu Arg Ser Ser Thr Ser Gln Asn Gln Ala Asn Ala Arg Leu Ser Asp
                85                  90                  95

Gln Phe Lys Asp Thr Asn Glu Thr Ser Gln Gln Leu Pro Thr Asn Val
            100                 105                 110

Ser Asp Asp Ser Ile Asn Gln Ser His Ser Glu Ala Asn Met Asn Asn
        115                 120                 125

Glu Pro Leu Lys Val Asp Asn Ser Thr Met Gln Ala His Ser Lys Ile
    130                 135                 140

Val Ser Asp Ser Asp Gly Asn Ala Ser Glu Asn Lys His His Lys Leu
145                 150                 155                 160

Thr Glu Asn Val Leu Ala Glu Ser Arg Ala Ser Lys Asn Asp Lys Glu
                165                 170                 175

Lys Glu Asn Leu Gln Glu Lys Asp Lys Ser Gln Gln Val His Pro Pro
            180                 185                 190

Leu Asp Lys Asn Ala Leu Gln Ala Phe Phe Asp Ala Ser Tyr His Asn
        195                 200                 205

Tyr Arg Met Ile Asp Arg Asp Arg Ala Asp Ala Thr Glu Tyr Gln Lys
    210                 215                 220

Val Lys Ser Thr Phe Asp Tyr Val Asn Asp Leu Leu Gly Asn Asn Gln
225                 230                 235                 240

Asn Ile Pro Ser Glu Gln Leu Val Ser Ala Tyr Gln Gln Leu Glu Lys
                245                 250                 255

Ala Leu Glu Leu Ala Arg Thr Leu Pro Gln Gln Ser Thr Thr Glu Lys
            260                 265                 270

Arg Gly Arg Arg Ser Thr Arg Ser Val Val Glu Asn Arg Ser Ser Arg
        275                 280                 285

Ser Asp Tyr Leu Asp Ala Arg Thr Glu Tyr Tyr Val Ser Lys Asp Asp
    290                 295                 300

Asp Asp Ser Gly Phe Pro Pro Gly Thr Phe Phe His Ala Ser Asn Arg
305                 310                 315                 320

Arg Trp Pro Tyr Asn Leu Pro Arg Ser Arg Asn Ile Leu Arg Ala Ser
                325                 330                 335
```

Asp Val Gln Gly Asn Ala Tyr Ile Thr Thr Lys Arg Leu Lys Asp Gly
                340                 345                 350

Tyr Gln Trp Asp Ile Leu Phe Asn Ser Asn His Lys Gly His Glu Tyr
            355                 360                 365

Met Tyr Tyr Trp Phe Gly Leu Pro Ser Asp Gln Thr Pro Thr Gly Pro
370                 375                 380

Val Thr Phe Thr Ile Ile Asn Arg Asp Gly Ser Ser Thr Ser Thr Gly
385                 390                 395                 400

Gly Val Gly Phe Gly Ser Gly Ala Pro Leu Pro Gln Phe Trp Arg Ser
                405                 410                 415

Ala Gly Ala Ile Asn Ser Ser Val Ala Asn Asp Phe Lys His Gly Ser
            420                 425                 430

Ala Thr Asn Tyr Ala Phe Tyr Asp Gly Val Asn Asn Phe Ser Asp Phe
        435                 440                 445

Ala Arg Gly Gly Glu Leu Tyr Phe Asp Arg Glu Gly Ala Thr Gln Thr
    450                 455                 460

Asn Lys Tyr Tyr Gly Asp Glu Asn Phe Ala Leu Leu Asn Ser Glu Lys
465                 470                 475                 480

Pro Asp Gln Ile Arg Gly Leu Asp Thr Ile Tyr Ser Phe Lys Gly Ser
                485                 490                 495

Gly Asp Val Ser Tyr Arg Ile Ser Phe Lys Thr Gln Gly Ala Pro Thr
            500                 505                 510

Ala Arg Leu Tyr Tyr Ala Ala Gly Ala Arg Ser Gly Glu Tyr Lys Gln
        515                 520                 525

Ala Thr Asn Tyr Asn Gln Leu Tyr Val Glu Pro Tyr Lys Asn Tyr Arg
    530                 535                 540

Asn Arg Val Gln Ser Asn Val Gln Val Lys Asn Arg Thr Leu His Leu
545                 550                 555                 560

Lys Arg Thr Ile Arg Gln Phe Asp Pro Thr Leu Gln Arg Thr Thr Asp
                565                 570                 575

Val Pro Ile Leu Asp Ser Asp Gly Ser Gly Ser Ile Asp Ser Val Tyr
            580                 585                 590

Asp Pro Leu Ser Tyr Val Lys Asn Val Thr Gly Thr Val Leu Gly Ile
        595                 600                 605

Tyr Pro Ser Tyr Leu Pro Tyr Asn Gln Glu Arg Trp Gln Gly Ala Asn
    610                 615                 620

Ala Met Asn Ala Tyr Gln Ile Glu Glu Leu Phe Ser Gln Glu Asn Leu
625                 630                 635                 640

Gln Asn Ala Ala Arg Ser Gly Arg Pro Ile Gln Phe Leu Val Gly Phe
                645                 650                 655

Asp Val Glu Asp Ser His His Asn Pro Glu Thr Leu Leu Pro Val Asn
            660                 665                 670

Leu Tyr Val Lys Pro Glu Leu Lys His Thr Ile Glu Leu Tyr His Asp
        675                 680                 685

Asn Glu Lys Gln Asp Arg Lys Glu Phe Ser Val Ser Lys
    690                 695                 700

<210> SEQ ID NO 15
<211> LENGTH: 9439
<212> TYPE: PRT
<213> ORGANISM: S. epidermidis

<400> SEQUENCE: 15

Met Ser Gly Thr Leu His Asn Thr Val Gly Ser Gly Ile Leu Pro Tyr

```
            1               5              10              15
        Gln Gln Glu Ile Arg Ile Lys Leu Thr Ser Asn Glu Pro Ile Lys Asp
                        20                  25                  30

Ser Glu Trp Ser Ile Thr Gly Tyr Pro Asn Thr Leu Thr Leu Gln Asn
                        35                  40                  45

Ala Val Gly Arg Thr Asn Asn Ala Thr Glu Lys Asn Leu Ala Leu Val
                    50                  55                  60

Gly His Ile Asp Pro Gly Asn Tyr Phe Ile Thr Val Lys Phe Gly Asp
         65                  70                  75                  80

Lys Val Glu Gln Phe Glu Ile Arg Ser Lys Pro Thr Pro Pro Arg Ile
                            85                  90                  95

Ile Thr Thr Ala Asn Glu Leu Arg Gly Asn Pro Asn His Lys Pro Glu
                        100                 105                 110

Ile Arg Val Thr Asp Ile Pro Asn Asp Thr Thr Ala Lys Ile Lys Leu
                        115                 120                 125

Val Met Gly Gly Thr Asp Gly Asp His Asp Pro Glu Ile Asn Pro Tyr
                    130                 135                 140

Thr Val Pro Glu Asn Tyr Thr Val Val Ala Glu Ala Tyr His Asp Asn
        145                 150                 155                 160

Asp Pro Ser Lys Asn Gly Val Leu Thr Phe Arg Ser Asp Tyr Leu
                        165                 170                 175

Lys Asp Leu Pro Leu Ser Gly Glu Leu Lys Ala Ile Val Tyr Tyr Asn
                        180                 185                 190

Gln Tyr Val Gln Ser Asn Phe Ser Lys Ser Val Pro Phe Ser Ser Asp
                        195                 200                 205

Thr Thr Pro Pro Thr Ile Asn Glu Pro Ala Gly Leu Val His Lys Tyr
                        210                 215                 220

Tyr Arg Gly Asp His Val Glu Ile Thr Leu Pro Val Thr Asp Asn Thr
        225                 230                 235                 240

Gly Gly Ser Gly Leu Arg Asp Val Asn Val Asn Leu Pro Gln Gly Trp
                        245                 250                 255

Thr Lys Thr Phe Thr Ile Asn Pro Asn Asn Asn Thr Glu Gly Thr Leu
                        260                 265                 270

Lys Leu Ile Gly Asn Ile Pro Ser Asn Glu Ala Tyr Asn Thr Thr Tyr
                        275                 280                 285

His Phe Asn Ile Thr Ala Thr Asp Asn Ser Gly Asn Thr Thr Asn Pro
                        290                 295                 300

Ala Lys Thr Phe Ile Leu Asn Val Gly Lys Leu Ala Asp Asp Leu Asn
        305                 310                 315                 320

Pro Val Gly Leu Ser Arg Asp Gln Leu Gln Leu Val Thr Asp Pro Ser
                        325                 330                 335

Ser Leu Ser Asn Ser Glu Arg Glu Val Lys Arg Lys Ile Ser Glu
                        340                 345                 350

Ala Asn Ala Asn Ile Arg Ser Tyr Leu Leu Gln Asn Asn Pro Ile Leu
                        355                 360                 365

Ala Gly Val Asn Gly Asp Val Thr Phe Tyr Tyr Arg Asp Gly Ser Val
                        370                 375                 380

Asp Val Ile Asp Ala Glu Asn Val Ile Thr Tyr Glu Pro Glu Arg Lys
        385                 390                 395                 400

Ser Ile Phe Ser Glu Asn Gly Asn Thr Asn Lys Lys Glu Ala Val Ile
                        405                 410                 415

Thr Ile Ala Arg Gly Gln Asn Tyr Thr Ile Gly Pro Asn Leu Arg Lys
                        420                 425                 430
```

```
Tyr Phe Ser Leu Ser Asn Gly Ser Asp Leu Pro Asn Arg Asp Phe Thr
        435                 440                 445

Ser Ile Ser Ala Ile Gly Ser Leu Pro Ser Ser Glu Ile Ser Arg
    450                 455                 460

Leu Asn Val Gly Asn Tyr Asn Tyr Arg Val Asn Ala Lys Asn Ala Tyr
465                 470                 475                 480

His Lys Thr Gln Gln Glu Leu Asn Leu Lys Leu Lys Ile Val Glu Val
            485                 490                 495

Asn Ala Pro Thr Gly Asn Asn Arg Val Tyr Arg Val Ser Thr Tyr Asn
                500                 505                 510

Leu Thr Asn Asp Glu Ile Asn Lys Ile Lys Gln Ala Phe Lys Ala Ala
            515                 520                 525

Asn Ser Gly Leu Asn Leu Asn Asp Asn Asp Ile Thr Val Ser Asn Asn
                530                 535                 540

Phe Asp His Arg Asn Val Ser Ser Val Thr Val Thr Ile Arg Lys Gly
545                 550                 555                 560

Asp Leu Ile Lys Glu Phe Ser Ser Asn Leu Asn Asn Met Asn Phe Leu
                565                 570                 575

Arg Trp Val Asn Ile Arg Asp Asp Tyr Thr Ile Ser Trp Thr Ser Ser
            580                 585                 590

Lys Ile Gln Gly Arg Asn Thr Asp Gly Gly Leu Glu Trp Ser Pro Asp
            595                 600                 605

His Lys Ser Leu Ile Tyr Lys Tyr Asp Ala Thr Leu Gly Arg Gln Ile
    610                 615                 620

Asn Thr Asn Asp Val Leu Thr Leu Leu Gln Ala Thr Ala Lys Asn Ser
625                 630                 635                 640

Asn Leu Arg Ser Asn Ile Asn Ser Asn Glu Lys Gln Leu Ala Glu Arg
                645                 650                 655

Gly Ser Asn Gly Tyr Ser Lys Ser Ile Ile Arg Asp Asp Gly Glu Lys
                660                 665                 670

Ser Tyr Leu Leu Asn Ser Asn Pro Ile Gln Val Leu Asp Leu Val Glu
    675                 680                 685

Pro Asp Asn Gly Tyr Gly Gly Arg Gln Val Ser His Ser Asn Val Ile
    690                 695                 700

Tyr Asn Glu Lys Asn Ser Ser Ile Val Asn Gly Gln Val Pro Glu Ala
705                 710                 715                 720

Asn Gly Ala Ser Ala Phe Asn Ile Asp Lys Val Val Lys Ala Asn Ala
                725                 730                 735

Ala Asn Asn Gly Ile Met Gly Val Ile Tyr Lys Ala Gln Leu Tyr Leu
                740                 745                 750

Ala Pro Tyr Ser Pro Lys Gly Tyr Ile Glu Lys Leu Gly Gln Asn Leu
    755                 760                 765

Ser Asn Thr Asn Asn Val Ile Asn Val Tyr Phe Val Pro Ser Asp Lys
    770                 775                 780

Val Asn Pro Ser Ile Thr Val Gly Asn Tyr Asp His His Thr Val Tyr
785                 790                 795                 800

Ser Gly Glu Thr Phe Lys Asn Thr Ile Asn Val Asn Asp Asn Tyr Gly
                805                 810                 815

Leu Asn Thr Val Ala Ser Thr Ser Asp Ser Ala Ile Thr Met Thr Arg
                820                 825                 830

Asn Asn Asn Glu Leu Val Gly Gln Ala Pro Asn Val Thr Asn Ser Ile
                835                 840                 845
```

```
Asn Lys Ile Val Lys Val Lys Ala Thr Asp Lys Ser Gly Asn Glu Ser
850                 855                 860
Ile Val Ser Phe Thr Val Asn Ile Lys Pro Leu Asn Glu Lys Tyr Arg
865                 870                 875                 880
Ile Thr Thr Ser Ser Ser Asn Gln Thr Pro Val Arg Ile Ser Asn Ile
                885                 890                 895
Gln Asn Asn Ala Asn Leu Ser Ile Glu Asp Gln Asn Arg Val Lys Ser
            900                 905                 910
Ser Leu Ser Met Thr Lys Ile Leu Gly Thr Arg Asn Tyr Val Asn Glu
        915                 920                 925
Ser Asn Asn Asp Val Arg Ser Gln Val Val Ser Lys Val Asn Arg Ser
    930                 935                 940
Gly Asn Asn Ala Thr Val Asn Val Thr Thr Phe Ser Asp Gly Thr
945                 950                 955                 960
Thr Asn Thr Ile Thr Val Pro Val Lys His Val Leu Leu Glu Val Val
                965                 970                 975
Pro Thr Thr Arg Thr Thr Val Arg Gly Gln Gln Phe Pro Thr Gly Lys
            980                 985                 990
Gly Thr Ser Pro Asn Asp Phe Phe Ser Leu Arg Thr Gly Gly Pro Val
        995                 1000                1005
Asp Ala Arg Ile Val Trp Val Asn Asn Gln Gly Pro Asp Ile Asn Ser
    1010                1015                1020
Asn Gln Ile Gly Arg Asp Leu Thr Leu His Ala Glu Ile Phe Phe Asp
1025                1030                1035                1040
Gly Glu Thr Thr Pro Ile Arg Lys Asp Thr Thr Tyr Lys Leu Ser Gln
                1045                1050                1055
Ser Ile Pro Lys Gln Ile Tyr Glu Thr Thr Ile Asn Gly Arg Phe Asn
            1060                1065                1070
Ser Ser Gly Asp Ala Tyr Pro Gly Asn Phe Val Gln Ala Val Asn Gln
        1075                1080                1085
Tyr Trp Pro Glu His Met Asp Phe Arg Trp Ala Gln Gly Ser Gly Thr
    1090                1095                1100
Pro Ser Ser Arg Asn Ala Gly Ser Phe Thr Lys Thr Val Thr Val Val
1105                1110                1115                1120
Tyr Gln Asn Gly Gln Thr Glu Asn Val Asn Val Leu Phe Lys Val Lys
                1125                1130                1135
Pro Asn Lys Pro Val Ile Asp Ser Asn Ser Val Ile Ser Lys Gly Gln
            1140                1145                1150
Leu Asn Gly Gln Gln Ile Leu Val Arg Asn Val Pro Gln Asn Ala Gln
        1155                1160                1165
Val Thr Leu Tyr Gln Ser Asn Gly Thr Val Ile Pro Asn Thr Asn Thr
    1170                1175                1180
Thr Ile Asp Ser Asn Gly Ile Ala Thr Val Thr Ile Gln Gly Thr Leu
1185                1190                1195                1200
Pro Thr Gly Asn Ile Thr Ala Lys Thr Ser Met Thr Asn Asn Val Thr
                1205                1210                1215
Tyr Thr Lys Gln Asn Ser Ser Gly Ile Ala Ser Asn Thr Thr Glu Asp
            1220                1225                1230
Ile Ser Val Phe Ser Glu Asn Ser Asp Gln Val Asn Val Thr Ala Gly
        1235                1240                1245
Met Gln Ala Lys Asn Asp Gly Ile Lys Ile Ile Lys Gly Thr Asn Tyr
    1250                1255                1260
Asn Phe Asn Asp Phe Asn Ser Phe Ile Ser Asn Ile Pro Ala His Ser
```

```
                1265                1270                1275                1280
            Thr Leu Thr Trp Asn Glu Glu Pro Asn Ser Trp Lys Asn Asn Ile Gly
                            1285                1290                1295

Thr Thr Thr Lys Thr Val Thr Val Thr Leu Pro Asn His Gln Gly Thr
                        1300                1305                1310

Arg Thr Val Asp Ile Pro Ile Thr Ile Tyr Pro Thr Val Thr Ala Lys
                        1315                1320                1325

Asn Pro Val Arg Asp Gln Lys Gly Arg Asn Leu Thr Asn Gly Thr Asp
                        1330                1335                1340

Val Tyr Asn Tyr Ile Ile Phe Glu Asn Asn Arg Leu Gly Gly Thr
            1345                1350                1355                1360

Ala Ser Trp Lys Asp Asn Arg Gln Pro Asp Lys Asn Ile Ala Gly Val
                            1365                1370                1375

Gln Asn Leu Ile Ala Leu Val Asn Tyr Pro Gly Ile Ser Thr Pro Leu
                        1380                1385                1390

Glu Val Pro Val Lys Val Trp Val Tyr Asn Phe Asp Phe Thr Gln Pro
                        1395                1400                1405

Ile Tyr Lys Ile Gln Val Gly Asp Thr Phe Pro Lys Gly Thr Trp Ala
                        1410                1415                1420

Gly Tyr Tyr Lys His Leu Glu Asn Gly Glu Gly Leu Pro Ile Asp Gly
            1425                1430                1435                1440

Trp Lys Phe Tyr Trp Asn Gln Gln Ser Thr Gly Thr Thr Ser Asp Gln
                            1445                1450                1455

Trp Gln Ser Leu Ala Tyr Thr Arg Thr Pro Phe Val Lys Thr Gly Thr
                        1460                1465                1470

Tyr Asp Val Val Asn Pro Ser Asn Trp Gly Val Trp Gln Thr Ser Gln
                        1475                1480                1485

Ser Ala Lys Phe Ile Val Thr Asn Ala Lys Pro Asn Gln Pro Thr Ile
                        1490                1495                1500

Thr Gln Ser Lys Thr Gly Asp Val Thr Val Thr Pro Gly Ala Val Arg
            1505                1510                1515                1520

Asn Ile Leu Ile Ser Gly Thr Asn Asp Tyr Ile Gln Ala Ser Ala Asp
                            1525                1530                1535

Lys Ile Val Ile Asn Lys Asn Gly Asn Lys Leu Thr Thr Phe Val Lys
                        1540                1545                1550

Asn Asn Asp Gly Arg Trp Thr Val Glu Thr Gly Ser Pro Asp Ile Asn
                        1555                1560                1565

Gly Ile Gly Pro Thr Asn Asn Gly Thr Ala Ile Ser Leu Ser Arg Leu
                        1570                1575                1580

Ala Val Arg Pro Gly Asp Ser Ile Glu Ala Ile Ala Thr Glu Gly Ser
            1585                1590                1595                1600

Gly Glu Thr Ile Ser Thr Ser Ala Thr Ser Glu Ile Tyr Ile Val Lys
                            1605                1610                1615

Ala Pro Gln Pro Glu Gln Val Ala Thr His Thr Tyr Asp Asn Gly Thr
                        1620                1625                1630

Phe Asp Ile Leu Pro Asp Asn Ser Arg Asn Ser Leu Asn Pro Thr Glu
                        1635                1640                1645

Arg Val Glu Ile Asn Tyr Thr Glu Lys Leu Asn Gly Asn Glu Thr Gln
                        1650                1655                1660

Lys Ser Phe Thr Ile Thr Lys Asn Asn Asn Gly Lys Trp Thr Ile Asn
            1665                1670                1675                1680

Asn Lys Pro Asn Tyr Val Glu Phe Asn Gln Asp Asn Gly Lys Val Val
                            1685                1690                1695
```

```
Phe Ser Ala Asn Thr Ile Lys Pro Asn Ser Gln Ile Thr Ile Thr Pro
        1700                1705                1710

Lys Ala Gly Gln Gly Asn Thr Glu Asn Thr Asn Pro Thr Val Ile Gln
        1715                1720                1725

Ala Pro Ala Gln His Thr Leu Thr Ile Asn Glu Ile Val Lys Glu Gln
        1730                1735                1740

Gly Gln Asn Val Thr Asn Asp Asp Ile Asn Ala Val Gln Val Pro
1745                1750                1755                1760

Asn Lys Asn Arg Val Ala Ile Lys Gln Gly Asn Ala Leu Pro Thr Asn
                1765                1770                1775

Leu Ala Gly Gly Ser Thr Ser His Ile Pro Val Val Ile Tyr Tyr Ser
        1780                1785                1790

Asp Gly Ser Ser Glu Glu Ala Thr Glu Thr Val Arg Thr Lys Val Asn
        1795                1800                1805

Lys Thr Glu Leu Ile Asn Ala Arg Arg Arg Leu Asp Glu Glu Ile Ser
        1810                1815                1820

Lys Glu Asn Lys Thr Pro Ser Ser Ile Arg Asn Phe Asp Gln Ala Met
1825                1830                1835                1840

Asn Arg Ala Gln Ser Gln Ile Asn Thr Ala Lys Ser Asp Ala Asp Gln
                1845                1850                1855

Val Ile Gly Thr Glu Phe Ala Thr Pro Gln Gln Val Asn Ser Ala Leu
        1860                1865                1870

Ser Lys Val Gln Ala Ala Gln Asn Lys Ile Asn Glu Ala Lys Ala Leu
        1875                1880                1885

Leu Gln Asn Lys Ala Asp Asn Ser Gln Leu Val Arg Ala Lys Glu Gln
        1890                1895                1900

Leu Gln Gln Ser Ile Gln Pro Ala Ala Ser Thr Asp Gly Met Thr Gln
1905                1910                1915                1920

Asp Ser Thr Arg Asn Tyr Asn Asn Lys Arg Gln Ala Ala Glu Gln Ala
                1925                1930                1935

Ile Gln His Ala Asn Ser Val Ile Asn Asn Gly Asp Ala Thr Ser Gln
        1940                1945                1950

Gln Ile Asn Asp Ala Lys Asn Thr Val Glu Gln Ala Gln Arg Asp Tyr
        1955                1960                1965

Val Glu Ala Lys Ser Asn Leu Arg Ala Asp Lys Ser Gln Leu Gln Ser
        1970                1975                1980

Ala Tyr Asp Thr Leu Asn Arg Asp Val Leu Thr Asn Asp Lys Lys Pro
1985                1990                1995                2000

Ala Ser Val Arg Arg Tyr Asn Glu Ala Ile Ser Asn Ile Arg Lys Glu
                2005                2010                2015

Leu Asp Thr Ala Lys Ala Asp Ala Ser Ser Thr Leu Arg Asn Thr Asn
        2020                2025                2030

Pro Ser Val Glu Gln Val Arg Asp Ala Leu Asn Lys Ile Asn Thr Val
        2035                2040                2045

Gln Pro Lys Val Asn Gln Ala Ile Ala Leu Leu Gln Pro Lys Glu Asn
        2050                2055                2060

Asn Ser Glu Leu Val Gln Ala Lys Lys Arg Leu Gln Asp Ala Val Asn
2065                2070                2075                2080

Asp Ile Pro Gln Thr Gln Gly Met Thr Gln Gln Thr Ile Asn Asn Tyr
                2085                2090                2095

Asn Asp Lys Gln Arg Glu Ala Glu Arg Ala Leu Thr Ala Gln Arg
                2100                2105                2110
```

-continued

```
Val Ile Asp Asn Gly Asp Ala Thr Thr Gln Glu Ile Thr Ser Glu Lys
            2115                2120                2125

Ser Lys Val Glu Gln Ala Met Gln Ala Leu Thr Asn Ala Lys Ser Asn
        2130                2135                2140

Leu Arg Ala Asp Lys Asn Glu Leu Gln Thr Ala Tyr Asn Lys Leu Ile
2145                2150                2155                2160

Glu Asn Val Ser Thr Asn Gly Lys Lys Pro Ala Ser Ile Arg Gln Tyr
            2165                2170                2175

Glu Thr Ala Lys Ala Arg Ile Gln Asn Gln Ile Asn Asp Ala Lys Asn
            2180                2185                2190

Glu Ala Glu Arg Ile Leu Gly Asn Asp Asn Pro Gln Val Ser Gln Val
            2195                2200                2205

Thr Gln Ala Leu Asn Lys Ile Lys Ala Ile Gln Pro Lys Leu Thr Glu
            2210                2215                2220

Ala Ile Asn Met Leu Gln Asn Lys Glu Asn Asn Thr Glu Leu Val Asn
2225                2230                2235                2240

Ala Lys Asn Arg Leu Glu Asn Ala Val Asn Asp Thr Asp Pro Thr His
            2245                2250                2255

Gly Met Thr Gln Glu Thr Ile Asn Asn Tyr Asn Ala Lys Lys Arg Glu
            2260                2265                2270

Ala Gln Asn Glu Ile Gln Lys Ala Asn Met Ile Ile Asn Asn Gly Asp
            2275                2280                2285

Ala Thr Ala Gln Asp Ile Ser Ser Glu Lys Ser Lys Val Glu Gln Val
            2290                2295                2300

Leu Gln Ala Leu Gln Asn Ala Lys Asn Asp Leu Arg Ala Asp Lys Arg
2305                2310                2315                2320

Glu Leu Gln Thr Ala Tyr Asn Lys Leu Ile Gln Asn Val Asn Thr Asn
            2325                2330                2335

Gly Lys Lys Pro Ser Ser Ile Gln Asn Tyr Lys Ser Ala Arg Arg Asn
            2340                2345                2350

Ile Glu Asn Gln Tyr Asn Thr Ala Lys Asn Glu Ala His Asn Val Leu
            2355                2360                2365

Glu Asn Thr Asn Pro Thr Val Asn Ala Val Glu Asp Ala Leu Arg Lys
            2370                2375                2380

Ile Asn Ala Ile Gln Pro Glu Val Thr Lys Ala Ile Asn Ile Leu Gln
2385                2390                2395                2400

Asp Lys Glu Asp Asn Ser Glu Leu Val Arg Ala Lys Glu Lys Leu Asp
            2405                2410                2415

Gln Ala Ile Asn Ser Gln Pro Ser Leu Asn Gly Met Thr Gln Glu Ser
            2420                2425                2430

Ile Asn Asn Tyr Thr Thr Lys Arg Arg Glu Ala Gln Asn Ile Ala Ser
            2435                2440                2445

Ser Ala Asp Thr Ile Ile Asn Asn Gly Asp Ala Ser Ile Glu Gln Ile
            2450                2455                2460

Thr Glu Asn Lys Ile Arg Val Glu Glu Ala Thr Asn Ala Leu Asn Glu
2465                2470                2475                2480

Ala Lys Gln His Leu Thr Ala Asp Thr Thr Ser Leu Lys Thr Glu Val
            2485                2490                2495

Arg Lys Leu Ser Arg Arg Gly Asp Thr Asn Asn Lys Lys Pro Ser Ser
            2500                2505                2510

Val Ser Ala Tyr Asn Asn Thr Ile His Ser Leu Gln Ser Glu Ile Thr
            2515                2520                2525

Gln Thr Glu Asn Arg Ala Asn Thr Ile Ile Asn Lys Pro Ile Arg Ser
```

```
                    2530            2535            2540
Val Glu Glu Val Asn Asn Ala Leu His Glu Val Asn Gln Leu Asn Gln
2545                2550            2555            2560

Arg Leu Thr Asp Thr Ile Asn Leu Leu Gln Pro Leu Ala Asn Lys Glu
            2565            2570            2575

Ser Leu Lys Glu Ala Arg Asn Arg Leu Glu Ser Lys Ile Asn Glu Thr
        2580            2585            2590

Val Gln Thr Asp Gly Met Thr Gln Gln Ser Val Glu Asn Tyr Lys Gln
        2595            2600            2605

Ala Lys Ile Lys Ala Gln Asn Glu Ser Ser Ile Ala Gln Thr Leu Ile
        2610            2615            2620

Asn Asn Gly Asp Ala Ser Asp Gln Glu Val Ser Thr Glu Ile Glu Lys
2625            2630            2635            2640

Leu Asn Gln Lys Leu Ser Glu Leu Thr Asn Ser Ile Asn His Leu Thr
            2645            2650            2655

Val Asn Lys Glu Pro Leu Glu Thr Ala Lys Asn Gln Leu Gln Ala Asn
            2660            2665            2670

Ile Asp Gln Lys Pro Ser Thr Asp Gly Met Thr Gln Gln Ser Val Gln
            2675            2680            2685

Ser Tyr Glu Arg Lys Leu Gln Glu Ala Lys Asp Lys Ile Asn Ser Ile
            2690            2695            2700

Asn Asn Val Leu Ala Asn Asn Pro Asp Val Asn Ala Ile Arg Thr Asn
2705            2710            2715            2720

Lys Val Glu Thr Glu Gln Ile Asn Asn Glu Leu Thr Gln Ala Lys Gln
            2725            2730            2735

Gly Leu Thr Val Asp Lys Gln Pro Leu Ile Asn Ala Lys Thr Ala Leu
            2740            2745            2750

Gln Gln Ser Leu Asp Asn Gln Pro Ser Thr Thr Gly Met Thr Glu Ala
            2755            2760            2765

Thr Ile Gln Asn Tyr Asn Ala Lys Arg Gln Lys Ala Glu Gln Val Ile
            2770            2775            2780

Gln Asn Ala Asn Lys Ile Ile Glu Asn Ala Gln Pro Ser Val Gln Gln
2785            2790            2795            2800

Val Ser Asp Glu Lys Ser Lys Val Glu Gln Ala Leu Ser Glu Leu Asn
            2805            2810            2815

Asn Ala Lys Ser Ala Leu Arg Ala Asp Lys Gln Glu Leu Gln Gln Ala
            2820            2825            2830

Tyr Asn Gln Leu Ile Gln Pro Thr Asp Leu Asn Asn Lys Lys Pro Ala
            2835            2840            2845

Ser Ile Thr Ala Tyr Asn Gln Arg Tyr Gln Gln Phe Ser Asn Glu Leu
            2850            2855            2860

Asn Ser Thr Lys Thr Asn Thr Asp Arg Ile Leu Lys Glu Gln Asn Pro
2865            2870            2875            2880

Ser Val Ala Asp Val Asn Asn Ala Leu Asn Lys Val Arg Glu Val Gln
            2885            2890            2895

Gln Lys Leu Asn Glu Ala Arg Ala Leu Leu Gln Asn Lys Glu Asp Asn
            2900            2905            2910

Ser Ala Leu Val Arg Ala Lys Glu Gln Leu Gln Gln Ala Val Asp Gln
            2915            2920            2925

Val Pro Ser Thr Glu Gly Met Thr Gln Gln Thr Lys Asp Asp Tyr Asn
            2930            2935            2940

Ser Lys Gln Gln Ala Ala Gln Gln Glu Ile Ser Lys Ala Gln Gln Val
2945            2950            2955            2960
```

```
Ile Asp Asn Gly Asp Ala Thr Thr Gln Gln Ile Ser Asn Ala Lys Thr
            2965                2970                2975

Asn Val Glu Arg Ala Leu Glu Ala Leu Asn Asn Ala Lys Thr Gly Leu
        2980                2985                2990

Arg Ala Asp Lys Glu Glu Leu Gln Asn Ala Tyr Asn Gln Leu Thr Gln
    2995                3000                3005

Asn Ile Asp Thr Ser Gly Lys Thr Pro Ala Ser Ile Arg Lys Tyr Asn
3010                3015                3020

Glu Ala Lys Ser Arg Ile Gln Thr Gln Ile Asp Ser Ala Lys Asn Glu
3025                3030                3035                3040

Ala Asn Ser Ile Leu Thr Asn Asp Asn Pro Gln Val Ser Gln Val Thr
            3045                3050                3055

Ala Ala Leu Asn Lys Ile Lys Ala Val Gln Pro Glu Leu Asp Lys Ala
        3060                3065                3070

Ile Ala Met Leu Lys Asn Lys Glu Asn Asn Ala Leu Val Gln Ala
            3075                3080                3085

Lys Gln Gln Leu Gln Gln Ile Val Asn Glu Val Asp Pro Thr Gln Gly
    3090                3095                3100

Met Thr Thr Asp Thr Ala Asn Asn Tyr Lys Ser Lys Lys Arg Glu Ala
3105                3110                3115                3120

Glu Asp Glu Ile Gln Lys Ala Gln Gln Ile Ile Asn Asn Gly Asp Ala
            3125                3130                3135

Thr Glu Gln Gln Ile Thr Asn Glu Thr Asn Arg Val Asn Gln Ala Ile
        3140                3145                3150

Asn Ala Ile Asn Lys Ala Lys Asn Asp Leu Arg Ala Asp Lys Ser Gln
    3155                3160                3165

Leu Glu Asn Ala Tyr Asn Gln Leu Ile Gln Asn Val Asp Thr Asn Gly
3170                3175                3180

Lys Lys Pro Ala Ser Ile Gln Gln Tyr Gln Ala Ala Arg Gln Ala Ile
3185                3190                3195                3200

Glu Thr Gln Tyr Asn Asn Ala Lys Ser Glu Ala His Gln Ile Leu Glu
            3205                3210                3215

Asn Ser Asn Pro Ser Val Asn Glu Val Ala Gln Ala Leu Gln Lys Val
        3220                3225                3230

Glu Ala Val Gln Leu Lys Val Asn Asp Ala Ile His Ile Leu Gln Asn
    3235                3240                3245

Lys Glu Asn Asn Ser Ala Leu Val Thr Ala Lys Asn Gln Leu Gln Gln
3250                3255                3260

Ser Val Asn Asp Gln Pro Leu Thr Thr Gly Met Thr Gln Asp Ser Ile
3265                3270                3275                3280

Asn Asn Tyr Glu Ala Lys Arg Asn Glu Ala Gln Ser Ala Ile Arg Asn
            3285                3290                3295

Ala Glu Ala Val Ile Asn Asn Gly Asp Ala Thr Ala Lys Gln Ile Ser
        3300                3305                3310

Asp Glu Lys Ser Lys Val Glu Gln Ala Leu Ala His Leu Asn Asp Ala
    3315                3320                3325

Lys Gln Gln Leu Thr Ala Asp Thr Thr Glu Leu Gln Thr Ala Val Gln
3330                3335                3340

Gln Leu Asn Arg Arg Gly Asp Thr Asn Lys Lys Pro Arg Ser Ile
3345                3350                3355                3360

Asn Ala Tyr Asn Lys Ala Ile Gln Ser Leu Glu Thr Gln Ile Thr Ser
            3365                3370                3375
```

```
Ala Lys Asp Asn Ala Asn Ala Val Ile Gln Lys Pro Ile Arg Thr Val
        3380                3385                3390

Gln Glu Val Asn Ala Leu Gln Gln Val Asn Gln Leu Asn Gln Gln
        3395                3400            3405

Leu Thr Glu Ala Ile Asn Gln Leu Gln Pro Leu Ser Asn Asn Asp Ala
        3410                3415                3420

Leu Lys Ala Ala Arg Leu Asn Leu Glu Asn Lys Ile Asn Gln Thr Val
3425            3430                3435                3440

Gln Thr Asp Gly Met Thr Gln Gln Ser Ile Glu Ala Tyr Gln Asn Ala
        3445                3450                3455

Lys Arg Val Ala Gln Asn Glu Ser Asn Thr Ala Leu Ala Leu Ile Asn
        3460                3465                3470

Asn Gly Asp Ala Asp Glu Gln Gln Ile Thr Thr Glu Thr Asp Arg Val
        3475                3480                3485

Asn Gln Gln Thr Thr Asn Leu Thr Gln Ala Ile Asn Gly Leu Thr Val
        3490                3495                3500

Asn Lys Glu Pro Leu Glu Thr Ala Lys Thr Ala Leu Gln Asn Asn Ile
3505            3510                3515                3520

Asp Gln Val Pro Ser Thr Asp Gly Met Thr Gln Gln Ser Val Ala Asn
        3525                3530                3535

Tyr Asn Gln Lys Leu Gln Ile Ala Lys Asn Glu Ile Asn Thr Ile Asn
        3540                3545                3550

Asn Val Leu Ala Asn Asn Pro Asp Val Asn Ala Ile Lys Thr Asn Lys
        3555                3560                3565

Ala Glu Ala Glu Arg Ile Ser Asn Asp Leu Thr Gln Ala Lys Asn Asn
        3570                3575                3580

Leu Gln Val Asp Thr Gln Pro Leu Glu Lys Ile Lys Arg Gln Leu Gln
3585            3590                3595                3600

Asp Glu Ile Asp Gln Gly Thr Asn Thr Asp Gly Met Thr Gln Asp Ser
        3605                3610                3615

Val Asp Asn Tyr Asn Asp Ser Leu Ser Ala Ala Ile Ile Glu Lys Gly
        3620                3625                3630

Lys Val Asn Lys Leu Leu Lys Arg Asn Pro Thr Val Glu Gln Val Lys
        3635                3640                3645

Glu Ser Val Ala Asn Ala Gln Gln Val Ile Gln Asp Leu Gln Asn Ala
        3650                3655                3660

Arg Thr Ser Leu Val Pro Asp Lys Thr Gln Leu Gln Glu Ala Lys Asn
3665            3670                3675                3680

Arg Leu Glu Asn Ser Ile Asn Gln Gln Thr Asp Thr Asp Gly Met Thr
        3685                3690                3695

Gln Asp Ser Leu Asn Asn Tyr Asn Asp Lys Leu Ala Lys Ala Arg Gln
        3700                3705                3710

Asn Leu Glu Lys Ile Ser Lys Val Leu Gly Gly Gln Pro Thr Val Ala
        3715                3720                3725

Glu Ile Arg Gln Asn Thr Asp Glu Ala Asn Ala His Lys Gln Ala Leu
        3730                3735                3740

Asp Thr Ala Arg Ser Gln Leu Thr Leu Asn Arg Glu Pro Tyr Ile Asn
3745            3750                3755                3760

His Ile Asn Asn Glu Ser His Leu Asn Asn Ala Gln Lys Asp Asn Phe
        3765                3770                3775

Lys Ala Gln Val Asn Ser Ala Pro Asn His Asn Thr Leu Glu Thr Ile
        3780                3785                3790

Lys Asn Lys Ala Asp Thr Leu Asn Gln Ser Met Thr Ala Leu Ser Glu
```

```
             3795                3800                3805

Ser Ile Ala Asp Tyr Glu Asn Gln Lys Gln Gln Glu Asn Tyr Leu Asp
         3810                3815                3820

Ala Ser Asn Asn Lys Arg Gln Asp Tyr Asp Asn Ala Val Asn Ala Ala
3825                3830                3835                3840

Lys Gly Ile Leu Asn Gln Thr Gln Ser Pro Thr Met Ser Ala Asp Val
             3845                3850                3855

Ile Asp Gln Lys Ala Glu Asp Val Lys Arg Thr Lys Thr Ala Leu Asp
         3860                3865                3870

Gly Asn Gln Arg Leu Glu Val Ala Lys Gln Gln Ala Leu Asn His Leu
     3875                3880                3885

Asn Thr Leu Asn Asp Leu Asn Asp Ala Gln Arg Gln Thr Leu Thr Asp
         3890                3895                3900

Thr Ile Asn His Ser Pro Asn Ile Asn Ser Val Asn Gln Ala Lys Glu
3905                3910                3915                3920

Lys Ala Asn Thr Val Asn Thr Ala Met Thr Gln Leu Lys Gln Thr Ile
             3925                3930                3935

Ala Asn Tyr Asp Asp Glu Leu His Asp Gly Asn Tyr Ile Asn Ala Asp
         3940                3945                3950

Lys Asp Lys Lys Asp Ala Tyr Asn Asn Ala Val Asn Asn Ala Lys Gln
     3955                3960                3965

Leu Ile Asn Gln Ser Asp Ala Asn Gln Ala Gln Leu Asp Pro Ala Glu
         3970                3975                3980

Ile Asn Lys Val Thr Gln Arg Val Asn Thr Thr Lys Asn Asp Leu Asn
3985                3990                3995                4000

Gly Asn Asp Lys Leu Ala Glu Ala Lys Arg Asp Ala Asn Thr Thr Ile
             4005                4010                4015

Asp Gly Leu Thr Tyr Leu Asn Glu Ala Gln Arg Asn Lys Ala Lys Glu
         4020                4025                4030

Asn Val Gly Lys Ala Ser Thr Lys Thr Asn Ile Thr Ser Gln Leu Gln
     4035                4040                4045

Asp Tyr Asn Gln Leu Asn Ile Ala Met Gln Ala Leu Arg Asn Ser Val
         4050                4055                4060

Asn Asp Val Asn Asn Val Lys Ala Asn Ser Asn Tyr Ile Asn Glu Asp
4065                4070                4075                4080

Asn Gly Pro Lys Glu Ala Tyr Asn Gln Ala Val Thr His Ala Gln Thr
             4085                4090                4095

Leu Ile Asn Ala Gln Ser Asn Pro Glu Met Ser Arg Asp Val Val Asn
         4100                4105                4110

Gln Lys Thr Gln Ala Val Asn Thr Ala His Gln Asn Leu His Gly Gln
     4115                4120                4125

Gln Lys Leu Glu Gln Ala Gln Ser Ser Ala Asn Thr Glu Ile Gly Asn
         4130                4135                4140

Leu Pro Asn Leu Thr Asn Thr Gln Lys Ala Lys Glu Lys Glu Leu Val
4145                4150                4155                4160

Asn Ser Lys Gln Thr Arg Thr Glu Val Gln Glu Leu Asn Gln Ala
             4165                4170                4175

Lys Ser Leu Asp Ser Ser Met Gly Thr Leu Lys Ser Leu Val Ala Lys
         4180                4185                4190

Gln Pro Thr Val Gln Lys Thr Ser Val Tyr Ile Asn Glu Asp Gln Pro
     4195                4200                4205

Glu Gln Ser Ala Tyr Asn Asp Ser Ile Thr Met Gly Gln Thr Ile Ile
         4210                4215                4220
```

-continued

```
Asn Lys Thr Ala Asp Pro Val Leu Asp Lys Thr Leu Val Asp Asn Ala
4225                4230                4235                4240

Ile Ser Asn Ile Ser Thr Lys Glu Asn Ala Leu His Gly Glu Gln Lys
                4245                4250                4255

Leu Thr Thr Ala Lys Thr Glu Ala Ile Asn Ala Leu Asn Thr Leu Ala
                4260                4265                4270

Asp Leu Asn Thr Pro Gln Lys Glu Ala Ile Lys Thr Ala Ile Asn Thr
            4275                4280                4285

Ala His Thr Arg Thr Asp Val Thr Ala Glu Gln Ser Lys Ala Asn Gln
            4290                4295                4300

Ile Asn Ser Ala Met His Thr Leu Arg Gln Asn Ile Ser Asp Asn Glu
4305                4310                4315                4320

Ser Val Thr Asn Glu Ser Asn Tyr Ile Asn Ala Glu Pro Glu Lys Gln
                4325                4330                4335

His Ala Phe Thr Glu Ala Leu Asn Asn Ala Lys Glu Ile Val Asn Glu
                4340                4345                4350

Gln Gln Ala Thr Leu Asp Ala Asn Ser Ile Asn Gln Lys Ala Gln Ala
            4355                4360                4365

Ile Leu Thr Thr Lys Asn Ala Leu Asp Gly Glu Glu Gln Leu Arg Arg
            4370                4375                4380

Ala Lys Glu Asn Ala Asp Gln Glu Ile Asn Thr Leu Asn Gln Leu Thr
4385                4390                4395                4400

Asp Ala Gln Arg Asn Ser Glu Lys Gly Leu Val Asn Ser Ser Gln Thr
                4405                4410                4415

Arg Thr Glu Val Ala Ser Gln Leu Ala Lys Ala Lys Glu Leu Asn Lys
                4420                4425                4430

Val Met Glu Gln Leu Asn His Leu Ile Asn Gly Lys Asn Gln Met Ile
            4435                4440                4445

Asn Ser Ser Lys Phe Ile Asn Glu Asp Ala Asn Gln Gln Gln Ala Tyr
            4450                4455                4460

Ser Asn Ala Ile Ala Ser Ala Glu Ala Leu Lys Asn Lys Ser Gln Asn
4465                4470                4475                4480

Pro Glu Leu Asp Lys Val Thr Ile Glu Gln Ala Ile Asn Asn Ile Asn
                4485                4490                4495

Ser Ala Ile Asn Asn Leu Asn Gly Glu Ala Lys Leu Thr Lys Ala Lys
                4500                4505                4510

Glu Asp Ala Val Ala Ser Ile Asn Asn Leu Ser Gly Leu Thr Asn Glu
            4515                4520                4525

Gln Lys Thr Lys Glu Asn Gln Ala Val Asn Gly Ala Gln Thr Arg Asp
            4530                4535                4540

Gln Val Ala Asn Lys Leu Arg Asp Ala Glu Ala Leu Asp Gln Ser Met
4545                4550                4555                4560

Gln Thr Leu Arg Asp Leu Val Asn Asn Gln Asn Ala Ile His Ser Thr
                4565                4570                4575

Ser Asn Tyr Phe Asn Glu Asp Ser Thr Gln Lys Asn Thr Tyr Asp Asn
                4580                4585                4590

Ala Ile Asp Asn Gly Ser Thr Tyr Ile Thr Gly Gln His Asn Pro Glu
            4595                4600                4605

Leu Asn Lys Ser Thr Ile Asp Gln Thr Ile Ser Arg Ile Asn Thr Ala
            4610                4615                4620

Lys Asn Asp Leu His Gly Val Glu Lys Leu Gln Arg Asp Lys Gly Thr
4625                4630                4635                4640
```

```
Ala Asn Gln Glu Ile Gly Gln Leu Gly Tyr Leu Asn Asp Pro Gln Lys
            4645                4650                4655

Ser Gly Glu Glu Ser Leu Val Asn Gly Ser Asn Thr Arg Ser Glu Val
            4660                4665                4670

Glu Glu His Leu Asn Glu Ala Lys Ser Leu Asn Asn Ala Met Lys Gln
            4675                4680                4685

Leu Arg Asp Lys Val Ala Glu Lys Thr Asn Val Lys Gln Ser Ser Asp
            4690                4695                4700

Tyr Ile Asn Asp Ser Thr Glu His Gln Arg Gly Tyr Asp Gln Ala Leu
4705                4710                4715                4720

Gln Glu Ala Glu Asn Ile Ile Asn Glu Ile Gly Asn Pro Thr Leu Asn
            4725                4730                4735

Lys Ser Glu Ile Glu Gln Lys Leu Gln Gln Leu Thr Asp Ala Gln Asn
            4740                4745                4750

Ala Leu Gln Gly Ser His Leu Leu Glu Glu Ala Lys Asn Asn Ala Ile
            4755                4760                4765

Thr Gly Ile Asn Lys Leu Thr Ala Leu Asn Asp Ala Gln Arg Gln Lys
            4770                4775                4780

Ala Ile Glu Asn Val Gln Ala Gln Gln Thr Ile Pro Ala Val Asn Gln
4785                4790                4795                4800

Gln Leu Thr Leu Asp Arg Glu Ile Asn Thr Ala Met Gln Ala Leu Arg
            4805                4810                4815

Asp Lys Val Gly Gln Gln Asn Asn Val His Gln Ser Asn Tyr Phe
            4820                4825                4830

Asn Glu Asp Glu Gln Pro Lys His Asn Tyr Asp Asn Ser Val Gln Ala
            4835                4840                4845

Gly Gln Thr Ile Ile Asp Lys Leu Gln Asp Pro Ile Met Asn Lys Asn
            4850                4855                4860

Glu Ile Glu Gln Ala Ile Asn Gln Ile Asn Thr Thr Gln Thr Ala Leu
4865                4870                4875                4880

Ser Gly Glu Asn Lys Leu His Thr Asp Gln Glu Ser Thr Asn Arg Gln
            4885                4890                4895

Ile Glu Gly Leu Ser Ser Leu Asn Thr Ala Gln Ile Asn Ala Glu Lys
            4900                4905                4910

Asp Leu Val Asn Gln Ala Lys Thr Arg Thr Asp Val Ala Gln Lys Leu
            4915                4920                4925

Ala Ala Ala Lys Glu Ile Asn Ser Ala Met Ser Asn Leu Arg Asp Gly
            4930                4935                4940

Ile Gln Asn Lys Glu Asp Ile Lys Arg Ser Ser Ala Tyr Ile Asn Ala
4945                4950                4955                4960

Asp Pro Thr Lys Val Thr Ala Tyr Asp Gln Ala Leu Gln Asn Ala Glu
            4965                4970                4975

Asn Ile Ile Asn Ala Thr Pro Asn Val Glu Leu Asn Lys Ala Thr Ile
            4980                4985                4990

Glu Gln Ala Leu Ser Arg Val Gln Gln Ala Gln Asp Leu Asp Gly
            4995                5000                5005

Val Gln Gln Leu Ala Asn Ala Lys Gln Ala Thr Gln Thr Val Asn
            5010                5015                5020

Gly Leu Asn Ser Leu Asn Asp Gly Gln Lys Arg Glu Leu Asn Leu Leu
5025                5030                5035                5040

Ile Asn Ser Ala Asn Thr Arg Thr Lys Val Gln Glu Glu Leu Asn Lys
            5045                5050                5055

Ala Thr Glu Leu Asn His Ala Met Glu Ala Leu Arg Asn Ser Val Gln
```

```
                  5060          5065              5070
Asn Val Asp Gln Val Lys Gln Ser Ser Asn Tyr Val Asn Glu Asp Gln
            5075            5080            5085

Pro Glu Gln His Asn Tyr Asp Asn Ala Val Asn Glu Ala Gln Ala Thr
            5090            5095            5100

Ile Asn Asn Asn Ala Gln Pro Val Leu Asp Lys Leu Ala Ile Glu Arg
5105            5110            5115            5120

Leu Thr Gln Thr Val Asn Thr Thr Lys Asp Ala Leu His Gly Ala Gln
            5125            5130            5135

Lys Leu Thr Gln Asp Gln Gln Ala Ala Glu Thr Gly Ile Arg Gly Leu
            5140            5145            5150

Thr Ser Leu Asn Glu Pro Gln Lys Asn Ala Glu Val Ala Lys Val Thr
            5155            5160            5165

Ala Ala Thr Thr Arg Asp Glu Val Arg Asn Ile Arg Gln Glu Ala Thr
            5170            5175            5180

Thr Leu Asp Thr Ala Met Leu Gly Leu Arg Lys Ser Ile Lys Asp Lys
5185            5190            5195            5200

Asn Asp Thr Lys Asn Ser Ser Lys Tyr Ile Asn Glu Asp His Asp Gln
            5205            5210            5215

Gln Gln Ala Tyr Asp Asn Ala Val Asn Asn Ala Gln Val Ile Asp
            5220            5225            5230

Glu Thr Gln Ala Thr Leu Ser Ser Asp Thr Ile Asn Gln Leu Ala Asn
            5235            5240            5245

Ala Val Thr Gln Ala Lys Ser Asn Leu His Gly Asp Thr Lys Leu Gln
            5250            5255            5260

His Asp Lys Asp Ser Ala Lys Gln Thr Ile Ala Gln Leu Gln Asn Leu
5265            5270            5275            5280

Asn Ser Ala Gln Lys His Met Glu Asp Ser Leu Ile Asp Asn Glu Ser
            5285            5290            5295

Thr Arg Thr Gln Val Gln His Asp Leu Thr Glu Ala Gln Ala Leu Asp
            5300            5305            5310

Gly Leu Met Gly Ala Leu Lys Glu Ser Ile Lys Asp Tyr Thr Asn Ile
            5315            5320            5325

Val Ser Asn Gly Asn Tyr Ile Asn Ala Glu Pro Ser Lys Lys Gln Ala
            5330            5335            5340

Tyr Asp Ala Ala Val Gln Asn Ala Gln Asn Ile Ile Asn Gly Thr Asn
5345            5350            5355            5360

Gln Pro Thr Ile Asn Lys Gly Asn Val Thr Thr Ala Thr Gln Thr Val
            5365            5370            5375

Lys Asn Thr Lys Asp Ala Leu Asp Gly Asp His Arg Leu Glu Glu Ala
            5380            5385            5390

Lys Asn Asn Ala Asn Gln Thr Ile Arg Asn Leu Ser Asn Leu Asn Asn
            5395            5400            5405

Ala Gln Lys Asp Ala Glu Lys Asn Leu Val Asn Ser Ala Ser Thr Leu
            5410            5415            5420

Glu Gln Val Gln Gln Asn Leu Gln Thr Ala Gln Gln Leu Asp Asn Ala
5425            5430            5435            5440

Met Gly Glu Leu Arg Gln Ser Ile Ala Lys Lys Asp Gln Val Lys Ala
            5445            5450            5455

Asp Ser Lys Tyr Leu Asn Glu Asp Pro Gln Ile Lys Gln Asn Tyr Asp
            5460            5465            5470

Asp Ala Val Gln Arg Val Glu Thr Ile Ile Asn Glu Thr Gln Asn Pro
            5475            5480            5485
```

```
Glu Leu Leu Lys Ala Asn Ile Asp Gln Ala Thr Gln Ser Val Gln Asn
        5490                5495                5500
Ala Glu Gln Ala Leu His Gly Ala Glu Lys Leu Asn Gln Asp Lys Gln
5505                5510                5515                5520
Thr Ser Ser Thr Glu Leu Asp Gly Leu Thr Asp Leu Thr Asp Ala Gln
            5525                5530                5535
Arg Glu Lys Leu Arg Glu Gln Ile Asn Thr Ser Asn Ser Arg Asp Asp
        5540                5545                5550
Ile Lys Gln Lys Ile Glu Gln Ala Lys Ala Leu Asn Asp Ala Met Lys
    5555                5560                5565
Lys Leu Lys Glu Gln Val Ala Gln Lys Asp Gly Val His Ala Asn Ser
        5570                5575                5580
Asp Tyr Thr Asn Glu Asp Ser Ala Gln Lys Asp Ala Tyr Asn Asn Ala
5585                5590                5595                5600
Leu Lys Gln Ala Glu Asp Ile Ile Asn Asn Ser Ser Asn Pro Asn Leu
            5605                5610                5615
Asn Ala Gln Asp Ile Thr Asn Ala Leu Asn Asn Ile Lys Gln Ala Gln
        5620                5625                5630
Asp Asn Leu His Gly Ala Gln Lys Leu Gln Asp Lys Asn Thr Thr
    5635                5640                5645
Asn Gln Ala Ile Gly Asn Leu Asn His Leu Asn Gln Pro Gln Lys Asp
        5650                5655                5660
Ala Leu Ile Gln Ala Ile Asn Gly Ala Thr Ser Arg Asp Gln Val Ala
5665                5670                5675                5680
Glu Lys Leu Lys Glu Ala Glu Ala Leu Asp Glu Ala Met Lys Gln Leu
            5685                5690                5695
Glu Asp Gln Val Asn Gln Asp Gln Ile Ser Asn Ser Ser Pro Phe
        5700                5705                5710
Ile Asn Glu Asp Ser Asp Lys Gln Lys Thr Tyr Asn Asp Lys Ile Gln
            5715                5720                5725
Ala Ala Lys Glu Ile Ile Asn Gln Thr Ser Asn Pro Thr Leu Asp Lys
        5730                5735                5740
Gln Lys Ile Ala Asp Thr Leu Gln Asn Ile Lys Asp Ala Val Asn Asn
5745                5750                5755                5760
Leu His Gly Asp Gln Lys Leu Ala Gln Ser Lys Gln Asp Ala Asn Asn
            5765                5770                5775
Gln Leu Asn His Leu Asp Asp Leu Thr Glu Glu Gln Lys Asn His Phe
            5780                5785                5790
Lys Pro Leu Ile Asn Asn Ala Asp Thr Arg Asp Glu Val Asn Lys Gln
        5795                5800                5805
Leu Glu Ile Ala Lys Gln Leu Asn Gly Asp Met Ser Thr Leu His Lys
        5810                5815                5820
Val Ile Asn Asp Lys Asp Gln Ile Gln His Leu Ser Asn Tyr Ile Asn
5825                5830                5835                5840
Ala Asp Asn Asp Lys Lys Gln Asn Tyr Asp Asn Ala Ile Lys Glu Ala
            5845                5850                5855
Glu Asp Leu Ile His Asn His Pro Asp Thr Leu Asp His Lys Ala Leu
            5860                5865                5870
Gln Asp Leu Leu Asn Lys Ile Asp Gln Ala His Asn Glu Leu Asn Gly
        5875                5880                5885
Glu Ser Arg Phe Lys Gln Ala Leu Asp Asn Ala Leu Asn Asp Ile Asp
        5890                5895                5900
```

```
Ser Leu Asn Ser Leu Asn Val Pro Gln Arg Gln Thr Val Lys Asp Asn
5905                5910                5915                5920

Ile Asn His Val Thr Thr Leu Glu Ser Leu Ala Gln Glu Leu Gln Lys
            5925                5930                5935

Ala Lys Glu Leu Asn Asp Ala Met Lys Ala Met Arg Asp Ser Ile Met
            5940                5945                5950

Asn Gln Glu Gln Ile Arg Lys Asn Ser Asn Tyr Thr Asn Glu Asp Leu
            5955                5960                5965

Ala Gln Gln Asn Ala Tyr Asn His Ala Val Asp Lys Ile Asn Asn Ile
            5970                5975                5980

Ile Gly Glu Asp Asn Ala Thr Met Asp Pro Gln Ile Ile Lys Gln Ala
5985                5990                5995                6000

Thr Gln Asp Ile Asn Thr Ala Ile Asn Gly Leu Asn Gly Asp Gln Lys
            6005                6010                6015

Leu Gln Asp Ala Lys Thr Asp Ala Lys Gln Gln Ile Thr Asn Phe Thr
            6020                6025                6030

Gly Leu Thr Glu Pro Gln Lys Gln Ala Leu Glu Asn Ile Ile Asn Gln
            6035                6040                6045

Gln Thr Ser Arg Ala Asn Val Ala Lys Gln Leu Ser His Ala Lys Phe
            6050                6055                6060

Leu Asn Gly Lys Met Glu Glu Leu Lys Val Ala Val Ala Lys Ala Ser
6065                6070                6075                6080

Leu Val Arg Gln Asn Ser Asn Tyr Ile Asn Glu Asp Val Ser Glu Lys
            6085                6090                6095

Glu Ala Tyr Glu Gln Ala Ile Ala Lys Gly Gln Glu Ile Ile Asn Ser
            6100                6105                6110

Glu Asn Asn Pro Thr Ile Ser Ser Thr Asp Ile Asn Arg Thr Ile Gln
            6115                6120                6125

Glu Ile Asn Asp Ala Glu Gln Asn Leu His Gly Asp Asn Lys Leu Arg
            6130                6135                6140

Gln Ala Gln Glu Ile Ala Lys Asn Glu Ile Gln Asn Leu Asp Gly Leu
6145                6150                6155                6160

Asn Ser Ala Gln Ile Thr Lys Leu Ile Gln Asp Ile Gly Arg Thr Thr
            6165                6170                6175

Thr Lys Pro Ala Val Thr Gln Lys Leu Glu Glu Ala Lys Ala Ile Asn
            6180                6185                6190

Gln Ala Met Gln Gln Leu Lys Gln Ser Ile Ala Asp Lys Asp Ala Thr
            6195                6200                6205

Leu Asn Ser Ser Asn Tyr Leu Asn Glu Asp Ser Glu Lys Lys Leu Ala
            6210                6215                6220

Tyr Asp Asn Ala Val Ser Gln Ala Glu Gln Leu Ile Asn Gln Leu Asn
6225                6230                6235                6240

Asp Pro Thr Met Asp Ile Ser Asn Ile Gln Ala Ile Thr Gln Lys Val
            6245                6250                6255

Ile Gln Ala Lys Asp Ser Leu His Gly Ala Asn Lys Leu Ala Gln Asn
            6260                6265                6270

Gln Ala Asp Ser Asn Leu Ile Ile Asn Gln Ser Thr Asn Leu Asn Asp
            6275                6280                6285

Lys Gln Lys Gln Ala Leu Asn Asp Leu Ile Asn His Ala Gln Thr Lys
            6290                6295                6300

Gln Gln Val Ala Glu Ile Ile Ala Gln Ala Asn Lys Leu Asn Asn Glu
6305                6310                6315                6320

Met Gly Thr Leu Lys Thr Leu Val Glu Glu Gln Ser Asn Val His Gln
```

```
                     6325            6330            6335
Gln Ser Lys Tyr Ile Asn Glu Asp Pro Gln Val Gln Asn Ile Tyr Asn
            6340            6345            6350

Asp Ser Ile Gln Lys Gly Arg Glu Ile Leu Asn Gly Thr Thr Asp Asp
            6355            6360            6365

Val Leu Asn Asn Lys Ile Ala Asp Ala Ile Gln Asn Ile His Leu
            6370            6375            6380

Thr Lys Asn Asp Leu His Gly Asp Gln Lys Leu Gln Lys Ala Gln Gln
6385            6390            6395            6400

Asp Ala Thr Asn Glu Leu Asn Tyr Leu Thr Asn Leu Asn Asn Ser Gln
            6405            6410            6415

Arg Gln Ser Glu His Asp Glu Ile Asn Ser Ala Pro Ser Arg Thr Glu
            6420            6425            6430

Val Ser Asn Asp Leu Asn His Ala Lys Ala Leu Asn Glu Ala Met Arg
            6435            6440            6445

Gln Leu Glu Asn Glu Val Ala Leu Glu Asn Ser Val Lys Lys Leu Ser
6450            6455            6460

Asp Phe Ile Asn Glu Asp Glu Ala Ala Gln Asn Glu Tyr Ser Asn Ala
6465            6470            6475            6480

Leu Gln Lys Ala Lys Asp Ile Ile Asn Gly Val Pro Ser Ser Thr Leu
            6485            6490            6495

Asp Lys Ala Thr Ile Glu Asp Ala Leu Leu Glu Leu Gln Asn Ala Arg
            6500            6505            6510

Glu Ser Leu His Gly Glu Gln Lys Leu Gln Glu Ala Lys Asn Gln Ala
            6515            6520            6525

Val Ala Glu Ile Asp Asn Leu Gln Ala Leu Asn Pro Gly Gln Val Leu
            6530            6535            6540

Ala Glu Lys Thr Leu Val Asn Gln Ala Ser Thr Lys Pro Glu Val Gln
6545            6550            6555            6560

Glu Ala Leu Gln Lys Ala Lys Glu Leu Asn Glu Ala Met Lys Ala Leu
            6565            6570            6575

Lys Thr Glu Ile Asn Lys Lys Glu Gln Ile Lys Ala Asp Ser Arg Tyr
            6580            6585            6590

Val Asn Ala Asp Ser Gly Leu Gln Ala Asn Tyr Asn Ser Ala Leu Asn
            6595            6600            6605

Tyr Gly Ser Gln Ile Ile Ala Thr Thr Gln Pro Pro Glu Leu Asn Lys
            6610            6615            6620

Asp Val Ile Asn Arg Ala Thr Gln Thr Ile Lys Thr Ala Glu Asn Asn
6625            6630            6635            6640

Leu Asn Gly Gln Ser Lys Leu Ala Glu Ala Lys Ser Asp Gly Asn Gln
            6645            6650            6655

Ser Ile Glu His Leu Gln Gly Leu Thr Gln Ser Gln Lys Asp Lys Gln
            6660            6665            6670

His Asp Leu Ile Asn Gln Ala Gln Thr Lys Gln Gln Val Asp Asp Ile
            6675            6680            6685

Val Asn Asn Ser Lys Gln Leu Asp Asn Ser Met Asn Gln Leu Gln Gln
            6690            6695            6700

Ile Val Asn Asn Asp Asn Thr Val Lys Gln Asn Ser Asp Phe Ile Asn
6705            6710            6715            6720

Glu Asp Ser Ser Gln Gln Asp Ala Tyr Asn His Ala Ile Gln Ala Ala
            6725            6730            6735

Lys Asp Leu Ile Thr Ala His Pro Thr Ile Met Asp Lys Asn Gln Ile
            6740            6745            6750
```

-continued

```
Asp Gln Ala Ile Glu Asn Ile Lys Gln Ala Leu Asn Asp Leu His Gly
            6755                6760                6765
Ser Asn Lys Leu Ser Glu Asp Lys Lys Glu Ala Ser Glu Gln Leu Gln
        6770                6775                6780
Asn Leu Asn Ser Leu Thr Asn Gly Gln Lys Asp Thr Ile Leu Asn His
6785                6790                6795                6800
Ile Phe Ser Ala Pro Thr Arg Ser Gln Val Gly Glu Lys Ile Ala Ser
                6805                6810                6815
Ala Lys Gln Leu Asn Asn Thr Met Lys Ala Leu Arg Asp Ser Ile Ala
            6820                6825                6830
Asp Asn Asn Glu Ile Leu Gln Ser Ser Lys Tyr Phe Asn Glu Asp Ser
        6835                6840                6845
Glu Gln Gln Asn Ala Tyr Asn Gln Ala Val Asn Lys Ala Lys Asn Ile
    6850                6855                6860
Ile Asn Asp Gln Pro Thr Pro Val Met Ala Asn Asp Glu Ile Gln Ser
6865                6870                6875                6880
Val Leu Asn Glu Val Lys Gln Thr Lys Asp Asn Leu His Gly Asp Gln
                6885                6890                6895
Lys Leu Ala Asn Asp Lys Thr Asp Ala Gln Ala Thr Leu Asn Ala Leu
            6900                6905                6910
Asn Tyr Leu Asn Gln Ala Gln Arg Gly Asn Leu Glu Thr Lys Val Gln
        6915                6920                6925
Asn Ser Asn Ser Arg Pro Glu Val Gln Lys Val Val Gln Leu Ala Asn
    6930                6935                6940
Gln Leu Asn Asp Ala Met Lys Lys Leu Asp Ala Ala Leu Thr Gly Asn
6945                6950                6955                6960
Asp Ala Ile Lys Gln Thr Ser Asn Tyr Ile Asn Glu Asp Thr Ser Gln
                6965                6970                6975
Gln Val Asn Phe Asp Glu Tyr Thr Asp Arg Gly Lys Asn Ile Val Ala
            6980                6985                6990
Glu Gln Thr Asn Pro Asn Met Ser Pro Thr Asn Ile Asn Thr Ile Ala
        6995                7000                7005
Asp Lys Ile Thr Glu Ala Lys Asn Asp Leu His Gly Val Gln Lys Leu
    7010                7015                7020
Lys Gln Ala Gln Gln Gln Ser Ile Asn Thr Ile Asn Gln Met Thr Gly
7025                7030                7035                7040
Leu Asn Gln Ala Gln Lys Glu Gln Leu Asn Gln Glu Ile Gln Gln Thr
                7045                7050                7055
Gln Thr Arg Ser Glu Val His Gln Val Ile Asn Lys Ala Gln Ala Leu
            7060                7065                7070
Asn Asp Ser Met Asn Thr Leu Arg Gln Ser Ile Thr Asp Glu His Glu
        7075                7080                7085
Val Lys Gln Thr Ser Asn Tyr Ile Asn Glu Thr Val Gly Asn Gln Thr
    7090                7095                7100
Ala Tyr Asn Asn Ala Val Asp Arg Val Lys Gln Ile Ile Asn Gln Thr
7105                7110                7115                7120
Ser Asn Pro Thr Met Asn Pro Leu Glu Val Glu Arg Ala Thr Ser Asn
                7125                7130                7135
Val Lys Ile Ser Lys Asp Ala Leu His Gly Glu Arg Glu Leu Asn Asp
            7140                7145                7150
Asn Lys Asn Ser Lys Thr Phe Ala Val Asn His Leu Asp Asn Leu Asn
        7155                7160                7165
```

```
Gln Ala Gln Lys Glu Ala Leu Thr His Glu Ile Glu Gln Ala Thr Ile
    7170                7175                7180

Val Ser Gln Val Asn Asn Ile Tyr Asn Lys Ala Lys Ala Leu Asn Asn
7185                7190                7195                7200

Asp Met Lys Lys Leu Lys Asp Ile Val Ala Gln Gln Asp Asn Val Arg
                7205                7210                7215

Gln Ser Asn Asn Tyr Ile Asn Glu Asp Ser Thr Pro Gln Asn Met Tyr
            7220                7225                7230

Asn Asp Thr Ile Asn His Ala Gln Ser Ile Ile Asp Gln Val Ala Asn
        7235                7240                7245

Pro Thr Met Ser His Asp Glu Ile Glu Asn Ala Ile Asn Asn Ile Lys
    7250                7255                7260

His Ala Ile Asn Ala Leu Asp Gly Glu His Lys Leu Gln Gln Ala Lys
7265                7270                7275                7280

Glu Asn Ala Asn Leu Leu Ile Asn Ser Leu Asn Asp Leu Asn Ala Pro
                7285                7290                7295

Gln Arg Asp Ala Ile Asn Arg Leu Val Asn Glu Ala Gln Thr Arg Glu
            7300                7305                7310

Lys Val Ala Glu Gln Leu Gln Ser Ala Gln Ala Leu Asn Asp Ala Met
        7315                7320                7325

Lys His Leu Arg Asn Ser Ile Gln Asn Gln Ser Ser Val Arg Gln Glu
    7330                7335                7340

Ser Lys Tyr Ile Asn Ala Ser Asp Ala Lys Lys Glu Gln Tyr Asn His
7345                7350                7355                7360

Ala Val Arg Glu Val Glu Asn Ile Ile Asn Glu Gln His Pro Thr Leu
                7365                7370                7375

Asp Lys Glu Ile Ile Lys Gln Leu Thr Asp Gly Val Asn Gln Ala Asn
            7380                7385                7390

Asn Asp Leu Asn Gly Val Glu Leu Leu Asp Ala Asp Lys Gln Asn Ala
        7395                7400                7405

His Gln Ser Ile Pro Thr Leu Met His Leu Asn Gln Ala Gln Gln Asn
    7410                7415                7420

Ala Leu Asn Glu Lys Ile Asn Asn Ala Val Thr Arg Thr Glu Val Ala
7425                7430                7435                7440

Ala Ile Ile Gly Gln Ala Lys Leu Leu Asp His Ala Met Glu Asn Leu
                7445                7450                7455

Glu Glu Ser Ile Lys Asp Lys Glu Gln Val Lys Gln Ser Ser Asn Tyr
            7460                7465                7470

Ile Asn Glu Asp Ser Asp Val Gln Glu Thr Tyr Asp Asn Ala Val Asp
        7475                7480                7485

His Val Thr Glu Ile Leu Asn Gln Thr Val Asn Pro Thr Leu Ser Ile
    7490                7495                7500

Glu Asp Ile Glu His Ala Ile Asn Glu Val Asn Gln Ala Lys Lys Gln
7505                7510                7515                7520

Leu Arg Gly Lys Gln Lys Leu Tyr Gln Thr Ile Asp Leu Ala Asp Lys
                7525                7530                7535

Glu Leu Ser Lys Leu Asp Asp Leu Thr Ser Gln Gln Ser Ser Ser Ile
            7540                7545                7550

Ser Asn Gln Ile Tyr Thr Ala Lys Thr Arg Thr Glu Val Ala Gln Ala
        7555                7560                7565

Ile Glu Lys Ala Lys Ser Leu Asn His Ala Met Lys Ala Leu Asn Lys
    7570                7575                7580

Val Tyr Lys Asn Ala Asp Lys Val Leu Asp Ser Ser Arg Phe Ile Asn
```

```
                  7585                7590                7595                7600
Glu Asp Gln Pro Glu Lys Lys Ala Tyr Gln Gln Ala Ile Asn His Val
                 7605                7610                7615

Asp Ser Ile Ile His Arg Gln Thr Asn Pro Glu Met Asp Pro Thr Val
             7620                7625                7630

Ile Asn Ser Ile Thr His Glu Leu Glu Thr Ala Gln Asn Asn Leu His
         7635                7640                7645

Gly Asp Gln Lys Leu Ala His Ala Gln Gln Asp Ala Ala Asn Val Ile
     7650                7655                7660

Asn Gly Leu Ile His Leu Asn Val Ala Gln Arg Glu Val Met Ile Asn
7665                7670                7675                7680

Thr Asn Thr Asn Ala Thr Thr Arg Glu Lys Val Ala Lys Asn Leu Asp
                7685                7690                7695

Asn Ala Gln Ala Leu Asp Lys Ala Met Glu Thr Leu Gln Gln Val Val
            7700                7705                7710

Ala His Lys Asn Asn Ile Leu Asn Asp Ser Lys Tyr Leu Asn Glu Asp
        7715                7720                7725

Ser Lys Tyr Gln Gln Gln Tyr Asp Arg Val Ile Ala Asp Ala Glu Gln
    7730                7735                7740

Leu Leu Asn Gln Thr Thr Asn Pro Thr Leu Glu Pro Tyr Lys Val Asp
7745                7750                7755                7760

Ile Val Lys Asp Asn Val Leu Ala Asn Glu Lys Ile Leu Phe Gly Ala
                7765                7770                7775

Glu Lys Leu Ser Tyr Asp Lys Ser Asn Ala Asn Asp Glu Ile Lys His
            7780                7785                7790

Met Asn Tyr Leu Asn Asn Ala Gln Lys Gln Ser Ile Lys Asp Met Ile
        7795                7800                7805

Ser His Ala Ala Leu Arg Thr Glu Val Lys Gln Leu Leu Gln Gln Ala
    7810                7815                7820

Lys Ile Leu Asp Glu Ala Met Lys Ser Leu Glu Asp Lys Thr Gln Val
7825                7830                7835                7840

Val Ile Thr Asp Thr Thr Leu Pro Asn Tyr Thr Glu Ala Ser Glu Asp
                7845                7850                7855

Lys Lys Glu Lys Val Asp Gln Thr Val Ser His Ala Gln Ala Ile Ile
            7860                7865                7870

Asp Lys Ile Asn Gly Ser Asn Val Ser Leu Asp Gln Val Arg Gln Ala
        7875                7880                7885

Leu Glu Gln Leu Thr Gln Ala Ser Glu Asn Leu Asp Gly Asp Gln Arg
    7890                7895                7900

Val Glu Glu Ala Lys Val His Ala Asn Gln Thr Ile Asp Gln Leu Thr
7905                7910                7915                7920

His Leu Asn Ser Leu Gln Gln Gln Thr Ala Lys Glu Ser Val Lys Asn
                7925                7930                7935

Ala Thr Lys Leu Glu Glu Ile Ala Thr Val Ser Asn Asn Ala Gln Ala
            7940                7945                7950

Leu Asn Lys Val Met Gly Lys Leu Glu Gln Phe Ile Asn His Ala Asp
        7955                7960                7965

Ser Val Glu Asn Ser Asp Asn Tyr Arg Gln Ala Asp Asp Lys Ile
    7970                7975                7980

Ile Ala Tyr Asp Glu Ala Leu Glu His Gly Gln Asp Ile Gln Lys Thr
7985                7990                7995                8000

Asn Ala Thr Gln Asn Glu Thr Lys Gln Ala Leu Gln Gln Leu Ile Tyr
                8005                8010                8015
```

```
Ala Glu Thr Ser Leu Asn Gly Phe Glu Arg Leu Asn His Ala Arg Pro
             8020                8025                8030

Arg Ala Leu Glu Tyr Ile Lys Ser Leu Glu Lys Ile Asn Asn Ala Gln
        8035                8040                8045

Lys Ser Ala Leu Glu Asp Lys Val Thr Gln Ser His Asp Leu Leu Glu
    8050                8055                8060

Leu Glu His Ile Val Asn Glu Gly Thr Asn Leu Asn Asp Ile Met Gly
8065                8070                8075                8080

Glu Leu Ala Asn Ala Ile Val Asn Asn Tyr Ala Pro Thr Lys Ala Ser
             8085                8090                8095

Ile Asn Tyr Ile Asn Ala Asp Asn Leu Arg Lys Asp Asn Phe Thr Gln
        8100                8105                8110

Ala Ile Asn Asn Ala Arg Asp Ala Leu Asn Lys Thr Gln Gly Gln Asn
    8115                8120                8125

Leu Asp Phe Asn Ala Ile Asp Thr Phe Lys Asp Asp Ile Phe Lys Thr
8130                8135                8140

Lys Asp Ala Leu Asn Gly Ile Glu Arg Leu Thr Ala Ala Lys Ser Lys
8145                8150                8155                8160

Ala Glu Lys Leu Ile Asp Ser Leu Lys Phe Ile Asn Lys Ala Gln Phe
             8165                8170                8175

Thr His Ala Asn Asp Glu Ile Met Asn Thr Asn Ser Ile Ala Gln Leu
        8180                8185                8190

Ser Arg Ile Val Asn Gln Ala Phe Asp Leu Asn Asp Ala Met Lys Ser
    8195                8200                8205

Leu Arg Asp Glu Leu Asn Asn Gln Ala Phe Pro Val Gln Ala Ser Ser
        8210                8215                8220

Asn Tyr Ile Asn Ser Asp Glu Asp Leu Lys Gln Gln Phe Asp His Ala
8225                8230                8235                8240

Leu Ser Asn Ala Arg Lys Val Leu Ala Lys Glu Asn Gly Lys Asn Leu
             8245                8250                8255

Asp Glu Lys Gln Ile Gln Gly Leu Lys Gln Val Ile Glu Asp Thr Lys
        8260                8265                8270

Asp Ala Leu Asn Gly Ile Gln Arg Leu Ser Lys Ala Lys Ala Lys Ala
    8275                8280                8285

Ile Gln Tyr Val Gln Ser Leu Ser Tyr Ile Asn Asp Ala Gln Arg His
        8290                8295                8300

Ile Ala Glu Asn Asn Ile His Asn Ser Asp Asp Leu Ser Ser Leu Ala
8305                8310                8315                8320

Asn Thr Leu Ser Lys Ala Ser Asp Leu Asp Asn Ala Met Lys Asp Leu
             8325                8330                8335

Arg Asp Thr Ile Glu Ser Asn Ser Thr Ser Val Pro Asn Ser Val Asn
        8340                8345                8350

Tyr Ile Asn Ala Asp Lys Asn Leu Gln Ile Glu Phe Asp Glu Ala Leu
    8355                8360                8365

Gln Gln Ala Ser Ala Thr Ser Ser Lys Thr Ser Glu Asn Pro Ala Thr
        8370                8375                8380

Ile Glu Glu Val Leu Gly Leu Ser Gln Ala Ile Tyr Asp Thr Lys Asn
8385                8390                8395                8400

Ala Leu Asn Gly Glu Gln Arg Leu Ala Thr Glu Lys Ser Lys Asp Leu
             8405                8410                8415

Lys Leu Ile Lys Gly Leu Lys Asp Leu Asn Lys Ala Gln Leu Glu Asp
        8420                8425                8430
```

```
Val Thr Asn Lys Val Asn Ser Ala Asn Thr Leu Thr Glu Leu Ser Gln
    8435            8440            8445

Leu Thr Gln Ser Thr Leu Glu Leu Asn Asp Lys Met Lys Leu Leu Arg
    8450            8455            8460

Asp Lys Leu Lys Thr Leu Val Asn Pro Val Lys Ala Ser Leu Asn Tyr
8465            8470            8475            8480

Arg Asn Ala Asp Tyr Asn Leu Lys Arg Gln Phe Asn Lys Ala Leu Lys
            8485            8490            8495

Glu Ala Lys Gly Val Leu Asn Lys Asn Ser Gly Thr Asn Val Asn Ile
            8500            8505            8510

Asn Asp Ile Gln His Leu Leu Thr Gln Ile Asp Asn Ala Lys Asp Gln
            8515            8520            8525

Leu Asn Gly Glu Arg Arg Leu Lys Glu His Gln Gln Lys Ser Glu Val
            8530            8535            8540

Phe Ile Ile Lys Glu Leu Asp Ile Leu Asn Asn Ala Gln Lys Ala Ala
8545            8550            8555            8560

Ile Ile Asn Gln Ile Arg Ala Ser Lys Asp Ile Lys Ile Ile Asn Gln
            8565            8570            8575

Ile Val Asp Asn Ala Ile Glu Leu Asn Asp Ala Met Gln Gly Leu Lys
            8580            8585            8590

Glu His Val Ala Gln Leu Thr Ala Thr Thr Lys Asp Asn Ile Glu Tyr
            8595            8600            8605

Leu Asn Ala Asp Glu Asp His Lys Leu Gln Tyr Asp Tyr Ala Ile Asn
            8610            8615            8620

Leu Ala Asn Asn Val Leu Asp Lys Glu Asn Gly Thr Asn Lys Asp Ala
8625            8630            8635            8640

Asn Ile Ile Ile Gly Met Ile Gln Asn Met Asp Asp Ala Arg Ala Leu
            8645            8650            8655

Leu Asn Gly Ile Glu Arg Leu Lys Asp Ala Gln Thr Lys Ala His Asn
            8660            8665            8670

Asp Ile Lys Asp Thr Leu Lys Arg Gln Leu Asp Glu Ile Glu His Ala
            8675            8680            8685

Asn Ala Thr Ser Asn Ser Lys Ala Gln Ala Lys Gln Met Val Asn Glu
            8690            8695            8700

Glu Ala Arg Lys Ala Leu Ser Asn Ile Asn Asp Ala Thr Ser Asn Asp
8705            8710            8715            8720

Leu Val Asn Gln Ala Lys Asp Glu Gly Gln Ser Ala Ile Glu His Ile
            8725            8730            8735

His Ala Asp Glu Leu Pro Lys Ala Lys Leu Asp Ala Asn Gln Met Ile
            8740            8745            8750

Asp Gln Lys Val Glu Asp Ile Asn His Leu Ile Ser Gln Asn Pro Asn
            8755            8760            8765

Leu Ser Asn Glu Glu Lys Asn Lys Leu Ile Ser Gln Ile Asn Lys Leu
            8770            8775            8780

Val Asn Gly Ile Lys Asn Glu Ile Gln Gln Ala Ile Asn Lys Gln Gln
8785            8790            8795            8800

Ile Glu Asn Ala Thr Thr Lys Leu Asp Glu Val Ile Glu Thr Thr Lys
            8805            8810            8815

Lys Leu Ile Ile Ala Lys Ala Glu Ala Lys Gln Met Ile Lys Glu Leu
            8820            8825            8830

Ser Gln Lys Lys Arg Asp Ala Ile Asn Asn Thr Asp Leu Thr Pro
            8835            8840            8845

Ser Gln Lys Ala His Ala Leu Ala Asp Ile Asp Lys Thr Glu Lys Asp
```

-continued

```
                 8850                8855                8860

Ala Leu Gln His Ile Glu Asn Ser Asn Ser Ile Asp Asp Ile Asn Asn
8865                8870                8875                8880

Asn Lys Glu His Ala Phe Asn Thr Leu Ala His Ile Ile Ile Trp Asp
                 8885                8890                8895

Thr Asp Gln Gln Pro Leu Val Phe Glu Leu Pro Glu Leu Ser Leu Gln
                 8900                8905                8910

Asn Ala Leu Val Thr Ser Glu Val Val His Arg Asp Glu Thr Ile
                 8915                8920                8925

Ser Leu Glu Ser Ile Ile Gly Ala Met Thr Leu Thr Asp Glu Leu Lys
                 8930                8935                8940

Val Asn Ile Val Ser Leu Pro Asn Thr Asp Lys Val Ala Asp His Leu
8945                8950                8955                8960

Thr Ala Lys Val Lys Val Ile Leu Ala Asp Gly Ser Tyr Val Thr Val
                 8965                8970                8975

Asn Val Pro Val Lys Val Glu Lys Glu Leu Gln Ile Ala Lys Lys
                 8980                8985                8990

Asp Ala Ile Lys Thr Ile Asp Val Leu Val Lys Gln Lys Ile Lys Asp
                 8995                9000                9005

Ile Asp Ser Asn Asn Glu Leu Thr Ser Thr Gln Arg Glu Asp Ala Lys
                 9010                9015                9020

Ala Glu Ile Glu Arg Leu Lys Lys Gln Ala Ile Asp Lys Val Asn His
9025                9030                9035                9040

Ser Lys Ser Ile Lys Asp Ile Glu Thr Val Lys Arg Thr Asp Phe Glu
                 9045                9050                9055

Glu Ile Asp Gln Phe Asp Pro Lys Arg Phe Thr Leu Asn Lys Ala Lys
                 9060                9065                9070

Lys Asp Ile Ile Thr Asp Val Asn Thr Gln Ile Gln Asn Gly Phe Lys
                 9075                9080                9085

Glu Ile Glu Thr Ile Lys Gly Leu Thr Ser Asn Glu Lys Thr Gln Phe
                 9090                9095                9100

Asp Lys Gln Leu Thr Ala Leu Gln Lys Glu Phe Leu Glu Lys Val Glu
9105                9110                9115                9120

His Ala His Asn Leu Val Glu Leu Asn Gln Leu Gln Gln Glu Phe Asn
                 9125                9130                9135

Asn Arg Tyr Lys His Ile Leu Asn Gln Ala His Leu Leu Gly Glu Lys
                 9140                9145                9150

His Ile Ala Glu His Lys Leu Gly Tyr Val Val Asn Lys Thr Gln
                 9155                9160                9165

Gln Ile Leu Asn Asn Gln Ser Ala Ser Tyr Phe Ile Lys Gln Trp Ala
                 9170                9175                9180

Leu Asp Arg Ile Lys Gln Ile Gln Leu Glu Thr Met Asn Ser Ile Arg
9185                9190                9195                9200

Gly Ala His Thr Val Gln Asp Val His Lys Ala Leu Leu Gln Gly Ile
                 9205                9210                9215

Glu Gln Ile Leu Lys Val Asn Val Ser Ile Ile Asn Gln Ser Phe Asn
                 9220                9225                9230

Asp Ser Leu His Asn Phe Asn Tyr Leu His Ser Lys Phe Asp Ala Arg
                 9235                9240                9245

Leu Arg Glu Lys Asp Val Ala Asn His Ile Val Gln Thr Glu Thr Phe
9250                9255                9260

Lys Glu Val Leu Lys Gly Thr Gly Val Glu Pro Gly Lys Ile Asn Lys
9265                9270                9275                9280
```

```
Glu Thr Gln Gln Pro Lys Leu His Lys Asn Asp Asp Ser Leu Phe
                9285                9290                9295

Lys His Leu Val Asp Asn Phe Gly Lys Thr Val Gly Val Ile Thr Leu
            9300                9305                9310

Thr Gly Leu Leu Ser Ser Phe Trp Leu Val Leu Ala Lys Arg Arg Lys
        9315                9320                9325

Lys Glu Glu Glu Glu Lys Gln Ser Ile Lys Asn His His Lys Asp Ile
    9330                9335                9340

Arg Leu Ser Asp Thr Asp Lys Ile Asp Pro Ile Val Ile Thr Lys Arg
9345                9350                9355                9360

Lys Ile Asp Lys Glu Glu Gln Ile Gln Asn Asp Asp Lys His Ser Ile
            9365                9370                9375

Pro Val Ala Lys His Lys Lys Ser Lys Glu Lys Gln Leu Ser Glu Glu
                9380                9385                9390

Asp Ile His Ser Ile Pro Val Val Lys Arg Lys Gln Asn Ser Asp Asn
            9395                9400                9405

Lys Asp Thr Lys Gln Lys Lys Val Thr Ser Lys Lys Lys Lys Thr Pro
        9410                9415                9420

Gln Ser Thr Lys Lys Val Val Lys Thr Lys Lys Arg Ser Lys Lys
9425                9430                9435

<210> SEQ ID NO 16
<211> LENGTH: 1115
<212> TYPE: PRT
<213> ORGANISM: S. aureus

<400> SEQUENCE: 16

Met Arg Asp Lys Lys Gly Pro Val Asn Lys Arg Val Asp Phe Leu Ser
1               5                   10                  15

Asn Lys Leu Asn Lys Tyr Ser Ile Arg Lys Phe Thr Val Gly Thr Ala
            20                  25                  30

Ser Ile Leu Ile Gly Ser Leu Met Tyr Leu Gly Thr Gln Gln Glu Ala
        35                  40                  45

Glu Ala Ala Glu Asn Asn Ile Glu Asn Pro Thr Thr Leu Lys Asp Asn
    50                  55                  60

Val Gln Ser Lys Glu Val Lys Ile Glu Glu Val Thr Asn Lys Asp Thr
65                  70                  75                  80

Ala Pro Gln Gly Val Glu Ala Lys Ser Glu Val Thr Ser Asn Lys Asp
                85                  90                  95

Thr Ile Glu His Glu Ala Ser Val Lys Ala Glu Asp Ile Ser Lys Lys
            100                 105                 110

Glu Asp Thr Pro Lys Glu Val Ala Asn Val Ala Glu Val Gln Pro Lys
        115                 120                 125

Ser Ser Val Thr His Asn Ala Glu Ala Pro Lys Val Arg Lys Ala Arg
    130                 135                 140

Ser Val Asp Glu Gly Ser Phe Asp Ile Thr Arg Asp Ser Lys Asn Val
145                 150                 155                 160

Val Glu Ser Thr Pro Ile Thr Ile Gln Gly Lys Glu His Phe Glu Gly
                165                 170                 175

Tyr Gly Ser Val Asp Ile Gln Lys Asn Pro Thr Asp Leu Gly Val Ser
            180                 185                 190

Glu Val Thr Arg Phe Asn Val Gly Asn Glu Ser Asn Gly Leu Ile Gly
        195                 200                 205

Ala Leu Gln Leu Lys Asn Lys Ile Asp Phe Ser Lys Asp Phe Asn Phe
```

```
                210                 215                 220
Lys Val Arg Val Ala Asn Asn His Gln Ser Asn Thr Thr Gly Ala Asp
225                 230                 235                 240

Gly Trp Gly Phe Leu Phe Ser Lys Gly Asn Ala Glu Glu Tyr Leu Thr
                245                 250                 255

Asn Gly Gly Ile Leu Gly Asp Lys Gly Leu Val Asn Ser Gly Gly Phe
                260                 265                 270

Lys Ile Asp Thr Gly Tyr Ile Tyr Thr Ser Ser Met Asp Lys Thr Glu
                275                 280                 285

Lys Gln Ala Gly Gln Gly Tyr Arg Gly Tyr Gly Ala Phe Val Lys Asn
                290                 295                 300

Asp Ser Ser Gly Asn Ser Gln Met Val Gly Glu Asn Ile Asp Lys Ser
305                 310                 315                 320

Lys Thr Asn Phe Leu Asn Tyr Ala Asp Asn Ser Thr Asn Thr Ser Asp
                325                 330                 335

Gly Lys Phe His Gly Gln Arg Leu Asn Asp Val Ile Leu Thr Tyr Val
                340                 345                 350

Ala Ser Thr Gly Lys Met Arg Ala Glu Tyr Ala Gly Lys Thr Trp Glu
                355                 360                 365

Thr Ser Ile Thr Asp Leu Gly Leu Ser Lys Asn Gln Ala Tyr Asn Phe
                370                 375                 380

Leu Ile Thr Ser Ser Gln Arg Trp Gly Leu Asn Gln Gly Ile Asn Ala
385                 390                 395                 400

Asn Gly Trp Met Arg Thr Asp Leu Lys Gly Ser Glu Phe Thr Phe Thr
                405                 410                 415

Pro Glu Ala Pro Lys Thr Ile Thr Glu Leu Glu Lys Lys Val Glu Glu
                420                 425                 430

Ile Pro Phe Lys Lys Glu Arg Lys Phe Asn Pro Asp Leu Ala Pro Gly
                435                 440                 445

Thr Glu Lys Val Thr Arg Glu Gly Gln Lys Gly Glu Lys Thr Ile Thr
                450                 455                 460

Thr Pro Thr Leu Lys Asn Pro Leu Thr Gly Glu Ile Ile Ser Lys Gly
465                 470                 475                 480

Glu Ser Lys Glu Glu Ile Thr Lys Asp Pro Ile Asn Glu Leu Thr Glu
                485                 490                 495

Tyr Gly Pro Glu Thr Ile Ala Pro Gly His Arg Asp Glu Phe Asp Pro
                500                 505                 510

Lys Leu Pro Thr Gly Glu Lys Glu Val Pro Gly Lys Pro Gly Ile
                515                 520                 525

Lys Asn Pro Glu Thr Gly Asp Val Val Arg Pro Val Asp Ser Val
530                 535                 540

Thr Lys Tyr Gly Pro Val Lys Gly Asp Ser Ile Val Glu Lys Glu Glu
545                 550                 555                 560

Ile Pro Phe Glu Lys Glu Arg Lys Phe Asn Pro Asp Leu Ala Pro Gly
                565                 570                 575

Thr Glu Lys Val Thr Arg Glu Gly Gln Lys Gly Glu Lys Thr Ile Thr
                580                 585                 590

Thr Pro Thr Leu Lys Asn Pro Leu Thr Gly Glu Ile Ile Ser Lys Gly
                595                 600                 605

Glu Ser Lys Glu Glu Ile Thr Lys Asp Pro Ile Asn Glu Leu Thr Glu
                610                 615                 620

Tyr Gly Pro Glu Thr Ile Ala Pro Gly His Arg Asp Glu Phe Asp Pro
625                 630                 635                 640
```

```
Lys Leu Pro Thr Gly Glu Lys Glu Val Pro Gly Lys Pro Gly Ile
            645                 650                 655

Lys Asn Pro Glu Thr Gly Asp Val Val Arg Pro Val Asp Ser Val
            660                 665                 670

Thr Lys Tyr Gly Pro Val Lys Gly Asp Ser Ile Val Glu Lys Glu
            675                 680                 685

Ile Pro Phe Lys Lys Glu Arg Lys Phe Asn Pro Asp Leu Ala Pro Gly
            690                 695                 700

Thr Glu Lys Val Thr Arg Glu Gly Gln Lys Gly Glu Lys Thr Ile Thr
705                 710                 715                 720

Thr Pro Thr Leu Lys Asn Pro Leu Thr Gly Glu Ile Ile Ser Lys Gly
            725                 730                 735

Glu Ser Lys Glu Glu Ile Thr Lys Asp Pro Ile Asn Glu Leu Thr Glu
            740                 745                 750

Tyr Gly Pro Glu Thr Ile Thr Pro Gly His Arg Asp Glu Phe Asp Pro
            755                 760                 765

Lys Leu Pro Thr Gly Glu Lys Glu Val Pro Gly Lys Pro Gly Ile
            770                 775                 780

Lys Asn Pro Glu Thr Gly Asp Val Val Arg Pro Val Asp Ser Val
785                 790                 795                 800

Thr Lys Tyr Gly Pro Val Lys Gly Asp Ser Ile Val Glu Lys Glu
            805                 810                 815

Ile Pro Phe Glu Lys Glu Arg Lys Phe Asn Pro Asp Leu Ala Pro Gly
            820                 825                 830

Thr Glu Lys Val Thr Arg Glu Gly Gln Lys Gly Glu Lys Thr Ile Thr
            835                 840                 845

Thr Pro Thr Leu Lys Asn Pro Leu Thr Gly Glu Ile Ile Ser Lys Gly
            850                 855                 860

Glu Ser Lys Glu Glu Ile Thr Lys Asp Pro Val Asn Glu Leu Thr Glu
865                 870                 875                 880

Phe Gly Gly Glu Lys Ile Pro Gln Gly His Lys Asp Ile Phe Asp Pro
            885                 890                 895

Asn Leu Pro Thr Asp Gln Thr Glu Lys Val Pro Gly Lys Pro Gly Ile
            900                 905                 910

Lys Asn Pro Asp Thr Gly Lys Val Ile Glu Glu Pro Val Asp Asp Val
            915                 920                 925

Ile Lys His Gly Pro Lys Thr Gly Thr Pro Gly Thr Lys Thr Val Glu
            930                 935                 940

Ile Pro Phe Glu Thr Lys Arg Glu Phe Asn Pro Lys Leu Gln Pro Gly
945                 950                 955                 960

Glu Glu Arg Val Lys Gln Glu Gly Gln Pro Gly Ser Lys Thr Ile Thr
            965                 970                 975

Thr Pro Ile Thr Val Asn Pro Leu Thr Gly Glu Lys Val Gly Glu Gly
            980                 985                 990

Gln Pro Thr Glu Glu Ile Thr Lys Gln Pro Val Asp Lys Ile Val Glu
            995                 1000                1005

Phe Gly Gly Glu Lys Pro Lys Asp Pro Lys Gly Pro Glu Asn Pro Glu
            1010                1015                1020

Lys Pro Ser Arg Pro Thr His Pro Ser Gly Pro Val Asn Pro Asn Asn
1025                1030                1035                1040

Pro Gly Leu Ser Lys Asp Arg Ala Lys Pro Asn Gly Pro Val His Ser
            1045                1050                1055
```

```
Met Asp Lys Asn Asp Lys Val Lys Ser Lys Ile Ala Lys Glu Ser
            1060                1065                1070

Val Ala Asn Gln Glu Lys Lys Arg Ala Glu Leu Pro Lys Thr Gly Leu
        1075                1080                1085

Glu Ser Thr Gln Lys Gly Leu Ile Phe Ser Ser Ile Ile Gly Ile Ala
        1090                1095                1100

Gly Leu Met Leu Leu Ala Arg Arg Arg Lys Asn
1105                1110                1115

<210> SEQ ID NO 17
<211> LENGTH: 1469
<212> TYPE: PRT
<213> ORGANISM: S. epidermidis

<400> SEQUENCE: 17

Met Gly Lys Arg Arg Gln Gly Pro Ile Asn Lys Lys Val Asp Phe Leu
1               5                   10                  15

Pro Asn Lys Leu Asn Lys Tyr Ser Ile Arg Lys Phe Thr Val Gly Thr
            20                  25                  30

Ala Ser Ile Leu Leu Gly Ser Thr Leu Ile Phe Gly Ser Ser Ser His
        35                  40                  45

Glu Ala Lys Ala Ala Glu Glu Lys Gln Val Asp Pro Ile Thr Gln Ala
    50                  55                  60

Asn Gln Asn Asp Ser Ser Glu Arg Ser Leu Glu Asn Thr Asn Gln Pro
65                  70                  75                  80

Thr Val Asn Asn Glu Ala Pro Gln Met Ser Ser Thr Leu Gln Ala Glu
                85                  90                  95

Glu Gly Ser Asn Ala Glu Ala Pro Asn Val Pro Thr Ile Lys Ala Asn
            100                 105                 110

Ser Asp Asn Asp Thr Gln Thr Gln Phe Ser Glu Ala Pro Thr Arg Asn
        115                 120                 125

Asp Leu Ala Arg Lys Glu Asp Ile Pro Ala Val Ser Lys Asn Glu Glu
    130                 135                 140

Leu Gln Ser Ser Gln Pro Asn Thr Asp Ser Lys Ile Glu Pro Thr Thr
145                 150                 155                 160

Ser Glu Pro Val Asn Leu Asn Tyr Ser Ser Pro Phe Met Ser Leu Leu
                165                 170                 175

Ser Met Pro Ala Asp Ser Ser Asn Asn Thr Lys Asn Thr Ile Asp
            180                 185                 190

Ile Pro Pro Thr Thr Val Lys Gly Arg Asp Asn Tyr Asp Phe Tyr Gly
        195                 200                 205

Arg Val Asp Ile Gln Ser Asn Pro Thr Asp Leu Asn Ala Thr Asn Leu
    210                 215                 220

Thr Arg Tyr Asn Tyr Gly Gln Pro Pro Gly Thr Thr Thr Ala Gly Ala
225                 230                 235                 240

Val Gln Phe Lys Asn Gln Val Ser Phe Asp Lys Asp Phe Asp Phe Asn
                245                 250                 255

Ile Arg Val Ala Asn Asn Arg Gln Ser Asn Thr Thr Gly Ala Asp Gly
            260                 265                 270

Trp Gly Phe Met Phe Ser Lys Lys Asp Gly Asp Phe Leu Lys Asn
        275                 280                 285

Gly Gly Ile Leu Arg Glu Lys Gly Thr Pro Ser Ala Ala Gly Phe Arg
    290                 295                 300

Ile Asp Thr Gly Tyr Tyr Asn Asn Asp Pro Leu Asp Lys Ile Gln Lys
305                 310                 315                 320
```

```
Gln Ala Gly Gln Gly Tyr Arg Gly Tyr Gly Thr Phe Val Lys Asn Asp
                325                 330                 335

Ser Gln Gly Asn Thr Ser Lys Val Gly Ser Gly Thr Pro Ser Thr Asp
            340                 345                 350

Phe Leu Asn Tyr Ala Asp Asn Thr Thr Asn Asp Leu Asp Gly Lys Phe
        355                 360                 365

His Gly Gln Lys Leu Asn Asn Val Asn Leu Lys Tyr Asn Ala Ser Asn
    370                 375                 380

Gln Thr Phe Thr Ala Thr Tyr Ala Gly Lys Thr Trp Thr Ala Thr Leu
385                 390                 395                 400

Ser Glu Leu Gly Leu Ser Pro Thr Asp Ser Tyr Asn Phe Leu Val Thr
                405                 410                 415

Ser Ser Gln Tyr Gly Asn Gly Asn Ser Gly Thr Tyr Ala Asp Gly Val
            420                 425                 430

Met Arg Ala Asp Leu Asp Gly Ala Thr Leu Thr Tyr Thr Pro Lys Ala
        435                 440                 445

Val Asp Gly Asp Pro Ile Thr Ser Thr Lys Glu Ile Pro Phe Asn Lys
    450                 455                 460

Lys Arg Glu Phe Asp Pro Asn Leu Ala Pro Gly Thr Glu Lys Val Val
465                 470                 475                 480

Gln Lys Gly Glu Pro Gly Ile Glu Thr Thr Thr Pro Thr Tyr Val
                485                 490                 495

Asn Pro Asn Thr Gly Glu Lys Val Gly Glu Gly Thr Pro Thr Thr Lys
            500                 505                 510

Ile Thr Lys Gln Pro Val Asp Glu Ile Val His Tyr Gly Gly Glu Glu
        515                 520                 525

Ile Lys Pro Gly His Lys Asp Glu Phe Asp Pro Asn Ala Pro Lys Gly
        530                 535                 540

Ser Gln Thr Thr Gln Pro Gly Lys Pro Gly Val Lys Asn Pro Asp Thr
545                 550                 555                 560

Gly Glu Val Val Thr Pro Pro Val Asp Val Thr Lys Tyr Gly Pro
                565                 570                 575

Val Asp Gly Asp Pro Ile Thr Ser Thr Glu Glu Ile Pro Phe Asp Lys
            580                 585                 590

Lys Arg Glu Phe Asn Pro Asp Leu Lys Pro Gly Glu Glu Arg Val Lys
        595                 600                 605

Gln Lys Gly Glu Pro Gly Thr Lys Thr Ile Thr Thr Pro Thr Thr Lys
610                 615                 620

Asn Pro Leu Thr Gly Glu Lys Val Gly Glu Gly Glu Pro Thr Glu Lys
625                 630                 635                 640

Ile Thr Lys Gln Pro Val Asp Glu Ile Thr Glu Tyr Gly Gly Glu Glu
                645                 650                 655

Ile Lys Pro Gly His Lys Asp Glu Phe Asp Pro Asn Ala Pro Lys Gly
            660                 665                 670

Ser Gln Glu Asp Val Pro Gly Lys Pro Gly Val Lys Asn Pro Asp Thr
        675                 680                 685

Gly Glu Val Val Thr Pro Pro Val Asp Val Thr Lys Tyr Gly Pro
    690                 695                 700

Val Asp Gly Asp Pro Ile Thr Ser Thr Glu Glu Ile Pro Phe Asp Lys
705                 710                 715                 720

Lys Arg Glu Phe Asp Pro Asn Leu Ala Pro Gly Thr Glu Lys Val Val
                725                 730                 735
```

Gln Lys Gly Glu Pro Gly Thr Lys Thr Ile Thr Pro Thr Thr Lys
                740                 745                 750

Asn Pro Leu Thr Gly Glu Lys Val Gly Glu Gly Glu Pro Thr Glu Lys
            755                 760                 765

Ile Thr Lys Gln Pro Val Asp Glu Ile Val His Tyr Gly Gly Glu Glu
        770                 775                 780

Ile Lys Pro Gly His Lys Asp Glu Phe Asp Pro Asn Ala Pro Lys Gly
785                 790                 795                 800

Ser Gln Glu Asp Val Pro Gly Lys Pro Gly Val Lys Asn Pro Asp Thr
                805                 810                 815

Gly Glu Val Val Thr Pro Pro Val Asp Asp Val Thr Lys Tyr Gly Pro
            820                 825                 830

Val Asp Gly Asp Pro Ile Thr Ser Thr Glu Glu Ile Pro Phe Asp Lys
        835                 840                 845

Lys Arg Glu Phe Asn Pro Asp Leu Lys Pro Gly Glu Glu Arg Val Lys
                850                 855                 860

Gln Lys Gly Glu Pro Gly Thr Lys Thr Ile Thr Thr Pro Thr Thr Lys
865                 870                 875                 880

Asn Pro Leu Thr Gly Glu Lys Val Gly Glu Gly Glu Pro Thr Glu Lys
                885                 890                 895

Val Thr Lys Gln Pro Val Asp Glu Ile Val His Tyr Gly Gly Glu Glu
            900                 905                 910

Ile Lys Pro Gly His Lys Asp Glu Phe Asp Pro Asn Ala Pro Lys Gly
        915                 920                 925

Ser Gln Glu Asp Val Pro Gly Lys Pro Gly Val Lys Asn Pro Asp Thr
                930                 935                 940

Gly Glu Val Val Thr Pro Pro Val Asp Asp Val Thr Lys Tyr Gly Pro
945                 950                 955                 960

Val Asp Gly Asp Pro Ile Thr Ser Thr Glu Glu Ile Pro Phe Asp Lys
                965                 970                 975

Lys Arg Glu Phe Asp Pro Asn Leu Ala Pro Gly Thr Glu Lys Val Val
            980                 985                 990

Gln Lys Gly Glu Pro Gly Thr Lys Thr Ile Thr Thr Pro Thr Thr Lys
        995                 1000                1005

Asn Pro Leu Thr Gly Glu Lys Val Gly Glu Gly Glu Pro Thr Glu Lys
    1010                1015                1020

Ile Thr Lys Gln Pro Val Asp Glu Ile Val His Tyr Gly Gly Glu Glu
1025                1030                1035                1040

Ile Lys Pro Gly His Lys Asp Glu Phe Asp Pro Asn Ala Pro Lys Gly
                1045                1050                1055

Ser Gln Thr Thr Gln Pro Gly Lys Pro Gly Val Lys Asn Pro Asp Thr
            1060                1065                1070

Gly Glu Val Val Thr Pro Pro Val Asp Asp Val Thr Lys Tyr Gly Pro
        1075                1080                1085

Val Asp Gly Asp Pro Ile Thr Ser Thr Glu Glu Ile Pro Phe Asp Lys
    1090                1095                1100

Lys Arg Glu Phe Asp Pro Asn Leu Ala Pro Gly Thr Glu Lys Val Val
1105                1110                1115                1120

Gln Lys Gly Glu Pro Gly Thr Lys Thr Ile Thr Thr Pro Thr Thr Lys
                1125                1130                1135

Asn Pro Leu Thr Gly Glu Lys Val Gly Glu Gly Glu Pro Thr Glu Lys
            1140                1145                1150

Ile Thr Lys Gln Pro Val Asp Glu Ile Val His Tyr Gly Gly Glu Gln

```
                  1155                1160                1165
Ile Pro Gln Gly His Lys Asp Glu Phe Asp Pro Asn Ala Pro Val Asp
        1170                1175                1180
Ser Lys Thr Glu Val Pro Gly Lys Pro Gly Val Lys Asn Pro Asp Thr
1185                1190                1195                1200
Gly Glu Val Val Thr Pro Pro Val Asp Asp Val Thr Lys Tyr Gly Pro
                    1205                1210                1215
Lys Val Gly Asn Pro Ile Thr Ser Thr Glu Glu Ile Pro Phe Asp Lys
            1220                1225                1230
Lys Arg Val Phe Asn Pro Asp Leu Lys Pro Gly Glu Glu Arg Val Lys
        1235                1240                1245
Gln Lys Gly Glu Pro Gly Thr Lys Thr Ile Thr Thr Pro Ile Leu Val
    1250                1255                1260
Asn Pro Ile Thr Gly Glu Lys Val Gly Glu Gly Lys Ser Thr Glu Lys
1265                1270                1275                1280
Val Thr Lys Gln Pro Val Asp Glu Ile Val Glu Tyr Gly Pro Thr Lys
                1285                1290                1295
Ala Glu Pro Gly Lys Pro Ala Glu Pro Gly Lys Pro Ala Glu Pro Gly
            1300                1305                1310
Lys Pro Ala Glu Pro Gly Lys Pro Ala Glu Pro Gly Thr Pro Ala Glu
        1315                1320                1325
Pro Gly Lys Pro Ala Glu Pro Gly Lys Pro Ala Glu Pro Gly Lys Pro
    1330                1335                1340
Ala Glu Pro Gly Lys Pro Ala Glu Pro Gly Lys Pro Ala Glu Pro Gly
1345                1350                1355                1360
Thr Pro Ala Glu Pro Gly Lys Pro Ala Glu Pro Gly Lys Pro Ala Glu
                1365                1370                1375
Pro Gly Lys Pro Ala Glu Pro Gly Thr Pro Ala Glu Pro Gly Lys Pro
            1380                1385                1390
Ala Glu Pro Gly Thr Pro Ala Glu Pro Gly Lys Pro Ala Glu Pro Gly
        1395                1400                1405
Thr Pro Thr Gln Ser Gly Ala Pro Glu Gln Pro Asn Arg Ser Met His
    1410                1415                1420
Ser Thr Asp Asn Lys Asn Gln Leu Pro Asp Thr Gly Glu Asn Arg Gln
1425                1430                1435                1440
Ala Asn Glu Gly Thr Leu Val Gly Ser Leu Leu Ala Ile Val Gly Ser
                1445                1450                1455
Leu Phe Ile Phe Gly Arg Arg Lys Lys Gly Asn Glu Lys
            1460                1465

<210> SEQ ID NO 18
<211> LENGTH: 167
<212> TYPE: PRT
<213> ORGANISM: S. aureus

<400> SEQUENCE: 18

Met Lys Lys Leu Tyr Thr Ser Tyr Gly Thr Tyr Gly Phe Leu His Gln
1               5                   10                  15
Ile Lys Ile Asn Asn Pro Thr His Gln Leu Phe Gln Phe Ser Ala Ser
            20                  25                  30
Asp Thr Ser Val Ile Phe Glu Glu Thr Asp Gly Glu Thr Val Leu Lys
        35                  40                  45
Ser Pro Ser Ile Tyr Glu Val Ile Lys Glu Ile Gly Glu Phe Ser Glu
    50                  55                  60
```

```
His His Phe Tyr Cys Ala Ile Phe Ile Pro Ser Thr Glu Asp His Ala
 65                  70                  75                  80

Tyr Gln Leu Glu Lys Lys Leu Ile Ser Val Asp Asp Asn Phe Arg Asn
                 85                  90                  95

Phe Gly Gly Phe Lys Ser Tyr Arg Leu Leu Arg Pro Ala Lys Gly Thr
            100                 105                 110

Thr Tyr Lys Ile Tyr Phe Gly Phe Ala Asp Arg His Ala Tyr Glu Asp
        115                 120                 125

Phe Lys Gln Ser Asp Ala Phe Asn Asp His Phe Ser Lys Asp Ala Leu
    130                 135                 140

Ser His Tyr Phe Gly Ser Ser Gly Gln His Ser Ser Tyr Phe Glu Arg
145                 150                 155                 160

Tyr Leu Tyr Pro Ile Lys Glu
                165

<210> SEQ ID NO 19
<211> LENGTH: 167
<212> TYPE: PRT
<213> ORGANISM: S. epidermidis

<400> SEQUENCE: 19

Met Tyr Leu Tyr Thr Ser Tyr Gly Thr Tyr Gln Phe Leu Asn Gln Ile
  1               5                  10                  15

Lys Leu Asn His Gln Glu Arg Ser Leu Phe Gln Phe Ser Thr Asn Asp
                 20                  25                  30

Ser Ser Ile Ile Leu Glu Glu Ser Glu Gly Lys Ser Ile Leu Lys His
             35                  40                  45

Pro Ser Ala Tyr Gln Val Ile Asp Ser Thr Gly Glu Phe Asn Glu His
 50                  55                  60

His Phe Tyr Ser Ala Ile Phe Val Pro Thr Ser Glu Asp His Arg Gln
 65                  70                  75                  80

Gln Leu Glu Lys Lys Leu Leu Leu Val Asp Val Pro Leu Arg Asn Phe
                 85                  90                  95

Gly Gly Phe Lys Ser Tyr Arg Leu Leu Lys Pro Thr Glu Gly Ser Thr
            100                 105                 110

Tyr Lys Ile Tyr Phe Gly Phe Ala Asn Arg Thr Ala Tyr Glu Asp Phe
        115                 120                 125

Lys Ala Ser Asp Ile Phe Asn Glu Asn Phe Ser Lys Ala Leu Ser
    130                 135                 140

Gln Tyr Phe Gly Ala Ser Gly Gln His Ser Ser Tyr Phe Glu Arg Tyr
145                 150                 155                 160

Leu Tyr Pro Ile Glu Asp His
                165

<210> SEQ ID NO 20
<211> LENGTH: 1141
<212> TYPE: PRT
<213> ORGANISM: S. aureus

<400> SEQUENCE: 20

Met Ile Asn Arg Asp Asn Lys Lys Ala Ile Thr Lys Lys Gly Met Ile
  1               5                  10                  15

Ser Asn Arg Leu Asn Lys Phe Ser Ile Arg Lys Tyr Thr Val Gly Thr
                 20                  25                  30

Ala Ser Ile Leu Val Gly Thr Thr Leu Ile Phe Gly Leu Gly Asn Gln
             35                  40                  45
```

```
Glu Ala Lys Ala Ala Glu Asn Thr Ser Thr Glu Asn Ala Lys Gln Asp
 50                  55                  60

Asp Ala Thr Thr Ser Asp Asn Lys Glu Val Val Ser Glu Thr Glu Asn
 65                  70                  75                  80

Asn Ser Thr Thr Glu Asn Asp Ser Thr Asn Pro Ile Lys Lys Glu Thr
                 85                  90                  95

Asn Thr Asp Ser Gln Pro Glu Ala Lys Glu Glu Ser Thr Thr Ser Ser
            100                 105                 110

Thr Gln Gln Gln Gln Asn Asn Val Thr Ala Thr Thr Glu Thr Lys Pro
        115                 120                 125

Gln Asn Ile Glu Lys Glu Asn Val Lys Pro Ser Thr Asp Lys Thr Ala
    130                 135                 140

Thr Glu Asp Thr Ser Val Ile Leu Glu Glu Lys Lys Ala Pro Asn Tyr
145                 150                 155                 160

Thr Asn Asn Asp Val Thr Thr Lys Pro Ser Thr Ser Glu Ile Gln Thr
                165                 170                 175

Lys Pro Thr Thr Pro Gln Glu Ser Thr Asn Ile Glu Asn Ser Gln Pro
            180                 185                 190

Gln Pro Thr Pro Ser Lys Val Asp Asn Gln Val Thr Asp Ala Thr Asn
        195                 200                 205

Pro Lys Glu Pro Val Asn Val Ser Lys Glu Glu Leu Lys Asn Asn Pro
    210                 215                 220

Glu Lys Leu Lys Glu Leu Val Arg Asn Asp Asn Thr Asp Arg Ser
225                 230                 235                 240

Thr Lys Pro Val Ala Thr Ala Pro Thr Ser Val Ala Pro Lys Arg Leu
                245                 250                 255

Asn Ala Lys Met Arg Phe Ala Val Ala Gln Pro Ala Ala Val Ala Ser
            260                 265                 270

Asn Asn Val Asn Asp Leu Ile Thr Val Thr Lys Gln Thr Ile Lys Val
        275                 280                 285

Gly Asp Gly Lys Asp Asn Val Ala Ala Ala His Asp Gly Lys Asp Ile
    290                 295                 300

Glu Tyr Asp Thr Glu Phe Thr Ile Asp Asn Lys Val Lys Lys Gly Asp
305                 310                 315                 320

Thr Met Thr Ile Asn Tyr Asp Lys Asn Val Ile Pro Ser Asp Leu Thr
                325                 330                 335

Asp Lys Asn Asp Pro Ile Asp Ile Thr Asp Pro Ser Gly Glu Val Ile
            340                 345                 350

Ala Lys Gly Thr Phe Asp Lys Ala Thr Lys Gln Ile Thr Tyr Thr Phe
        355                 360                 365

Thr Asp Tyr Val Asp Lys Tyr Glu Asp Ile Lys Ala Arg Leu Thr Leu
    370                 375                 380

Tyr Ser Tyr Ile Asp Lys Gln Ala Val Pro Asn Glu Thr Ser Leu Asn
385                 390                 395                 400

Leu Thr Phe Ala Thr Ala Gly Lys Glu Thr Ser Gln Asn Val Ser Val
                405                 410                 415

Asp Tyr Gln Asp Pro Met Val His Gly Asp Ser Asn Ile Gln Ser Ile
            420                 425                 430

Phe Thr Lys Leu Asp Glu Asn Lys Gln Thr Ile Glu Gln Gln Ile Tyr
        435                 440                 445

Val Asn Pro Leu Lys Lys Thr Ala Thr Asn Thr Lys Val Asp Ile Ala
    450                 455                 460

Gly Ser Gln Val Asp Asp Tyr Gly Asn Ile Lys Leu Gly Asn Gly Ser
```

```
              465                 470                 475                 480
         Thr Ile Ile Asp Gln Asn Thr Glu Ile Lys Val Tyr Lys Val Asn Pro
                             485                 490                 495
         Asn Gln Gln Leu Pro Gln Ser Asn Arg Ile Tyr Asp Phe Ser Gln Tyr
                         500                 505                 510
         Glu Asp Val Thr Ser Gln Phe Asp Asn Lys Lys Ser Phe Ser Asn Asn
                     515                 520                 525
         Val Ala Thr Leu Asp Phe Gly Asp Ile Asn Ser Ala Tyr Ile Ile Lys
                 530                 535                 540
         Val Val Ser Lys Tyr Thr Pro Thr Ser Asp Gly Glu Leu Asp Ile Ala
         545                 550                 555                 560
         Gln Gly Thr Ser Met Arg Thr Thr Asp Lys Tyr Gly Tyr Tyr Asn Tyr
                             565                 570                 575
         Ala Gly Tyr Ser Asn Phe Ile Val Thr Ser Asn Asp Thr Gly Gly Gly
                         580                 585                 590
         Asp Gly Thr Val Lys Pro Glu Glu Lys Leu Tyr Lys Ile Gly Asp Tyr
                     595                 600                 605
         Val Trp Glu Asp Val Asp Lys Asp Gly Val Gln Gly Thr Asp Ser Lys
         610                 615                 620
         Glu Lys Pro Met Ala Asn Val Leu Val Thr Leu Thr Tyr Pro Asp Gly
         625                 630                 635                 640
         Thr Thr Lys Ser Val Arg Thr Asp Ala Asn Gly His Tyr Glu Phe Gly
                             645                 650                 655
         Gly Leu Lys Asp Gly Glu Thr Tyr Thr Val Lys Phe Glu Thr Pro Ala
                         660                 665                 670
         Gly Tyr Leu Pro Thr Lys Val Asn Gly Thr Thr Asp Gly Glu Lys Asp
                     675                 680                 685
         Ser Asn Gly Ser Ser Ile Thr Val Lys Ile Asn Gly Lys Asp Asp Met
         690                 695                 700
         Ser Leu Asp Thr Gly Phe Tyr Lys Glu Pro Lys Tyr Asn Leu Gly Asp
         705                 710                 715                 720
         Tyr Val Trp Glu Asp Thr Asn Lys Asp Gly Ile Gln Asp Ala Asn Glu
                             725                 730                 735
         Pro Gly Ile Lys Asp Val Lys Val Thr Leu Lys Asp Ser Thr Gly Lys
                         740                 745                 750
         Val Ile Gly Thr Thr Thr Thr Asp Ala Ser Gly Lys Tyr Lys Phe Thr
                     755                 760                 765
         Asp Leu Asp Asn Gly Asn Tyr Thr Val Glu Phe Glu Thr Pro Ala Gly
         770                 775                 780
         Tyr Thr Pro Thr Val Lys Asn Thr Thr Ala Glu Asp Lys Asp Ser Asn
         785                 790                 795                 800
         Gly Leu Thr Thr Thr Gly Val Ile Lys Asp Ala Asp Asn Met Thr Leu
                             805                 810                 815
         Asp Ser Gly Phe Tyr Lys Thr Pro Lys Tyr Ser Leu Gly Asp Tyr Val
                         820                 825                 830
         Trp Tyr Asp Ser Asn Lys Asp Gly Lys Gln Asp Ser Thr Glu Lys Gly
                     835                 840                 845
         Ile Lys Asp Val Lys Val Thr Leu Leu Asn Glu Lys Gly Glu Val Ile
         850                 855                 860
         Gly Thr Thr Lys Thr Asp Glu Asn Gly Lys Tyr Arg Phe Asp Asn Leu
         865                 870                 875                 880
         Asp Ser Gly Lys Tyr Lys Val Ile Phe Glu Lys Pro Ala Gly Leu Thr
                             885                 890                 895
```

-continued

```
Gln Thr Val Thr Asn Thr Thr Glu Asp Asp Lys Asp Ala Asp Gly Gly
            900                 905                 910

Glu Val Asp Val Thr Ile Thr Asp His Asp Asp Phe Ile Leu Asp Asn
            915                 920                 925

Gly Tyr Phe Glu Glu Asp Thr Ser Asp Ser Asp Ser Asp Ser
            930                 935                 940

Asp Ser Asp Ser Asp Ser Asp Ser Asp Ser Asp Ser Asp Ser Asp Ser
945                 950                 955                 960

Asp Ser Asp Ser Asp Ser Asp Ser Asp Ser Asp Ser Asp Ser
            965                 970                 975

Asp Ser Asp Ser Asp Ser Asp Ser Asp Ser Asp Ser Asp Ser
            980                 985                 990

Asp Ser Asp Ser Asp Ser Asp Ser Asp Ser Asp Ser Asp Ser
            995                1000                1005

Asp Ser Asp Ser Asp Ser Asp Ser Asp Ser Asp Ser Asp Ser
           1010                1015                1020

Asp Ser Asp Ser Asp Ser Asp Ser Asp Ser Asp Ser Asp Ser
1025                1030                1035                1040

Asp Ser Asp Ser Asp Ser Asp Ser Asp Ser Asp Ser Asp Ser
           1045                1050                1055

Asp Ser Asp Ser Asp Ser Asp Ser Asp Ser Asp Ser Asp Ser
           1060                1065                1070

Asp Ser Asp Ser Asp Ser Asp Ser Asp Ala Gly Lys His Thr Pro Val
           1075                1080                1085

Lys Pro Met Ser Thr Thr Lys Asp His His Asn Lys Ala Lys Ala Leu
           1090                1095                1100

Pro Glu Thr Gly Ser Glu Asn Asn Gly Ser Asn Asn Ala Thr Leu Phe
1105                1110                1115                1120

Gly Gly Leu Phe Ala Ala Leu Gly Ser Leu Leu Leu Phe Gly Arg Arg
           1125                1130                1135

Lys Lys Gln Asn Lys
           1140

<210> SEQ ID NO 21
<211> LENGTH: 1056
<212> TYPE: PRT
<213> ORGANISM: S. epidermidis

<400> SEQUENCE: 21

Met Ile Asn Lys Lys Asn Asn Leu Leu Thr Lys Lys Pro Ile Ala
1               5                  10                  15

Asn Lys Ser Asn Lys Tyr Ala Ile Arg Lys Phe Thr Val Gly Thr Ala
            20                  25                  30

Ser Ile Val Ile Gly Ala Thr Leu Leu Phe Gly Leu Gly His Asn Glu
        35                  40                  45

Ala Lys Ala Glu Glu Asn Ser Val Gln Asp Val Lys Asp Ser Asn Thr
    50                  55                  60

Asp Asp Glu Leu Ser Asp Ser Asn Asp Gln Ser Ser Asp Glu Glu Lys
65                  70                  75                  80

Asn Asp Val Ile Asn Asn Gln Ser Ile Thr Asp Asp Asn Asn
            85                  90                  95

Gln Ile Ile Lys Lys Glu Glu Thr Asn Asn Tyr Asp Gly Ile Glu Lys
            100                 105                 110

Arg Ser Glu Asp Arg Thr Glu Ser Thr Thr Asn Val Asp Glu Asn Glu
```

```
              115                 120                 125
Ala Thr Phe Leu Gln Lys Thr Pro Gln Asp Asn Thr His Leu Thr Glu
              130                 135                 140
Glu Glu Val Lys Glu Ser Ser Ser Val Glu Ser Ser Asn Ser Ser Ile
145                 150                 155                 160
Asp Thr Ala Gln Gln Pro Ser His Thr Thr Ile Asn Arg Glu Glu Ser
              165                 170                 175
Val Gln Thr Ser Asp Asn Val Glu Asp Ser His Val Ser Asp Phe Ala
              180                 185                 190
Asn Ser Lys Ile Lys Glu Ser Asn Thr Glu Ser Gly Lys Glu Glu Asn
              195                 200                 205
Thr Ile Glu Gln Pro Asn Lys Val Lys Glu Asp Ser Thr Thr Ser Gln
210                 215                 220
Pro Ser Gly Tyr Thr Asn Ile Asp Glu Lys Ile Ser Asn Gln Asp Glu
225                 230                 235                 240
Leu Leu Asn Leu Pro Ile Asn Glu Tyr Glu Asn Lys Ala Arg Pro Leu
              245                 250                 255
Ser Thr Thr Ser Ala Gln Pro Ser Ile Lys Arg Val Thr Val Asn Gln
              260                 265                 270
Leu Ala Ala Glu Gln Gly Ser Asn Val Asn His Leu Ile Lys Val Thr
              275                 280                 285
Asp Gln Ser Ile Thr Glu Gly Tyr Asp Ser Glu Gly Val Ile Lys
290                 295                 300
Ala His Asp Ala Glu Asn Leu Ile Tyr Asp Val Thr Phe Glu Val Asp
305                 310                 315                 320
Asp Lys Val Lys Ser Gly Asp Thr Met Thr Val Asp Ile Asp Lys Asn
              325                 330                 335
Thr Val Pro Ser Asp Leu Thr Asp Ser Phe Thr Ile Pro Lys Ile Lys
              340                 345                 350
Asp Asn Ser Gly Glu Ile Ile Ala Thr Gly Thr Tyr Asp Asn Lys Asn
              355                 360                 365
Lys Gln Ile Thr Tyr Thr Phe Thr Asp Tyr Val Asp Lys Tyr Glu Asn
              370                 375                 380
Ile Lys Ala His Leu Lys Leu Thr Ser Tyr Ile Asp Lys Ser Lys Val
385                 390                 395                 400
Pro Asn Asn Asn Thr Lys Leu Asp Val Glu Tyr Lys Thr Ala Leu Ser
              405                 410                 415
Ser Val Asn Lys Thr Ile Thr Val Glu Tyr Gln Arg Pro Asn Glu Asn
              420                 425                 430
Arg Thr Ala Asn Leu Gln Ser Met Phe Thr Asn Ile Asp Thr Lys Asn
              435                 440                 445
His Thr Val Glu Gln Thr Ile Tyr Ile Asn Pro Leu Arg Tyr Ser Ala
              450                 455                 460
Lys Glu Thr Asn Val Asn Ile Ser Gly Asn Gly Asp Glu Gly Ser Thr
465                 470                 475                 480
Ile Ile Asp Asp Ser Thr Ile Ile Lys Val Tyr Lys Val Gly Asp Asn
              485                 490                 495
Gln Asn Leu Pro Asp Ser Asn Arg Ile Tyr Asp Tyr Ser Glu Tyr Glu
              500                 505                 510
Asp Val Thr Asn Asp Asp Tyr Ala Gln Leu Gly Asn Asn Asn Asp Val
              515                 520                 525
Asn Ile Asn Phe Gly Asn Ile Asp Ser Pro Tyr Ile Ile Lys Val Ile
              530                 535                 540
```

```
Ser Lys Tyr Asp Pro Asn Lys Asp Tyr Thr Thr Ile Gln Gln Thr
545                 550                 555                 560

Val Thr Met Gln Thr Thr Ile Asn Glu Tyr Thr Gly Glu Phe Arg Thr
                565                 570                 575

Ala Ser Tyr Asp Asn Thr Ile Ala Phe Ser Thr Ser Ser Gly Gln Gly
                580                 585                 590

Gln Gly Asp Leu Pro Pro Glu Lys Thr Tyr Lys Ile Gly Asp Tyr Val
            595                 600                 605

Trp Glu Asp Val Asp Lys Asp Gly Ile Gln Asn Thr Asn Asp Asn Glu
610                 615                 620

Lys Pro Leu Ser Asn Val Leu Val Thr Leu Thr Tyr Pro Asp Gly Thr
625                 630                 635                 640

Ser Lys Ser Val Arg Thr Asp Glu Asp Gly Lys Tyr Gln Phe Asp Gly
                645                 650                 655

Leu Lys Asn Gly Leu Thr Tyr Lys Ile Thr Phe Glu Thr Pro Glu Gly
                660                 665                 670

Tyr Thr Pro Thr Leu Lys His Ser Gly Thr Asn Pro Ala Leu Asp Ser
                675                 680                 685

Glu Gly Asn Ser Val Trp Val Thr Ile Asn Gly Gln Asp Asp Met Thr
690                 695                 700

Ile Asp Ser Gly Phe Tyr Gln Thr Pro Lys Tyr Ser Leu Gly Asn Tyr
705                 710                 715                 720

Val Trp Tyr Asp Thr Asn Lys Asp Gly Ile Gln Gly Asp Glu Lys
                725                 730                 735

Gly Ile Ser Gly Val Lys Val Thr Leu Lys Asp Glu Asn Gly Asn Ile
                740                 745                 750

Ile Ser Thr Thr Thr Thr Asp Glu Asn Gly Lys Tyr Gln Phe Asp Asn
                755                 760                 765

Leu Asn Ser Gly Asn Tyr Ile Val His Phe Asp Lys Pro Ser Gly Met
                770                 775                 780

Thr Gln Thr Thr Thr Asp Ser Gly Asp Asp Asp Glu Gln Asp Ala Asp
785                 790                 795                 800

Gly Glu Glu Val His Val Thr Ile Thr Asp His Asp Asp Phe Ser Ile
                805                 810                 815

Asp Asn Gly Tyr Tyr Asp Asp Glu Ser Asp Ser Asp Ser Asp Ser Asp
                820                 825                 830

Ser Asp Ser Asp Ser Asp Ser Asp Ser Asp Ser Asp Ser Asp Ser Asp
                835                 840                 845

Ser Asp Ser Asp Ser Asp Ser Asp Ser Asp Ser Asp Ser Asp Ser Asp
                850                 855                 860

Ser Asp Ser Asp Ser Asp Ser Asp Ser Asp Ser Asp Ser Asp Ser Asp
865                 870                 875                 880

Ser Asp Ser Asp Ser Asp Ser Asp Ser Asp Ser Asp Ser Asp Ser Asp
                885                 890                 895

Ser Asp Ser Asp Ser Asp Ser Asp Ser Asp Ser Asp Ser Asp Ser Asp
                900                 905                 910

Ser Asp Ser Asp Ser Asp Ser Asp Ser Asp Ser Asp Ser Asp Ser Asp
                915                 920                 925

Ser Asp Ser Asp Ser Asp Ser Asp Ser Asp Ser Asp Ser Asp Ser Asp
                930                 935                 940

Ser Asp Ser Asp Ser Asp Ser Asp Ser Asp Ser Asp Ser Asp Ser Asp
945                 950                 955                 960
```

-continued

```
Ser Asp Ser Asp Ser Asp Ser Asp Ser Asp Ser Asp Ser Asp
                965                 970                 975

Ser Asp Ser Asp Ser Asp Ser Asp Ser Asp Ser Asp Ser Asp
            980                 985                 990

Ser Asp Ser Asp Ser Asp Asn Asp Ser Asp Leu Gly Asn Ser
            995                1000                1005

Ser Asp Lys Ser Thr Lys Asp Lys Leu Pro Asp Thr Gly Ala Asn Glu
        1010                1015                1020

Asp Tyr Gly Ser Lys Gly Thr Leu Leu Gly Thr Leu Phe Ala Gly Leu
    1025                1030                1035                1040

Gly Ala Leu Leu Leu Gly Lys Arg Arg Lys Asn Arg Lys Asn Lys Asn
            1045                1050                1055

<210> SEQ ID NO 22
<211> LENGTH: 486
<212> TYPE: PRT
<213> ORGANISM: S. aureus

<400> SEQUENCE: 22

Met Ser Asn Asn Phe Lys Asp Asp Phe Glu Lys Asn Arg Gln Ser Ile
  1               5                  10                  15

Asp Thr Asn Ser His Gln Asp His Thr Glu Asp Val Glu Lys Asp Gln
             20                  25                  30

Ser Glu Leu Glu His Gln Asp Thr Ile Glu Asn Thr Glu Gln Gln Phe
         35                  40                  45

Pro Pro Arg Asn Ala Gln Arg Lys Arg Arg Arg Asp Leu Ala Thr
     50                  55                  60

Asn His Asn Lys Gln Val His Asn Glu Ser Gln Thr Ser Glu Asp Asn
 65                  70                  75                  80

Val Gln Asn Glu Ala Gly Thr Ile Asp Asp Arg Gln Val Glu Ser Ser
                 85                  90                  95

His Ser Thr Glu Ser Gln Glu Pro Ser His Gln Asp Ser Thr Pro Gln
            100                 105                 110

His Glu Glu Glu Tyr Tyr Asn Lys Asn Ala Phe Ala Met Asp Lys Ser
        115                 120                 125

His Pro Glu Pro Ile Glu Asp Asn Asp Lys His Glu Thr Ile Lys Asp
    130                 135                 140

Ala Glu Asn Asn Thr Glu His Ser Thr Val Ser Asp Lys Ser Ile Ala
145                 150                 155                 160

Glu Gln Ser Gln Gln Pro Lys Pro Tyr Phe Ala Thr Gly Ala Asn Gln
                165                 170                 175

Ala Asn Thr Ser Lys Asp Lys His Asp Asp Val Thr Val Lys Gln Asp
            180                 185                 190

Lys Asp Glu Ser Lys Asp His His Ser Gly Lys Lys Gly Ala Ala Ile
        195                 200                 205

Gly Ala Gly Thr Ala Gly Val Ala Gly Ala Gly Ala Met Gly Val
    210                 215                 220

Ser Lys Ala Lys Lys His Ser Asn Asp Ala Gln Asn Lys Ser Asn Ser
225                 230                 235                 240

Asp Lys Ser Asn Asn Ser Thr Glu Asp Lys Ala Ser Gln Asp Lys Ser
                245                 250                 255

Lys Asp His His Asn Gly Lys Lys Gly Ala Ala Ile Gly Ala Gly Thr
            260                 265                 270

Ala Gly Leu Ala Gly Gly Ala Ala Ser Lys Ser Ala Ser Ala Ala Ser
        275                 280                 285
```

-continued

```
Lys Pro His Ala Ser Asn Asn Ala Ser Gln Asn His Asp Glu His Asp
    290                 295                 300

Asn His Asp Arg Asp Lys Glu Arg Lys Lys Gly Gly Met Ala Lys Val
305                 310                 315                 320

Leu Leu Pro Leu Ile Ala Ala Val Leu Ile Ile Gly Ala Leu Ala Ile
                325                 330                 335

Phe Gly Gly Met Ala Leu Asn Asn His Asn Asn Gly Thr Lys Glu Asn
                340                 345                 350

Lys Ile Ala Asn Thr Asn Lys Asn Asn Ala Asp Glu Ser Lys Asp Lys
                355                 360                 365

Asp Thr Ser Lys Asp Ala Ser Lys Asp Lys Ser Lys Thr Asp Ser
    370                 375                 380

Asp Lys Ser Lys Glu Asp Gln Asp Lys Ala Thr Lys Asp Glu Ser Asp
385                 390                 395                 400

Asn Asp Gln Asn Asn Ala Asn Gln Ala Asn Gln Ala Gln Asn Asn
                405                 410                 415

Gln Asn Gln Gln Gln Ala Asn Gln Asn Gln Gln Gln Gln Gln Gln Arg
                420                 425                 430

Gln Gly Gly Gly Gln Arg His Thr Val Asn Gly Gln Glu Asn Leu Tyr
                435                 440                 445

Arg Ile Ala Ile Gln Tyr Tyr Gly Ser Gly Ser Pro Glu Asn Val Glu
    450                 455                 460

Lys Ile Arg Arg Ala Asn Gly Leu Ser Gly Asn Asn Ile Arg Asn Gly
465                 470                 475                 480

Gln Gln Ile Val Ile Pro
                485

<210> SEQ ID NO 23
<211> LENGTH: 472
<212> TYPE: PRT
<213> ORGANISM: S. epidermidis

<400> SEQUENCE: 23

Met Ile Glu Leu Ile Lys Met Glu Gly Met Ile Val Val Ser Asn Asn
1               5                   10                  15

Asn Phe Lys Asp Asp Phe Glu Lys Asn Arg Gln Ser Ile Asn Pro Asp
                20                  25                  30

Glu Gln Gln Thr Glu Leu Lys Glu Asp Asp Lys Thr Asn Glu Asn Lys
                35                  40                  45

Lys Glu Ala Asp Ser Gln Asn Ser Leu Ser Asn Ser Asn Gln Gln
50                  55                  60

Phe Pro Pro Arg Asn Ala Gln Arg Arg Lys Arg Arg Glu Thr Ala
65                  70                  75                  80

Thr Asn Gln Ser Lys Gln Gln Asp Asp Lys His Gln Lys Asn Ser Asp
                85                  90                  95

Ala Lys Thr Thr Glu Gly Ser Leu Asp Asp Arg Tyr Asp Glu Ala Gln
                100                 105                 110

Leu Gln Gln Gln His Asp Lys Ser Gln Gln Asn Lys Thr Glu Lys
                115                 120                 125

Gln Ser Gln Asp Asn Arg Met Lys Asp Gly Lys Asp Ala Ala Ile Val
                130                 135                 140

Asn Gly Thr Ser Glu Ser Pro Glu His Lys Ser Lys Ser Thr Gln Asn
145                 150                 155                 160

Arg Pro Gly Pro Lys Ala Gln Gln Gln Lys Arg Lys Ser Glu Ser Thr
```

165                 170                 175

Gln Ser Lys Pro Ser Thr Asn Lys Asp Lys Ala Ala Thr Gly Ala
            180                 185                 190

Gly Ile Ala Gly Ala Ala Gly Val Ala Gly Ala Ala Glu Thr Ser Lys
        195                 200                 205

Arg His His Asn Lys Lys Asp Lys Gln Asp Ser Lys His Ser Asn His
210                 215                 220

Glu Asn Asp Glu Lys Ser Val Lys Asn Asp Asp Gln Lys Gln Ser Lys
225                 230                 235                 240

Lys Gly Lys Lys Ala Ala Val Gly Ala Gly Ala Ala Gly Val Gly
            245                 250                 255

Ala Ala Gly Val Ala His His Asn Asn Gln Asn Lys His His Asn Glu
        260                 265                 270

Glu Lys Asn Ser Asn Gln Asn Asn Gln Tyr Asn Asp Gln Ser Glu Gly
        275                 280                 285

Lys Lys Lys Gly Gly Phe Met Lys Ile Leu Leu Pro Leu Ile Ala Ala
        290                 295                 300

Ile Leu Ile Leu Gly Ala Ile Ala Ile Phe Gly Gly Met Ala Leu Asn
305                 310                 315                 320

Asn His Asn Asp Ser Lys Ser Asp Gln Lys Ile Ala Asn Gln Ser
                325                 330                 335

Lys Lys Asp Ser Asp Lys Lys Asp Gly Ala Gln Ser Glu Asp Asn Lys
            340                 345                 350

Asp Lys Lys Ser Asp Ser Asn Lys Asp Lys Lys Ser Asp Ser Asp Lys
        355                 360                 365

Asn Ala Asp Asp Asp Ser Asp Asn Ser Ser Asn Pro Asn Ala Thr
370                 375                 380

Ser Thr Asn Asn Asn Asp Asn Val Ala Asn Asn Ser Asn Tyr Thr
385                 390                 395                 400

Asn Gln Asn Gln Gln Asp Asn Ala Asn Gln Asn Ser Asn Asn Gln Gln
                405                 410                 415

Ala Thr Gln Gly Gln Gln Ser His Thr Val Tyr Gly Gln Glu Asn Leu
            420                 425                 430

Tyr Arg Ile Ala Ile Gln Tyr Tyr Gly Glu Gly Thr Gln Ala Asn Val
        435                 440                 445

Asp Lys Ile Lys Arg Ala Asn Gly Leu Ser Ser Asn Asn Ile His Asn
        450                 455                 460

Gly Gln Thr Leu Val Ile Pro Gln
465                 470

<210> SEQ ID NO 24
<211> LENGTH: 165
<212> TYPE: PRT
<213> ORGANISM: S. aureus

<400> SEQUENCE: 24

Met Lys Asn Lys Leu Ile Ala Lys Ser Leu Leu Thr Ile Ala Ala Ile
1               5                   10                  15

Gly Ile Thr Thr Thr Thr Ile Ala Ser Thr Ala Asp Ala Ser Glu Gly
            20                  25                  30

Tyr Gly Pro Arg Glu Lys Lys Pro Val Ser Ile Asn His Asn Ile Val
        35                  40                  45

Glu Tyr Asn Asp Gly Thr Phe Lys Tyr Gln Ser Arg Pro Lys Phe Asn
    50                  55                  60

```
Ser Thr Pro Lys Tyr Ile Lys Phe Lys His Asp Tyr Asn Ile Leu Glu
 65                  70                  75                  80

Phe Asn Asp Gly Thr Phe Glu Tyr Gly Ala Arg Pro Gln Phe Asn Lys
                 85                  90                  95

Pro Ala Ala Lys Thr Asp Ala Thr Ile Lys Lys Glu Gln Lys Leu Ile
            100                 105                 110

Gln Ala Gln Asn Leu Val Arg Glu Phe Glu Lys Thr His Thr Val Ser
        115                 120                 125

Ala His Arg Lys Ala Gln Lys Ala Val Asn Leu Val Ser Phe Glu Tyr
    130                 135                 140

Lys Val Lys Met Val Leu Gln Glu Arg Ile Asp Asn Val Leu Lys
145                 150                 155                 160

Gln Gly Leu Val Arg
            165

<210> SEQ ID NO 25
<211> LENGTH: 319
<212> TYPE: PRT
<213> ORGANISM: S. aureus

<400> SEQUENCE: 25

Met Lys Thr Arg Ile Val Ser Val Thr Thr Leu Leu Leu Gly
  1               5                  10                  15

Ser Ile Leu Met Asn Pro Val Ala Asn Ala Asp Ser Asp Ile Asn
                 20                  25                  30

Ile Lys Thr Gly Thr Thr Asp Ile Gly Ser Asn Thr Thr Val Lys Thr
             35                  40                  45

Gly Asp Leu Val Thr Tyr Asp Lys Glu Asn Gly Met His Lys Lys Val
 50                  55                  60

Phe Tyr Ser Phe Ile Asp Asp Lys Asn His Asn Lys Lys Leu Leu Val
 65                  70                  75                  80

Ile Arg Thr Lys Gly Thr Ile Ala Gly Gln Tyr Arg Val Tyr Ser Glu
             85                  90                  95

Glu Gly Ala Asn Lys Ser Gly Leu Ala Trp Pro Ser Ala Phe Lys Val
        100                 105                 110

Gln Leu Gln Leu Pro Asp Asn Glu Val Ala Gln Ile Ser Asp Tyr Tyr
    115                 120                 125

Pro Arg Asn Ser Ile Asp Thr Lys Glu Tyr Met Ser Thr Leu Thr Tyr
130                 135                 140

Gly Phe Asn Gly Asn Val Thr Gly Asp Asp Thr Gly Lys Ile Gly Gly
145                 150                 155                 160

Leu Ile Gly Ala Asn Val Ser Ile Gly His Thr Leu Lys Tyr Val Gln
                165                 170                 175

Pro Asp Phe Lys Thr Ile Leu Glu Ser Pro Thr Asp Lys Lys Val Gly
            180                 185                 190

Trp Lys Val Ile Phe Asn Asn Met Val Asn Gln Asn Trp Gly Pro Tyr
        195                 200                 205

Asp Arg Asp Ser Trp Asn Pro Val Tyr Gly Asn Gln Leu Phe Met Lys
    210                 215                 220

Thr Arg Asn Gly Ser Met Lys Ala Ala Glu Asn Phe Leu Asp Pro Asn
225                 230                 235                 240

Lys Ala Ser Ser Leu Leu Ser Ser Gly Phe Ser Pro Asp Phe Ala Thr
                245                 250                 255

Val Ile Thr Met Asp Arg Lys Ala Ser Lys Gln Gln Thr Asn Ile Asp
            260                 265                 270
```

```
Val Ile Tyr Glu Arg Val Arg Asp Asp Tyr Gln Leu His Trp Thr Ser
            275                 280                 285

Thr Asn Trp Lys Gly Thr Asn Thr Lys Asp Lys Trp Thr Asp Arg Ser
        290                 295                 300

Ser Glu Arg Tyr Lys Ile Asp Trp Glu Lys Glu Glu Met Thr Asn
305                 310                 315

<210> SEQ ID NO 26
<211> LENGTH: 428
<212> TYPE: PRT
<213> ORGANISM: S. aureus

<400> SEQUENCE: 26

Met His Met Lys Asn Lys Tyr Ile Ser Lys Leu Leu Val Gly Ala Ala
1               5                   10                  15

Thr Ile Thr Leu Ala Thr Met Ile Ser Asn Gly Glu Ala Lys Ala Ser
            20                  25                  30

Glu Asn Thr Gln Gln Thr Ser Thr Lys His Gln Thr Thr Gln Asn Asn
        35                  40                  45

Tyr Val Thr Asp Gln Gln Lys Ala Phe Tyr Gln Val Leu His Leu Lys
    50                  55                  60

Gly Ile Thr Glu Glu Gln Arg Asn Gln Tyr Ile Lys Thr Leu Arg Glu
65                  70                  75                  80

His Pro Glu Arg Ala Gln Glu Val Phe Ser Glu Ser Leu Lys Asp Ser
                85                  90                  95

Lys Asn Pro Asp Arg Arg Val Ala Gln Gln Asn Ala Phe Tyr Asn Val
            100                 105                 110

Leu Lys Asn Asp Asn Leu Thr Glu Gln Glu Lys Asn Asn Tyr Ile Ala
        115                 120                 125

Gln Ile Lys Glu Asn Pro Asp Arg Ser Gln Gln Val Trp Val Glu Ser
    130                 135                 140

Val Gln Ser Ser Lys Ala Lys Glu Arg Gln Asn Ile Glu Asn Ala Asp
145                 150                 155                 160

Lys Ala Ile Lys Asp Phe Gln Asp Asn Lys Ala Pro His Asp Lys Ser
                165                 170                 175

Ala Ala Tyr Glu Ala Asn Ser Lys Leu Pro Lys Asp Leu Arg Asp Lys
            180                 185                 190

Asn Asn Arg Phe Val Glu Lys Val Ser Ile Glu Lys Ala Ile Val Arg
        195                 200                 205

His Asp Glu Arg Val Lys Ser Ala Asn Asp Ala Ile Ser Lys Leu Asn
    210                 215                 220

Glu Lys Asp Ser Ile Glu Asn Arg Arg Leu Ala Gln Arg Glu Val Asn
225                 230                 235                 240

Lys Ala Pro Met Asp Val Lys Glu His Leu Gln Lys Gln Leu Asp Ala
                245                 250                 255

Leu Val Ala Gln Lys Asp Ala Glu Lys Lys Val Ala Pro Lys Val Glu
            260                 265                 270

Ala Pro Gln Ile Gln Ser Pro Gln Ile Glu Lys Pro Lys Ala Glu Ser
        275                 280                 285

Pro Lys Val Glu Val Pro Gln Ser Lys Leu Leu Gly Tyr Tyr Gln Ser
    290                 295                 300

Leu Lys Asp Ser Phe Asn Tyr Gly Tyr Lys Tyr Leu Thr Asp Thr Tyr
305                 310                 315                 320

Lys Ser Tyr Lys Glu Lys Tyr Asp Thr Ala Lys Tyr Tyr Tyr Asn Thr
```

```
            325                 330                 335
Tyr Tyr Lys Tyr Lys Gly Ala Ile Asp Gln Thr Val Leu Thr Val Leu
            340                 345                 350

Gly Ser Gly Ser Lys Ser Tyr Ile Gln Pro Leu Lys Val Asp Asp Lys
            355                 360                 365

Asn Gly Tyr Leu Ala Lys Ser Tyr Ala Gln Val Arg Asn Tyr Val Thr
            370                 375                 380

Glu Ser Ile Asn Thr Gly Lys Val Leu Tyr Thr Phe Tyr Gln Asn Pro
385                 390                 395                 400

Thr Leu Val Lys Thr Ala Ile Lys Ala Gln Glu Thr Ala Ser Ser Ile
            405                 410                 415

Lys Asn Thr Leu Ser Asn Leu Leu Ser Phe Trp Lys
            420                 425

<210> SEQ ID NO 27
<211> LENGTH: 350
<212> TYPE: PRT
<213> ORGANISM: S. aureus

<400> SEQUENCE: 27

Met Thr Lys His Tyr Leu Asn Ser Lys Tyr Gln Ser Glu Gln Arg Ser
1               5                   10                  15

Ser Ala Met Lys Lys Ile Thr Met Gly Thr Ala Ser Ile Ile Leu Gly
            20                  25                  30

Ser Leu Val Tyr Ile Gly Ala Asp Ser Gln Gln Val Asn Ala Ala Thr
            35                  40                  45

Glu Ala Thr Asn Ala Thr Asn Asn Gln Ser Thr Gln Val Ser Gln Ala
            50                  55                  60

Thr Ser Gln Pro Ile Asn Phe Gln Val Gln Lys Asp Gly Ser Ser Glu
65                  70                  75                  80

Lys Ser His Met Asp Asp Tyr Met Gln His Pro Gly Lys Val Ile Lys
            85                  90                  95

Gln Asn Asn Lys Tyr Tyr Phe Gln Thr Val Leu Asn Asn Ala Ser Phe
            100                 105                 110

Trp Lys Glu Tyr Lys Phe Tyr Asn Ala Asn Asn Gln Glu Leu Ala Thr
            115                 120                 125

Thr Val Val Asn Asp Asn Lys Lys Ala Asp Thr Arg Thr Ile Asn Val
            130                 135                 140

Ala Val Glu Pro Gly Tyr Lys Ser Leu Thr Thr Lys Val His Ile Val
145                 150                 155                 160

Val Pro Gln Ile Asn Tyr Asn His Arg Tyr Thr Thr His Leu Glu Phe
            165                 170                 175

Glu Lys Ala Ile Pro Thr Leu Ala Asp Ala Ala Lys Pro Asn Asn Val
            180                 185                 190

Lys Pro Val Gln Pro Lys Pro Ala Gln Pro Lys Thr Pro Thr Glu Gln
            195                 200                 205

Thr Lys Pro Val Gln Pro Lys Val Glu Lys Val Lys Pro Thr Val Thr
            210                 215                 220

Thr Thr Ser Lys Val Glu Asp Asn His Ser Thr Lys Val Val Ser Thr
225                 230                 235                 240

Asp Thr Thr Lys Asp Gln Thr Lys Thr Gln Thr Ala His Thr Val Lys
            245                 250                 255

Thr Ala Gln Thr Ala Gln Glu Gln Asn Lys Val Gln Thr Pro Val Lys
            260                 265                 270
```

-continued

```
Asp Val Ala Thr Ala Lys Ser Glu Ser Asn Asn Gln Ala Val Ser Asp
            275                 280                 285

Asn Lys Ser Gln Gln Thr Asn Lys Val Thr Lys His Asn Glu Thr Pro
290                 295                 300

Lys Gln Ala Ser Lys Ala Lys Glu Leu Pro Lys Thr Gly Leu Thr Ser
305                 310                 315                 320

Val Asp Asn Phe Ile Ser Thr Val Ala Phe Thr Leu Ala Leu Leu
                325                 330                 335

Gly Ser Leu Ser Leu Leu Leu Phe Lys Arg Lys Glu Ser Lys
            340                 345                 350

<210> SEQ ID NO 28
<211> LENGTH: 645
<212> TYPE: PRT
<213> ORGANISM: S. aureus

<400> SEQUENCE: 28

Met Asn Lys Gln Gln Lys Glu Phe Lys Ser Phe Tyr Ser Ile Arg Lys
1               5                   10                  15

Ser Ser Leu Gly Val Ala Ser Val Ala Ile Ser Thr Leu Leu Leu Leu
            20                  25                  30

Met Ser Asn Gly Glu Ala Gln Ala Ala Ala Glu Glu Thr Gly Gly Thr
        35                  40                  45

Asn Thr Glu Ala Gln Pro Lys Thr Glu Ala Val Ala Ser Pro Thr Thr
    50                  55                  60

Thr Ser Glu Lys Ala Pro Glu Thr Lys Pro Val Ala Asn Ala Val Ser
65                  70                  75                  80

Val Ser Asn Lys Glu Val Glu Ala Pro Thr Ser Glu Thr Lys Glu Ala
                85                  90                  95

Lys Glu Val Lys Glu Val Lys Ala Pro Lys Glu Thr Lys Ala Val Lys
            100                 105                 110

Pro Ala Ala Lys Ala Thr Asn Asn Thr Tyr Pro Ile Leu Asn Gln Glu
        115                 120                 125

Leu Arg Glu Ala Ile Lys Asn Pro Ala Ile Lys Asp Lys Asp His Ser
130                 135                 140

Ala Pro Asn Ser Arg Pro Ile Asp Phe Glu Met Lys Lys Glu Asn Gly
145                 150                 155                 160

Glu Gln Gln Phe Tyr His Tyr Ala Ser Ser Val Lys Pro Ala Arg Val
                165                 170                 175

Ile Phe Thr Asp Ser Lys Pro Glu Ile Glu Leu Gly Leu Gln Ser Gly
            180                 185                 190

Gln Phe Trp Arg Lys Phe Glu Val Tyr Glu Gly Asp Lys Lys Leu Pro
        195                 200                 205

Ile Lys Leu Val Ser Tyr Asp Thr Val Lys Asp Tyr Ala Tyr Ile Arg
210                 215                 220

Phe Ser Val Ser Asn Gly Thr Lys Ala Val Lys Ile Val Ser Ser Thr
225                 230                 235                 240

His Phe Asn Asn Lys Glu Glu Lys Tyr Asp Tyr Thr Leu Met Glu Phe
                245                 250                 255

Ala Gln Pro Ile Tyr Asn Ser Ala Asp Lys Phe Lys Thr Glu Glu Asp
            260                 265                 270

Tyr Lys Ala Glu Lys Leu Leu Ala Pro Tyr Lys Lys Ala Lys Thr Leu
        275                 280                 285

Glu Arg Gln Val Tyr Glu Leu Asn Lys Ile Gln Asp Lys Leu Pro Glu
290                 295                 300
```

```
Lys Leu Lys Ala Glu Tyr Lys Lys Leu Glu Asp Thr Lys Ala
305                 310                 315                 320

Leu Asp Glu Gln Val Lys Ser Ala Ile Thr Glu Phe Gln Asn Val Gln
                325                 330                 335

Pro Thr Asn Glu Lys Met Thr Asp Leu Gln Asp Thr Lys Tyr Val Val
            340                 345                 350

Tyr Glu Ser Val Glu Asn Asn Glu Ser Met Met Asp Thr Phe Val Lys
        355                 360                 365

His Pro Ile Lys Thr Gly Met Leu Asn Gly Lys Lys Tyr Met Val Met
370                 375                 380

Glu Thr Thr Asn Asp Asp Tyr Trp Lys Asp Phe Met Val Glu Gly Gln
385                 390                 395                 400

Arg Val Arg Thr Ile Ser Lys Asp Ala Lys Asn Asn Thr Arg Thr Ile
                405                 410                 415

Ile Phe Pro Tyr Val Glu Gly Lys Thr Leu Tyr Asp Ala Ile Val Lys
            420                 425                 430

Val His Val Lys Thr Ile Asp Tyr Asp Gly Gln Tyr His Val Arg Ile
        435                 440                 445

Val Asp Lys Glu Ala Phe Thr Lys Ala Asn Thr Asp Lys Ser Asn Lys
    450                 455                 460

Lys Glu Gln Gln Asp Asn Ser Ala Lys Lys Glu Ala Thr Pro Ala Thr
465                 470                 475                 480

Pro Ser Lys Pro Thr Pro Ser Pro Val Glu Lys Glu Ser Gln Lys Gln
                485                 490                 495

Asp Ser Gln Lys Asp Asp Asn Lys Gln Leu Pro Ser Val Glu Lys Glu
            500                 505                 510

Asn Asp Ala Ser Ser Glu Ser Gly Lys Asp Lys Thr Pro Ala Thr Lys
        515                 520                 525

Pro Thr Lys Gly Glu Val Glu Ser Ser Ser Thr Thr Pro Thr Lys Val
    530                 535                 540

Val Ser Thr Thr Gln Asn Val Ala Lys Pro Thr Thr Ala Ser Ser Lys
545                 550                 555                 560

Thr Thr Lys Asp Val Val Gln Thr Ser Ala Gly Ser Ser Glu Ala Lys
                565                 570                 575

Asp Ser Ala Pro Leu Gln Lys Ala Asn Ile Lys Asn Thr Asn Asp Gly
            580                 585                 590

His Thr Gln Ser Gln Asn Asn Lys Asn Thr Gln Glu Asn Lys Ala Lys
        595                 600                 605

Ser Leu Pro Gln Thr Gly Glu Glu Ser Asn Lys Asp Met Thr Leu Pro
    610                 615                 620

Leu Met Ala Leu Leu Ala Leu Ser Ser Ile Val Ala Phe Val Leu Pro
625                 630                 635                 640

Arg Lys Arg Lys Asn
            645

<210> SEQ ID NO 29
<211> LENGTH: 953
<212> TYPE: PRT
<213> ORGANISM: S. aureus

<400> SEQUENCE: 29

Met Asn Asn Lys Lys Thr Ala Thr Asn Arg Lys Gly Met Ile Pro Asn
1               5                   10                  15

Arg Leu Asn Lys Phe Ser Ile Arg Lys Tyr Ser Val Gly Thr Ala Ser
```

-continued

```
                20                  25                  30
Ile Leu Val Gly Thr Thr Leu Ile Phe Gly Leu Ser Gly His Glu Ala
            35                  40                  45
Lys Ala Ala Glu His Thr Asn Gly Glu Leu Asn Gln Ser Lys Asn Glu
        50                  55                  60
Thr Thr Ala Pro Ser Glu Asn Lys Thr Glu Lys Val Asp Ser Arg
 65                  70                  75                  80
Gln Leu Lys Asp Asn Thr Gln Thr Ala Thr Ala Asp Gln Pro Lys Val
                85                  90                  95
Thr Met Ser Asp Ser Ala Thr Val Lys Glu Thr Ser Ser Asn Met Gln
            100                 105                 110
Ser Pro Gln Asn Ala Thr Ala Ser Gln Ser Thr Thr Gln Thr Ser Asn
        115                 120                 125
Val Thr Thr Asn Asp Lys Ser Ser Thr Thr Tyr Ser Asn Glu Thr Asp
        130                 135                 140
Lys Ser Asn Leu Thr Gln Ala Lys Asn Val Ser Thr Thr Pro Lys Thr
145                 150                 155                 160
Thr Thr Ile Lys Gln Arg Ala Leu Asn Arg Met Ala Val Asn Thr Val
            165                 170                 175
Ala Ala Pro Gln Gln Gly Thr Asn Val Asn Asp Lys Val His Phe Thr
            180                 185                 190
Asn Ile Asp Ile Ala Ile Asp Lys Gly His Val Asn Lys Thr Thr Gly
        195                 200                 205
Asn Thr Glu Phe Trp Ala Thr Ser Ser Asp Val Leu Lys Leu Lys Ala
        210                 215                 220
Asn Tyr Thr Ile Asp Asp Ser Val Lys Glu Gly Asp Thr Phe Thr Phe
225                 230                 235                 240
Lys Tyr Gly Gln Tyr Phe Arg Pro Gly Ser Val Arg Leu Pro Ser Gln
            245                 250                 255
Thr Gln Asn Leu Tyr Asn Ala Gln Gly Asn Ile Ile Ala Lys Gly Ile
            260                 265                 270
Tyr Asp Ser Lys Thr Asn Thr Thr Thr Tyr Thr Phe Thr Asn Tyr Val
        275                 280                 285
Asp Gln Tyr Thr Asn Val Ser Gly Ser Phe Glu Gln Val Ala Phe Ala
        290                 295                 300
Lys Arg Glu Asn Ala Thr Thr Asp Lys Thr Ala Tyr Lys Met Glu Val
305                 310                 315                 320
Thr Leu Gly Asn Asp Thr Tyr Ser Lys Asp Val Ile Val Asp Tyr Gly
            325                 330                 335
Asn Gln Lys Gly Gln Gln Leu Ile Ser Ser Thr Asn Tyr Ile Asn Asn
            340                 345                 350
Glu Asp Leu Ser Arg Asn Met Thr Val Tyr Val Asn Gln Pro Lys Lys
        355                 360                 365
Thr Tyr Thr Lys Glu Thr Phe Val Thr Asn Leu Thr Gly Tyr Lys Phe
        370                 375                 380
Asn Pro Asp Ala Lys Asn Phe Lys Ile Tyr Glu Val Thr Asp Gln Asn
385                 390                 395                 400
Gln Phe Val Asp Ser Phe Thr Pro Asp Thr Ser Lys Leu Lys Asp Val
            405                 410                 415
Thr Gly Gln Phe Asp Val Ile Tyr Ser Asn Asp Asn Lys Thr Ala Thr
            420                 425                 430
Val Asp Leu Leu Asn Gly Gln Ser Ser Asp Lys Gln Tyr Ile Ile
        435                 440                 445
```

```
Gln Gln Val Ala Tyr Pro Asp Asn Ser Ser Thr Asp Asn Gly Lys Ile
    450                 455                 460

Asp Tyr Thr Leu Glu Thr Gln Asn Gly Lys Ser Ser Trp Ser Asn Ser
465                 470                 475                 480

Tyr Ser Asn Val Asn Gly Ser Thr Ala Asn Gly Asp Gln Lys Lys
            485                 490                 495

Tyr Asn Leu Gly Asp Tyr Val Trp Glu Asp Thr Asn Lys Asp Gly Lys
            500                 505                 510

Gln Asp Ala Asn Glu Lys Gly Ile Lys Gly Val Tyr Val Ile Leu Lys
            515                 520                 525

Asp Ser Asn Gly Lys Glu Leu Asp Arg Thr Thr Thr Glu Asn Gly
    530                 535                 540

Lys Tyr Gln Phe Thr Gly Leu Ser Asn Gly Thr Tyr Ser Val Glu Phe
545                 550                 555                 560

Ser Thr Pro Ala Gly Tyr Thr Pro Thr Ala Asn Ala Gly Thr Asp
            565                 570                 575

Asp Ala Val Asp Ser Asp Gly Leu Thr Thr Gly Val Ile Lys Asp
            580                 585                 590

Ala Asp Asn Met Thr Leu Asp Ser Gly Phe Tyr Lys Thr Pro Lys Tyr
            595                 600                 605

Ser Leu Gly Asp Tyr Val Trp Tyr Asp Ser Asn Lys Asp Gly Lys Gln
    610                 615                 620

Asp Ser Thr Glu Lys Gly Ile Lys Gly Val Lys Val Thr Leu Gln Asn
625                 630                 635                 640

Glu Lys Gly Glu Val Ile Gly Thr Thr Glu Thr Asp Glu Asn Gly Lys
            645                 650                 655

Tyr Arg Phe Asp Asn Leu Asp Ser Gly Lys Tyr Lys Val Ile Phe Glu
            660                 665                 670

Lys Pro Ala Gly Leu Thr Gln Thr Gly Thr Asn Thr Thr Glu Asp Asp
            675                 680                 685

Lys Asp Ala Asp Gly Gly Glu Val Asp Val Thr Ile Thr Asp His Asp
            690                 695                 700

Asp Phe Thr Leu Asp Asn Gly Tyr Tyr Glu Glu Glu Thr Ser Asp Ser
705                 710                 715                 720

Asp Ser Asp Ser Asp Ser Asp Ser Asp Ser Asp Ser Asp Ser Asp Ser
            725                 730                 735

Asp Ser Asp Ser Asp Ser Asp Ser Asp Ser Asp Ser Asp Ser Asp Ser
            740                 745                 750

Asp Ser Asp Ser Asp Ser Asp Ser Asp Ser Asp Ser Asp Ser Asp Ser
            755                 760                 765

Asp Ser Asp Ser Glu Ser Asp Ser Asp Ser Asp Ser Asp Ser Asp Ser
            770                 775                 780

Asp Ser Asp Ser Asp Ser Asp Ser Asp Ser Asp Ser Asp Ser Asp Ser
785                 790                 795                 800

Asp Ser Asp Ser Asp Ser Asp Ser Asp Ser Asp Ser Asp Ser Asp Ser
            805                 810                 815

Asp Ser Asp Ser Asp Ser Asp Asn Asp Ser Asp Ser Asp Ser Asp Ser
            820                 825                 830

Asp Ser Asp Ser Asp Ser Asp Ser Asp Ser Asp Ser Asp Ser Asp Ser
            835                 840                 845

Asp Ser Asp Ser Asp Ser Asp Ser Asp Ser Asp Ser Asp Ser Asp Ser
            850                 855                 860
```

```
Asp Ser Asp Ser Asp Ser Asp Ser Asp Ser Asp Ser
865                 870                 875                 880

Asp Ser Asp Ser Asp Ser Asp Ser Asp Ser Ala Gly Lys
                885                 890                 895

His Thr Pro Thr Lys Pro Met Ser Thr Val Lys Asp Gln His Lys Thr
            900                 905                 910

Ala Lys Ala Leu Pro Glu Thr Gly Ser Glu Asn Asn Asn Ser Asn Asn
            915                 920                 925

Gly Thr Leu Phe Gly Gly Phe Ala Ala Leu Gly Ser Leu Leu Leu
            930                 935                 940

Phe Gly Arg Arg Lys Lys Gln Asn Lys
945                 950

<210> SEQ ID NO 30
<211> LENGTH: 935
<212> TYPE: PRT
<213> ORGANISM: S. aureus

<400> SEQUENCE: 30

Met Asn Met Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
            35                  40                  45

Ser Ala Ser Asn Glu Ser Lys Ser Asn Asp Ser Ser Val Ser Ala
50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
            85                  90                  95

Glu Thr Thr Gln Ser Ser Ser Thr Asn Ala Thr Thr Glu Glu Thr Pro
            100                 105                 110

Val Thr Gly Glu Ala Thr Thr Thr Thr Thr Asn Gln Ala Asn Thr Pro
            115                 120                 125

Ala Thr Thr Gln Ser Ser Asn Thr Asn Ala Glu Glu Leu Val Asn Gln
            130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
            165                 170                 175

Asp Thr Ser Thr Glu Ala Thr Pro Ser Asn Asn Glu Ser Ala Pro Gln
            180                 185                 190

Asn Thr Asp Ala Ser Asn Lys Asp Val Val Ser Gln Ala Val Asn Pro
            195                 200                 205

Ser Thr Pro Arg Met Arg Ala Phe Ser Leu Ala Ala Val Ala Ala Asp
            210                 215                 220

Ala Pro Ala Ala Gly Thr Asp Ile Thr Asn Gln Leu Thr Asp Val Lys
225                 230                 235                 240

Val Thr Ile Asp Ser Gly Thr Val Tyr Pro His Gln Ala Gly Tyr
            245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
            275                 280                 285
```

```
Thr Ser Thr Ala Lys Val Pro Pro Ile Met Ala Gly Asp Gln Val Leu
    290                 295                 300
Ala Asn Gly Val Ile Asp Ser Asp Gly Asn Val Ile Tyr Thr Phe Thr
305                 310                 315                 320
Asp Tyr Val Asp Asn Lys Glu Asn Val Thr Ala Asn Ile Thr Met Pro
                325                 330                 335
Ala Tyr Ile Asp Pro Glu Asn Val Thr Lys Thr Gly Asn Val Thr Leu
            340                 345                 350
Thr Thr Gly Ile Gly Thr Asn Thr Ala Ser Lys Thr Val Leu Ile Asp
        355                 360                 365
Tyr Glu Lys Tyr Gly Gln Phe His Asn Leu Ser Ile Lys Gly Thr Ile
    370                 375                 380
Asp Gln Ile Asp Lys Thr Asn Asn Thr Tyr Arg Gln Thr Ile Tyr Val
385                 390                 395                 400
Asn Pro Ser Gly Asp Asn Val Val Leu Pro Ala Leu Thr Gly Asn Leu
                405                 410                 415
Ile Pro Asn Thr Lys Ser Asn Ala Leu Ile Asp Ala Lys Asn Thr Asp
            420                 425                 430
Ile Lys Val Tyr Arg Val Asp Asn Ala Asn Asp Leu Ser Glu Ser Tyr
        435                 440                 445
Tyr Val Asn Pro Ser Asp Phe Glu Asp Val Thr Asn Gln Val Arg Ile
    450                 455                 460
Ser Phe Pro Asn Ala Asn Gln Tyr Lys Val Glu Phe Pro Thr Asp Asp
465                 470                 475                 480
Asp Gln Ile Thr Thr Pro Tyr Ile Val Val Asn Gly His Ile Asp
                485                 490                 495
Pro Ala Ser Thr Gly Asp Leu Ala Leu Arg Ser Thr Phe Tyr Gly Tyr
                500                 505                 510
Asp Ser Asn Phe Ile Trp Arg Ser Met Ser Trp Asp Asn Glu Val Ala
            515                 520                 525
Phe Asn Asn Gly Ser Gly Ser Gly Asp Gly Ile Asp Lys Pro Val Val
        530                 535                 540
Pro Glu Gln Pro Asp Glu Pro Gly Glu Ile Glu Pro Ile Pro Glu Asp
545                 550                 555                 560
Ser Asp Ser Asp Pro Gly Ser Asp Ser Gly Ser Asp Ser Asn Ser Asp
                565                 570                 575
Ser Gly Ser Asp Ser Gly Ser Asp Ser Thr Ser Asp Ser Gly Ser Asp
            580                 585                 590
Ser Ala Ser Asp Ser Asp Ser Ala Ser Asp Ser Asp Ser Ala Ser Asp
        595                 600                 605
Ser Asp Ser Ala Ser Asp Ser Asp Ser Ala Ser Asp Ser Asp Ser Ala
    610                 615                 620
Ser Asp Ser Asp Ser Ala Ser Asp Ser Asp Ser Ala Ser Asp Ser Asp
625                 630                 635                 640
Ser Ala Ser Asp Ser Asp Ser Ala Ser Asp Ser Asp Ser Ala Ser Asp
                645                 650                 655
Ser Asp Ser Ala Ser Asp Ser Ala Ser Asp Ser Asp Ser Asp
            660                 665                 670
Ser Asp Ser Asp Ser Asp Ser Asp Ser Asp Ser Asp Ser Asp Ser Asp
        675                 680                 685
Ser Asp Ser Asp Ser Asp Ser Asp Ser Asp Ser Asp Ser Asp Ser Asp
    690                 695                 700
```

```
Ser Asp Ser Asp Ser Asp Ser Asp Ser Asp Ser Asp Ser Asp Ser Asp
705                 710                 715                 720

Ser Asp Ser Asp Ser Asp Ser Asp Ser Asp Ser Asp Ser Asp Ser Asp
            725                 730                 735

Ser Asp Ser Asp Ser Asp Ser Asp Ser Asp Ser Asp Ser Asp Ser Asp
            740                 745                 750

Ser Asp Ser Asp Ser Asp Ser Asp Ser Asp Ser Asp Ser Asp Ser Ala
            755                 760                 765

Ser Asp Ser Asp Ser Asp Ser Asp Ser Glu Ser Asp Ser Asp Ser Asp
770                 775                 780

Ser Asp Ser Asp Ser Asp Ser Asp Ser Asp Ser Asp Ser Asp Ser Asp
785                 790                 795                 800

Ser Glu Ser Asp Ser Asp Ser Asp Ser Asp Ser Asp Ser Glu Ser Asp
                805                 810                 815

Ser Asp Ser Asp Ser Asp Ser Asp Ser Asp Ser Ala Ser Asp Ser Asp
            820                 825                 830

Ser Gly Ser Asp Ser Asp Ser Ser Asp Ser Asp Ser Asp Ser Thr
            835                 840                 845

Ser Asp Thr Gly Ser Asp Asn Asp Ser Asp Ser Asp Ser Asn Ser Asp
850                 855                 860

Ser Glu Ser Gly Ser Asn Asn Asn Val Val Pro Pro Asn Ser Pro Lys
865                 870                 875                 880

Asn Gly Thr Asn Ala Ser Asn Lys Asn Glu Ala Lys Asp Ser Lys Glu
                885                 890                 895

Pro Leu Pro Asp Thr Gly Ser Glu Asp Glu Ala Asn Thr Ser Leu Ile
            900                 905                 910

Trp Gly Leu Leu Ala Ser Leu Gly Ser Leu Leu Leu Phe Arg Arg Lys
            915                 920                 925

Lys Glu Asn Lys Asp Lys Lys
            930                 935

<210> SEQ ID NO 31
<211> LENGTH: 1038
<212> TYPE: PRT
<213> ORGANISM: S. aureus

<400> SEQUENCE: 31

Met Lys Asn Asn Leu Arg Tyr Gly Ile Arg Lys His Lys Leu Gly Ala
1               5                   10                  15

Ala Ser Val Phe Leu Gly Thr Met Ile Val Val Gly Met Gly Gln Asp
            20                  25                  30

Lys Glu Ala Ala Ala Ser Glu Gln Lys Thr Thr Thr Val Glu Glu Asn
        35                  40                  45

Gly Asn Ser Ala Thr Asp Asn Lys Thr Ser Glu Thr Gln Thr Thr Ala
    50                  55                  60

Thr Asn Val Asn His Ile Glu Glu Thr Gln Ser Tyr Asn Ala Thr Val
65                  70                  75                  80

Thr Glu Gln Pro Ser Asn Ala Thr Gln Val Thr Thr Glu Glu Ala Pro
                85                  90                  95

Lys Ala Val Gln Ala Pro Gln Thr Ala Gln Pro Ala Asn Val Glu Thr
            100                 105                 110

Val Lys Glu Glu Glu Lys Pro Gln Val Lys Glu Thr Thr Gln Pro Gln
        115                 120                 125

Asp Asn Ser Gly Asn Gln Arg Gln Val Asp Leu Thr Pro Lys Lys Val
    130                 135                 140
```

-continued

```
Thr Gln Asn Gln Gly Thr Glu Thr Gln Val Glu Val Ala Gln Pro Arg
145                 150                 155                 160

Thr Ala Ser Glu Ser Lys Pro Arg Val Thr Arg Ser Ala Asp Val Ala
            165                 170                 175

Glu Ala Lys Glu Ala Ser Asp Val Ser Glu Val Lys Gly Thr Asp Val
        180                 185                 190

Thr Ser Lys Val Thr Val Glu Ser Gly Ser Ile Glu Ala Pro Gln Gly
    195                 200                 205

Asn Lys Val Glu Pro His Ala Gly Gln Arg Val Val Leu Lys Tyr Lys
210                 215                 220

Leu Lys Phe Ala Asp Gly Leu Lys Arg Gly Asp Tyr Phe Asp Phe Thr
225                 230                 235                 240

Leu Ser Asn Asn Val Asn Thr Tyr Gly Val Ser Thr Ala Arg Lys Val
            245                 250                 255

Pro Glu Ile Lys Asn Gly Ser Val Val Met Ala Thr Gly Glu Ile Leu
        260                 265                 270

Gly Asn Gly Asn Ile Arg Tyr Thr Phe Thr Asn Glu Ile Glu His Lys
    275                 280                 285

Val Glu Val Thr Ala Asn Leu Glu Ile Asn Leu Phe Ile Asp Pro Lys
290                 295                 300

Thr Val Gln Ser Asn Gly Glu Gln Lys Ile Thr Ser Lys Leu Asn Gly
305                 310                 315                 320

Glu Glu Thr Glu Lys Thr Ile Pro Val Val Tyr Asn Pro Gly Val Ser
            325                 330                 335

Asn Ser Tyr Thr Asn Val Asn Gly Ser Ile Glu Thr Phe Asn Lys Glu
        340                 345                 350

Ser Asn Lys Phe Thr His Ile Ala Tyr Ile Lys Pro Met Asn Gly Asn
    355                 360                 365

Gln Ser Asn Thr Val Ser Val Thr Gly Thr Leu Thr Glu Gly Ser Asn
370                 375                 380

Leu Ala Gly Gly Gln Pro Thr Val Lys Val Tyr Glu Tyr Leu Gly Lys
385                 390                 395                 400

Lys Asp Glu Leu Pro Gln Ser Val Tyr Ala Asn Thr Ser Asp Thr Asn
            405                 410                 415

Lys Phe Lys Asp Val Thr Lys Glu Met Asn Gly Lys Leu Ser Val Gln
        420                 425                 430

Asp Asn Gly Ser Tyr Ser Leu Asn Leu Asp Lys Leu Asp Lys Thr Tyr
    435                 440                 445

Val Ile His Tyr Thr Gly Glu Tyr Leu Gln Gly Ser Asp Gln Val Asn
450                 455                 460

Phe Arg Thr Glu Leu Tyr Gly Tyr Pro Glu Arg Ala Tyr Lys Ser Tyr
465                 470                 475                 480

Tyr Val Tyr Gly Gly Tyr Arg Leu Thr Trp Asp Asn Gly Leu Val Leu
            485                 490                 495

Tyr Ser Asn Lys Ala Asp Gly Asn Gly Lys Asn Gly Gln Ile Ile Gln
        500                 505                 510

Asp Asn Asp Phe Glu Tyr Lys Glu Asp Thr Ala Lys Gly Thr Met Ser
    515                 520                 525

Gly Gln Tyr Asp Ala Lys Gln Ile Ile Glu Thr Glu Asn Gln Asp
530                 535                 540

Asn Thr Pro Leu Asp Ile Asp Tyr His Thr Ala Ile Asp Gly Glu Gly
545                 550                 555                 560
```

```
Gly Tyr Val Asp Gly Tyr Ile Glu Thr Ile Glu Thr Asp Ser Ser
                565                 570                 575

Ala Ile Asp Ile Asp Tyr His Thr Ala Val Asp Ser Glu Val Gly His
            580                 585                 590

Val Gly Gly Tyr Thr Glu Ser Ser Glu Glu Ser Asn Pro Ile Asp Phe
            595                 600             605

Glu Glu Ser Thr His Glu Asn Ser Lys His His Ala Asp Val Val Glu
        610                 615                 620

Tyr Glu Glu Asp Thr Asn Pro Gly Gly Gln Val Thr Thr Glu Ser
625                 630                 635                 640

Asn Leu Val Glu Phe Asp Glu Glu Ser Thr Lys Gly Ile Val Thr Gly
                645                 650                 655

Ala Val Ser Asp His Thr Thr Ile Glu Asp Thr Lys Glu Tyr Thr Thr
            660                 665                 670

Glu Ser Asn Leu Ile Glu Leu Val Asp Glu Leu Pro Glu Glu His Gly
        675                 680                 685

Gln Ala Gln Gly Pro Ile Glu Glu Ile Thr Glu Asn Asn His His Ile
    690                 695                 700

Ser His Ser Gly Leu Gly Thr Glu Asn Gly His Gly Asn Tyr Gly Val
705                 710                 715                 720

Ile Glu Glu Ile Glu Glu Asn Ser His Val Asp Ile Lys Ser Glu Leu
                725                 730                 735

Gly Tyr Glu Gly Gly Gln Asn Ser Gly Asn Gln Ser Phe Glu Glu Asp
            740                 745                 750

Thr Glu Glu Asp Lys Pro Lys Tyr Glu Gln Gly Gly Asn Ile Val Asp
        755                 760                 765

Ile Asp Phe Asp Ser Val Pro Gln Ile His Gly Gln Asn Lys Gly Asp
770                 775                 780

Gln Ser Phe Glu Glu Asp Thr Glu Lys Asp Lys Pro Lys Tyr Glu His
785                 790                 795                 800

Gly Gly Asn Ile Ile Asp Ile Asp Phe Asp Ser Val Pro Gln Ile His
                805                 810                 815

Gly Phe Asn Lys His Asn Glu Ile Ile Glu Glu Asp Thr Asn Lys Asp
            820                 825                 830

Lys Pro Asn Tyr Gln Phe Gly Gly His Asn Ser Val Asp Phe Glu Glu
        835                 840                 845

Asp Thr Leu Pro Lys Val Ser Gly Gln Asn Glu Gly Gln Gln Thr Ile
    850                 855                 860

Glu Glu Asp Thr Thr Pro Pro Thr Pro Pro Thr Pro Glu Val Pro Ser
865                 870                 875                 880

Glu Pro Glu Thr Pro Met Pro Pro Thr Pro Glu Val Pro Ser Glu Pro
                885                 890                 895

Glu Thr Pro Thr Pro Pro Thr Pro Glu Val Pro Ser Glu Pro Glu Thr
            900                 905                 910

Pro Thr Pro Pro Thr Pro Glu Val Pro Ser Glu Pro Glu Thr Pro Thr
        915                 920                 925

Pro Pro Thr Pro Glu Val Pro Ser Glu Pro Glu Thr Pro Thr Pro Pro
    930                 935                 940

Thr Pro Glu Val Pro Ala Glu Pro Gly Lys Pro Val Pro Pro Ala Lys
945                 950                 955                 960

Glu Glu Pro Lys Lys Pro Ser Lys Pro Val Glu Gln Gly Lys Val Val
                965                 970                 975

Thr Pro Val Ile Glu Ile Asn Glu Lys Val Lys Ala Val Ala Pro Thr
```

```
                    980              985                 990
Lys Lys Ala Gln Ser Lys Lys Ser Glu Leu Pro Glu Thr Gly Gly Glu
                995                1000               1005

Glu Ser Thr Asn Lys Gly Met Leu Phe Gly Gly Leu Phe Ser Ile Leu
   1010                1015               1020

Gly Leu Ala Leu Leu Arg Arg Asn Lys Lys Asn Asn Lys Ala
1025                1030               1035

<210> SEQ ID NO 32
<211> LENGTH: 877
<212> TYPE: PRT
<213> ORGANISM: S. aureus

<400> SEQUENCE: 32

Met Lys Lys Arg Ile Asp Tyr Leu Ser Asn Lys Gln Asn Lys Tyr Ser
 1               5                  10                  15

Ile Arg Arg Phe Thr Val Gly Thr Thr Ser Val Ile Val Gly Ala Thr
                20                  25                  30

Ile Leu Phe Gly Ile Gly Asn His Gln Ala Gln Ala Ser Glu Gln Ser
                35                  40                  45

Asn Asp Thr Thr Gln Ser Ser Lys Asn Asn Ala Ser Ala Asp Ser Glu
 50                  55                  60

Lys Asn Asn Met Ile Glu Thr Pro Gln Leu Asn Thr Thr Ala Asn Asp
65                  70                  75                  80

Thr Ser Asp Ile Ser Ala Asn Thr Asn Ser Ala Asn Val Asp Ser Thr
                85                  90                  95

Thr Lys Pro Met Ser Thr Gln Thr Ser Asn Thr Thr Thr Thr Glu Pro
               100                 105                 110

Ala Ser Thr Asn Glu Thr Pro Gln Pro Thr Ala Ile Lys Asn Gln Ala
              115                 120                 125

Thr Ala Ala Lys Met Gln Asp Gln Thr Val Pro Gln Glu Ala Asn Ser
130                 135                 140

Gln Val Asp Asn Lys Thr Thr Asn Asp Ala Asn Ser Ile Ala Thr Asn
145                 150                 155                 160

Ser Glu Leu Lys Asn Ser Gln Thr Leu Asp Leu Pro Gln Ser Ser Pro
                165                 170                 175

Gln Thr Ile Ser Asn Ala Gln Gly Thr Ser Lys Pro Ser Val Arg Thr
                180                 185                 190

Arg Ala Val Arg Ser Leu Ala Val Ala Glu Pro Val Val Asn Ala Ala
                195                 200                 205

Asp Ala Lys Gly Thr Asn Val Asn Asp Lys Val Thr Ala Ser Asn Phe
210                 215                 220

Lys Leu Glu Lys Thr Thr Phe Asp Pro Asn Gln Ser Gly Asn Thr Phe
225                 230                 235                 240

Met Ala Ala Asn Phe Thr Val Thr Asp Lys Val Lys Ser Gly Asp Tyr
                245                 250                 255

Phe Thr Ala Lys Leu Pro Asp Ser Leu Thr Gly Asn Gly Asp Val Asp
                260                 265                 270

Tyr Ser Asn Ser Asn Asn Thr Met Pro Ile Ala Asp Ile Lys Ser Thr
                275                 280                 285

Asn Gly Asp Val Val Ala Lys Ala Thr Tyr Asp Ile Leu Thr Lys Thr
                290                 295                 300

Tyr Thr Phe Val Phe Thr Asp Tyr Val Asn Asn Lys Glu Asn Ile Asn
305                 310                 315                 320
```

-continued

Gly Gln Phe Ser Leu Pro Leu Phe Thr Asp Arg Ala Lys Ala Pro Lys
            325                 330                 335

Ser Gly Thr Tyr Asp Ala Asn Ile Asn Ile Ala Asp Glu Met Phe Asn
        340                 345                 350

Asn Lys Ile Thr Tyr Asn Tyr Ser Ser Pro Ile Ala Gly Ile Asp Lys
            355                 360                 365

Pro Asn Gly Ala Asn Ile Ser Ser Gln Ile Ile Gly Val Asp Thr Ala
370                 375                 380

Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
                405                 410                 415

Ile Glu Glu Ser Ser Gly Lys Val Ser Ala Thr Asp Thr Lys Leu Arg
            420                 425                 430

Ile Phe Glu Val Asn Asp Thr Ser Lys Leu Ser Asp Ser Tyr Tyr Ala
        435                 440                 445

Asp Pro Asn Asp Ser Asn Leu Lys Glu Val Thr Asp Gln Phe Lys Asn
    450                 455                 460

Arg Ile Tyr Tyr Glu His Pro Asn Val Ala Ser Ile Lys Phe Gly Asp
465                 470                 475                 480

Ile Thr Lys Thr Tyr Val Val Leu Val Glu Gly His Tyr Asp Asn Thr
                485                 490                 495

Gly Lys Asn Leu Lys Thr Gln Val Ile Gln Glu Asn Val Asp Pro Val
            500                 505                 510

Thr Asn Arg Asp Tyr Ser Ile Phe Gly Trp Asn Asn Glu Asn Val Val
        515                 520                 525

Arg Tyr Gly Gly Gly Ser Ala Asp Gly Asp Ser Ala Val Asn Pro Lys
530                 535                 540

Asp Pro Thr Pro Gly Pro Pro Val Asp Pro Glu Pro Ser Pro Asp Pro
545                 550                 555                 560

Glu Pro Glu Pro Thr Pro Asp Pro Glu Pro Ser Pro Asp Pro Glu Pro
                565                 570                 575

Glu Pro Ser Pro Asp Pro Asp Pro Asp Ser Asp Ser Asp Ser Asp Ser
            580                 585                 590

Gly Ser Asp Ser Asp Ser Gly Ser Asp Ser Asp Ser Glu Ser Asp Ser
        595                 600                 605

Asp Ser Asp Ser Asp Ser Asp Ser Asp Ser Asp Ser Asp Ser Glu Ser
    610                 615                 620

Asp Ser Asp Ser Glu Ser Asp Ser Asp Ser Asp Ser Asp Ser Asp Ser
625                 630                 635                 640

Asp Ser Asp Ser Asp Ser Glu Ser Asp Ser Asp Ser Asp Ser Asp Ser
                645                 650                 655

Asp Ser Asp Ser Asp Ser Asp Ser Glu Ser Asp Ser Asp Ser Glu Ser
            660                 665                 670

Asp Ser Glu Ser Asp Ser Asp Ser Asp Ser Asp Ser Asp Ser Asp Ser
        675                 680                 685

Asp Ser Asp Ser Asp Ser Asp Ser Asp Ser Asp Ser Asp Ser Asp Ser
    690                 695                 700

Asp Ser Asp Ser Asp Ser Asp Ser Glu Ser Asp Ser Asp Ser Asp Ser
705                 710                 715                 720

Asp Ser Asp Ser Asp Ser Asp Ser Asp Ser Asp Ser Asp Ser Asp Ser
                725                 730                 735

Asp Ser Asp Ser Asp Ser Asp Ser Asp Ser Asp Ser Asp Ser Asp Ser

```
                    740                 745                 750
Asp Ser Asp Ser Asp Ser Asp Ser Asp Ser Asp Ser
            755                 760                 765

Asp Ser Asp Ser Asp Ser Asp Ser Asp Ser Asp Ser
            770                 775                 780

Asp Ser Asp Ser Asp Ser Asp Ser Asp Ser Asp Ser
785                 790                 795                 800

Asp Ser Asp Ser Arg Val Thr Pro Pro Asn Asn Glu Gln Lys Ala Pro
            805                 810                 815

Ser Asn Pro Lys Gly Glu Val Asn His Ser Asn Lys Val Ser Lys Gln
            820                 825                 830

His Lys Thr Asp Ala Leu Pro Glu Thr Gly Asp Lys Ser Glu Asn Thr
            835                 840                 845

Asn Ala Thr Leu Phe Gly Ala Met Met Ala Leu Gly Ser Leu Leu
            850                 855                 860

Leu Phe Arg Lys Arg Lys Gln Asp His Lys Glu Lys Ala
865                 870                 875

<210> SEQ ID NO 33
<211> LENGTH: 658
<212> TYPE: PRT
<213> ORGANISM: S. aureus

<400> SEQUENCE: 33

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
                20                  25                  30

Ser Lys Glu Ser Arg Val Asn Glu Lys Ser Lys Gly Ala Thr Val
            35                  40                  45

Ser Asp Tyr Tyr Tyr Trp Lys Ile Ile Asp Ser Leu Glu Ala Gln Phe
    50                  55                  60

Thr Gly Ala Ile Asp Leu Leu Glu Asp Tyr Lys Tyr Gly Asp Pro Ile
65              70                  75                  80

Tyr Lys Glu Ala Lys Asp Arg Leu Met Thr Arg Val Leu Gly Glu Asp
                85                  90                  95

Gln Tyr Leu Leu Lys Lys Ile Asp Glu Tyr Glu Leu Tyr Lys Lys
            100                 105                 110

Trp Tyr Lys Ser Ser Asn Lys Asn Thr Asn Met Leu Thr Phe His Lys
        115                 120                 125

Tyr Asn Leu Tyr Asn Leu Thr Met Asn Glu Tyr Asn Asp Ile Phe Asn
    130                 135                 140

Ser Leu Lys Asp Ala Val Tyr Gln Phe Asn Lys Glu Val Lys Glu Ile
145                 150                 155                 160

Glu His Lys Asn Val Asp Leu Lys Gln Phe Asp Lys Asp Gly Glu Asp
                165                 170                 175

Lys Ala Thr Lys Glu Val Tyr Asp Leu Val Ser Glu Ile Asp Thr Leu
            180                 185                 190

Val Val Thr Tyr Tyr Ala Asp Lys Asp Tyr Gly Glu His Ala Lys Glu
        195                 200                 205

Leu Arg Ala Lys Leu Asp Leu Ile Leu Gly Asp Thr Asp Asn Pro His
    210                 215                 220

Lys Ile Thr Asn Glu Arg Ile Lys Lys Glu Met Ile Asp Asp Leu Asn
225                 230                 235                 240
```

-continued

```
Ser Ile Ile Asp Asp Phe Phe Met Glu Thr Lys Gln Asn Arg Pro Asn
            245                 250                 255

Ser Ile Thr Lys Tyr Asp Pro Thr Lys His Asn Phe Lys Glu Lys Ser
        260                 265                 270

Glu Asn Lys Pro Asn Phe Asp Lys Leu Val Glu Thr Lys Lys Ala
    275                 280                 285

Val Lys Glu Ala Asp Glu Ser Trp Lys Asn Lys Thr Val Lys Lys Tyr
290                 295                 300

Glu Glu Thr Val Thr Lys Ser Pro Val Val Lys Glu Lys Lys Val
305                 310                 315                 320

Glu Glu Pro Gln Leu Pro Lys Val Gly Asn Gln Gln Glu Val Lys Thr
                325                 330                 335

Thr Ala Gly Lys Ala Glu Glu Thr Thr Gln Pro Val Ala Gln Pro Leu
            340                 345                 350

Val Lys Ile Pro Gln Glu Thr Ile Tyr Gly Glu Thr Val Lys Gly Pro
        355                 360                 365

Glu Tyr Pro Thr Met Glu Asn Lys Thr Leu Gln Gly Glu Ile Val Gln
    370                 375                 380

Gly Pro Asp Phe Leu Thr Met Glu Gln Asn Arg Pro Ser Leu Ser Asp
385                 390                 395                 400

Asn Tyr Thr Gln Pro Thr Thr Pro Asn Pro Ile Leu Glu Gly Leu Glu
                405                 410                 415

Gly Ser Ser Ser Lys Leu Glu Ile Lys Pro Gln Gly Thr Glu Ser Thr
            420                 425                 430

Leu Lys Gly Ile Gln Gly Glu Ser Ser Asp Ile Glu Val Lys Pro Gln
        435                 440                 445

Ala Thr Glu Thr Thr Glu Ala Ser Gln Tyr Gly Pro Arg Pro Gln Phe
    450                 455                 460

Asn Lys Thr Pro Lys Tyr Val Lys Tyr Arg Asp Ala Gly Thr Gly Ile
465                 470                 475                 480

Arg Glu Tyr Asn Asp Gly Thr Phe Gly Tyr Glu Ala Arg Pro Arg Phe
                485                 490                 495

Asn Lys Pro Ser Glu Thr Asn Ala Tyr Asn Val Thr Thr Asn Gln Asp
            500                 505                 510

Gly Thr Val Ser Tyr Gly Ala Arg Pro Thr Gln Asn Lys Pro Ser Glu
        515                 520                 525

Thr Asn Ala Tyr Asn Val Thr Thr His Ala Asn Gly Gln Val Ser Tyr
    530                 535                 540

Gly Ala Arg Pro Thr Gln Lys Lys Pro Ser Lys Thr Asn Ala Tyr Asn
545                 550                 555                 560

Val Thr Thr His Ala Asn Gly Gln Val Ser Tyr Gly Ala Arg Pro Thr
                565                 570                 575

Gln Lys Lys Pro Ser Lys Thr Asn Ala Tyr Asn Val Thr Thr His Ala
            580                 585                 590

Asn Gly Gln Val Ser Tyr Gly Ala Arg Pro Thr Tyr Lys Lys Pro Ser
        595                 600                 605

Glu Thr Asn Ala Tyr Asn Val Thr Thr His Ala Asn Gly Gln Val Ser
    610                 615                 620

Tyr Gly Ala Arg Pro Thr Gln Lys Lys Pro Ser Glu Thr Asn Ala Tyr
625                 630                 635                 640

Asn Val Thr Thr His Ala Asp Gly Thr Ala Thr Tyr Gly Pro Arg Val
                645                 650                 655

Thr Lys
```

<210> SEQ ID NO 34
<211> LENGTH: 1602
<212> TYPE: DNA
<213> ORGANISM: S. aureus

<400> SEQUENCE: 34

| | | | | | | |
|---|---|---|---|---|---|---|
| atgttacaag | taactgatgt | gagtttacgt | tttggagatc | gtaaactatt | tgaagatgta | 60 |
| aatattaaat | ttacagaagg | taattgttat | ggattaattg | gtgcgaatgg | tgcaggtaaa | 120 |
| tcaacattct | aaaaatatt | atctggtgaa | ttagattctc | aaacaggaca | tgtttcatta | 180 |
| ggtaaaaatg | aacgtctagc | tgttttaaaa | caggaccact | atgcttatga | agatgaacgc | 240 |
| gtgcttgatg | ttgtaattaa | aggtcacgaa | cgtctttatg | aggttatgaa | agaaaaagat | 300 |
| gaaatctata | tgaagccaga | tttcagtgat | gaagatggta | tccgtgctgc | tgaacttgaa | 360 |
| ggtgaatttg | cagaaatgaa | tggttggaat | gctgaagctg | atgctgctaa | ccttttatct | 420 |
| ggtttaggta | tcgatccaac | tttacacgat | aaaaaaatgg | ctgaattaga | aacaaccaa | 480 |
| aaaattaaag | tattattagc | gcaaagttta | ttcggtgaac | cagacgtact | attactggat | 540 |
| gagcctacta | acggtctcga | tattccagca | atcagttggt | tagaagattt | cttaattaac | 600 |
| tttgataata | ctgttatcgt | agtatcgcat | gaccgtcatt | tcttaaataa | tgtatgtact | 660 |
| catatcgctg | atttagactt | cggtaaaatt | aaagttatg | ttggtaacta | tgattttgg | 720 |
| tatcaatcta | gtcagttagc | tcaaaagatg | gctcaagaac | aaaacaagaa | aaagaagaa | 780 |
| aaaatgaaag | agttcaggga | ctttattgca | cgtttctcag | ctaacgcttc | taaatctaaa | 840 |
| caagcaacaa | gtcgtaaaaa | acaacttgag | aaaattgaat | tagatgatat | tcaaccatca | 900 |
| tcaagaagat | atcctttcgt | taaattcacg | cctgagcgtg | agattggtaa | cgacttatta | 960 |
| atcgttcaaa | atctttctaa | aacaattgac | ggcgaaaaag | tattagataa | tgtatcattc | 1020 |
| acaatgaatc | caaatgataa | agcgatttta | attggagata | gtgaaattgc | aaaaacaaca | 1080 |
| ttacttaaaa | tattagctgg | cgaaatggaa | ccagacgaag | gttcatttaa | atggggtgtt | 1140 |
| actacatcat | taagttactt | ccctaaagat | aactcagagt | tctttgaggg | tgtaaatatg | 1200 |
| aatctcgttg | attggttaag | acaatatgct | cctgaagatg | aacaaacaga | acatttta | 1260 |
| cgtggtttct | taggtcgtat | gttatttagt | ggtgaagaag | ttaagaaaaa | agctagtgtg | 1320 |
| ctttcaggtg | gagaaaaagt | acgttgtatg | ctaagtaaaa | tgatgttatc | aagtgcgaat | 1380 |
| gtacttttac | ttgacgaacc | tactaaccac | ttagacttag | aaagtattac | tgctgtcaat | 1440 |
| gatggtctta | atcatttaa | aggttctatc | atctttactt | cttatgactt | cgaatttatc | 1500 |
| aacacgattg | caaccgtgt | tatcgattta | aataaacaag | gcggcgtttc | aaaagaaatt | 1560 |
| ccatatgaag | aatacttgca | agaaatcggc | gttttaaaat | aa | | 1602 |

<210> SEQ ID NO 35
<211> LENGTH: 1608
<212> TYPE: DNA
<213> ORGANISM: S. epidermidis

<400> SEQUENCE: 35

| | | | | | | |
|---|---|---|---|---|---|---|
| atgttacaag | taactgatgt | aagtttacgt | tttggtgatc | gtaaactatt | tgaagatgta | 60 |
| aatataaaat | ttacagaggg | taattgttat | ggattaattg | gtgcaaatgg | tgctgggaaa | 120 |
| tctacattct | tgaagatttt | atcaggcgaa | attgattcac | agactggtca | tgtatctcta | 180 |
| ggtaaagatg | agcgtttggc | tgtgttaaaa | caagatcatt | ttgcttatga | agatgaacgt | 240 |

| | |
|---|---|
| gttttagatg ttgtgattaa aggacatgaa cgtttgtatc aagtgatgaa agagaaagat | 300 |
| gaaatttata tgaaacctga tttcagcgat gaggacggta ttcgcgctgc agaacttgaa | 360 |
| ggagaatttg cagaaatgaa cggttggaat gctgaagctg atgctgctaa cttattatca | 420 |
| ggattaggca tagaacctga cttacatgat aaaaatatgt ctgaacttga aaataatcaa | 480 |
| aaagttaagg tattgttagc tcaaagttta tttggtgatc ctgacgttct tttactagat | 540 |
| gagcctacca atggtttaga tataccagca ataagttggt tagaagactt tttaattaat | 600 |
| tttgaaaata ctgtcattgt cgtttcgcat gaccgtcact tcttaaataa tgtttgtact | 660 |
| catattgctg atttagactt tggcaaaatt aaacttatg ttggtaacta tgattttgg | 720 |
| tatcaatcaa gtcaattagc acaaaaaatg cacaagaac aaataagaa aaagaagaa | 780 |
| aaaatgaaag agttacagga tttcatcgca cgcttctcag caaatgcttc taaatctaaa | 840 |
| caggcaacaa gtcgtaagaa acaattagaa aaaattgaat tagatgatat ccagccatca | 900 |
| tctcgtagat acccttacgt gaaatttact cctgaacgtg aaattggaaa tgatttactt | 960 |
| acagtagaaa atctttctaa aacaattgac ggcgaaaaag tactagacaa tgtttcattc | 1020 |
| actatgaatc ctaatgataa agctatttta gttggtgata gcgaaattgc taaaacaaca | 1080 |
| ttgttaaaaa ttttagctgg agaaatgaa ccagatgaag gtacatttaa atggggtgta | 1140 |
| acgacatctt taagttactt ccctaaagat aactctgagt tctttgatgg tgtcgatatg | 1200 |
| aatttagttg aatggttacg tcaatacgct ccagaagatg aacaaactga acatttta | 1260 |
| cgtggtttct taggtcgcat gttatttagt ggtgaggaag ttaagaaaaa agcaagcgtg | 1320 |
| cttttcaggtg gagaaaaagt acgttgcatg ttaagtaaaa tgatgttatc aagtgctaac | 1380 |
| gtacttttac ttgatgagcc aacaaaccat ttagatttgg aaagtatcac tgctgtaaat | 1440 |
| gacggattaa aatcatttaa aggttctatc atcttcactt cttatgattt tgaatttatt | 1500 |
| aatacaatcg caaatcgagt gattgacttg aatcaagctg gtgcccttc taaagaagta | 1560 |
| ccttatgagg aatacttaca agaaattggt gtattacaaa ataattaa | 1608 |

<210> SEQ ID NO 36
<211> LENGTH: 1305
<212> TYPE: DNA
<213> ORGANISM: S. aureus

<400> SEQUENCE: 36

| | |
|---|---|
| atgccaatta ttacagatgt ttacgctcgc gaagtcttag actctcgtgg taacccaact | 60 |
| gttgaagtag aagtattaac tgaaagtggc gcatttggtc gtgcattagt accatcaggt | 120 |
| gcttcaactg gtgaacacga agctgttgaa ttacgtgatg gagacaaatc acgttattta | 180 |
| ggtaaaggtg ttactaaagc agttgaaaac gttaatgaaa tcatcgcacc agaaattatt | 240 |
| gaaggtgaat tttcagtatt agatcaagta tctattgata aaatgatgat cgcattagac | 300 |
| ggtactccaa acaaaggtaa attaggtgca atgctatttt aggtgtatc tatcgcagta | 360 |
| gcacgtgcag cagctgactt attaggtcaa ccactttaca aatatttagg tggattaat | 420 |
| ggtaagcagt taccagtacc aatgatgaac atcgttaatg gtggttctca ctcagatgct | 480 |
| ccaattgcat tccaagaatt catgatttta cctgtaggtg ctacaacgtt caaagaatca | 540 |
| ttacgttggg gtactgaaat tttccacaac ttaaaatcaa ttttaagcaa acgtggttta | 600 |
| gaaactgcag taggtgacga aggtggtttc gctcctaaat tgaaggtac tgaagatgct | 660 |
| gttgaaacaa ttatccaagc aatcgaagca gctggttaca aaccaggtga gaagtattc | 720 |
| ttaggatttg actgtgcatc atcagaattc tatgaaaatg gtgtatatga ctacagtaag | 780 |

```
ttcgaaggcg aacacggtgc aaaacgtaca gctgcagaac aagttgacta cttagaacaa      840
ttagtagaca aatatcctat cattacaatt gaagacggta tggacgaaaa cgactgggat      900
ggttggaaac aacttacaga acgtatcggt gaccgtgtac aattagtagg tgacgattta      960
ttcgtaacaa acactgaaat tttagcaaaa ggtattgaaa acggaattgg taactcaatc     1020
ttaattaaag ttaaccaaat cggtacatta actgaaacat tgatgcaat cgaaatggct     1080
caaaaagctg gttacacagc agtagtttct caccgttcag gtgaaacaga agatacaaca     1140
attgctgata ttgctgttgc tacaaacgct ggtcaaatta aaactggttc attatcacgt     1200
actgaccgta ttgctaaata caatcaatta ttacgtatcg aagatgaatt atttgaaact     1260
gctaaatatg acggtatcaa atcattctat aacttagata aataa                    1305
```

<210> SEQ ID NO 37
<211> LENGTH: 1305
<212> TYPE: DNA
<213> ORGANISM: S. epidermidis

<400> SEQUENCE: 37

```
atgccaatta ttacagatgt ttacgctcgc gaagtcttag actcacgtgg taacccaaca       60
gttgaagttg aagtattaac tgaaagcggt gctttcggac gtgcattagt accttctggt      120
gcttctactg gtgaacatga agcagttgaa ttacgtgatg gagataaatc acgttattta      180
ggtaaaggtg tgactaaagc ggtagaaaat gttaacgaaa tgatcgcacc agaaatcgtt      240
gaaggtgaat tttcagtttt agatcaagta tctattgata aatgatgat tcaattagac      300
ggtacacaca acaaaggtaa attaggtgca atgccatttt aggtgttttc tattgccgta      360
gctcgtgcag ctgctgactt attaggtcaa ccattatata atatttagg tggatttaat      420
ggtaaacaat tgccagtacc tatgatgaat attgttaatg gtggttctca ctcagatgca      480
ccaattgctt tccaagagtt catgattta cctgtaggtg ctgagtcatt caaagaatca      540
ttacgttggg gtgcagaaat cttccataac cttaaatcaa tcttaagtga acgtggttta      600
gaaactgcag taggtgatga aggtggtttc gctcctagat ttgaaggcac tgaagacgct      660
gtagaaacta ttattaaagc tatcgaaaaa gcaggataca aaccaggtga agatgtattc      720
ttaggatttg actgtgcttc ttctgaattc tatgaaaatg gtgtttatga ttacactaaa      780
ttcgaaggtg aacacggtgc taaacgtagt gcagcagagc aagttgacta cttagaagaa      840
ttaattggta aatatccaat catcactatt gaagatggta tggatgaaaa cgattgggaa      900
ggttggaaac aattaactga tcgtatcggt gataaagttc aattagttgg tgatgattta      960
ttcgtaacta acactgaaat tttatctaaa ggtatcgaac aaggtattgg taactcaatc     1020
ttaatcaaag taaccaaat cggtacatta actgaaacat tcgatgctat tgaaatggct     1080
caaaaagctg gatatactgc ggttgtatct caccgttctg gtgaaactga agatactaca     1140
attgctgata tcgcagttgc tacaaatgca ggccaaatta aaacaggttc attatctaga     1200
actgaccgta ttgctaaata caatcaatta ttacgtattg aagatgaatt atacgaaaca     1260
gctaaatttg aaggaattaa atctttctac aatttagata aataa                    1305
```

<210> SEQ ID NO 38
<211> LENGTH: 768
<212> TYPE: DNA
<213> ORGANISM: S. aureus

<400> SEQUENCE: 38

| | |
|---|---|
| atgaaaaaaa tcgttacagc tacaatcgct acagcaggac ttgccactat cgcatttgca | 60 |
| ggacatgatg cacaagccgc agaacaaaat aacaatggat ataattctaa tgacgctcaa | 120 |
| tcatacagct atacgtatac aattgatgca caaggtaatt atcattacac ttggacagga | 180 |
| aattggaatc caagtcaatt aacgcaaaac aacacatact actacaacaa ctacaatact | 240 |
| tatagttata caatgcatc ttacaataac tactataatc attcatatca atacaataac | 300 |
| tatacaaaca atagccaaac agcaacaaat aactattata ctggtggttc aggtgcaagt | 360 |
| tatagcacaa caagtaataa tgttcatgtg actacaactg cagcgccatc ttcaaatggt | 420 |
| cgttcaattt ctaatggtta tgcatcagga agtaacttat atacttcagg acaatgtact | 480 |
| tattatgtat ttgatcgtgt tggtgggaaa attggttcaa catgggtaa cgcaagtaat | 540 |
| tgggctaacg cagctgcatc atctggctat acagtgaaca atacaccaaa agttggtgct | 600 |
| atcatgcaaa caacacaagg ctattacggt catgttgctt acgttgaagg cgttaacagc | 660 |
| aacggttctg ttcgtgtttc agaaatgaac tatggacatg gtgctggtgt ggttacgtct | 720 |
| cgtacaattt cagcaaacca agcaggttca tataatttca ttcattaa | 768 |

<210> SEQ ID NO 39
<211> LENGTH: 804
<212> TYPE: DNA
<213> ORGANISM: S. aureus

<400> SEQUENCE: 39

| | |
|---|---|
| atgaagaaaa tcgctacagc tactatcgca actgcaggat cgctacaat cgcaattgca | 60 |
| tcaggaaatc aagctcatgc ttctgagcaa gataactacg ttataatcc aaacgaccca | 120 |
| acatcatata gctatactta cactattgat gcacaaggta actaccatta cacatggaaa | 180 |
| ggtaactggc atccaagtca attaaaccaa gataatggct actacagcta ttactactac | 240 |
| aatggctaca ataactacaa caattacaac aatggttata gctacaataa ttacagccgt | 300 |
| tacaacaact actcaaataa taatcaatca tataactaca ataactataa tagttacaac | 360 |
| acaaacagct accgtactgg tggtttaggt gcaagctaca gcacttcaag caacaatgtt | 420 |
| caagtaacta caactatggc tccatcatca atggccgtt caatctcaag tggttatact | 480 |
| tcaggacgta acttatacac ttctggtcaa tgtacatact acgtatttga tcgtgtaggt | 540 |
| ggtaaaatcg gttcaacttg ggcaatgca agtaactggg ctaacgcagc tgcaagagct | 600 |
| ggttacacag tgaacaatac accaaaagct ggtgcaatta tgcaaacaac tcaaggtgca | 660 |
| tacggtcacg ttgcatacgt tgaaagtgtt aacagcaatg gttcagtaag agtttcagaa | 720 |
| atgaactatg gttatggccc aggtgttgta acttcacgta caatctcagc tagccaagct | 780 |
| gctggttata acttcattca ctaa | 804 |

<210> SEQ ID NO 40
<211> LENGTH: 774
<212> TYPE: DNA
<213> ORGANISM: S. epidermidis

<400> SEQUENCE: 40

| | |
|---|---|
| atgaaaaaaa tcgctacagc tacaattgca actgcaggaa tcgctacttt cgcatttgca | 60 |
| caccatgacg cacaagcagc agaacaaaat aatgatgggt acaatccaaa cgacccttat | 120 |
| tcatatagct acacttacac aatcgatgct gaaggtaact accactacac ttggaaaggt | 180 |
| aactggagtc cagatcgtgt aaatacttca tataactata ataattataa taactacaac | 240 |
| tactatggtt acaataacta tagcaactac aataactaca gtaattacaa caattacaac | 300 |

```
aactatcaat caaacaacac gcaatcacaa agaacaactc aaccgactgg tggtttaggc    360
gcaagctatt caacatcaag tagtaatgtt cacgttacaa caacttctgc gccatcatca    420
aacggtgtat ctttatcaaa cgctcgctca gcatctggta acttatacac ttcaggtcaa    480
tgtacatatt atgtatttga cagagtaggt ggcaaaatcg gttcaacgtg gggtaacgca    540
aacaactggg caaacgctgc agcacgttct ggttacacag taaacaattc gcctgctaaa    600
ggtgcaatct acaaacgtc acaaggtgca tacggacacg tagcatacgt tgaaggtgta    660
aacagcaatg gttcaatcag agtttcagaa atgaactacg gtcacggtgc aggtgttgtc    720
acttcacgta caatctctgc gagccaagct gcttcatata actatattca ctaa           774
```

<210> SEQ ID NO 41
<211> LENGTH: 930
<212> TYPE: DNA
<213> ORGANISM: S. aureus

<400> SEQUENCE: 41

```
atgaaaaaat tagtaccttt attattagcc ttattacttc tagttgctgc atgtggtact     60
ggtggtaaac aaagcagtga taagtcaaat ggcaaattaa agtagtaac gacgaattca    120 attttatatg atatggctaa aaatgttggt ggagacaacg tcgatattca tagtattgta    180
cctgttggtc aagatcctca tgaatatgaa gttaaaccta agatattaa aaagttaact    240 gacgctgacg ttatttata caacggatta aatttagaga ctggtaacgg ttggtttgaa    300
aaagccttag aacaggctgg taaatcatta aaagataaaa agttatcgc agtatcaaaa    360 gatgttaaac ctatctattt aaacggtgaa gaaggcaaca agataaaca agatccacac    420 gcatggttaa gttagataa tggtattaaa tacgtaaaaa caattcaaca acatttatc    480 gataacgaca aaaacataa agcagattat gaaaagcaag gtaacaaata cattgctcaa    540
ttggaaaaat taaataatga cagtaaagac aaatttaatg acattccaaa agaacaacgt    600
gccatgatta caagtgaagg tgccttcaag tacttctcaa acaatacgg tattacacca    660 ggttatattt gggaaattaa cactgaaaaa caaggtacac ctgaacaaat gagacaagct    720
attgagtttg ttaaaaagca caattaaaa cacttattag tagaaacaag tgttgataag    780
aaagcaatgg aaagtttatc tgaagaaacg aagaaagata tctttggtga agtgtacaca    840
gattcaatcg gtaagaagg cactaaaggt gactcttact acaaaatgat gaaatcaaat    900
attgaaactg tacacggaag catgaaataa                                     930
```

<210> SEQ ID NO 42
<211> LENGTH: 930
<212> TYPE: DNA
<213> ORGANISM: S. epidermidis

<400> SEQUENCE: 42

```
gtgaaaaaa ttctcgcttt agcaatagca tttttaatta tccttgccgc atgtgggaat      60
cacagtaacc atgaacatca ctcacatgaa ggaaaattaa agttgtaac tacaaactct    120 attctctatg acatggttaa acgtgtcggt ggaaataagg tcgatgttca tagcatcgtt    180
ccagtaggac aagaccccaca tgaatatgag gttaaaccta agatattaa agcattaaca    240 gatgctgacg ttgtatttta aacggttta aacctagaaa ctggaaatgg ttggtttgaa    300
aaagcacttg accaagcagg aaaatcaaca aaagataaaa atgtgatagc agcatcaaat    360
aatgttaaac caatatactt aaatggtgag gaaggtaaca aaaacaaaca agatccacat    420
```

```
gcatggttaa gtttagagaa tggaattaaa tacgtaaaaa caatacaaaa atcactagaa    480
catcatgata aaaagataa gtctacatat gaaaaacaag ggaatgcata tatatcaaaa    540
ttagaagaac ttaataaaga tagtaaaaat aaatttgatg acatacccaa aaatcaacgt    600
gccatgatga caagtgaagg tgcatttaaa tattttgctc aacaattcga tgttaaacca    660
ggttatattt gggagataaa cacagaaaaa caaggtacac ctggtcaaat gaaacaagcc    720
attaaatttg ttaagataa tcatttaaaa catttattag tcgaaacaag cgtagataaa    780
aaagctatgc aaagtttatc agaagaaact aagaaagata tttatggtga agtatttacc    840
gactctatag gtaaggaagg tactaaaggt gactcatact ataaaatgat gaaatctaat    900
attgatacaa tacatggtag tatgaaataa                                     930

<210> SEQ ID NO 43
<211> LENGTH: 702
<212> TYPE: DNA
<213> ORGANISM: S. aureus

<400> SEQUENCE: 43
atgaaaaaga caattatggc atcatcatta gcagtggcat taggtgtaac aggttacgca     60
gcaggtacag acatcaagc acacgctgct gaagtaaacg ttgatcaagc acacttagtt    120
gacttagcgc ataatcacca agatcaatta aatgcagctc caatcaaaga tggtgcatat    180
gacatccact ttgtaaaaga tggtttccaa tataacttta cttcaaatgg tactacatgg    240
tcatggagct atgaagcagc taatggtcaa actgctggtt tctcaaacgt tgcaggtgca    300
gactacacta cttcatacaa ccaaggttca gatgtacaat cagtaagcta caatgcacaa    360
tcaagtaact caaacgttga agctgtttca gctccaactt accataacta cagcacttca    420
actacttcaa gttcagtgag attaagcaat ggtaatactg caggtgctac tggttcatca    480
gcagctcaaa tcatggctca acgtactggt gtttcagctt ctacatgggc tgcaatcatc    540
gctcgtgaat caaatggtca agtaaatgct tacaacccat caggtgcttc aggtttattc    600
caaactatgc caggttgggg tccgacaaac actgttgacc aacaaatcaa cgcagctgtt    660
aaagcataca aagcacaagg tttaggtgct tggggattct aa                      702

<210> SEQ ID NO 44
<211> LENGTH: 708
<212> TYPE: DNA
<213> ORGANISM: S. epidermidis

<400> SEQUENCE: 44
atgaaaaaaa cagttatcgc ttctacatta gcagtatctt taggaattgc aggttacggt     60
ttatcaggac atgaagcaca cgcttcagaa actacaaacg ttgataaagc acacttagta    120
gatttagcac aacataatcc tgaagaatta aatgctaaac cagttcaagc tggtgcttac    180
gatattcatt tcgtagacaa tggataccaa tacaacttca cttcaaatgg ttctgaatgg    240
tcatggagct acgctgtagc tggttcagat gctgattaca cagaatcatc atcaaaccaa    300
gaagtaagtg caaatacaca atctagtaac acaaatgtac aagctgtttc agctccaact    360
tcttcagaaa gtcgtagcta cagcacatca actacttcat actcagcacc aagccataac    420
tacagctctc acagtagttc agtaagatta tcaaatggta atactgctgg ttctgtaggt    480
tcatatgctg ctgctcaaat ggctgcacgt actggtgtat ctgcttcaac atgggaacac    540
atcattgcta gagaatcaaa tggtcaatta catgcacgta atgcttcagg tgctgctgga    600
ttattccaaa ctatgccagg ttggggttca actggttcag taaatgatca aatcaatgcc    660
```
gcttataaag catataaagc acaaggttta tctgcttggg gtatgtaa        708

<210> SEQ ID NO 45
<211> LENGTH: 11670
<212> TYPE: DNA
<213> ORGANISM: S. aureus

<400> SEQUENCE: 45
gtgaattatc gtgataaaat tcaaaagttt agtattcgta aatatacagt tggtacattt     60
tcaactgtca ttgcgacatt ggtatttta ggattcaata catcacaagc acatgctgct    120
gaaacaaatc aaccagcaag cgtggttaaa cagaaacaac aaagtaataa tgaacagact    180
gagaatcgag aatctcaagt acaaaattct caaaattcac aaaatagtca atcattatcc    240
gctactcatg aaaatgagca accaaataat agtcaagcta atttagtaaa tcaaaaagta    300
gcgcaatcat ctactactaa tgatgaacaa ccagcatctc aaaatgtaaa tacaaagaaa    360
gattcggcaa cggctgcgac aacacaacca gataaagaag aaagtaagca taaacaaaac    420
gaaagtcaat ctgctaataa aaatggaaac gacaatagag cggctcatgt agaaaatcat    480
gaagcaaatg tagtaacagc ttcagattca tctgataatg gtaacgtaca acatgaccga    540
aatgaattac aagcattttt tgatgcaaat tatcatgatt atcgctttat tgaccgtgaa    600
aatgcagatt ctggcacatt taactatgta aaaggcattt ttgacaagat taatacttta    660
ttaggcagta atgatccaat taacaataaa gacttgcaac ttgcatacaa agaattggaa    720
caagctgttg cttttaattcg tacaatgcct caacgtcaac aaactagccg tcgatcaaac    780
agaattcaaa cgcgttctgt tgagtctaga gctgcagagc ctagatcagt atcagactat    840
caaaatgcaa attcatcata ttatgttgaa aatgctaatg atggttcagg atatcctgta    900
ggtacatata tcaatgcttc tagtaaaggg gcgccatata atttaccaac tacaccatgg    960
aatacattga aggcctctga ctcaaaggaa attgctctta tgacagcgaa acaaactgga   1020
gatggctacc aatgggttat taagtttaat aaaggacatg ctccacatca aaatatgatt   1080
ttctggtttg cattaccagc agaccaagtg ccagtaggaa gaactgactt tgtaacagtt   1140
aattcagatg gaacaaatgt acaatggagt catggagcag gagcaggtgc aaataaacca   1200
cttcaacaaa tgtgggaata tggagtaaat gatcctgatc gttcacatga cttaaaaata   1260
agaaatagaa gtggccaagt aatatatagc tggccaactg tccatgttta ttctttagaa   1320
gattatctca gcgagtgatt attttagt gaagctggag cgacacctgc tactaaagca   1380
tttggtagac aaaatttga atatattaat ggtcaaaaac ctgctgaatc accgggtgtt   1440
cctaaagttt atactttcat cggtcaaggt gatgcaagtt atacaatttc atttaaaaca   1500
caaggtccaa ctgttaataa attgtattat gcagcaggtg ggcgtgcttt agagtacaat   1560
caattattta tgtacagtca actatacgtc gaatcaacgc aagaccatca acaacgtctt   1620
aatggtttaa gacaagtggt taatcgtaca tatcgcatag gtacaactaa acgtgtagaa   1680
gtgagtcaag gaaatgtaca aacgaaaaag gtattagaaa gtacaaacct aaatatagat   1740 gatttgttg atgatccttt aagttatgtt aagacgccga gtaataaagt gttaggtttt   1800
tacccaacta atgcaaatac taacgctttt agaccggggg gcgttcaaga attaaatgaa   1860
tatcaattaa gtcaattatt tactgatcaa aaattacaag aagcagcaag aactagaaac   1920
ccaataagat taatgattgg tttcgactat cctgatggtt atggtaatag tgaaacttta   1980
gttcctgtta acttaacggt attacctgaa atccaacata atattaaatt ctttaaaaat   2040

```
gacgatactc aaaatattgc tgaaaaacca ttttcaaaac aagctgggca tccagttttc   2100
tatgtatatg caggtaacca agggaatgct tccgtgaatt taggtggtag cgtaacatct   2160
attcaaccat tacgtattaa tttaacaagt aatgagaatt ttacagataa agattggcaa   2220
attacaggta ttccgcgtac attacacatt gaaaactcga caaatagaac taataatgct   2280
agagaacgta acattgaact tgttggtaat ttattaccag gggattactt tggtacgata   2340
cgttttggac gtaaagaaca attatttgaa attcgtgtta aaccacatac accaacaatt   2400
acaacgacag ctgagcaatt aagaggtaca gcattacaaa aagtgcctgt taatatttcg   2460
ggaataccgt tggatccatc ggcattggtt tatttagttg caccaacaaa tcaaactacg   2520
aatggtggta gtgaggcaga tcaaatacca tctggttata cgatacttgc gactggtaca   2580
cctgatgggg tgcataatac aattactata cgaccgcaag attatgttgt attcatacca   2640
cctgtaggta aacaaattag agcagtagtt tattataata agtagttgc atctaatatg    2700 agtaatgctg ttactatttt gccagatgac attccaccaa caatcaataa tcctgttgga   2760
ataaatgcca aatactatcg aggcgacgaa gtcaactta caatgggagt ctctgataga    2820
cattctggta taaaaaatac aactattact actttgccaa gtggttggac atcaaattta    2880
actaaatccg caacaaaaa cggctcatta gctattacag gtagagtctc tatgaatcag    2940
gcatttaaca gtgatattac atttaaagta tcagcgacag acaatgtcaa taatacgaca   3000
aatgatagtc aatctaaaca tgtgtcaatt catgtaggta aaattagtga agatgctcat   3060
ccgattgtat taggaaatac tgagaaagtt gtagtagtca atccgactgc tgtatctaat   3120
gatgaaaagc aaagcataat tactgccttt atgaataaaa accaaaatat aagaggatat   3180
ttagcatcaa ctgatccagt aactgtcgat aataatggta acgtcacatt acattaccgt   3240
gatggctcat caacaacgct tgatgctaca aatgtgatga catacgaacc agttgtgaaa   3300
tctgaatatc aaactgccaa tgctgctaaa acagcaacgg taacgattgc taaaggacaa   3360
tcatttaata ttggtgatat taaacaatat tttactttaa gtaatggaca agctattcca   3420
aatggcacat ttacaaatat tacatctgat agaactattc caactgcaca agaagttagt   3480
caaatgaatg caggtacgca gttatatcat atagttgctt caaatgcata tcataaagac   3540
actgaagatt tctatattag ttttaaaatc gttgatgtga acaacctgaa aggcgatcaa   3600
cgtgtctatc gtacgtcaac atatgattta accactgatg aaatctcaaa agtaaaacaa   3660
gcttttatta atgcaaatag agatgtaatt acgcttgccg aaggtgatat ttcagttaca   3720
aatacaccta atggtgctaa tgtaagtact attacagtaa atattaataa aggtcgatta   3780
acgaaatcat tcgcgtctaa cctagctaat atgaatttct tgcgttgggt taatttccca   3840
caagattata cagtgacatg gacgaatgca aaaattgcaa acagaccaac agatggtggt   3900
ttatcatggt ccgatgacca taaatctta atttatcgtt atgatgctac attaggcaca    3960
caaattacaa ctaatgatat tttaacgatg ctaaaagcga ctactacagt gcctggattg   4020
cgtaataata ttactggtaa tgaaaagca caagcagaag caggtggaag accaaactat    4080
agaacaactg gttattcaca atcaaatgcg acaactgatg gtcaacgtca atttacgttg   4140
aatggtcaag tgattcaaat attagacatc atcaaccctt caaacggtta tggtgggcaa   4200
cctgttacaa attcaaatac tcgtgcaaac catagtaact caactgttgt taacgtaaac   4260
gaaccggcag ctaatggtgc tggcgcattt acaattgacc acgttgtaaa aagtaattct   4320
acacataatg caagtgatgc agtttataaa gcgcagttat acttaacgcc atatggtcca   4380
aaacaatatg ttgaacattt aaatcaaaat acaggaaata ctactgacgc tattaacatt   4440
```

```
tattttgtac caagtgactt agtgaatcca acaatttcag taggtaatta cactaatcat    4500
caagtgttct caggtgaaac atttacaaat acgattacag cgaatgataa ctttggtgtg    4560
caatcggtaa ctgtaccaaa tacatcacaa attacaggta ctgttgataa taaccatcaa    4620
catgtttctg caacggcacc aaatgtgaca tcagcaacta gtaagacaat caatttatta    4680
gcaactgata caagtggtaa tacagctaca acttcattca atgtaacagt gaaacctttg    4740
cgtgataaat atcgagttgg tacttcatca acggctgcta atcctgttag aattgccaat    4800
atttcgaata atgcgacagt atcacaagct gatcaaacga caattattaa ttcgttaacg    4860
tttacaagta atgcaccaaa tagaaactat gcaacagcaa gcgcaaatga aatcactagt    4920
aaaacagtta gtaatgtcag tcgtactgga aataatgcca atgtcacagt aactgttact    4980
catcaagatg aacaacatc aacagtgact gtacctgtaa agcatgtcat tccagaaatc    5040
gttgcacatt cgcattacac tgtacaaggc caagacttcc cagcaggtaa tggttctagt    5100
gcagcagatt actttaagtt atctaatggt agtgccattc cagatgcaac gattacatgg    5160
gtaagtggac aagcgccaaa taaagataat acacgtattg gtgaagatat aacagtaact    5220
gcacatatct taattgatgg cgaaacaacg ccgattacga aaacagcaac atataaagta    5280
gtaagaactg taccgaaaca tgtctttgaa acagccagag gtgttttata cccaggtgtt    5340
tcagatatgt atgatgcgaa acaatatgtt aagccagtaa ataattcttg gtcgacaaat    5400
gcgcaacata tgaattttca atttgttgga acatatggtc ctaacaaaga tgttgtaggt    5460
atatcaacgc gtcttattag agtgacttat gataatagac aaactgaaga tttaactatt    5520
ttatctaaag ttaaacctga cccaccaaga attgacgcaa actctgtgac atataaagca    5580
ggtcttacaa accaagaaat taagttaat aacgtattaa ataactcgtc agtaaaatta    5640
tttaaagcag ataatacacc attaaatgtc acaaatatta ctcatggtag tggttttagt    5700
tcggttgtga cagtaagtga cgcgttacca aatggcggaa ttaaagcaaa atcttcaatt    5760
tcaatgaaca atgtgacgta tacgacgcaa gacgaacatg gtcaagttgt tacagtaaca    5820
agaaatgaat ctgttgattc aaatgatagt gcttctgtta cagtaacacc acaattacaa    5880
gcaactactg aaggcgctgt atttattaaa ggtggcgacg ttttgatttt cggtcatgta    5940
gaacgattta ttcaaaatcc gccacatggg gcaacggtcg catggcatga tagtccagat    6000
acatggaaga atacagtcgg caacacacat aaaactgcgg ttgtaacatt acctagtggt    6060
caaggtacgc gtaatgttga agttccagtc aaagtttatc cagttgctaa tgctaaggcg    6120
ccatcacgta tgtgaaagg tcaaaatttg acacatggta caaacgctat tgattacatt    6180
acatttgatc caaatactaa tacgaatggt attacagcag catgggcaaa tagacaacaa    6240
ccaaataacc agcaagcagg cgttcaacat ttaaatgtcg atgtcacata tccaggtatt    6300
tcagctgcta aacgagttcc tgtaactgtg aacgtatatc aatttgaatt ccctcaaact    6360
acttatacaa caacagttgg tggcacttta gcaagtggta cgcaagcatc aggatatgca    6420
catatgcaaa acgcttcagg tttaccaaca gatggattta cgtataaatg gaatcgtgat    6480
actacgggta caaacgatgc aaactgggca gcaatgaata aaccaaatac tgcacaagtc    6540
gttaatgcaa aatatgatgt catctataat ggacatacat ttgcaacatc tttaccagcg    6600
aaatttgtag taaagatgt tcaaccagcg aaaccaactg tcactgaaac agcggcagga    6660
gcgattacaa ttgcacctgg tgcgaaccaa acagtcaata tcatgctggt aatgttacg    6720 acatatgctg acaaattagt tattaaacgt aatggaaatg ttgtaacgac atttacacgt    6780
```

```
cgtaataata cgagcccatg ggtgaaagaa gcatcagcag ataatgtaac aggtattgtt    6840
ggaactaata atggtattac tgtggcagca ggtactttca atcctgctga tacaattcaa    6900
gttgttgcaa cacaaggtag tggcgaaaca atcagtgacg agcaacgtag tgatgatttc    6960
acagttgtcg caccacaacc gaaccaagcg actacgaaaa tttggcaaaa tggtcatatt    7020
gatatcacgc ctaataatcc atcaggacat ttaattaatc aacacaagc aatggatatt     7080 gcttacactg aaaagtggg taatggtgca gaacatagta agacaattaa tgttgttcgt    7140
ggtcaaaata atcaatggac aattgcgaat aagcctgact atgtaacgtt agatgcacaa    7200
actggtaaag tgacgttcaa tgccaatact ataaaaccaa attcatcaat cacaattact    7260
ccgaaagcag gtacaggtca ctcagtaagt agtaatccaa gtacattaac tgcaccggca    7320
gctcatactg tcaacacaac tgaaattgtg aaagattatg gttcaaatgt aacagcagct    7380
gaaattaaca atgcagttca agttgctaat aaacgtactg caacgattaa aaatggcaca    7440
gcaatgccta ctaatttagc tggtggtagc acaacgacga ttcctgtgac agtaacttac    7500
aatgatggta gtactgaaga agtacaagag tccatttca caaaagcgga taaacgtgag    7560
ttaatcacag ctaaaaatca tttagatgat ccagtaagca ctgaaggtaa aaagccaggt    7620
acaattacgc agtacaataa tgcaatgcat aatgcgcaac aacaaatcaa taccgcgaaa    7680
acagaagcac aacaagtgat taataatgag cgtgcaacac cacaacaagt ttctgacgca    7740
ctaactaaag ttcgtgcagc acaaactaag attgatcaag ctaaagcatt acttcaaaat    7800
aaagaagata atagccaatt agtaacgtct aaaaataact tacaaagttc tgtgaaccaa    7860
gtaccatcaa ctgctggtat gacgcaacaa agtattgata actataatgc gaagaagcgt    7920
gaagcagaaa ctgaaataac tgcagctcaa cgtgttattg acaatggcga tgcaactgca    7980
caacaaattt cagatgaaaa acatcgtgtc gataacgcat taacagcatt aaaccaagcg    8040
aaacatgatt taactgcaga tacacatgcc ttagagcaag cagtgcaaca attgaatcgc    8100
acaggtacaa cgactggtaa gaagccggca agtattactg cttacaataa ttcgattcgt    8160
gcacttcaaa gtgacttaac aagtgctaaa aatagcgcta atgctatcat tcagaagcca    8220
ataagaacag tgcaagaggt acaatctgcg ttaacaaatg taaatcgtgt caatgagcga    8280
ttaacgcaag caattaatca attagtacct ttagctgata atagtgcttt aagaactgct    8340
aagacgaaac ttgatgaaga aatcaataaa tcagtaacta ctgatggtat gacacaatca    8400
tcaatccaag catatgaaaa tgctaaacgt gcaggtcaaa cagaaacaac aaatgcacaa    8460
aatgttatta acaatggtga cgcgacagac caacaaattg ccgcagaaaa aacaaaagta    8520
gaagaaaaat ataatagctt aaaacaagca attgctggat taacaccaga cttggcacca    8580
ttacaaactg caaaaactca gttgcaaaat gatattgatc agccaacgag tacgactggt    8640
atgacaagcg catctgttgc tgcatttaat gacaaacttt cagcagctag aactaaaatt    8700
caagaaattg atcgcgtact agcatctcat ccagatgtag caacgattcg tcaaaacgtg    8760
acagcagcga atgctgctaa aacagcactt gatcaagcgc gcaatggctt aacagtcgat    8820
aaagcacctt tagaaaatgc gaaaaatcaa ctacaacata gtattgatac gcaaacaagt    8880
acaactggta tgcacaagaa ctctataaat gcatacaatg cgaagttaac agctgcacgt    8940
aataaggttc aacaaatcaa tcaagtatta gcaggttcac ctactgtaga tcaaattaat    9000
acaaatacgt ctgcagcaaa tcaagcgaaa tctgatttag atcatgcacg tcaagcgtta    9060
acaccagata aagcgccgct tcaaaatgcg aaaacgcaat tagaacaaag cattaatcaa    9120
ccaacagata caacaggtat gacaaccgct tcgttaaatg catacaacca aaaattacaa    9180
```

```
gcagcacgtc aaaagttaac tgaaattaat caagtgttga atggcaaccc aactgtccaa   9240
aatatcaatg ataaagtggc agaggcaaac caagctaagg atcaattaaa tacagcacgt   9300
caaggtttaa cattagatag acagccagcg ttaacaacat tacatggtgc atctaactta   9360
aaccaagcac aacaaaataa tttcacgcaa caaattaatg ctgctcaaaa tcatgctgcg   9420
cttgaaacaa ttaagtctaa cattacggct ttaaatactg cgatgacgaa attaaaagac   9480
agtgttgcgg ataataatac aattaaatca ggtcaaaatt acactgacgc aacaccagct   9540
aataaacaag cctatgataa tgcagttaat gcggctaaag gtgtcattgg agaaacgact   9600
aatccaacga tggatgttaa cacagtgaac caaaaagcag catctgttaa atcgacgaaa   9660
gatgctttag atggtcaaca aaacttacaa cgtgcgaaaa cagaagcaac aaatgcgatt   9720
acgcatgcaa gtgatttaaa ccaagcacaa aagaatgcat taacacaaca agtgaatagt   9780
gcacaaaacg tgcaagcagt aaatgatatt aaacaaacga ctcaaagctt aaatactgct   9840
atgacaggtt taaacgtggg cgttgctaat cataaccaag tcgtacaaag tgataattat   9900
gtcaacgcag atactaataa gaaaaatgat tacaacaatg catcaaccca tgcgaatgac   9960
attattaatg gtaatgcaca acatccagtt ataacaccaa gtgatgttaa caatgctttta  10020 tcaaatgtca caagtaaaga acatgcattg aatggtgaag ctaagttaaa tgctgcgaaa  10080
caagaagcga atactgcatt aggtcattta aacaatttaa ataatgtaca acgtcaaaac  10140
ttacaatcgc aaattaatgg tgcgcatcaa attgatgcag ttaatacaat taagcaaaat  10200
gcaacaaact tgaatagtgc aatgggtaac ttaagacaag ctgttgcaga taaagatcaa  10260
gtgaaacgta cagaagatta tgcggatgca gatacagcta aacaaaatgc atataacagt  10320
gcagtttcaa gtgctgaaac aattattaat caaacagcta atccgacaat gtctgttgat  10380
gatgttaatc gtgcaacttc agctgttact actaataaaa atgcattaaa tggtgatgaa  10440
aaattagtac aatctaaaac agatgctgca agagcaattg atgcattacc acatttaaat  10500
aatgcacaaa aagcagatgt taaatctaaa attaatgctg catcaaatat tgctggtgta  10560
aataccgtta acaacaagg tacagattta aatacagcga tgggtaactt gcagggtgca  10620
atcaatgatg aacaaacgac gcttaatagt caaaattatc aagatgcgac acctagtaag  10680
aaaacagcat acacaaatgc ggtgcaagct gcgaaagata ttttaaataa atcaaatggt  10740
caaaataaaa cgaaagatca agttactgaa gcgatgaatc aagtgaattc ggctaaaaat  10800
aacttagatg gtacgcgttt attagatcaa gcgaagcaaa cagcgaaaca gcagttaaat  10860
aatatgacgc atttaacaac tgcacaaaaa acgaatttaa caaatcaaat taatagtggt  10920
actactgttg ctggtgttca tacggttcaa tcaaatgcca acacattaga tcaagcgatg  10980
aatacgttaa gacaaagtat tgctaacaat gatgcgacta agcaagtgaa agattacgta  11040
gatgctaata atgataagca aacagcatat aacaacgcgg tagctgctgc tgaaacgatt  11100
attaatgcga atagtaatcc agaaatgaat ccaagtacga ttacacaaaa agcagagcaa  11160
gtgaatagtt ctaaaacggc acttaacggt gatgaaaact tagctacggc aaaacaaaat  11220
gcgaaaacgt acttaaacac attaacgagt attacagatg ctcaaaagaa caatttgatt  11280
agtcaaatta gtagtgcgac aagagtgagt ggtgttgata ctgtaaaaca aaatgcacaa  11340
catttagatc aagctatggc taacttacaa aatggtatta acaacgaatc tcaagtgaaa  11400
tcatctgaga aatatcgtga tgctgataca aataaacaac aagagtatga taatgctatt  11460
actgcagcga aagcgatttt aaataaatcg acaggtccaa cactgcgcca aaatgcagtt  11520
```

```
gaagcagcat tgcaacgtgt taatactgcg aaagatgcat tgaatggtga tgcaaaatta   11580
attgcagctc aaaacgcagc gaaacaacat ttaggtactt taacgcatat cactacagca   11640
caacgcaatg atttaacaaa tcaaatttca                                    11670
```

<210> SEQ ID NO 46
<211> LENGTH: 20139
<212> TYPE: DNA
<213> ORGANISM: S. aureus

<400> SEQUENCE: 46

```
atgggtaact tacaaacggc tatcaacgat aagtcaggaa cattagcgag ccaaaacttc     60
ttggatgctg atgagcaaaa acgtaatgct tacaatcaag ctatatcagc tgccgaaacc    120
attttaaata aacaaactgg accgaataca gcgaaaacag cggttgaaca agcacttaat    180
aatgttaata gtgcgaaaca tgcattaaat ggtacgcaaa acttaaataa tgcgaaacaa    240
gcagcgatta cagcaattaa tggcgcatct gatttaaatc aaaaacaaaa agatgcatta    300
aaagcacaag ctaatggtgc tcaacgcgta tctaatgcaa atgatgtaca acgtaatgcg    360
actgaactga cacggcaat gggtcaatta caacatgcca tcgcagataa gacgaatacg    420
ttagcaagca gtaaatatgt caacgccgat agcactaaac aaaatgctta cacaactaaa    480
gttaccaatg ctgaacatat tattagcggt acgccaacgg ttgttacaac accttcagaa    540
gtaacagctg cagctaatca gtaaacagc gcgaaacaag aattaaatgg tgacgaaaga    600
ttacgtgttg caaacaaaa cgccaatact gctattgatg cattaacgca attaaatact    660
cctcaaaaag ctaaattaaa agaacaagtg ggacaagcca atagattaga agacgtacaa    720
tctgttcaaa caaatggaca atcattgaac aatgcaatga aaggcttaag agatagtatt    780
gctaacgaaa aacagtcaa agcaagtcaa aactatacag acgcaagtcc gaataaccaa    840
tcaacatata atagcgctgt gtcaaatgcg aaaggtatca ttaatcaaac taacaatcca    900
actatggata ctagtgcgat tacccaagct acaacacaag tgaataatgc taaaaatggt    960
ttaaacggtg ctgaaaactt aagaaatgca caaaacactg ctaagcaaaa cttaaatacg   1020
ttatcacact taacaaataa ccaaaaatct gcaatctcat cacaaattga tcgtgcaggt   1080
catgtgagtg aggtaacagc tgctaaaaat gcagcaactg agttaaacgc gcaaatgggc   1140
aacttggaac aagctatcca tgatcaaaac acagttaaac aaggtgttaa cttcactgat   1200
gcagataaag ctaacgtga tgcttataca aatgcggtaa gcagagcaga aacaattctg   1260
aataaaacgc aaggtgcaaa tacgtctaaa caagatgttg aagcggctat tcaaaatgtt   1320
acaagtgcta aaaatgcatt gaatggtgat caaaacgtta caaatgcgaa gaatgcagct   1380
aaaaatgcat taataacttt aacgtcaatt aataatgcac aaaaacgtga cttaacaact   1440
aaaattgatc aagcaacaac agtagctggt gttgaagcgg tatctaatac aggtacacaa   1500
ttgaatacag cgatggctaa cttgcaaaat ggtattaatg ataaagcgaa tactttagcg   1560
agcgaaaact atcatgatgc tgattcagat aagaaaactg cttatactca agccgttacg   1620
aacgcagaaa atattttaaa taaaaatagt ggatcaaatt tagataaagc tgccgttgaa   1680
aacgcgttgt cacaagtgac aaatgcgaaa ggtgccctaa atggtaacca taatttagag   1740
caagctaaat caaatgcaaa cactactata aacggccttc aacatttaac aacagcacaa   1800
aaagataaat tgaacaacaa agtgcaacaa gcacaaatg ttgcaggtgt agatactgtt   1860
aaatcaagtg ccaacacatt aaatggtgct atgggtacgt taagaaatag catacaagat   1920
aacacagcta cgaaaaatgg ccaaaactat cttgatgcta cagaacgtaa caaaacaaac   1980
```

```
tataacaatg ctgttgatag tgctaatggt gtcattaatg caacaagcaa tccaaatatg    2040
gatgctaatg caattaacca aatcgctaca caagtgacat caacgaaaaa tgcattagat    2100
ggtacacata atttaacgca agcgaaacaa acagcaacaa atgccatcga tggtgctact    2160
aacttaaata aagcgcaaaa agatgcgtta aaagcacaag ttacaagtgc gcaacgtgtt    2220
gcaaatgtaa caagtatcca acaaactgca aatgaactta atacagctat gggtcaatta    2280
caacatggta ttgatgatga aaatgcaaca aaacaaactc aaaatatcg tgacgctgaa     2340 caaagtaaga aaactgctta tgatcaagct gtagctgctg cgaaagcaat tttaaataaa    2400
caaacaggtt ccaattcaga taaagcagca gttgaccgtg cattacaaca agtaacaagt    2460
acgaaagatg cattgaatgg ggatgctaaa ctggcagaag cgaaagcggc agctagacaa    2520
aacttaggta cttaaaacca tattacgaat gcacaacgta ctgcgttaga aggtcaaatc    2580
aatcaagcga cgactgttga tggcgttaat actgtaaaaa caaatgccaa tacattagac    2640
ggcgctatga atagcttaca aggtgcaatc aatgataaag atgcgacatt aagaaatcaa    2700
aattatcttg atgcagatga atcaaaacga aatgcatata cgcaagctgt cacagcggct    2760
gaaggcattt taaataaaca aacaggtggt aacacatcta aagcagacgt tgataatgca    2820
ttaaatgcag ttacaagagc gaaagcggct ttaaatggtg ctgaaaactt aagaaatgcg    2880
aaaacttcag caacaaatac gattaatggt ttacctaact taacacaatt acaaaaagac    2940
aacttgaagc atcaagttga acaagcgcaa aatgtagttg gtgtaaatgg tgttaaagat    3000
aaaggtaata cattaaatac tgccatgggt gcattacgta caagtatcca aaatgataat    3060
acgacgaaaa caagtcaaaa ttatcttgat gcatctgata gcaacaaaaa taattacaat    3120
actgctgtaa ataatgcaaa tggtgttatt aatgcaacga acaatccaaa tatggatgct    3180
aatgcgatta atgacatggc aaatcaagtc aatacaacaa aagcagcgtt aaatggtgca    3240
caaaacttag ctcaagctaa aacaaatgcg acgaacacaa ttaacaacgc gcaagactta    3300
aaccaaaaac aaaaagatgc attaaaaaca caagttaaca atgcacaacg tgtatctgat    3360
gcaaataacg ttcaacatac agctactgaa ttgaacggtg cgatgacagc acttaaagca    3420
gctattgcgg ataaagaaag aacaaaagca agcggtaatt atgtcaatgc tgatcaagaa    3480
aaacgtcaag cgtatgattc aaaagtgact aacgctgaaa atatcattaa tggtacacca    3540
aatgcgacat taacagtcaa tgacgtaaat agtgcggcat cacaagtcaa tgcggctaaa    3600
acagcattaa atggtgataa caacttacgt gtagcgaaag agcatgctaa caatacaatt    3660
gacggcttag cacaattgaa taatgtacaa aaagcaaaat taaagaaaca agttcaaagt    3720
gcaactacat tagatggtgt tcaaactgtt aaaaatagtt ctcaaacgtt gaatacagcg    3780
atgaaaggct taagagatag tattgcgaat gaagcaacga ttaaagcagg tcaaaactac    3840
actgacgcaa gtccaaataa tcgtaacgag tacgacagcg cagttactgc agcaaaagca    3900
atcattaatc aaacatcgaa cccaacgatg gaaccaaata ctattacgca agcaacatca    3960
caagtgacaa ctaaagaaca tgcattaaat ggtgcgcaaa acttagctca agctaagaca    4020
acagcgaaaa acaacttgaa taacttaaca tcaattaaca atgcacaaaa agatgcgtta    4080
acgcgtaaca ttgatggtgc aactacagta gctggtgtaa atcaagaaac tgcaaaagca    4140
acagaattaa ataacgcaat gcacagttta caaaatggta tcaatgatga gacacaaaca    4200
aaacaaactc agaaatacct agatgctgag ccaagtaaga aatcagctta tgatcaagca    4260
gtaaatgcag caaaagcaat tttaacaaaa gctagtggtc aaaatgtaga caagcagca     4320
```

```
gttgaacaag cattacaaaa tgtgaacagt acgaagacgg cgttgaacgg tgatgcgaaa    4380
ttaaatgaag ctaaagctgc tgcgaaacaa acgttaggta cattaacaca cattaataat    4440
gcacaacgta atgcgttaga taatgaaatt acacaagcaa caaatgttga aggtgttaat    4500
acagttaaag ccaaagcgca acaattagat ggtgctatgg gtcaattaga acatcaatt     4560 cgtgataaag acacgacgtt acaaagtcaa aattatcaag atgctgatga tgctaaacga    4620
acggcttatt ctcaagcagt aaatgcagca gcaactattt taaataaaac agctggagga    4680
aatacaccta aagcagatgt cgaaagagca atgcaagctg ttacacaagc caatactgca    4740
ttaaacggta ttcaaaactt agaacgtgcg aaacaggctg cgaacacagc gattacaaat    4800
gcttcggact taaatacaaa acaaaaagaa gcattgaaag cacaagtaac aagtgcagga    4860
cgcgtatctg cagcaaatgg tgttgaacat actgcgactg aattaaatac tgcgatgaca    4920
gctttaaaac gtgccattgc tgataaagct gacacaaaag ctagtggtaa ttatgtcaat    4980
gctgatgcga ataaacgcca agcatatgat gaaaaagtga cagctgcaga acatatcgtt    5040
agtggtacac caacaccaac gttaacacca tcagatgtta caaatgcagc aacgcaagta    5100
acgaatgcga agacgcagtt aaacggtaat cataatttag aagtagcgaa acaaaatgct    5160
aacacagcaa ttgatggttt aacttctttta aatggtccgc aaaaagcaaa acttaaagaa    5220
caagtgggtc aagcgacgac gttgccaaat gttcaaactg ttcgtgataa tgcacaaaca    5280
ttaaacactg caatgaaagg tctacgagat agcattgcga atgaagcaac gattaaagca    5340
ggtcaaaact acacagatgc aagtcaaaac aaacaaaatg actacaacaa tgcagtcact    5400
gcagcaaaag caatcattgg tcaaacaact agtccatcaa tgattgcgca agaaattaat    5460
caagcgaaag accaagtgac agctaaacaa caagcgttaa acggtcaaga aacttaaga    5520 actgcgcaaa caaatgcgaa gcaacatttg aatggcttaa gtgacttaac taatgcacaa    5580
aaagatgcag cgaaacgcca aatcgaaggt gcaacgcatg ttaatgaagt aacacaagcg    5640
caaaataatg cggacgcatt aaatacagct atgacgaact tgaaaaatgg tattcaagat    5700
caaaatacga ttaagcaagg tgttaacttc actgatgcag atgaagcgaa acgtaatgca    5760
tatacaaatg cagtgacgca agctgaacaa atttaaaata agcacaagg tccaaatact    5820 gcaaaagacg gtgtcgaaac tgcgttacaa aatgtacaac gtgctaaaaa cgaattgaac    5880
ggtaatcaaa atgttgcgaa cgctaagaca actgcgaaaa atgcattgaa taaccttaca    5940
tcaattaata atgcacaaaa agcagcattg aaatcacaaa ttgaaggtgc gacaacagtt    6000
gcaggtgtaa atcaagtgtc tacaatggca tctgaattaa atactgcaat gagcaactta    6060
caacgtggta ttaatgacga agcagctaca aaagcagctc agaaatatac tgaagcagat    6120
agagataaac aaactgcata caatgatgct gtaacagcag ctaaaacgtt attagataaa    6180
acagctggtt caaatgacaa taaagtagcc gttgaacaag cattacaacg tgtgaatact    6240
gctaaaacag cattaaatgg tgacgcgcga ttaaatgaag cgaagaacac agctaaacaa    6300
caattagcga caatgtcaca tttaactaat gctcaaaaag caaacttaac agaacaaatt    6360
gaacgtggta caactgttgc tggtgttcaa ggcatccaag caaatgctgg tactttaaat    6420
caagcaatga atcaattaag acaaagtatt gcttctaaag atgcgactaa atcaagcgaa    6480
gattatcaag acgcgaatgc agattacaa aatgcataca atgatgcggt aactaatgct    6540
gaaggtatta ttagtgcaac gaataacct gaaatgaatc ctgatacaat taaccaaaa    6600 gcgagccaag tgaacagtgc gaagtctgca ttgaacggtg atgaaaaatt agcagcgta    6660 aaacaaactg cgaaatcaga tatcggtcgt ttgacagact tgaacaatgc acaacgaact    6720
```

```
gcggcaaatg ctgaagtgga tcaagcacca atcttgcag  ctgtcacagc ggctaaaaat   6780
aaagcaacat cgttaaacac agcgatgggt aatttgaaac atgcacttgc tgaaaaggat   6840
aatacgaaac gtagtgtcaa ttacacagat gcggatcaac caaaacaaca agcgtatgat   6900
actgcagtta cacaagcaga agcaattact aatgcaaatg gcagtaacgc gaatgaaaca   6960
caagttcaag cagcgcttaa ccaattgaat caagctaaaa acgacttgaa tggtgataat   7020
aaagttgctc aagcgaaaga aacagcaaaa cgtgcattag cttcatatag taacttgaat   7080
aacgcgcaat caactgcagc aactagtcaa attgacaatg caacgacagt agcagacgta   7140
actgctgcac aaaatactgc taatgaatta aatacagcaa tgggtcaact tcaaaatggt   7200
attaatgacc aaaacactgt taaacaacaa gtgaacttta cagatgctga ccaaggtaag   7260
aaagatgctt acacaaatgc tgttacgaat gctcaaggta ttttagataa agcaaacggt   7320
caaaatatga caaaagcaca agttgaagct gcattaaatc aagtaacgac tgctaagaat   7380
gctttaaacg gtgatgcaaa tgtaagacaa gcaaaatcag atgcgaaagc aaacttaggt   7440
acattaacac acttaaataa tgcacaaaaa caagatttaa catcacaaat cgaaggtgca   7500
acaacagtca acggtgtaaa tagtgttaaa acgaaagcac aagacttaga tggtgcaatg   7560
caacgattag agtcagcaat cgcaaataaa gatcaaacta aagcgagcga aaactacatt   7620
gacgcagatc caactaagaa aacagcattt gataatgcca tcacacaagc tgaatcttac   7680
ttaaataaag atcatggtac gaataaagat aagcaagctg ttgaacaagc aattcaaagt   7740
gtaacgtcta ctgaaaatgc tttgaacggt gacgcgaact acaatgcgc  taaaactgaa   7800 gctacacaag ctatcgataa cttgacacaa ttgaatacac cgcaaaaaac agcattgaaa   7860
caacaagtga atgctgcaca acgcgtatca ggtgtaactg atctgaaaaa tagtgctaca   7920
tcacttaata atgcgatgga tcaattaaaa caagcaattg gtgatcatga cacaattgta   7980
gctggtggta attacactaa cgcaagtcct gataaacaag gtgcttacac tgatgcatat   8040
aatgctgcga agaatatcgt aaatggttca cctaatgtga ttacaaatgc agcagatgtt   8100
actgcggcaa cacaacgtgt caataatgct gaaacaagtt taaatggtga tacaaactta   8160
gcaactgcga agcaacaagc taaagatgca ttacgtcaaa tgcacatttt atctgatgca   8220
caaaaacaaa gtattactgg tcaaattgat agcgcgacac aagtaactgg tgtacaaagt   8280
gtgaaagaca atgcaacaaa tcttgacaat gcaatgaatc aacttcgaaa tagtattgcg   8340
aataaagatg aagtaaaagc gagtcaacca tatgttgatg cagatacaga taaacaaaat   8400
gcatacaata cagcagttac aagtgctgaa aatatcatta atgcaacgag tcagccaaca   8460
cttgatccat ctgcagtaac acaagcagct aatcaagtga acactaacaa aactgcgctt   8520
aatggtgcgc aaaacttagc aaataaaaag caagaaacaa ctgctaacat caaccgatta   8580
agtcatttaa acaatgctca aaagcaagat ttaaatacac aagtgacaaa tgcaccaaat   8640
attagcacag taaatcaagt gaaaactaaa gctgaacaat tagatcaagc aatggaacgt   8700
ttaatcaacg gaatccaaga caaagatcaa gtgaaacaaa gtgttaactt tacagatgca   8760
gatccagaaa aacaaacagc atacaacaat gcggtaactg ctgctgaaaa tattattaat   8820
caagcaaatg gtacaaatgc gaaccaatca caagttgaag cagcactttc aactgtaaca   8880
actactaaac aagcgttgaa tggtgataga aaagtaacag atgctaaaaa caatgcaaac   8940
caaacattat ctcgcgttaga taacttaaac aatgcacaaa aaggtgctgt tactggaaac   9000
atcaatcaag cgcacactgt agctgaagta acgcaagcca ttcaaaccgc tcaggaactg   9060
```

```
aatacagcga tgggtaactt gaaaaatagc ttgaatgata aagcacactac acttggcagt   9120 caaaactttg cagatgcaga tccagagaag aaaaatgcat acaatgaagc ggttcgtaat   9180
gctgaaaata ttttaaataa atctacaggt acgaacgtgc ctaaagatca agttgaagca   9240
gctatgaatc aagtgaatac tacaaaagca gcgcttaatg gtactcaaaa ccttgaaaaa   9300
gcgaaacaac acgcaaatac agcaattgac ggtttaagcc atttaacaaa tgcacaaaaa   9360
gaggcattaa aacaattggt acaacaatcg actactgttg cagaagcaca aggtaatgaa   9420 caaaagcaa acaatgttga tgcagcaatg gacaaattac gtcaaagtat tgcagataat   9480
gcgacaacaa aacaaaacca aaattatact gatgcaagtc cgaataaaaa ggatgcgtac   9540
aataatgctg tcacaactgc acaaggtatt attgatcaaa ctacaaaccc ttcattagat   9600
ccgactgtta tcaatcaagc tgctggacaa gtaagcacgt ctaaaaatgc tttaaatggt   9660
aatgaaaact tagaggcagc gaagcaacaa gcaacgcaat ctttaggttc attagacaac   9720
ttaaataatg cgcaaaaaca agctgttact aatcaaatta atggcgcgca tactgttgat   9780
gaagcaaatc aaattaagca aaatgcgcaa aacttaaata ctgcgatggg taacttgaaa   9840
caagcgatag ctgataaaga tgctacgaaa gcaacagtta acttcactga tgcagatcaa   9900
gcaaaacaac aagcatataa cactgcagtt acaaatgctg aaaatatcat ttcaaaagct   9960
aatggtggta atgcaacaca aactgaagtt gaacaagcaa tccaacaagt aaatgcagca  10020
aaacaagcat taaatggtaa tgccaacgtt caacatgcaa aagacgaagc aacagcatta  10080
attaataact ctaatgatct taaccaagca cagaaagatg cattaaaaca acaagtacaa  10140
aatgcaacta ctgtagctgg tgtaaacaat gttaaacaaa cggcgcaaga gttaaacaat  10200
gcgatgacac aattaaaaca aggcattgca gataaagaac aaacaaaagc tgatggtaac  10260
tttgtcaatg cagattctga caagcaaaat gcatataatc aagcagtagc gaaagctgaa  10320
gcattaatta gtggtacgcc tgatgttgtc gttacaccta gcgaaattac tgcagcgtta  10380
aataaagtta cgcaagctaa aaatgattta aatggtaata caaacttagc aacggcgaaa  10440
caaaatgttc aacatgctat tgatcaattg ccaaacttaa accaagcgca acgtgatgaa  10500
tacagcaaac aaatcacgca agcaacactt gtaccaaacg tcaatgctat tcaacaagcg  10560
gcaacaacgc ttaatgacgc gatgacacaa ttgaaacaag gtattgcgaa taaagcacaa  10620
attaaaggta gcgagaacta tcacgatgct gatactgaca agcaaacagc atatgataat  10680
gcagtaacaa aagcagaaga attgttaaaa caaacaacaa atccaacaat ggatccaaat  10740
acaattcaac aagcattaac taaagtgaat gacacaaatc aagcacttaa cggtaatcaa  10800
aaattagctg atgccaaaca agatgctaag acaacacttg gtacactaga tcatttaaat  10860
gatgctcaaa aacaagcgct aacaactcaa gttgaacaag caccagatat tgcaacagtt  10920
aataatgtta agcaaaatgc tcaaaatctg aataatgcta tgactaactt aaacaatgca  10980
ttacaagata aaactgagac attaaatagc attaacttta ctgatgcaga tcaagctaag  11040
aaagatgatt atactaatgc ggtttcacat gcagaaggta ttttatctaa agcaaatggc  11100
agcaatgcaa gtcaaactga agtggaacaa gcgatgcaac gtgtgaacga agcgaaacaa  11160
gcattgaatg gtaatgacaa tgtacaacgt gcaaagatg cagcgaaaca agtaattaca  11220
aatgcaaatg atttaaatca agcgcaaaaa gatgcattaa aacaacaagt cgatgctgcg  11280
caaactgttg caaatgtaaa cacgattaag caaacagcac aagatttaaa tcaagcaatg  11340
acacaattga aacaaggtat tgcagataaa gaccaaacta aagcaaatgg taactttgtc  11400
aatgctgata ctgataagca aaatgcatat aacaatgcgg tagcgcatgc tgaacaaatc  11460
```

```
attagtggta caccaaatgc aaacgtggat ccacaacaag tggctcaagc gttacaacaa    11520
gtgaatcaag ctaagggtga tttaaacggt aaccacaact tacaagttgc taaagacaat    11580
gcaaatacag ccattgatca gttaccaaac ttaaatcaac cacaaaaaac agcattaaaa    11640
gaccaagtgt cgcatgcaga acttgttaca ggtgttaatg ctattaagca aaatgctgat    11700
gcgttaaata atgcaatggg tacgttgaaa caacaaattc aagcgaatag tcaagtacca    11760
caatcagttg actttacaca agcggatcaa gacaaacaac aagcttataa caatgcagct    11820
aaccaagcgc aacaaatcgc aaatggcaca ccaacacctg tattggcgcc tgatacagta    11880
acaaaagcag ttacaactat gaatcaagcg aaagatgcat taaacggtga tgaaaaatta    11940
gcgcaagcga acaagatgc tttagcaaat cttgatacgt tacgtgactt aaatcaacca    12000
caacgtgatg cattacgaaa ccaaatcaat caagcacaag ctttagctac agttgaacaa    12060
actaaacaaa atgcacaaaa tgtgaataca gcaatgggta acttgaaaca aggtattgca    12120
aataaagata ctgtgaaagc aagtgagaac taccacgatg ctgatgtcga taagcaaaca    12180
gcatatacaa atgcagtgtc tcaagcggaa ggtattatca atcaaacgac aaatccaacg    12240
cttaacccag atgacattac tcgtgcatta actcaagtga ctgatgctaa aaatagctta    12300
aacggtgaag ctaaattagc cactgaaaag caaaatgcta agatgccgt aagtggaatg    12360 acgcatttaa acgatgctca aaaacaagca ttaaaggtc aaatcgatca atcgcctgaa    12420
attgctacag tgaaccaagt taaacaaaca gcaacgagcc tagatcaagc aatggatcaa    12480
ttatcacaag ctattaatga taaagatcaa atattagcgg acggtaatta cttaaatgca    12540
gatcctgaca aacaaaatgc gtataaacag gcagtagcaa aagctgaagc attattgaat    12600
aaacaaagtg gtactaatga agtcaagca caagttgaaa gcatcactaa tgaagtgaac    12660
gcagcgaaac aagcattaaa tggtaatgac aatttggcaa atgcaaaaca acaagcaaaa    12720
caacaattgg cgaacttaac acacttaaat gatgcacaaa aacaatcatt tgaaagtcaa    12780
attacacaag cgccacttgt tacagatgtc actacgatta atcaaaaagc acaaacgtta    12840
gatcatgcga tggaattatt aagaaatagt gttgcggata tcaaacgac attagcgtct    12900 gaagattatc atgatgcaac tgcgcaaaga caaaatgact ataacaaagc tgtaacagct    12960
gctaataata tcattaatca aactacatcg cctacgatga atccagatga tgttaatggt    13020
gcaacgacac aagtgaataa tacgaaagtt gcattagatg gtgatgaaaa ccttgcagca    13080
gctaaacaac aagcaaacaa cagacttgat caattagatc atttgaataa tgcgcaaaag    13140
caacagttac aatcacaaat tacgcaatca tctgatattg ctgcagttaa tggtcacaaa    13200
caaacagcag aatctttaaa tactgcgatg ggtaacttaa ttaatgcgat tgcagatcat    13260
caagccgttg acaacgtgg taacttcatc aatgctgata ctgataaaca aactgcttat    13320
aatacagcgg taaatgaagc agcagcaatg attaacaaac aaactggtca aaatgcgaac    13380
caaacagaag tagaacaagc tattactaaa gttcaaacaa cacttcaagc gttaaatgga    13440
gatcataatt tacaagttgc taaaacaaat gcgacgcaag caattgatgt tttaacaagc    13500
ttaaatgatc ctcaaaaaac agcattaaaa gaccaagtta cagctgcaac tttagtaact    13560
gcagttcatc aaattgaaca aaatgcgaat acgcttaacc aagcaatgca tggtttaaga    13620
cagagcattc aagataacgc agcaactaaa gcaaatagca aatatatcaa cgaagatcaa    13680
ccagagcaac aaaactatga tcaagctgtt caagccgcaa ataatattat caatgaacaa    13740
actgcaacat tagataataa tgcgattaat caagtagcgg caactgtgaa tacaacgaaa    13800
```

```
gcagcattac atggtgatgt gaaattacaa aatgataaag atcatgctaa acaaacggtt   13860
agccaattag cacatctaaa caatgcacaa aaacatatgg aagatacgtt aattgatagt   13920
gaaacaacta gaacagcagt taagcaagat ttgactgaag tacaagcatt agatcaactt   13980
atggatgcat tacaacaaag tattgctgac aaagatgcaa cacgtgcgag cagtgcatat   14040
gtcaatgcag aaccgaataa aaaacaagcc tatgatgaag cagttcaaaa tgctgagtct   14100
atcattgcag gattaaataa tccaactatc aataaaggta atgtatcaag tgcgactcaa   14160
gcagtaatat catctaaaaa tgcattagat ggtgttgaac gattagctca agataagcaa   14220
actgctggaa attctctaaa tcatttagat caattaacac cagctcaaca acaagcgcta   14280
gaaaatcaaa ttaataatgc aacaacttgt gataaagtgg ctgaaatcat tgcacaagcg   14340
caagcattaa atgaagcgat gaaagcatta aagaaagta ttaaggatca accacaaact   14400
```
(Note: the row at 14400 in source reads: `caagcattaa atgaagcgat gaaagcatta aagaaagta ttaaggatca accacaaact`)

```
gaagcaagta gtaaatttat taacgaggat caagcgcaaa aagatgcata tacgcaagca   14460
gtacaacacg cgaaagattt gattaacaaa acaactgatc ctacattagc taaatcaatc   14520
attgatcaag cgacacaggc agtgactgat gctaaaaaca atttacatgg tgatcaaaaa   14580
ctagctcaag ataagcaacg tgcaacagaa acgttaaata acttgtctaa cttgaataca   14640
ccacaacgtc aagcacttga aaatcaaatc aataatgcag caactcgtgg tgaagtagca   14700
caaaaattaa ctgaagcaca agcacttaac caagcaatgg aagctttacg taatagcatt   14760
caagatcaac aacaaacaga atctggtagc aagtttatta tgaagataa accgcaaaaa   14820
```
(14820 row: `caagatcaac aacaaacaga atctggtagc aagtttatta tgaagataa accgcaaaaa`)

```
gatgcttacc aagcagcagt tcaaaatgca aaagatttaa ttaaccaaac aggtaatcca   14880
acgcttgata agcacaagt tgaacaattg acacatgctt ttaaacaagc taaagataac   14940
ctacacggtg atcaaaaact tgcagacgat aaacaacatg cggttactga tttaaatcaa   15000
ttaaatggtt tgaataatcc gcaacgtcaa gcacttgaaa gccaaataaa caacgcagca   15060
actcgtggcg aagtagcgca aaaattagct gaagcaaaag cgcttgatca agcaatgcaa   15120
gcattacgaa atagtattca agatcaacaa caaacggaag cgggtagcaa gtttatcaat   15180
gaagataaac cgcaaaaaga tgcttaccaa gcagcagttc aaaatgcaaa agatttaatt   15240
aaccaaacag gtaatccaac actcgacaaa tcacaagtag aacaattaac acaagcagta   15300
acaactgcaa aagataatct acatggtgat caaaaacttg ctcgtgatca acaacaagca   15360
gtaacaactg taaatgcatt gccaaactta aatcatgcac aacaacaaac attaactgat   15420
gctataaatg cagcgcctac aagaacagag gttgcacaac atgttcaaac tgctactgaa   15480
cttgatcacg cgatggaaac attgaaaaat aaagttgatc aagtgaatac agataaggct   15540
caaccaaatt acactgaagc gtcaactgat aaaaagaag cagtagatca agcgttacaa   15600
```
(15600 row: `caaccaaatt acactgaagc gtcaactgat aaaaagaag cagtagatca agcgttacaa`)

```
gctgcacaaa gcattacaga tccaactaat ggttcaaatg cgaataaaga cgctgtagaa   15660
caagcattaa ctaagcttca agaaaaagtg aatgagttaa atggtaatga gagagtcgct   15720
gaagctaaaa cacaagcgaa acaaactatt gaccaattaa cacatttaaa tgctgatcaa   15780
attgcaactg ctaaacaaaa tattgatcaa gcgacgaaac ttcaaccaat cgctgaatta   15840
gtagatcaag caacgcaatt gaaccaatca atggatcaat tacaacaagc agttaatgaa   15900
catgctaacg ttgagcaaac tatagattac acacaagcag attcagataa gcaaaaggct   15960
tataaacaag cgattgctga tgctgaaaat gtattgaaac aaaatgcgaa taagcaacaa   16020
gtggatcaag cacttcaaaa tattttaaat gcaaaacaag cattaaatgg tgatgaacgt   16080
gtagcacttg ctaaaacaaa tggtaaacat gacatcgacc aattgaatgc attaaacaat   16140
gctcaacaag atggatttaa aggtcgcatc gatcaatcaa acgatttaaa tcaaatccaa   16200
```

```
caaattgtag atgaggctaa ggcacttaat cgtgcaatgg atcaattgtc acaagaaatc  16260
actggcaatg aaggacgcac gaaaggtagc acgaactatg tcaatgcaga tacacaagtc  16320
aaacaagtat atgatgaagc ggttgataaa gcgaaacaag cacttgataa atcgtctggg  16380
caaaacttaa ctgcagaaca agttatcaaa ttaaatgatg cagtcactgc agctaagaaa  16440
gcattaaatg gtgaagaaag acttaataat cgtaaagctg aagcattaca aagattggat  16500
caattaacac atctaaacaa tgctcaaaga caattagcaa tccaacaaat taataatgct  16560
gaaacgctaa ataaagcatc tcgagcaatt aatagagcaa ctaaattaga taatgcaatg  16620
ggtgcagtac aacaatatat tgacgaacag caccttggtg ttatcagcag cacaaattac  16680
atcaatgcag atgacaattt gaaagcaaat tatgataatg caattgcgaa tgcagcacat  16740
gagttagata aagtgcaagg taatgcaatt gcaaaagctg aagcagagca attgaaacaa  16800
aatattatcg atgctcaaaa tgcattaaat ggagaccaaa accttgcaaa tgccaaagat  16860
aaagcaaatg cgtttgttaa ttcgttaaat ggattaaatc aacagcaaca agatcttgca  16920
cataaagcaa ttaacaatgc cgatactgta tcagatgtaa cagatattgt taataatcaa  16980
attgacttaa atgatgcaat ggaaacattg aaacatttag ttgacaatga aattccaaat  17040
gcagagcaaa ctgtcaatta ccaaaacgct gacgataatg ctaaaacaaa cttcgatgat  17100
gccaaacgtc tagcaaatac attgctaaat agtgataaca caaatgtgaa tgatatcaat  17160
ggcgcaatcc aagcagtcaa tgatgcaatc cataatctta atggtgatca acgactacaa  17220
gatgctaaag acaaggcaat tcaatcaatt aatcaagctt tagctaataa gctaaaagaa  17280
atcgaagctt caaatgcgac ggatcaagac aagcttattg cgaaaaataa agcagaagaa  17340
ttggcaaaca gcatcatcaa caacattaat aaagcaacaa gtaatcaggc tgtatctcaa  17400
gttcaaacag caggcaacca cgcgattgaa caagtgcatg ctaatgaaat accaaaagca  17460
aaaattgatg ccaataaaga cgttgataag caagttcaag cattaattga cgaaattgat  17520
cgaaatccaa atctaacaga taaggaaaaa caagcactta agatcgtat taatcaaata  17580 cttcaacaag gtcataacga cattaacaat gcgctgacta agaagaaat tgaacaagct  17640 aaagcacaac ttgcgcaagc attacaagac atcaaagatt tagtgaaagc taagaagat  17700 gcgaaacaag atgttgataa acaagttcaa gcattaattg acgaaatcga tcaaaatcca  17760
aatctaacag ataaggaaaa acaagcactt aaagatcgta ttaatcaaat acttcaacaa  17820
ggtcataacg gcattaacaa tgcgatgact aaagaagaaa ttgaacaagc caaagcacaa  17880
cttgcacaag cattaaaaga aattaaagat ttagtgaaag ctaaagaaaa tgcgaaacaa  17940
gatgttgata acaagttca agcattaatt gacgaaatcg atcaaaatcc aaatctaaca  18000
gataaggaaa acaagcgct taagatcga atcaatcaaa tactgcaaca aggtcataac  18060
gacattaaca atgcgatgac taaagaagaa attgaacaag ccaaagcaca acttgcacaa  18120
gcattacaag acatcaaaga tttagtgaaa gctaaagaag atgcgaaaaa tgcaataaaa  18180
gccttagcta atgcgaagcg tgatcaaatc aattcaaatc cagatttaac acctgagcaa  18240
aaagcaaaag cgctcaaaga aattgacgaa gctgaaaaac gagcactaca aaacgttgag  18300
aatgctcaaa ctatagatca attaaatcga ggattaaact taggtttaga tgacattaga  18360
aatacacatg tatgggaggt tgatgaacaa cctgctgtaa atgaaatttt tgaagcaaca  18420
cctgagcaaa tcctagttaa tggtgaactc attgtcatc gtgatgacat cattacagaa  18480
caagatattc ttgcacacat aaacttaatt gatcagcttt cagcagaagt tattgataca  18540
```

```
ccatcaactg caacgatttc tgatagctta acagcaaaag ttgaagttac attgcttgat    18600
ggatcaaaag tgattgttaa tgttcctgta aaagttgtag aaaaagaatt gtcagtagtc    18660
aaacaacagg caattgaatc aatcgaaaat gcggcacaac aaaagattga tgaaatcaat    18720
aatagtgtga cattaacact ggaacaaaaa gaagctgcaa ttgcagaagt taataagctt    18780
aaacaacaag caattgatca tgttaacaat gcacctgatg ttcattcagt tgaagaaatt    18840
caacaacaag aacaagcgta tattgaacaa tttaatccag aacaatttac gattgaacaa    18900
gcaaaatcaa atgcaattaa atcgattgaa gatgcaattc aacatatgat tgatgaaatc    18960
aaagctcgta ctgatctaac agataaagag aagcaagaag ctattgctaa gttaaatcaa    19020
ttaaaagaac aagcaattca agcgattcaa cgtgcgcaaa gcatcagtga aataactgag    19080
caattggaac aatttaaagc tcaaatgaaa gcagctaatc aacagcaaaa agaactagct    19140
aaacgcaagc aagaagctat tagtagaatt aaagactttt caaatgaaaa aataaatagt    19200
attcgaaata gtgaaattgg cacagctgat gaaaaacaag cagcaatgaa tcaaattaac    19260
gaaattgtgc ttgaaacaat tagagatatt aataatgcgc atacattaca gcaagttgag    19320
gctgcattga acaatggtat tgctcgaatt tcagcagtac aaattgtaat atctgatcgt    19380
gctaaacaat cgtcaagtac tggaaatgaa tctaatagcc atttaacaat tggttatgga    19440
actgcaaatc atccatttaa cagttcgact attggacata aaaagaaact tgatgaagat    19500
gatgacattg atccacttca tatgcgtcac tttagtaata atttcggtaa tgttattaaa    19560
aacgctattg gtgtggtggg tatctctggc ttactagcta gtttctggtt cttcattgcc    19620
aaacgtcgtc gtaaagaaga tgaagaggaa gaattagaaa taagagataa taataaagat    19680
tcaataaaag agactttaga cgatacaaaa catttaccac tttttatttgc gaaacgtcgc    19740 agaaaagaag atgaagaaga tgttactgtt gaagaaaaag attcgctaaa taatggcgag    19800
tcactcgata agttaaaaca tacgccgttc ttcttaccaa aacgtcgtcg taaagaagat    19860
gaagaagatg tggaagttac aaatgaaaac acagatgaaa aagtgttgaa agataacgaa    19920
cattcaccac tcttattcgc aaaacgacgc aaagataaag aggaagatgt tgaaacaaca    19980
actagtattg aatctaaaga tgaggacgtt cctttattat tggctaaaaa gaaaaatcaa    20040
aaagataacc aatccaaaga caaaaagtca gcatcaaaaa atacttctaa aaaggtagca    20100
gctaaaaaga agaaaaagaa atctaagaaa aataaaaaa                          20139
```

<210> SEQ ID NO 47
<211> LENGTH: 2103
<212> TYPE: DNA
<213> ORGANISM: S. epidermidis

<400> SEQUENCE: 47

```
ttgaataatc gtgataaatt acaaaaattt agtattcgaa aatacgcaat tggaacattt      60
tctactgtga ttgcaacact tgtgttcatg ggtatcaata caaaccatgc aagtgccgac     120
gagttgaatc aaaatcaaaa gttaattaaa caattaaatc aaacagatga tgatgattcg     180
aatacgcata gtcaagaaat cgaaataaac aaacaaaatt ctagtgggca gactgaatca     240
ttacgttcat caactagtca aaatcaagca atgcacgca tgtcggatca attcaaagac      300
actaatgaaa catcgcaaca attacctaca aatgtttcgg atgatagtat caatcaatcg     360
catagtgaag caaatatgaa taacgaacca ttgaaagttg ataatagtac tatgcaagca     420
catagtaaaa tagtaagcga tagcgatggg aatgcttctg aaaataaaca tcataaacta     480
acagaaaatg tacttgcaga aagccgagca agtaaaaatg acaaagagaa agagaatcta     540
```

```
caagagaaag ataaatcgca gcaagtacat ccaccattag ataaaaatgc attacaagct    600 tttttttgacg catcatatca caattacaga atgattgata gagatcgtgc ggatgcaaca    660
gaatatcaaa aagtcaaatc tacttttgac tacgtcaatg acttactagg taataatcaa    720
aatattcctt cagaacagct tgtttcggca tatcaacaat tagagaaagc attagaactt    780
gcacgtacgt taccacaaca atctactaca gaaaaacgtg gtagaagaag tacgagaagt    840
gttgttgaga atcgttcatc aagaagcgat tacttagatg ctagaactga atattatgtt    900
tcaaaagacg atgatgattc tggttttccct cctggtactt tcttccatgc ttcaaataga    960
agatggcctt ataattttacc aagatctagg aacatcttac gtgcttctga tgtacaaggt   1020
aatgcttata tcactacaaa acgacttaaa gatggatatc aatgggatat tttatttaat   1080
agtaatcata aagggcatga atatatgtac tattggtttg acttccaag tgatcaaaca    1140 ccaactggtc cagtaacttt cactattatc aaccgtgatg gttcaagtac atctactggt   1200
ggcgttggat ttggatcagg tgcaccacta cctcaatttt ggagatcagc aggtgctatt   1260
aattctagcg tagcgaatga ttttaaacat ggctccgcta caaattatgc attttatgat   1320
ggtgttaata ttttttctga ctttgctaga gggggagaat tatacttcga cagagaaggc   1380
gctacacaaa ctaataaata ttatggcgat gaaaacttcg cattgctaaa tagtgagaaa   1440
ccagatcaaa taagaggatt agatacaata tatagtttta aaggtagtgg tgatgtaagt   1500
tatcgtattt catttaaaac tcaaggagct ccaactgcaa gattgtatta tgctgctggc   1560
gcgcgttctg gtaatataaa acaagcaacg aactataacc aactctatgt cgaaccttat   1620
aagaattatc gaaatcgagt acagtcaaat gtccaagtta aaaatcgtac acttcattta   1680 aaagaacaa tcagacaatt cgatcctaca ttacagagaa ctactgatgt tcctattttg   1740
gatagtgacg gttccggaag tattgattcg gtatacgacc cattaagtta tgtaaagaat   1800
gtgactggta cagtcctagg tatttatcca tcttatcttc cttataatca ggaaagatgg   1860
cagggagcta atgcaatgaa tgcctatcaa attgaagaac ttttttcaca agaaaatctt   1920
caaaatgcag cacgttcagg ccgtccaatt caatttcttg taggttttga tgttgaagat   1980
agccatcata accctgaaac tcttttacca gtaaattat atgtaaaacc tgagttaaaa   2040
catacaattg agttatatca cgataatgaa aaacaagata gaaaggaatt ttcagtatcg   2100
aaa                                                                   2103
```

<210> SEQ ID NO 48
<211> LENGTH: 28317
<212> TYPE: DNA
<213> ORGANISM: S. epidermidis

<400> SEQUENCE: 48

```
atgagtggaa cgcttcataa cactgtagga tcaggaatat taccttatca acaagagata     60
cgtatcaaac ttactagtaa tgaaccaatt aaagatagtg aatggtctat tacaggatat    120
cctaacacgc ttacattaca aaacgctgtg gtagaacaa taatgctac tgaaaaaaac    180 ttagctcttg ttggtcatat tgatccagga aattatttca tcactgttaa gtttggtgat    240
aaagtagaac aatttgaaat tagatcaaaa ccaactccac caagaatcat tacaactgct    300
aatgaattac gtggaaatcc taaccataag cctgaaataa gagtaacaga tataccaaat    360
gatactactg ctaaaatcaa acttgtgatg ggcggaaccg atggcgatca tgatccagaa    420
ataaatccat atactgtccc tgaaaactac acagtagttg cagaagcata ccatgataat    480
```

```
gatccaagta aaaatggggt cttaacattc cgttcatcag actaccttaa agatctacca    540
ttaagcggtg aattaaaggc aattgtttat tacaatcaat atgtacaatc aaactttagt    600
aaaagcgttc cgtttagtag cgatacaaca ccacctacaa ttaatgaacc ggcaggacta    660
gttcataagt attacagggg agatcatgta gaaattactc ttccagtcac tgataatact    720
ggcggttcag gtttaagaga tgtaaacgtc aatttacctc aaggttggac aaaaaccttt    780
acaatcaatc ctaataataa tactgagggt acgcttaagt taattggtaa tatacctagt    840
aatgaagcat ataatacgac atatcatttc aatattactg caaccgataa ttctggaaat    900
acaacaaatc cagctaaaac ctttatttta aatgttggta agttggctga tgatttaaat    960
ccagtcggat tatctagaga tcaactacaa ttagtgacag acccttcttc attatctaat   1020
tccgaacgag aagaggtaaa aagaaaaata agtgaagcaa atgctaatat aagatcatat   1080
ttattacaaa ataacccaat actcgctgga gtaaacggcg atgttacatt ttattataga   1140
gatggttctg tagatgttat tgatgctgaa aatgtaatca catatgagcc cgaaagaaaa   1200
tccattttca gtgaaaatgg taatacaaat aaaaaagaag cagtaatcac tattgctaga   1260
ggacaaaact ataccattgg tccaaactta agaaaatatt tctcattaag taatggttcg   1320
gatttaccta atagagattt cacctctata tcagctattg gatctttacc ttcatcgagt   1380
gaaattagtc gactcaatgt tggaaattat aactatagag ttaatgctaa aaatgcttat   1440
cataagactc aacaagaact taatttaaaa cttaaaatag tagaggttaa tgcacctact   1500
ggtaataatc gtgtatatag agttagtact tataatttaa ctaatgatga atcaataaaa   1560
atcaaacaag catttaaagc agctaattct ggacttaatt taaacgataa cgatatcact   1620
gtttcgaata actttgacca tagaaatgtt agtagtgtga cagtaactat acgtaagggc   1680
gatttgataa aagagttttc atcaaatctc aataatatga atttcttacg ttgggttaat   1740
ataagggatg attataccat ttcgtggact tctagtaaga ttcaaggtag aaatacagat   1800
ggtggattag aatggtcacc agatcataaa tcacttattt ataaatatga tgcaacatta   1860
ggtagacaaa taaatactaa tgacgtgtta actttacttc aagcaacagc taaaaactca   1920
aatttacgtt caaatatcaa tagtaatgaa aaacagttag cagaacgagg gtctaatggg   1980
tattctaaat ctataattag agatgatggc gagaaatctt atttacttaa ctcaaatcct   2040
attcaagtat tagacttagt agaaccagat aatggttacg gtggacgtca agtcagtcat   2100
tctaacgtta tatataatga aaaaaattct tctatcgtaa atggtcaagt tccagaagct   2160
aatggggcat ccgcttttaa tattgataaa gttgttaaag ctaatgcggc aaataatggt   2220
attatgggtg ttatctataa ggcacaatta tacttagcac catacagtcc aaaaggttac   2280
attgaaaaat taggccaaaa tttaagcaat accaataacg tgattaatgt ttattttgtg   2340
ccttctgata aagtaaatcc tagtataact gtaggtaatt acgaccatca tacggtatat   2400
tctggtgaaa catttaaaaa tactatcaat gtaaatgata attatggatt aaatacagta   2460
gcttctacaa gtgatagtgc aattactatg accagaaaca caacgagtt agtaggtcag   2520
gctcctaatg ttactaatag cataaataaa attgtaaaag ttaaagccac agataaaagt   2580
ggaaatgaaa gtattgtttc tttcacagta aatataaaac cattaaacga gaaatataga   2640
ataacaactt catcaagtaa tcaaacacca gtgagaatta gtaatattca aaacaatgct   2700
aacctttcaa ttgaagatca aaatagagta aaatcttcac tcagcatgac taaaattttta  2760
ggtacaagaa attatgtcaa tgagtcaaat aatgacgttc gtagtcaagt tgtaagtaaa   2820
gtaaatagaa gtgggaacaa tgctacagtt aatgttacaa ctacattttc tgatggtaca   2880
```

```
actaatacaa taaccgttcc agttaaacat gtgttattag aagttgtacc tactactaga    2940
acaacagtaa gaggacaaca atttccaacc ggcaaaggaa cttccccaaa tgatttcttt    3000
agtttaagaa cgggaggtcc agttgatgcg agaatagttt gggttaataa tcagggaccc    3060
gatataaata gtaatcaaat tggtagagat ttaacattac acgctgaaat attcttttgat   3120
ggtgaaacaa caccaattag aaaagatact acttacaaac ttagtcaatc tattccaaag    3180
caaatatatg aaacaactat caatggtcga tttaattcat caggtgatgc atatccagga    3240
aattttgttc aagcagtaaa tcaatattgg ccagaacata tggacttcag atgggcccaa    3300
ggatcaggca caccaagttc tcgtaatgca ggttcattta ctaaaacagt tacggtagtt    3360
tatcaaaacg gccaaactga aaacgttaat gtactattca aagtcaaacc aaataaacct    3420
gttattgata gtaatagtgt gatttcaaaa ggacaattaa atggtcaaca aattttagtt    3480
cgaaatgttc cacaaaatgc acaagtcact ctatatcaat caaatggaac tgttattcct    3540
aatacaaata caactataga ttctaatggt atagctactg taacaattca aggcactcta    3600
ccaaccggaa atattactgc taaaacctca atgacaaata atgtaacgta cactaaacaa    3660
aatagtagtg gaattgcttc aaatacaact gaagatataa gtgttttttc agaaaacagt    3720
gatcaagtaa atgttaccgc tggcatgcaa gctaaaaatg atggtattaa aataattaaa    3780
ggtacaaact ataattttaa tgacttcaat agtttcataa gtaatatacc agcccattct    3840
actcttacat ggaacgagga gcctaatagt tggaaaaaca acatcggtac tacaacaaaa    3900
actgttacag ttactctacc taatcatcaa ggtacgagaa ctgtagatat tccaataaca    3960
atctatccaa cagttacagc taagaatcca gtaagagatc aaaaaggacg aaacttaacc    4020
aatggtactg acgtttataa ttatattatt tttgaaaata ataccgtct tggaggaaca    4080
gcttcttgga aagacaatcg tcaacctgat aaaaacatag ccggtgtaca aaatttaatt    4140
gcacttgtta attatcctgg catatctaca ccattagaag ttcctgttaa agtgtgggta    4200
tataattttg atttcactca acctatctac aaaattcaag taggagatac attccctaaa    4260
ggaacatggg caggctatta caaacatctt gaaaatggag agggattacc aatagatggt    4320
tggaaatttt attggaacca gcaaagtaca ggaactacta gtgatcaatg gcaatcatta    4380
gcatatacta gaactccttt tgttaaaact ggtacttatg atgtcgttaa tcctagcaac    4440
tggggtgttt ggcaaacatc acaatcagct aaatttatag ttacaaatgc taaacctaat    4500
caaccaacca taactcagtc taaaactggt gatgtaacag taacacctgg tgctgtgcgt    4560
aatatactaa taagtgggac aaatgattat atccaagcat ctgcagataa gattgttatt    4620
aataaaaatg gaaataaatt aactacattt gttaaaaata atgatggtcg ttggactgtt    4680
gaaactgggt caccctgacat aaatggtatc ggaccaacaa ataacggaac tgctatatct    4740
ttaagtcgat tagcagttag acctggggat tcaatagaag caatagcgac tgaaggttcc    4800
ggagaaacta taagtacttc agcaactagt gaatttata ttgtcaaagc tccacaacct    4860
gaacaagtag caactcatac ttatgataat ggaacattcg atatattacc tgacaattca    4920
cgtaattctt taaatccaac tgaacgtgtc gaaattaatt acactgaaaa attaaatggc    4980
aatgaaacac aaaaatcatt cactattact aaaaataaca acggcaaatg gacgataaat    5040
aataaaccaa attatgtcga gttcaatcag gataatggta agttgtatt ttcggccaat    5100
acaattaaac ctaattctca aattacaata actcctaaag caggtcaggg taacactgaa    5160
aacacaaatc ctactgtaat tcaagcacct gcgcaacata ctttaacaat caatgaaatt    5220
```

```
gttaaagaac agggtcaaaa tgtgactaat gatgatatta ataatgcggt tcaagtgcca     5280
aataaaaata gagttgcgat taaacaagga aacgctcttc caacaaattt agctggtggt     5340
agtacatcac atattccagt agttatttat tacagtgatg gaagttctga agaagctact     5400
gagactgtta gaactaaagt taataaaacc gaattaatca atgctcgtcg tcgactagat     5460
gaagaaatta gtaaagagaa caaaacacca tcaagtatca gaaactttga tcaagctatg     5520
aatcgtgctc aatcacaaat taatacagct aaaagtgatg ctgaccaagt tataggcaca     5580
gaatttgcaa cacctcaaca agtaaattca gctttatcta aagttcaagc ggcacaaaat     5640
aaaataaatg aagctaaagc attattacaa aacaaggctg ataatagtca acttgtgaga     5700
gcaaaagaac aattacaaca atcgattcaa ccagccgctt caactgatgg tatgactcaa     5760
gatagcacaa ggaactacaa caataaacgc caagcagctg aacaagcaat acaacatgca     5820
aatagcgtta taataatgg agatgcaaca tcccaacaaa ttaatgatgc taaaaacaca     5880
gttgaacagg cacagagaga ttatgttgaa gctaaaagca acttacgtgc tgataagtca     5940
cagttacaaa gcgcttatga tacgttaaat agagatgttt taacaaatga taaaaagcca     6000
gcatctgtaa gacgctataa tgaagccatt tcaaatatta gaaagaatt agatacagct     6060 aaagcggatg caagtagtac tttgcgaaac accaatcctt ccgttgaaca agttagagac     6120
gctttaaata aaataaatac tgttcaacct aaagtgaatc aagcaattgc tttacttcaa     6180
ccaaaagaaa ataattcaga acttgtacaa gctaaaaaac gtttacaaga cgctgtaaat     6240
gacatacctc aaacacaagg tatgacacaa caaacaatta ataattataa tgacaaacaa     6300
cgtgaagctg aaagagcact acatctgca caaagagtga ttgataatgg ggatgctaca     6360
actcaagaaa ttacttctga aaaatctaaa gtagagcaag caatgcaagc tttaactaat     6420
gctaaaagta atctgagagc tgataagaat gagttacaga ctgcatataa caaattaatt     6480
gagaacgtat ctaccaatgg taaaaaaccg gcgagtatac gtcaatacga aacagccaaa     6540
gccagaatac aaaatcaaat taatgatgct aaaaatgaag cggagcgaat tttaggtaat     6600
gataatccac aagtatcaca agtaactcaa gcattgaaca aaatcaaagc tattcaacca     6660
aaattaacag aagctatcaa catgcttcaa aacaaagaaa ataatacaga attagtcaat     6720
gctaaaaaca gacttgaaaa tgcagtaaat gatacagatc caacacacgg tatgactcaa     6780
gaaacaatta ataattacaa cgctaaaaag cgagaagctc aaaatgaaat acaaaaagcg     6840
aacatgatta ttaataatgg agatgctact gctcaagata tttcttctga aaaatctaaa     6900
gtagagcaag tattacaagc attacaaaat gctaagaatg acttaagagc tgataaaaga     6960
gaattacaga ctgcatacaa taaacttata caaaatgtta ataccaatgg taaaaaacca     7020
tctagtattc aaaactataa gtctgcaaga cgaaatatcg aaaaccaata taataccgct     7080
aaaaatgaag cacataatgt tcttgaaaat acaaaccctca ctgtaaatgc agtagaagat     7140
gctttacgta agataaatgc aattcaacca gaggttacaa aagctattaa tatacttcaa     7200
gataaagaag ataatagcga acttgttaga gcaaagaaa aattagatca agcgattaat     7260
agtcaaccat cactaaatgg tatgactcaa gaatctatta ataattacac aacaaaacgt     7320
agagaagcac aaaatatagc aagttctgct gacactatta ttaataatgg ggatgcatct     7380
attgaacaaa taacagaaaa taaaattcga gttgaagagg caactaatgc acttaacgaa     7440 gcaaacaac atttaacggc agatacaact tctttaaaaa ctgaagtacg gaaattaagt     7500
aggagaggcg acacaaacaa caaaaagcct agcagtgtta gtgcttataa caatactatt     7560
cattcgctac aatctgaaat tacacagact gaaaatagag caaatactat catcaataag     7620
```

```
cctattcgtt ctgttgaaga agtaaataat gcattgcatg aagtaaacca attgaaccaa    7680
cgcttaacag atacaattaa cttattacaa cctttagcga ataagaaaag cttaaaagaa    7740
gctcgtaatc gacttgaaag taaaattaat gaaaccgttc aaacagacgg tatgactcaa    7800
caatctgttg agaattataa gcaagctaaa ataaaagctc aaaatgaatc tagtattgca    7860
caaactctta ttaataatgg tgatgcatct gatcaagaag tttctacaga aatagaaaaa    7920
ttaaatcaaa agctgtctga attaacaaat tcaatcaatc acttaacagt taataaagaa    7980
cctttagaaa ctgccaaaaa tcagttacaa gcaaatattg accaaaaacc tagcactgat    8040
ggtatgacgc aacaatctgt acaaagctat gaacgtaaac tacaagaagc caaagataaa    8100
ataaactcaa ttaataatgt cttagctaac aatccagatg ttaatgctat cagaacaaac    8160
aaagttgaga cggaacaaat caataatgaa ttaacacagg cgaaacaagg tcttactgtt    8220
gataaacaac cattgattaa tgcaaaaact gctttgcaac aaagtctaga taatcaacca    8280
agtactactg gtatgactga agcaacaatt caaaattata cgctaaacg tcaaaaagca    8340 gagcaagtta tacaaaatgc aaataaaatt attgaaaacg ctcaacctag tgtacaacaa    8400
gtgtctgatg agaaatctaa ggtagagcaa gcactcagtg aattgaacaa cgccaaatca    8460
gcgcttagag ctgataaaca agaattacag caagcatata atcagttgat tcaaccaacg    8520
gatttaaata ataagaaacc agcttctatc actgcgtaca atcaaagata tcaacaattt    8580
agtaacgaat tgaacagcac taaaacaaat acagatcgca ttttaaaaga gcaaaatcca    8640
agtgtagctg atgtcaacaa tgcactaaat aaagtaagag aagtacaaca aaaattaaac    8700
gaagccagag cacttttaca aaataaagaa gataatagtg cactagttcg agccaaagaa    8760
caacttcaac aggcagttga ccaagtccct tcaacagaag gtatgacgca acaaactaaa    8820
gatgattaca attcaaaaca acaagctgct caacaagaaa tatcaaaagc acaacaagtt    8880
atcgataatg gcgatgcgac tacacaacaa atttctaacg ccaaaacaaa tgttgaacgc    8940
gctttagaag cattaaataa tgcaaaaact ggtttaagag cagataaaga ggaacttcaa    9000
aatgcatata atcaattaac tcaaaatatt gatacgagcg gtaaaacgcc tgcaagtatc    9060
aggaaataca atgaagctaa gtcacgtatt caaactcaaa ttgattcagc taaaaatgaa    9120
gcaaacagta ttttaacaaa tgacaatcct caagtatcac aagtgactgc tgcgttaaac    9180
aaaataaaag ctgttcaacc tgaattagat aaagcgatag caatgcttaa aaataaagag    9240
aataataatg cattggttca agcgaaacaa caacttcaac aaattgttaa tgaagtagat    9300
ccaacacaag gcatgacaac agatactgct aataactata atcaaaaaa acgtgaagct    9360 gaagatgaaa tacaaaaagc tcaacaaatc attaacaatg gcgatgccac tgagcaacaa    9420
attactaacg aaacaaatag agtaaatcaa gcgattaatg caataaacaa agccaaaaac    9480
gatttacgtg ctgataagtc tcaattggaa aatgcttata accaattaat acaaaatgtt    9540
gatacaaatg gtaaaaaacc tgctagtatt caacaatacc aagctgctcg acaagctatt    9600
gagacgcaat acaataacgc taaatcagaa gcacatcaaa ttcttgaaaa tagtaaccct    9660
tcagttaatg aagtagcaca agcattacaa aaagttgaag ctgtacaact taaagttaat    9720
gacgcgattc atatacttca aaataaagag aataatagtg cacttgtcac agctaaaaat    9780
caacttcagc aatcagttaa tgatcaacca ttaacaacag gtatgactca agattctatt    9840
aataactatg aagctaagag aaatgaggct caaagtgcta tcagaaatgc agaagctgtc    9900
atcaacaatg gcgatgcaac tgcaaaacaa atttcagacg agaaatctaa agttgaacaa    9960
```

```
gcactagcac atttgaatga tgctaaacag caattaactg cagatactac tgaattacaa    10020
acagcagttc aacaattaaa cagaagaggc gatacaaata ataaaaagcc aagaagtatc    10080
aatgcatata ataaagcaat tcaatcatta gaaacacaaa ttacttctgc taaagataat    10140
gccaacgctg tgatacaaaa acctatacgt actgttcaag aggtaaataa tgcattacaa    10200
caagtaaatc agttgaatca acaattaact gaagcaatta atcaacttca accgctatca    10260
aataatgatg cattaaaagc tgcaagatta aatttagaaa ataaaattaa tcaaactgta    10320
caaactgatg gtatgacaca acaatctata gaggcttatc aaaacgctaa acgcgtagcc    10380
caaaatgaat ctaacactgc tttagcatta attaataacg gcgatgccga tgaacaacaa    10440
attacaactg aaacagaccg agtcaatcag caaactacaa acttaactca agcaattaac    10500
gggttaacag ttaataaaga accattagaa accgctaaaa cagcgttaca aaataacatc    10560
gaccaggtac ctagtacaga tggtatgact cagcaatctg ttgcaaatta taatcaaaaa    10620
ctacaaatag ctaaaaacga aattaacaca attaataacg ttttagcgaa caatccagat    10680
gttaatgcaa tcaaaacgaa taagcagaa gcggaacgaa tcagtaacga tttaacacaa    10740
gctaagaata acttacaagt tgatactcaa cctttagaaa aaataaaaag acaacttcaa    10800
gatgaaattg atcaaggtac taacacagat ggaatgactc aagattcagt ggataattac    10860
aatgatagct taagtgcagc aattatagaa aaaggcaaag taaataaatt acttaaacgt    10920
aatccgacag tagaacaagt taaagagagc gttgctaatg cacaacaagt catacaagat    10980
ttacaaaatg ctcgaacttc acttgttcca gacaaaactc aacttcaaga agctaaaaat    11040
agattagaaa acagtattaa ccaacaaaca gatactgacg gcatgactca agattcgctt    11100
aacaattata atgataaatt agcaaaagct agacaaaacc ttgaaaaaat atctaaagtt    11160
ttaggtggtc aacctactgt agctgaaatt agacaaaata cagatgaagc aaatgcacat    11220
aaacaagcat tagacactgc acgttctcaa cttacattaa atagagagcc atatatcaat    11280
catattaata atgaaagtca tttaaataac gcgcaaaaag ataattttaa agctcaagtt    11340
aactcagcac ctaatcataa tactttagaa acgattaaaa ataaggctga tactttaaat    11400
caatctatga cagcattaag tgaaagtatt gcagattacg aaaatcaaaa acaacaagaa    11460
aattatttag atgcatctaa caataaacgt caagactatg acaatgcagt caatgcggct    11520
aaaggtattt taaccaaaac tcaaagtccg acaatgagtg ctgatgtgat tgatcaaaaa    11580
gctgaagatg ttaaacgtac gaaaactgcg ttagatggaa atcaaagatt agaagttgct    11640
aaacaacaag cacttaatca tttaaatacc ttaaatgatt taaacgatgc tcagcgacaa    11700
actttaactg atactataaa tcactctcca aacatcaatt cagtgaatca agctaaagaa    11760
aaagctaata ctgttaacac agcaatgact caactgaaac aaactattgc taactatgac    11820
gatgaattgc atgacggcaa ttacattaat gcagataaag acaaaaaaga tgcttataat    11880
aacgctgtta acaatgctaa acaactgatt aatcaatctg atgctaatca agcacaactt    11940
gatccagctg aaattaataa agttacacaa agagtcaata cgactaaaaa tgatctaaat    12000
ggtaatgaca aattggctga agctaaaaga gatgctaata caaccattga tggtttaact    12060
tatctaaatg aagctcaacg taacaaagct aagaaaatg taggcaaagc ttctacaaaa    12120
acaaatatta cgagtcagtt acaagattac aatcaattga atattgctat gcaagcatta    12180
cgtaacagtg tgaacgacgt taacaatgtt aaagcaaata gcaattatat aaatgaagat    12240
aatggtccaa aagaagctta caatcaagcc gttactcatg ctcaaacatt gataaatgca    12300
caatctaacc ctgaaatgag ccgtgacgta gtaaatcaaa aaacacaagc agtaaatact    12360
```

```
gcccatcaga atttacatgg acaacaaaag ttagaacaag cacaaagtag tgctaataca    12420
gaaatcggta acttaccaaa cttaactaat actcaaaaag ctaaagaaaa ggaactggta    12480
aatagtaaac aaactcgtac ggaagtacaa gaacaactta accaagctaa gtcactagat    12540
agttctatgg gcacgttaaa atcattagtt gctaaacaac ctacagtaca aaaacaagt    12600 gtttatatta acgaagatca acctgagcaa tctgcctaca atgattccat tacaatggga    12660
caaactataa ttaataaaac agctgatcca gtacttgata aaactttagt tgataacgca    12720
atcagtaaca tttcaactaa agagaatgca ctgcatggtg aacaaaaatt aacaactgct    12780
aaaacggaag caattaatgc acttaataca ttagctgatt taaacacacc tcagaaagag    12840
gctattaaaa cagctattaa cactgctcat acaagaactg atgtaactgc agagcaaagt    12900
aaggctaatc aaataaatag tgcaatgcac acgttgagac aaaacatttc tgacaacgaa    12960
tcagtaacaa acgaaagtaa ttatattaac gctgaacccg aaaaacaaca tgcctttact    13020
gaggctctaa ataatgctaa agaaatagtt aatgaacaac aagccactct tgatgccaat    13080
tcaattaacc aaaaagcaca agcgattctt actactaaaa atgctttaga tggtgaagaa    13140
caattacgtc gtgctaaaga aaatgccgat caagaaatca atacgttaaa tcaattgact    13200
gatgcgcaaa gaaatagtga aaaaggttta gtcaacagtt ctcaaactag aacagaagtt    13260
gcttctcaat tagcaaaagc taaagaacta aataaggtga tggaacaact gaatcacctt    13320
atcaatggta aaaaccaaat gataaatagc agtaaattta tcaatgaaga tgcgaaccaa    13380
caacaagcat attcaaatgc gattgcaagt gcagaagcgc ttaaaaacaa atcacaaaac    13440
cctgaattag ataaagtaac aattgaacaa gcaattaata atattaattc tgcaattaac    13500
aatctaaacg gtgaagctaa actgactaaa gctaaagaag atgctgttgc ttcaataaac    13560
aacctaagcg gattaacaaa cgagcaaaaa acaaaagaaa atcaagccgt taatggcgct    13620
caaactagag accaagttgc taataaatta cgtgatgctg aagcattaga tcaatcaatg    13680
caaacattac gtgacttagt taacaatcaa aatgcaatac attcaacaag taattatttt    13740
aacgaggatt caactcaaaa gaatacttat gataatgcaa ttgataatgg ctcgacatat    13800
ataactggtc aacacaatcc agaattaaat aaatctacta ttgatcaaac gattagccga    13860
attaacacag ctaaaaatga tttacatggt gtagaaaagt tacaaagaga taagggaact    13920
gctaatcaag aaattggaca attaggttat ttaaatgacc ctcaaaaatc tggtgaggaa    13980
tccttagtca acggttcaaa tacacgttct gaagtagaag agcatcttaa tgaagctaaa    14040
tcattaaata atgcaatgaa acaattaaga gataaagtag ctgaaaagac taatgtcaaa    14100
caaagtagcg attacattaa tgattcaact gaacatcaac gtgggtatga tcaagcactt    14160
caagaagcag aaaatattat taatgaaatc ggtaatccaa cattaaataa atcggaaatt    14220
gaacaaaagt tacaacaatt gactgacgct caaaatgcgt tacaaggttc acatctatta    14280
gaagaagcta aaaataatgc gattactgga atcaataaac ttacagcatt aaatgatgca    14340
caacgtcaaa aagcaattga aaatgttcaa gcacagcaga caatcccagc agttaatcaa    14400
caattaactt tggatagaga aataaatact gcaatgcaag ctttacgaga taaagtaggc    14460
caacaaaata acgttcacca acaaagtaat tatttcaatg aagatgaaca accaaaacat    14520
aactatgata attctgtaca agccggtcaa actattattg ataaacttca agatccaatc    14580
atgaacaaaa atgaaattga gcaggctatt aatcaaatca atcgactca aacagcgtta    14640 agtggagaaa ataaattaca cactgaccaa gaaagcacaa atagacaaat agaaggttta    14700
```

```
tctagtttga acacagctca aatcaacgcc gaaaaagatt tagtcaatca agctaaaaca   14760
agaacagatg ttgctcaaaa gttagctgca gctaaagaaa taaattctgc tatgagtaat   14820
ttaagagatg gcattcaaaa taaagaggac atcaaacgta gcagtgcata tatcaacgca   14880
gatccgacta aagttacagc ttacgatcaa gcactacaga acgcagaaaa tatcatcaat   14940
gccacaccaa acgtagagct taataaagct acaattgaac aagcgctatc acgcgttcaa   15000
caagcacaac aagatcttga tggtgttcaa caattagcta atgctaaaca acaagctaca   15060
caaactgtca atgggttaaa tagcttaaat gacggtcaaa agcgtgaatt aaatctatta   15120
attaattcag ctaatacccg tacaaaagta caagaagaat taaacaaagc aactgaattg   15180
aaccatgcga tggaagcttt aagaaacagt gttcaaaacg ttgatcaagt aaaacaaagt   15240
agcaattatg tcaatgaaga tcaacctgaa cagcacaatt atgataatgc tgtcaatgaa   15300
gctcaagcta caatcaacaa caatgctcaa cctgttctag acaaattagc tatagaacgt   15360
ttaactcaaa ctgttaacac tacaaaagat gcattacatg gtgctcaaaa actgacacaa   15420
gaccaacaag ctgctgaaac tggaatacgt ggtttaacga gtctcaatga acctcagaaa   15480
aatgctgaag tagctaaagt aactgcagca caaacacgtg atgaagtgag aaatattcgt   15540
caagaagcaa caacattaga tactgcaatg cttggtttac gtaaaagcat taagataaa    15600 aacgatacta aaaatagtag taaatatatt aatgaggatc atgaccaaca acaagcttat   15660
gacaatgctg taaataatgc tcaacaagtt atcgatgaaa ctcaagcaac gttaagctca   15720
gatacaatca atcaattggc aaatgccgta actcaagcta atctaatct tcatggagat    15780 actaaactac aacacgataa agatagtgct aaacaaacga ttgctcaatt acagaatttg   15840
aattcagctc aaaaacatat ggaagattct ttaattgata tgaatctac acgtacgcaa    15900 gtccaacacg atttaacaga agctcaagct ttagatggtt taatgggtgc cttaaaagaa   15960
agtattaaag attatactaa tattgtttca acggtaatt acatcaatgc ggaaccatct    16020
aagaaacaag catatgatgc agctgtacaa aatgctcaaa atataataaa tggaacgaat   16080
caaccaacaa ttaataaagg taatgtcact acagcaacac aaaccgtgaa aaatactaaa   16140
gatgccttag acggtgatca tagattagag gaagctaaaa ataatgccaa tcaaacaatc   16200
agaaatctat ctaatttgaa caatgcccaa aaagatgcag agaaaaatct agttaatagc   16260
gcatcaacat tagaacaagt tcaacaaaac ttacaaaccg ctcaacaatt agataatgct   16320
atgggtgagt tacgacaaag tattgctaaa aaagatcaag tgaaagcaga tagtaaatat   16380
ctaaatgaag atcctcaaat taagcaaaac tatgatgatg cagttcaacg tgttgaaact   16440
attattaacg aaactcaaaa ccctgaatta cttaaagcaa acattgacca agcaactcaa   16500
tccgttcaaa atgcagaaca agctttacat ggtgctgaaa aattaaatca agacaaacaa   16560
acgtcttcga cagaactaga tggattaaca gatttaacag atgcacaacg tgaaaaactc   16620
agagaacaaa ttaacacttc taatagtaga atgatattta gcaaaaaat tgagcaagca   16680 aaagcactaa atgacgcaat gaaaaaactt aaagaacaag ttgcgcaaaa agatggtgtt   16740
catgctaaca gtgattatac aaatgaagat tctgcacaaa aagatgcgta taataatgca   16800
cttaaacaag cggaagacat tattaataac agctcaaatc ctaacttaaa tgcacaagac   16860
attactaatg ctttaaataa tattaaacaa gcacaagata accttcatgg agctcaaaaa   16920
ttacagcaag acaaaaatac aactaatcaa gccattggta acttaaatca tcttaatcaa   16980
cctcaaaaag atgcgcttat acaagctatt aatggagcta catctaggga ccaagttgca   17040
gaaaaactta agaggccga agcgcttgat gaagctatga aacaacttga agatcaagtg   17100
```

```
aatcaagatg atcaaatttc aaatagcagc ccattcataa atgaagactc agacaaacaa   17160
aaaacttata atgataaaat ccaagctgca aaagaaataa ttaatcaaac atctaatcca   17220
accttagata aacaaaaaat tgctgataca cttcaaaata ttaaagatgc agtgaataat   17280
ttacatggtg atcaaaaatt agctcaatct aaacaagatg ctaataatca attaaatcat   17340
ttagatgact taaccgaaga acaaaaaaac cattttaaac cgttaattaa taatgctgat   17400
actcgagatg aggtaaataa acaactagag attgctaaac aattaaatgg tgatatgagt   17460
acacttcata aagtcataaa tgataaagat caaattcaac atttaagcaa ttacattaat   17520
gctgataatg ataaaaaaca aaattatgat aatgctatta agaagctgag ggatttaatt   17580
cataatcatc cagatacatt agatcataaa gcattacaag atttattaaa caagatagac   17640
caagcgcata acgaattaaa tggagaatcc agatttaaac aggctttaga caatgcttta   17700
aacgacatag atagcttaaa cagtctcaat gttccacaac gccaaactgt taaggataac   17760
atcaaccatg tgacaactct agaaagttta gctcaagaat tgcagaaagc aaaagagctt   17820
aatgatgcta tgaaagcaat gagagatagc attatgaatc aagagcaaat tcgtaaaaat   17880
agcaattata ctaatgaaga cttagctcaa caaaatgcct ataatcatgc agtagataaa   17940
ataaataaca ttattggtga agacaatgcg acgatggatc ctcaaataat caaacaagca   18000
actcaagata taaatacagc tataaatgga ttaaatggag atcaaaaact tcaagatgca   18060
aagacagatg ctaaacaaca aattactaac tttactggtt taactgaacc acaaaaacaa   18120
gcattggaaa acatcattaa ccaacaaaca agcagagcaa atgttgctaa acagttaagt   18180
catgctaaat tcttaaatgg aaaaatggaa gaattaaaag ttgcagtagc caaagcgtca   18240
ttagtaagac aaaatagtaa ctatattaat gaagatgtct ctgaaaaaga agcatatgaa   18300
caagctatcg caaaaggtca ggaaataatt aattcagaaa ataatccaac aataagtagt   18360
actgatatca atcgtaccat tcaagaaatt aatgatgctg aacaaaatct tcatggtgat   18420
aataaattaa gacaagcaca ggaaattgca aagaatgaaa tacaaaatct agacggatta   18480
aattcagctc aaataacaaa attaatccaa gatataggca gaacaacaac taaacctgca   18540
gtaactcaga aactagaaga agcaaaagca ataaccaag ctatgcaaca acttaaacaa   18600
agtatagccg ataaggatgc tactctaaat tctagtaact atctcaatga agattctgag   18660
aaaaagttag cgtacgataa tgctgtaagc caagctgaac aactcataaa tcaacttaac   18720
gacccaacta tggatataag taatattcaa gctattactc aaaaggtcat tcaagcaaaa   18780
gattcattgc acggtgcgaa taaacttgca caaaatcaag cagattcaaa tttaataata   18840
aatcaatcaa caaatttaaa tgataaacaa aagcaagcat taaatgactt aattaatcat   18900
gctcaaacta aacagcaagt ggcagaaata attgcacaag ctaataagtt aaataacgaa   18960
atgggcacac taaaaacact cgtagaagaa cagtcaaacg ttcatcaaca aagtaaatat   19020
attaatgaag atccgcaagt tcaaaatatt tataatgact ccattcaaaa aggtcgagaa   19080
atattaaacg gcactacaga tgatgtttta aacaacaata aaatagcaga tgccattcaa   19140
aacattcatt taactaaaaa cgatttacat ggtgatcaaa aattacaaaa agcacaacaa   19200
gatgcaacca atgaattaaa ctatttaaca aatctaaaca attctcaaag acaaagcgag   19260
catgatgaga ttaactctgc tccttcaaga actgaagttt ctaatgattt aaatcatgct   19320
aaagcactta atgaagctat gcgtcaactt gagaatgaag ttgctcttga aaacagtgtt   19380
aaaaaattaa gcgactttat caatgaagat gaagcggcac aaaatgaata tagtaatgca   19440
```

```
cttcaaaaag ctaaagacat tatcaacggc gttccaagta gcactttaga taaagctaca   19500
attgaagatg cttttattaga attgcaaaat gctagagaaa gtttacatgg tgagcaaaaa   19560
cttcaagagg ctaaaaatca agctgttgct gaaattgata atttacaagc attaaatcct   19620
ggacaggttc ttgctgaaaa aacattagtt aaccaagcat caaccaaacc agaagttcaa   19680
gaagccttac aaaaagcaaa agaacttaat gaagctatga aagcactgaa aactgaaata   19740
aataaaaaag aacaaatcaa ggctgatagt agatatgtaa atgctgacag tggtcttcaa   19800
gcaaattaca attctgcgtt aaattatggt tctcaaatta ttgcaactac ccaaccacca   19860
gagcttaata aagatgtaat aaatagagca actcaaacga ttaaaactgc tgaaaataat   19920
ttaaatgggc aatctaaatt agcagaggct aagtcagacg gaaatcaaag catcgaacat   19980
ttgcaaggat taacacaatc acaaaaagat aaacaacatg atttaattaa tcaagctcaa   20040
actaaacaac aggtagatga tatcgtaaat aactctaaac aattagataa ctctatgaat   20100
caactacaac aaattgttaa caatgacaat acagtaaaac aaaatagtga tttcattaat   20160
gaagattcca gccaacagga tgcttataat catgcaattc aagcagcaaa agatttgata   20220
actgctcatc caactatcat ggataaaaat caaatagatc aagctattga aaatatcaaa   20280
caagcactta atgatttaca cggtagtaat aaactatcag aagataaaaa agaagcttca   20340
gaacaactac aaaaccttaa tagcttgacg aacgggcaaa aagatacgat tttaaatcat   20400
attttcagtg caccaacaag aagccaagta ggagaaaaaa ttgcaagtgc taaacaatta   20460
aataatacaa tgaaagcact tagagattct attgctgata ataatgaaat tttacaaagt   20520
agtaagtact tcaatgaaga ttctgaacaa caaaatgctt ataatcaagc cgtaaataaa   20580
gctaaaaata taattaatga tcaaccaaca ccagtaatgg caaatgatga gattcaaagt   20640
gtcctaaatg aagttaaaca aactaaagat aatttacatg gtgatcaaaa acttgctaac   20700
gacaagacag atgctcaagc aacattaaat gcgttaaatt acttaaatca agcgcaaaga   20760
ggtaatcttg aaactaaagt tcaaaactct aattctagac cagaagtaca aaaagtagtt   20820
caattagcaa atcaacttaa tgatgcgatg aaaaaattag atgatgcttt aactggtaat   20880
gacgcaataa aacaaacgag taattatatt aatgaagata cttctcaaca agttaacttt   20940
gatgagtata cagatagagg taaaaacata gttgctgaac aaacaaatcc aaatatgtct   21000
ccaactaata ttaacactat tgctgataaa attactgaag ctaaaaacga tttacatggc   21060
gtacaaaaac taaacaagc tcaacaacag tccatcaata ctattaatca aatgactggt   21120
ctaaaccaag ctcaaaaaga acaattaaat caagaaattc aacaaactca acccgttct   21180 gaagtacatc aagtaattaa taaagcacaa gctttaaatg attcaatgaa tactttacgt   21240
caaagtatta ctgatgaaca tgaagttaaa caaacaagta actacatcaa tgaaactgtt   21300
ggtaatcaaa ctgcatataa caatgccgtt gatcgtgtaa aacaaataat caatcaaaca   21360
tctaatccaa ctatgaatcc tttagaggtg gaacgtgcaa catcaaatgt aaaaatttct   21420
aaagatgcac ttcatggtga acgtgaattg aatgacaata aaaattcaaa aacttttgca   21480
gtcaatcact tagataacct caatcaagct caaaagaag cattaactca tgaaattgaa   21540
caagcaacta tagtttcaca agtaaataat atctataaca aagcgaaagc tttaaataat   21600
gatatgaaaa aacttaaaga tatcgttgct caacaagata atgtgagaca atcaaacaat   21660
tatataaacg aggatagtac acctcaaaat atgtacaacg atacaattaa tcatgcacaa   21720
tcaatcattg atcaagtagc aaaccctacg atgtctcatg acgaaataga gaatgcaatc   21780
aataacataa agcatgccat caatgcactc gatggagaac ataaattaca acaagcaaaa   21840
```

```
gaaaatgcaa acttattgat taatagttta aacgatttaa atgcaccaca aagagatgcc    21900
ataaatagat tggttaatga agctcaaaca agagaaaaag tagctgaaca acttcaaagt    21960
gctcaagctt taaatgacgc tatgaagcat ttaagaaaca gcattcaaaa tcaatcatcc    22020
gtaagacaag agagcaaata tattaatgca agtgatgcta aaaagagca atataatcac     22080 gcagttagag aagtcgaaaa tattatcaat gaacaacatc caacattgga taaagaaata    22140
attaagcaac taacggatgg tgtaaatcaa gcgaataatg acttaaatgg cgttgaatta    22200
ttagatgctg ataagcaaaa cgcacatcaa tcgatacctA cattgatgca cttaaatcaa    22260
gcacaacaaa acgcattaaa tgaaaaaatt aataacgcag ttaccagaac tgaagttgcg    22320
gctattattg gccaagcaaa actactcgat catgctatgg agaatttaga agaaagtatc    22380
aaagataaag agcaagtcaa acagtcaagt aactatatta tgaagattc tgatgttcaa     22440 gaaacatacg ataacgccgt tgatcatgtg acagaaatac ttaatcaaac agtaaatcca    22500
actttatcta ttgaagatat agagcatgct atcaacgaag ttaatcaagc gaaaaaacaa    22560
ctcagaggta acaaaaaact ttatcaaact atcgatttag ctgataaaga attaagtaaa    22620
ttggatgatt taacatcaca acaaagcagt tcaatatcta atcaaatata tactgctaaa    22680
acgagaacag aagttgccca agcaattgaa aaagcaaaat cattaaatca tgcaatgaaa    22740
gcacttaaca aagtatataa aaatgcagat aaagtgttag atagtagtcg attcattaac    22800
gaagatcaac ctgaaaaaaa ggcgtatcaa caagctataa atcatgttga ttcaatcatt    22860
catagacaaa caaatcctga aatggatcca acagtaatca atagcataac tcatgaactc    22920
gaaacagctc aaaataactt acatggtgat cagaaacttg ctcatgcaca acaagatgcc    22980
gctaatgtaa ttaatggtct aattcatctt aatgttgctc aacgtgaggt aatgataaat    23040
acgaatacaa atgctacaac acgcgaaaaa gttgcaaaga acttagataa tgctcaagct    23100
cttgataaag ctatggaaac actacaacaa gtagttgctc ataaaaataa tatattgaac    23160
gatagtaaat atttaaatga agattcaaaa tatcaacaac aatacgatcg agttattgct    23220
gatgccgaac aactacttaa tcagacaaca atccaacat tagaaccttta taaagtcgat    23280 attgttaagg ataatgtcct agctaacgaa aaaatactat ttggcgcaga aaaactatca    23340
tatgacaaat caaatgcaaa tgatgaaatt aaacatatga attatcttaa taatgcacaa    23400
aagcaatcta taaagatat gatttctcac gcagcattaa gaactgaagt taaacaactt     23460
ctgcaacaag ctaaaatcct tgatgaagcc atgaaatcac ttgaagataa aactcaagta    23520
gtgattacag atactacttt gcctaattac actgaagctt cagaggataa aaaggaaaaa    23580
gtagaccaaa ctgtatcaca tgctcaagcg attattgata aataaatgg ctcaaatgta     23640 agtttagatc aagtacgaca agcactagaa caattaactc aagcatcaga aaacctcgat    23700
ggtgatcagc gagttgaaga agctaaagtt catgctaatc aaacaattga tcaattaaca    23760
catcttaatt cattacaaca acaaactgcg aagagaagtg ttaaaaacgc aacaaaacta    23820
gaagaaatcg ctactgttag taacaatgct caggcattaa acaaagtaat gggtaaatta    23880
gaacaattca ttaatcatgc tgattctgtt gaaaatagtg ataattatag acaagccgac    23940
gacgacaaaa tcatcgctta tgatgaagca cttgaacatg acaagatat acaaaaaact     24000 aacgcaaccc aaaatgaaac aaaacaagcg ttacaacaat taatatatgc agaaacatcg    24060
ttaaatggtt tcgaaagatt aaatcatgct agaccacgag ctttagaata tatcaaatca    24120
ctagaaaaaa taaacaatgc tcaaaagtct gctttagagg ataaagtaac gcaatcgcat    24180
```

```
gatttattag aattagaaca tattgtcaac gagggcacaa acctcaatga cattatgggt   24240
gaattagcta acgcaatcgt taataactat gctccaacca aagcaagtat aaattatatt   24300
aacgccgata acctacgcaa agataacttt actcaagcta tcaacaatgc acgtgatgca   24360
ctcaacaaaa ctcaaggtca gaacttagat ttcaatgcaa ttgatacatt taaagatgat   24420
atattcaaaa ctaaagatgc acttaacggt attgaacgtt taacagctgc aaaatcaaaa   24480
gcagaaaaac taattgatag tttaaaattt attaataaag ctcaattcac acatgcaaat   24540
gatgaaatta tgaatactaa ttctattgca caattgtcta gaatcgtgaa tcaagcattt   24600
gatttaaatg atgcaatgaa atctttaaga gatgaactta ataatcaagc ttttcctgtc   24660
caagcaagct caaattatat aaattcagat gaagatttaa acaacaatt tgaccatgct   24720 ttaagtaatg ctcgaaaagt tcttgcaaaa gaaaatggta aaaatttaga tgaaaaacaa   24780
attcagggac tcaaacaagt gattgaggat actaaagatg cttaaatgg tatccaacgt   24840 ttatcaaaag ctaaagctaa agcaattcaa tacgtacaat ctttatctta tatcaatgat   24900
gcacagcgtc atattgctga aataatatt cacaactctg atgattatc atctttagca   24960 aatacattat ctaaagctag tgatttagat aatgcaatga agacttacg agatactata   25020 gaaagtaatt caacttctgt tccaaatagt gtgaattata ttaatgctga taagaattta   25080
caaattgaat ttgatgaggc gctacaacaa gcaagtgcaa caagttctaa aacttcagaa   25140
aatccagcaa cgattgaaga agtattaggt cttagtcaag ccatttacga tacaaaaaat   25200
gcattaaatg gtgaacaacg acttgcaact gagaagagca aagatctaaa attaataaaa   25260
ggattaaaag atttaaataa agcacaactt gaagatgtca caaacaaggt aaattcagca   25320
aatactttaa cagagttatc tcagctcact caatcaacgt tagaattaaa cgataaaatg   25380
aaattattga gagataagct taaaacttta gtaaatcctg ttaaagcaag tttaaattat   25440
agaaacgctg attataattt aaaacgtcaa tttaacaaag ctttaaaaga agctaaaggc   25500
gtattaaata aaaatagcgg tacaaatgtc aatatcaatg acattcaaca tcttttaaca   25560
caaatagata atgctaaaga ccaattaaat ggtgaacgac gtctaaaaga acatcaacaa   25620
aaatctgaag tatttattat taagaatta gatatactta ataatgctca aaaagctgca   25680
ataattaatc agattagagc gtctaaagac attaaaataa ttaatcaaat cgttgataat   25740
gcaatagaat taaatgatgc tatgcaaggt ttaaagaac atgtagctca attaacagca   25800
actacaaaag acaacattga atatttaaat gctgatgaag accataaatt acaatatgat   25860
tacgctatca acttagcgaa taatgttctt gacaaagaaa acggtacaaa taagacgct   25920 aatatcataa ttggaatgat tcaaaacatg gatgatgcta gagcacttct aaatggaatt   25980
gaaagactta agatgctca aacaaaagca cataatgaca ttaaagatac gctcaaacgt   26040
caacttgatg aaattgaaca cgctaatgca acatcaaatt ctaaagctca agctaaacaa   26100
atggtaaatg aggaagctag aaaagcgctt tctaatatta tgacgcaac atcaaatgat   26160 ttagttaatc aagcaaaaga tgaagggcaa tctgcaattg aacacataca tgcagatgaa   26220
ttacctaaag caaaactaga tgctaatcaa atgattgacc aaaaagttga agatataaat   26280
cacttaatta gtcaaaatcc aaacttatca atgaagaaa aaaataaact aatatctcaa   26340
attaataagt tagtaaatgg aattaagaat gaaattcaac aagctataaa caacaacaa   26400 atagaaaatg ctacaacaaa actagatgaa gtcattgaaa ctactaaaaa attaattatc   26460
gccaaagcag aagctaaaca aatgataaaa gagttatcac aaaagaaacg agatgcaata   26520
aataacaaca ctgatttaac accttctcaa aaggcacatg ctttagcaga tattgataaa   26580
```

-continued

```
acagaaaaag atgcacttca acatatcgaa aattctaatt caattgatga tatcaataac    26640
aataaagagc atgcatttaa tactttagct catatcatta tttgggatac tgatcagcaa    26700
ccattagttt ttgaactacc tgaattgagc cttcaaaatg ctctagtaac aagtgaggtg    26760
gttgttcaca gagatgaaac tatttcatta gaatctataa ttggagctat gactttaact    26820
gatgaactta aagtcaatat tgtttcatta ccgaacactg ataaagtagc tgatcaccta    26880
accgctaaag ttaaggttat tttagctgat ggctcatatg tcactgtaaa tgttccagtc    26940
aaagttgtag aaaaagaatt acaaatagct aaaaaggatg ctataaaaac aattgatgtt    27000
ctggtaaaac aaaaaatcaa agatatagat tctaataacg aattaacgtc tactcaacgt    27060
gaagatgcaa aagctgaaat tgaaagattg aaaaagcaag ccatcgataa agtgaatcat    27120
tcaaaatcga ttaaagatat tgaaacagta aaacgaactg attttgaaga aatagatcag    27180
tttgatccta aacgctttac gctaaataaa gctaaaaagg atatcattac tgatgttaat    27240
actcaaatcc aaaatggttt caagaaaatt gaaacaataa aaggtttaac ttctaatgaa    27300
aaaactcagt ttgataaaca attaactgca ctacaaaaag aattttttaga aaagtcgag    27360 catgctcata atttagtaga attaaatcaa ttacaacaag agtttaataa tagatataaa    27420
catattttaa accaagcaca tttactaggt gaaaaacata tagcagaaca taaattagga    27480
tatgttgtag taaacaaaac tcagcaaata ctaataatc aatctgcttc ttactttata    27540
aaacaatggg cacttgatag aattaaacaa attcaactag aaacgatgaa ttcaattcgt    27600
ggtgcgcata ccgtacaaga tgtacacaaa gcattattac aaggtataga gcaaatcttg    27660
aaagtaaatg taagtattat aaatcaatct ttcaacgatt ccttgcataa ctttaattat    27720
cttcattcaa aatttgatgc tagattaaga gaaaaggatg ttgcaaacca tatcgtacaa    27780
actgaaacat tcaaagaagt tctaaaagga acgggtgttg aaccaggtaa aatcaacaaa    27840
gaaacacagc aaccaaaact tcataagaat gataatgata gcctattcaa acatttagtt    27900
gataatttcg gcaaaactgt aggtgttatt acattaactg gtttactttc tagtttctgg    27960
ttagttttgg ctaaaagacg taaaaaagaa gaagaagaaa aacaatcgat aaaaaatcat    28020
cacaaagata ttcgtctttc agatactgat aaaaatagatc caattgtaat aactaagcgt    28080
aaaatagata aagaagaaca aattcaaaac gatgacaaac attcaattcc agttgctaaa    28140
cataagaaat ctaagaaaaa gcaattgagt gaagaggata ttcattcaat ccccgtcgtt    28200
aagcgtaaac aaaacagtga taacaaagat acaaaacaga gaaagttac ttctaaaaag    28260 aagaaaacgc ctcagtcaac taaaaaagtt gtaaaaacca aaaagcgttc taaaaag       28317
```

<210> SEQ ID NO 49
<211> LENGTH: 3348
<212> TYPE: DNA
<213> ORGANISM: S. aureus

<400> SEQUENCE: 49

```
atgagagata agaaaggacc ggtaaataaa agagtagatt ttctatcaaa taaattgaat      60
aaatattcaa taagaaaatt tacagttgga acagcatcta ttttaattgg ctcactaatg     120
tatttgggaa ctcaacaaga agcagaagca gctgaaaaca atattgagaa tccaactaca     180
ttaaaagata atgtccaatc aaaagaagtg aagattgaag aagtaacaaa caaagacact     240
gcaccacaag gtgtagaagc taaatctgaa gtaacttcaa acaaagacac aatcgaacat     300
gaagcatcag taaaagctga agatatatca aaaaaggagg atacaccaaa agaagtagct     360
```

```
aatgttgctg aagttcagcc gaaatcgtca gtcactcata acgcagaggc acctaaggtt      420
agaaaagctc gttctgttga tgaaggctct tttgatatta caagagattc taaaaatgta      480
gttgaatcta ccccaattac aattcaaggt aaagaacatt ttgaaggtta cggaagtgtt      540
gatatacaaa aaaacccaac agatttaggg gtatcagagg taaccaggtt taatgttggt      600
aatgaaagta atggtttgat aggagcttta caattaaaaa ataaaataga ttttagtaag      660
gatttcaatt ttaaagttag agtggcaaat aaccatcaat caaataccac aggtgctgat      720
ggttgggggt tcttatttag taaaggaaat gcagaagaat atttaactaa tggtggaatc      780
cttggggata aaggtctggt aaattcaggc ggatttaaaa ttgatactgg atacatttat      840
acaagttcca tggacaaaac tgaaaagcaa gctggacaag gttatagagg atacggagct      900
tttgtgaaaa atgacagttc tggtaattca caaatggttg gagaaaatat tgataaatca      960
aaaactaatt ttttaaacta tgcggacaat tcaactaata catcagatgg aaagtttcat     1020
gggcaacgtt taaatgatgt catcttaact tatgttgctt caactggtaa aatgagagca     1080
gaatatgctg gtaaaacttg ggagacttca ataacagatt taggtttatc taaaaatcag     1140
gcatataatt tcttaattac atctagtcaa agatggggcc ttaatcaagg gataaatgca     1200
aatggctgga tgagaactga cttgaaaggt tcagagttta cttttacacc agaagcgcca     1260 aaacaataa  cagaattaga aaaaaaagtt gaagagattc cattcaagaa agaacgtaaa     1320
tttaatccgg atttagcacc agggacagaa aaagtaacaa gagaaggaca aaaaggtgag     1380
aagacaataa caacaccaac actaaaaaat ccattaactg gagaaattat tagtaaaggt     1440
gaatcgaaag aagagatcac aaaagatccg attaatgaat taacagaata cggaccagaa     1500
acgatagcac caggtcatcg agacgaattt gatccgaagt taccaacagg agagaaagaa     1560
gaagttccag gtaaaccagg aattaagaat ccagaaacag gagacgtagt tagaccaccg     1620
gtcgatagtg taacaaaata tggacctgta aaaggagact cgattgtaga aaaagaagaa     1680
attccattcg agaagaacg taaatttaat cctgatttag caccaggaac agaaaaagta     1740
acaagagaag gacaaaaagg tgagaagaca ataacgacac caacactaaa aaatccatta     1800
actggagaaa ttattagtaa aggtgaatcg aagaagagag tcacaaaaga tccgattaat     1860
gaattaacag aatacggacc tgaaacaata gcgccaggtc atcgagacga atttgatccg     1920
aagttaccaa caggagagaa agaagaagtt ccaggtaaac caggaattaa gaatccagaa     1980
acaggagacg tagttagacc gccggtcgat agcgtaacaa aatatggacc tgtaaaagga     2040
gactcgattg tagaaaaaga gaaattcca ttcaagaaag aacgtaaatt taatcctgat     2100
ttagcaccag ggacagaaaa agtaacaaga gaaggacaaa aggtgagaa gacaataacg     2160 acgccaacac taaaaaatcc attaactgga gaaattatta gtaaaggtga atcgaaagaa     2220
gaaatcacaa aagatccgat taatgaatta acagaatacg gaccagaaac gataacacca     2280
ggtcatcgag acgaatttga tccgaagtta ccaacaggag agaaaggaa agttccaggt     2340 aaaccaggaa ttaagaatcc agaaacagga gatgtagtta gaccaccggt cgatagcgta     2400
acaaaatatg gacctgtaaa aggagactcg attgtagaaa aagaagaaat tccattcgag     2460
aaagaacgta aatttaatcc tgatttagca ccagggacag aaaagtaac aagaagga      2520 caaaaaggtg agaagacaat aacgacgcca acactaaaaa atccattaac tggagaaatt     2580
attagtaaag gtgaatcgaa agaagaaatc acaaaagatc cagttaatga attaacagaa     2640
ttcggtggcg agaaaatacc gcaaggtcat aaagatatct ttgatccaaa cttaccaaca     2700
gatcaaacgg aaaaagtacc aggtaaacca ggaatcaaga atccagacac aggaaaagtg     2760
```

| | |
|---|---|
| atcgaagagc cagtggatga tgtgattaaa cacggaccaa aaacgggtac accagaaaca | 2820 |
| aaaacagtag agataccgtt tgaaacaaaa cgtgagttta tccaaaatt acaacctggt | 2880 |
| gaagagcgag tgaaacaaga aggacaacca ggaagtaaga caatcacaac accaatcaca | 2940 |
| gtgaacccat taacaggtga aaaagttggc gagggtcaac caacagaaga gatcacaaaa | 3000 |
| caaccagtag ataagattgt agagttcggt ggagagaaac caaagatcc aaaaggacct | 3060 |
| gaaaacccag agaagccgag cagaccaact catccaagtg gcccagtaaa tcctaacaat | 3120 |
| ccaggattat cgaaagacag agcaaaacca atgggcccag ttcattcaat ggataaaaat | 3180 |
| gataaagtta aaaaatctaa aattgctaaa gaatcagtag ctaatcaaga gaaaaaacga | 3240 |
| gcagaattac aaaaacagg tttagaaagc acgcaaaaag gtttgatctt tagtagtata | 3300 |
| attggaattg ctggattaat gttattggct cgtagaagaa agaattaa | 3348 |

<210> SEQ ID NO 50
<211> LENGTH: 4410
<212> TYPE: DNA
<213> ORGANISM: S. epidermidis

<400> SEQUENCE: 50

| | |
|---|---|
| atgggcaaac gtagacaagg tcctattaat aaaaaagtgg atttttttacc taacaaatta | 60 |
| aacaagtatt ctataagaaa attcactgtt ggtacggcct caatattact tggttcgaca | 120 |
| cttattttttg gaagtagtag ccatgaagcg aaagctgcag aagaaaaaca agttgatcca | 180 |
| attacacaag ctaatcaaaa tgatagtagt gaaagatcac ttgaaaacac aaatcaacct | 240 |
| actgtaaaca atgaagcacc acagatgtct tctacattgc aagcagaaga aggaagcaat | 300 |
| gcagaagcac cgaatgttcc aactatcaaa gctaattcag ataatgatac acaaacacaa | 360 |
| ttttcagaag cccctacaag aaatgaccta gctagaaaag aagtatatccc tgctgtttct | 420 |
| aaaaacgagg aattacaatc atcacaacca aacactgaca gtaaaataga acctacaact | 480 |
| tcagaacctg tgaatttaaa ttatagttct ccgtttatgt ccttattaag catgcctgct | 540 |
| gatagttcat ccaataacac taaaaatata atagatatac cgccaactac ggttaaaggt | 600 |
| agagataatt acgattttta cggtagagta gatatccaaa gtaatcctac agatttaaat | 660 |
| gcgacaaatt taacgagata taattatgga cagccacctg gtacaacaac agctggtgca | 720 |
| gttcaattta aaaatcaagt tagttttgat aaagatttcg acttaacat tagagtagca | 780 |
| aacaatcgtc aaagtaatac aactggtgca gatggttggg gctttatgtt cagcaagaaa | 840 |
| gatggggatg atttcctaaa aaacggtggt atcttacgtg aaaaaggtac acctagtgca | 900 |
| gctggtttca gaattgatac aggatattat aataacgatc cattagataa aatacagaaa | 960 |
| caagctggtc aaggctatag agggtatggg acatttgtta aaaatgactc ccaaggtaat | 1020 |
| acttctaaag taggatcagg tactccatca acagattttc ttaactacgc agataatact | 1080 |
| actaatgatt tagatggtaa attccatggt caaaaattaa ataatgttaa tttgaaatat | 1140 |
| aatgcttcaa atcaaacttt tacagctact tatgctggta aaacttggac ggctacgtta | 1200 |
| tctgaattag gattgagtcc aactgatagt tacaattttt tagttacatc aagtcaatat | 1260 |
| ggaaatggta atagtggtac atacgcagat ggcgttatga gagctgattt agatggtgca | 1320 |
| acattgacat atactcctaa agcagtcgat ggagacccaa ttcatcaac taaggaaata | 1380 |
| ccatttaata aaaaacgcga atttgatcca aacttagcgc caggtacaga aaaagtcgtt | 1440 |
| caaaaaggtg aaccaggaat tgaaacaaca acaacaccaa cttatgtcaa tcctaatact | 1500 |

```
ggagaaaaag taggtgaagg cacacctaca acaaagatca ctaaacaacc agtggatgaa    1560
atcgttcatt atggtggcga agaaatcaag ccaggacata agatgaatt  tgatccaaat    1620 gcaccgaaag gtagtcaaac aacgcaacca ggtaagccag gagttaaaaa tcctgataca    1680
ggcgaagtag tcacaccacc agtggatgat gtgacaaaat atggtccagt tgatggagat    1740
ccgattacgt caacggaaga aattccattc gacaagaaac gtgaattcaa tcctgattta    1800
aaaccaggtg aagagcgtgt taaacaaaaa ggtgaaccag gaacaaaaac aattacaaca    1860
ccaacaacta gaacccatt  aacaggggaa aaagttggcg aaggtgaacc aacagaaaaa    1920
ataacaaaac aaccagtaga tgaaatcaca gaatatggtg cgaagaaat  caagccaggc    1980 cataaggatg aatttgatcc gaacgcaccg aaaggtagcc aagaggacgt tccaggtaaa    2040
ccaggagtta aaaatcctga tacaggcgaa gtagtcacac caccagtgga tgatgtgaca    2100
aaatatggtc cagttgatgg agatccgatt acgtcaacgg aagaaattcc gtttgataaa    2160
aaacgcgaat ttgatccaaa cttagcgcca ggtacagaga agtcgttca  aaaaggtgaa    2220 ccaggaacaa aaacaattac aacaccaaca actaagaacc cattaacagg agaaaaagtt    2280
ggcgaaggtg aaccaacaga aaaaataaca aacaaccag  tggatgaaat cgttcattat    2340
ggtggcgaag aaatcaagcc aggccataag gatgaatttg atccgaacgc accgaaaggt    2400
agccaagagg acgttccagg taagccagga gttaaaaatc ctgatacagg cgaagtagtc    2460
acaccaccag tggatgatgt gacaaaatat ggtccagttg atggagatcc gattacgtca    2520
acggaagaaa ttccattcga caagaaacgt gaattcaatc ctgatttaaa accaggtgaa    2580
gagcgtgtta acaaaaagg  tgaaccagga acaaaaacaa ttacaacacc aacaactaag    2640
aacccattaa caggggaaaa agttggcgaa ggtgaaccaa cagaaaaagt aacaaaacaa    2700
ccagtggatg aaatcgttca ttatggtggc gaagaaatca agccaggcca taaggatgaa    2760
tttgatccaa atgcaccgaa aggtagccaa gaagacgttc caggtaaacc aggagttaaa    2820
aaccctgata caggcgaagt agttactcca ccagtggatg atgtgacaaa atatggtcca    2880
gttgatggag atccgattac gtcaacggaa gaaattccgt ttgataaaaa acgcgaattt    2940
gatccaaact agcgccagg  tacagagaaa gtcgttcaaa aggtgaacc  aggaacaaaa    3000 acaattacaa caccaacaac taagaaccca ttaacaggag aaaaagttgg cgaaggtgaa    3060
ccaacagaaa aataacaaa  acaaccagtg gatgagatcg ttcattatgg tggcgaagaa    3120
atcaagccag gccataagga tgaatttgat ccgaacgcac cgaaaggtag tcaaacaacg    3180
caaccaggta gccaggagt  taaaaatcct gatacaggcg aagtagtcac accaccagtg    3240
gatgatgtga caaaatatgg tccagttgat ggagatccga ttacgtcaac ggaagaaatt    3300
ccgtttgata aaaacgcga  atttgatcca aacttagcgc aggtacagag aaagtcgtt     3360 caaaaaggtg aaccaggaac aaaacaatt  acaacgccaa caactaagaa cccattaaca    3420
ggagaaaaag ttggcgaagg tgaaccaaca gaaaaaataa caaaacaacc agtggatgag    3480
attgttcatt atggtggtga acaaatacca caaggtcata agatgaatt  tgatccaaat    3540 gcacctgtag atagtaaaac tgaagttcca ggtaaaccag gagttaaaaa tcctgataca    3600
ggtgaagttt taccccacc  agtggatgat gtgacaaaat atggtccgaa agttggtaat    3660
ccaatcacat caacggaaga gattccattt gataagaaac gtgtatttaa tcctgattta    3720
aaaccaggtg aagagcgcgt taaacaaaaa ggtgaaccag gaacaaaaac aattacaaca    3780
ccaatattag ttaatcctat tacaggagaa aaagttggcg aaggtaaatc aacagaaaaa    3840
gtcactaaac aacctgttga cgaaattgtt gagtatggtc aacaaaaagc agaaccaggt    3900
```

```
aaaccagcgg aaccaggtaa accagcggaa ccaggtaaac cagcggaacc aggtaaacca    3960
gcggaaccag gtacgccagc agaaccaggt aaaccagcgg aaccaggtaa accagcggaa    4020
ccaggtaaac cagcggaacc aggtaaacca gcggaaccag gtaaaccagc ggaaccaggt    4080
acgccagcag aaccaggtaa accagcggaa ccaggtaaac cagcggaacc aggtaaacca    4140
gcggaaccag gtacgccagc agaaccaggt aaaccagcgg aaccaggtac gccagcagaa    4200
ccaggtaaac cagcggaacc aggtacgcca acacaatcag gtgcaccaga caaccaaat     4260 agatcaatgc attcaacaga taataaaaat caattacctg atacaggtga aaatcgtcaa    4320
gctaatgagg gaactttagt cggatctcta ttagcaattg tcggatcatt gttcatattt    4380
ggtcgtcgta aaaaggtaa tgaaaaataa                                       4410

<210> SEQ ID NO 51
<211> LENGTH: 504
<212> TYPE: DNA
<213> ORGANISM: S. aureus

<400> SEQUENCE: 51
atgaagaaac tatatacatc ttatggcact tatggatttt tacatcaaat aaaaatcaat      60
aacccgaccc atcaactatt ccaattttca gcatcagata cttcagttat ttttgaagaa     120
actgatggtg agactgtttt aaaatcacct tcaatatatg aagttattaa agaaattggt     180
gaattcagtg aacatcattt ctattgtgca atcttcattc cttcaacaga agatcatgca     240
tatcaacttg aaagaaaact gattagtgta gacgataatt tcagaaactt tggtggcttt     300
aaaagctatc gtttgttaag acctgctaaa ggtacaacat ataaaattta tttcggattt     360
gctgatcgac atgcatacga agactttaag caatctgatg cctttaatga ccatttttca     420
aaagacgcat taagtcatta ctttggttca agcggacaac attcaagtta ttttgaaaga    480
tatctatacc caataaaaga atag                                            504

<210> SEQ ID NO 52
<211> LENGTH: 504
<212> TYPE: DNA
<213> ORGANISM: S. epidermidis

<400> SEQUENCE: 52
atgtatttat atacatctta tgggacttac caattttaa atcaaattaa acttaatcat       60
caagaacgta gtttatttca attttccact aatgattcct caataatctt agaagagtct     120
gagggaaaat caatcttaaa acatcctagt gcatatcaag tgattgatag cacaggtgaa    180
tttaacgaac atcatttta tagtgctatt tttgtcccta catctgaaga tcatcgtcaa      240
cagctagaga aaaaattatt actcgtagac gtacctttaa gaaattttgg tggttttaaa     300
agctatcgtt tattaaaacc cactgagggg tctacctaca aaatttactt tggttttgca     360
aatcgaacag catatgaaga tttcaaagct tctgatatat ttaatgaaaa cttttcaaaa    420
gatgcattga gccaatactt tggtgctagt ggtcaacatt ctagctactt tgaaagatat    480
ttatatccaa tagaagatca ttaa                                            504

<210> SEQ ID NO 53
<211> LENGTH: 3426
<212> TYPE: DNA
<213> ORGANISM: S. aureus

<400> SEQUENCE: 53
```

```
atgattaaca gggataataa aaaggcaata acaaaaaagg gtatgatttc aaatcgctta    60
aacaaatttt cgattagaaa gtatactgta ggaactgcat cgattttagt aggtacgaca   120
ttgattttg  gtctagggaa ccaagaagct aaagctgctg aaaacactag tacagaaaat   180
gcgaaacaag atgatgcaac gactagtgat aataaagaag tagtgtcgga aactgaaaat   240
aattcgacaa cagaaaatga ttcaacaaat ccaattaaga aagaaacaaa tactgattca   300
caaccagaag ctaagaagaa atcaactaca tcaagtactc aacaacagca aaataacgtt   360
acagctacaa ctgaaactaa gcctcaaaac attgaaaaag aaaatgttaa accttcaact   420
gataaaactg cgacagaaga tacatctgtt attttagaag agaagaaagc accaaattat   480
acaaataacg atgtaactac aaaaccatct acaagtgaaa ttcaaacaaa accaactaca   540
cctcaagaat ctacaaatat tgaaaattca caaccgcaac caacgccttc aaaagtagac   600
aatcaagtta cagatgcaac taatccaaaa gaaccagtaa atgtgtcaaa agaagaactt   660
aaaaataatc ctgagaaatt aaaagaatta gttagaaatg ataacaatac agatcgttca   720
actaaaccag ttgctacagc tccaacaagt gttgcaccaa acgattaaa  tgcgaaaatg   780
cgttttgcag ttgcacaacc agcagcagtt gcttcaaata atgtaaatga cttaattaca   840
gttacgaaac agacgatcaa agttggcgat ggtaaagata atgtggcagc agcgcatgac   900
ggtaaagata ttgaatatga tacagagttt acaattgaca ataaagtcaa aaaaggcgat   960
acaatgacga ttaattatga taagaatgta attccttcgg atttaacaga taaaaatgat  1020
cctatcgata ttactgatcc atcaggagag gtcattgcca aggaacatt  tgataaagcg  1080
actaagcaaa tcacatatac atttacagat tatgtagata aatatgaaga tataaaagca  1140
cgtttaactt tatactcata tattgataag caagcagtac ctaatgaaac tagtttgaat  1200
ttaacgtttg caacagcagg taaagaaact agccaaaacg tttctgttga ttatcaagac  1260
ccaatggttc atggtgattc aaacattcaa tctatcttta caagttaga  tgaaaacaaa  1320
caaactattg aacaacaaat ttatgttaat cctttgaaaa aaacagcaac taacactaaa  1380
gttgatatag ctggtagtca agtagatgat tatggaaata ttaaactagg aaatggtagt  1440
accattattg accaaaatac agaaataaaa gtttataaag ttaaccctaa tcaacaattg  1500
cctcaaagta atagaatcta tgattttagt caatacgaag atgtaacaag tcaatttgat  1560
aataaaaaat catttagtaa aatgtagca  acattggatt ttggtgatat taattcagcc  1620
tatattatca aagttgttag taaatataca cctacatcag atggcgaact agatattgct  1680
caaggtacta gtatgagaac aactgataaa tatggttatt ataattatgc aggatattca  1740
aacttcatcg taacttctaa tgacactggc ggtggcgacg gtactgttaa acctgaagaa  1800
aagttataca aaattggtga ctatgtatgg gaagacgttg ataaagacgg tgtccaaggt  1860
acagattcga agaaaagcc  aatggcaaac gttttagtta cattaactta cccggacggt  1920
actacaaaat cagtaagaac agatgctaac ggtcattatg aattcggtgg tttgaaagac  1980
ggagaaactt atacagttaa attcgaaacg ccagctggat atcttccaac aaaagtaaat  2040
ggaacaactg atggtgaaaa agactcaaat ggtagttcta taactgttaa aattaatggt  2100
aaagatgata tgtctttaga cactggtttt tataaagaac taaatataa  tcttggtgac  2160
tatgtatggg aagatacaaa taagatggt  atccaagatg ctaatgaacc tggtatcaaa  2220
gatgttaagg ttacattaaa agatagtact ggaaaagtta ttggtacaac tactactgat  2280
gcctcgggta atataaatt  tacagattta gataatggta actatacagt agaatttgaa  2340
acaccagcag gttacacgcc aacggttaaa aatactacag ctgaagataa agattctaat  2400
```

-continued

```
ggtttaacaa caacaggtgt cattaaagat gcagataata tgacattaga cagtggtttc    2460
tataaaacac caaaatacag tttaggtgat tatgtttggt acgacagtaa taagacggt     2520 aaacaagatt caactgaaaa aggtatcaaa gatgttaaag ttactttatt aaatgaaaaa    2580
ggcgaagtaa ttggaacaac taaaacagat gaaaatggta aatatcgttt cgataattta    2640
gatagcggta atacaaagt tatttttgaa aagcctgctg gcttaacaca aacagttaca     2700 aatcaactg aagatgataa agatgccgat ggtggcgaag ttgacgtaac aattacggat     2760
catgatgatt tcatacttga taacggatac ttcgaagaag atacatcaga cagtgattca    2820
gactcagaca gtgattcaga ctcagacagc gactcagatt cagacagtga ttcagactca    2880
gatagcgatt cagattcaga cagcgactca gactcagata gcgactcaga ctcagacagc    2940
gactcagact cagatagcga ctcagattcg dacagcgatt cagactcaga tagcgactca    3000
gattcagaca gcgattcaga ctcagatagc gactcagatt cagacagtga ctcagactca    3060
gatagcgact cagactcaga cagtgactca gactcagaca gcgattcaga ttcagatagc    3120
gactcagatt cggacagtga ttcagactca gatagcgact cagattcaga cagcgactca    3180
gactcagata gcgactcaga ctcagacagt gattcagact cagatagcga ttcggactcg    3240
gatgcaggaa acatacacc tgttaaacca atgagtacta ctaaagacca tcacaataaa     3300
gcaaaagcat taccagaaac aggtagtgaa ataacggct caaataacgc aacgttattt     3360
ggtggattat ttgcagcatt aggttcatta ttgttattcg gtcgtcgcaa aaaacaaaac    3420
aaataa                                                              3426
```

<210> SEQ ID NO 54
<211> LENGTH: 3171
<212> TYPE: DNA
<213> ORGANISM: S. epidermidis

<400> SEQUENCE: 54

```
atgattaata aaaaaaataa tttactaact aaaaagaaac ctatagcaaa taaatccaat     60
aaatatgcaa ttagaaaatt cacagtaggt acagcgtcta ttgtaatagg tgcaacatta    120
ttgtttggtt taggtcataa tgaggccaaa gccgaggaga attcagtaca agacgttaaa    180
gattcgaata cggatgatga attatcagac agcaatgatc agtctagtga tgaagaaaag    240
aatgatgtga tcaataataa tcagtcaata aacaccgacg ataataacca aataattaaa    300
aaagaagaaa cgaataacta cgatggcata gaaaaacgct cagaagatag aacagagtca    360
acaacaaatg tagatgaaaa cgaagcaaca ttttacaaa agacccctca agataatact     420
catcttacag aagaagaggt aaaagaatcc tcatcagtcg aatcctcaaa ttcatcaatt    480
gatactgccc aacaaccatc tcacacaaca ataaatagaa agaatctgt tcaaacaagt     540 gataatgtag aagattcaca cgtatcagat tttgctaact ctaaaataaa agagagtaac    600
actgaatctg gtaaagaaga gaatactata gagcaaccta taaagtaaa agaagattca    660 acaacaagtc agccgtctgg ctatacaaat atagatgaaa aaatttcaaa tcaagatgag    720
ttattaaatt taccaataaa tgaatatgaa aataaggcta gaccattatc tacaacatct    780
gcccaaccat cgattaaacg tgtaaccgta atcaattag cggcggaaca aggttcgaat     840
gttaatcatt taattaaagt tactgatcaa agtattactg aaggatatga tgatagtgaa    900
ggtgttatta agcacatga tgctgaaaac ttaatctatg atgtaacttt tgaagtagat     960
gataaggtga atctggtga tacgatgaca gtggatatag ataagaatac agttccatca    1020
```

```
gatttaaccg atagctttac aataccaaaa ataaaagata attctggaga aatcatcgct    1080
acaggtactt atgataacaa aaataaacaa atcacctata cttttacaga ttatgtagat    1140
aagtatgaaa atattaaagc acaccttaaa ttaacgtcat acattgataa atcaaaggtt    1200
ccaaataata ataccaagtt agatgtagaa tataaaacgg ccctttcatc agtaaataaa    1260
acaattacgg ttgaatatca aagacctaac gaaaatcgga ctgctaacct tcaaagtatg    1320
tttacaaaca tagatacgaa aaatcataca gttgagcaaa cgatttatat taaccctctt    1380
cgttattcag ccaaggaaac aaatgtaaat atttcaggga atggtgatga aggttcaaca    1440
attatagacg atagcacaat aattaaagtt tataaggttg gagataatca aaatttacca    1500
gatagtaaca gaatttatga ttacagtgaa tatgaagatg tcacaaatga tgattatgcc    1560
caattaggaa ataataatga tgtgaatatt aattttggta atatagattc accatatatt    1620
attaaagtta ttagtaaata tgaccctaat aaggatgatt acacgactat acagcaaact    1680
gtgacaatgc agacgactat aaatgagtat actggtgagt ttagaacagc atcctatgat    1740
aatacaattg ctttctctac aagttcaggt caaggacaag gtgacttgcc tcctgaaaaa    1800
acttataaaa tcggagatta cgtatgggaa gatgtagata agatggtat tcaaaataca    1860 aatgataatg aaaaaccgct tagtaatgta ttggtaactt tgacgtatcc tgatggaact    1920
tcaaaatcag tcagaacaga tgaagatggg aaatatcaat ttgatggatt gaaaaacgga    1980
ttgacttata aaattacatt cgaaacacct gaaggatata cgccgacgct taaacattca    2040
ggaacaaatc ctgcactaga ctcagaaggt aattctgtat gggtaactat taatggacaa    2100
gacgatatga cgattgatag tggatttat caaacaccta atacagctt agggaactat    2160 gtatggtatg acactaataa agatggtatt caaggtgatg atgaaaaagg aatctctgga    2220
gttaaagtga cgttaaaaga tgaaaacgga aatatcatta gtacaactac aaccgatgaa    2280
aatggaaagt atcaatttga taatttaaat agtggtaatt atattgttca ttttgataaa    2340
ccttcaggta tgactcaaac aacaacagat tctggtgatg atgacgaaca ggatgctgat    2400
ggggaagaag ttcatgtaac aattactgat catgatgact ttagtataga taacggatac    2460
tatgatgacg aatcggattc cgatagtgac tcagacagcg actcagattc cgatagtgat    2520
tcagactccg atagcgactc ggattcagac agcgactcag attcagacag cgactcggat    2580
tctgatagcg actcggattc agacagcgac tcagactcag acagtgattc agattcagac    2640
agcgactcag attccgatag tgattcagac tcagacagcg actcagattc tgatagtgat    2700
tcagactcag acagtgattc agattcagac agcgactcag attccgatag tgattcagac    2760
tcagacagcg actcagattc cgatagtgat tcagactcag acagcgactc agattctgat    2820
agtgattcag actcagacag tgattcagat tccgatagtg attcagactc cgatagcgac    2880
tcagactcgg atagtgactc agattctgat agtgattcag actcagacag tgattcggat    2940
tccgatagtg attcagactc agacagcgac tcagattctg atagtgattc agactcagac    3000
aacgactcag atttaggcaa tagctcagat aagagtacaa aagataaatt acctgataca    3060
ggagctaatg aagattatgg ctctaaaggc acgttacttg gaactctgtt tgcaggttta    3120
ggagcgttat tattagggaa acgtcgcaaa aatagaaaaa ataaaaatta a             3171
```

<210> SEQ ID NO 55
<211> LENGTH: 1461
<212> TYPE: DNA
<213> ORGANISM: S. aureus

<400> SEQUENCE: 55

```
atgtctaata attttaaaga tgactttgaa aaaaatcgtc aatcgataga cacaaattca      60
catcaagacc atacggaaga tgttgaaaaa gaccaatcag aattagaaca tcaggataca     120
atagagaata cggagcaaca gtttccgcca agaaatgccc aaagaagaaa aagacgccgt     180
gatttagcaa cgaatcataa taaacaagtt cacaatgaat cacaaacatc tgaagacaat     240
gttcaaaatg aggctggcac aatagatgat cgtcaagtcg aatcatcaca cagtactgaa     300
agtcaagaac ctagccatca agacagtaca cctcaacatg aagaggaata ttataataag     360
aatgcttttg caatggataa atcacatcca gaaccaatcg aagacaatga taaacacgag     420
actattaaag atgcagaaaa taacactgag cattcaacag tttctgataa gagtatagct     480
gaacaatctc agcaacctaa accatatttt gcaacaggtg ctaaccaagc aaatacatca     540
aaagataaac atgatgatgt aactgttaag caagacaaag atgaatctaa agatcatcat     600
agtggtaaaa aaggcgcagc aattggtgct ggaacagcgg gtgttgcagg tgcagctggt     660
gcaatgggtg tttctaaagc taagaaacat tcaaatgacg ctcaaaacaa aagtaattct     720
gacaagtcga ataactcgac tgaggataaa gcgtctcaag ataagtctaa agatcatcat     780
aatggcaaaa aaggtgcagc gatcggtgct ggaacagcag gtttggctgg aggcgcagca     840
agtaaaagtg cttctgccgc ttcaaaacca catgcctcta ataatgcaag ccaaaaccat     900
gatgaacatg acaatcatga cagagataaa gaacgtaaaa aaggtggcat ggccaaagta     960
ttgttaccat taattgcagc tgtactaatt atcggtgcat tagcgatatt tggaggcatg    1020
gcattaaaca atcataataa tggtacaaaa gaaaataaaa tcgcgaatac aaataaaaat    1080
aatgctgatg aaagtaaaga caaagacaca tctaaagacg cttctaaaga taaatcaaaa    1140
tctacagaca gtgataaatc aaaagaggat caagacaaag cgactaaaga tgaatctgat    1200
aatgatcaaa acaacgctaa tcaagcgaac aatcaagcac aaaataatca aaatcaacaa    1260
caagctaatc aaaatcaaca acagcaacaa caacgtcaag gtggtggcca agacatacat    1320
gtgaatggtc aagaaaactt ataccgtatc gcaattcaat actacggttc aggttcaccg    1380
gaaaatgttg aaaaaattag acgtgccaat ggtttaagtg gtaacaatat tagaaacggt    1440
caacaaatcg ttattccata a                                              1461

<210> SEQ ID NO 56
<211> LENGTH: 1419
<212> TYPE: DNA
<213> ORGANISM: S. epidermidis

<400> SEQUENCE: 56
gtgattgaat taattaaaat ggaagggatg atagttgtgt ctaataataa ttttaaagat      60
gatttcgaaa agaatcgtca atctattaat ccagacgaac agcaaacaga attaaaagaa     120
gatgataaaa caaatgaaaa taaaaaagaa gctgactctc aaaacagttt atctaataac     180
tcaaatcaac aatttcctcc gagaaatgcc caacgacgaa aaagacgtag agagacagca     240
actaatcaaa gcaaacaaca agacgacaaa catcaaaaaa atagtgacgc taaaactaca     300
gaaggttcat tagatgaccg ttatgacgaa gcacagttac agcaacaaca tgataaatcg     360
caacaacaaa ataaaactga aaaacaatca agataata gaatgaaaga tggaaaagat     420
gcagctattg taaatggaac atctgagtca ccagaacata aatcaaaatc aacacaaaat     480
agacccggcc ctaaagctca acaacaaaag cgtaaatcag aaagtacgca atcaaaaccg     540
tcaacaaaca aagataaaaa agcagctaca ggtgctggaa tagctggtgc agctggtgtt     600
```

```
gctggtgcag cagaaacatc caaacgtcat cataataaaa aagataaaca agattctaaa       660
cactcaaacc atgagaatga cgaaaaatct gttaaaaatg atgaccaaaa gcaatctaaa       720
aaaggcaaaa aagcagcagt cggtgctggc gcagctgcag gagttggtgc ggctggtgtt       780
gcgcatcata ataatcaaaa taaacatcat aatgaggaaa aaaattctaa tcaaaacaat       840
cagtacaatg accaatcaga aggtaagaaa aaaggtggtt tcatgaaaat cttgttacca       900
cttatagcag ccattcttat tctaggtgca atagcaatat tcggtggtat ggctctaaat       960
aatcacaacg atagtaaaag tgatgaccaa aaaatagcga atcaaagtaa gaaagactca      1020
gataaaaaag atggtgcgca atccgaagat aacaaagaca aaaaatctga tagtaacaaa      1080
gacaaaaaat ctgattctga taagaacgca gatgatgact ctgataatag ttcctcaaat      1140
cctaacgcta cttcaactaa taataacgat aatgtagcca ataataactc aaattataca      1200
aaccaaaatc aacaagataa tgcaaaccaa aatagcaata atcaacaggc aactcaaggt      1260
caacaatcac atacagtata cggtcaagaa aacttatatc gtatcgccat acaatattat      1320
ggagaaggaa ctcaagctaa cgtagataaa attaaacgtg cgaatggatt aagcagtaat      1380
aatattcata atggtcaaac attagttatt cctcaataa                             1419

<210> SEQ ID NO 57
<211> LENGTH: 498
<212> TYPE: DNA
<213> ORGANISM: S. aureus

<400> SEQUENCE: 57
atgaaaaata aattgatagc aaaatcttta ttaacaatag cggcaattgg tattactaca        60
actacaattg cgtcaacagc agatgcgagc gaaggatacg gtccaagaga aagaaaccca       120
gtgagtatta atcacaatat cgtagagtac aatgatggta cttttaaata tcaatctaga       180
ccaaaattta actcaacacc taaatatatt aaattcaaac atgactataa tattttagaa       240
tttaacgatg gtacattcga atatggtgca cgtccacaat ttaataaacc agcagcgaaa       300
actgatgcaa ctattaaaaa agaacaaaaa ttgattcaag ctcaaaatct tgtgagagaa       360
tttgaaaaaa cacatactgt cagtgcacac agaaaagcac aaaaggcagt caacttagtt       420
tcgtttgaat acaaagtgaa gaaaatggtc ttacaagagc gaattgataa tgtattaaaa       480
caaggattag tgagataa                                                    498

<210> SEQ ID NO 58
<211> LENGTH: 960
<212> TYPE: DNA
<213> ORGANISM: S. aureus

<400> SEQUENCE: 58
atgaaaacac gtatagtcag ctcagtaaca acaacactat tgctaggttc catattaatg        60
aatcctgtcg ctaatgccgc agattctgat attaatatta aaaccggtac tacagatatt       120
ggaagcaata ctacagtaaa aacaggtgat ttagtcactt atgataaaga aaatggcatg       180
cacaaaaaag tattttatag ttttatcgat gataaaaatc acaataaaaa actgctagtt       240
attagaacga aagtaccat tgctggtcaa tatagagttt atagcgaaga aggtgctaac       300
aaaagtggtt tagcctggcc ttcagccttt aaggtacagt tgcaactacc tgataatgaa       360
gtagctcaaa tatctgatta ctatccaaga aattcgattg atacaaaaga gtatatgagt       420 acttttaactt atggattcaa cggtaatgtt actggtgatg atacaggaaa attggcggc      480 cttattggtg caaatgtttc gattggtcat acactgaaat atgttcaacc tgatttcaaa      540
```

| | | |
|---|---|---|
| acaattttag agagcccaac tgataaaaaa gtaggctgga aagtgatatt taacaatatg | 600 | |
| gtgaatcaaa attggggacc atatgataga gattcttgga acccggtata tggcaatcaa | 660 | |
| cttttcatga aaactagaaa tggttctatg aaagcagcag agaacttcct tgatcctaac | 720 | |
| aaagcaagtt ctctattatc ttcagggttt tcaccagact tcgctacagt tattactatg | 780 | |
| gatagaaaag catccaaaca acaaacaaat atagatgtaa tatacgaacg agttcgtgat | 840 | |
| gactaccaat tgcattggac ttcaacaaat tggaaaggta ccaatactaa agataaatgg | 900 | |
| acagatcgtt cttcagaaag atataaaatc gattgggaaa agaagaaat gacaaattaa | 960 | |

<210> SEQ ID NO 59
<211> LENGTH: 1287
<212> TYPE: DNA
<213> ORGANISM: S. aureus

<400> SEQUENCE: 59

| | | |
|---|---|---|
| atacacatga aaataaaata tatctcgaag ttgctagttg gggcagcaac aattacttta | 60 | |
| gctacaatga tttcaaatgg ggaagcaaaa gcgagtgaaa acacgcaaca aacttcaact | 120 | |
| aagcaccaaa caactcaaaa caactacgta acagatcaac aaaaagcttt ttatcaagta | 180 | |
| ttacatctaa aaggtatcac agaagaacaa cgtaaccaat acatcaaaac attacgcgaa | 240 | |
| cacccagaac gtgcacaaga agtattctct gaatcactta agacagcaa gaacccagac | 300 | |
| cgacgtgttg cacaacaaaa cgcttttttac aatgttctta aaaatgataa cttaactgaa | 360 | |
| caagaaaaaa ataattacat tgcacaaatt aaagaaaacc ctgatagaag ccaacaagtt | 420 | |
| tgggtagaat cagtacaatc ttctaaagct aaagaacgtc aaaatattga aaatgcggat | 480 | |
| aaagcaatta aagatttcca agataacaaa gcaccacacg ataaatcagc agcatatgaa | 540 | |
| gctaactcaa aattacctaa agatttacgc gataaaaata accgctttgt agaaaaagtt | 600 | |
| tcaattgaaa aagcaatcgt tcgtcatgat gagcgtgtga atcagcaaa tgatgcaatc | 660 | |
| tcaaaattaa atgaaaaaga ttcaattgaa acagacgtt tagcacaacg tgaagttaac | 720 | |
| aaagcaccta tggatgtaaa agagcattta cagaaacaat tagacgcatt agtagctcaa | 780 | |
| aaagatgctg aaaagaaagt ggcgccaaaa gttgaggctc ctcaaattca atcaccacaa | 840 | |
| attgaaaaac ctaaagcaga atcaccaaaa gttgaagtcc ctcaatctaa attattaggt | 900 | |
| tactaccaat cattaaaaga ttcatttaac tatggttaca gtatttaac agatacttat | 960 | |
| aaaagctata agaaaaaata tgatacagca aagtactact ataatacgta ctataaatac | 1020 | |
| aaaggtgcga ttgatcaaac agtattaaca gtactaggta gtggttctaa atcttacatc | 1080 | |
| caaccattga agttgatga taaaaacggc tacttagcta atcatatgc acaagtaaga | 1140 | |
| aactatgtaa ctgagtcaat caatactggt aaagtattat atactttcta ccaaaaccca | 1200 | |
| acattagtaa aaacagctat taaagctcaa gaaactgcat catcaatcaa aaatacatta | 1260 | |
| agtaatttat tatcattctg gaaataa | 1287 | |

<210> SEQ ID NO 60
<211> LENGTH: 1053
<212> TYPE: DNA
<213> ORGANISM: S. aureus

<400> SEQUENCE: 60

| | | |
|---|---|---|
| atgacaaaac attatttaaa cagtaagtat caatcagaac aacgttcatc agctatgaaa | 60 | |
| aagattacaa tgggtacagc atctatcatt ttaggttccc ttgtatacat aggcgcagac | 120 | |

-continued

| | |
|---|---|
| agccaacaag tcaatgcggc aacagaagct acgaacgcaa ctaataatca aagcacacaa | 180 |
| gtttctcaag caacatcaca accaattaat ttccaagtgc aaaaagatgg ctcttcagag | 240 |
| aagtcacaca tggatgacta tatgcaacac cctggtaaag taattaaaca aaataataaa | 300 |
| tattatttcc aaaccgtgtt aaacaatgca tcattctgga aagaatacaa attttacaat | 360 |
| gcaaacaatc aagaattagc aacaactgtt gttaacgata ataaaaagc ggatactaga | 420 |
| acaatcaatg ttgcagttga acctggatat aagagcttaa ctactaaagt acatattgtc | 480 |
| gtgccacaaa ttaattacaa tcatagatat actacgcatt tggaatttga aaaagcaatt | 540 |
| cctacattag ctgacgcagc aaaaccaaac aatgttaaac cggttcaacc aaaaccagct | 600 |
| caacctaaaa cacctactga gcaaactaaa ccagttcaac ctaaagttga aaaagttaaa | 660 |
| cctactgtaa ctacaacaag caaagttgaa gacaatcact ctactaaagt tgtaagtact | 720 |
| gacacaacaa aagatcaaac taaaacacaa actgctcata cagttaaaac agcacaaact | 780 |
| gctcaagaac aaaataaagt tcaaacacct gttaaagatg ttgcaacagc gaaatctgaa | 840 |
| agcaacaatc aagctgtaag tgataataaa tcacaacaaa ctaacaaagt tacaaaacat | 900 |
| aacgaaacgc ctaaacaagc atctaaagct aaagaattac caaaaactgg tttaacttca | 960 |
| gttgataact ttattagcac agttgccttc gcaacacttg ccctttagg ttcattatct | 1020 |
| ttattacttt tcaaaagaaa agaatctaaa taa | 1053 |

<210> SEQ ID NO 61
<211> LENGTH: 1938
<212> TYPE: DNA
<213> ORGANISM: S. aureus

<400> SEQUENCE: 61

| | |
|---|---|
| atgaacaaac agcaaaaaga atttaaatca ttttattcaa ttagaaagtc atcactaggc | 60 |
| gttgcatctg tagcgattag tacactttta ttattaatgt caaatggcga agcacaagca | 120 |
| gcagctgaag aaacaggtgg tacaaataca gaagcacaac caaaaactga agcagttgca | 180 |
| agtccaacaa caacatctga aaaagctcca gaaactaaac cagtagctaa tgctgtctca | 240 |
| gtatctaata agaagttga ggccctact tctgaaacaa aagaagctaa agaagttaaa | 300 |
| gaagttaaag cccctaagga acaaaagca gttaaaccag cagcaaaagc cactaacaat | 360 |
| acatatccta ttttgaatca ggaacttaga gaagcgatta aaaaccctgc aataaaagat | 420 |
| aaagatcata gcgcaccaaa ctctcgtcca attgattttg aaatgaaaaa agaaaatggt | 480 |
| gagcaacaat tttatcatta tgccagctct gttaaacctg ctagagttat tttcactgat | 540 |
| tcaaaaccag aaattgaatt aggattacaa tcaggtcaat tttggagaaa atttgaagtt | 600 |
| tatgaaggtg acaaaaagtt gccaattaaa ttagtatcat acgatactgt taaagattac | 660 |
| gcttacattc gcttctctgt ttcaaatgga acaaaagccg ttaaaattgt aagttcaact | 720 |
| cacttcaata caaagaaga aaaatacgat tacacattaa tggaattcgc acaaccaatt | 780 |
| tataacagtg cagataaatt caaaactgaa gaagattata agctgaaaaa attattagcg | 840 |
| ccatataaaa aagcgaaaac actagaaaga caagtttatg aattaaataa aattcaagat | 900 |
| aaacttcctg aaaaattaaa ggctgagtac aagaagaaat tagaggatac aaagaaagct | 960 |
| ttagatgagc aagtgaaatc agctattact gaattccaaa atgtacaacc aacaaatgaa | 1020 |
| aaaatgactg atttacaaga tacaaaatat gttgtttatg aaagtgttga gaataacgaa | 1080 |
| tctatgatgg atactttgt taaacaccct attaaaacag gtatgcttaa cggcaaaaaa | 1140 |
| tatatggtca tggaaactac taatgacgat tactggaaag atttcatggt tgaaggtcaa | 1200 |

-continued

```
cgtgttagaa ctataagcaa agatgctaaa aataatacta gaacaattat tttcccatat    1260
gttgaaggta aaactctata tgatgctatc gttaaagttc acgtaaaaac gattgattat    1320
gatggacaat accatgtcag aatcgttgat aagaagcat  ttacaaaagc caataccgat    1380
aaatctaaca aaaagaaca  acaagataac tcagctaaga aggaagctac tccagctacg    1440
cctagcaaac caacaccatc acctgttgaa aagaatcac  aaaaacaaga cagccaaaaa    1500
gatgacaata acaattacc  aagtgttgaa aagaaaatg  acgcatctag tgagtcaggt    1560
aaagacaaaa cgcctgctac aaaaccaact aaggtgaag  tagaatcaag tagtacaact    1620
ccaactaagg tagtatctac gactcaaaat gttgcaaaac caacaactgc ttcatcaaaa    1680
acaacaaaag atgttgttca aacttcagca ggttctagcg aagcaaaaga tagtgctcca    1740
ttacaaaaag caaacattaa aaacacaaat gatggacaca ctcaaagcca aaacaataaa    1800
aatacacaag aaaataaagc aaaatcatta ccacaaactg gtgaagaatc aaataaagat    1860
atgacattac cattaatggc attactagct ttaagtagca tcgttgcatt cgtattacct    1920
agaaaacgta aaaactaa                                                  1938
```

<210> SEQ ID NO 62
<211> LENGTH: 2862
<212> TYPE: DNA
<213> ORGANISM: S. aureus

<400> SEQUENCE: 62

```
atgaataata aaagacagc  aacaaataga aaaggcatga taccaaatcg attaaacaaa      60
ttttcgataa gaaagtattc tgtaggtact gcttcaattt tagtagggac aacattgatt     120
tttgggttaa gtggtcatga agctaaagcg gcagaacata cgaatggaga attaaatcaa     180
tcaaaaaatg aaacgacagc cccaagtgag aataaaacaa ctgaaaaagt tgatagtcgt     240
caactaaaag acaatacgca aactgcaact gcagatcagc ctaaagtgac aatgagtgat     300
agtgcaacag ttaagaaaac tagtagtaac atgcaatcac cacaaaacgc tacagctagt     360
caatctacta cacaaactag caatgtaaca acaaatgata aatcatcaac tacatatagt     420
aatgaaactg ataaagtaa  tttaacacaa gcaaaaaacg tttcaactac acctaaaaca     480
acgactatta acaaagagc  tttaaatcgc atggcagtga atactgttgc agctccacaa     540
caaggaacaa atgttaatga taagtacat  tttacgaaca ttgatattgc gattgataaa     600
ggacatgtta ataaaacaac aggaaatact gaattttggg caacttcaag tgatgtttta     660
aaattaaaag cgaattacac aatcgatgat tctgttaaag agggcgatac atttactttt     720
aaatatggtc aatatttccg tccaggttct gtaagattac cttcacaaac tcaaaattta     780
tataatgccc aagtaatat  tattgcaaaa ggtatttacg atagtaaaac aaatacaaca     840
acgtatactt ttacgaatta tgtagatcaa tacacaaatg ttagcggtag ctttgaacaa     900
gtcgcatttg cgaaacgtga aaatgcaaca actgataaaa ctgcttataa aatgaagtta     960
actttaggta atgatacata tagtaaagat gtcattgtcg attatggtaa tcaaaaaggt    1020
caacaactta tttcgagtac aaattatatt aataatgaag atttgtcacg taatatgact    1080
gtttatgtaa atcaacctaa aaagacctat acaaagaaa  catttgtaac aaatttaact    1140
ggttataaat ttaatccaga tgctaaaaac ttcaaaattt acgaagtgac agatcaaaat    1200
caatttgtgg atagtttcac cccagatact tcaaaactta agatgttac  tggtcaattc    1260
gatgttattt atagtaatga taataagacg gcgacagtag atttattgaa tggtcaatct    1320
```

-continued

```
agtagtgata aacagtacat cattcaacaa gttgcttatc cagataatag ttcaacagat   1380
aatgggaaaa ttgattatac tttagaaaca caaaatggaa aaagtagttg gtcaaacagt   1440
tattcaaatg tgaatggctc atcaactgca aatggcgacc aaaagaaata taatctaggt   1500
gactatgtat gggaagatac aaataaagat ggtaaacaag atgccaatga aaaagggatt   1560
aaaggtgttt atgtcattct taaagatagt aacggtaaag aattagatcg tacgacaaca   1620
gatgaaaatg gtaaatatca gttcactggt ttaagcaatg gaacttatag tgtagagttt   1680
tcaacaccag ccggttatac accgacaact gcaaatgcag gtacagatga tgctgtagat   1740
tctgatggac taactacaac aggtgtcatt aaagacgctg acaacatgac attagatagt   1800
ggattctaca aaacaccaaa atatagttta ggtgattatg tttggtacga cagtaataaa   1860
gatggtaaac aagattcgac tgaaaaagga attaaaggtg ttaaagttac tttgcaaaac   1920
gaaaaaggcg aagtaattgg tacaactgaa acagatgaaa atggtaaata ccgctttgat   1980
aatttagata gtggtaaata caaagttatc tttgaaaagc ctgctggttt aactcaaaca   2040
ggtacaaata caactgaaga tgataaagat gccgatggtg gcgaagttga tgtaacaatt   2100
acggatcatg atgatttcac acttgataat ggctactacg aagaagaaac atcagatagt   2160
gactcagatt cggacagcga ttcagactca gatagcgact cagattcaga tagtgactca   2220
gactcagata gcgactcaga ctcagatagc gactcagaca gcgactcaga ctcagatagt   2280
gattcagatt cggacagcga ctcagattca gacagcgaat cagattcgga tagcgactca   2340
gactcagata gcgactcaga cagcgactca gattcagaca gtgactcaga ctcagacagc   2400
gactcagatt cagacagcga ttcagattcg gatagcgact cagattcaga tagcgattcg   2460
gactcagaca cgactcaga ttctgacagc gattcagact cagatagcga ctcagattca   2520
gacagcgact cagattcaga cagcgattca gattcagata gcgattcaga ttcagacagc   2580
gactcagatt cagatagcga ctcagactca gacagcgatt cagactcaga tagcgactca   2640
gacagcgatt cagattcgga tagcgattca gattcagatg caggtaaaca tactccgact   2700
aaaccaatga gtacggttaa agatcagcat aaaacagcta aagcattacc agaaacaggt   2760
agtgaaaata taattcaaa taatggcaca ttattcggtg gattattcgc ggcattagga   2820
tcattattgt tattcggtcg tcgtaaaaaa caaaataaat aa   2862
```

<210> SEQ ID NO 63
<211> LENGTH: 2808
<212> TYPE: DNA
<213> ORGANISM: S. aureus

<400> SEQUENCE: 63

```
atgaatatga agaaaaaaga aaacacgca attcggaaaa aatcgattgg cgtggcttca     60
gtgcttgtag gtacgttaat cggttttgga ctactcagca gtaaagaagc agatgcaagt    120
gaaaatagtg ttacgcaatc tgatagcgca agtaacgaaa gcaaagtaa tgattcaagt    180 agcgttagtg ctgcacctaa aacagacgac acaaacgtga gtgatactaa acatcgtca    240 aacactaata tggcgaaac gagtgtggcg caaaatccag cacaacagga acgacacaa    300 tcatcatcaa caaatgcaac tacgaagaa acgccggtaa ctggtgaagc tactactacg    360
acaacgaatc aagctaatac accggcaaca actcaatcaa gcaatacaaa tgcggaggaa    420
ttagtgaatc aaacaagtaa tgaaacgact tctaatgata ctaatacagt atcatctgta    480
aattcacctc aaaattctac aaatgcggaa atgttcaa caacgcaaga tacttcaact    540
gaagcaacac cttcaaacaa tgaatcagct ccacagaata cagatgcaag taataaagat    600
```

```
gtagttagtc aagcggttaa tccaagtacg cctagaatga gagcatttag tttagcggca      660
gtagctgcag atgcaccggc agctggcaca gatattacga atcagttgac agatgtgaaa      720
gttactattg actctggtac gactgtgtat ccgcaccaag caggttatgt caaactgaat      780
tatggttttt cagtgcctaa ttctgctgtt aaaggtgaca cattcaaaat aactgtacct      840
aaagaattaa acttaaatgg tgtaacttca actgctaaag tgccaccaat tatggctgga      900
gatcaagtat tggcaaatgg tgtaatcgat agtgatggta atgttatttta tacatttaca     960 gactatgttg ataataaaga aaatgtaaca gctaatatta ctatgccagc ttatattgac     1020
cctgaaaatg ttacaaagac aggtaatgtg acattgacaa ctggcatagg aaccaatact     1080
gctagtaaga cagtattaat cgactatgag aaatatggac aattccataa tttatcaatt     1140
aaaggtacga ttgatcaaat cgataaaaca ataatacgt atcgccaaac aatttatgtc      1200
aatccaagcg gagataacgt tgtgttacct gccttaacag gtaatttaat tcctaataca     1260
aagagtaatg cgttaataga tgcaaaaaac actgatatta aagtttatag agtcgataat     1320
gctaatgatt tatctgaaag ttattatgtg aatcctagcg attttgaaga tgtaactaat     1380
caagttagaa tttcatttcc aaatgctaat caatacaaag tagaatttcc tacgacgat      1440 gaccaaatta caacaccgta tattgtagtt gttaatggcc atattgatcc tgctagtaca     1500
ggtgatttag cactacgttc gacattttat ggttatgatt ctaattttat atggagatct     1560
atgtcatggg acaacgaagt agcatttaat aacggatcag gttctggtga cggtatcgat     1620
aaaccagttt ttcctgaaca acctgatgag cctggtgaaa ttgaaccaat tccagaggat     1680
tcagattctg acccaggttc agattctggc agcgattcta attcagatag cggttcagat     1740
tctggcagtg attctacatc agatagtggt tcagattcag cgagtgattc agattcagca     1800
agtgattcag actcagcgag tgattcagat tcagcaagtg attcagattc agcaagtgat     1860
tcagattcag caagtgattc agactcagca agtgattcag attcagcaag tgattcagat     1920
tcagcaagcg attcagattc agcgagcgat tcagattcag cgagcgattc agattcagcg     1980
agtgattccg actcagcgag cgattcagac tcagatagtg actcagattc cgatagcgat     2040
tccgactcag atagcgactc agattcagac agcgattctg actcagacag cgattctgac     2100
tcagacagtg actcagattc cgatagcgat tctgactcag acagtgactc agattccgat     2160
agcgattcag attcagacag tgattcagac tcagatagcg attcagattc cgacagtgac     2220
tcagactcag acagcgattc agattccgat agcgattcag attccgacag tgactcagat     2280
tccgatagtg actcggattc agcgagtgat tcagattcag atagcgattc agaatcagat     2340
agtgactcag actcagacag tgattcagat tcagatagtg actcagactc agacagcgat     2400
tcagaatcag atagtgactc cgattcagac agcgattcag aatcagatag tgactccgat     2460
tcagatagcg attcggattc agcgagtgat tcagactcag gtagtgactc cgattcatca     2520
agtgattcag attccgattc aacgagtgac acaggatcag caacgactc agacagtgat      2580 tcaaatagcg attccgagtc aggttctaac aataatgtag ttccgcctaa ttcacctaaa     2640
aatggtacta atgcttctaa taaaaatgag gctaaagata gtaaagaacc attaccagat     2700
acaggttctg aagatgaagc gaatacgtca ctaatttggg gattattagc atcattaggt     2760
tcattactac ttttcagaag aaaaaaagaa aataaagata gaaataa                   2808
```

<210> SEQ ID NO 64
<211> LENGTH: 3117
<212> TYPE: DNA

<213> ORGANISM: S. aureus

<400> SEQUENCE: 64

```
gtgaaaaaca atcttaggta cggcattaga aacataaat tgggagcagc atcagtattc      60
ttaggaacaa tgatcgttgt tgggatggga caagataaag aagctgcagc atcagaacaa     120
aagacaacta cagtagaaga aaatgggaat tcagctactg ataataaaac aagtgaaaca     180
caaacaactg ctactaacgt taatcatata gaagaaactc aatcatataa cgcaacagta     240
acagaacaac cgtcaaacgc aacacaagta acaactgaag aagcaccaaa agcagtacaa     300
gcaccacaaa ctgcacaacc agcaaatgta gaaacagtta agaagaaga gaaacctcaa     360
gttaaggaaa cgacacaacc tcaagacaat agcggaaatc aaagacaagt agatttaaca     420
cctaaaaagg ttacacaaaa tcaagggaca gaaacacaag ttgaagtggc acagccaaga     480
acggcatcag aaagtaagcc acgtgtgaca agatcagcag atgtagcgga agctaaggaa     540
gctagtgacg tttcagaagt taaggcaca gatgttacaa gtaaagttac agtagaaagt     600
ggttctattg aggcacctca aggaaataaa gtagagccac atgctggtca acgtgtcgta     660
ttgaaataca aattgaaatt cgcagatgga ttaaaaagag gagattattt tgatttaca     720
ttatcaaata atgtaaatac ttatggggtt tcaacagcta gaaaggtacc agagattaaa     780
aatggctcag ttgtaatggc tacaggtgag atcttaggga atggtaacat aagatataca     840
tttactaacg aaattgaaca caaggtagag gtaacagcta atttagaaat caacttattt     900
attgacccta aaactgtaca agcaatgga gaacaaaaga ttacttctaa attaaatggt     960
gaagaaacag aaaaaacaat accagttgtt tataatccag gtgttagcaa tagttataca    1020
aatgtaaatg gatcaattga acatttaat aaagaatcta ataaatttac acatatagct    1080
tatattaagc caatgaatgg aaaccagtca aacactgtat cagtaacagg gacgttgact    1140
gaaggtagta atttagctgg tggacaacct actgttaaag tatatgaata tctagggaaa    1200
aaagatgaat tgccacaaag tgtttatgca aatacatcag atactaacaa attcaaagat    1260
gtaacaaagg aaatgaatgg aaaattgagt gtgcaagaca atggtagtta ctcattgaat    1320
ttagataagt tggataaaac gtatgtcatt cattatacag gtaatatttt gcaagggtca    1380
gatcaggtta attttagaac tgaattatat gggtatccag aacgagcata taaatcttac    1440
tatgtttatg ggggatatcg tttaacttgg gataatggtt tagttttata tagcaataaa    1500
gctgacggca atggtaaaaa tggacaaatt attcaagata tgattttga atataagaa     1560
gatactgcaa aaggaactat gagcgggcag tacgatgcca agcaaattat tgaaacagaa    1620
gaaaatcaag acaatacacc gcttgacatt gattaccaca cagctataga tggtgagggt    1680
ggttatgttg atgggtatat tgaaacaata gaagaaacgg attcatcagc tattgatatc    1740
gattaccata ctgctgtgga tagtgaagtg ggtcacgttg gaggatacac tgagtcctct    1800
gaggaatcaa atccaattga ctttgaagaa tcgacacatg aaaattcaaa acatcacgct    1860
gatgttgttg aatatgaaga ggatacaaat ccaggtggtg gccaagtaac aactgagtct    1920
aacttagttg aatttgacga agagtctaca aaaggtattg taactggcgc agtgagcgac    1980
catacaacaa ttgaagatac gaaagaatat acgactgaaa gtaatctgat tgaactagta    2040
gatgaactac ctgaagaaca tggtcaagca caaggaccaa tcgaggaaat tactgaaaac    2100
aatcatcata tttctcattc tggttaggga actgaaaatg gtcacggtaa ttatggcgtg    2160
attgaagaaa tcgaagaaaa tagccacgtt gatattaaga gtgaattagg ttacgaaggt    2220
ggccaaaata gcggtaacca gtcattcgag gaagacacag aagaagacaa acctaaatat    2280
```

```
gaacaaggtg gcaatatcgt agatatcgat ttcgacagtg tacctcaaat tcatggtcaa    2340
aataaaggtg accagtcatt cgaagaagat acagagaaag acaagcctaa atatgaacat    2400
ggcggtaata tcattgatat cgacttcgac agtgtgccac aaattcatgg attcaataag    2460
cataatgaaa ttattgaaga agatacaaac aaagataaac ctaattatca attcggtgga    2520
cacaatagtg ttgactttga agaagataca cttccaaaag taagcggcca aaatgaaggt    2580
caacaaacga ttgaagaaga tacaacgccg ccaacgccac cgacaccaga agtaccgagt    2640
gagccggaaa caccaatgcc accgacacca gaagtaccga gtgagccgga acaccaacg     2700 ccaccaacac cagaggtacc aagtgagccg gaaacaccaa caccaccgac tccggaagta    2760
ccaagtgagc cggaaacacc aacaccaccg acaccagaag tgccgagtga gccagaaaca    2820
ccaacaccgc caacaccaga ggtaccagct gaacctggta aaccagtacc acccgcaaaa    2880
gaagaaccta aaagccttc taaaccagtg gaacaaggta agtagtaac acctgttatt      2940 gaaatcaatg aaaaggttaa agcagtggca ccaactaaaa aagcacaatc taagaaatct    3000
gaactacctg aaacaggtgg agaagaatca acaaacaaag gtatgttgtt cggcggatta    3060
ttcagcattc taggtttagc attattacgc agaaataaaa agaataacaa agcataa      3117

<210> SEQ ID NO 65
<211> LENGTH: 2634
<212> TYPE: DNA
<213> ORGANISM: S. aureus

<400> SEQUENCE: 65
ttgaaaaaaa gaattgatta tttgtcgaat aagcagaata agtattcgat tagacgtttt    60
acagtaggta ccacatcagt aatagtaggg gcaactatac tatttgggat aggcaatcat   120
caagcacaag cttcagaaca atcgaacgat acaacgcaat cttcgaaaaa taatgcaagt   180
gcagattccg aaaaaaacaa tatgatagaa acacctcaat taaatacaac ggctaatgat   240
acatctgata ttagtgcaaa cacaaacagt gcgaatgtag atagcacaac aaaaccaatg   300
tctacacaaa cgagcaatac cactacaaca gagccagctt caacaaatga acaccctcaa   360
ccgacggcaa ttaaaaatca agcaactgct gcaaaaatgc aagatcaaac tgttcctcaa   420
gaagcaaatt ctcaagtaga taataaaaca cgaatgatg ctaatagcat agcaacaaac    480
agtgagctta aaaattctca acattagat ttaccacaat catcaccaca aacgatttcc    540
aatgcgcaag gaactagtaa accaagtgtt agaacgagag ctgtacgtag tttagctgtt   600
gctgaaccgg tagtaaatgc tgctgatgct aaaggtacaa atgtaaatga taagttacg    660 gcaagtaatt tcaagttaga aaagactaca tttgaccta atcaaagtgg taacacattt    720
atggcggcaa attttacagt gacagataaa gtgaaatcag gggattattt tacagcgaag   780
ttaccagata gtttaactgg taatggagac gtggattatt ctaattcaaa taatacgatg   840
ccaattgcag acattaaaag tacgaatggc gatgttgtag ctaaagcaac atatgatatc   900
ttgactaaga cgtatacatt tgtctttaca gattatgtaa ataataaaga aaatattaac   960
ggacaatttt cattaccttt atttacagac cgagcaaagg cacctaaatc aggaacatat   1020
gatgcgaata ttaatattgc ggatgaaatg tttaataata aaattactta taactatagt   1080
tcgccaattg caggaattga taaaccaaat ggcgcgaaca tttcttctca aattattggt   1140
gtagatacag cttcaggtca aaacacatac aagcaaacag tatttgttaa ccctaagcaa   1200
cgagttttag gtaatacgtg ggtgtatatt aaaggctacc aagataaaat cgaagaaagt   1260
```

| | |
|---|---|
| agcggtaaag taagtgctac agatacaaaa ctgagaattt ttgaagtgaa tgatacatct | 1320 |
| aaattatcag atagctacta tgcagatcca aatgactcta accttaaaga agtaacagac | 1380 |
| caatttaaaa atagaatcta ttatgagcat ccaaatgtag ctagtattaa atttggtgat | 1440 |
| attactaaaa catatgtagt attagtagaa gggcattacg acaatacagg taagaactta | 1500 |
| aaaactcagg ttattcaaga aaatgttgat cctgtaacaa atagagacta cagtattttc | 1560 |
| ggttggaata atgagaatgt tgtacgttat ggtggtggaa gtgctgatgg tgattcagca | 1620 |
| gtaaatccga aagacccaac tccagggccg ccggttgacc cagaaccaag tccagaccca | 1680 |
| gaaccagaac caacgccaga tccagaacca agtccagacc cagaaccgga accaagccca | 1740 |
| gacccggatc cggattcgga ttcagacagt gactcaggct cagacagcga ctcaggttca | 1800 |
| gatagcgact cagaatcaga tagcgattcg gattcagaca gtgattcaga ttcagacagc | 1860 |
| gactcagaat cagatagcga ttcagaatca gatagcgact cagattcaga tagcgattca | 1920 |
| gattcagata gcgattcaga atcagatagc gattcggatt cagacagtga ttcagattca | 1980 |
| gacagcgact cagaatcaga tagcgactca gaatcagata gtgagtcaga ttcagacagt | 2040 |
| gactcggact cagacagtga ttcagactca gatagcgatt cagactcaga tagcgattca | 2100 |
| gactcagaca gcgattcaga ttcagacagc gactcagaat cagacagcga ctcagactca | 2160 |
| gatagcgact cagactcaga cagcgactca gattcagata gcgattcaga ctcagacagc | 2220 |
| gactcagact cagacagcga ctcagactca gatagcgatt cagactcaga cagcgactca | 2280 |
| gattcagata gcgattcgga ctcagacagc gattcagatt cagacagcga ctcagactcg | 2340 |
| gatagcgatt cagattcaga cagcgactca gactcggata gcgactcgga ttcagatagt | 2400 |
| gactccgatt caagagttac accaccaaat aatgaacaga aagcaccatc aaatcctaaa | 2460 |
| ggtgaagtaa accattctaa taaggtatca aaacaacaca aaactgatgc tttaccagaa | 2520 |
| acaggagata agagcgaaaa cacaaatgca actttatttg gtgcaatgat ggcattatta | 2580 |
| ggatcattac tattgtttag aaaacgcaag caagatcata agaaaaagc gtaa | 2634 |

<210> SEQ ID NO 66
<211> LENGTH: 1977
<212> TYPE: DNA
<213> ORGANISM: S. aureus

<400> SEQUENCE: 66

| | |
|---|---|
| atgaaaaagc aaataatttc gctaggcgca ttagcagttg catctagctt atttacatgg | 60 |
| gataacaaag cagatgcgat agtaacaaag gattatagta agaatcaag agtgaatgag | 120 |
| aaaagtaaaa agggagctac tgtttcagat tattactatt ggaaaataat tgatagttta | 180 |
| gaggcacaat ttactggagc aatagactta ttggaagatt ataaatatgg agatcctatc | 240 |
| tataaagaag cgaaagatag attgatgaca agagtattag gagaagacca gtatttatta | 300 |
| aagaaaaaga ttgatgaata tgagctttat aaaaagtggt ataaaagttc aaataagaac | 360 |
| actaatatgc ttactttcca taaatataat ctttacaatt taacaatgaa tgaatataac | 420 |
| gatattttta actctttgaa agatgcagtt tatcaattta ataagaagt taagaaaata | 480 |
| gagcataaaa atgttgactt gaagcagttt gataaagatg gagaagacaa ggcaactaaa | 540 |
| gaagtttatg accttgtttc tgaaattgat acattagttg taacttatta tgctgataag | 600 |
| gattatgggg agcatgcgaa agagttacga gcaaaactgg acttaatcct tggagataca | 660 |
| gacaatccac ataaaattac aaatgagcgt ataaaaaaag aaatgatcga tgacttaaat | 720 |
| tcaattatag atgatttctt tatggagact aaacaaaata gaccgaattc tataacaaaa | 780 |

-continued

```
tatgatccaa caaaacacaa ttttaaagag aagagtgaaa ataaacctaa ttttgataaa      840
ttagttgaag aaacaaaaaa agcagttaaa gaagcagacg aatcttggaa aaataaaact      900
gtcaaaaaat acgaggaaac tgtaacaaaa tctcctgttg taaaagaaga gaagaaagtt      960
gaagaacctc aattacctaa agttggaaac cagcaagagg ttaaaactac ggctggtaaa     1020
gctgaagaaa caacacaacc agtggcacag ccattagtaa aaattccaca agaaacaatc     1080
tatggtgaaa ctgtaaaagg tccagaatat ccaacgatgg aaaataaaac gttacaaggt     1140
gaaatcgttc aaggtcccga ttttctaaca atggaacaaa acagaccatc tttaagcgat     1200
aattatactc aaccgacgac accgaaccct attttagaag gtcttgaagg tagctcatct     1260
aaacttgaaa taaaccaca aggtactgaa tcaacgttga aaggtattca aggagaatca     1320
agtgatattg aagttaaacc tcaagcaact gaaacaacag aagcttctca atatggtccg     1380
agaccgcaat taacaaaac acctaagtat gtgaaatata gagatgctgg tacaggtatc     1440
cgtgaataca acgatggaac atttggatat gaagcgagac aagattcaa caagccaagt     1500
gaaacaaatg catacaacgt aacgacaaat caagatggca gtatcata cggagctcgc     1560
ccaacacaaa acaagccaag tgaaacaaac gcatataacg taacaacaca tgcaaatggt     1620
caagtatcat acggtgctcg cccaacacaa aaaaagccaa gcaaacaaa tgcatacaac     1680
gtaacaacac atgcaaatgg tcaagtatca tatggcgctc gcccgacaca aaaaaagcca     1740
agcaaaacaa atgcatataa cgtaacaaca catgcaaatg gtcaagtatc atacggagct     1800
cgcccgacat acaagaagcc aagcgaaaca aatgcataca acgtaacaac acatgcaaat     1860
ggtcaagtat catatggcgc tcgcccgaca caaaaaaagc caagcgaaac aaacgcatat     1920
aacgtaacaa cacatgcaga tggtactgcg acatatgggc ctagagtaac aaaataa        1977
```

<210> SEQ ID NO 67
<211> LENGTH: 960
<212> TYPE: PRT
<213> ORGANISM: S. aureus

<400> SEQUENCE: 67

```
Met Lys Ser Asn Leu Arg Tyr Gly Ile Arg Lys His Lys Leu Gly Ala
  1               5                  10                  15

Ala Ser Val Phe Leu Gly Thr Met Ile Val Gly Met Gly Gln Glu
             20                  25                  30

Lys Glu Ala Ala Ala Ser Glu Gln Asn Asn Thr Thr Val Glu Glu Ser
         35                  40                  45

Gly Ser Ser Ala Thr Glu Ser Lys Ala Ser Glu Thr Gln Thr Thr Thr
     50                  55                  60

Asn Asn Val Asn Thr Ile Asp Glu Thr Gln Ser Tyr Ser Ala Thr Ser
 65                  70                  75                  80

Thr Glu Gln Pro Ser Lys Ser Thr Gln Val Thr Thr Glu Ala Pro
             85                  90                  95

Thr Thr Val Gln Ala Pro Lys Val Glu Thr Glu Met Lys Ser Gln Glu
            100                 105                 110

Asp Leu Pro Ser Glu Lys Val Ala Asp Lys Glu Thr Thr Gly Thr Gln
        115                 120                 125

Val Asp Ile Ala Gln Pro Ser Asn Val Ser Glu Ile Lys Pro Arg Met
    130                 135                 140

Lys Arg Ser Ala Asp Val Thr Ala Val Ser Glu Lys Glu Val Ala Glu
145                 150                 155                 160
```

```
Glu Ala Lys Ala Thr Gly Thr Asp Val Thr Asn Lys Val Glu Val Thr
            165                 170                 175

Glu Ser Ser Leu Glu Gly His Asn Lys Asp Ser Asn Ile Val Asn Pro
            180                 185                 190

His Asn Ala Gln Arg Val Thr Leu Lys Tyr Lys Trp Lys Phe Gly Glu
            195                 200                 205

Gly Ile Lys Ala Gly Asp Tyr Phe Asp Phe Thr Leu Ser Asp Asn Val
            210                 215                 220

Glu Thr His Gly Ile Ser Thr Leu Arg Lys Val Pro Glu Ile Lys Ser
225                 230                 235                 240

Ser Thr Glu Asp Lys Val Met Ala Asn Gly Gln Val Ile Asn Glu Arg
                245                 250                 255

Thr Ile Arg Tyr Thr Phe Thr Asp Tyr Ile Asn Asn Lys Lys Asp Leu
            260                 265                 270

Thr Ala Glu Leu Asn Leu Asn Leu Phe Ile Asp Pro Thr Thr Val Thr
            275                 280                 285

Lys Gln Gly Ser Gln Lys Val Glu Val Thr Leu Gly Gln Asn Lys Val
            290                 295                 300

Ser Lys Glu Phe Asp Ile Lys Tyr Leu Asp Gly Val Lys Asp Arg Met
305                 310                 315                 320

Gly Val Thr Val Asn Gly Arg Ile Asp Thr Leu Asn Lys Glu Glu Gly
                325                 330                 335

Lys Phe Ser His Phe Ala Tyr Val Lys Pro Asn Asn Gln Ser Leu Thr
            340                 345                 350

Ser Val Thr Val Thr Gly Gln Val Thr Ser Gly Tyr Lys Gln Ser Ala
            355                 360                 365

Asn Asn Pro Thr Val Lys Val Tyr Lys His Ile Gly Ser Asp Glu Leu
            370                 375                 380

Ala Glu Ser Val Tyr Ala Lys Leu Asp Asp Thr Ser Lys Phe Glu Asp
385                 390                 395                 400

Val Thr Glu Lys Val Asn Leu Ser Tyr Thr Ser Asn Gly Gly Tyr Thr
            405                 410                 415

Leu Asn Leu Gly Asp Leu Asp Asn Ser Lys Asp Tyr Val Ile Lys Tyr
            420                 425                 430

Glu Gly Glu Tyr Asp Gln Asn Ala Lys Asp Leu Asn Phe Arg Thr His
            435                 440                 445

Leu Ser Gly Tyr His Lys Tyr Tyr Pro Tyr Tyr Tyr Pro Tyr
            450                 455                 460

Tyr Pro Val Gln Leu Thr Trp Asn Asn Gly Val Ala Phe Tyr Ser Asn
465                 470                 475                 480

Asn Ala Lys Gly Asp Gly Lys Asp Lys Pro Asn Asp Pro Ile Ile Glu
            485                 490                 495

Lys Ser Glu Pro Ile Asp Leu Asp Ile Lys Ser Glu Pro Pro Val Glu
            500                 505                 510

Lys His Glu Leu Thr Gly Thr Ile Glu Glu Ser Asn Asp Ser Lys Pro
            515                 520                 525

Ile Asp Phe Glu Tyr His Thr Ala Val Glu Gly Ala Glu Gly His Ala
            530                 535                 540

Glu Gly Ile Ile Glu Thr Glu Glu Asp Ser Ile His Val Asp Phe Glu
545                 550                 555                 560

Glu Ser Thr His Glu Asn Ser Lys His His Ala Asp Val Val Glu Tyr
            565                 570                 575

Glu Glu Asp Thr Asn Pro Gly Gly Gly Gln Val Thr Thr Glu Ser Asn
```

580                 585                 590
Leu Val Glu Phe Asp Glu Glu Ser Thr Lys Gly Ile Val Thr Gly Ala
            595                 600                 605

Val Ser Asp His Thr Thr Val Glu Asp Thr Lys Glu Tyr Thr Thr Glu
610                 615                 620

Ser Asn Leu Ile Glu Leu Val Asp Glu Leu Pro Glu Glu His Gly Gln
625                 630                 635                 640

Ala Gln Gly Pro Ile Glu Ile Thr Glu Asn Asn His His Ile Ser
            645                 650                 655

His Ser Gly Leu Gly Thr Glu Asn Gly His Gly Asn Tyr Gly Val Ile
            660                 665                 670

Asp Glu Ile Glu Glu Asn Ser His Val Asp Ile Lys Ser Glu Leu Gly
            675                 680                 685

Tyr Glu Gly Gly Gln Asn Ser Gly Asn Gln Ser Phe Glu Glu Asp Thr
            690                 695                 700

Glu Glu Asp Lys Pro Lys Tyr Glu Gln Gly Gly Asn Ile Val Asp Ile
705                 710                 715                 720

Asp Phe Asp Ser Val Pro Gln Ile His Gly Gln Asn Asn Gly Asn Gln
                725                 730                 735

Ser Phe Glu Glu Asp Thr Glu Glu Asp Lys Pro Lys Tyr Glu Gln Gly
            740                 745                 750

Gly Asn Ile Ile Asp Ile Asp Phe Asp Ser Val Pro Gln Ile His Gly
            755                 760                 765

Phe Asn Lys His Asn Glu Ile Ile Glu Glu Asp Thr Asn Lys Asp Lys
770                 775                 780

Pro Asn Tyr Gln Phe Gly Gly His Asn Ser Val Asp Phe Glu Glu Asp
785                 790                 795                 800

Thr Leu Pro Lys Val Ser Gly Gln Asn Glu Gly Gln Gln Thr Ile Glu
                805                 810                 815

Glu Asp Thr Thr Pro Thr Pro Thr Pro Glu Val Pro Ser Glu
            820                 825                 830

Pro Glu Thr Pro Thr Pro Thr Pro Glu Val Pro Ser Glu Pro Gly
            835                 840                 845

Glu Pro Thr Pro Lys Pro Glu Val Pro Ser Glu Pro Glu Thr Pro
850                 855                 860

Val Pro Pro Thr Pro Glu Val Pro Ser Glu Pro Gly Lys Pro Val Pro
865                 870                 875                 880

Pro Ala Lys Glu Glu Pro Lys Lys Pro Ser Lys Pro Val Glu Gln Gly
                885                 890                 895

Lys Val Val Thr Pro Val Ile Glu Ile Asn Glu Lys Val Lys Ala Val
            900                 905                 910

Ala Pro Thr Lys Gln Lys Gln Ser Lys Lys Ser Glu Leu Pro Glu Thr
            915                 920                 925

Gly Gly Glu Glu Ser Thr Asn Lys Gly Met Leu Phe Gly Gly Leu Phe
            930                 935                 940

Ser Ile Leu Gly Leu Val Leu Leu Arg Arg Asn Lys Lys Asn Asn Lys
945                 950                 955                 960

<210> SEQ ID NO 68
<211> LENGTH: 578
<212> TYPE: PRT
<213> ORGANISM: S. aureus

<400> SEQUENCE: 68

```
Met Lys Phe Lys Ser Leu Ile Thr Thr Thr Leu Ala Leu Gly Val Ile
  1               5                  10                  15

Ala Ser Thr Gly Ala Asn Phe Asn Thr Asn Glu Ala Ser Ala Ala Ala
             20                  25                  30

Lys Pro Leu Asp Lys Ser Ser Ser Thr Leu His His Gly His Ser Asn
             35                  40                  45

Ile Gln Ile Pro Tyr Thr Ile Thr Val Asn Gly Thr Ser Gln Asn Ile
 50                  55                  60

Leu Ser Ser Leu Thr Phe Asn Lys Asn Gln Asn Ile Ser Tyr Lys Asp
 65                  70                  75                  80

Ile Glu Asn Lys Val Lys Ser Val Leu Tyr Phe Asn Arg Gly Ile Ser
                 85                  90                  95

Asp Ile Asp Leu Arg Leu Ser Lys Gln Ala Glu Tyr Thr Val His Phe
            100                 105                 110

Lys Asn Gly Thr Lys Arg Val Ile Asp Leu Lys Ser Gly Ile Tyr Thr
            115                 120                 125

Ala Asp Leu Ile Asn Thr Ser Asp Ile Lys Ala Ile Ser Val Asn Val
            130                 135                 140

Asp Thr Lys Lys Gln Pro Lys Asp Lys Ala Lys Ala Asn Val Gln Val
145                 150                 155                 160

Pro Tyr Thr Ile Thr Val Asn Gly Thr Ser Gln Asn Ile Leu Ser Asn
                165                 170                 175

Leu Thr Phe Asn Lys Asn Gln Asn Ile Ser Tyr Lys Asp Leu Glu Gly
                180                 185                 190

Lys Val Lys Ser Val Leu Glu Ser Asn Arg Gly Ile Thr Asp Val Asp
            195                 200                 205

Leu Arg Leu Ser Lys Gln Ala Lys Tyr Thr Val Asn Phe Lys Asn Gly
            210                 215                 220

Thr Lys Lys Val Ile Asp Leu Lys Ser Gly Ile Tyr Thr Ala Asn Leu
225                 230                 235                 240

Ile Asn Ser Ser Asp Ile Lys Ser Ile Asn Ile Asn Val Asp Thr Lys
                245                 250                 255

Lys His Ile Glu Asn Lys Ala Lys Arg Asn Tyr Gln Val Pro Tyr Ser
            260                 265                 270

Ile Asn Leu Asn Gly Thr Ser Thr Asn Ile Leu Ser Asn Leu Ser Phe
            275                 280                 285

Ser Asn Lys Pro Trp Thr Asn Tyr Lys Asn Leu Thr Ser Gln Ile Lys
            290                 295                 300

Ser Val Leu Lys His Asp Arg Gly Ile Ser Glu Gln Asp Leu Lys Tyr
305                 310                 315                 320

Ala Lys Lys Ala Tyr Tyr Thr Val Tyr Phe Lys Asn Gly Gly Lys Arg
                325                 330                 335

Ile Leu Gln Leu Asn Ser Lys Asn Tyr Thr Ala Asn Leu Val His Ala
            340                 345                 350

Lys Asp Val Lys Arg Ile Glu Ile Thr Val Lys Thr Gly Thr Lys Ala
            355                 360                 365

Lys Ala Asp Arg Tyr Val Pro Tyr Thr Ile Ala Val Asn Gly Thr Ser
            370                 375                 380

Thr Pro Ile Leu Ser Lys Leu Lys Ile Ser Asn Lys Gln Leu Ile Ser
385                 390                 395                 400

Tyr Lys Tyr Leu Asn Asp Lys Val Lys Ser Val Leu Lys Ser Glu Arg
                405                 410                 415

Gly Ile Ser Asp Leu Asp Leu Lys Phe Ala Lys Gln Ala Lys Tyr Thr
```

```
                420             425             430
Val Tyr Phe Lys Asn Gly Lys Lys Gln Val Val Asn Leu Lys Ser Asp
        435             440             445

Ile Phe Thr Pro Asn Leu Phe Ser Ala Lys Asp Ile Lys Lys Ile Asp
        450             455             460

Ile Asp Val Lys Gln Tyr Thr Lys Ser Lys Lys Ile Asn Lys Ser
465             470             475             480

Asn Asn Val Lys Phe Pro Val Thr Ile Asn Lys Phe Glu Asn Ile Val
                485             490             495

Ser Asn Glu Phe Val Phe Tyr Asn Ala Ser Lys Ile Thr Ile Asn Asp
            500             505             510

Leu Ser Ile Lys Leu Lys Ser Ala Met Ala Asn Asp Gln Gly Ile Thr
        515             520             525

Lys His Asp Ile Gly Leu Ala Glu Arg Ala Val Tyr Lys Val Tyr Phe
        530             535             540

Lys Asn Gly Ser Ser Lys Tyr Val Asp Leu Lys Thr Glu Tyr Lys Asp
545             550             555             560

Glu Arg Val Phe Lys Ala Thr Asp Ile Lys Lys Val Asp Ile Glu Leu
                565             570             575

Lys Phe

<210> SEQ ID NO 69
<211> LENGTH: 895
<212> TYPE: PRT
<213> ORGANISM: S. aureus

<400> SEQUENCE: 69

Met Asn Lys His His Pro Lys Leu Arg Ser Phe Tyr Ser Ile Arg Lys
1               5               10              15

Ser Thr Leu Gly Val Ala Ser Val Ile Val Ser Thr Leu Phe Leu Ile
            20              25              30

Thr Ser Gln His Gln Ala Gln Ala Ala Glu Asn Thr Asn Thr Ser Asp
        35              40              45

Lys Ile Ser Glu Asn Gln Asn Asn Asn Ala Thr Thr Thr Gln Pro Pro
    50              55              60

Lys Asp Thr Asn Gln Thr Gln Pro Ala Thr Gln Pro Ala Asn Thr Ala
65              70              75              80

Lys Asn Tyr Pro Ala Ala Asp Glu Ser Leu Lys Asp Ala Ile Lys Asp
                85              90              95

Pro Ala Leu Glu Asn Lys Glu His Asp Ile Gly Pro Arg Glu Gln Val
            100             105             110

Asn Phe Gln Leu Leu Asp Lys Asn Asn Glu Thr Gln Tyr Tyr His Phe
        115             120             125

Phe Ser Ile Lys Asp Pro Ala Asp Val Tyr Tyr Thr Lys Lys Lys Ala
    130             135             140

Glu Val Glu Leu Asp Ile Asn Thr Ala Ser Thr Trp Lys Lys Phe Glu
145             150             155             160

Val Tyr Glu Asn Asn Gln Lys Leu Pro Val Arg Leu Val Ser Tyr Ser
                165             170             175

Pro Val Pro Glu Asp His Ala Tyr Ile Arg Phe Pro Val Ser Asp Gly
            180             185             190

Thr Gln Glu Leu Lys Ile Val Ser Ser Thr Gln Ile Asp Asp Gly Glu
        195             200             205

Glu Thr Asn Tyr Asp Tyr Thr Lys Leu Val Phe Ala Lys Pro Ile Tyr
```

```
            210                 215                 220
Asn Asp Pro Ser Leu Val Lys Ser Asp Thr Asn Asp Ala Val Val Thr
225                 230                 235                 240

Asn Asp Gln Ser Ser Ser Val Ala Ser Asn Gln Thr Asn Thr Asn Thr
                    245                 250                 255

Ser Asn Gln Asn Ile Ser Thr Ile Asn Asn Ala Asn Asn Gln Pro Gln
                260                 265                 270

Ala Thr Thr Asn Met Ser Gln Pro Ala Gln Pro Lys Ser Ser Thr Asn
            275                 280                 285

Ala Asp Gln Ala Ser Ser Gln Pro Ala His Glu Thr Asn Ser Asn Gly
        290                 295                 300

Asn Thr Asn Asp Lys Thr Asn Glu Ser Ser Asn Gln Ser Asp Val Asn
305                 310                 315                 320

Gln Gln Tyr Pro Pro Ala Asp Glu Ser Leu Gln Asp Ala Ile Lys Asn
                    325                 330                 335

Pro Ala Ile Ile Asp Lys Glu His Thr Ala Asp Asn Trp Arg Pro Ile
                340                 345                 350

Asp Phe Gln Met Lys Asn Asp Lys Gly Glu Arg Gln Phe Tyr His Tyr
            355                 360                 365

Ala Ser Thr Val Glu Pro Ala Thr Val Ile Phe Thr Lys Thr Gly Pro
        370                 375                 380

Ile Ile Glu Leu Gly Leu Lys Thr Ala Ser Thr Trp Lys Lys Phe Glu
385                 390                 395                 400

Val Tyr Glu Gly Asp Lys Lys Leu Pro Val Glu Leu Val Ser Tyr Asp
                    405                 410                 415

Ser Asp Lys Asp Tyr Ala Tyr Ile Arg Phe Pro Val Ser Asn Gly Thr
                420                 425                 430

Arg Glu Val Lys Ile Val Ser Ser Ile Glu Tyr Gly Glu Asn Ile His
            435                 440                 445

Glu Asp Tyr Asp Tyr Thr Leu Met Val Phe Ala Gln Pro Ile Thr Asn
        450                 455                 460

Asn Pro Asp Asp Tyr Val Asp Glu Glu Thr Tyr Asn Leu Gln Lys Leu
465                 470                 475                 480

Leu Ala Pro Tyr His Lys Ala Lys Thr Leu Glu Arg Gln Val Tyr Glu
                    485                 490                 495

Leu Glu Lys Leu Gln Glu Lys Leu Pro Glu Lys Tyr Lys Ala Glu Tyr
                500                 505                 510

Lys Lys Lys Leu Asp Gln Thr Arg Val Glu Leu Ala Asp Gln Val Lys
            515                 520                 525

Ser Ala Val Thr Glu Phe Glu Asn Val Thr Pro Thr Asn Asp Gln Leu
        530                 535                 540

Thr Asp Leu Gln Glu Ala His Phe Val Val Phe Glu Ser Glu Glu Asn
545                 550                 555                 560

Ser Glu Ser Val Met Asp Gly Phe Val Glu His Pro Phe Tyr Thr Ala
                    565                 570                 575

Thr Leu Asn Gly Gln Lys Tyr Val Val Met Lys Thr Lys Asp Asp Ser
                580                 585                 590

Tyr Trp Lys Asp Leu Ile Val Glu Gly Lys Arg Val Thr Thr Val Ser
            595                 600                 605

Lys Asp Pro Lys Asn Asn Ser Arg Thr Leu Ile Phe Pro Tyr Ile Pro
        610                 615                 620

Asp Lys Ala Val Tyr Asn Ala Ile Val Lys Val Val Ala Asn Ile
625                 630                 635                 640
```

```
Gly Tyr Glu Gly Gln Tyr His Val Arg Ile Ile Asn Gln Asp Ile Asn
                645                 650                 655

Thr Lys Asp Asp Asp Thr Ser Gln Asn Asn Thr Ser Glu Pro Leu Asn
            660                 665                 670

Val Gln Thr Gly Gln Glu Gly Lys Val Ala Asp Thr Asp Val Ala Glu
        675                 680                 685

Asn Ser Ser Thr Ala Thr Asn Pro Lys Asp Ala Ser Asp Lys Ala Asp
    690                 695                 700

Val Ile Glu Pro Glu Ser Asp Val Val Lys Asp Ala Asp Asn Asn Ile
705                 710                 715                 720

Asp Lys Asp Val Gln His Asp Val Asp His Leu Ser Asp Met Ser Asp
                725                 730                 735

Asn Asn His Phe Asp Lys Tyr Asp Leu Lys Glu Met Asp Thr Gln Ile
            740                 745                 750

Ala Lys Asp Thr Asp Arg Asn Val Asp Lys Asp Ala Asp Asn Ser Val
        755                 760                 765

Gly Met Ser Ser Asn Val Asp Thr Asp Lys Asp Ser Asn Lys Asn Lys
    770                 775                 780

Asp Lys Val Ile Gln Leu Asn His Ile Ala Asp Lys Asn Asn His Thr
785                 790                 795                 800

Gly Lys Ala Ala Lys Leu Asp Val Val Lys Gln Asn Tyr Asn Thr
                805                 810                 815

Asp Lys Val Thr Asp Lys Lys Thr Thr Glu His Leu Pro Ser Asp Ile
            820                 825                 830

His Lys Thr Val Asp Lys Thr Val Thr Lys Glu Lys Ala Gly Thr
        835                 840                 845

Pro Ser Lys Glu Asn Lys Leu Ser Gln Ser Lys Met Leu Pro Lys Thr
    850                 855                 860

Gly Glu Thr Thr Ser Ser Gln Ser Trp Trp Gly Leu Tyr Ala Leu Leu
865                 870                 875                 880

Gly Met Leu Ala Leu Phe Ile Pro Lys Phe Arg Lys Glu Ser Lys
                885                 890                 895

<210> SEQ ID NO 70
<211> LENGTH: 747
<212> TYPE: PRT
<213> ORGANISM: S. aureus

<400> SEQUENCE: 70

Met Ala Glu Thr Thr Gln Asp Gln Thr Thr Asn Lys Asn Val Leu Asp
 1               5                  10                  15

Ser Asn Lys Val Lys Ala Thr Thr Glu Gln Ala Lys Ala Glu Val Lys
                20                  25                  30

Asn Pro Thr Gln Asn Ile Ser Gly Thr Gln Val Tyr Gln Asp Pro Ala
            35                  40                  45

Ile Val Gln Pro Lys Thr Ala Asn Asn Lys Thr Gly Asn Ala Gln Val
        50                  55                  60

Ser Gln Lys Val Asp Thr Ala Gln Val Asn Gly Asp Thr Arg Ala Asn
65                  70                  75                  80

Gln Ser Ala Thr Thr Asn Asn Thr Gln Pro Val Ala Lys Ser Thr Ser
                85                  90                  95

Thr Thr Ala Pro Lys Thr Asn Thr Asn Val Thr Asn Ala Gly Tyr Ser
            100                 105                 110

Leu Val Asp Asp Glu Asp Asp Asn Ser Glu Asn Gln Ile Asn Pro Glu
```

```
            115                 120                 125
Leu Ile Lys Ser Ala Ala Lys Pro Ala Ala Leu Glu Thr Gln Tyr Lys
    130                 135                 140

Thr Ala Ala Pro Lys Ala Ala Thr Thr Ser Ala Pro Lys Ala Lys Thr
145                 150                 155                 160

Glu Ala Thr Pro Lys Val Thr Thr Phe Ser Ala Ser Ala Gln Pro Arg
                165                 170                 175

Ser Val Ala Ala Thr Pro Lys Thr Ser Leu Pro Lys Tyr Lys Pro Gln
            180                 185                 190

Val Asn Ser Ser Ile Asn Asp Tyr Ile Cys Lys Asn Leu Lys Ala
        195                 200                 205

Pro Lys Ile Glu Glu Asp Tyr Thr Ser Tyr Phe Pro Lys Tyr Ala Tyr
    210                 215                 220

Arg Asn Gly Val Gly Arg Pro Glu Gly Ile Val Val His Asp Thr Ala
225                 230                 235                 240

Asn Asp Arg Ser Thr Ile Asn Gly Glu Ile Ser Tyr Met Lys Asn Asn
                245                 250                 255

Tyr Gln Asn Ala Phe Val His Ala Phe Val Asp Gly Asp Arg Ile Ile
            260                 265                 270

Glu Thr Ala Pro Thr Asp Tyr Leu Ser Trp Gly Val Gly Ala Val Gly
        275                 280                 285

Asn Pro Arg Phe Ile Asn Val Glu Ile Val His Thr His Asp Tyr Ala
    290                 295                 300

Ser Phe Ala Arg Ser Met Asn Asn Tyr Ala Asp Tyr Ala Ala Thr Gln
305                 310                 315                 320

Leu Gln Tyr Tyr Gly Leu Lys Pro Asp Ser Ala Glu Tyr Asp Gly Asn
                325                 330                 335

Gly Thr Val Trp Thr His Tyr Ala Val Ser Lys Tyr Leu Gly Gly Thr
            340                 345                 350

Asp His Ala Asp Pro His Gly Tyr Leu Arg Ser His Asn Tyr Ser Tyr
        355                 360                 365

Asp Gln Leu Tyr Asp Leu Ile Asn Glu Lys Tyr Leu Ile Lys Met Gly
    370                 375                 380

Lys Val Ala Pro Trp Gly Thr Gln Ser Thr Thr Thr Pro Thr Thr Pro
385                 390                 395                 400

Ser Lys Pro Thr Thr Pro Ser Lys Pro Ser Thr Gly Lys Leu Thr Val
                405                 410                 415

Ala Ala Asn Asn Gly Val Ala Gln Ile Lys Pro Thr Asn Ser Gly Leu
            420                 425                 430

Tyr Thr Thr Val Tyr Asp Lys Thr Gly Lys Ala Thr Asn Glu Val Gln
        435                 440                 445

Lys Thr Phe Ala Val Ser Lys Thr Ala Thr Leu Gly Asn Gln Lys Phe
    450                 455                 460

Tyr Leu Val Gln Asp Tyr Asn Ser Gly Asn Lys Phe Gly Trp Val Lys
465                 470                 475                 480

Glu Gly Asp Val Val Tyr Asn Thr Ala Lys Ser Pro Val Asn Val Asn
                485                 490                 495

Gln Ser Tyr Ser Ile Lys Pro Gly Thr Lys Leu Tyr Thr Val Pro Trp
            500                 505                 510

Gly Thr Ser Lys Gln Val Ala Gly Ser Val Ser Gly Ser Gly Asn Gln
        515                 520                 525

Thr Phe Lys Ala Ser Lys Gln Gln Gln Ile Asp Lys Ser Ile Tyr Leu
    530                 535                 540
```

```
Tyr Gly Ser Val Asn Gly Lys Ser Gly Trp Val Ser Lys Ala Tyr Leu
545                 550                 555                 560

Val Asp Thr Ala Lys Pro Thr Pro Thr Pro Thr Lys Pro Ser Thr
                565                 570                 575

Pro Thr Thr Asn Asn Lys Leu Thr Val Ser Ser Leu Asn Gly Val Ala
                580                 585                 590

Gln Ile Asn Ala Lys Asn Asn Gly Leu Phe Thr Thr Val Tyr Asp Lys
                595                 600                 605

Thr Gly Lys Pro Thr Lys Glu Val Gln Lys Thr Phe Ala Val Thr Lys
                610                 615                 620

Glu Ala Ser Leu Gly Gly Asn Lys Phe Tyr Leu Val Lys Asp Tyr Asn
625                 630                 635                 640

Ser Pro Thr Leu Ile Gly Trp Val Lys Gln Gly Asp Val Ile Tyr Asn
                645                 650                 655

Asn Ala Lys Ser Pro Val Asn Val Met Gln Thr Tyr Thr Val Lys Pro
                660                 665                 670

Gly Thr Lys Leu Tyr Ser Val Pro Trp Gly Thr Tyr Lys Gln Glu Ala
                675                 680                 685

Gly Ala Val Ser Gly Thr Gly Asn Gln Thr Phe Lys Ala Thr Lys Gln
690                 695                 700

Gln Gln Ile Asp Lys Ser Ile Tyr Leu Phe Gly Thr Val Asn Gly Lys
705                 710                 715                 720

Ser Gly Trp Val Ser Lys Ala Tyr Leu Ala Val Pro Ala Ala Pro Lys
                725                 730                 735

Lys Ala Val Ala Gln Pro Lys Thr Ala Val Lys
                740                 745

<210> SEQ ID NO 71
<211> LENGTH: 482
<212> TYPE: PRT
<213> ORGANISM: S. aureus

<400> SEQUENCE: 71

Met Ala Tyr Thr Val Thr Lys Pro Gln Thr Thr Gln Thr Val Ser Lys
1               5                   10                  15

Ile Ala Gln Val Lys Pro Asn Asn Thr Gly Ile Arg Ala Ser Val Tyr
                20                  25                  30

Glu Lys Thr Ala Lys Asn Gly Ala Lys Tyr Ala Asp Arg Thr Phe Tyr
                35                  40                  45

Val Thr Lys Glu Arg Ala His Gly Asn Glu Thr Tyr Val Leu Leu Asn
50                  55                  60

Asn Thr Ser His Asn Ile Pro Leu Gly Trp Phe Asn Val Lys Asp Leu
65                  70                  75                  80

Asn Val Gln Asn Leu Gly Lys Glu Val Lys Thr Thr Gln Lys Tyr Thr
                85                  90                  95

Val Asn Lys Ser Asn Asn Gly Leu Ser Met Val Pro Trp Gly Thr Lys
                100                 105                 110

Asn Gln Val Ile Leu Thr Gly Asn Asn Ile Ala Gln Gly Thr Phe Asn
                115                 120                 125

Ala Thr Lys Gln Val Ser Val Gly Lys Asp Val Tyr Leu Tyr Gly Thr
                130                 135                 140

Ile Asn Asn Arg Thr Gly Trp Val Asn Ala Lys Asp Leu Thr Ala Pro
145                 150                 155                 160

Thr Ala Val Lys Pro Thr Thr Ser Ala Ala Lys Asp Tyr Asn Tyr Thr
```

```
                    165                 170                 175
Tyr Val Ile Lys Asn Gly Asn Gly Tyr Tyr Val Thr Pro Asn Ser
                180                 185                 190
Asp Thr Ala Lys Tyr Ser Leu Lys Ala Phe Asn Glu Gln Pro Phe Ala
                195                 200                 205
Val Val Lys Glu Gln Val Ile Asn Gly Gln Thr Trp Tyr Tyr Gly Lys
            210                 215                 220
Leu Ser Asn Gly Lys Leu Ala Trp Ile Lys Ser Thr Asp Leu Ala Lys
225                 230                 235                 240
Glu Leu Ile Lys Tyr Asn Gln Thr Gly Met Thr Leu Asn Gln Val Ala
                245                 250                 255
Gln Ile Gln Ala Gly Leu Gln Tyr Lys Pro Gln Val Gln Arg Val Pro
                260                 265                 270
Gly Lys Trp Thr Asp Ala Lys Phe Asn Asp Val Lys His Ala Met Asp
                275                 280                 285
Thr Lys Arg Leu Ala Gln Asp Pro Ala Leu Lys Tyr Gln Phe Leu Arg
            290                 295                 300
Leu Asp Gln Pro Gln Asn Ile Ser Ile Asp Lys Ile Asn Gln Phe Leu
305                 310                 315                 320
Lys Gly Lys Gly Val Leu Glu Asn Gln Gly Ala Ala Phe Asn Lys Ala
                325                 330                 335
Ala Gln Met Tyr Gly Ile Asn Glu Val Tyr Leu Ile Ser His Ala Leu
                340                 345                 350
Leu Glu Thr Gly Asn Gly Thr Ser Gln Leu Ala Lys Gly Ala Asp Val
                355                 360                 365
Val Asn Asn Lys Val Val Thr Asn Ser Asn Thr Lys Tyr His Asn Val
            370                 375                 380
Phe Gly Ile Ala Ala Tyr Asp Asn Asp Pro Leu Arg Glu Gly Ile Lys
385                 390                 395                 400
Tyr Ala Lys Gln Ala Gly Trp Asp Thr Val Ser Lys Ala Ile Val Gly
                405                 410                 415
Gly Ala Lys Phe Ile Gly Asn Ser Tyr Val Lys Ala Gly Gln Asn Thr
                420                 425                 430
Leu Tyr Lys Met Arg Trp Asn Pro Ala His Pro Gly Thr His Gln Tyr
            435                 440                 445
Ala Thr Asp Val Asp Trp Ala Asn Ile Asn Ala Lys Ile Ile Lys Gly
                450                 455                 460
Tyr Tyr Asp Lys Ile Gly Glu Val Gly Lys Tyr Phe Asp Ile Pro Gln
465                 470                 475                 480
Tyr Lys

<210> SEQ ID NO 72
<211> LENGTH: 706
<212> TYPE: PRT
<213> ORGANISM: S. aureus

<400> SEQUENCE: 72

Asp Arg Val Leu Ala Ser His Pro Asp Val Ala Thr Ile Arg Gln Asn
 1               5                  10                  15
Val Thr Ala Ala Asn Ala Ala Lys Ser Ala Leu Asp Gln Ala Arg Asn
                20                  25                  30
Gly Leu Thr Val Asp Lys Ala Pro Leu Glu Asn Ala Lys Asn Gln Leu
            35                  40                  45
Gln His Ser Ile Asp Thr Gln Thr Ser Thr Thr Gly Met Thr Gln Asp
```

```
                50                  55                  60
Ser Ile Asn Ala Tyr Asn Ala Lys Leu Thr Ala Ala Arg Asn Lys Ile
 65                  70                  75                  80

Gln Gln Ile Asn Gln Val Leu Ala Gly Ser Pro Thr Val Glu Gln Ile
                 85                  90                  95

Asn Thr Asn Thr Ser Thr Ala Asn Gln Ala Lys Ser Asp Leu Asp His
                100                 105                 110

Ala Arg Gln Ala Leu Thr Pro Asp Lys Ala Pro Leu Gln Thr Ala Lys
                115                 120                 125

Thr Gln Leu Glu Gln Ser Ile Asn Gln Pro Thr Asp Thr Thr Gly Met
130                 135                 140

Thr Thr Ala Ser Leu Asn Ala Tyr Asn Gln Lys Leu Gln Ala Ala Arg
145                 150                 155                 160

Gln Lys Leu Thr Glu Ile Asn Gln Val Leu Asn Gly Asn Pro Thr Val
                165                 170                 175

Gln Asn Ile Asn Asp Lys Val Thr Glu Ala Asn Gln Ala Lys Asp Gln
                180                 185                 190

Leu Asn Thr Ala Arg Gln Gly Leu Thr Leu Asp Arg Gln Pro Ala Leu
                195                 200                 205

Thr Thr Leu His Gly Ala Ser Asn Leu Asn Gln Ala Gln Gln Asn Asn
210                 215                 220

Phe Thr Gln Gln Ile Asn Ala Ala Gln Asn His Ala Ala Leu Glu Thr
225                 230                 235                 240

Ile Lys Ser Asn Ile Thr Ala Leu Asn Thr Ala Met Thr Lys Leu Lys
                245                 250                 255

Asp Ser Val Ala Asp Asn Asn Thr Ile Lys Ser Asp Gln Asn Tyr Thr
                260                 265                 270

Asp Ala Thr Pro Ala Asn Lys Gln Ala Tyr Asp Asn Ala Val Asn Ala
                275                 280                 285

Ala Lys Gly Val Ile Gly Glu Thr Thr Asn Pro Thr Met Asp Val Asn
                290                 295                 300

Thr Val Asn Gln Lys Ala Ala Ser Val Lys Ser Thr Lys Asp Ala Leu
305                 310                 315                 320

Asp Gly Gln Gln Asn Leu Gln Arg Ala Lys Thr Glu Ala Thr Asn Ala
                325                 330                 335

Ile Thr His Ala Ser Asp Leu Asn Gln Ala Gln Lys Asn Ala Leu Thr
                340                 345                 350

Gln Gln Val Asn Ser Ala Gln Asn Val Gln Ala Val Asn Asp Ile Lys
                355                 360                 365

Gln Thr Thr Gln Ser Leu Asn Thr Ala Met Thr Gly Leu Lys Arg Gly
                370                 375                 380

Val Ala Asn His Asn Gln Val Val Gln Ser Asp Asn Tyr Val Asn Ala
385                 390                 395                 400

Asp Thr Asn Lys Lys Asn Asp Tyr Asn Asn Ala Tyr Asn His Ala Asn
                405                 410                 415

Asp Ile Ile Asn Gly Asn Ala Gln His Pro Val Ile Thr Pro Ser Asp
                420                 425                 430

Val Asn Asn Ala Leu Ser Asn Val Thr Ser Lys Glu His Ala Leu Asn
                435                 440                 445

Gly Glu Ala Lys Leu Asn Ala Ala Lys Gln Glu Ala Asn Thr Ala Leu
                450                 455                 460

Gly His Leu Asn Asn Leu Asn Asn Ala Gln Arg Gln Asn Leu Gln Ser
465                 470                 475                 480
```

```
Gln Ile Asn Gly Ala His Gln Ile Asp Ala Val Asn Thr Ile Lys Gln
                485                 490                 495

Asn Ala Thr Asn Leu Asn Ser Ala Met Gly Asn Leu Arg Gln Ala Val
            500                 505                 510

Ala Asp Lys Asp Gln Val Lys Arg Thr Glu Asp Tyr Ala Asp Ala Asp
        515                 520                 525

Thr Ala Lys Gln Asn Ala Tyr Asn Ser Ala Val Ser Ser Ala Glu Thr
    530                 535                 540

Ile Ile Asn Gln Thr Thr Asn Pro Thr Met Ser Val Asp Asp Val Asn
545                 550                 555                 560

Arg Ala Thr Ser Ala Val Thr Ser Asn Lys Asn Ala Leu Asn Gly Tyr
                565                 570                 575

Glu Lys Leu Ala Gln Ser Lys Thr Asp Ala Ala Arg Ala Ile Asp Ala
            580                 585                 590

Leu Pro His Leu Asn Asn Ala Gln Lys Ala Asp Val Lys Ser Lys Ile
        595                 600                 605

Asn Ala Ala Ser Asn Ile Ala Gly Val Asn Thr Val Lys Gln Gln Gly
    610                 615                 620

Thr Asp Leu Asn Thr Ala Met Gly Asn Leu Gln Gly Ala Ile Asn Asp
625                 630                 635                 640

Glu Gln Thr Thr Leu Asn Ser Gln Asn Tyr Gln Asp Ala Thr Pro Ser
                645                 650                 655

Lys Lys Thr Ala Tyr Thr Asn Ala Val Gln Ala Ala Lys Asp Ile Leu
            660                 665                 670

Asn Lys Ser Asn Gly Gln Asn Lys Thr Lys Asp Gln Val Thr Glu Ala
        675                 680                 685

Met Asn Gln Val Asn Ser Ala Lys Asn Asn Leu Asp Gly Thr Arg Leu
    690                 695                 700

Leu Asp
705

<210> SEQ ID NO 73
<211> LENGTH: 241
<212> TYPE: PRT
<213> ORGANISM: S. aureus

<400> SEQUENCE: 73

Ala Ser Thr Gln His Thr Val Gln Ser Gly Glu Ser Leu Trp Ser Ile
  1               5                  10                  15

Ala Gln Lys Tyr Asn Thr Ser Val Glu Ser Ile Lys Gln Asn Asn Gln
            20                  25                  30

Leu Asp Asn Asn Leu Val Phe Pro Gly Gln Val Ile Ser Val Gly Gly
        35                  40                  45

Ser Asp Ala Gln Asn Thr Ser Asn Thr Ser Pro Gln Ala Gly Ser Ala
    50                  55                  60

Ser Ser His Thr Val Gln Ala Gly Glu Ser Leu Asn Ile Ile Ala Ser
65                  70                  75                  80

Arg Tyr Gly Val Ser Val Asp Gln Leu Met Ala Ala Asn Asn Leu Arg
                85                  90                  95

Gly Tyr Leu Ile Met Pro Asn Gln Thr Leu Gln Ile Pro Asn Gly Gly
            100                 105                 110

Ser Gly Gly Thr Thr Pro Thr Ala Thr Thr Gly Ser Asn Gly Asn Ala
        115                 120                 125

Ser Ser Phe Asn His Gln Asn Leu Tyr Thr Ala Gly Gln Cys Thr Trp
```

```
            130                 135                 140
Tyr Val Phe Asp Arg Arg Ala Gln Ala Gly Ser Pro Ile Ser Thr Tyr
145                 150                 155                 160

Trp Ser Asp Ala Lys Tyr Trp Ala Gly Asn Ala Ala Asn Asp Gly Tyr
                165                 170                 175

Gln Val Asn Asn Thr Pro Ser Val Gly Ser Ile Met Gln Ser Thr Pro
            180                 185                 190

Gly Pro Tyr Gly His Val Ala Tyr Val Glu Arg Val Asn Gly Asp Gly
                195                 200                 205

Ser Ile Leu Ile Ser Glu Met Asn Tyr Thr Tyr Gly Pro Tyr Asn Met
            210                 215                 220

Asn Tyr Arg Thr Ile Pro Ala Ser Glu Val Ser Ser Tyr Ala Phe Ile
225                 230                 235                 240

His

<210> SEQ ID NO 74
<211> LENGTH: 995
<212> TYPE: PRT
<213> ORGANISM: S. aureus

<400> SEQUENCE: 74

Met Asn Asn Lys Lys Thr Ala Thr Asn Arg Lys Gly Met Ile Pro Asn
1               5                   10                  15

Arg Leu Asn Lys Phe Ser Ile Arg Lys Tyr Ser Val Gly Thr Ala Ser
                20                  25                  30

Ile Leu Val Gly Thr Thr Leu Ile Phe Gly Leu Ser Gly His Glu Ala
            35                  40                  45

Lys Ala Ala Glu His Thr Asn Gly Glu Leu Asn Gln Ser Lys Asn Glu
        50                  55                  60

Thr Thr Ala Pro Ser Glu Asn Lys Thr Thr Lys Val Asp Ser Arg
65                  70                  75                  80

Gln Leu Lys Asp Asn Thr Gln Thr Ala Thr Ala Asp Gln Pro Lys Val
                85                  90                  95

Thr Met Ser Asp Ser Ala Thr Val Lys Glu Thr Ser Ser Asn Met Gln
            100                 105                 110

Ser Pro Gln Asn Ala Thr Ala Asn Gln Ser Thr Thr Lys Thr Ser Asn
        115                 120                 125

Val Thr Thr Asn Asp Lys Ser Ser Thr Thr Tyr Ser Asn Glu Thr Asp
130                 135                 140

Lys Ser Asn Leu Thr Gln Ala Lys Asp Val Ser Thr Thr Pro Lys Thr
145                 150                 155                 160

Thr Thr Ile Lys Pro Arg Thr Leu Asn Arg Met Ala Val Asn Thr Val
                165                 170                 175

Ala Ala Pro Gln Gln Gly Thr Asn Val Asn Asp Lys Val His Phe Ser
            180                 185                 190

Asn Ile Asp Ile Ala Ile Asp Lys Gly His Val Asn Gln Thr Thr Gly
        195                 200                 205

Lys Thr Glu Phe Trp Ala Thr Ser Ser Asp Val Leu Lys Leu Lys Ala
    210                 215                 220

Asn Tyr Thr Ile Asp Asp Ser Val Lys Glu Gly Asp Thr Phe Thr Phe
225                 230                 235                 240

Lys Tyr Gly Gln Tyr Phe Arg Pro Gly Ser Val Arg Leu Pro Ser Gln
                245                 250                 255

Thr Gln Asn Leu Tyr Asn Ala Gln Gly Asn Ile Ile Ala Lys Gly Ile
```

```
                260                 265                 270
Tyr Asp Ser Thr Thr Asn Thr Thr Tyr Thr Phe Thr Asn Tyr Val
            275                 280                 285

Asp Gln Tyr Thr Asn Val Arg Gly Ser Phe Glu Gln Val Ala Phe Ala
290                 295                 300

Lys Arg Lys Asn Ala Thr Thr Asp Lys Thr Ala Tyr Lys Met Glu Val
305                 310                 315                 320

Thr Leu Gly Asn Asp Thr Tyr Ser Glu Glu Ile Ile Val Asp Tyr Gly
            325                 330                 335

Asn Lys Lys Ala Gln Pro Leu Ile Ser Ser Thr Asn Tyr Ile Asn Asn
            340                 345                 350

Glu Asp Leu Ser Arg Asn Met Thr Ala Tyr Val Asn Gln Pro Lys Asn
            355                 360                 365

Thr Tyr Thr Lys Gln Thr Phe Val Thr Asn Leu Thr Gly Tyr Lys Phe
            370                 375                 380

Asn Pro Asn Ala Lys Asn Phe Lys Ile Tyr Glu Val Thr Asp Gln Asn
385                 390                 395                 400

Gln Phe Val Asp Ser Phe Thr Pro Asp Thr Ser Lys Leu Lys Asp Val
                405                 410                 415

Thr Asp Gln Phe Asp Val Ile Tyr Ser Asn Asp Asn Lys Thr Ala Thr
            420                 425                 430

Val Asp Leu Met Lys Gly Gln Thr Ser Ser Asn Lys Gln Tyr Ile Ile
            435                 440                 445

Gln Gln Val Ala Tyr Pro Asp Asn Ser Ser Thr Asp Asn Gly Lys Ile
        450                 455                 460

Asp Tyr Thr Leu Asp Thr Asp Lys Thr Lys Tyr Ser Trp Ser Asn Ser
465                 470                 475                 480

Tyr Ser Asn Val Asn Gly Ser Ser Thr Ala Asn Gly Asp Gln Lys Lys
                485                 490                 495

Tyr Asn Leu Gly Asp Tyr Val Trp Glu Asp Thr Asn Lys Asp Gly Lys
            500                 505                 510

Gln Asp Ala Asn Glu Lys Gly Ile Lys Gly Val Tyr Val Ile Leu Lys
            515                 520                 525

Asp Ser Asn Gly Lys Glu Leu Asp Arg Thr Thr Asp Glu Asn Gly
            530                 535                 540

Lys Tyr Gln Phe Thr Gly Leu Ser Asn Gly Thr Tyr Ser Val Glu Phe
545                 550                 555                 560

Ser Thr Pro Ala Gly Tyr Thr Pro Thr Ala Asn Val Gly Thr Asp
                565                 570                 575

Asp Ala Val Asp Ser Asp Gly Leu Thr Thr Gly Val Ile Lys Asp
                580                 585                 590

Ala Asp Asn Met Thr Leu Asp Ser Gly Phe Tyr Lys Thr Pro Lys Tyr
            595                 600                 605

Ser Leu Gly Asp Tyr Val Trp Tyr Asp Ser Asn Lys Asp Gly Lys Gln
            610                 615                 620

Asp Ser Thr Glu Lys Gly Ile Lys Gly Val Lys Val Thr Leu Gln Asn
625                 630                 635                 640

Glu Lys Gly Glu Val Ile Gly Thr Thr Glu Thr Asp Glu Asn Gly Lys
                645                 650                 655

Tyr Arg Phe Asp Asn Leu Asp Ser Gly Lys Tyr Lys Val Ile Phe Glu
            660                 665                 670

Lys Pro Ala Gly Leu Thr Gln Thr Gly Thr Asn Thr Thr Glu Asp Asp
            675                 680                 685
```

```
Lys Asp Ala Asp Gly Gly Glu Val Asp Val Thr Ile Thr Asp His Asp
        690             695                 700
Asp Phe Thr Leu Asp Asn Gly Tyr Tyr Glu Glu Thr Ser Asp Ser
705                 710                 715                 720
Asp Ser Asp Ser Asp Ser Asp Ser Asp Ser Asp Ser Asp Ser
            725                 730                 735
Asp Ser Asp Ser Asp Ser Asp Ser Asp Ser Asp Ser Asp Ser
            740                 745                 750
Asp Ser Asp Ser Asp Ser Asp Ser Asp Ser Asp Ser Asp Ser
            755                 760                 765
Asp Ser Asp Ser Asp Ser Asp Ser Asp Ser Asp Ser Asp Ser
770                 775                 780
Asp Ser Asp Ser Asp Ser Asp Ser Asp Ser Asp Ser Asp Ser
785                 790                 795                 800
Asp Ser Asp Ser Asp Ser Asp Ser Asp Ser Asp Ser Asp Ser
            805                 810                 815
Asp Ser Asp Ser Asp Ser Asp Ser Asp Ser Asp Ser Asp Ser
            820                 825                 830
Asp Ser Asp Ser Asp Ser Asp Ser Asp Ser Asp Ser Asp Ser
            835                 840                 845
Asp Ser Asp Ser Asp Ser Asp Ser Asn Asp Ser Asp Ser Asp Ser
850                 855                 860
Asp Ser Asp Ser Asp Ser Asp Ser Asp Ser Asp Ser Asp Ser
865                 870                 875                 880
Asp Ser Asp Ser Asp Ser Asp Ser Asp Ser Asp Ser Asp Ser
            885                 890                 895
Asp Ser Asp Ser Asp Ser Asp Ser Asp Ser Asp Ser Asp Ser
            900                 905                 910
Asp Ser Asp Ser Asp Ser Asp Ser Asp Asn Asp Ser Asp Ser
            915                 920                 925
Asp Ser Asp Ser Asp Ser Asp Ala Gly Lys His Thr Pro Ala Lys Pro
            930                 935                 940
Met Ser Thr Val Lys Asp Gln His Lys Thr Ala Lys Ala Leu Pro Glu
945                 950                 955                 960
Thr Gly Ser Glu Asn Asn Asn Ser Asn Asn Gly Thr Leu Phe Gly Gly
                965                 970                 975
Leu Phe Ala Ala Leu Gly Ser Leu Leu Leu Phe Gly Arg Arg Lys Lys
            980                 985                 990
Gln Asn Lys
        995

<210> SEQ ID NO 75
<211> LENGTH: 2186
<212> TYPE: PRT
<213> ORGANISM: S. aureus

<400> SEQUENCE: 75

Met Asn Leu Leu Lys Lys Asn Lys Tyr Ser Ile Arg Lys Tyr Lys Val
1               5                   10                  15

Gly Ile Phe Ser Thr Leu Ile Gly Thr Val Leu Leu Leu Ser Asn Pro
            20                  25                  30

Asn Gly Ala Gln Ala Leu Thr Thr Asp Asn Asn Val Gln Ser Asp Thr
        35                  40                  45

Asn Gln Ala Thr Pro Val Asn Ser Gln Asp Lys Asp Val Ala Asn Asn
```

```
            50                  55                  60
Arg Gly Leu Ala Asn Ser Ala Gln Asn Thr Pro Asn Gln Ser Ala Thr
 65                  70                  75                  80

Thr Asn Gln Ala Thr Asn Gln Ala Leu Val Asn His Asn Asn Gly Ser
                     85                  90                  95

Ile Val Asn Gln Ala Thr Pro Thr Ser Val Gln Ser Ser Thr Pro Ser
                    100                 105                 110

Ala Gln Asn Asn His Thr Asp Gly Asn Thr Thr Ala Thr Glu Thr
                    115                 120                 125

Val Ser Asn Ala Asn Asn Asp Val Val Ser Asn Asn Thr Ala Leu
                    130                 135                 140

Asn Val Pro Thr Lys Thr Asn Glu Asn Gly Ser Gly Gly His Leu Thr
145                 150                 155                 160

Leu Lys Glu Ile Gln Glu Asp Val Arg His Ser Ser Asn Lys Pro Glu
                    165                 170                 175

Leu Val Ala Ile Ala Glu Pro Ala Ser Asn Arg Pro Lys Lys Arg Ser
                    180                 185                 190

Arg Arg Ala Ala Pro Ala Asp Pro Asn Ala Thr Pro Ala Asp Pro Ala
                    195                 200                 205

Ala Ala Ala Val Gly Asn Gly Gly Ala Pro Val Ala Ile Thr Ala Pro
210                 215                 220

Tyr Thr Pro Thr Thr Asp Pro Asn Ala Asn Asn Ala Gly Gln Asn Ala
225                 230                 235                 240

Pro Asn Glu Val Leu Ser Phe Asp Asp Asn Gly Ile Arg Pro Ser Thr
                    245                 250                 255

Asn Arg Ser Val Pro Thr Val Asn Val Val Asn Asn Leu Pro Gly Phe
                    260                 265                 270

Thr Leu Ile Asn Gly Gly Lys Val Gly Val Phe Ser His Ala Met Val
                    275                 280                 285

Arg Thr Ser Met Phe Asp Ser Gly Asp Asn Lys Asn Tyr Gln Ala Gln
                    290                 295                 300

Gly Asn Val Ile Ala Leu Gly Arg Ile His Gly Thr Asp Thr Asn Asp
305                 310                 315                 320

His Gly Asp Phe Asn Gly Ile Glu Lys Ala Leu Thr Val Asn Pro Asn
                    325                 330                 335

Ser Glu Leu Ile Phe Glu Phe Asn Thr Met Thr Thr Lys Asn Gly Gln
                    340                 345                 350

Gly Ala Thr Asn Val Ile Ile Lys Asn Ala Asp Thr Asn Asp Thr Ile
                    355                 360                 365

Ala Glu Lys Thr Val Glu Gly Gly Pro Thr Leu Arg Leu Phe Lys Val
                    370                 375                 380

Pro Asp Asn Val Arg Asn Leu Lys Ile Gln Phe Val Pro Lys Asn Asp
385                 390                 395                 400

Ala Ile Thr Asp Ala Arg Gly Ile Tyr Gln Leu Lys Asp Gly Tyr Lys
                    405                 410                 415

Tyr Tyr Ser Phe Val Asp Ser Ile Gly Leu His Ser Gly Ser His Val
                    420                 425                 430

Phe Val Glu Arg Arg Thr Met Asp Pro Thr Ala Thr Asn Asn Lys Glu
                    435                 440                 445

Phe Thr Val Thr Thr Ser Leu Lys Asn Asn Gly Asn Ser Gly Ala Ser
                    450                 455                 460

Leu Asp Thr Asn Asp Phe Val Tyr Gln Val Gln Leu Pro Glu Gly Val
465                 470                 475                 480
```

-continued

```
Glu Tyr Val Asn Asn Ser Leu Thr Lys Asp Phe Pro Ser Asn Asn Ser
                485                 490                 495
Gly Val Asp Val Asn Asp Met Asn Val Thr Tyr Asp Ala Ala Asn Arg
            500                 505                 510
Val Ile Thr Ile Lys Ser Thr Gly Gly Thr Ala Asn Ser Pro Ala
        515                 520                 525
Arg Leu Met Pro Asp Lys Ile Leu Asp Leu Arg Tyr Lys Leu Arg Val
    530                 535                 540
Asn Asn Val Pro Thr Pro Arg Thr Val Thr Phe Asn Glu Thr Leu Thr
545                 550                 555                 560
Tyr Lys Thr Tyr Thr Gln Asp Phe Ile Asn Ser Ala Ala Glu Ser His
                565                 570                 575
Thr Val Ser Thr Asn Pro Tyr Thr Ile Asp Ile Ile Met Asn Lys Asp
            580                 585                 590
Ala Leu Gln Ala Glu Val Asp Arg Arg Ile Gln Gln Ala Asp Tyr Thr
        595                 600                 605
Phe Ala Ser Leu Asp Ile Phe Asn Gly Leu Lys Arg Arg Ala Gln Thr
    610                 615                 620
Ile Leu Asp Glu Asn Arg Asn Asn Val Pro Leu Asn Lys Arg Val Ser
625                 630                 635                 640
Gln Ala Tyr Ile Asp Ser Leu Thr Asn Gln Met Gln His Thr Leu Ile
                645                 650                 655
Arg Ser Val Asp Ala Glu Asn Ala Val Asn Lys Lys Val Asp Gln Met
            660                 665                 670
Glu Asp Leu Val Asn Gln Asn Asp Glu Leu Thr Asp Glu Glu Lys Gln
        675                 680                 685
Ala Ala Ile Gln Val Ile Glu Glu His Lys Asn Glu Ile Ile Gly Asn
    690                 695                 700
Ile Gly Asp Gln Thr Thr Asp Asp Gly Val Thr Arg Ile Lys Asp Gln
705                 710                 715                 720
Gly Ile Gln Thr Leu Ser Gly Asp Thr Ala Thr Pro Val Val Lys Pro
                725                 730                 735
Asn Ala Lys Lys Ala Ile Arg Asp Lys Ala Thr Lys Gln Arg Glu Ile
            740                 745                 750
Ile Asn Ala Thr Pro Asp Ala Thr Glu Asp Glu Ile Gln Asp Ala Leu
        755                 760                 765
Asn Gln Leu Ala Thr Asp Glu Thr Asp Ala Ile Asp Asn Val Thr Asn
    770                 775                 780
Ala Thr Thr Asn Ala Asp Val Glu Thr Ala Lys Asn Asn Gly Ile Asn
785                 790                 795                 800
Thr Ile Gly Ala Val Pro Gln Val Thr His Lys Lys Ala Ala Arg
                805                 810                 815
Asp Ala Ile Asn Gln Ala Thr Ala Thr Lys Arg Gln Ile Asn Ser
            820                 825                 830
Asn Arg Glu Ala Thr Gln Glu Lys Asn Ala Ala Leu Asn Glu Leu
        835                 840                 845
Thr Gln Ala Thr Asn His Ala Leu Glu Gln Ile Asn Gln Ala Thr Thr
    850                 855                 860
Asn Ala Asn Val Asp Asn Ala Lys Gly Asp Gly Leu Asn Ala Ile Asn
865                 870                 875                 880
Pro Ile Ala Pro Val Thr Val Lys Gln Ala Ala Arg Asp Ala Val
                885                 890                 895
```

```
Ser His Asp Ala Gln Gln His Ile Ala Glu Ile Asn Ala Asn Pro Asp
                900                 905                 910
Ala Thr Gln Glu Glu Arg Gln Ala Ala Ile Asp Lys Val Asn Ala Ala
            915                 920                 925
Val Thr Ala Ala Asn Thr Asn Ile Leu Asn Ala Asn Thr Asn Ala Asp
        930                 935                 940
Val Glu Gln Val Lys Thr Asn Ala Ile Gln Gly Ile Gln Ala Ile Thr
945                 950                 955                 960
Pro Ala Thr Lys Val Lys Thr Asp Ala Lys Asn Ala Ile Asp Lys Ser
                965                 970                 975
Ala Glu Thr Gln His Asn Thr Ile Phe Asn Asn Asp Ala Thr Leu
            980                 985                 990
Glu Glu Gln Gln Ala Ala Gln Gln Leu Leu Asp Gln Ala Val Ala Thr
        995                 1000                1005
Ala Lys Gln Asn Ile Asn Ala Ala Asp Thr Asn Gln Glu Val Ala Gln
        1010                1015                1020
Ala Lys Asp Gln Gly Thr Gln Asn Ile Val Val Ile Gln Pro Ala Thr
1025                1030                1035                1040
Gln Val Lys Thr Asp Thr Arg Asn Val Val Asn Asp Lys Ala Arg Glu
            1045                1050                1055
Ala Ile Thr Asn Ile Asn Ala Thr Thr Gly Ala Thr Arg Glu Glu Lys
        1060                1065                1070
Gln Glu Ala Ile Asn Arg Val Asn Thr Leu Lys Asn Arg Ala Leu Thr
        1075                1080                1085
Asp Ile Gly Val Thr Ser Thr Thr Ala Met Val Asn Ser Ile Arg Asp
        1090                1095                1100
Asp Ala Val Asn Gln Ile Gly Ala Val Gln Pro His Val Thr Lys Lys
1105                1110                1115                1120
Gln Thr Ala Thr Gly Val Leu Asn Asp Leu Ala Thr Ala Lys Lys Gln
            1125                1130                1135
Glu Ile Asn Gln Asn Thr Asn Ala Thr Thr Glu Glu Lys Gln Val Ala
        1140                1145                1150
Leu Asn Gln Val Asp Gln Glu Leu Ala Thr Ala Ile Asn Asn Ile Asn
        1155                1160                1165
Gln Ala Asp Thr Asn Ala Glu Val Asp Gln Ala Gln Gln Leu Gly Thr
        1170                1175                1180
Lys Ala Ile Asn Ala Ile Gln Pro Asn Ile Val Lys Lys Pro Ala Ala
1185                1190                1195                1200
Leu Ala Gln Ile Asn Gln His Tyr Asn Ala Lys Leu Ala Glu Ile Asn
            1205                1210                1215
Ala Thr Pro Asp Ala Thr Asn Asp Glu Lys Asn Ala Ala Ile Asn Thr
        1220                1225                1230
Leu Asn Gln Asp Arg Gln Gln Ala Ile Glu Ser Ile Lys Gln Ala Asn
            1235                1240                1245
Thr Asn Ala Glu Val Asp Gln Ala Ala Thr Val Ala Glu Asn Asn Ile
        1250                1255                1260
Asp Ala Val Gln Val Asp Val Val Lys Lys Gln Ala Ala Arg Asp Lys
1265                1270                1275                1280
Ile Thr Ala Glu Val Ala Lys Arg Ile Glu Ala Val Lys Gln Thr Pro
            1285                1290                1295
Asn Ala Thr Asp Glu Glu Lys Gln Ala Ala Val Asn Gln Ile Asn Gln
        1300                1305                1310
Leu Lys Asp Gln Ala Ile Asn Gln Ile Asn Gln Asn Gln Thr Asn Asp
```

-continued

```
            1315                1320                1325

Gln Val Asp Thr Thr Thr Asn Gln Ala Val Asn Ala Ile Asp Asn Val
            1330                1335                1340

Glu Ala Glu Val Val Ile Lys Thr Lys Ala Ile Ala Asp Ile Glu Lys
1345                1350                1355                1360

Ala Val Lys Glu Lys Gln Gln Gln Ile Asp Asn Ser Leu Asp Ser Thr
                1365                1370                1375

Asp Asn Glu Lys Glu Val Ala Ser Gln Ala Leu Ala Lys Glu Lys Glu
            1380                1385                1390

Lys Ala Leu Ala Ala Ile Asp Gln Ala Gln Thr Asn Ser Gln Val Asn
        1395                1400                1405

Gln Ala Ala Thr Asn Gly Val Ser Ala Ile Lys Ile Gln Pro Glu
    1410                1415                1420

Thr Lys Val Lys Pro Ala Ala Arg Glu Lys Ile Asn Gln Lys Ala Asn
1425                1430                1435                1440

Glu Leu Arg Ala Lys Ile Asn Gln Asp Lys Glu Ala Thr Ala Glu Glu
                1445                1450                1455

Arg Gln Val Ala Leu Asp Lys Ile Asn Glu Phe Val Asn Gln Ala Met
            1460                1465                1470

Thr Asp Ile Thr Asn Asn Arg Thr Asn Gln Gln Val Asp Asp Thr Thr
        1475                1480                1485

Ser Gln Ala Leu Asp Ser Ile Ala Leu Val Thr Pro Asp His Ile Val
    1490                1495                1500

Arg Ala Ala Ala Arg Asp Ala Val Lys Gln Gln Tyr Glu Ala Lys Lys
1505                1510                1515                1520

Arg Glu Ile Glu Gln Ala Glu His Ala Thr Asp Glu Glu Lys Gln Val
                1525                1530                1535

Ala Leu Asn Gln Leu Ala Asn Asn Glu Lys Arg Ala Leu Gln Asn Ile
            1540                1545                1550

Asp Gln Ala Ile Ala Asn Asn Asp Val Lys Arg Val Glu Thr Asn Gly
        1555                1560                1565

Ile Ala Thr Leu Lys Gly Val Gln Pro His Ile Val Ile Lys Pro Glu
    1570                1575                1580

Ala Gln Gln Ala Ile Lys Ala Ser Ala Glu Asn Gln Val Glu Ser Ile
1585                1590                1595                1600

Lys Asp Thr Pro His Ala Thr Val Asp Glu Leu Asp Glu Ala Asn Gln
                1605                1610                1615

Leu Ile Ser Asp Thr Leu Lys Gln Ala Gln Gln Glu Ile Glu Asn Thr
            1620                1625                1630

Asn Gln Asp Ala Ala Val Thr Asp Val Arg Asn Gln Thr Ile Lys Ala
        1635                1640                1645

Ile Glu Gln Ile Lys Pro Lys Val Arg Arg Lys Arg Ala Ala Leu Asp
    1650                1655                1660

Ser Ile Glu Glu Asn Asn Lys Asn Gln Leu Asp Ala Ile Arg Asn Thr
1665                1670                1675                1680

Leu Asp Thr Thr Gln Asp Glu Arg Asp Val Ala Ile Asp Thr Leu Asn
                1685                1690                1695

Lys Ile Val Asn Thr Ile Lys Asn Asp Ile Ala Gln Asn Lys Thr Asn
            1700                1705                1710

Ala Glu Val Asp Arg Thr Glu Thr Asp Gly Asn Asp Asn Ile Lys Val
        1715                1720                1725

Ile Leu Pro Lys Val Gln Val Lys Pro Ala Ala Arg Gln Ser Val Gly
    1730                1735                1740
```

```
Val Lys Ala Glu Ala Gln Asn Ala Leu Ile Asp Gln Ser Asp Leu Ser
1745                1750                1755                1760

Thr Glu Glu Glu Arg Leu Ala Ala Lys His Leu Val Gln Ala Leu
                1765                1770                1775

Asn Gln Ala Ile Asp Gln Ile Asn His Ala Asp Lys Thr Ala Gln Val
            1780                1785                1790

Asn Gln Asp Ser Ile Asn Ala Gln Asn Ile Ile Ser Lys Ile Lys Pro
            1795                1800                1805

Ala Thr Thr Val Lys Ala Thr Ala Leu Gln Gln Ile Gln Asn Ile Ala
            1810                1815                1820

Thr Asn Lys Ile Asn Leu Ile Lys Ala Asn Asn Glu Ala Thr Asp Glu
1825                1830                1835                1840

Glu Gln Asn Ile Ala Ile Ala Gln Val Glu Lys Glu Leu Ile Lys Ala
                1845                1850                1855

Lys Gln Gln Ile Ala Ser Ala Val Thr Asn Ala Asp Val Ala Tyr Leu
            1860                1865                1870

Leu His Asp Glu Lys Asn Glu Ile Arg Glu Ile Glu Pro Val Ile Asn
            1875                1880                1885

Arg Lys Ala Ser Ala Arg Glu Gln Leu Thr Thr Leu Phe Asn Asp Lys
            1890                1895                1900

Lys Gln Ala Ile Glu Ala Asn Ile Gln Ala Thr Val Glu Glu Arg Asn
1905                1910                1915                1920

Ser Ile Leu Ala Gln Leu Gln Asn Ile Tyr Asp Thr Ala Ile Gly Gln
            1925                1930                1935

Ile Asp Gln Asp Arg Ser Asn Ala Gln Val Asp Lys Thr Ala Ser Leu
            1940                1945                1950

Asn Leu Gln Thr Ile His Asp Leu Asp Val His Pro Ile Lys Lys Pro
            1955                1960                1965

Asp Ala Glu Lys Thr Ile Asn Asp Asp Leu Ala Arg Val Thr Ala Leu
            1970                1975                1980

Val Gln Asn Tyr Arg Lys Val Ser Asn Arg Asn Lys Ala Asp Ala Leu
1985                1990                1995                2000

Lys Ala Ile Thr Ala Leu Lys Leu Gln Met Asp Glu Glu Leu Lys Thr
                2005                2010                2015

Ala Arg Thr Asn Ala Asp Val Asp Ala Val Leu Lys Arg Phe Asn Val
                2020                2025                2030

Ala Leu Ser Asp Ile Glu Ala Val Ile Thr Glu Lys Glu Asn Ser Leu
                2035                2040                2045

Leu Arg Ile Asp Asn Ile Ala Gln Gln Thr Tyr Ala Lys Phe Lys Ala
            2050                2055                2060

Ile Ala Thr Pro Glu Gln Leu Ala Lys Val Lys Val Leu Ile Asp Gln
2065                2070                2075                2080

Tyr Val Ala Asp Gly Asn Arg Met Ile Asp Glu Asp Ala Thr Leu Asn
                2085                2090                2095

Asp Ile Lys Gln His Thr Gln Phe Ile Val Asp Glu Ile Leu Ala Ile
            2100                2105                2110

Lys Leu Pro Ala Glu Ala Thr Lys Val Ser Pro Lys Glu Ile Gln Pro
            2115                2120                2125

Ala Pro Lys Val Cys Thr Pro Ile Lys Lys Glu Glu Thr His Glu Ser
            2130                2135                2140

Arg Lys Val Glu Lys Glu Leu Pro Asn Thr Gly Ser Glu Gly Met Asp
2145                2150                2155                2160
```

```
Leu Pro Leu Lys Glu Phe Ala Leu Ile Thr Gly Ala Ala Leu Leu Ala
            2165                2170                2175
Arg Arg Arg Thr Lys Asn Glu Lys Glu Ser
        2180                2185
```

<210> SEQ ID NO 76
<211> LENGTH: 773
<212> TYPE: PRT
<213> ORGANISM: S. aureus

<400> SEQUENCE: 76

```
Glu Glu Asn Ser Val Gln Asp Val Lys Asp Ser Asn Thr Asp Asp Glu
 1               5                  10                  15
Leu Ser Asp Ser Asn Asp Gln Ser Ser Asp Glu Glu Lys Asn Asp Val
            20                  25                  30
Ile Asn Asn Asn Gln Ser Ile Asn Thr Asp Asp Asn Asn Gln Ile Ile
        35                  40                  45
Lys Lys Glu Glu Thr Asn Asn Tyr Asp Gly Ile Glu Lys Arg Ser Glu
 50                  55                  60
Asp Arg Thr Glu Ser Thr Thr Asn Val Asp Glu Asn Glu Ala Thr Phe
 65                  70                  75                  80
Leu Gln Lys Thr Pro Gln Asp Asn Thr His Leu Thr Glu Glu Val
            85                  90                  95
Lys Glu Ser Ser Ser Val Glu Ser Asn Ser Ser Ile Asp Thr Ala
            100                 105                 110
Gln Gln Pro Ser His Thr Thr Ile Asn Arg Glu Glu Ser Val Gln Thr
        115                 120                 125
Ser Asp Asn Val Glu Asp Ser His Val Ser Asp Phe Ala Asn Ser Lys
130                 135                 140
Ile Lys Glu Ser Asn Thr Glu Ser Gly Lys Glu Glu Asn Thr Ile Glu
145                 150                 155                 160
Gln Pro Asn Lys Val Lys Glu Asp Ser Thr Thr Ser Gln Pro Ser Gly
                165                 170                 175
Tyr Thr Asn Ile Asp Glu Lys Ile Ser Asn Gln Asp Glu Leu Leu Asn
            180                 185                 190
Leu Pro Ile Asn Glu Tyr Glu Asn Lys Ala Arg Pro Leu Ser Thr Thr
        195                 200                 205
Ser Ala Gln Pro Ser Ile Lys Arg Val Thr Val Asn Gln Leu Ala Ala
    210                 215                 220
Glu Gln Gly Ser Asn Val Asn His Leu Ile Lys Val Thr Asp Gln Ser
225                 230                 235                 240
Ile Thr Glu Gly Tyr Asp Asp Ser Glu Gly Val Ile Lys Ala His Asp
                245                 250                 255
Ala Glu Asn Leu Ile Tyr Asp Val Thr Phe Glu Val Asp Lys Val
            260                 265                 270
Lys Ser Gly Asp Thr Met Thr Val Asp Ile Asp Lys Asn Thr Val Pro
        275                 280                 285
Ser Asp Leu Thr Asp Ser Phe Thr Ile Pro Lys Ile Lys Asp Asn Ser
    290                 295                 300
Gly Glu Ile Ile Ala Thr Gly Thr Tyr Asp Asn Lys Asn Lys Gln Ile
305                 310                 315                 320
Thr Tyr Thr Phe Thr Asp Tyr Val Asp Lys Tyr Glu Asn Ile Lys Ala
                325                 330                 335
His Leu Lys Leu Thr Ser Tyr Ile Asp Lys Ser Lys Val Pro Asn Asn
            340                 345                 350
```

-continued

```
Asn Thr Lys Leu Asp Val Glu Tyr Lys Thr Ala Leu Ser Ser Val Asn
            355                 360                 365
Lys Thr Ile Thr Val Glu Tyr Gln Arg Pro Asn Glu Asn Arg Thr Ala
        370                 375                 380
Asn Leu Gln Ser Met Phe Thr Asn Ile Asp Thr Lys Asn His Thr Val
385                 390                 395                 400
Glu Gln Thr Ile Tyr Ile Asn Pro Leu Arg Tyr Ser Ala Lys Glu Thr
                405                 410                 415
Asn Val Asn Ile Ser Gly Asn Gly Asp Glu Gly Ser Thr Ile Ile Asp
            420                 425                 430
Asp Ser Thr Ile Ile Lys Val Tyr Lys Val Gly Asp Asn Gln Asn Leu
        435                 440                 445
Pro Asp Ser Asn Arg Ile Tyr Asp Tyr Ser Glu Tyr Glu Asp Val Thr
        450                 455                 460
Asn Asp Asp Tyr Ala Gln Leu Gly Asn Asn Asn Asp Val Asn Ile Asn
465                 470                 475                 480
Phe Gly Asn Ile Asp Ser Pro Tyr Ile Ile Lys Val Ile Ser Lys Tyr
                485                 490                 495
Asp Pro Asn Lys Asp Asp Tyr Thr Thr Ile Gln Gln Thr Val Thr Met
            500                 505                 510
Gln Thr Thr Ile Asn Glu Tyr Thr Gly Glu Phe Arg Thr Ala Ser Tyr
        515                 520                 525
Asp Asn Thr Ile Ala Phe Ser Thr Ser Gly Gln Gly Gln Gly Asp
        530                 535                 540
Leu Pro Pro Glu Lys Thr Tyr Lys Ile Gly Asp Tyr Val Trp Glu Asp
545                 550                 555                 560
Val Asp Lys Asp Gly Ile Gln Asn Thr Asn Asp Asn Glu Lys Pro Leu
                565                 570                 575
Ser Asn Val Leu Val Thr Leu Thr Tyr Pro Asp Gly Thr Ser Lys Ser
            580                 585                 590
Val Arg Thr Asp Glu Asp Gly Lys Tyr Gln Phe Asp Gly Leu Lys Asn
        595                 600                 605
Gly Leu Thr Tyr Lys Ile Thr Phe Glu Thr Pro Glu Gly Tyr Thr Pro
        610                 615                 620
Thr Leu Lys His Ser Gly Thr Asn Pro Ala Leu Asp Ser Glu Gly Asn
625                 630                 635                 640
Ser Val Trp Val Thr Ile Asn Gly Gln Asp Asp Met Thr Ile Asp Ser
                645                 650                 655
Gly Phe Tyr Gln Thr Pro Lys Tyr Ser Leu Gly Asn Tyr Val Trp Tyr
            660                 665                 670
Asp Thr Asn Lys Asp Gly Ile Gln Gly Asp Asp Glu Lys Gly Ile Ser
        675                 680                 685
Gly Val Lys Val Thr Leu Lys Asp Glu Asn Gly Asn Ile Ile Ser Thr
        690                 695                 700
Thr Thr Thr Asp Glu Asn Gly Lys Tyr Gln Phe Asp Asn Leu Asn Ser
705                 710                 715                 720
Gly Asn Tyr Ile Val His Phe Asp Lys Pro Ser Gly Met Thr Gln Thr
                725                 730                 735
Thr Thr Asp Ser Gly Asp Asp Glu Gln Asp Ala Asp Gly Glu Glu
            740                 745                 750
Val His Val Thr Ile Thr Asp His Asp Phe Ser Ile Asp Asn Gly
        755                 760                 765
```

Tyr Tyr Asp Asp Glu
    770

<210> SEQ ID NO 77
<211> LENGTH: 2886
<212> TYPE: DNA
<213> ORGANISM: S. aureus

<400> SEQUENCE: 77

| | | | | | |
|---|---|---|---|---|---|
| gtgaaaagca | atcttagata | cggcataaga | aaacacaaat | tgggagcggc | ctcagtattc | 60 |
| ttaggaacaa | tgatcgttgt | tggaatggga | caagaaaaag | aagctgcagc | atcggaacaa | 120 |
| aacaatacta | cagtagagga | aagtgggagt | tcagctactg | aaagtaaagc | aagcgaaaca | 180 |
| caaacaacta | caaataacgt | taatacaata | gatgaaacac | aatcatacag | cgcgacatca | 240 |
| actgagcaac | catcaaaatc | aactcaagta | acaacagaag | aagcaccaac | aactgtgcaa | 300 |
| gcaccaaaag | tagaaaccga | aatgaaatca | aagaagatt | taccatcaga | aaaagttgct | 360 |
| gataaggaaa | ctacaggaac | tcaagttgac | atagctcaac | caagtaacgt | ctcagaaatt | 420 |
| aaaccaagaa | tgaaaagatc | agctgacgtt | acagcagttt | cagagaaaga | agtagcggaa | 480 |
| gaagctaaag | cgacaggtac | agatgtaaca | aataaagtgg | aagttactga | aagctctta | 540 |
| gaaggacata | taaagattc | gaatattgtt | aatccgcata | atgctcaaag | agtaacttta | 600 |
| aaatacaaat | ggaaatttgg | agaaggaatt | aaggcaggag | attattttga | tttcacatta | 660 |
| agtgataatg | ttgaaacaca | tggtatatca | acactgcgta | aagttccgga | gataaaaagt | 720 |
| tcaacagaag | ataaagttat | ggcaaatggt | caagttataa | atgaacgtac | aattcgctat | 780 |
| acatttactg | attatataaa | taacaaaaaa | gatttaactg | ctgaattaaa | cttaaaccta | 840 |
| ttcattgacc | caacaacagt | gacaaagcaa | gggagtcaaa | aagttgaagt | aacactaggt | 900 |
| caaaataaag | tctcaaaaga | atttgatatc | aaatatttag | acggcgttaa | agatagaatg | 960 |
| ggtgttactg | ttaatggtcg | tattgatact | ttgaataaag | aagagggtaa | atttagccat | 1020 |
| tttgcatatg | tgaagcctaa | caaccagtcg | ttaacttctg | tcacagtaac | tggtcaagta | 1080 |
| acatctggat | ataaacaaag | tgctaataat | ccaacagtca | aagtatataa | acacattggt | 1140 |
| tcagatgaat | tagctgaaag | tgtttatgca | aagcttgatg | ataccagtaa | atttgaagat | 1200 |
| gtgactgaaa | aagtaaatct | atcttacaca | agtaatggtg | ggtacacatt | gaaccttggc | 1260 |
| gatttagata | ttcgaaaga | ctatgtaatt | aaatatgaag | gtgaatatga | tcaaaatgct | 1320 |
| aaggatctaa | atttccgaac | acatctttca | ggatatcata | atactacccc | atactatcct | 1380 |
| tattacccgt | attatccagt | tcaattaact | tggaacaacg | tgttgcatt | ttactctaat | 1440 |
| aatgctaaag | gcgatggtaa | agataaacca | aatgatccta | tcattgagaa | gagtgaacca | 1500 |
| attgatttag | acattaaatc | agagccacca | gtggagaagc | atgaattgac | tggtacaatc | 1560 |
| gaagaaagta | acgattctaa | gccaattgat | tttgaatatc | atacagctgt | tgaaggtgca | 1620 |
| gaaggtcatg | cagaaggtat | tattgaaact | gaagaagatt | ctattcatgt | ggattttgaa | 1680 |
| gaatctacac | atgaaaattc | aaaacatcac | gctgatgttg | ttgaatatga | agaggataca | 1740 |
| aacccaggtg | gtggccaagt | aacaactgag | tctaacttag | ttgaatttga | cgaagagtct | 1800 |
| acaaaaggta | ttgtaactgg | cgcagtgagc | gaccataaca | cagttgaaga | tacgaaagaa | 1860 |
| tatacaactg | aaagtaatct | gattgaatta | gtggatgaat | tacctgaaga | acatggtcaa | 1920 |
| gcacaagggc | caatcgagga | aattactgaa | acaatcatc | atatttctca | ttctggttta | 1980 |
| ggaactgaaa | atggtcacgg | taattatggc | gtgattgatg | aaatcgaaga | aaatagccac | 2040 |

```
gttgatatta agagtgaatt aggttatgaa ggtggccaaa atagcggtaa tcagtcattc    2100
gaggaagaca cagaagaaga taaacctaaa tatgaacaag gtggtaatat cgtagatatc    2160
gatttcgaca gtgtacctca aattcatggt caaaataatg gtaaccagtc attcgaggaa    2220
gacacagaag aagacaagcc taagtatgaa caaggtggta acatcattga tatcgacttc    2280
gacagtgtgc cacaaattca tggattcaat aagcataatg aaattattga agaagataca    2340
aacaaagata aacctaatta tcaatttggt ggacacaaca gtgttgattt tgaagaagat    2400
acacttccaa aagtaagtgg tcaaaatgaa ggtcaacaaa cgattgaaga agatacaacg    2460
ccgccaacac cgccaacacc agaggtacca agtgagccgg aaacaccaac accaccaaca    2520
ccagaagtac cgagtgagcc aggcgaacca acgccaccaa accggaagt accaagtgag    2580 ccggaaacac cagtaccacc aacaccagag gtaccatctg aacctggtaa accagtacca    2640
cctgctaaag aagaacctaa aaaaccttct aaaccagtgg aacaaggtaa ggtagtaaca    2700
cctgttattg aaatcaatga aaaggttaaa gcagtggcac caactaaaca aaaacaatct    2760
aagaaatctg aactacctga aacaggtgga gaagaatcaa caaacaaagg tatgttgttc    2820
ggcggattat tcagcattct aggtttagta ttattacgca gaaataaaaa gaataacaaa    2880
gcataa                                                              2886

<210> SEQ ID NO 78
<211> LENGTH: 1737
<212> TYPE: DNA
<213> ORGANISM: S. aureus

<400> SEQUENCE: 78
atgaaattta agtcattgat tacaacaaca ttagcattag gcgttatagc atcaacagga      60
gcaaacttta tactaacga agcatctgcc gcagctaagc cattagataa atcatcaagt     120
acattacacc atggacattc taacatccag attccatata caattactgt gaacggtaca     180
agccaaaaca ttttatcaag cttaacattt aataagaatc aaaatattag ttataaagat     240
atagagaata aagttaaatc agttttatac tttaatagag gtattagtga tatcgattta     300
agactttcaa agcaagcgga atatacggtt cattttaaaa atggaacaaa aagagttatc     360
gatttgaaat caggtatcta cacagctgac ttaatcaata caagtgacat taaagctatc     420
agtgttaacg tagatactaa aaagcaacct aaagataaag ctaaagcaaa tgttcaagtg     480
ccatatacaa tcacagtgaa cggcacaagc caaaacattt tatcaaacct aacatttaat     540
aaaaatcaaa atattagtta caagatttta gagggtaaag ttaaatcagt tttagaatca     600
aatagaggta ttactgatgt tgatttaaga ctttcgaagc aagcgaaata cagttaat      660 tttaaaaatg gaacgaagaa agttatcgat ttgaaatcag gtatttacac agcgaattta     720
atcaattcaa gtgatattaa agtatcaat attaacgtag atacaaaaaa acatatcgaa     780
aataaagcta aagaaaacta tcaagttcca tattcaatta atctaaatgg tacatctaca     840
aacattttat cgaatctttc attttcaaat aaaccttgga caaattacaa aaatttaact     900
agtcaaataa aatcagtact gaagcatgat agaggtatta gtgaacaaga tttaaaatat     960
gctaagaaag cttattatac tgtttatttt aaaaatggtg gtaaaagaat cttacagtta    1020
aattcaaaaa attacacagc aaacttagtt catgcgaaag atgttaagag aattgaaatt    1080
actgttaaaa caggaactaa agcgaaagca gacagatatg taccatacac aattgcagta    1140
aatggcacat caacaccaat tttatcaaaa ctaaaaattt cgaataaaca attaattagt    1200
tacaaatatt taaacgacaa agtgaaatct gtattaaaaa gtgaaagagg tatcagtgat    1260
```

```
cttgacttaa aatttgcgaa acaagcaaaa tatacagtat atttcaaaaa tggaaagaaa    1320
caagtagtga atttaaaatc agacatcttt acacctaatt tatttagtgc caaagatatt    1380
aaaaagattg atattgatgt aaacaatac actaaatcaa aaaaaaaaat aaataaatct     1440
aataatgtga aattcccagt aacaataaat aaatttgaaa acatagtttc aaatgaattt    1500
gtgttctata atgcaagcaa aattacaatt aatgatttaa gtataaaact taaatcagca    1560
atggcaaatg atcaagggat aactaaacat gacataggac ttgctgaacg cgcagtgtat    1620
aaagtgtatt ttaaaaatgg ttcgtcaaaa tatgtagact taaaaactga gtataaagat    1680
gaaagagtat ttaaagcaac tgacattaaa aaggtagata ttgaacttaa attctaa      1737
```

<210> SEQ ID NO 79
<211> LENGTH: 2688
<212> TYPE: DNA
<213> ORGANISM: S. aureus

<400> SEQUENCE: 79

```
atgaacaaac atcacccaaa attaaggtct ttctattcta ttagaaaatc aactctaggc      60
gttgcatcgg tcattgtcag tacactattt ttaattactt ctcaacatca agcacaagca    120
gcagaaaata caaatacttc agataaaatc tcggaaaatc aaaataataa tgcaactaca    180
actcagccac ctaaggatac aaatcaaaca caacctgcta cgcaaccagc aaacactgcg    240
aaaaactatc ctgcagcgga tgaatcactt aaagatgcaa ttaaagatcc tgcattagaa    300
aataagaaac atgatatagg tccaagagaa caagtcaatt tccagttatt agataaaaac    360
aatgaaacgc agtactatca cttttttcagc atcaaagatc cagcagatgt gtattacact    420
aaaaagaaag cagaagttga attagacatc aatactgctt caacatggaa gaagtttgaa    480
gtctatgaaa acaatcaaaa attgccagtg agacttgtat catatagtcc tgtaccagaa    540
gaccatgcct atattcgatt cccagtttca gatggcacac aagaattgaa aattgtttct    600
tcgactcaaa ttgatgatgg agaagaaaca aattatgatt atactaaatt agtatttgct    660
aaacctattt ataacgatcc ttcacttgta aaatcagata caaatgatgc agtagtaacg    720
aatgatcaat caagttcagt cgcaagtaat caaacaaaca cgaatacatc taatcaaaat    780
atatcaacga tcaacaatgc taataatcaa ccgcaggcaa cgaccaatat gagtcaacct    840
gcacaaccaa atcgtcaac gaatgcagat caagcgtcaa gccaaccagc tcatgaaaca    900
aattctaatg gtaatactaa cgataaaacg aatgagtcaa gtaatcagtc ggatgttaat    960
caacagtatc caccagcaga tgaatcacta caagatgcaa ttaaaaaccc ggctatcatc   1020
gataaagaac atacagctga taattggcga ccaattgatt tcaaatgaa aatgataaa    1080 ggtgaaagac agttctatca ttatgctagt actgttgaac cagcaactgt catttttaca   1140
aaaacaggac caataattga attaggttta agacagcttt caacatggaa gaaatttgaa   1200
gtttatgaag gtgacaaaaa gttaccagtc gaattagtat catatgattc tgataaagat   1260
tatgcctata ttcgtttccc agtatctaat ggtacgagag aagttaaaat tgtgtcatct   1320
attgaatatg gtgagaacat ccatgaagac tatgattata cgctaatggt ctttgcacag   1380
cctattacta ataccccaga cgactatgtg gatgaagaaa catacaattt acaaaaatta   1440
ttagctccgt atcacaaagc taaaacgtta gaaagacaag tttatgaatt agaaaaatta   1500
caagagaaat tgccagaaaa atataaggcg aatataaaa agaaattaga tcaaactaga   1560
gtagagttag ctgatcaagt taaatcagca gtgacggaat ttgaaaatgt tacacctaca   1620
```

| | |
|---|---|
| aatgatcaat taacagattt acaagaagcg cattttgttg tttttgaaag tgaagaaaat | 1680 |
| agtgagtcag ttatggacgg ctttgttgaa catccattct atacagcaac tttaaatggt | 1740 |
| caaaaatatg tagtgatgaa acaaaggat gacagttact ggaaagattt aattgtagaa | 1800 |
| ggtaaacgtg tcactactgt ttctaaagat cctaaaaata attctagaac gctgattttc | 1860 |
| ccatatatac ctgacaaagc agtttacaat gcgattgtta aagtcgttgt ggcaaacatt | 1920 |
| ggttatgaag gtcaatatca tgtcagaatt ataaatcagg atatcaatac aaaagatgat | 1980 |
| gatacatcac aaaataacac gagtgaaccg ctaaatgtac aaacaggaca agaaggtaag | 2040 |
| gttgctgata cagatgtagc tgaaaatagc agcactgcaa caaatcctaa agatgcgtct | 2100 |
| gataaagcag atgtgataga accagagtct gacgtggtta agatgctga taataatatt | 2160 |
| gataaagatg tgcaacatga tgttgatcat ttatccgata tgtcggataa taatcacttc | 2220 |
| gataaatatg atttaaaaga aatggatact caaattgcca agatactga tagaaatgtg | 2280 |
| gataaagatg ccgataatag cgttggtatg tcatctaatg tcgatactga taaagactct | 2340 |
| aataaaaata aagacaaagt catacagctg aatcatattg ccgataaaaa taatcatact | 2400 |
| ggaaaagcag caaagcttga cgtagtgaaa caaaattata ataatacaga caaagttact | 2460 |
| gacaaaaaaa caactgaaca tctgccgagt gatattcata aaactgtaga taaacagtg | 2520 |
| aaaacaaaag aaaaagccgg cacaccatcg aaagaaaaca aacttagtca atctaaaatg | 2580 |
| ctaccaaaaa ctggagaaac aacttcaagc caatcatggt ggggcttata tgcgttatta | 2640 |
| ggtatgttag ctttattcat tcctaaattc agaaaagaat ctaaataa | 2688 |

<210> SEQ ID NO 80
<211> LENGTH: 2238
<212> TYPE: DNA
<213> ORGANISM: S. aureus

<400> SEQUENCE: 80

| | |
|---|---|
| gctgagacga cacaagatca aactactaat aaaaacgttt tagatagtaa taaagttaaa | 60 |
| gcaactactg aacaagcaaa agctgaggta aaaaatccaa cgcaaaacat ttctggcact | 120 |
| caagtatatc aagaccctgc tattgtccaa ccaaaaacag caaataacaa acaggcaat | 180 |
| gctcaagtaa gtcaaaaagt tgatactgca caagtaaatg gtgacactcg tgctaatcaa | 240 |
| tcagcgacta caaataatac gcagcctgtt gcaaagtcaa caagcactac agcacctaaa | 300 |
| actaacacta atgttacaaa tgctggttat agtttagttg atgatgaaga tgataattca | 360 |
| gaaaatcaaa ttaatccaga attaattaaa tcagctgcta aacctgcagc tcttgaaacg | 420 |
| caatataaaa ccgcagcacc taaagctgca actacatcag cacctaaagc taaaactgaa | 480 |
| gcgacaccta agtaactac ttttagcgct tcagcacaac caagatcagt tgctgcaaca | 540 |
| ccaaaaacga gtttgccaaa atataaacca caagtaaact cttcaattaa cgattacatt | 600 |
| tgtaaaaata acttaaaagc acctaaaatt gaagaagatt atacatctta cttccctaaa | 660 |
| tacgcatacc gtaacggcgt aggtcgtcct gaaggtatcg tagttcatga tacagctaat | 720 |
| gatcgttcga cgataaatgg tgaaattagt tatatgaaaa ataactatca aaacgcattc | 780 |
| gtacatgcat tgttgatgg ggatcgtata atcgaaacag caccaacgga ttacttatct | 840 |
| tggggtgtcg gtgcagtcgg taaccctaga ttcatcaatg ttgaaatcgt acacacacac | 900 |
| gactatgctt catttgcacg ttcaatgaat aactatgctg actatgcagc tacacaatta | 960 |
| caatattatg gtttaaaacc agacagtgct gagtatgatg gaaatggtac agtatggact | 1020 |
| cactacgctg taagtaaaata tttaggtggt actgaccatg ccgatccaca tggatattta | 1080 |

```
agaagtcata attatagtta tgatcaatta tatgacttaa ttaatgaaaa atatttaata    1140
aaaatgggta aagtggcgcc atggggtacg caatctacaa ctacccctac tacaccatca    1200
aaaccaacaa caccgtcgaa accatcaact ggtaaattaa cagttgctgc aaacaatggt    1260
gtcgcacaaa tcaaaccaac aaatagtggt ttatatacta ctgtatacga caaaactggt    1320
aaagcaacta atgaagttca aaaaacattt gctgtatcta aaacagctac attaggtaat    1380
caaaaattct atcttgttca agattacaat tctggtaata aatttggttg ggttaaagaa    1440
ggcgatgtgg tttacaacac agctaaatca cctgtaaatg taaatcaatc atattcaatc    1500
aaacctggta cgaaacttta tacagtacct tggggtacat ctaaacaagt tgctggtagt    1560
gtgtctggct ctggaaacca aacatttaag gcttcaaagc aacaacaaat tgataaatca    1620
atttatttat atggctctgt gaatggtaaa tctggttggg taagtaaagc atatttagtt    1680
gatactgcta aacctacgcc tacaccaaca cctaagccat caacacctac aacaaataat    1740
aaattaacag tttcatcatt aaacggtgtt gctcaaatta atgctaaaaa caatggctta    1800
ttcactacag tttatgacaa aactggtaag ccaacgaaag aagttcaaaa acatttgct    1860 gtaacaaaag aagcaagttt aggtggaaac aaattctact tagttaaaga ttacaatagt    1920
ccaactttaa ttggttgggt taaacaaggt gacgttattt ataacaatgc aaaatcacct    1980
gtaaatgtaa tgcaaacata tacagtaaaa ccaggcacta aattatattc agtaccttgg    2040
ggcacttata acaagaagc tggtgcagtt tctggtacag gtaaccaaac ttttaaagcg    2100
actaagcaac aacaaattga taaatctatc tatttatttg gaactgtaaa tggtaaatct    2160
ggttgggtaa gtaaagcata tttagctgta cctgctgcac ctaaaaaagc agtagcacaa    2220
ccaaaaacag ctgtaaaa                                                  2238

<210> SEQ ID NO 81
<211> LENGTH: 1443
<212> TYPE: DNA
<213> ORGANISM: S. aureus

<400> SEQUENCE: 81
gcttatactg ttactaaacc acaaacgact caaacagtta gcaagattgc tcaagttaaa     60
ccaaacaaca ctggtattcg tgcttctgtt tatgaaaaaa cagcgaaaaa cggtgcgaaa    120
tatgcagacc gtacgttcta tgtaacaaaa gagcgtgctc atggtaatga acgtatgta    180 ttattaaaca atacaagcca taacatccca ttaggttggt tcaatgtaaa agacttaaat    240
gttcaaaact taggcaaaga agttaaaacg actcaaaaat atactgttaa taaatcaaat    300
aacggcttat caatggttcc ttggggtact aaaaaccaag tcatttttaac aggcaataac    360 attgctcaag gtacatttaa tgcaacgaaa caagtatctg taggcaaaga tgtttattta    420
tacggtacta ttaataaccg cactggttgg gtaaatgcaa aagatttaac tgcaccaact    480
gctgtgaaac caactacatc agctgccaaa gattataact acacttatgt aattaaaaat    540
ggtaatggtt attactatgt aacaccaaat tctgatacag ctaaatactc attaaaagca    600
tttaatgaac aaccattcgc agttgttaaa gaacaagtca ttaatggaca aacttggtac    660
tatggtaaat tatctaacgg taaattagca tggattaaat caactgattt agctaaagaa    720
ttaattaagt ataatcaaac aggtatgaca ttaaaccaag ttgctcaaat acaagctggt    780
ttacaatata aaccacaagt acaacgtgta ccaggtaagt ggacagatgc taaatttaat    840
gatgttaagc atgcaatgga tacgaagcgt ttagctcaag atccagcatt aaaatatcaa    900
```

| | |
|---|---|
| ttcttacgct tagaccaacc acaaaatatt tctattgata aaattaatca attcttaaaa | 960 |
| ggtaaaggtg tattagaaaa ccaaggtgct gcatttaaca aagctgctca aatgtatggc | 1020 |
| attaatgaag tttatcttat ctcacatgcc ctattagaaa caggtaacgg tacttctcaa | 1080 |
| ttagcgaaag gtgcagatgt agtgaacaac aaagttgtaa ctaactcaaa cacgaaatac | 1140 |
| cataacgtat ttggtattgc tgcatatgat aacgatcctt tacgtgaagg tattaaatat | 1200 |
| gctaaacaag ctggttggga cacagtatca aaagcaatcg ttggtggtgc taaattcatc | 1260 |
| ggcaactcat atgtaaaagc tggtcaaaat acactttaca aaatgagatg gaatcctgca | 1320 |
| catccaggaa cacaccaata tgctacagat gtagattggg ctaacatcaa tgctaaaatc | 1380 |
| atcaaaggct actatgataa aattggcgaa gtcggcaaat acttcgacat cccacaatat | 1440 |
| aaa | 1443 |

<210> SEQ ID NO 82
<211> LENGTH: 2118
<212> TYPE: DNA
<213> ORGANISM: S. aureus

<400> SEQUENCE: 82

| | |
|---|---|
| gatcgtgtat tagcctcaca tccagatgtt gcgacaatac gtcaaaacgt gacagcagcg | 60 |
| aatgccgcta atcagcact tgatcaagca cgtaatggct taacagtcga taaagcgcct | 120 |
| ttagaaaatg cgaaaaatca actacaacat agtattgaca cgcaaacaag tacaactggt | 180 |
| atgacacaag actctataaa tgcatacaat gcgaagttaa cagctgcacg taataagatt | 240 |
| caacaaatca atcaagtatt agcaggttca ccgactgtag aacaaattaa tacaaatacg | 300 |
| tctacagcaa atcaagctaa atctgattta gatcatgcac gtcaagcttt aacaccagat | 360 |
| aaagcgccgc ttcaaactgc gaaaacgcaa ttagaacaaa gcattaatca accaacggat | 420 |
| acaacaggta tgacgaccgc ttcgttaaat gcgtacaacc aaaaattaca agcagcgcgt | 480 |
| caaaagttaa ctgaaattaa tcaagtgttg aatggcaacc caactgtcca aaatatcaat | 540 |
| gataaagtga cagaggcaaa ccaagctaag gatcaattaa atacagcacg tcaaggttta | 600 |
| acattagata gacagccagc gttaacaaca ttacatggtg catctaactt aaaccaagca | 660 |
| caacaaaata atttcacgca acaaattaat gctgctcaaa atcatgctgc gcttgaaaca | 720 |
| attaagtcta acattacggc tttaaatact gcgatgacga aattaaaaga cagtgttgcg | 780 |
| gataataata caattaaatc agatcaaaat tacactgacg caacaccagc taataaacaa | 840 |
| gcgtatgata atgcagttaa tgcggctaaa ggtgtcattg gagaaacgac taatccaacg | 900 |
| atggatgtta acacagtgaa ccaaaaagca gcatctgtta atcgacgaa agatgcttta | 960 |
| gatggtcaac aaaacttaca acgtgcgaaa acagaagcaa caaatgcgat tacgcatgca | 1020 |
| agtgatttaa accaagcaca aaagaatgca ttaacacaac aagtgaatag tgcacaaaac | 1080 |
| gtgcaagcag taaatgatat taaacaaacg actcaaagct taaatactgc tatgacaggt | 1140 |
| ttaaaacgtg gcgttgctaa tcataaccaa gtcgtacaaa gtgataatta tgtcaacgca | 1200 |
| gatactaata agaaaaatga ttacaacaat gcatacaacc atgcgaatga cattattaat | 1260 |
| ggtaatgcac aacatccagt tataacacca agtgatgtta acaatgcttt atcaaatgtc | 1320 |
| acaagtaaag aacatgcatt gaatggtgaa gctaagttaa atgctgcgaa acaagaagcg | 1380 |
| aatactgcat taggtcattt aaacaattta aataatgcac aacgtcaaaa cttacaatcg | 1440 |
| caaattaatg gtgcgcatca aattgatgca gttaatacaa ttaagcaaaa tgcaacaaac | 1500 |
| ttgaatagtg caatgggtaa cttaagacaa gctgttgcag ataaagatca agtgaaacgt | 1560 |

| acagaagatt atgcggatgc agatacagct aaacaaaatg catataacag tgcagtttca | 1620 |
| agtgccgaaa caatcattaa tcaaacaaca atccaacga tgtctgttga tgatgttaat | 1680 |
| cgtgcaactt cagctgttac ttctaataaa aatgcattaa atggttatga aaaattagca | 1740 |
| caatctaaaa cagatgctgc aagagcaatt gatgcattac cacatttaaa taatgcacaa | 1800 |
| aaagcagatg ttaaatctaa aattaatgct gcatcaaata ttgctggcgt aaatactgtt | 1860 |
| aaacaacaag gtacagattt aaatacacg atgggtaact tgcaaggtgc aatcaatgat | 1920 |
| gaacaaacga cgcttaatag tcaaaactat caagatgcga caccctagtaa gaaaacagca | 1980 |
| tacacaaatg cggtacaagc tgcgaaagat attttaaata aatcaaatgg tcaaaataaa | 2040 |
| acgaaagatc aagttactga agcgatgaat caagtgaatt ctgctaaaaa taacttagat | 2100 |
| ggtacgcgtt tattagat | 2118 |

<210> SEQ ID NO 83
<211> LENGTH: 726
<212> TYPE: DNA
<213> ORGANISM: S. aureus

<400> SEQUENCE: 83

| gcttctacac aacatacagt acaatctggt gaatcattat ggagtattgc tcaaaaatac | 60 |
| aacacttcag tagagagtat taaacaaaat aaccaattag ataacaactt ggtattccct | 120 |
| ggtcaagtta tctcagtagg tggaagtgat gcacaaaata cgtcaaacac ttctccacaa | 180 |
| gctggttcag catcatctca tactgtacaa gctggtgaat cattaaatat cattgctagc | 240 |
| agatatggtg tttcagttga tcaattaatg gcagccaata acttacgtgg ttatttaatt | 300 |
| atgcctaacc aaacattaca aattcctaat ggtggatcag gtggtacaac accaacagct | 360 |
| acaacaggta gcaatggcaa tgcatcatct tttaatcacc aaaatttata cactgctggt | 420 |
| caatgtacat ggtacgtatt tgaccgtcgt gctcaagctg gtagtccaat tagcacatat | 480 |
| tggtcagacg ctaagtattg ggctggtaac gcagctaatg atggttacca agtaaacaac | 540 |
| acaccatcag ttggttcaat tatgcaaagc acacctggtc catatggtca tgttgcttat | 600 |
| gttgaacgtg tcaatggtga tggtagtatc ttgatttctg aaatgaatta cacatatggt | 660 |
| ccatacaata tgaactaccg tacaattcca gcttcagaag tttctagcta tgcattcatc | 720 |
| cattaa | 726 |

<210> SEQ ID NO 84
<211> LENGTH: 2988
<212> TYPE: DNA
<213> ORGANISM: S. aureus

<400> SEQUENCE: 84

| atgaataata aaaagacagc aacaaataga aaaggcatga taccaaatcg attaaacaaa | 60 |
| ttttcgataa gaaagtattc tgtaggtact gcttcaattt tagtagggac aacattgatt | 120 |
| tttgggttaa gtggtcatga agctaaagcg gcagaacata cgaatggaga attaaatcaa | 180 |
| tcaaaaaatg aaacgacagc cccaagtgag aataaaacaa ctaaaaaagt tgatagtcgt | 240 |
| caactaaaag acaatacgca aactgcaact gcagatcagc taaagtgac aatgagtgat | 300 |
| agtgcaacag ttaagaaaac tagtagtaac atgcaatcac cacaaaacgc tacagctaat | 360 |
| caatctacta caaaaactag caatgtaaca acaaatgata atcatcaac tacatatagt | 420 |
| aatgaaactg ataaaagtaa tttaacacaa gcaaaagatg tttcaactac acctaaaaca | 480 |

```
acgactatta aaccaagaac tttaaatcgc atggcagtga atactgttgc agctccacaa    540
caaggaacaa atgttaatga taaagtacat ttttcaaata ttgacattgc gattgataaa    600
ggacatgtta atcagactac tggtaaaact gaattttggg caacttcaag tgatgtttta    660
aaattaaaag caaattacac aatcgatgat tctgttaaag agggcgatac atttactttt    720
aaatatggtc aatatttccg tccaggatca gtaagattac cttcacaaac tcaaaattta    780
tataatgccc aaggtaatat tattgcaaaa ggtatttatg atagtacaac aaacacaaca    840
acatatactt ttacgaacta tgtagatcaa tatacaaatg ttagaggtag ctttgaacaa    900
gttgcatttg cgaaacgtaa aaatgcaaca actgataaaa cagcttataa aatggaagta    960
actttaggta atgatacata tagcgaagaa atcattgtcg attatggtaa taaaaaagca   1020
caaccgctta tttcaagtac aaactatatt aacaatgaag atttatcgcg taatatgact   1080
gcatatgtaa atcaacctaa aaatacatat actaaacaaa cgtttgttac taatttaact   1140
ggatataaat ttaatccaaa tgcaaaaaac ttcaaaattt acgaagtgac agatcaaaat   1200
caatttgtgg atagtttcac ccctgatact tcaaaactta agatgttac  tgatcaattc   1260
gatgttattt atagtaatga taataaaaca gctacagtcg atttaatgaa aggccaaaca   1320
agcagcaata aacaatacat cattcaacaa gttgcttatc cagataatag ttcaacagat   1380
aatggaaaaa ttgattatac tttagacact gacaaaacta aatatagttg gtcaaatagt   1440
tattcaaatg tgaatggctc atcaactgct aatggcgacc aaaagaaata taatctaggt   1500
gactatgtat gggaagatac aaataaagat ggtaaacaag atgccaatga aaaagggatt   1560
aaaggtgttt atgtcattct taaagatagt aacggtaaag aattagatcg tacgacaaca   1620
gatgaaaatg gtaaatatca gttcactggt ttaagcaatg gaacttatag tgtagagttt   1680
tcaacaccag ccggttatac accgacaact gcaaatgtag gtacagatga tgctgtagat   1740
tctgatggac taactacaac aggtgtcatt aaagacgctg acaacatgac attagatagt   1800
ggattctaca aaacaccaaa atatagtta  ggtgattatg tttggtacga cagtaataaa   1860
gatggtaaac aagattcgac tgaaaaagga attaaggtg  ttaaagttac tttgcaaaac   1920
gaaaaaggcg aagtaattgg tacaactgaa acagatgaaa atggtaaata ccgctttgat   1980
aatttagata gtggtaaata caaagttatc tttgaaaaac ctgctggctt aactcaaaca   2040
ggtacaaata caactgaaga tgataaagat gccgatggtg gcgaagttga tgtaacaatt   2100
acggatcatg atgatttcac acttgataat ggctactacg aagaagaaac atcagatagc   2160
gactcagatt ctgacagcga ttcagactca gatagcgact cagattcaga tagcgactca   2220
gattcagaca gcgattcaga cagcgactca gactcagata gcgattcaga ttcagacagc   2280
gactcagact cagacagcga ttcagactcg gatagcgact cagactcaga tagcgactca   2340
gattcggata gcgactcaga ctcagatagc gattcagatt cagatagcga ttcggactca   2400
gacagtgatt cagattcaga ctcagatagc gactcagatt ctgacagcga ttcagactca   2460
gacagcgact cagactcaga cagtgattca gattcagaca gcgactcaga ttcagatagc   2520
gactcagact cagatagcga ctcagattca gatagcgatt cggactcaga caacgactca   2580
gattcagata gcgattcaga ttcagatagc gactcagatt cggacagcga ttcagactca   2640
gatagcgatt cagactcaga cagcgattca gattcagata gcgactcaga ctcagatagc   2700
gactcagact cggatagcga ttcagattca gacagcgact cagattcaga tagcgattcg   2760
gactcagaca cgactcaga  ttcagatagc gattcagatt cagatgcagg taaacatact   2820
ccggctaaac caatgagtac ggttaaagat cagcataaaa cagctaaagc attaccagaa   2880
```

```
acaggtagtg aaaataataa ttcaaataat ggcacattat tcggtggatt attcgcggca    2940
ttaggatcat tattgttatt cggtcgtcgt aaaaaacaaa ataaataa                 2988

<210> SEQ ID NO 85
<211> LENGTH: 6561
<212> TYPE: DNA
<213> ORGANISM: S. aureus

<400> SEQUENCE: 85
atgaatttgt aaagaaaaa taaatatagt attaggaagt ataaagtagg catattctct       60
actttaatcg gaacagtttt attactttca aacccaaatg gtgcacaagc cttaactacg     120
gataataatg tacaaagcga tactaatcaa gcaacacctg taaattcaca agataaagat     180
gttgctaata atagaggttt agcaaatagt gcgcagaata cacctaatca atctgcaaca     240
accaatcaag caacgaatca agcattggtt aatcataata atggtagtat agtaaatcaa     300
gctacgccaa catcagtgca atcaagtacg ccttcagcac aaaacaataa tcatacagat     360
ggcaatacaa cagcaactga gacagtgtca aacgctaata ataatgatgt agtgtcgaat     420
aataccgcat taaatgtacc aactaaaaca aatgaaaatg gttcaggagg acatctaact     480
ttaaaggaaa ttcaagaaga tgttcgtcat tcttcaaata aaccagagct agttgcaatt     540
gctgaaccag catctaatag accgaaaaag agaagtagac gtgcggcacc ggcagatcct     600
aatgcaactc cagcagatcc agcggctgca gcggtaggaa acggtggtgc accagttgca     660
attacagcgc catatacgcc aacaactgat cctaatgcca ataatgcagg acaaaatgca     720
cctaacgaag tgctgtcatt tgatgacaat ggtattagac caagtaccaa ccgttctgtg     780
ccaacagtaa acgttgttaa taacttgccg ggcttcacac taatcaatgg tgcaaagta     840 ggggtgttta gtcatgcaat ggtaagaacg agcatgtttg attcaggaga taataagaac     900
tatcaagcac aaggaaatgt aattgcatta ggtcgtatac atggaactga tacgaatgac     960
catggcgatt ttaatggtat cgagaaagca ttaacagtaa atccgaattc tgaattaatc    1020
tttgaattta atacaatgac tactaaaaac ggtcaaggcg caacaaatgt tattatcaaa    1080
aatgctgata ctaatgatac gattgctgaa aagactgttg aaggcggtcc aactttgcgt    1140
ttatttaaag tacctgataa tgtgagaaat ctcaaaattc aatttgtacc taaaaatgac    1200
gcaataacag atgcgcgtgg catttatcaa ctaaagatg gttacaaata ctatagcttt    1260
gttgactcta tcggacttca ttctgggtca catgtttttg ttgaaagacg aacaatggat    1320
ccaacagcaa caaataataa agagtttact gtaacaacat cattaaagaa taatggtaat    1380
tctggtgctt ctctagatac aaatgacttt gtatatcaag ttcaattacc tgaaggtgtt    1440
gaatatgtga acaattcatt gactaaagat tttccaagta acaattcagg cgttgatgtt    1500
aatgatatga atgttacata tgatgcagca atcgtgtga taacaattaa aagtactgga    1560
ggaggtacag caaactctcc ggcacgactt atgcctgata aaatactcga tttaagatat    1620
aaattacgtg taaataatgt gccgacacca agaacagtaa catttaacga gacattaacg    1680
tataaaacat atacacaaga tttcattaat tcagctgcag aaagtcatac tgtaagtaca    1740
aatccatata ctatcgatat catcatgaat aaagatgcat tacaagccga agttgacaga    1800
cgtattcaac aagctgatta tacatttgcg tcattagata tctttaatgg tctgaaacga    1860
cgcgcacaaa cgattttaga tgaaaatcgt aacaatgtac cattaaataa aagagtttct    1920
caagcatata ttgattcatt aactaatcaa atgcaacata cgttaattcg aagtgttgat    1980
```

```
gctgaaaatg cagttaataa aaaagttgac caaatggaag atttagttaa tcaaaatgat    2040
gaattgacag atgaagaaaa acaagcagca atacaagtta tcgaggaaca taaaaatgaa    2100
ataattggta atattggtga ccaaacgact gatgatggcg ttactagaat caaagatcaa    2160
ggtatacaga ccttaagtgg ggatactgca acaccggttg ttaaaccaaa tgctaaaaaa    2220
gcaatacgtg ataaagcaac gaaacaaagg gaaattatca atgcaacacc agatgctact    2280
gaagacgaga ttcaagatgc actaaatcaa ttagctacgg atgaaacaga tgctattgat    2340
aatgttacga atgctactac aaatgctgac gttgaaacag ctaaaaataa tggcatcaat    2400
actattggag cagttgttcc tcaagtaact cataaaaaag ctgcaagaga tgcaattaac    2460
caagcaacag caacgaaaag acaacaaata aatagtaata gagaagcaac tcaggaagag    2520
aaaaatgcag cattgaacga attaactcaa gcaaccaacc atgctttaga acaaatcaat    2580
caagcaacaa caaatgctaa tgttgataac gccaaaggag atggtctaaa tgccattaat    2640
ccaattgctc ctgtaactgt tgttaagcaa gctgcaaggg atgccgtatc acatgatgca    2700
caacaacata tcgcagagat caatgctaat cctgatgcga ctcaagaaga aagacaagca    2760
gcaattgaca aagtgaatgc tgctgtaact gcagcaaaca caaacatttt aaacgctaat    2820
accaatgctg atgttgaaca gtaaagacaa atgcgattc aaggaataca agcaattaca    2880
ccagctacaa aagtaaaaac agatgcaaaa aatgccatcg ataaaagtgc ggaaacgcaa    2940
cataatacga tatttaataa taatgatgcg acgctcgaag aacaacaagc agcacaacaa    3000
ttacttgatc aagctgtagc cacagcgaag caaaatatta atgcagcaga tacgaatcaa    3060
gaagttgcac aagcaaaaga tcagggcaca caaaatatag tagtgattca accggcaaca    3120
caagttaaaa cggatactcg caatgttgta aatgataaag cgcgagaggc gataacaaat    3180
atcaatgcta caactggcgc gactcgagaa gagaaacaag aagcgataaa tcgtgtcaat    3240
acacttaaaa atagagcatt aactgatatt ggtgtgacgt ctactactgc gatggtcaat    3300
agtattagag acgatgcagt caatcaaatc ggcgcagttc aaccgcatgt aacgaagaaa    3360
caaactgcta caggtgtatt aaatgattta gcaactgcta aaaagcaaga aattaatcaa    3420
aacacaaatg caacaactga agaaaagcaa gtggctttaa atcaagtgga tcaagagtta    3480
gcaacggcaa ttaataatat aaatcaagct gatacaaatg cggaagtaga tcaagcgcaa    3540
caattaggta caaaagcaat taatgcgatt cagccaaata ttgttaaaaa acctgcagca    3600
ttagcacaaa tcaatcagca ttataatgct aaattagctg aaatcaatgc tacaccagat    3660
gcaacgaatg atgagaaaaa tgctgcgatc aatactttaa atcaagacag acaacaagct    3720
attgaaagta ttaacaagc taacacaaat gcagaagtag accaagctgc gacagtagca    3780
gagaataata tcgatgctgt tcaagttgat gtagtaaaaa acaagcagc gcgagataaa    3840 atcactgctg aagtggcgaa gcgtattgaa gcggttaaac aaacacctaa tgcaactgac    3900
gaagaaaagc aggctgctgt taatcaaatc aatcaactta agatcaagc aattaatcaa    3960 attaatcaaa accaaacaaa tgatcaggta gacacaacta caaatcaagc ggtaaatgct    4020
atagataatg ttgaagctga agtagtaatt aaaacaaagg caattgcaga tattgaaaaa    4080
gctgttaaag aaaagcaaca gcaaattgat aatagtcttg attcaacaga taatgagaaa    4140
gaagttgctt cacaagcatt agctaaagaa aagaaaaag cacttgcagc tattgaccaa    4200
gctcaaacga atagtcaggt gaatcaagca gcaacaaatg gtgtatcagc gattaaaatt    4260
attcaacctg aaacaaaagt taaaccagct gcacgtgaaa aaatcaatca aaaagcgaat    4320
gaattacgtg ctaagattaa tcaggataaa gaagcaacag cagaagaaag acaagtagca    4380
```

```
ctagataaaa tcaatgaatt tgtaaatcaa gccatgacag atattacgaa taatagaaca    4440
aatcaacaag ttgatgatac aacaagtcaa gcgcttgata gcattgcttt agtgacgcct    4500
gaccatattg ttagagcagc tgctagagat gcagttaagc aacaatatga agctaaaaag    4560
cgcgaaattg agcaagcgga acatgcgact gatgaagaaa aacaagttgc tttaaatcaa    4620
ttagcgaata atgaaaaacg tgcattacaa aacatcgatc aagcaatagc gaataatgat    4680
gtgaaacgtg ttgaaacaaa tggcattgct acactaaaag gtgtacaacc tcatattgta    4740
attaagcctg aagcacaaca agcaataaaa gcaagtgcag aaaatcaagt agaatcaata    4800
aaagatacac cacatgcaac agttgatgaa ttagatgaag cgaatcaatt aattagcgac    4860
acactcaaac aagcgcaaca agaaatagaa aatacaaatc aagatgctgc tgttactgat    4920
gttagaaatc aaacaatcaa ggcaatagag caaataaaac ctaaagtaag acgtaaacga    4980
gctgcgcttg atagcattga agaaaataat aaaaatcaac tcgatgcaat ccgaaatacg    5040
ttggatacta ctcaagatga aagagatgtt gctattgata ctttaaataa aattgtaaat    5100
acaattaaaa atgacattgc acaaaacaaa acgaatgcag aagtggatcg aactgagact    5160
gatggcaacg acaacatcaa agtgatttta cctaaagttc aagttaaacc agcagcgcgt    5220
caatctgttg gtgtaaaagc cgaagctcaa aatgcactaa tcgatcaaag cgatttatca    5280
actgaagaag aaagactagc tgctaaacat ttagtagaac aagcacttaa tcaggctatt    5340
gatcagatca atcatgcaga taagactgcc caagttaatc aagatagtat aaatgctcaa    5400
aatattattt caaaaattaa accagcgaca acagttaaag caacagcatt acaacaaatt    5460
caaaatatcg ctacaaataa aattaattta attaaagcaa ataacgaagc gacagatgaa    5520
gaacaaaata ttgcaatagc acaagttgaa aaagagttaa ttaaagctaa acaacaaatt    5580
gctagtgcag tgactaatgc agatgtggca tatttattgc atgatgagaa aaacgaaatt    5640
cgtgaaatcg aacctgttat taacagaaag gcgtctgctc gagaacaatt gacaacatta    5700
ttcaacgata aaaaacaagc aattgaagcg aatattcaag caacggtaga agaaagaaat    5760
agtatattag cacagttaca aaatatttat gacactgcta ttggacaaat tgatcaagat    5820
cgtagcaatg cacaagttga taaaacagca tcattaaatc tacaaacaat acatgattta    5880
gatgtacatc ctattaaaaa gccagatgct gaaaaaacga ttaatgatga tcttgcacgc    5940
gtcactgctt tagtgcaaaa ttatcgaaaa gtaagtaatc gtaataaggc tgatgcatta    6000
aaagctataa ctgctttaaa attacaaatg gatgaagaat taaaaacagc acgcactaat    6060
gctgatgttg atgcagtttt aaaacgattt aatgttgcat taagcgatat agaagcagta    6120
attactgaaa agaaaaatag cttactgcga attgataaca ttgctcaaca aacatatgcg    6180
aaattcaaag cgatcgcaac accagaacaa ttagctaaag taaaagtatt aattgatcaa    6240
tatgttgcag atggcaatag aatgattgat gaagatgcga cattaaatga catcaaacaa    6300
cacacgcaat tcattgttga tgaattttta gcaattaaat taccagctga agcgacgaaa    6360
gtatcaccaa agaaattca gccagctcca aaagtttgta cgcctattaa aaaagaagag    6420
acacatgaat cgcgcaaagt tgaaaaagaa cttccaaata caggttctga aggaatggat    6480
ttaccattga agaatttgc actgattaca ggtgcggctt tgttagctag aagacgtact    6540
aaaaacgaaa aagaatcata a                                             6561
```

<210> SEQ ID NO 86
<211> LENGTH: 2319
<212> TYPE: DNA

<213> ORGANISM: S. aureus

<400> SEQUENCE: 86

```
gaggagaatt cagtacaaga cgttaaagat tcgaatacgg atgatgaatt atcagacagc      60
aatgatcagt ctagtgatga agaaaagaat gatgtgatca ataataatca gtcaataaac     120
accgacgata ataaccaaat aattaaaaaa gaagaaacga ataactacga tggcatagaa     180
aaacgctcag aagatagaac agagtcaaca acaaatgtag atgaaaacga agcaacattt     240
ttacaaaaga cccctcaaga taatactcat cttacagaag aagaggtaaa agaatcctca     300
tcagtcgaat cctcaaattc atcaattgat actgcccaac aaccatctca cacaacaata     360
aatagagaag aatctgttca acaagtgat aatgtagaag attcacacgt atcagatttt     420
gctaactcta aaataaaaga gagtaacact gaatctggta agaagagaa tactatagag     480
caacctaata aagtaaaaga gattcaaca acaagtcagc cgtctggcta tacaaatata     540
gatgaaaaaa tttcaaatca agtgagtta ttaaatttac caataaatga atatgaaaat     600
aaggctagac cattatctac aacatctgcc caaccatcga ttaaacgtgt aaccgtaaat     660
caattagcgg cggaacaagg ttcgaatgtt aatcatttaa ttaaagttac tgatcaaagt     720
attactgaag gatatgatga tagtgaaggt gttattaaag cacatgatgc tgaaaactta     780
atctatgatg taacttttga agtagatgat aaggtgaaat ctggtgatac gatgacagtg     840
gatatagata agaatacagt tccatcagat ttaaccgata gctttacaat accaaaaata     900
aaagataatt ctggagaaat catcgctaca ggtacttatg ataacaaaaa taaacaaatc     960
acctatactt ttacagatta tgtagataag tatgaaaata ttaaagcaca ccttaaatta    1020
acgtcataca ttgataaatc aaaggttcca aataataata ccaagttaga tgtagaatat    1080
aaaacggccc tttcatcagt aaataaaaca attacgttg aatatcaaag acctaacgaa    1140
aatcggactg ctaaccttca agtatgtttt acaaacatag atacgaaaaa tcatacagtt    1200
gagcaaacga tttatattaa ccctcttcgt tattcagcca aggaaacaaa tgtaaatatt    1260
tcagggaatg gtgatgaagg ttcaacaatt atagacgata gcacaataat taaagtttat    1320
aaggttggag ataatcaaaa tttaccagat agtaacagaa tttatgatta cagtgaatat    1380
gaagatgtca caaatgatga ttatgcccaa ttaggaaata ataatgatgt gaatattaat    1440
tttggtaata tagattcacc atatattatt aaagttatta gtaaatatga ccctaataag    1500
gatgattaca cgactataca gcaaactgtg acaatgcaga cgactataaa tgagtatact    1560
ggtgagttta aacagcatc ctatgataat acaattgctt tctctacaag ttcaggtcaa    1620
ggacaaggtg acttgcctcc tgaaaaaact tataaaatcg gagattacgt atgggaagat    1680
gtagataaag atggtattca aaatacaaat gataatgaaa accgcttag taatgtattg    1740
gtaactttga cgtatcctga tggaacttca aaatcagtca gaacagatga agatgggaaa    1800
tatcaatttg atggattgaa aaacggattg acttataaaa ttacattcga aacacctgaa    1860
ggatatacgc cgacgcttaa acattcagga acaaatcctg cactagactc agaaggtaat    1920
tctgtatggg taactattaa tggacaagac gatatgacga ttgatagtgg attttatcaa    1980
acacctaaat acagcttagg gaactatgta tggtatgaca ctaataaaga tggtattcaa    2040
ggtgatgatg aaaaaggaat ctctggagtt aaagtgacgt taaagatga aaacggaaat    2100
atcattagta caactacaac cgatgaaaat ggaaagtatc aatttgataa tttaaatagt    2160
ggtaattata ttgttcattt tgataaacct tcaggtatga ctcaaacaac aacagattct    2220
ggtgatgatg acgaacagga tgctgatggg gaagaagttc atgtaacaat tactgatcat    2280
```

```
gatgacttta gtatagataa cggatactat gatgacgaa                              2319
```

<210> SEQ ID NO 87
<211> LENGTH: 774
<212> TYPE: PRT
<213> ORGANISM: Artificial Sequence
<220> FEATURE:
<223> OTHER INFORMATION: Staphylococcus epidermidis

<400> SEQUENCE: 87

```
Met Glu Glu Asn Ser Val Gln Asp Val Lys Asp Ser Asn Thr Asp Asp
 1               5                  10                  15

Glu Leu Ser Asp Ser Asn Asp Gln Ser Ser Asp Glu Glu Lys Asn Asp
            20                  25                  30

Val Ile Asn Asn Asn Gln Ser Ile Asn Thr Asp Asp Asn Asn Gln Ile
        35                  40                  45

Ile Lys Lys Glu Glu Thr Asn Asn Tyr Asp Gly Ile Glu Lys Arg Ser
    50                  55                  60

Glu Asp Arg Thr Glu Ser Thr Thr Asn Val Asp Glu Asn Glu Ala Thr
65                  70                  75                  80

Phe Leu Gln Lys Thr Pro Gln Asp Asn Thr His Leu Thr Glu Glu Glu
                85                  90                  95

Val Lys Glu Ser Ser Ser Val Glu Ser Ser Asn Ser Ser Ile Asp Thr
            100                 105                 110

Ala Gln Gln Pro Ser His Thr Thr Ile Asn Arg Glu Glu Ser Val Gln
        115                 120                 125

Thr Ser Asp Asn Val Glu Asp Ser His Val Ser Asp Phe Ala Asn Ser
    130                 135                 140

Lys Ile Lys Glu Ser Asn Thr Glu Ser Gly Lys Glu Glu Asn Thr Ile
145                 150                 155                 160

Glu Gln Pro Asn Lys Val Lys Glu Asp Ser Thr Thr Ser Gln Pro Ser
                165                 170                 175

Gly Tyr Thr Asn Ile Asp Glu Lys Ile Ser Asn Gln Asp Glu Leu Leu
            180                 185                 190

Asn Leu Pro Ile Asn Glu Tyr Glu Asn Lys Ala Arg Pro Leu Ser Thr
        195                 200                 205

Thr Ser Ala Gln Pro Ser Ile Lys Arg Val Thr Val Asn Gln Leu Ala
    210                 215                 220

Ala Glu Gln Gly Ser Asn Val Asn His Leu Ile Lys Val Thr Asp Gln
225                 230                 235                 240

Ser Ile Thr Glu Gly Tyr Asp Asp Ser Glu Gly Val Ile Lys Ala His
                245                 250                 255

Asp Ala Glu Asn Leu Ile Tyr Asp Val Thr Phe Glu Val Asp Asp Lys
            260                 265                 270

Val Lys Ser Gly Asp Thr Met Thr Val Asp Ile Asp Lys Asn Thr Val
        275                 280                 285

Pro Ser Asp Leu Thr Asp Ser Phe Thr Ile Pro Lys Ile Lys Asp Asn
    290                 295                 300

Ser Gly Glu Ile Ile Ala Thr Gly Thr Tyr Asp Asn Lys Asn Lys Gln
305                 310                 315                 320

Ile Thr Tyr Thr Phe Thr Asp Tyr Val Asp Lys Tyr Glu Asn Ile Lys
                325                 330                 335

Ala His Leu Lys Leu Thr Ser Tyr Ile Asp Lys Ser Lys Val Pro Asn
            340                 345                 350
```

```
Asn Asn Thr Lys Leu Asp Val Glu Tyr Lys Thr Ala Leu Ser Ser Val
            355                 360                 365

Asn Lys Thr Ile Thr Val Glu Tyr Gln Arg Pro Asn Glu Asn Arg Thr
    370                 375                 380

Ala Asn Leu Gln Ser Met Phe Thr Asn Ile Asp Thr Lys Asn His Thr
385                 390                 395                 400

Val Glu Gln Thr Ile Tyr Ile Asn Pro Leu Arg Tyr Ser Ala Lys Glu
                405                 410                 415

Thr Asn Val Asn Ile Ser Gly Asn Gly Asp Glu Gly Ser Thr Ile Ile
            420                 425                 430

Asp Asp Ser Thr Ile Ile Lys Val Tyr Lys Val Gly Asp Asn Gln Asn
        435                 440                 445

Leu Pro Asp Ser Asn Arg Ile Tyr Asp Tyr Ser Glu Tyr Glu Asp Val
    450                 455                 460

Thr Asn Asp Asp Tyr Ala Gln Leu Gly Asn Asn Asn Asp Val Asn Ile
465                 470                 475                 480

Asn Phe Gly Asn Ile Asp Ser Pro Tyr Ile Ile Lys Val Ile Ser Lys
                485                 490                 495

Tyr Asp Pro Asn Lys Asp Asp Tyr Thr Thr Ile Gln Gln Thr Val Thr
            500                 505                 510

Met Gln Thr Thr Ile Asn Glu Tyr Thr Gly Glu Phe Arg Thr Ala Ser
        515                 520                 525

Tyr Asp Asn Thr Ile Ala Phe Ser Thr Ser Ser Gly Gln Gly Gln Gly
    530                 535                 540

Asp Leu Pro Pro Glu Lys Thr Tyr Lys Ile Gly Asp Tyr Val Trp Glu
545                 550                 555                 560

Asp Val Asp Lys Asp Gly Ile Gln Asn Thr Asn Asp Asn Glu Lys Pro
                565                 570                 575

Leu Ser Asn Val Leu Val Thr Leu Thr Tyr Pro Asp Gly Thr Ser Lys
            580                 585                 590

Ser Val Arg Thr Asp Glu Asp Gly Lys Tyr Gln Phe Asp Gly Leu Lys
        595                 600                 605

Asn Gly Leu Thr Tyr Lys Ile Thr Phe Glu Thr Pro Glu Gly Tyr Thr
    610                 615                 620

Pro Thr Leu Lys His Ser Gly Thr Asn Pro Ala Leu Asp Ser Glu Gly
625                 630                 635                 640

Asn Ser Val Trp Val Thr Ile Asn Gly Gln Asp Met Thr Ile Asp
                645                 650                 655

Ser Gly Phe Tyr Gln Thr Pro Lys Tyr Ser Leu Gly Asn Tyr Val Trp
            660                 665                 670

Tyr Asp Thr Asn Lys Asp Gly Ile Gln Gly Asp Asp Glu Lys Gly Ile
        675                 680                 685

Ser Gly Val Lys Val Thr Leu Lys Asp Glu Asn Gly Asn Ile Ile Ser
    690                 695                 700

Thr Thr Thr Thr Asp Glu Asn Gly Lys Tyr Gln Phe Asp Asn Leu Asn
705                 710                 715                 720

Ser Gly Asn Tyr Ile Val His Phe Asp Lys Pro Ser Gly Met Thr Gln
                725                 730                 735

Thr Thr Thr Asp Ser Gly Asp Asp Glu Gln Asp Ala Asp Gly Glu
            740                 745                 750

Glu Val His Val Thr Ile Thr Asp His Asp Asp Phe Ser Ile Asp Asn
        755                 760                 765

Gly Tyr Tyr Asp Asp Glu
```

770

<210> SEQ ID NO 88
<211> LENGTH: 128
<212> TYPE: PRT
<213> ORGANISM: Artificial Sequence
<220> FEATURE:
<223> OTHER INFORMATION: Staphylococcus aureus

<400> SEQUENCE: 88

Met Asp Val Asn Thr Val Asn Gln Lys Ala Ala Ser Val Lys Ser Thr
1               5                   10                  15

Lys Asp Ala Leu Asp Gly Gln Gln Asn Leu Gln Arg Ala Lys Thr Glu
            20                  25                  30

Ala Thr Asn Ala Ile Thr His Ala Ser Asp Leu Asn Gln Ala Gln Lys
        35                  40                  45

Asn Ala Leu Thr Gln Gln Val Asn Ser Ala Gln Asn Val His Ala Val
    50                  55                  60

Asn Asp Ile Lys Gln Thr Thr Gln Ser Leu Asn Thr Ala Met Thr Gly
65                  70                  75                  80

Leu Lys Arg Gly Val Ala Asn His Asn Gln Val Val Gln Ser Asp Asn
                85                  90                  95

Tyr Val Asn Ala Asp Thr Asn Lys Lys Asn Asp Tyr Asn Asn Ala Tyr
            100                 105                 110

Asn His Ala Asn Asp Ile Ile Asn Gly Asn Ala Gln His Pro Val Ile
        115                 120                 125

<210> SEQ ID NO 89
<211> LENGTH: 52
<212> TYPE: PRT
<213> ORGANISM: Artificial Sequence
<220> FEATURE:
<223> OTHER INFORMATION: Staphylococcus aureus

<400> SEQUENCE: 89

Gln Thr Thr Gln Asn Asn Tyr Val Thr Asp Gln Gln Lys Ala Phe Tyr
1               5                   10                  15

Gln Val Leu His Leu Lys Gly Ile Thr Glu Gln Arg Asn Gln Tyr
            20                  25                  30

Ile Lys Thr Leu Arg Glu His Pro Glu Arg Ala Gln Glu Val Phe Ser
        35                  40                  45

Glu Ser Leu Lys
    50

<210> SEQ ID NO 90
<211> LENGTH: 36
<212> TYPE: PRT
<213> ORGANISM: Artificial Sequence
<220> FEATURE:
<223> OTHER INFORMATION: Staphylococcus aureus

<400> SEQUENCE: 90

Val Lys Asn Asn Leu Arg Tyr Gly Ile Arg Lys His Lys Leu Gly Ala
1               5                   10                  15

Ala Ser Val Phe Leu Gly Thr Met Ile Val Val Gly Met Gly Gln Asp
            20                  25                  30

Lys Glu Ala Ala
        35

<210> SEQ ID NO 91

```
<211> LENGTH: 6
<212> TYPE: PRT
<213> ORGANISM: Artificial Sequence
<220> FEATURE:
<223> OTHER INFORMATION: Staphylococcus aureus

<400> SEQUENCE: 91

Asp Arg His Phe Leu Asn
 1               5

<210> SEQ ID NO 92
<211> LENGTH: 4
<212> TYPE: PRT
<213> ORGANISM: Artificial Sequence
<220> FEATURE:
<223> OTHER INFORMATION: Staphylococcus aureus

<400> SEQUENCE: 92

Gly Asn Tyr Asp
 1

<210> SEQ ID NO 93
<211> LENGTH: 5
<212> TYPE: PRT
<213> ORGANISM: Artificial Sequence
<220> FEATURE:
<223> OTHER INFORMATION: Staphylococcus aureus

<400> SEQUENCE: 93

Arg Arg Tyr Pro Phe
 1               5

<210> SEQ ID NO 94
<211> LENGTH: 6
<212> TYPE: PRT
<213> ORGANISM: Artificial Sequence
<220> FEATURE:
<223> OTHER INFORMATION: Staphylococcus aureus

<400> SEQUENCE: 94

Lys Thr Thr Leu Leu Lys
 1               5

<210> SEQ ID NO 95
<211> LENGTH: 7
<212> TYPE: PRT
<213> ORGANISM: Artificial Sequence
<220> FEATURE:
<223> OTHER INFORMATION: Staphylococcus aureus

<400> SEQUENCE: 95

Gly Val Thr Thr Ser Leu Ser
 1               5

<210> SEQ ID NO 96
<211> LENGTH: 5
<212> TYPE: PRT
<213> ORGANISM: Artificial Sequence
<220> FEATURE:
<223> OTHER INFORMATION: Staphylococcus aureus

<400> SEQUENCE: 96

Val Asp Trp Leu Arg
 1               5

<210> SEQ ID NO 97
<211> LENGTH: 4
```

```
<212> TYPE: PRT
<213> ORGANISM: Artificial Sequence
<220> FEATURE:
<223> OTHER INFORMATION: Staphylococcus aureus

<400> SEQUENCE: 97

Arg Gly Phe Leu
 1

<210> SEQ ID NO 98
<211> LENGTH: 15
<212> TYPE: PRT
<213> ORGANISM: Artificial Sequence
<220> FEATURE:
<223> OTHER INFORMATION: Staphylococcus aureus

<400> SEQUENCE: 98

Lys Ile Lys Val Tyr Val Gly Asn Tyr Asp Phe Trp Tyr Gln Ser
 1               5                  10                  15

<210> SEQ ID NO 99
<211> LENGTH: 16
<212> TYPE: PRT
<213> ORGANISM: Artificial Sequence
<220> FEATURE:
<223> OTHER INFORMATION: Staphylococcus aureus

<400> SEQUENCE: 99

Thr Val Ile Val Val Ser His Asp Arg His Phe Leu Tyr Asn Asn Val
 1               5                  10                  15

<210> SEQ ID NO 100
<211> LENGTH: 15
<212> TYPE: PRT
<213> ORGANISM: Artificial Sequence
<220> FEATURE:
<223> OTHER INFORMATION: Staphylococcus aureus

<400> SEQUENCE: 100

Thr Glu Thr Phe Leu Arg Gly Phe Leu Gly Arg Met Leu Phe Ser
 1               5                  10                  15

<210> SEQ ID NO 101
<211> LENGTH: 895
<212> TYPE: PRT
<213> ORGANISM: Staphylococcus aureus

<400> SEQUENCE: 101

Met Asn Lys His His Pro Lys Leu Arg Ser Phe Tyr Ser Ile Arg Lys
 1               5                  10                  15

Ser Thr Leu Gly Val Ala Ser Val Ile Val Ser Thr Leu Phe Leu Ile
                20                  25                  30

Thr Ser Gln His Gln Ala Gln Ala Ala Glu Asn Thr Asn Thr Ser Asp
            35                  40                  45

Lys Ile Ser Glu Asn Gln Asn Asn Ala Thr Thr Thr Gln Pro Pro
        50                  55                  60

Lys Asp Thr Asn Gln Thr Gln Pro Ala Thr Gln Pro Ala Asn Thr Ala
 65                  70                  75                  80

Lys Asn Tyr Pro Ala Ala Asp Glu Ser Leu Lys Asp Ala Ile Lys Asp
                85                  90                  95

Pro Ala Leu Glu Asn Lys Glu His Asp Ile Gly Pro Arg Glu Gln Val
                100                 105                 110

Asn Phe Gln Leu Leu Asp Lys Asn Asn Glu Thr Gln Tyr Tyr His Phe
```

```
                115                 120                 125
        Phe Ser Ile Lys Asp Pro Ala Asp Val Tyr Thr Lys Lys Lys Ala
        130                 135                 140

Glu Val Glu Leu Asp Ile Asn Thr Ala Ser Thr Trp Lys Lys Phe Glu
        145                 150                 155                 160

Val Tyr Glu Asn Asn Gln Lys Leu Pro Val Arg Leu Val Ser Tyr Ser
                            165                 170                 175

Pro Val Pro Glu Asp His Ala Tyr Ile Arg Phe Pro Val Ser Asp Gly
                        180                 185                 190

Thr Gln Glu Leu Lys Ile Val Ser Ser Thr Gln Ile Asp Asp Gly Glu
                    195                 200                 205

Glu Thr Asn Tyr Asp Tyr Thr Lys Leu Val Phe Ala Lys Pro Ile Tyr
            210                 215                 220

Asn Asp Pro Ser Leu Val Lys Ser Asp Thr Asn Asp Ala Val Val Thr
        225                 230                 235                 240

Asn Asp Gln Ser Ser Ser Val Ala Ser Asn Gln Thr Asn Thr Asn Thr
                            245                 250                 255

Ser Asn Gln Asn Ile Ser Thr Ile Asn Asn Ala Asn Asn Gln Pro Gln
                        260                 265                 270

Ala Thr Thr Asn Met Ser Gln Pro Ala Gln Pro Lys Ser Ser Thr Asn
                    275                 280                 285

Ala Asp Gln Ala Ser Ser Gln Pro Ala His Glu Thr Asn Ser Asn Gly
            290                 295                 300

Asn Thr Asn Asp Lys Thr Asn Glu Ser Ser Asn Gln Ser Asp Val Asn
        305                 310                 315                 320

Gln Gln Tyr Pro Pro Ala Asp Glu Ser Leu Gln Asp Ala Ile Lys Asn
                            325                 330                 335

Pro Ala Ile Ile Asp Lys Glu His Thr Ala Asp Asn Trp Arg Pro Ile
                        340                 345                 350

Asp Phe Gln Met Lys Asn Asp Lys Gly Glu Arg Gln Phe Tyr His Tyr
                    355                 360                 365

Ala Ser Thr Val Glu Pro Ala Thr Val Ile Phe Thr Lys Thr Gly Pro
            370                 375                 380

Ile Ile Glu Leu Gly Leu Lys Thr Ala Ser Thr Trp Lys Lys Phe Glu
        385                 390                 395                 400

Val Tyr Glu Gly Asp Lys Lys Leu Pro Val Glu Leu Val Ser Tyr Asp
                            405                 410                 415

Ser Asp Lys Asp Tyr Ala Tyr Ile Arg Phe Pro Val Ser Asn Gly Thr
                        420                 425                 430

Arg Glu Val Lys Ile Val Ser Ser Ile Glu Tyr Gly Glu Asn Ile His
                    435                 440                 445

Glu Asp Tyr Asp Tyr Thr Leu Met Val Phe Ala Gln Pro Ile Thr Asn
            450                 455                 460

Asn Pro Asp Asp Tyr Val Asp Glu Glu Thr Tyr Asn Leu Gln Lys Leu
        465                 470                 475                 480

Leu Ala Pro Tyr His Lys Ala Lys Thr Leu Glu Arg Gln Val Tyr Glu
                            485                 490                 495

Leu Glu Lys Leu Gln Glu Lys Leu Pro Glu Lys Tyr Lys Ala Glu Tyr
                        500                 505                 510
```

```
Lys Lys Lys Leu Asp Gln Thr Arg Val Glu Leu Ala Asp Gln Val Lys
            515                 520                 525

Ser Ala Val Thr Glu Phe Glu Asn Val Thr Pro Thr Asn Asp Gln Leu
530                 535                 540

Thr Asp Leu Gln Glu Ala His Phe Val Val Phe Glu Ser Glu Glu Asn
545                 550                 555                 560

Ser Glu Ser Val Met Asp Gly Phe Val Glu His Pro Phe Tyr Thr Ala
                565                 570                 575

Thr Leu Asn Gly Gln Lys Tyr Val Val Met Lys Thr Lys Asp Asp Ser
            580                 585                 590

Tyr Trp Lys Asp Leu Ile Val Glu Gly Lys Arg Val Thr Thr Val Ser
        595                 600                 605

Lys Asp Pro Lys Asn Asn Ser Arg Thr Leu Ile Phe Pro Tyr Ile Pro
    610                 615                 620

Asp Lys Ala Val Tyr Asn Ala Ile Val Lys Val Val Ala Asn Ile
625                 630                 635                 640

Gly Tyr Glu Gly Gln Tyr His Val Arg Ile Ile Asn Gln Asp Ile Asn
                645                 650                 655

Thr Lys Asp Asp Asp Thr Ser Gln Asn Asn Thr Ser Glu Pro Leu Asn
            660                 665                 670

Val Gln Thr Gly Gln Glu Gly Lys Val Ala Asp Thr Asp Val Ala Glu
        675                 680                 685

Asn Ser Ser Thr Ala Thr Asn Pro Lys Asp Ala Ser Asp Lys Ala Asp
    690                 695                 700

Val Ile Glu Pro Glu Ser Asp Val Val Lys Asp Ala Asp Asn Asn Ile
705                 710                 715                 720

Asp Lys Asp Val Gln His Asp Val Asp His Leu Ser Asp Met Ser Asp
                725                 730                 735

Asn Asn His Phe Asp Lys Tyr Asp Leu Lys Glu Met Asp Thr Gln Ile
            740                 745                 750

Ala Lys Asp Thr Asp Arg Asn Val Asp Lys Asp Ala Asp Asn Ser Val
        755                 760                 765

Gly Met Ser Ser Asn Val Asp Thr Asp Lys Asp Ser Asn Lys Asn Lys
770                 775                 780

Asp Lys Val Ile Gln Leu Asn His Ile Ala Asp Lys Asn Asn His Thr
785                 790                 795                 800

Gly Lys Ala Ala Lys Leu Asp Val Val Lys Gln Asn Tyr Asn Asn Thr
                805                 810                 815

Asp Lys Val Thr Asp Lys Lys Thr Glu His Leu Pro Ser Asp Ile
            820                 825                 830

His Lys Thr Val Asp Lys Thr Val Lys Thr Lys Glu Lys Ala Gly Thr
        835                 840                 845

Pro Ser Lys Glu Asn Lys Leu Ser Gln Ser Lys Met Leu Pro Lys Thr
850                 855                 860

Gly Glu Thr Thr Ser Ser Gln Ser Trp Trp Gly Leu Tyr Ala Leu Leu
865                 870                 875                 880

Gly Met Leu Ala Leu Phe Ile Pro Lys Phe Arg Lys Glu Ser Lys
                885                 890                 895

<210> SEQ ID NO 102
<211> LENGTH: 5
<212> TYPE: PRT
<213> ORGANISM: Artificial Sequence
<220> FEATURE:
<223> OTHER INFORMATION: in silico derived motif
```

```
<220> FEATURE:
<221> NAME/KEY: VARIANT
<222> LOCATION: 3
<223> OTHER INFORMATION: Xaa = Any Amino Acid

<400> SEQUENCE: 102

Leu Pro Xaa Thr Gly
 1               5
```